US011834458B2

(12) United States Patent
Hung et al.

(10) Patent No.: US 11,834,458 B2
(45) Date of Patent: Dec. 5, 2023

(54) ANTI-CANCER NUCLEAR HORMONE RECEPTOR-TARGETING COMPOUNDS

(71) Applicant: Nuvation Bio Inc., New York, NY (US)

(72) Inventors: David Hung, New York, NY (US); Jayakanth Kankanala, Saint Paul, MN (US); Christopher Paul Miller, San Mateo, CA (US); Jeremy David Pettigrew, Vancouver (CA); Son Minh Pham, San Francisco, CA (US); Ihab S. Darwish, San Carlos, CA (US)

(73) Assignee: NUVATION BIO INC., New York, NY (US)

( * ) Notice: Subject to any disclaimer, the term of this patent is extended or adjusted under 35 U.S.C. 154(b) by 0 days.

(21) Appl. No.: 17/701,425

(22) Filed: Mar. 22, 2022

(65) Prior Publication Data
US 2022/0340587 A1 Oct. 27, 2022

Related U.S. Application Data

(60) Provisional application No. 63/165,087, filed on Mar. 23, 2021.

(51) Int. Cl.
*C07D 491/22* (2006.01)
*A61K 31/4745* (2006.01)
*C07D 471/14* (2006.01)

(52) U.S. Cl.
CPC ......... *C07D 491/22* (2013.01); *C07D 471/14* (2013.01)

(58) Field of Classification Search
CPC ..... C07D 491/22; C07F 7/02; A61K 31/4745; A61P 35/00
USPC .................. 546/48, 41, 14; 514/283, 279
See application file for complete search history.

(56) References Cited

U.S. PATENT DOCUMENTS

| | | | |
|---|---|---|---|
| 6,074,625 A | 6/2000 | Hawthorne et al. | |
| 6,462,038 B1 | 10/2002 | Higuchi et al. | |
| 6,777,427 B2 | 8/2004 | Miyakawa et al. | |
| 7,037,919 B1 | 5/2006 | Hanada et al. | |
| 7,038,041 B2 | 5/2006 | Ray et al. | |
| 7,220,730 B2 | 5/2007 | Baranowska-Kortylewicz et al. | |
| 7,449,464 B2 | 11/2008 | Martin et al. | |
| 8,012,976 B2 | 6/2011 | Wang et al. | |
| 7,981,889 B2 | 7/2011 | Martin et al. | |
| 8,129,380 B2 | 3/2012 | Menear et al. | |
| 8,252,802 B2 | 8/2012 | Foote et al. | |
| 8,629,167 B2 | 1/2014 | Miller | |
| 8,785,501 B2 | 7/2014 | Witt-Enderby et al. | |
| 8,871,765 B2 | 10/2014 | Shrivastava | |
| 9,056,140 B2 | 6/2015 | Stoloff et al. | |
| 9,963,433 B2 | 5/2018 | Qin | |
| 10,300,143 B2 | 5/2019 | Sengupta et al. | |
| 10,723,717 B2 | 7/2020 | Crew et al. | |
| 10,730,870 B2 | 8/2020 | Crew et al. | |
| 11,034,669 B2 | 6/2021 | Chakravarty et al. | |
| 11,292,782 B2 | 4/2022 | Chakravarty et al. | |
| 2003/0059465 A1 | 3/2003 | Unger et al. | |
| 2005/0069495 A1 | 3/2005 | Baranowska-Kortylewicz et al. | |
| 2005/0096381 A1 | 5/2005 | Kohen et al. | |
| 2005/0227919 A1 | 10/2005 | Ashworth et al. | |
| 2005/0245485 A1 | 11/2005 | Lanter et al. | |
| 2005/0250741 A1 | 11/2005 | Lanter et al. | |
| 2005/0277660 A1 | 12/2005 | Miyakawa | |
| 2005/0277681 A1 | 12/2005 | Hanney et al. | |
| 2006/0063819 A1 | 3/2006 | Lanter et al. | |
| 2006/0128737 A1 | 6/2006 | Miyakawa et al. | |
| 2006/0142387 A1 | 6/2006 | Cadilla et al. | |
| 2006/0148893 A1 | 7/2006 | Blanc et al. | |
| 2006/0160845 A1 | 7/2006 | Schlienger et al. | |
| 2006/0211756 A1 | 9/2006 | Zhang et al. | |
| 2009/0257999 A1 | 10/2009 | Fink | |
| 2010/0003192 A1 | 1/2010 | Sherman et al. | |
| 2011/0028420 A1 | 2/2011 | Boulares et al. | |
| 2011/0053923 A1 | 3/2011 | Foote et al. | |
| 2011/0104074 A1 | 5/2011 | Kakar | |
| 2011/0305631 A1 | 12/2011 | Govindan et al. | |
| 2012/0046461 A1 | 2/2012 | Hanson | |
| 2013/0156698 A1 | 6/2013 | Zhou et al. | |
| 2013/0309170 A1 | 11/2013 | Reiner et al. | |
| 2014/0080905 A1 | 3/2014 | Dalton et al. | |
| 2015/0110742 A1 | 4/2015 | Spiegel et al. | |
| 2015/0284416 A1 | 10/2015 | Zhao | |
| 2015/0322155 A1 | 11/2015 | Zhao | |
| 2016/0058872 A1 | 3/2016 | Crew et al. | |
| 2016/0176916 A1 | 6/2016 | Bradner et al. | |
| 2016/0214972 A1 | 7/2016 | Jin et al. | |
| 2017/0008904 A1 | 1/2017 | Crew et al. | |
| 2017/0217903 A1 | 8/2017 | Qin et al. | |
| 2017/0233365 A1 | 8/2017 | Hilderbrand et al. | |

(Continued)

FOREIGN PATENT DOCUMENTS

| | | |
|---|---|---|
| CN | 101948500 A | 1/2011 |
| CN | 101967172 A | 2/2011 |

(Continued)

OTHER PUBLICATIONS

Berge, S.M. et al. (Jan. 1977). "Pharmaceuticals Salts," J. Pharmaceutical Sciences 66(1):1-19.
Chekler, E.L.P. (Mar. 27, 2014, e-pub. Feb. 17, 2014). "1-(2-Hydroxy-2-methyl-3-phenoxypropanoyl) indoline-4-carbonitrile Derivatives as Potent and Tissue Selective Androgen Receptor Modulators," J. Med. Chem. 57(6):2462-2471.
Gillmore, A.T. et al. (Novmeber 14, 2012). "Multkilogram Scale-Up of a Reductive Alkylation Route to a Novel PARP Inhibitor," Org. Process Res. Dev. 16(12):1897-1904.
Guo, C. et al. (Sep. 21, 2011). "Discovery of Aryloxy Tetramethylcyclobutanes as Novel Androgen Receptor Antagonists," J. Medicinal Chemistry 54:7693-7704.
Hughes-Davies, L. (Nov. 26, 2003) "EMSY Links the BRCA2 Pathway to Sporadic Breast and Ovarian Cancer," Cell 115:523-535.

(Continued)

Primary Examiner — Charanjit Aulakh
(74) Attorney, Agent, or Firm — MORRISON & FOERSTER LLP

(57) ABSTRACT

The disclosure relates to anti-cancer compounds derived from nuclear steroid receptor binders, to products containing the same, as well as to methods of their use and preparation.

34 Claims, No Drawings

(56) References Cited

U.S. PATENT DOCUMENTS

| | | |
|---|---|---|
| 2017/0319543 A1 | 11/2017 | Ashworth et al. |
| 2017/0327469 A1 | 11/2017 | Crew et al. |
| 2018/0052180 A1 | 2/2018 | Jose et al. |
| 2018/0099940 A1 | 4/2018 | Crew et al. |
| 2018/0215731 A1 | 8/2018 | Crew et al. |
| 2018/0228907 A1 | 8/2018 | Crew et al. |
| 2018/0346461 A1 | 12/2018 | Crew et al. |
| 2019/0111010 A1 | 4/2019 | Narayanan et al. |
| 2019/0365904 A1 | 12/2019 | Low et al. |
| 2019/0375732 A1 | 12/2019 | Hung et al. |
| 2020/0055825 A1 | 2/2020 | Crew et al. |
| 2020/0155689 A1 | 5/2020 | Crew et al. |
| 2020/0155690 A1 | 5/2020 | Crew et al. |
| 2020/0172480 A1 | 6/2020 | Zhao et al. |
| 2020/0199098 A1 | 6/2020 | Chakravarty et al. |
| 2020/0239433 A1 | 7/2020 | Chakravarty et al. |
| 2020/0281955 A1 | 9/2020 | Xu et al. |
| 2020/0297725 A1 | 9/2020 | Crews et al. |
| 2020/0360523 A1 | 11/2020 | Hung et al. |
| 2020/0392131 A1 | 12/2020 | Crew et al. |
| 2021/0214316 A1 | 7/2021 | Pham et al. |
| 2022/0380364 A1 | 12/2022 | Hung et al. |
| 2023/0122310 A1 | 4/2023 | Hung et al. |

FOREIGN PATENT DOCUMENTS

| | | |
|---|---|---|
| CN | 101967173 A | 2/2011 |
| CN | 102492009 A | 6/2012 |
| CN | 102492010 A | 6/2012 |
| CN | 102516347 A | 6/2012 |
| CN | 102532237 A | 7/2012 |
| CN | 104292290 A | 1/2015 |
| CN | 107266520 A | 10/2017 |
| CN | 107286166 A | 10/2017 |
| CN | 105315294 A | 5/2018 |
| EP | 0699754 A1 | 3/1996 |
| EP | 0705903 A1 | 4/1996 |
| JP | 5934986 B2 | 3/2013 |
| WO | WO 1990010638 A1 | 9/1990 |
| WO | WO 1996000090 A1 | 1/1996 |
| WO | WO 1996013613 A1 | 5/1996 |
| WO | 200127086 A1 | 4/2001 |
| WO | 2003034987 A2 | 5/2003 |
| WO | WO 2003079965 A2 | 10/2003 |
| WO | WO 2003101995 A2 | 11/2003 |
| WO | 2004000816 A1 | 12/2003 |
| WO | 2004013104 A1 | 2/2004 |
| WO | 2004035736 A2 | 4/2004 |
| WO | 2004041277 A1 | 5/2004 |
| WO | WO 2004080976 A1 | 9/2004 |
| WO | WO 2004093807 A2 | 11/2004 |
| WO | 2004113309 A1 | 12/2004 |
| WO | 2005000795 A2 | 1/2005 |
| WO | WO 2005034856 A2 | 4/2005 |
| WO | 2005085185 A1 | 9/2005 |
| WO | WO 2005086974 A2 | 9/2005 |
| WO | 2005108351 A1 | 11/2005 |
| WO | 2005115361 A2 | 12/2005 |
| WO | WO 2005118612 A1 | 12/2005 |
| WO | 2006044707 A1 | 4/2006 |
| WO | 2006106108 A1 | 6/2006 |
| WO | 2006124447 A2 | 11/2006 |
| WO | 2006133216 A2 | 12/2006 |
| WO | 2007002181 A2 | 1/2007 |
| WO | WO 2007035927 A2 | 3/2007 |
| WO | WO 2008090379 A1 | 7/2008 |
| WO | WO 2009005839 A2 | 1/2009 |
| WO | WO 2009029375 A1 | 3/2009 |
| WO | 2009114459 A2 | 9/2009 |
| WO | WO 2009155431 A1 | 12/2009 |
| WO | WO 2010085747 A1 | 7/2010 |
| WO | WO 2010108251 A2 | 9/2010 |
| WO | 2011079245 A1 | 6/2011 |
| WO | WO 2011130697 A2 | 10/2011 |
| WO | WO 2012014221 A1 | 2/2012 |
| WO | WO 2012050868 A1 | 4/2012 |
| WO | WO 2012074840 A2 | 6/2012 |
| WO | 2012123820 A1 | 9/2012 |
| WO | WO 2012134446 A1 | 10/2012 |
| WO | WO 2013028495 A1 | 2/2013 |
| WO | WO 2013106643 A2 | 7/2013 |
| WO | 2013170147 A1 | 11/2013 |
| WO | WO 2014080251 A1 | 5/2014 |
| WO | WO 2014108452 A1 | 7/2014 |
| WO | 2014191726 A1 | 12/2014 |
| WO | WO 2014201026 A2 | 12/2014 |
| WO | WO 2015038649 A1 | 3/2015 |
| WO | WO 2015095755 A1 | 6/2015 |
| WO | WO 2015134464 A2 | 9/2015 |
| WO | WO 2015143004 A1 | 9/2015 |
| WO | WO 2015151078 A2 | 10/2015 |
| WO | WO 2015151080 A2 | 10/2015 |
| WO | WO 2015151081 A2 | 10/2015 |
| WO | WO 2015155753 A2 | 10/2015 |
| WO | WO 2016059622 A2 | 4/2016 |
| WO | WO 2016077505 A2 | 5/2016 |
| WO | 2016118666 A1 | 7/2016 |
| WO | WO 2016149668 A1 | 9/2016 |
| WO | 2016196337 A1 | 12/2016 |
| WO | WO 2016197032 A1 | 12/2016 |
| WO | WO 2016197114 A1 | 12/2016 |
| WO | WO 2017011590 A1 | 1/2017 |
| WO | 2017075495 A1 | 5/2017 |
| WO | WO 2017170564 A1 | 10/2017 |
| WO | 2017199042 A1 | 11/2017 |
| WO | WO 2017214491 A1 | 12/2017 |
| WO | 2018038680 A1 | 3/2018 |
| WO | 2018071606 A1 | 4/2018 |
| WO | WO 2018111990 A1 | 6/2018 |
| WO | WO 2018156815 A1 | 8/2018 |
| WO | WO 2018185526 A1 | 10/2018 |
| WO | WO 2018234636 A1 | 12/2018 |
| WO | WO 2019023553 A1 | 1/2019 |
| WO | WO 2019100973 A1 | 5/2019 |
| WO | 2019199816 A1 | 10/2019 |
| WO | WO 2019199634 A1 | 10/2019 |
| WO | WO 2019222272 A1 | 11/2019 |
| WO | WO 2019241231 A1 | 12/2019 |
| WO | 2020023851 A1 | 1/2020 |
| WO | WO 2020113088 A1 | 6/2020 |
| WO | WO 2020113094 A1 | 6/2020 |
| WO | WO 2020232119 A1 | 11/2020 |
| WO | WO 2020257998 A1 | 12/2020 |
| WO | 2021013735 A1 | 1/2021 |
| WO | WO 2021055705 A1 | 3/2021 |
| WO | WO 2021097046 A1 | 5/2021 |
| WO | 2021127443 A1 | 6/2021 |
| WO | WO 2021212638 A1 | 10/2021 |
| WO | WO 2022035818 A2 | 2/2022 |
| WO | WO 2022040635 A1 | 2/2022 |
| WO | 2022087125 A1 | 4/2022 |
| WO | 2022098544 A1 | 5/2022 |
| WO | 2022228387 A1 | 11/2022 |
| WO | 2022235585 A1 | 11/2022 |

OTHER PUBLICATIONS

Huxley, M. et al. (2010). "An Androgenic Steroid Delivery Vector That Imparts Activity to a Non-Conventional Platinum(II) Metallo-Drug," Dalton Trans. 39:11353-11364.

International Preliminary Report on Patentability, dated May 17, 2022, for PCT Application No. PCT/US2020/060165, filed Nov. 12, 2020, 9 pages.

International Preliminary Report on Patentability, dated Nov. 16, 2021, for PCT Application No. PCT/US2020/032675, filed May 13, 2020, 8 pages.

International Search Report and Written Opinion, dated Aug. 22, 2022, PCT Application No. PCT/US2022/027334, filed May 2, 2022, 14 pages.

Jadhavar, P.S. et al. (Nov. 1, 2016, e-pub. Oct. 4, 2016). "Targeting Prostate Cancer with Compounds Possessing Dual Activity as Androgen Receptor Antagonists and HDAC6 Inhibitors," Bioorg. Med. Chem. Letter 26:5222-5228.

(56) References Cited

OTHER PUBLICATIONS

Janatová, M. et al. (2003). "Detection Of The Most Frequent Mutations in BRCA1 Gene On Polyacrylamide Gels Containing Spreadex Polymer NAB," Neoplasma 50(4):246-250.
Jasin, M. (2002). "Homologous Repair of DNA Damage And Tumorigenesis:The BRCA Connection," Oncogene 21 (58):8981-8993.
Khanna, K.K. (Mar. 2001). "DNA Double-Strand Breaks: Signaling, Repair And The Cancer Connection," Nat. Genet. 27(3):247-254.
Menear, K.A. et al. (Oct. 23, 2008, e-pub. Sep. 19, 2008). "4-[3-(4-Cyclopropanecarbonylpiperazine-1-Carbonyl)-4-Fluorobenzyl]-2H-Phthalazin-1-One: A Novel Bioavailable Inhibitor Of Poly(ADP-Ribose) Polymerase-1," J. Med. Chem. 51(20):6581-6591.
Mortensen, D.S. et al. (Jul. 23, 2015, e-pub. Jun. 23, 2015). "Optimization of a Series of Triazole Containing Mammalian Target of Rapamycin (mTOR) Kinase Inhibitors and the Discovery of CC-115," J. Med. Chem. 58(14):5599-5608.
Murai, J. et al. (Nov. 1, 2012). "Differential Trapping of PARP1 and PARP2 by Clinical PARP Inhibitors," Cancer Research 72(21):5588-5599, 22 pages.
Neuhausen, S.L. et al. (1992). "Mutation Testing of Early-Onset Breast Cancer Genes BRCA1 and BRCA2," Genet. Test 1(2):75-83.
Radice, P. (Sep. 2002). "Mutations of BRCA Genes in Hereditary Breast and Ovarian Cancer," J. Exp. Clin. Cancer Res. 21(Suppl. 3):9-12.
Tutt, A. et al. (Dec. 2002). "The Relationship Between The Roles Of BRCA Genes In DNA Repair And Cancer Predisposition," Trends Mol. Med. 8(12):571-576.
Wood, R.D. et al. (Feb. 16, 2001). "Human DNA Repair Genes," Science 291:1284-1289.
Ahmed et al., "Synthesis, characterization, and estrogen receptor binding affinity of flavone-, indole-, and furan-estradiol conjugates," Bioorganic & Medicinal Chemistry Letters, 2007, vol. 17, pp. 3212-3216.
Beretta et al., "Androgen Receptor-Directed Molecular Conjugates for Targeting Prostate Cancer," Frontiers in Chemistry, 2019, vol. 7, Article 369, pp. 1-8.
Bertrand et al., "A Gold(III) Pincer Ligand Scaffold for the Synthesis of Binuclear and Bioconjugated Complexes: Synthesis and Anticancer Potential," Chemistry—A European Journal, 2018, vol. 24, Issue 14, pp. 3613-3622.
Biersack et al., "Metallodrug Conjugates with Steroids and Selective Estrogen Receptor Modulators (SERM)," Current Medicinal Chemistry, 2009, vol. 16, pp. 2324-2337.
Borsari et al., "Designing Chimeric Molecules for Drug Discovery by Leveraging Chemical Biology," Journal of Medicinal Chemistry, 2020, vol. 63, Issue 5, pp. 1908-1928.
Brix et al., "Androgen-linked alkylating agents: biological activity in methylnitrosourea-induced rat mammary carcinoma," Journal of Cancer Research and Clinical Oncology, 1990, vol. 116, pp. 538-549.
Burke et al., "Design, Synthesis, and Biological Evaluation of Doxorubicin-Formaldehyde Conjugates Targeted to Breast Cancer Cells," Journal of Medicinal Chemistry, 2004, vol. 47, Issue 5, pp. 1193-1206.
Cheng et al., "MicroRNA silencing for cancer therapy targeted to the tumour microenvironment," Nature, 2015, vol. 518, No. 7537, pp. 107-110.
Cogan et al., "Studies of Targeting and Intracellular Trafficking of an Anti-Androgen Doxorubicin-Formaldehyde Conjugate in PC-3 Prostate Cancer Cells Bearing Androgen Receptor-GFP Chimera," Journal of Medicinal Chemistry, 2004, vol. 47, No. 23, pp. 5690-5699.
Dao et al., "Design, Synthesis, and Initial Biological Evaluation of a Steroidal Anti-estrogen-Doxorubicin Bioconjugate for Targeting Estrogen Receptor-Positive Breast Cancer Cells," Bioconjugate Chemistry, 2012, vol. 23, No. 4, pp. 785-795.
Dao et al., "Targeting the Estrogen Receptor using Steroid-Therapeutic Drug Conjugates (Hybrids)," Bioconjugate Chemistry, 2012, vol. 23, No. 11, pp. 2139-2158.
Dawicki-McKenna et al., "PARP-1 Activation Requires Local Unfolding of an Autoinhibitory Domain," Molecular Cell, 2015, vol. 60, Issue 5, pp. 755-768.
Devraj et al., "Design, Synthesis, and Biological Evaluation of Ellipticine-Estradiol Conjugates," Journal of Medicinal Chemistry, 1996, vol. 39, No. 17, pp. 3367-3374.
Ding et al., "Design of a platinum-acridine-endoxifen conjugate targeted at hormone-dependent breast cancer," Chemical Communications, 2013, vol. 49, No. 24, pp. 2415-2417.
Dizio et al., "Progestin-Rhenium Complexes: Metal-Labeled Steroids with High Receptor Binding Affinity, Potential Receptor-Directed Agents for Diagnostic Imaging or Therapy," Bioconjugate Chemistry, 1991, vol. 2, No. 5, pp. 353-366.
French et al., "A Synthesis of 7α-substituted estradiols: synthesis and biological evaluation of a 7α-pentyl-substituted BODIPY fluorescent conjugate and a fluorine-18-labeled 7α-pentylestradiol analog," Steroids, 1993, vol. 58, No. 4, pp. 157-169.
Fröhlich et al., "Synthesis of Artemisinin-Estrogen Hybrids Highly Active Against HCMV, P. Falciparum, and Cervical and Breast Cancer," ACS Medicinal Chemistry Letters, 2018, vol. 9, No. 11, pp. 1128-1133.
George et al., "Design, synthesis, and evaluation of the antiproliferative activity of hydantoin-derived antiandrogen-genistein conjugates," Bioorganic & Medicinal Chemistry, 2018, vol. 26, No. 8, pp. 1481-1487.
Gryder et al., "Histone Deacetylase Inhibitors Equipped with Estrogen Receptor Modulation Activity," Journal of Medicinal Chemistry, 2013, vol. 56, No. 14, pp. 5782-5796.
Gryder et al., "Selectively Targeting Prostate Cancer with Antiandrogen Equipped Histone Deacetylase Inhibitors," ACS Chemical Biology, 2013, vol. 8, No. 11, pp. 2550-2560.
Hanson et al., "Convergent synthesis of a steroidal antiestrogen-mitomycin C hybrid using "click" chemistry," Organic & Biomolecular Chemistry, 2012, vol. 10, No. 42, pp. 8501-8508.
Hasan et al., "Pharmacological, Mechanistic, and Pharmacokinetic Assessment of Novel Melatonin- Tamoxifen Drug Conjugates as Breast Cancer Drugs," Molecular Pharmacology, 2019, vol. 96, No. 2, pp. 272-296.
He et al., "Synthesis and Characterization of Nonsteroidal-Linked $M(CO)_3^+(M=^{99m}Tc, Re)$ Compounds Based on the Androgen Receptor Targeting Molecule Flutamide," Bioconjugate Chemistry, 2009, vol. 20, No. 1, pp. 78-86.
Hendricks et al., "Synthesis and preliminary evaluation steroidal antiestrogen-geldanamycin conjugates," 2013, vol. 23, Issue 12, pp. 3635-3639.
Hillier et al., "DNA adducts formed by a novel antitumor agent 11B-dichloro in vitro and in vivo," Molecular Cancer Therapies, 2006, vol. 5, No. 4, pp. 977-984.
Hödl et al., "Syntheses and Antigestagenic Activity of Mifepristone Derivatives," Journal of Medicinal Chemistry, 2009, vol. 52, No. 5, pp. 1268-1274.
Hu et al., "A study on platinum(IV) species containing an estrogen receptor modulator to reverse tamoxifen resistance of breast cancer," Metallomics, 2018, vol. 10, No. 2, pp. 346-359.
Huxley et al., An androgenic steroid delivery vector that imparts activity to a non-conventional platinum(II) metallo-drug, Dalton Transactions, 2010, vol. 39, No. 47, pp. 11353-11364.
International Preliminary Report on Patentability, dated Sep. 30, 2019 for PCT/US2019/32295, 7 pages.
International Search Report and Written Opinion, dated Sep. 30, 2019 for PCT/US2019/32295, 11 pages.
International Search Report and Written Opinion, dated Sep. 28, 2020 for PCT/US2020/032672, 11 pages.
International Search Report and Written Opinion, dated Mar. 15, 2021 for PCT/US2020/060165, 18 pages.
International Search Report and Written Opinion, dated May 11, 2022, regarding Application No. PCT/US2022/021390, 17 pages.
Ishiki et al., "Biological Properties of Conjugates of Mitomycin C with Estradiol Benzoate and Estradiol: Their Stability Characteris-

(56) References Cited

OTHER PUBLICATIONS tics in Biological Media and Their Binding Abilities to Estrogen Receptor," Biological and Pharmaceutical Bulletin, 1997, vol. 20, No. 10, pp. 1096-1102.
Jones et al., "Target Directed Enediyne Prodrugs: Cytotoxic Estrogen Conjugates," Tetrahedron Letters, 1996, vol. 37, No. 21, pp. 3643-3646.
Jones et al., "Target-Directed Enediynes: Designed Estramycins," The Journal of Organic Chemistry, 2001, vol. 66, No. 11, pp. 3688-3695.
Juráek et al., "Trilobolide-steroid hybrids: Synthesis, cytotoxic and antimycobacterial activity," Steroids, 2017, vol. 117, pp. 97-104.
Kamal et al., "Synthesis and biological evaluation of estradiol linked pyrrolo [2,1-c][1,4] benzodiazepine (PBD) conjugates as potential anticancer agents," Bioorganic & Medicinal Chemistry, 2011, vol. 19, Issue 8, pp. 2565-2581.
Kasiotis et al., "Synthesis and biological evaluation of novel daunorubicin-estrogen conjugates," Steroids, 2001, vol. 66, No. 10, pp. 785-791.
Katzenellenbogen, "Designing Effective Hybrid Toxins," Chemistry & Biology, 2005, vol. 12, No. 7, pp. 719-724.
Keely et al., "Design, Synthesis and Biochemical Evaluation of Estrogen Receptor Ligand Conjugates as Tumour Targeting Agents," Letters in Drug Design & Discovery, 2012, vol. 9, No. 3, pp. 295-304.
Keely et al., "Design, Synthesis and Biochemical Evaluation of Novel Selective Estrogen Receptor Ligand Conjugates Incorporating an Endoxifen-Combretastatin Hybrid Scaffold," Biomedicines, 2016, vol. 4, No. 3, pp. 1-34.
Keely et al., "Targeting Tumors Using Estrogen Receptor Ligand Conjugates," Current Cancer Drug Targets, 2009, vol. 9, No. 3, pp. 370-380.
Kelly et al., "Novel Selective Estrogen Receptor Ligand Conjugates Incorporating Endoxifen-Combretastatin and Cyclofenil-Combretastatin Hybrid Scaffolds: Synthesis and Biochemical Evaluation," Molecules, 2017, vol. 22, No. 9, pp. 1-50.
Khan et al., "Synthesis and Biological Activities of Phthalocyanine-Estradiol Conjugates," Bioorganic & Medicinal Chemistry Letters, 2003, vol. 13, No. 7, pp. 1287-1290.
Koseki et al., "Influence of Hydrolysis Susceptibility and Hydrophobicity of SN-38 Nano-Prodrugs on Their Anticancer Activity," Bulletin of the Chemical Society of Japan, 2019, vol. 92, No. 8, pp. 1305-1313.
Kreis et al., "Unique synergism or antagonism of combinations of chemotherapeutic and hormonal agents in human prostate cancer cell lines," British Journal of Urology, 1997, vol. 79, No. 2, pp. 196-202.
Leah et al., (Abstract) Testosterone conjugated DNA methylating agents targeted to prostate cancer cells, SERMACS-695, American Chemistry Society, Meeting Abstract, 2016, AN: 2016:1708008.
Levine et al., "Targeting the Androgen Receptor with Steroid Conjugates: Miniperspective," Journal of Medicinal Chemistry, 2014, vol. 57, No. 20, pp. 8224-8237.
Li et al., "Synthesis and Biological Activity of Some Bile Acid-Based Camptothecin Analogues," Molecules, 2014, vol. 19, No. 3, pp. 3761-3776.
Liu et al., "Design, Synthesis, and Bioactivities of Steroid-Linked Taxol Analogues as Potential Targeted Drugs for Prostate and Breast Cancer," Journal of Natural Products, 2004, vol. 67, No. 2, pp. 152-159.
Lowder et al., "Testosterone conjugated DNA methylating agents targeted to prostate cancer cells," SERMACS-695, 68th Southeastern Regional Meeting of the American Chemistry Society, Meeting Abstract, 2016, AN: 2016:1708008.
Lv et al., "Enhancement of therapeutic effect in breast cancer with a steroid-conjugated ruthenium complex," New Journal of Chemistry, 2019, vol. 43, No. 8, pp. 3419-3427.
Marchal et al., "Synthesis of prodigiosene-estrogen conjugates: optimization of protecting group strategies and anticancer properties, " Canadian Journal of Chemistry, 2015, vol. 93, No. 5, pp. 526-535.
Marquis et al., "Disruption of Gene Expression and Induction of Apoptosis in Prostate Cancer Cells by a DNA-Damaging Agent Tethered to an Androgen Receptor Ligand," Chemistry & Biology, 2005, vol. 12, No. 7, pp. 779-787.
Mitra et al., "A Rationally Designed Genotoxin that Selectively Destroys Estrogen Receptor-Positive Breast Cancer Cells," Journal of the American Chemical Society, 2002, vol. 124, No. 9, pp. 1862-1863.
Morioka et al., "Design, synthesis, and biological evaluation of novel estradiol-bisphosphonate conjugates as bone-specific estrogens," Bioorganic & Medicinal Chemistry, 2010, vol. 18, No. 3, pp. 1143-1148.
Narayanan et al., "Selective androgen receptor modulators in preclinical and clinical development," Nuclear Receptor Signaling, 2008, vol. 6, No. 1, pp. 1-26.
Ning et al., "Novel Hybrid Conjugates with Dual Suppression of Estrogenic and Inflammatory Activities Display Significantly Improved Potency against Breast Cancer," Journal of Medicinal Chemistry, 2018, vol. 61, No. 18, pp. 8155-8173.
O'Connor et al., "Targeting the DNA Damage Response in Cancer," Molecular Cell, 2015, vol. 60, No. 4, pp. 547-560.
Ota et al., "Targeting Cancer with PCPA-Drug Conjugates: LSD1 Inhibition-Triggered Release of 4-Hydroxytamoxifen," Angewandte Chemie International Edition, 2016, vol. 55, pp. 16115-16118.
Palermo et al., "Incorporation of histone deacetylase inhibitory activity into the core of tamoxifen—a new hybrid design paradigm," Bioorganic & Medicinal Chemistry, 2018, vol. 26, Issue 15, pp. 4428-4440.
Patel et al., "A Chimeric SERM-Histone Deacetylase Inhibitor Approach to Breast Cancer Therapy," ChemMedChem, 2014, vol. 9, No. 3, pp. 602-613.
Powell et al., "Cyano-nilutamide conjugates with a DNA minor groove methylating agent for selective destruction of prostate cancer cells," 67th Southeast/71st Southwest Joint Regional Meeting of the American Chemical Society, 2015, SERMACS-SWRM-317, Meeting Abstract.
Premnauth et al., "Reactive oxygen species (ROS)-dependent release of an anticancer drug from a targeting peptide," Chemical Abstracts, 2019.
PubChem-CID-2375, Create Date: Mar. 25, 2005, p. 2, Fig.
PubChem-CID-11297720, Create Date: Oct. 26, 2006, p. 2, Fig.
Qin et al., "Theranostic Pt(IV) Conjugate with Target Selectivity for Androgen Receptor," Inorganic Chemistry, 2018, vol. 57, No. 9, pp. 5019-5029.
Ragozin et al., "Biolabile Peptidyl Delivery Systems Toward Sequential Drug Release," Biopolymers, 2016, vol. 106, No. 1, pp. 119-132.
Rapozzi et al., "Androgen Receptor Targeted Conjugate for Bimodal Photodynamic Therapy of Prostate Cancer in Vitro," Bioconjugate Chemistry, 2015, vol. 26, No. 8, pp. 1662-1671.
Rink et al., "Synthesis and biological activity of DNA damaging agents that form decoy binding sites for the estrogen receptor," Proceedings of the National Academy of Sciences, 1996, vol. 93, No. 26, pp. 15063-15068.
Sadler et al., "Internalization of a C17α-alkynylestradiol-porphyrin conjugate into estrogen receptor positive MCF-7 breast cancer cells," Bioorganic & Medicinal Chemistry Letters, 2011, vol. 21, No. 15, pp. 4638-4641.
Saha et al., "Design, synthesis, cytocidal activity and estrogen receptor α affinity of doxorubicin conjugates at 16α-position of estrogen for site-specific treatment of estrogen receptor positive breast cancer," Steroids, 2012, vol. 77, Issue 11, pp. 1113-1122.
Sanchez-Cano et al., "Conjugation of testosterone modifies the interaction of mono-functional cationic platinum (II) complexes with DNA, causing significant alterations to the DNA helix," Dalton Transactions, 2010, vol. 39, No. 47, pp. 11365-11374.
Sharifi et al., "A bifunctional colchicinoid that binds to the androgen receptor," Molecular Cancer Therapeutics, 2007, vol. 6, Issue 8, pp. 2328-2336.

(56) References Cited

OTHER PUBLICATIONS

Sharma et al., "Design, synthesis, and evaluation of estradiol-linked genotoxicants as anti-cancer agents," Bioorganic & Medicinal Chemistry Letters, 2004, vol. 14, No. 14, pp. 3829-3833.

Shen et al., "Synthesis and Anti-tumor Activity of Novel Steroidal Conjugates of Campothecin," Chinese Journal of New Drugs, 2013, pp. 585-589, vol. 22, Issue 5.

Shi et al., "Antitumor agents 290. Design, synthesis, and biological evaluation of new LNCaP and PC-3 cytotoxic curcumin analogs conjugated with anti-androgens, " Bioorganic & Medicinal Chemistry, 2012, vol. 20, No. 13, pp. 4020-4031.

Shibata et al., "Development of Protein Degradation Inducers of Androgen Receptor by Conjugation of Androgen Receptor Ligands and Inhibitor of Apoptosis Protein Ligands," Journal of Medicinal Chemistry, 2018, vol. 61, No. 2, pp. 543-575.

Steffen et al., "Structural implications for selective targeting of PARPs," Frontiers in Oncology, 2013, vol. 3, Article 301, pp. 1-14.

Sundaram et al., "Luteinizing hormone-releasing hormone receptor-targeted deslorelin-docetaxel conjugate enhances efficacy of docetaxel in prostate cancer therapy," Molecular Cancer Therapeutics, 2009, pp. 1655-1665.

Suzuki et al., "Target-selective degradation of proteins by a light-activated 2-phenylquinoline-estradiol hybrid," Chemical Communications, 2007, pp. 4260-4262.

Swamy et al., "An Estradiol-Porphyrin Conjugate Selectively Localizes Into Estrogen Receptor-Positive Breast Cancer Cells," Bioorganic & Medicinal Chemistry, 2002, vol. 10, pp. 3237-3243.

Tang et al., "Novel Bioactive Hybrid Compound Dual Targeting Estrogen Receptor and Histone Deacetylase for the Treatment of Breast Cancer," Journal of Medicinal Chemistry, 2015, vol. 58, No. 11, pp. 4550-4572.

Teutsch et al., "Synthesis of a fluorescent steroid derivative with high affinities for the glucocorticoid and progesterone receptors," Steroids, 1994, vol. 59, No. 1, pp. 22-26.

Tikhe et al., "Design, Synthesis, and Evaluation of 3,4-Dihydro-2H-[1,4]diazepino[6,7,1-hi]indol-1-ones as Inhibitors of Poly(ADP-Ribose) Polymerase," Journal of Medicinal Chemistry, 2004, vol. 47, pp. 5467-5481.

Wang et al., "Discovery and Characterization of (8S,9R)-5-Fluoro-8-(4-fluorophenyl)-9-(1-methyl-1H- 1,2,4-triazol-5-yl)-2,7,8,9-tetrohydro-3H-pyrido[4,3,2-de]phthalazin-3-one (BMN 673,Talazoparib), a Novel, Highly Potent, and Orally Efficacious Poly(ADP-ribose) Polymerase-1/2 Inhibitor, as an Anticancer Agent," Journal of Medicinal Chemistry, 2016, vol. 59, pp. 335-357.

Weinstain et al., "Fluorescent Ligand for Human Progesterone Receptor Imaging in Live Cells," Bioconjugate Chemistry, 2013, vol. 24, pp. 766-771.

Zeinyeh et al., "Progesterone-adenine hybrids as bivalent inhibitors of P-glycoprotein-mediated multidrug efflux: Design, synthesis, characterization and biological evaluation," Steroids, 2012, vol. 77, Issue 12, pp. 1177-1191.

Zhang et al., "Antagonizing the Androgen Receptor with a Biomimetic Acyltransferase," ACS Chemical Biology, 2016, vol. 11, No. 10, pp. 2797-2802.

Zhang et al., "Tamoxifen-zinc(II) phthalocyanine conjugates for target-based photodynamic therapy and hormone therapy," Journal of Porphyrins and Phthalocyanines, 2019, vol. 23, No. 10, pp. 1073-1083.

Zolottsev et al., "Conjugates of 17-substituted testosterone and epitestosterone with pyropheophorbide a differing in the length of linkers," Steroids, 2018, vol. 138, pp. 82-90.

Delfosse, V. et al. (2015, e-pub. Dec. 15, 2014). "A Structural Perspective on Nuclear Receptors as Targets of Environmental Compounds," Acta Pharmacologica 36:88-101.

Kronenberger, T. et al. (Jun. 3, 2015). "Chapter 5—Nuclear Receptor Modulators—Current Approaches and Future Perspectives," in Drug Discovery and Development—From Molecules to Medicine, pp. 107-130.

Peng, K.-W. et al. (Dec. 18, 2009). "Selective Estrogen Receptor Modulator Delivery of Quinone Warheads to DNA Triggering Apoptosis in Breast Cancer Cells," ACS Chemical Biology 4(12):1039-1049, 21 pages.

Wang, F.-Z. et al. (2014, Jun. 14, 2014). "The Checkpoint 1 Kinase Inhibitor LY2603618 Induces Cell Cycle Arrest, DNA Damage Response and Autophagy in Cancer Cells," Apoptosis 19(9):1389-1398.

ANTI-CANCER NUCLEAR HORMONE RECEPTOR-TARGETING COMPOUNDS

CROSS REFERENCE TO RELATED APPLICATIONS

This application claims the benefit under 35 U.S.C. § 119(e) to U.S. Provisional Application No. 63/165,087, filed Mar. 23, 2021, which is hereby incorporated by reference in its entirety.

BACKGROUND

Topoisomerase inhibitors are chemical compounds that block the action of topoisomerases, which are broken into two broad subtypes, type I topoisomerases (TopI) and type II topoisomerases (TopII). Topoisomerase plays important roles in cellular reproduction and DNA organization, as they mediate the cleavage of single and double stranded DNA to relax supercoils, untangle catenanes, and condense chromosomes in eukaryotic cells. Topoisomerase inhibitors influence these essential cellular processes. Some topoisomerase inhibitors prevent topoisomerases from performing DNA strand breaks, while others associate with topoisomerase-DNA complexes and prevent the re-ligation step of the topoisomerase mechanism. These topoisomerase-DNA-inhibitor complexes are cytotoxic agents, as the un-repaired single and double stranded DNA breaks that they cause can lead to apoptosis and cell death. Because of this ability to induce apoptosis, topoisomerase inhibitors have gained interest as therapeutics against infectious and cancerous cells.

Camptothecin (CPT) is a topoisomerase poison. It was isolated from the bark and stem of *Camptotheca acuminata* (*Camptotheca*, Happy tree), a tree native to China used as a cancer treatment in traditional Chinese medicine. CPT showed remarkable anticancer activity in preliminary clinical trials especially against breast, ovarian, colon, lung, and stomach cancers. However, it has low solubility and adverse effects have been reported when used therapeutically, so synthetic and medicinal chemists have developed numerous syntheses of camptothecin and various derivatives to increase the benefits of the chemical, with good results. Four CPT analogues have been approved and are used in cancer chemotherapy today, topotecan, irinotecan, belotecan, and trastuzumab deruxtecan. In addition to being an anti-tumor agent, camptothecin has also shown anti-HIV activity because it interrupts self-association of the viral-infectivity factor found in many retroviruses including HIV.

The future likely also holds many alternative uses for topoisomerase poisons, including lupus, rare brain disorders, sepsis, and viral and trypanosomal infections. As additional roles of Top1 (such as newly-discovered regulatory functions) emerge, and Top1 continues to be implicated in disease states, new drug discovery (and drug repurposing) efforts will continue for years to come.

SUMMARY

Provided herein are compounds comprising a nuclear payload, such as a topoisomerase inhibitor, topoisomerase poison, or analog thereof, and a nuclear receptor-targeting epitope. Compounds described herein are designed to bind nuclear receptors within the cell and allow the compound, with its nuclear payload, to accumulate in the nucleus. Not wishing to be bound by theory, one potential mode of enhanced utility is that this approach may provide for compounds having cell-type selectivity, not merely improved potency, working toward a higher therapeutic index. However, it may be that the compounds may be active by other modes, such as, but not limited to, passive localization in the nucleus.

Further, the compounds described herein offer targeted delivery of a nuclear payload. The compounds both target and localize within tumor tissue. The transport of the compound, which comprises at least one nuclear receptor-targeting epitope, such as a nuclear steroid receptor-targeting epitope, covalently attached to at least one nuclear payload, to the nucleus allows for accumulation of the nuclear payload in the nucleus, enhancing tumor cell death. By doing so, compounds described in this disclosure may exhibit superior efficacy. In addition, the compounds described in this disclosure will, by accumulating in the nucleus of nuclear receptor positive cells, such as steroid receptor positive cells, spare cells that do not express the specific nuclear steroid receptor, and therefore reduce side effects.

In certain embodiments, provided is a compound of Formula I, II, or III, or stereoisomer, mixture of stereoisomers, hydrate, solvate, isotopically enriched analog, or pharmaceutically acceptable salt thereof:

$$A^1\text{-}(L^1\text{-}B^1)_{m'} \qquad\qquad I$$

$$A^1\text{-}L^1\text{-}(B^1)_{m'} \qquad\qquad II$$

$$A^1\text{-}L^1\text{-}B^1 \qquad\qquad III$$

wherein:
$A^1$ is a nuclear payload (i.e., a topoisomerase inhibitor);
m' is 1, 2 or 3;
each $B^1$ is independently a nuclear receptor-targeting epitope; and
each $L^1$ is independently a covalent bond or a linking moiety.

In certain embodiments, provided is a compound of Formula III, or stereoisomer, mixture of stereoisomers, hydrate, solvate, isotopically enriched analog or pharmaceutically acceptable salt thereof:

$$A^1\text{-}L^1\text{-}B^1 \qquad\qquad III$$

wherein:
$B^1$ is a nuclear receptor-targeting epitope;
$L^1$ is a covalent bond or a linking moiety; and
$A^1$ is a topoisomerase inhibitor.

Also provided is a compound of Table 1, or stereoisomer, mixture of stereoisomers, hydrate, solvate, isotopically enriched analog, or pharmaceutically acceptable salt thereof.

Also provided is a composition comprising a compound as described herein or stereoisomer, mixture of stereoisomers, hydrate, solvate, isotopically enriched analog, or pharmaceutically acceptable salt thereof, and a pharmaceutically acceptable excipient.

Also provided is a method of treating or preventing cancer, comprising administering an effective amount of a compound or composition as described herein to an individual in need thereof. The cancer can be a blood cancer, lung cancer, breast cancer, fallopian tube cancer, brain cancer, head and neck cancer, esophageal cancer, ovarian cancer, pancreatic cancer, peritoneal cancer, prostate cancer or skin cancer, such as, but not limited to, liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, Waldenström macroglobulinemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoides, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, trophoblastic neoplasms, or prostatic carcinoma.

Also provided is a method of treating or preventing a cancer, comprising administering an effective amount of a compound or composition as described herein to an individual in need thereof. In certain embodiments, the cancer is neuroblastoma, brainstem glioma, Ewing's, non-small cell lung cancer, colorectal cancer, breast cancer, non-Hodgkin lymphoma, endometrial cancer, or oligodendroglioma.

Also provided is a method of treating or preventing a neuro-genetic disease or disorder, comprising administering an effective amount of a compound or composition as described herein to an individual in need thereof. In certain embodiments, the neuro-genetic disease or disorder is Angelman's syndrome.

Also provided is a method of treating or preventing breast cancer, comprising administering an effective amount of a compound or composition as described herein to an individual in need thereof. In certain embodiments, the breast cancer is hormone receptor-positive metastatic breast cancer.

Also provided is a method of treating or preventing prostate cancer, comprising administering an effective amount of a compound or composition as described herein to an individual in need thereof. In certain embodiments, the breast cancer is metastatic castration-resistant prostate cancer (mCRPC).

Also provided is a method of treating or preventing cancer, comprising administering an effective amount of a compound or composition as described herein, or a pharmaceutically acceptable salt or solvate thereof, in combination with an additional chemotherapeutic agent, to an individual in need thereof.

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

The term "about" refers to a variation of $\pm 1\%$, $\pm 3\%$, $\pm 5\%$, or $\pm 10\%$ of the value specified. For example, "about 50" can in some embodiments includes a range of from 45 to 55. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. Also, the singular forms "a" and "the" include plural references unless the context clearly dictates otherwise. Thus, e.g., reference to "the compound" includes a plurality of such compounds and reference to "the assay" includes reference to one or more compounds and equivalents thereof known to those skilled in the art.

"Alkyl" refers to and includes saturated linear and branched univalent hydrocarbon structures and combination thereof, having the number of carbon atoms designated (i.e., $C_1$-$C_{10}$ or $C_{1-10}$ means one to ten carbons). Particular alkyl groups are those having 1 to 20 carbon atoms (a "$C_1$-$C_{20}$ alkyl"). In one embodiment, alkyl groups are those having 1 to 12 carbon atoms (a "$C_1$-$C_{12}$ alkyl"), 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ or $C_{2-10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like. Similarly, the terms "alkenylene," "alkynylene," "heteroalkylene," "cycloalkylene," "heterocyclylene," "arylene," and "heteroarylene" refer to alkenyl, alkynyl, heteroalkyl, cycloalkyl, heterocyclyl, aryl, and heteroaryl residues, respectively, as defined herein, but having bivalency.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ or $C_{2-10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Amino" refers to amine of formula —N($R^N$)$_2$, where each $R^N$ is independently hydrogen, alkyl, alkenyl, alkynyl, haloalkyl, cycloalkyl, heterocyclyl, aryl, or heteroaryl, wherein each is optionally substituted, such as by one or more (e.g., 1-5 or 1-3) substituents (e.g., halo, cyano, hydroxy, —NH$_2$, —NH(alkyl), —N(alkyl)$_2$, alkyl, alkenyl, alkynyl, haloalkyl, alkoxy, or haloalkoxy).

"Aryl" refers to and includes polyunsaturated aromatic hydrocarbon groups. Aryl may contain additional fused rings (e.g., from 1 to 3 rings). In one variation, the aryl group contains from 6 to 14 annular carbon atoms. In some embodiments, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, but are not limited to, phenyl, naphthyl, and the like. It is understood that Aryl does not encompass or overlap in any way with heteroaryl defined below. It is understood that, if one or more aryl groups are fused with a heteroaryl, the resulting ring system is heteroaryl. It is understood that, if one or more aryl groups are fused with a heterocyclyl, the resulting ring system is heterocyclyl.

"Carbonyl" refers to the group C=O.

"Cycloalkyl" refers to and includes cyclic hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantyl. A cycloalkyl comprising more than one ring may be fused, spiro or bridged, or combinations thereof. In some embodiments, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). It is understood that the term cycloalkyl is intended to encompass any non-aromatic ring which may be fused to an aryl ring, regardless of the attachment to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. In some embodiments, halo groups include fluoro, chloro, bromo and iodo. Where a residue is substituted by more than one halogen, it may be referred to by using a prefix corresponding to the number of halogen moieties attached, e.g., dihaloaryl, dihaloalkyl, trihaloaryl etc. refer to aryl and alkyl substituted by two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." In some embodiments, perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NH—, —O—, —S—, —S(O)—, —S(O)$_2$—. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.), and amines (e.g., —CH$_2$NHCH$_3$, —CH(CH$_3$)NHCH$_3$, —CH$_2$CH$_2$NHCH$_3$, —CH$_2$CH$_2$NHCH$_2$CH$_2$NHCH$_3$, etc. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. In some embodiments, heteroaryl includes unsaturated aromatic cyclic groups having from 1 to 10 annular carbon atoms and from 1 to 4 annular heteroatoms. In some embodiments, heteroaryl includes 5-12 membered ring systems, 5-10 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. A heteroaryl group can be attached to the remainder of the molecule at an annular carbon or at an annular heteroatom. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above. Examples of heteroaryl groups include, but are not limited to, pyridyl, pyrimidyl, thiophenyl, furanyl, thiazolyl, pyrazolyl, oxazolyl, isooxazolyl, imidazolyl, quinolyl, isoquinolyl, benzimidazolyl, benzpyrazolyl, benzotriazolyl, indole, benzothiazyl, benzoxazolyl, benzisoxazolyl, imidazopyridinyl, and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. It is understood that any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. In some embodiments, heteroaryl includes 3-12 membered ring systems, 3-10 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. A heterocycle comprising more than one ring may be fused, spiro or bridged, or any combination thereof. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, dihydrooxazolyl, dihydroisoxazolyl, dioxolanyl, morpholinyl, dioxanyl, tetrahydrothiophenyl, and the like.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different, provided that the group's normal valence is not exceeded. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 0 to 2, 0 to 5, 1 to 2, 2 to 5, 3 to 5, 2 to 3, 2 to 4, 3 to 4, 1 to 3, 1 to 4 or 1 to 5 substituents.

Provided are also are stereoisomers, mixture of stereoisomers, tautomers, hydrates, solvates, isotopically enriched analog, and pharmaceutically acceptable salts of the compounds described herein.

The compounds disclosed herein, or their pharmaceutically acceptable salts, may include an asymmetric center and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposeable mirror images of one another and "diastereomers," which refers to stereoisomers that have at least two asymmetric atoms, but which are not mirror-images of each other. Thus, all stereoisomers (for example, geometric isomers, optical isomers and the like) of the present compounds (including those of the salts, solvates and hydrates of the compounds), such as those which may exist due to asymmetric carbons on various substituents, including enantiomeric forms (which may exist even in the absence of asymmetric carbons), rotameric forms, atropisomers, and diastereomeric forms, are contemplated.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds may be atropisomers and are considered as part of this disclosure. Stereoisomers can also be separated by use of chiral HPLC.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Any compound or structure given herein, is also intended to represent unlabeled forms as well as isotopically labeled forms of the compounds. These forms of compounds may also be referred to as an "isotopically enriched analog." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^{3}H$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Such compounds may exhibit increased resistance to metabolism and are thus useful for increasing the half-life of any compound when administered to a mammal, particularly a human. Such compounds are synthesized by means well known in the art, for example by employing starting materials in which one or more hydrogens have been replaced by deuterium.

Certain compounds disclosed herein contain one or more ionizable groups (groups from which a proton can be removed (e.g., —COOH) or added (e.g., amines) or which can be quaternized (e.g., amines)). All possible ionic forms of such molecules and salts thereof are intended to be included individually in the disclosure herein. With regard to salts of the compounds described herein, one of ordinary skill in the art can select from among a wide variety of available counterions those that are appropriate. In specific applications, the selection of a given anion or cation for preparation of a salt may result in increased or decreased solubility of that salt.

As used herein, the term "non-biocleavable linking moiety" is intended to refer to a linking moiety which is not readily hydrolyzed under physiological conditions. As used herein, the term "biocleavable linking moiety" is intended to refer to a linking moiety which is readily hydrolyzed under physiological conditions. In certain embodiments, at least one linking moiety is hydrolyzed under intracellular conditions (e.g., low pH).

As used herein, the term "cancer" refers to a class of diseases of mammals characterized by uncontrolled cellular growth. The term "cancer" is used interchangeably with the terms "tumor," "solid tumor," "malignancy," "hyperproliferation" and "neoplasm." Cancer includes all types of hyperproliferative growth, hyperplasic growth, neoplastic growth, cancerous growth or oncogenic processes, metastatic tissues or malignantly transformed cells, tissues, or organs, irrespective of histopathologic type or stage of invasiveness. Illustrative examples include, lung, prostate, head and neck, breast and colorectal cancer, melanomas and gliomas (such as a high-grade glioma, including glioblastoma multiforme (GBM), the most common and deadliest of malignant primary brain tumors in adult humans).

The phrase "solid tumor" includes, for example, lung cancer, head and neck cancer, brain cancer, oral cancer, colorectal cancer, breast cancer, prostate cancer, pancreatic cancer, and liver cancer. Other types of solid tumors are named for the particular cells that form them, for example, sarcomas formed from connective tissue cells (for example, bone cartilage, fat), carcinomas formed from epithelial tissue cells (for example, breast, colon, pancreas) and lymphomas formed from lymphatic tissue cells (for example, lymph nodes, spleen, thymus). Treatment of all types of solid tumors regardless of naming convention is within the scope of this disclosure.

"Chemotherapeutic agent" refers to any substance capable of reducing or preventing the growth, proliferation, or spread of a cancer cell, a population of cancer cells, tumor, or other malignant tissue. The term is intended also to encompass radiotherapy, or any antitumor or anticancer agent.

As used herein, "treatment" or "treating" is an approach for obtaining a beneficial or desired result, such as a clinical result. For purposes of this disclosure, beneficial or desired clinical results include, but are not limited to, alleviation of a symptom and/or diminishment of the extent of a symptom and/or preventing a worsening of a symptom associated with a disease or condition. In some embodiments, "treatment" or "treating" is an approach for obtaining a beneficial or desired result, such as a clinical result. For purposes of this disclosure, beneficial or desired clinical results include, but are not limited to, alleviation of a symptom and/or diminishment of the extent of a symptom, or a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. In some embodiments, treatment of a disease or condition with a compound of the disclosure or a pharmaceutically acceptable salt thereof is accompanied by no or fewer side effects than are associated with currently available therapies for the disease or condition and/or improves the quality of life of the individual.

The terms "inhibit," "inhibiting," and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

As used herein, by "combination therapy" is meant a therapy that includes two or more different compounds. Thus, in one aspect, a combination therapy comprising a compound detailed herein and anther compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the disclosure alone. In some embodiments, a lower amount of each compound is used as part of a combination therapy compared to the amount generally used for individual therapy. In some embodiments, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. In some embodiments, the use of a small amount of compound results in a reduction in the number, severity, frequency, and/or duration of one or more side-effects associated with the compound.

As used herein, the term "effective amount" intends such amount of a compound of the disclosure which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, the term "antagonist" or "inhibitor" refers to a compound, the presence of which results in a decrease in the magnitude of a biological activity of a target protein or enzyme. For example, a "topoisomerase inhibitor" is any compound that inhibits the function of one or more topoisomerase.

As used herein, the $IC_{50}$ refers to an amount, concentration or dosage of a particular test compound that achieves a 50% inhibition of a maximal response, such as modulation of a topoisomerase, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

The term "cancer," as used herein refers to an abnormal growth of cells which tend to proliferate in an uncontrolled way and, in some cases, to metastasize (spread). The types of cancer include, but are not limited to, solid tumors (such as those of the bladder, bowel, brain, breast, endometrium, heart, kidney, lung, lymphatic tissue (lymphoma), ovary, pancreas or other endocrine organ (thyroid)), prostate, skin (melanoma) or hematological tumors (such as the leukemias).

The term "carrier," as used herein, refers to relatively nontoxic chemical compounds or agents that facilitate the incorporation of a compound into cells or tissues.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. In some embodiments, pharmaceutically acceptable carriers or excipients have met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, J. Pharm. Sci. 1977 January; 66(1):1-19. Pharmaceutically acceptable salts can be prepared in situ in the manufacturing process, or by separately reacting a purified compound of the disclosure in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (directly compressible), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Compounds

Provided herein are targeted compounds for treating cancer. The compounds described herein are capable of targeting the nucleus of a cell by recognition and binding of a nuclear receptor-targeting epitope to the respective binding site and delivering the nuclear payload to the nucleus of the cell. The nuclear payload then is capable of binding to one or more target sites within the nucleus and/or disrupting one or more cellular processes, causing the cell to die.

In certain embodiments, the nuclear payload is bonded to the nuclear receptor-targeting epitope(s) via a linking moiety. In certain embodiments, the linking moiety provides a single or mono-linkage, meaning that the linker is only conjugated to one atom of each of the payload and the epitope.

Accordingly, provided is a compound of Formula I, or stereoisomer, mixture of stereoisomers, hydrate, solvate, isotopically enriched analog, or pharmaceutically acceptable salt thereof:

$$A^1\text{-}(L^1\text{-}B^1)_{m'} \qquad \text{I}$$

wherein:

$A^1$ is a nuclear payload (i.e., a topoisomerase inhibitor);

m' is 1, 2 or 3;

each $B^1$ is independently a nuclear receptor-targeting epitope; and each $L^1$ is independently a covalent bond or a linking moiety.

In certain embodiments, one or more nuclear receptor-targeting epitopes are bonded to a nuclear payload via a single linking moiety. Accordingly, also provided is a compound of Formula II, or stereoisomer, mixture of stereoisomers, hydrate, solvate, isotopically enriched analog, or pharmaceutically acceptable salt thereof:

$A^1\text{-}L^1\text{-}(B^1)_{m'}$  II wherein:
$A^1$ is a nuclear payload (i.e., a topoisomerase inhibitor);
m' is 1, 2 or 3;
each $B^1$ is independently a nuclear receptor-targeting epitope; and
$L^1$ is a linking moiety.

In certain embodiments, provided is a compound comprising a nuclear payload bonded to a nuclear receptor-targeting epitope, optionally via a linking moiety. Accordingly, provided is a compound of Formula III, or stereoisomer, mixture of stereoisomers, hydrate, solvate, isotopically enriched analog, or pharmaceutically acceptable salt thereof:

$A^1\text{-}L^1\text{-}B^1$  III wherein:
$A^1$ is a nuclear payload (i.e., a topoisomerase inhibitor);
$B^1$ is a nuclear receptor-targeting epitope; and
$L^1$ is a covalent bond or a linking moiety.

In certain embodiments of Formula I, II or III, $A^1$ is:

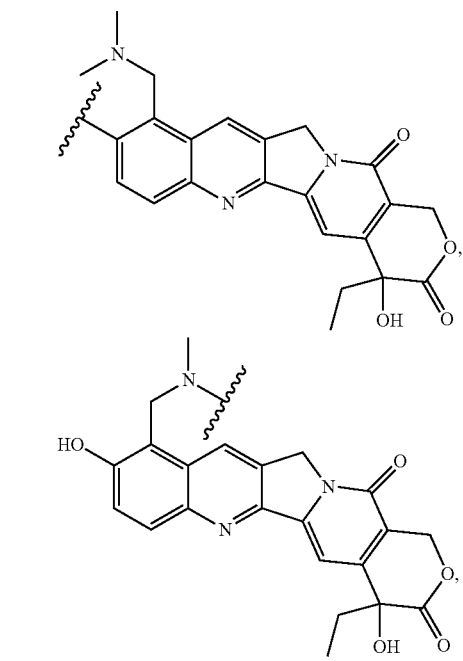

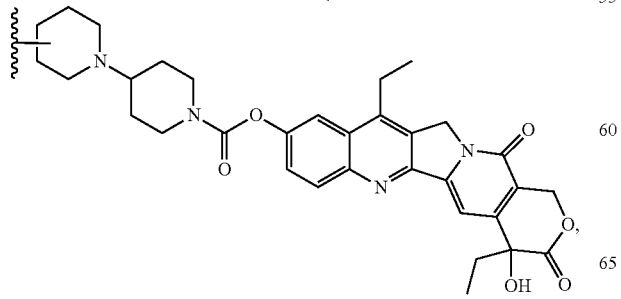

-continued

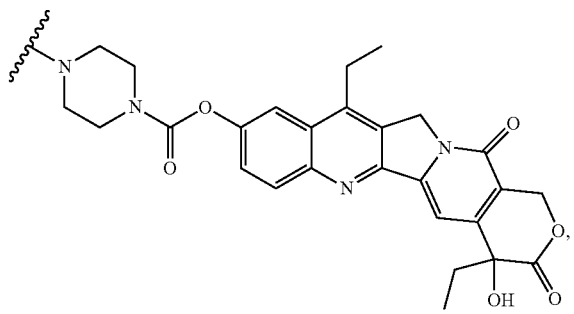

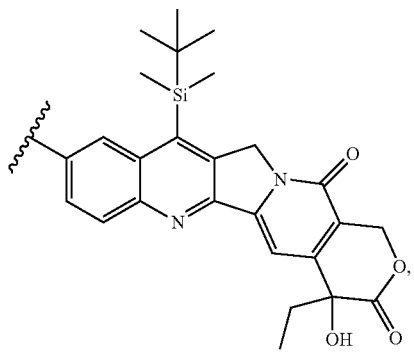

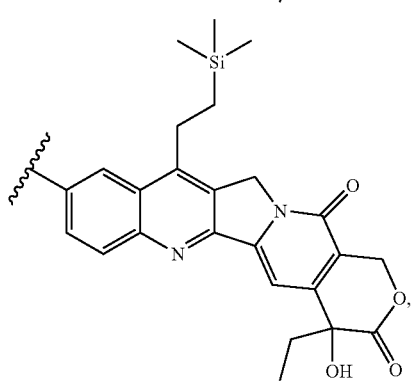

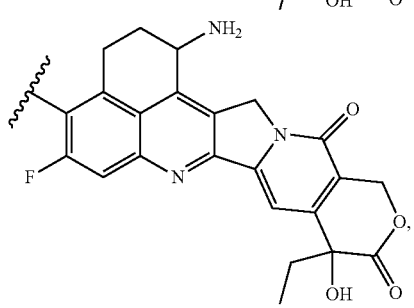

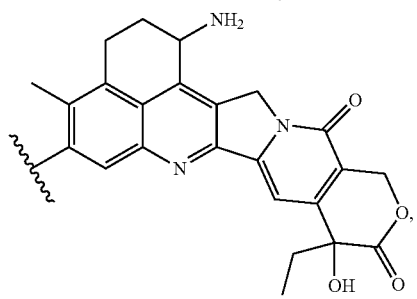

-continued
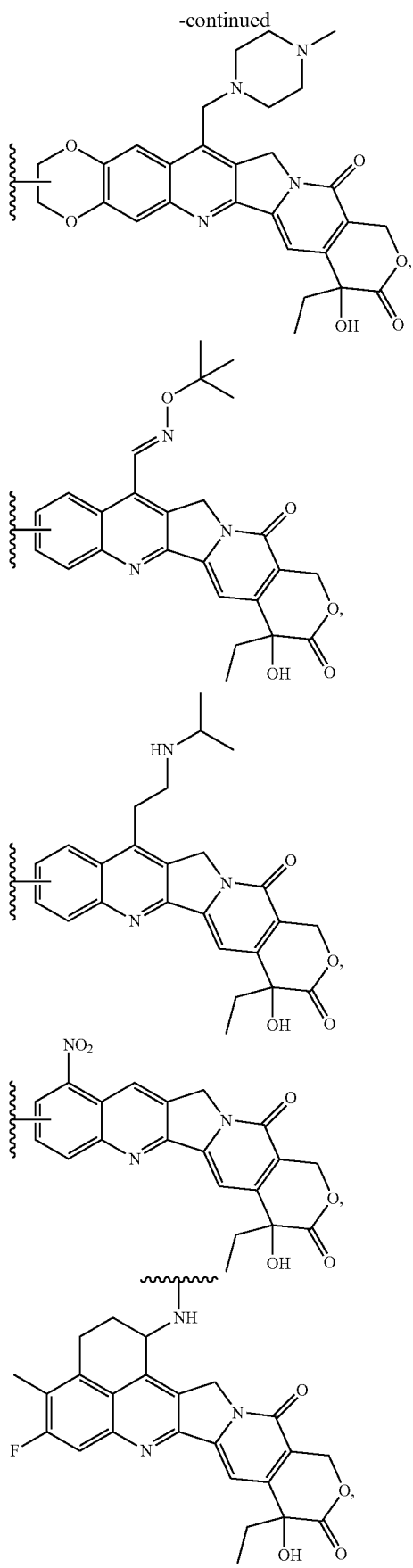
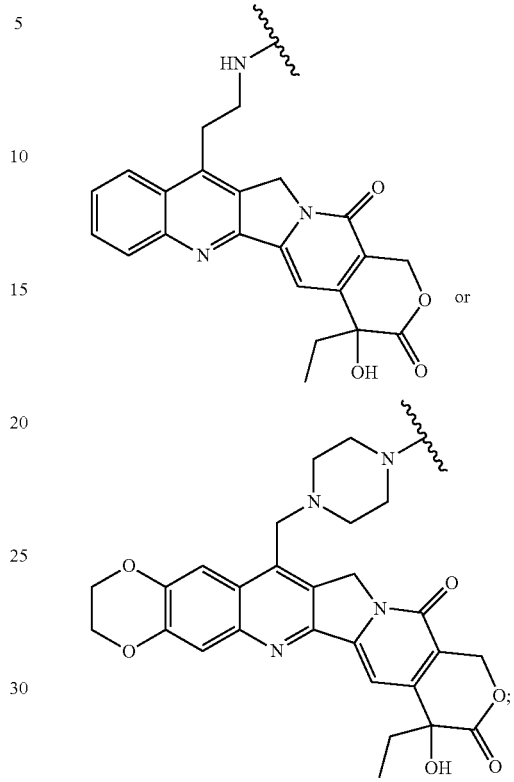
where the wavy line indicates the point of attachment to at least one nuclear steroid receptor-targeting epitope, optionally via a linking moiety (e.g., -L$^1$-B$^1$).
In certain embodiments of Formula I, II or III, A$^1$ is:
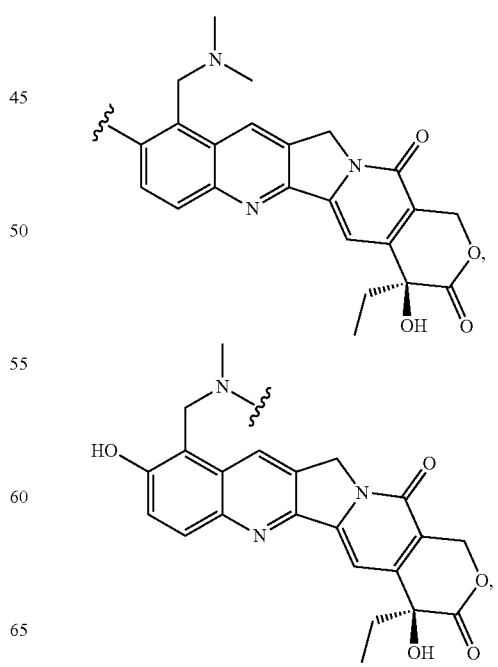

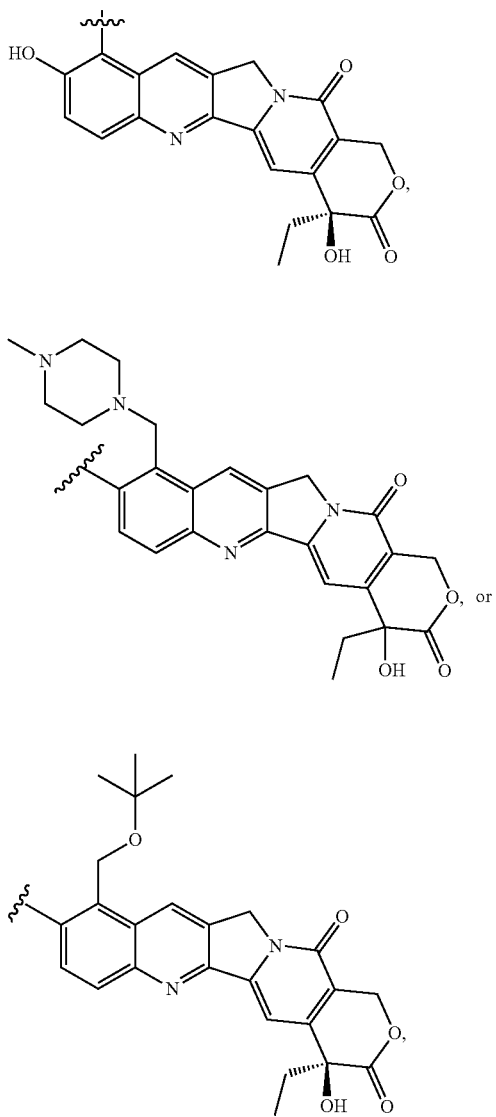

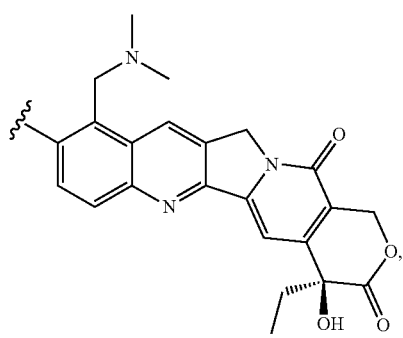

wherein the wavy bond refers to the point of connection to $L^1$. In certain embodiments, $A^1$ is:

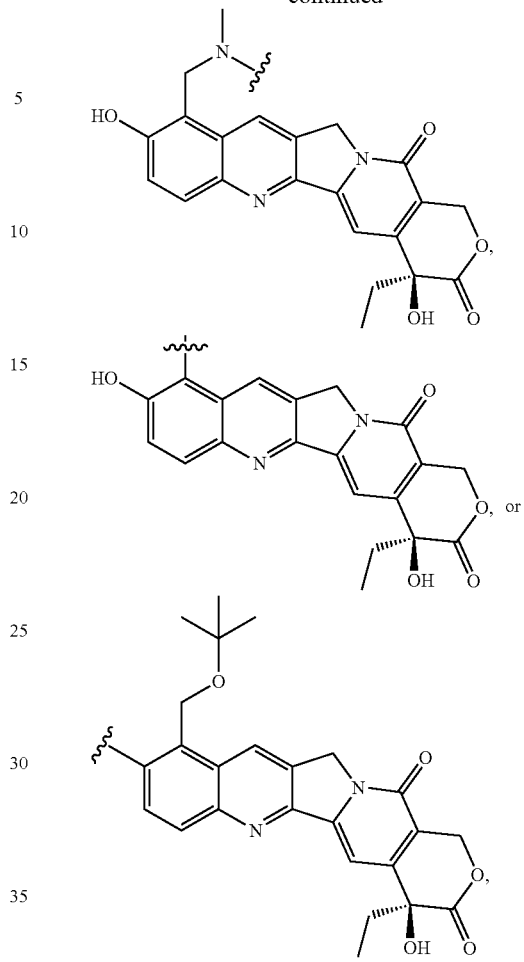

wherein the wavy bond refers to the point of connection to $L^1$.

In certain embodiments, any of the compounds disclosed herein (e.g., a compound of Formula I, II, or III) comprises a topoisomerase inhibitor analog, which even after modification to arrive at the compounds described herein, exhibit a biological activity which is comparable to that observed in the original, unmodified topoisomerase inhibitor. In certain embodiments, the topoisomerase inhibitor analogs maintain the ability to inhibit a topoisomerase. In certain embodiments, the topoisomerase inhibitor analogs exhibit a binding activity which is at least about 98%, about 95%, about 90%, about 85%, about 80%, about 75%, about 70%, about 65%, about 60%, about 55%, or about 50% of that observed in the original, unmodified topoisomerase inhibitor.

In certain embodiments, any of the compounds disclosed herein (e.g., a compound of Formula I, II, or III), $B^1$ binds to an estrogen receptor, glucocorticoid receptor, progesterone receptor, or androgen receptor. In certain embodiments, $B^1$ binds to estrogen receptor. In certain embodiments, $B^1$ binds to glucocorticoid receptor. In certain embodiments, $B^1$ binds to progesterone receptor. In certain embodiments, $B^1$ binds to androgen receptor. Exemplary estrogen receptor, glucocorticoid receptor, progesterone receptor, or androgen receptor binders are described herein Nuclear Payloads In certain embodiments, the nuclear payload (i.e., $A^1$) in the compounds described herein, is a topoisomerase inhibitor. As used herein, the term "topoisomerase inhibitor" refers to a chemical compound or moiety that blocks the action of a topoisomerase (or DNA topoisomerase), which are enzymes that participate in the overwinding or underwinding of DNA.

Topoisomerases, which are broken into two broad sub-types, type I topoisomerases (TopI) and type II topoisomerases (TopII), play important roles in cellular reproduction and DNA organization as they mediate the cleavage of single and double stranded DNA to relax supercoils, untangle catenanes, and condense chromosomes in eukaryotic cells. Topoisomerase inhibitors influence these essential cellular processes. In certain embodiments, the topoisomerase inhibitor prevents a topoisomerase from performing DNA strand breaks. In certain embodiments, the topoisomerase inhibitor is referred to as a topoisomerase poison, and associates with topoisomerase-DNA complexes to prevent the re-ligation step of the topoisomerase mechanism. These topoisomerase-DNA-inhibitor complexes are cytotoxic agents, as the un-repaired single and double stranded DNA breaks that they cause can lead to apoptosis and cell death. Because of this ability to induce apoptosis, topoisomerase inhibitors have been used as therapeutics against infectious and cancerous cells.

In certain embodiments, the nuclear payload (i.e., $A^1$) of the compounds described herein, is derived from camptothecin (CPT). As such, in certain embodiments, the nuclear payload (i.e., $A^1$) of the compounds described herein, is a camptothecin (CPT) analog. In certain embodiments, the nuclear payload (i.e., $A^1$) of the compounds described herein, is derived from topotecan, irinotecan (CPT-11), silatecan (DB-67, AR-67), cositecan (BNP-1350), exatecan, lurtotecan, gimatecan (ST1481), belotecan (CKD-602), or rubitecan, or an analog thereof.

In certain embodiments, the term "derived from" or "analog" as used in reference to a nuclear payload (i.e., $A^1$), means that at most, one non-hydrogen atom of an original, unmodified nuclear payload (i.e., a known topoisomerase inhibitor) is replaced by a covalent bond to the nuclear receptor-targeting epitope, optionally via a linking moiety. Exemplary non-hydrogen atoms include, but are not limited to, —CH$_3$, —OH, =O, and —NH$_2$. In certain embodiments, the term "derived from" as used in reference to a nuclear payload (i.e., $A^1$), means that one or more atoms (e.g., hydrogen, methyl, or hydroxy) of an original, unmodified nuclear payload (i.e., a topoisomerase inhibitor) is replaced by a direct covalent bond to $L^1$. Exemplary non-hydrogen atoms include, but are not limited to, —CH$_3$, —OCH$_3$, —OH, =O, —NH$_2$, —N(CH$_3$)$_2$, and the like. In certain embodiments, one hydrogen atom bound to a heteroatom (e.g., N, O, or S) of an original, unmodified nuclear payload (i.e., a known topoisomerase inhibitor) is replaced by a covalent bond to $L^1$. In certain embodiments, the term "derived from" means that one or more atoms (e.g., hydrogen, methyl, or hydroxy) is replaced by a direct covalent bond to $L^1$.

In certain embodiments, one or more atoms one or more atoms (e.g., hydrogen, methyl, hydroxy, amino, etc.) on the nuclear payload (i.e., $A^1$) as disclosed herein is replaced for attachment to the remainder of the compound (e.g., the moiety -$L^1$-$B^1$). In certain embodiments, a hydrogen atom on a nuclear receptor-targeting epitope disclosed herein is replaced for attachment to the remainder of the compound. In certain embodiments, the hydrogen atom is on a heteroatom. In certain embodiments, the hydrogen atom is on a halogen. In certain embodiments, the hydrogen atom is on a nitrogen. In certain embodiments, the hydrogen atom is on an oxygen. In certain embodiments, the hydrogen atom is on a carbon (e.g., methyl group). The analogs are derived from the known nuclear payload described herein (e.g., topoisomerase inhibitor or $A^1$) and are modified to be conjugated to at least one nuclear hormone receptor-targeting epitope, optionally via a linking moiety. The analogs, even after modification to arrive at the compounds described herein, maintain biological activity, which is comparable to that observed in the original, unmodified topoisomerase inhibitor. In certain embodiments, the compounds exhibit a binding activity or inhibition which is at least about 98%, about 95%, about 90%, about 85%, about 80%, about 75%, about 70%, about 65%, about 60%, about 55%, or about 50%, or about 5-50% of that observed in the original, unmodified topoisomerase inhibitor. In certain embodiments, the compound as described herein exhibits an IC$_{50}$ of less than about 500 nM, or less than about 400 nM, or less than about 350 nM, or less than about 300 nM, or less than about 200 nM, or less than about 100 nM, or less than about 50 nM.

In certain embodiments of Formula I, II or III, $A^1$ is a compound of Formula IA:

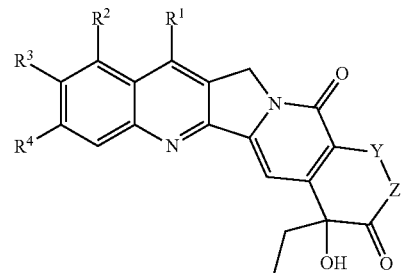

IA wherein:
Y is a bond, —CH$_2$—, or —CH$_2$—CH$_2$—;
Z is a bond or O;
$R^1$, $R^2$, $R^3$ and $R^4$ are each independently hydrogen, halo, cyano, nitro, —OR$^{15}$, —SR$^{15}$, —NR$^{15}$R$^{16}$, C$_{1-12}$ alkyl, C$_{2-12}$ alkenyl, C$_{2-12}$ alkynyl, C$_{3-10}$ cycloalkyl, heterocyclyl, aryl, heteroaryl, —C(=O)R$^{15}$, —C(=O)OR$^{15}$, —OC(=O)R$^{15}$, —C(=O)NR$^{15}$R$^{16}$, —NR$^{15}$C(=O)R$^{16}$, —NR$^{15}$C(=O)OR$^{16}$, —S(=O)$_{1-2}$R$^{15}$, —S(=O)$_{1-2}$NR$^{15}$R$^{16}$, —NR$^{15}$S(=O)$_{1-2}$R$^{16}$, —Si(R$^{15}$)$_3$, or —C=NOR$^{15}$, wherein each alkyl, alkenyl, alkynyl, cycloalkyl, heterocyclyl, aryl and heteroaryl of R$^1$, R$^2$, R$^3$ and R$^4$ are independently optionally substituted with one or more R$^{10}$ as valency permits;

or R$^1$ and R$^2$ are taken together with the atoms to which they are attached to form a C$_{3-10}$ cycloalkyl, heterocyclyl, aryl, or heteroaryl, optionally substituted with one or more R$^{10}$ as valency permits;

or R$^2$ and R$^3$ are taken together with the atoms to which they are attached to form a C$_{3-10}$ cycloalkyl, heterocyclyl, aryl, or heteroaryl, optionally substituted with one or more R$^{10}$ as valency permits;

or R$^3$ and R$^4$ are taken together with the atoms to which they are attached to form a C$_{3-10}$ cycloalkyl, heterocyclyl, aryl, or heteroaryl, optionally substituted with one or more R$^{10}$ as valency permits;

each R$^{10}$ is independently halo, cyano, nitro, —OR$^{17}$, —SR$^{17}$, —SF$_5$, —NR$^{17}$R$^{18}$, C$_{1-12}$ alkyl, C$_{2-12}$ alkenyl, C$_{2-12}$ alkynyl, C$_{3-10}$ cycloalkyl, heterocyclyl, aryl, heteroaryl, —C(=O)R$^{17}$, —C(=O)OR$^{17}$, —OC(=O)OR$^{17}$, —OC(=O)R$^{17}$, —C(=O)NR$^{17}$R$^{18}$, —OC(=O)NR$^{17}$R$^{18}$, —NR⁷C(=O)NR¹⁷R¹⁸, —S(=O)₁₋₂R¹⁷, —S(=O)₁₋₂NR¹⁷R¹⁸, —NR¹⁷S(=O)₁₋₂R¹⁸, —NR¹⁷S(=O)₁₋₂NR¹⁷R¹⁸, —NR¹⁷C(=O)R¹⁸, —NR¹⁷C(=O)OR¹⁸, —Si(R¹⁷)₃, or —C=NOR¹⁷, wherein each alkyl, alkenyl, alkynyl, cycloalkyl, heterocyclyl, aryl and heteroaryl of R¹⁰ are independently optionally substituted with one or more halo or C₁₋₁₂ alkyl optionally substituted by oxo, halo, hydroxyl or amino as valency permits; and each R¹⁵ and R¹⁶ is independently hydrogen, C₁₋₁₂ alkyl, C₂₋₁₂ alkenyl, C₂₋₁₂ alkynyl, or C₃₋₁₂ cycloalkyl, wherein each alkyl, alkenyl, alkynyl, or cycloalkyl is optionally independently substituted with oxo, halo, hydroxyl or amino as valency permits; or R¹⁵ and R¹⁶ are taken together with the atoms to which they are attached to form heterocyclyl optionally substituted by halo or C₁₋₁₂ alkyl optionally substituted by oxo, halo, hydroxyl or amino; and each R¹⁷ and R¹⁸ is independently hydrogen, C₁₋₁₂ alkyl, C₂₋₁₂ alkenyl, C₂₋₁₂ alkynyl, or C₃₋₁₂ cycloalkyl, wherein each C₁₋₁₂ alkyl, C₂₋₁₂ alkenyl, C₂₋₁₂ alkynyl, or C₃₋₁₂ cycloalkyl is optionally substituted with oxo, halo, hydroxyl or amino as valency permits; or R¹⁷ and R¹⁸ are taken together with the atoms to which they are attached to form heterocyclyl optionally substituted by halo or C₁₋₁₂ alkyl optionally substituted by oxo, halo, hydroxyl or amino;

wherein one or more atoms of Formula IA (e.g., hydrogen, methyl, or hydroxy) is replaced by a direct covalent bond L¹.

In embodiments where L¹ is a bond, the phrase "is replaced by a direct covalent bond L¹" means that the group is replaced by a direct covalent bond to B¹.

In certain embodiments, a hydrogen atom of Formula IA is replaced by a direct covalent bond to L¹.

In certain embodiments one or more atoms (e.g., hydrogen, methyl, or hydroxy) in one of R¹, R², and R³ is replaced by a direct covalent bond to L¹.

In certain embodiments Y is —CH₂—.

In certain embodiments Z is O.

In certain embodiments Y is —CH₂— and Z is O.

In certain embodiments of the various Formulas described herein, the terms heterocyclyl, aryl, or heteroaryl, refer to a 3-10 membered heterocyclyl, 6-10-membered aryl, or 5-10 membered heteroaryl.

In certain embodiments, provided is a compound of Formula IA-1, or stereoisomer, mixture of stereoisomers, hydrate, solvate, isotopically enriched analog, or pharmaceutically acceptable salt thereof:

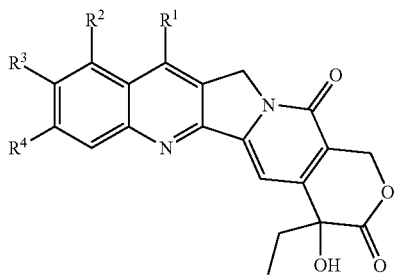

IA-1 wherein:

R¹, R², R³ and R⁴ are each independently hydrogen, halo, cyano, nitro, —OR¹⁵, —SR¹⁵, —NR¹⁵R¹⁶, C₁₋₁₂ alkyl, C₂₋₁₂ alkenyl, C₂₋₁₂ alkynyl, C₃₋₁₀ cycloalkyl, heterocyclyl, aryl, heteroaryl, —C(=O)R¹⁵, —C(=O)OR¹⁵, —OC(=O)R¹⁵, —C(=O)NR¹⁵R¹⁶, —NR¹⁵C(=O)R¹⁶, —S(=O)₁₋₂R¹⁵, —S(=O)₁₋₂NR¹⁵R¹⁶, —NR¹⁵S(=O)₁₋₂R¹⁶, —Si(R¹⁵)₃, or —C=NOR¹⁵, wherein each alkyl, alkenyl, alkynyl, cycloalkyl, heterocyclyl, aryl and heteroaryl of R¹, R², R³ and R⁴ are independently optionally substituted with one or more R¹⁰ as valency permits;

or R¹ and R² are taken together with the atoms to which they are attached to form a C₃₋₁₀ cycloalkyl, heterocyclyl, aryl, or heteroaryl, optionally substituted with one or more R¹⁰ as valency permits;

or R² and R³ are taken together with the atoms to which they are attached to form a C₃₋₁₀ cycloalkyl, heterocyclyl, aryl, or heteroaryl, optionally substituted with one or more R¹⁰ as valency permits;

or R³ and R⁴ are taken together with the atoms to which they are attached to form a C₃₋₁₀ cycloalkyl, heterocyclyl, aryl, or heteroaryl, optionally substituted with one or more R¹⁰ as valency permits;

each R¹⁰ is independently halo, cyano, nitro, —OR¹⁷, —SR¹⁷, —SF₅, —NR¹⁷R¹⁸, C₁₋₁₂ alkyl, C₂₋₁₂ alkenyl, C₂₋₁₂ alkynyl, C₃₋₁₀ cycloalkyl, heterocyclyl, aryl, heteroaryl, —C(=O)R¹⁷, —C(=O)OR¹⁷, —OC(=O)OR¹⁷, —OC(=O)R¹⁷, —C(=O)NR¹⁷R¹⁸, —OC(=O)NR¹⁷R¹⁸, —NR⁷C(=O)NR¹⁷R¹⁸, —S(=O)₁₋₂R¹⁷, —S(=O)₁₋₂NR¹⁷R¹⁸, —NR¹⁷S(=O)₁₋₂R¹⁸, —NR¹⁷S(=O)₁₋₂NR¹⁷R¹⁸, —NR¹⁷C(=O)R¹⁸, —NR¹⁷C(=O)OR¹⁸, —Si(R¹⁷)₃, or —C=NOR¹⁷, wherein each alkyl, alkenyl, alkynyl, cycloalkyl, heterocyclyl, aryl and heteroaryl of R¹⁰ are independently optionally substituted with one or more halo or C₁₋₁₂ alkyl optionally substituted by oxo, halo, hydroxyl or amino as valency permits; and each R¹⁵ and R¹⁶ is independently hydrogen, C₁₋₁₂ alkyl, C₂₋₁₂ alkenyl, C₂₋₁₂ alkynyl, or C₃₋₁₂ cycloalkyl, wherein each C₁₋₁₂ alkyl, C₂₋₁₂ alkenyl, C₂₋₁₂ alkynyl, or C₃₋₁₂ cycloalkyl is optionally independently substituted with oxo, halo, hydroxyl or amino as valency permits; or R¹⁵ and R¹⁶ are taken together with the atoms to which they are attached to form heterocyclyl optionally substituted by halo or C₁₋₁₂ alkyl optionally substituted by oxo, halo, hydroxyl or amino; and each R¹⁷ and R¹⁸ is independently hydrogen, C₁₋₁₂ alkyl, C₂₋₁₂ alkenyl, C₂₋₁₂ alkynyl, or C₃₋₁₂ cycloalkyl, wherein each C₁₋₁₂ alkyl, C₂₋₁₂ alkenyl, C₂₋₁₂ alkynyl, or C₃₋₁₂ cycloalkyl is optionally substituted with oxo, halo, hydroxyl or amino as valency permits; or R¹⁷ and R¹⁸ are taken together with the atoms to which they are attached to form heterocyclyl optionally substituted by halo or C₁₋₁₂ alkyl optionally substituted by oxo, halo, hydroxyl or amino;

where one or more atoms (e.g., hydrogen, methyl, hydroxy, etc.) is replaced by a direct covalent bond to at least one nuclear receptor-targeting epitope(s), optionally via a linking moiety (e.g., -L¹-B¹) as defined herein. In certain embodiments, a hydrogen atom of Formula IA-1 is replaced by a direct covalent bond to L¹.

In certain embodiments of Formula I, II or III, A¹ is a compound of Formula IB:

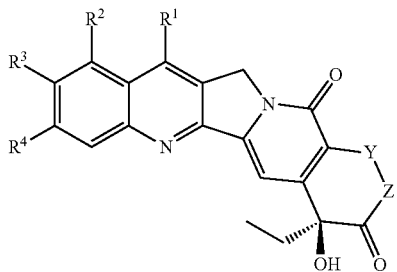

IB wherein:
R$^1$ is hydrogen, —C=NOR$^{15}$, or C$_{1-6}$ alkyl optionally substituted with one or more R$^{10}$;
R$^2$ is hydrogen, C$_{1-6}$ alkyl, —N(R$^{17}$R$^{18}$)$_2$, —NO$_2$, —C$_{1-6}$ alkylene-O—C$_{1-6}$ alkyl, or —C$_{1-6}$ alkylene-N(R$^{17}$R$^{18}$)$_2$; or
R$^1$ and R$^2$ are taken together with the atoms to which they are attached to form a C$_{3-10}$ cycloalkyl optionally substituted with one or more R$^{10}$;
R$^3$ is hydrogen, hydroxy, halo, C$_{1-6}$ alkyl, or —O—C$_{1-6}$ alkyl;
R$^4$ is hydrogen, halo, C$_{1-6}$ alkyl, or —O—C$_{1-6}$ alkyl; or
R$^3$ and R$^4$ together form a —O—CH$_2$—O— or —O—CH$_2$CH$_2$—O—;
Y is a bond, —CH$_2$—, or —CH$_2$—CH$_2$—; and
Z is a bond or O;
where one or more atoms in one of R$^1$, R$^2$, and R$^3$ is replaced by a direct covalent bond to L$^1$.

In certain embodiments, a hydrogen atom of Formula IB is replaced by a direct covalent bond to L$^1$.

In certain embodiments, provided is a compound of Formula IB, or stereoisomer, mixture of stereoisomers, hydrate, solvate, isotopically enriched analog, or pharmaceutically acceptable salt thereof:

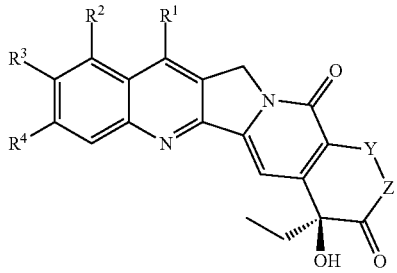

IB wherein:
R$^1$ is hydrogen or -L$^1$-B$^1$;
R$^2$ is hydrogen, NH$_2$, NO$_2$, or -L$^1$-B$^1$;
R$^3$ is hydrogen, halo, methyl, methoxy, or -L$^1$-B$^1$;
R$^4$ is hydrogen, halo, methyl, or methoxy; or
R$^3$ and R$^4$ together form a —O—CH$_2$—O— or —O—CH$_2$CH$_2$—O—;
Y is a bond, —CH$_2$—, or —CH$_2$—CH$_2$—; and
Z is a bond or O.

In certain embodiments, only one of R$^1$, R$^2$ or R$^3$ is -L$^1$-B$^1$. In certain embodiments, R$^1$ is -L$^1$-B$^1$. In certain embodiments, R$^2$ is -L$^1$-B$^1$. In certain embodiments, R$^3$ is -L$^1$-B$^1$.

In certain embodiments, provided is a compound of Formula IC, or stereoisomer, mixture of stereoisomers, hydrate, solvate, isotopically enriched analog, or pharmaceutically acceptable salt thereof:

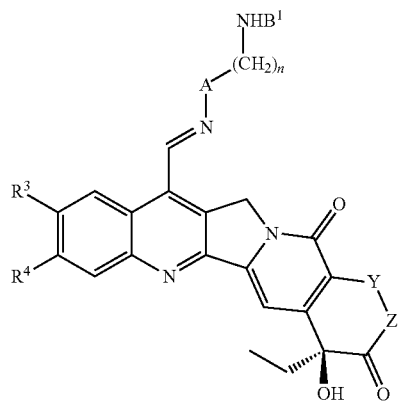

IC wherein:
B$^1$ is a nuclear receptor-targeting epitope as defined herein;
n is 2, 3 or 4;
A is O or NH;
R$^3$ is hydrogen, halo, methyl, or methoxy;
R$^4$ is hydrogen, halo, methyl, methoxy; or
R$^3$ and R$^4$ together form a —O—CH$_2$—O— or —O—CH$_2$CH$_2$—O—;
Y is a bond, —CH$_2$—, or —CH$_2$—CH$_2$—; and
Z is a bond or O.

In certain embodiments, provided is a compound of Formula ID, or stereoisomer, mixture of stereoisomers, hydrate, solvate, isotopically enriched analog, or pharmaceutically acceptable salt thereof:

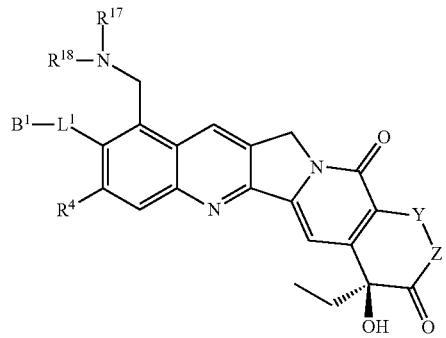

ID wherein:
L$^1$ is a linking moiety;
B$^1$ is a nuclear receptor-targeting epitope as defined herein;
R$^4$ is hydrogen, halo, methyl, or methoxy;
each of R$^{17}$ and R$^{18}$ is independently hydrogen, C$_{1-12}$ alkyl, C$_{2-12}$ alkenyl, or C$_{2-12}$ alkynyl, wherein each C$_{1-12}$ alkyl, C$_{2-12}$ alkenyl, or C$_{2-12}$ alkynyl is optionally substituted with oxo, halo, hydroxyl or amino as valency permits; or R$^{17}$ and R$^{18}$ are taken together with the atoms to which they are attached to form heterocyclyl optionally substituted by halo or C$_{1-12}$ alkyl optionally substituted by oxo, halo, hydroxyl or amino;

Y is a bond, —CH$_2$—, or —CH$_2$—CH$_2$—; and
Z is a bond or O.

In certain embodiments, provided is a compound of Formula IE, or stereoisomer, mixture of stereoisomers, hydrate, solvate, isotopically enriched analog, or pharmaceutically acceptable salt thereof:

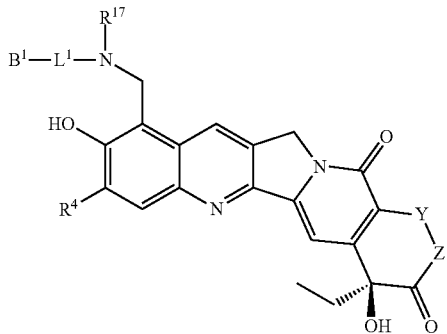

IE wherein:
L$^1$ is a linking moiety;
B$^1$ is a nuclear receptor-targeting epitope as defined herein;
R$^4$ is hydrogen, halo, methyl, or methoxy;
R$^{17}$ is hydrogen, C$_{1-12}$ alkyl, C$_{2-12}$ alkenyl, or C$_{2-12}$ alkynyl, wherein each C$_{1-12}$ alkyl, C$_{2-12}$ alkenyl, or C$_{2-12}$ alkynyl is optionally substituted with oxo, halo, hydroxyl or amino as valency permits;
Y is a bond, —CH$_2$—, or —CH$_2$—CH$_2$—; and
Z is a bond or O.

In certain embodiments, provided is a compound of Formula IF, or stereoisomer, mixture of stereoisomers, hydrate, solvate, isotopically enriched analog, or pharmaceutically acceptable salt thereof:

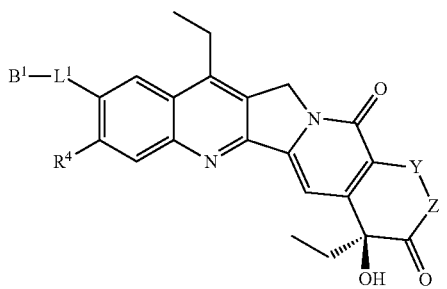

IF wherein:
L$^1$ is a linking moiety;
B$^1$ is a nuclear receptor-targeting epitope as defined herein;
R$^4$ is hydrogen, halo, methyl, or methoxy;
Y is a bond, —CH$_2$—, or —CH$_2$—CH$_2$—; and
Z is a bond or O.

In certain embodiments, provided is a compound of Formula IG, or stereoisomer, mixture of stereoisomers, hydrate, solvate, isotopically enriched analog, or pharmaceutically acceptable salt thereof:

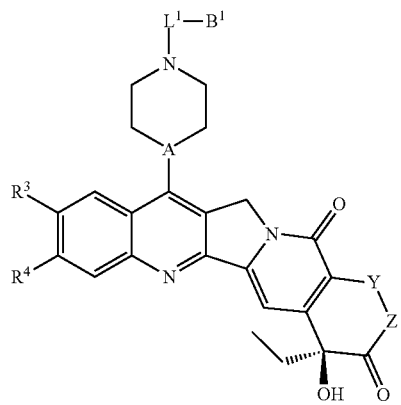

IG wherein:
B$^1$ is a nuclear receptor-targeting epitope as defined herein;
A is N or CH;
R$^3$ is hydrogen, halo, methyl, or methoxy;
R$^4$ is hydrogen, halo, methyl, methoxy; or
R$^3$ and R$^4$ together form a —O—CH$_2$—O— or —O—CH$_2$CH$_2$—O—;
Y is a bond, —CH$_2$—, or —CH$_2$—CH$_2$—; and
Z is a bond or O.

In certain embodiments, provided is a compound of Formula IH, or stereoisomer, mixture of stereoisomers, hydrate, solvate, isotopically enriched analog, or pharmaceutically acceptable salt thereof:

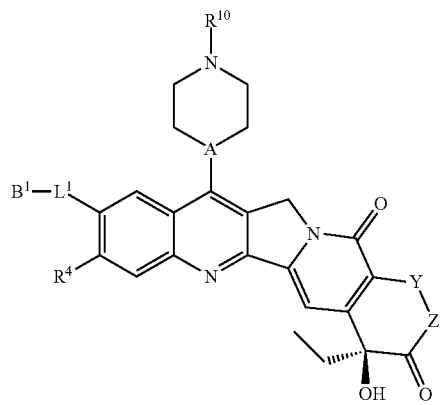

IH wherein:
B$^1$ is a nuclear receptor-targeting epitope as defined herein;
A is N or CH;
R$^4$ is hydrogen, halo, methyl, methoxy; or
each R$^{10}$ is independently halo, cyano, nitro, —OR$^{17}$, —SR$^{17}$, —SF$_5$, —NR$^{17}$R$^{18}$, C$_{1-12}$ alkyl, C$_{2-12}$ alkenyl, C$_{2-12}$ alkynyl, C$_{3-10}$ cycloalkyl, heterocyclyl, aryl, heteroaryl, —C(=O)R$^{17}$, —C(=O)OR$^{17}$, —OC(=O)OR$^{17}$, —OC(=O)R$^{17}$, —C(=O)NR$^{17}$R$^{18}$, —OC(=O)NR$^{17}$R$^{18}$, —NR$^7$C(=O)NR$^{17}$R$^{18}$, —S(=O)$_{1-2}$R$^{17}$, —S(=O)$_{1-2}$NR$^{17}$R$^{18}$, —NR$^{17}$S(=O)$_{1-2}$R$^{18}$, —NR$^{17}$S(=O)$_{1-2}$NR$^{17}$R$^{18}$, —NR$^{17}$C(=O)R$^{18}$, —NR$^{17}$C(=O)OR$^{18}$, —Si(R$^{17}$)$_3$, or —C=NOR$^{17}$, wherein each alkyl, alkenyl, alkynyl, cycloalkyl, heterocyclyl, aryl and heteroaryl of R$^{10}$ are independently optionally substituted with one or more halo or C$_{1-12}$ alkyl optionally substituted by oxo, halo, hydroxyl or amino as valency permits;

each R$^{17}$ and R$^{18}$ is independently hydrogen, C$_{1-12}$ alkyl, C$_{2-12}$ alkenyl, C$_{2-12}$ alkynyl, or C$_{3-12}$ cycloalkyl, wherein each C$_{1-12}$ alkyl, C$_{2-12}$ alkenyl, C$_{2-12}$ alkynyl, or C$_{3-12}$ cycloalkyl is optionally substituted with oxo, halo, hydroxyl or amino as valency permits; or R$^{17}$ and R$^{18}$ are taken together with the atoms to which they are attached to form heterocyclyl optionally substituted by halo or C$_{1-12}$ alkyl optionally substituted by oxo, halo, hydroxyl or amino;

Y is a bond, —CH$_2$—, or —CH$_2$—CH$_2$—; and

Z is a bond or O.

In certain embodiments, provided is a compound of Formula IJ, or stereoisomer, mixture of stereoisomers, hydrate, solvate, isotopically enriched analog, or pharmaceutically acceptable salt thereof:

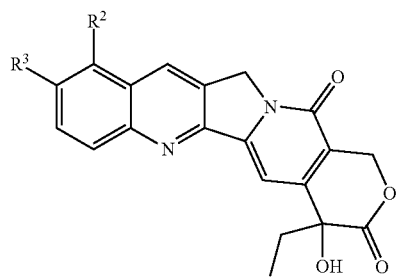

IJ wherein:

R$^3$ is hydrogen, hydroxy, —CH$_2$NH$_2$, or —C(=O)H;

R$^2$ is hydrogen when R$^3$ is —CH$_2$NH$_2$ or —C(=O)H; or

R$^2$ is —C(=O)H or —CH$_2$R$^{11}$ when R$^3$ is hydrogen or hydroxy;

R$^{11}$ is —OR$^{12}$, —SR$^{12}$, —CH$_2$NH$_2$, —NR$^{12}$R$^{13}$, or —N$^+$R$^{12}$R$^{13}$R$^{14}$;

R$^{12}$, R$^{13}$ and R$^{14}$ are each independently hydrogen, C$_{1-6}$ alkyl, C$_{2-6}$ hydroxyalkyl, C$_{1-6}$ dialkylamino, C$_{1-6}$ dialkylamino-C$_{2-6}$ alkyl, C$_{1-6}$ alkylamino-C$_{2-6}$ alkyl, C$_{2-6}$ aminoalkyl or a 3-7 member unsubstituted or substituted ring; and when R$^{11}$ is —NR$^{12}$R$^{13}$, the R$^{12}$ and R$^{13}$ groups may be combined together with the nitrogen atom to which they are bonded to form heterocyclic ring provided that such heterocyclic ring is selected from morpholino, N-methylpiperazinyl, or 4'-piperidinopiperidinyl, each which may contain additional heteroatoms;

or a pharmaceutically acceptable salt, hydrate or solvate thereof;

where an atom (e.g., hydrogen, carbon or heteroatom) is replaced by a direct covalent bond to at least one nuclear receptor-targeting epitope(s), optionally via a linking moiety (e.g., -L$^1$-B$^1$) as defined herein.

In certain embodiments, the nuclear payload is derived from topotecan, or an analog thereof (i.e., topotecan-containing analogs). In certain embodiments, provided is a compound of Formula IK:

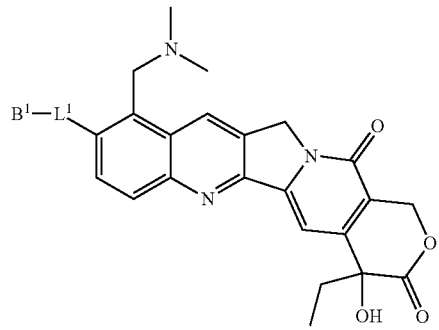

IK wherein B$^1$ is a nuclear receptor-targeting epitope; and L$^1$ is a covalent bond or a linking moiety.

In certain embodiments, the nuclear payload is derived from irinotecan (CPT-11), or an analog thereof (i.e., irinotecan-containing analogs). In certain embodiments, provided is a compound of Formula IL:

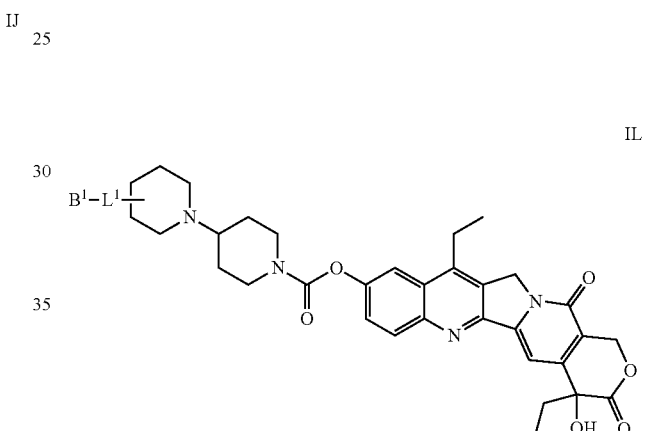

IL wherein B$^1$ is a nuclear receptor-targeting epitope; and L$^1$ is a covalent bond or a linking moiety. In certain embodiments, provided is a compound of Formula IM:

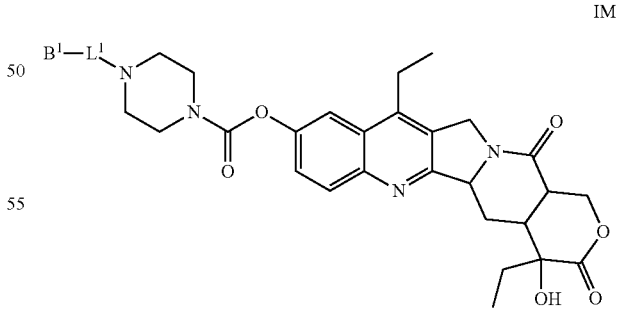

IM wherein B$^1$ is a nuclear receptor-targeting epitope; and L$^1$ is a covalent bond or a linking moiety.

In certain embodiments, the nuclear payload is derived from silatecan (DB-67, AR-67), or an analog thereof (i.e., silatecan-containing analogs). In certain embodiments, provided is a compound of Formula IN:

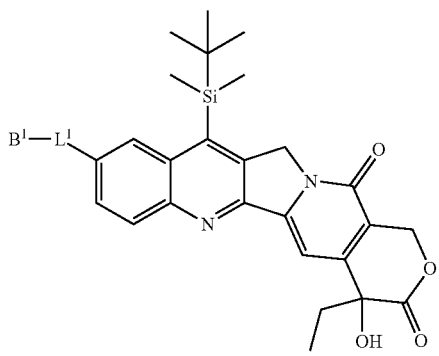

wherein B¹ is a nuclear receptor-targeting epitope; and L¹ is a covalent bond or a linking moiety.

In certain embodiments, the nuclear payload is derived from cositecan (BNP-1350), or an analog thereof (i.e., cositecan-containing analogs). In certain embodiments, provided is a compound of Formula IO:

IO

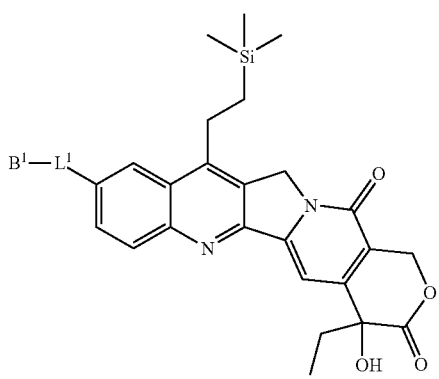

wherein B¹ is a nuclear receptor-targeting epitope; and L¹ is a covalent bond or a linking moiety.

In certain embodiments, the nuclear payload is derived from exatecan, or an analog thereof (i.e., exatecan-containing analogs). In certain embodiments, provided is a compound of Formula IP:

IP

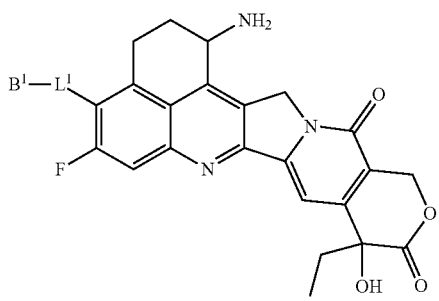

wherein B¹ is a nuclear receptor-targeting epitope; and L¹ is a covalent bond or a linking moiety. In certain embodiments, provided is a compound of Formula IQ:

IQ

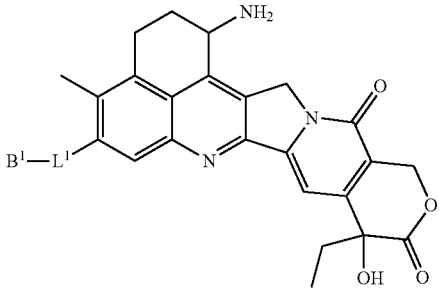

wherein B¹ is a nuclear receptor-targeting epitope; and L¹ is a covalent bond or a linking moiety.

In certain embodiments, the nuclear payload is derived from lurtotecan, or an analog thereof (i.e., lurtotecan-containing analogs). In certain embodiments, provided is a compound of Formula IR:

IR

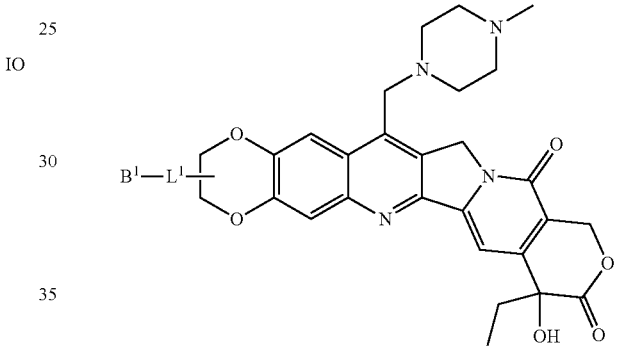

wherein B¹ is a nuclear receptor-targeting epitope; and L¹ is a covalent bond or a linking moiety.

In certain embodiments, the nuclear payload is derived from gimatecan (ST1481), or an analog thereof (i.e., gimatecan-containing analogs). In certain embodiments, provided is a compound of Formula IS:

IS

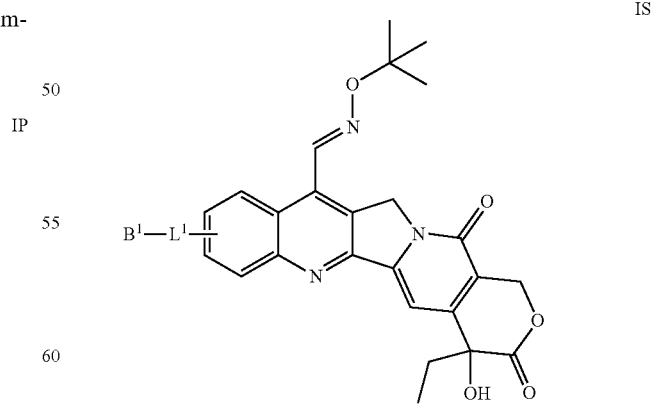

wherein B¹ is a nuclear receptor-targeting epitope; and L¹ is a covalent bond or a linking moiety.

In certain embodiments, the nuclear payload is derived from belotecan (CKD-602), or an analog thereof (i.e., belotecan-containing analogs). In certain embodiments, provided is a compound of Formula IT:

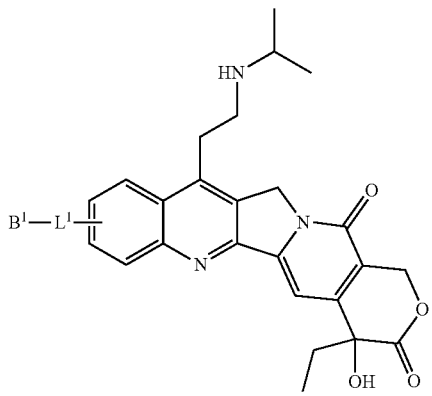

IT wherein B¹ is a nuclear receptor-targeting epitope; and L¹ is a covalent bond or a linking moiety.

In certain embodiments, the nuclear payload is derived from rubitecan, or an analog thereof (i.e., rubitecan-containing analogs). In certain embodiments, provided is a compound of Formula IU:

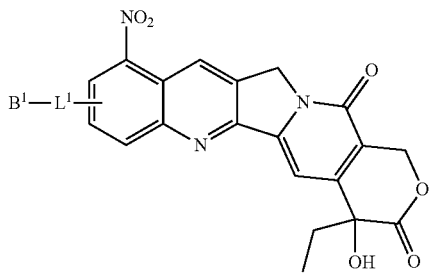

IU wherein B¹ is a nuclear receptor-targeting epitope; and L¹ is a covalent bond or a linking moiety.

In certain embodiments, the nuclear payload (i.e., A¹) is derived from:

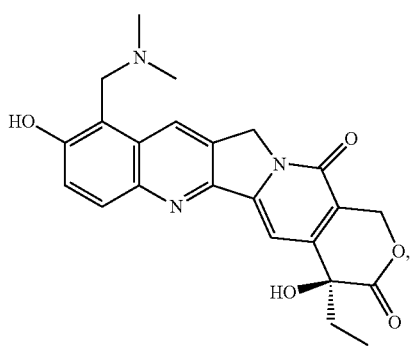

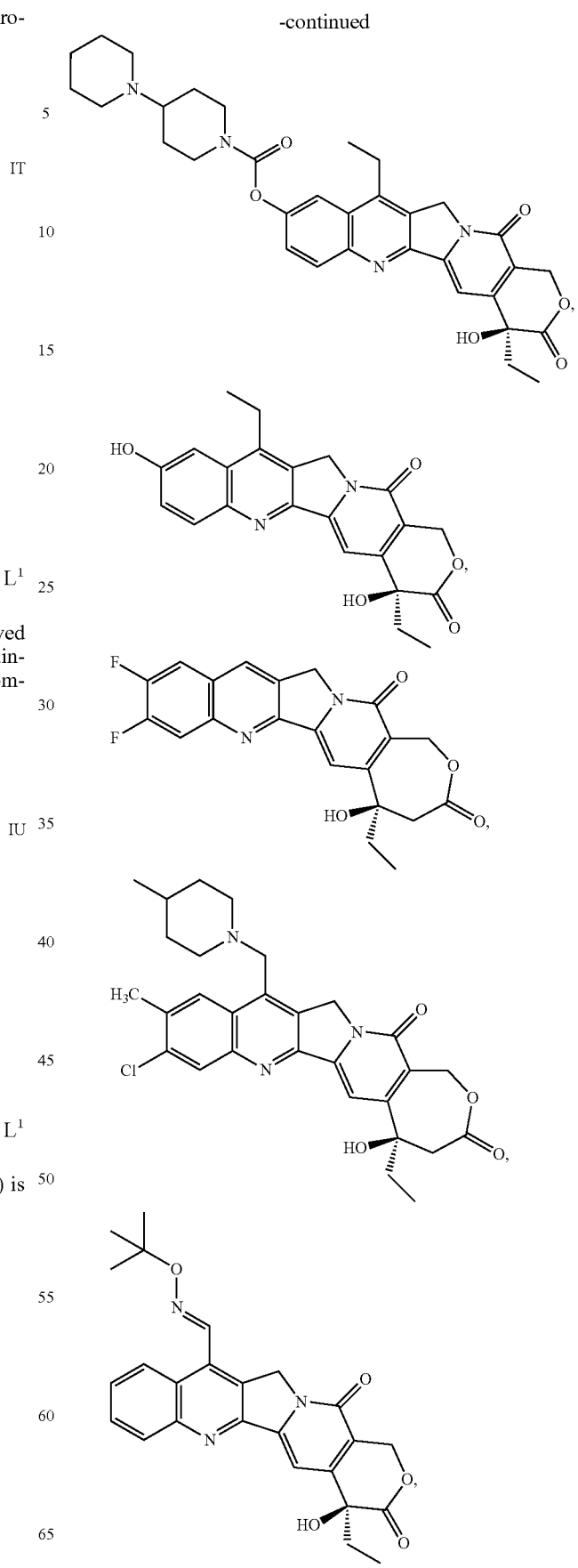

33
-continued
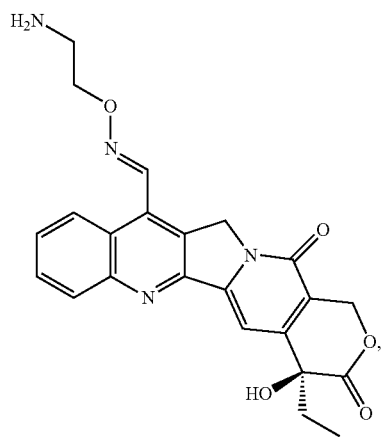
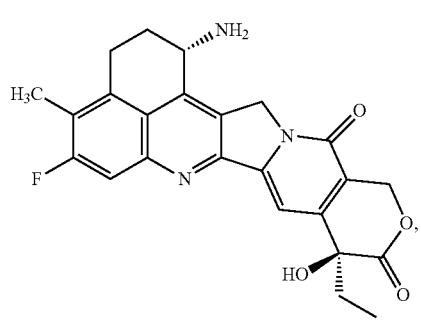
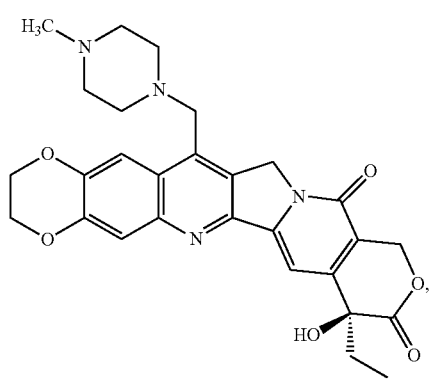
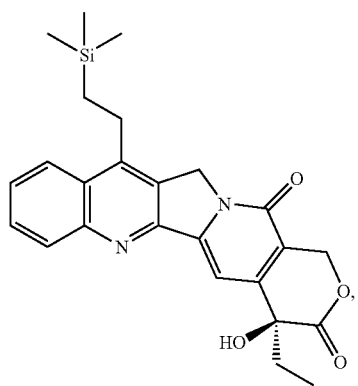
34
-continued
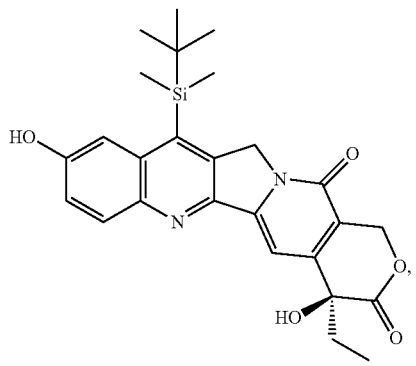
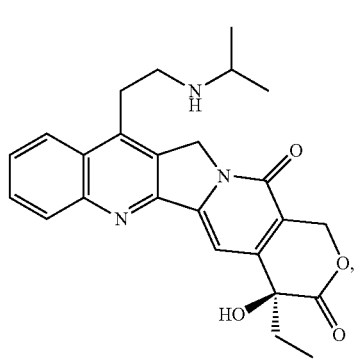
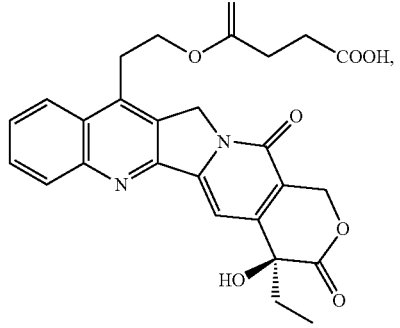
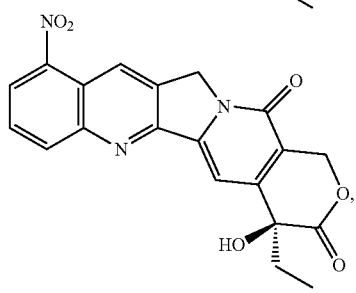
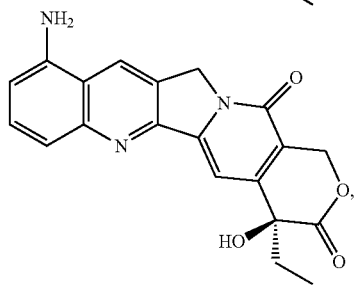

35
-continued
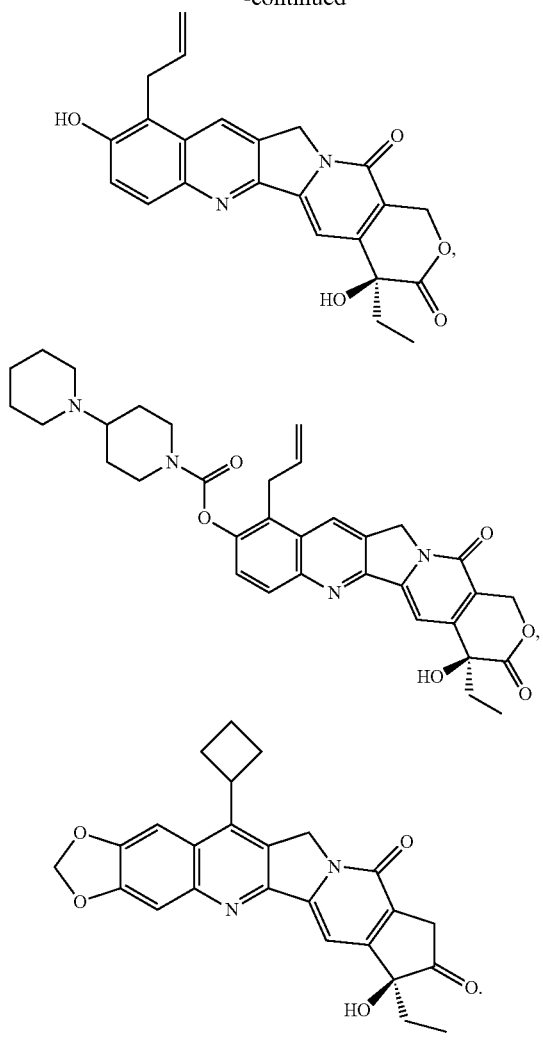
In certain embodiments, the nuclear payload or $A^1$ is derived from:
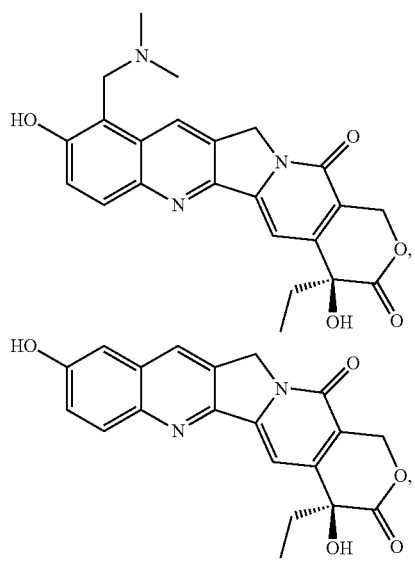
36
-continued
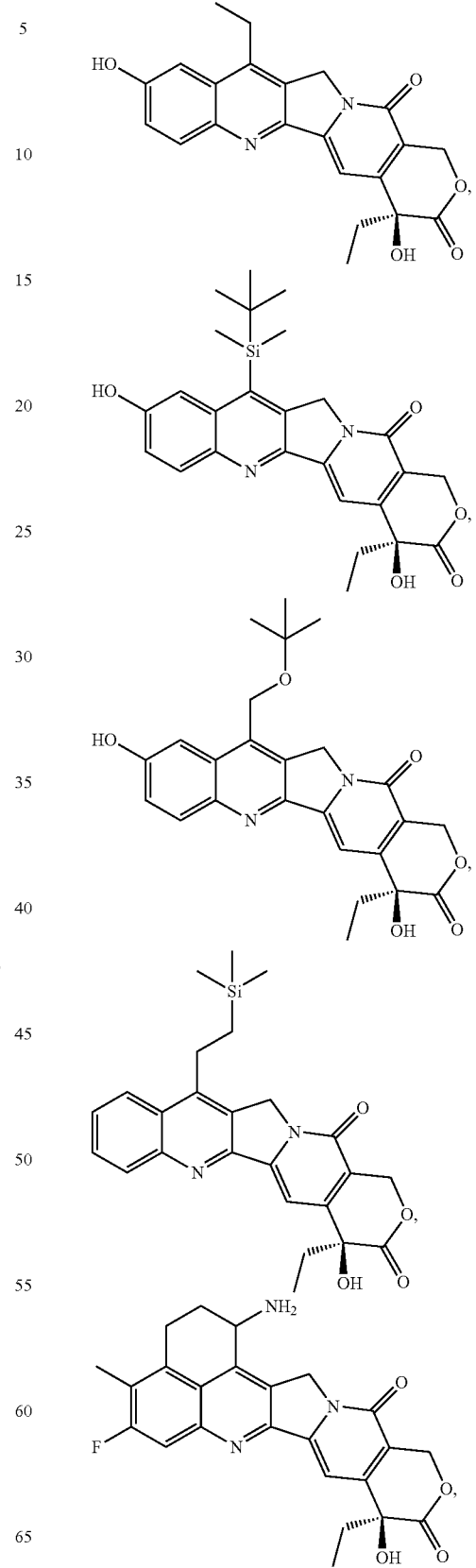

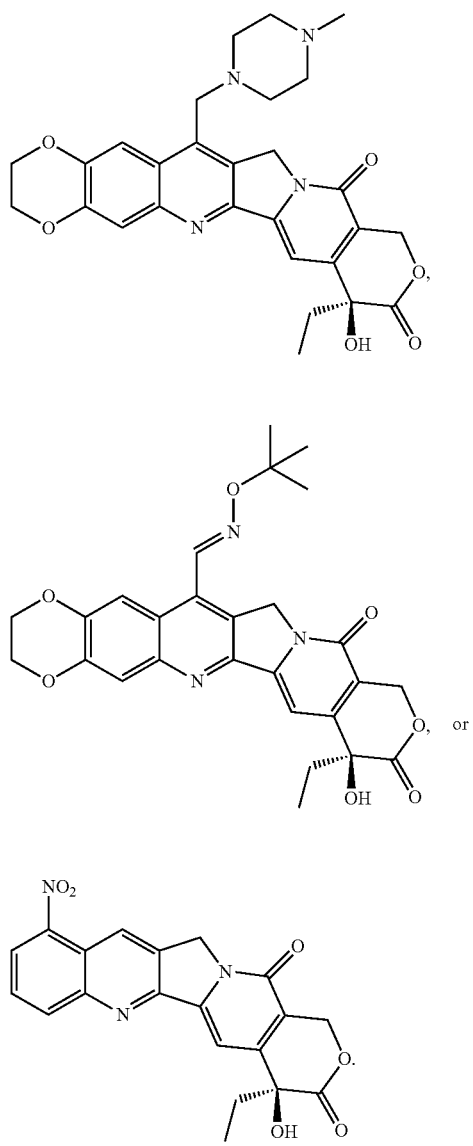
In certain embodiments, the nuclear payload is derived from:
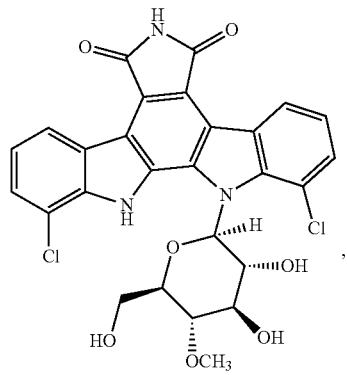
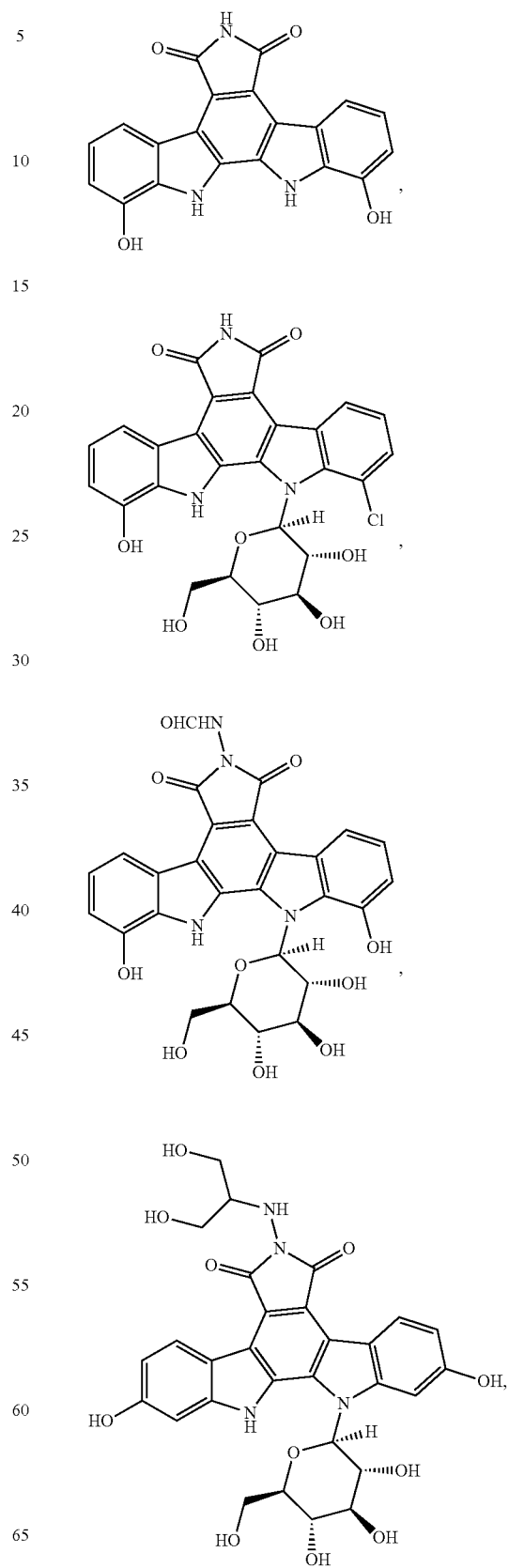

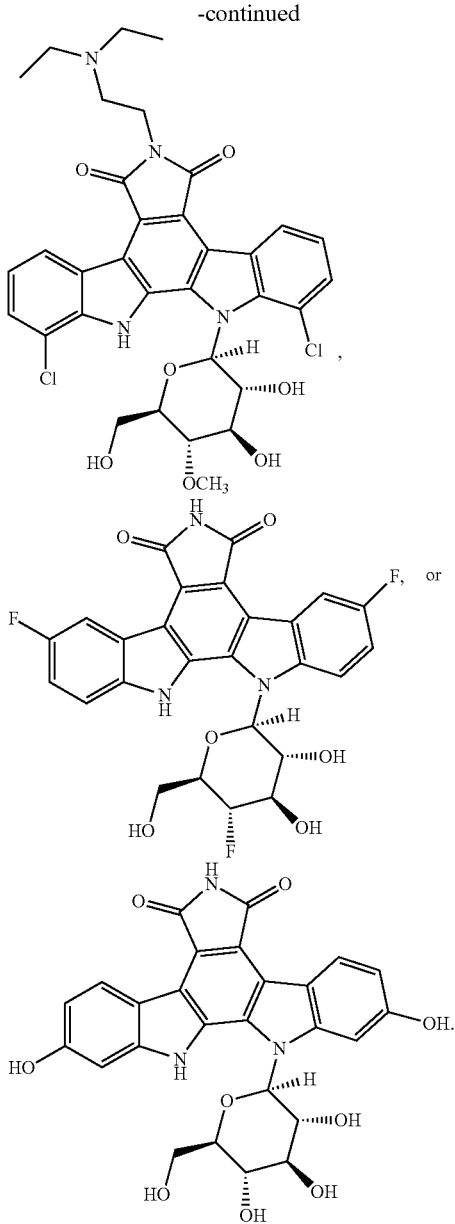
In certain embodiments, the nuclear payload is derived from:
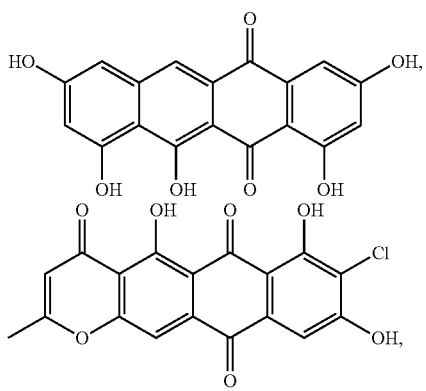
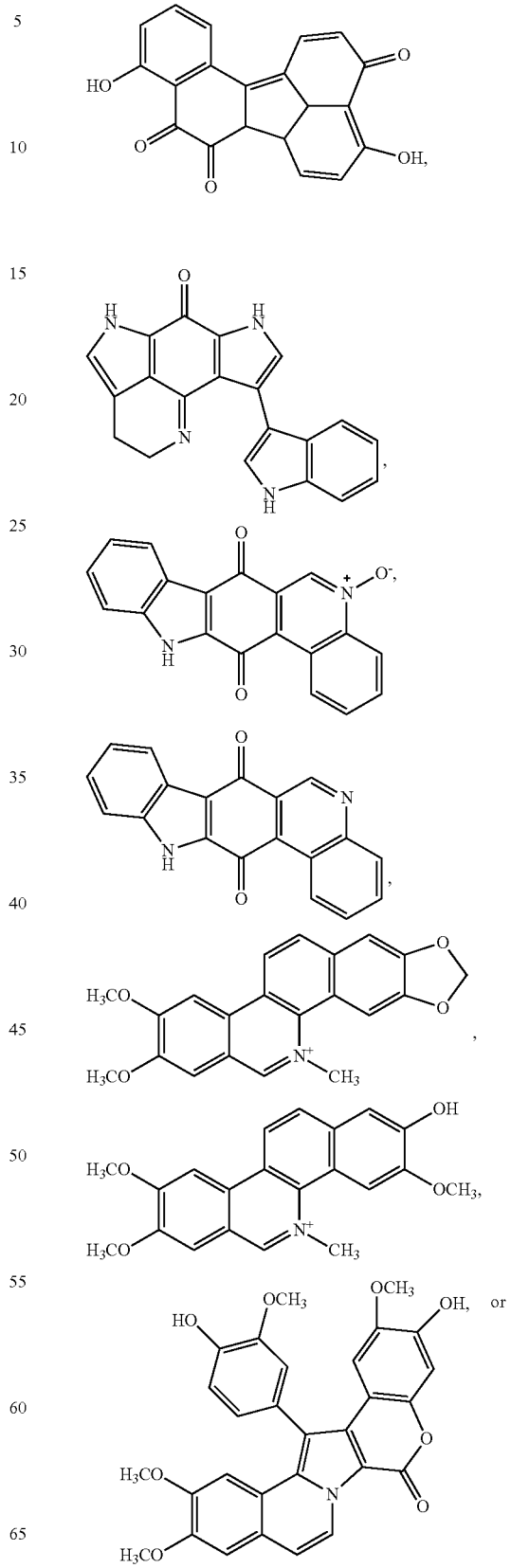

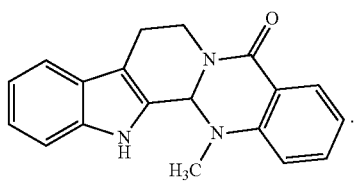
In certain embodiments, the nuclear payload is derived from:
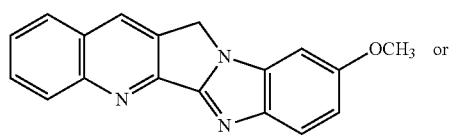
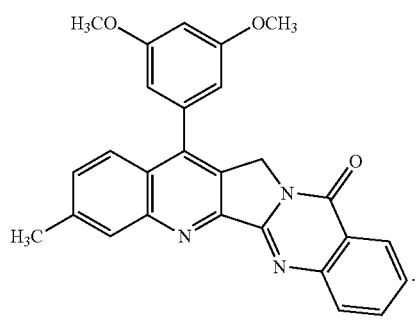
In certain embodiments, the nuclear payload is derived from:
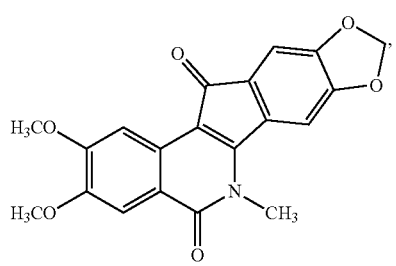
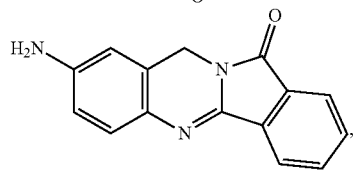
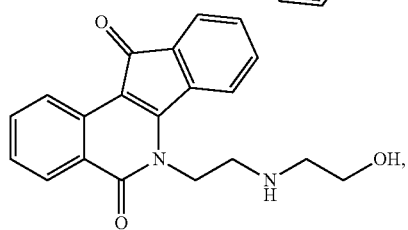
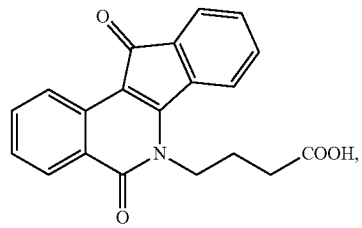
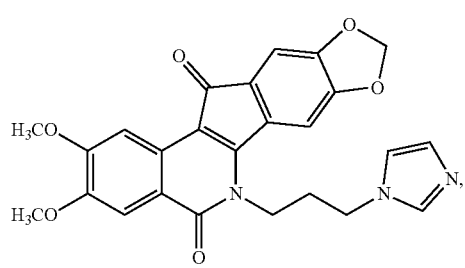
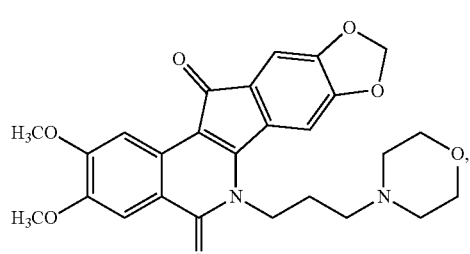
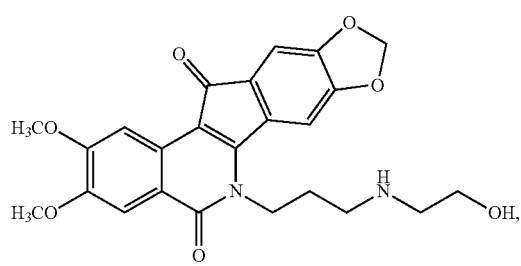
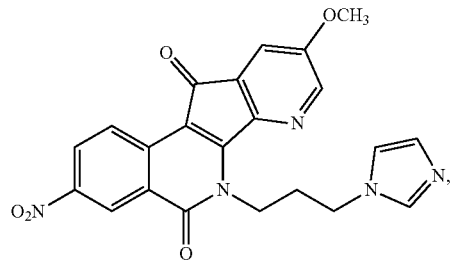
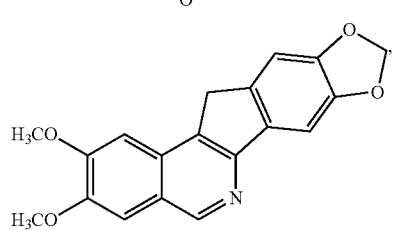

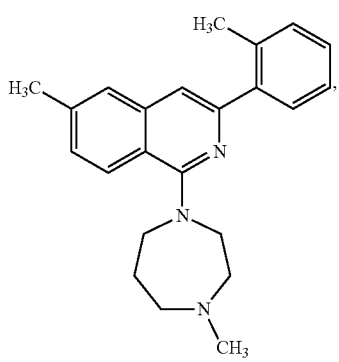
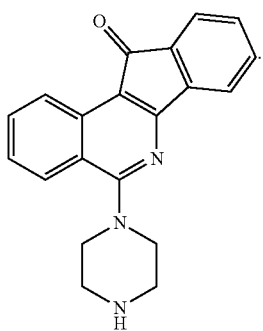
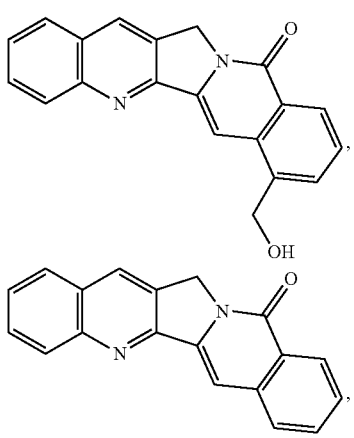
In certain embodiments, the nuclear payload is derived from:
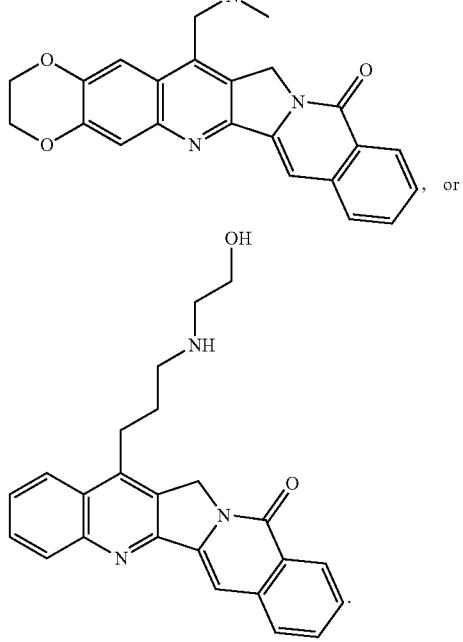
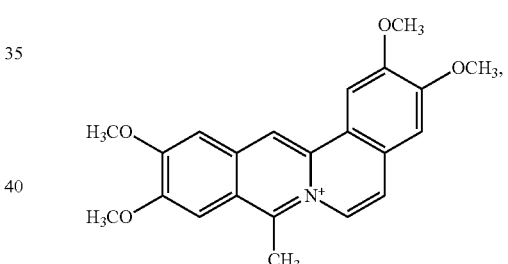
In certain embodiments, the nuclear payload is derived from:
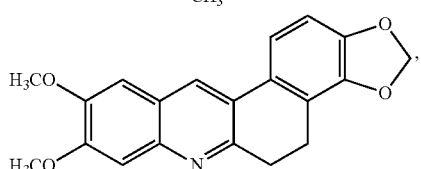
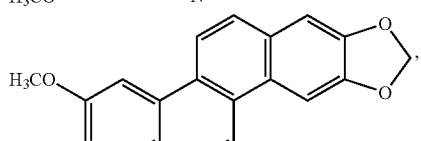
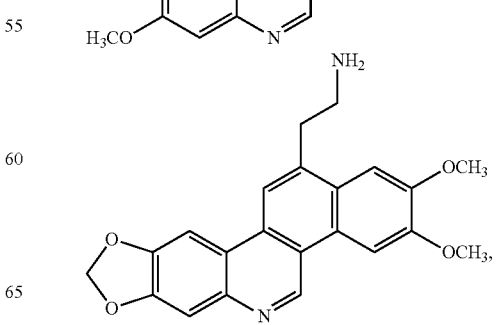

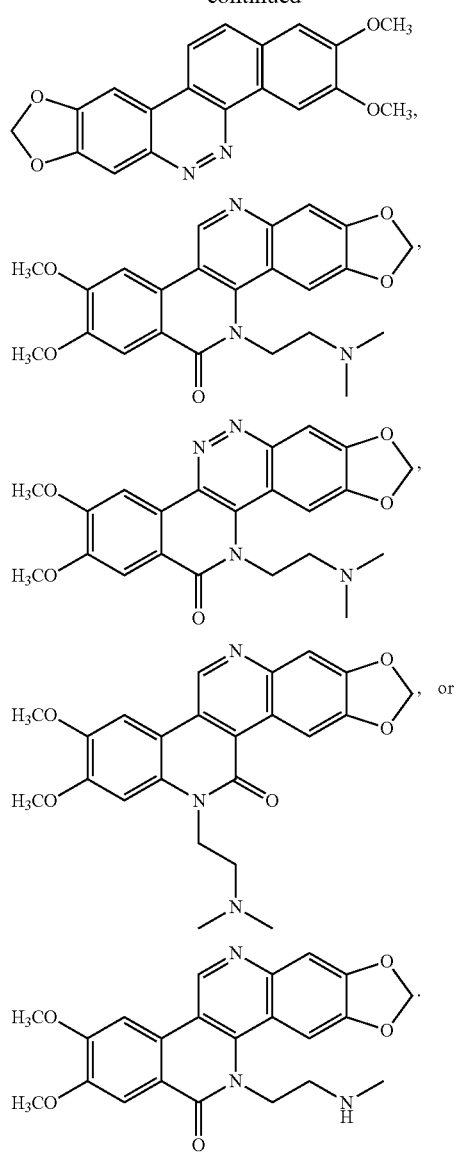
In certain embodiments, the nuclear payload is derived from:
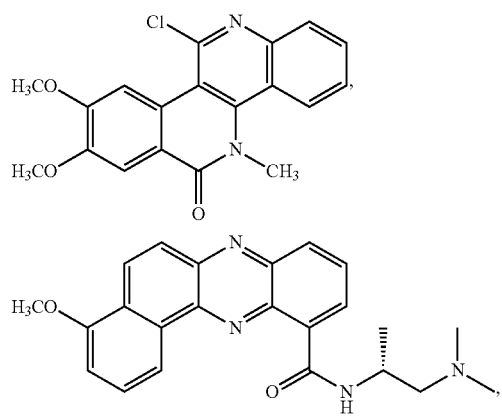
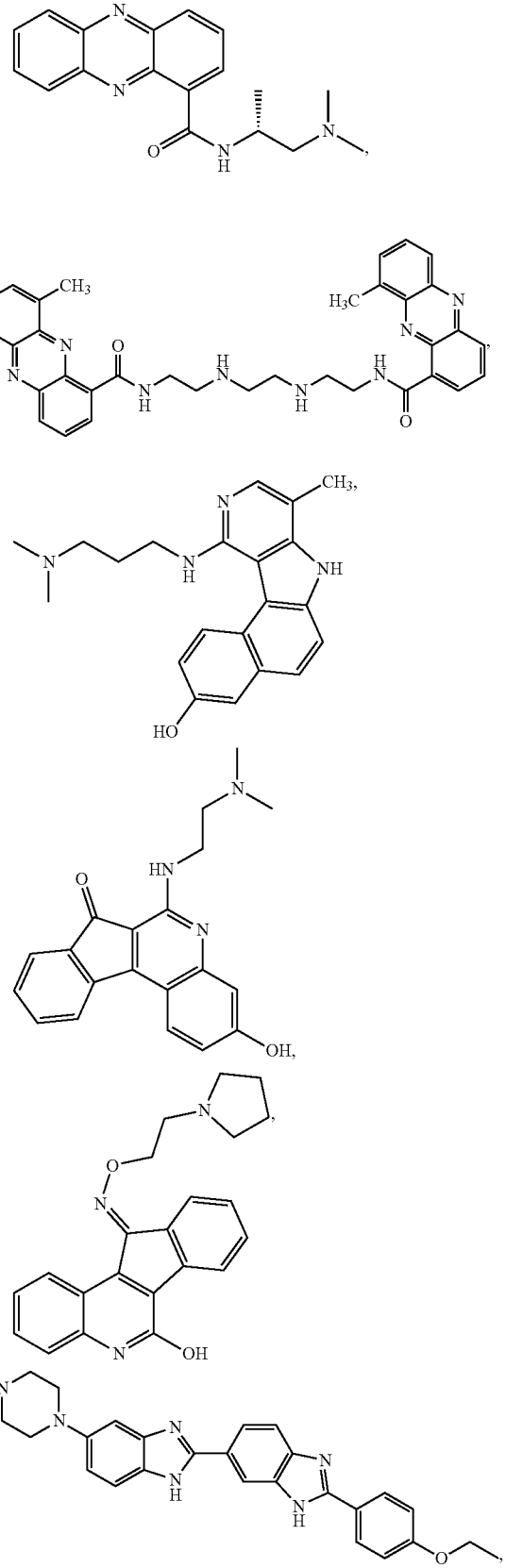

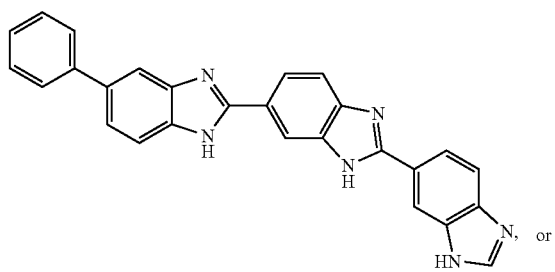
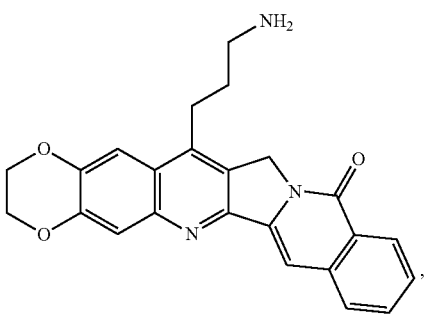
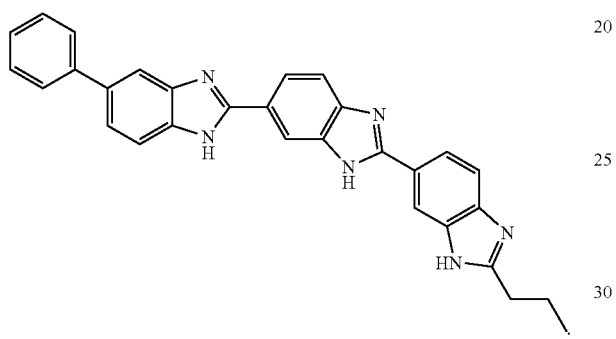
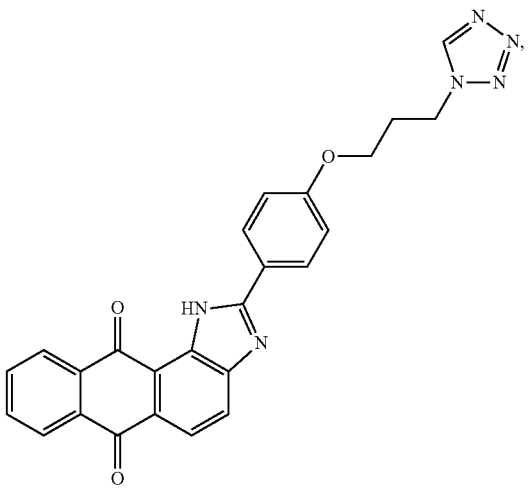
In certain embodiments, the nuclear payload is derived from:
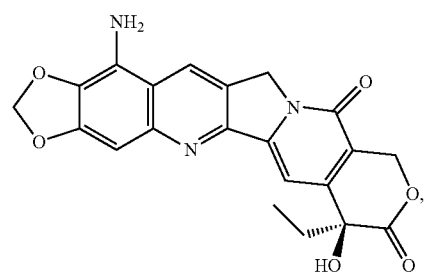
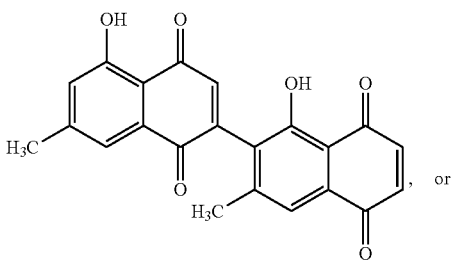
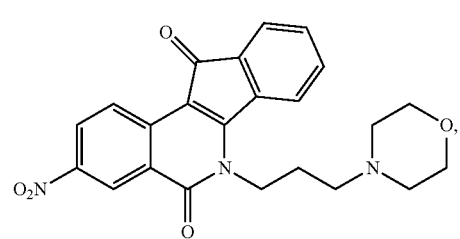
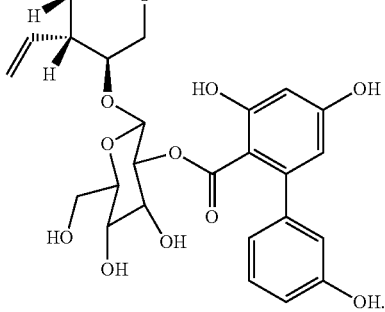

In certain embodiments, the nuclear payload is derived from:

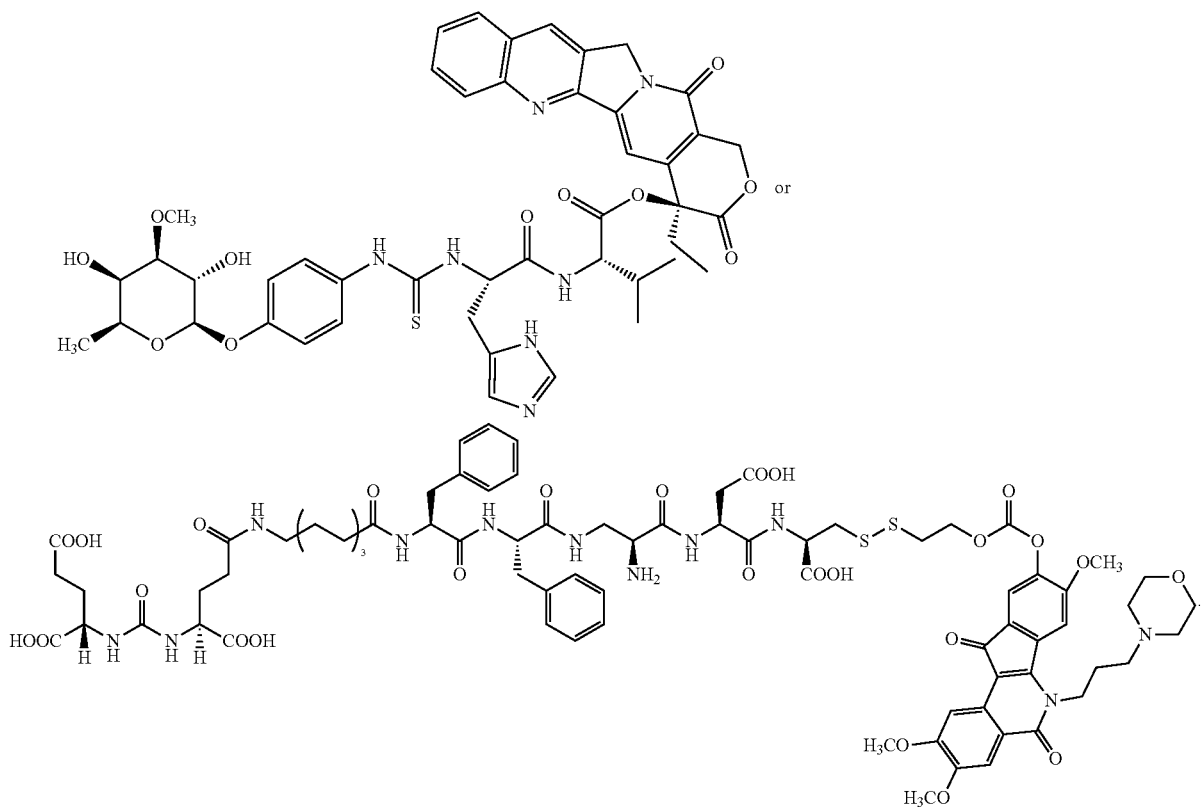

Nuclear Receptor-Targeting Epitopes

In certain embodiments, $B^1$ is a nuclear hormone receptor-targeting epitope. In certain embodiments, $B^1$ is a nuclear steroid receptor-targeting epitope. As used herein, "nuclear receptor-targeting epitope" refers to the portion of the compound described herein (e.g., $B^1$) which portion is derived from a nuclear targeting agent as disclosed herein and interacts with a ligand-binding domain of the target nuclear receptor, i.e., the portion of the compound which drives a ligand-binding interaction. The nuclear receptor-targeting epitope serves to associate the compound with a target nuclear receptor, e.g. a nuclear steroid receptor, facilitate the localization of compound to nuclear steroid receptor-expressing cells, and translocate the nuclear payload from the cytosol to nucleus, allowing the compound to accumulate in the nucleus. The level of accumulation can be controlled by selecting the appropriate nuclear receptor-targeting epitope. For example, the compounds described herein can accumulate in the nucleus to varying degrees, high in the case of a full agonist (e.g., dihydrotestosterone (DHT)), moderate in the case of a partial agonist (e.g., bicalutamide), and low, in the case of antagonists (e.g., enzalutamide), through nuclear translocation of the nuclear steroid receptor which happens, following epitope binding to the receptor.

The steroid receptor target can be any steroid receptor, including, but not limited to, those which are over-expressed on cancer cells. In certain embodiments, at least one nuclear steroid receptor-targeting epitope is capable of binding to a ligand binding domain of a nuclear steroid receptor, such as a ligand binding domain on an estrogen receptor, glucocorticoid receptor, progesterone receptor or androgen receptor.

Exemplary nuclear steroid receptor-targeting epitopes include those derived from an androgen receptor agonist, an androgen receptor antagonist, a selective androgen-receptor modulator (SARM), an estrogen receptor agonist, an estrogen receptor antagonist, a selective estrogen receptor modulator (SERM), a glucocorticoid receptor antagonist, a glucocorticoid receptor agonist, a selective glucocorticoid receptor modulator (SGRM), a progesterone receptor antagonist, a progesterone receptor agonist, a selective progesterone receptor modulator (SPRM), or a combination thereof.

The nuclear steroid receptor-targeting epitopes are typically capable of binding to a nuclear steroid receptor with an $IC_{50}$ of less than about 500 nM, or less than about 400 nM, or less than about 300 nM, or less than about 200 nM, or less than about 100 nM, or with an $EC_{50}$ of less than about 1 μM, or less than about 900 nM, or less than about 800 nM, or less than about 700 nM, or less than about 600 nM, or less than about 500 nM, or less than about 400 nM, or less than about 3400 nM, or less than about 200 nM, or less than about 100 nM.

In certain embodiments, the nuclear hormone receptor binding affinity of a compound of this invention can be defined according to its affinity relative to a reference nuclear hormone receptor binding compound. For example, some compounds of this invention can bind to the estrogen receptor. In some instances, a compound disclosed herein binds the human estrogen receptor with an affinity of at least 0.1%, 1%, 5%, 10%, 20%, 30%, 40%, 50%, 60%, 70%, 80%, 90%, or 100% of that of 17b-estradiol.

By way of additional examples, some compounds of this invention can bind to the human androgen receptor. In some instances, a compound disclosed herein binds the androgen receptor with an affinity of at least 0.1%, 1%, 5%, 10%, 20%, 30%, 40%, 50%, 60%, 70%, 80%, 90%, or 100% of that of dihydrotestosterone (DHT).

By way of additional examples, some compounds of this invention can bind to the human progestin receptor. In some instances, a compound disclosed herein binds the progestin receptor with an affinity of at least 0.1%, 1%, 5%, 10%, 20%, 30%, 40%, 50%, 60%, 70%, 80%, 90%, or 100% of that of progesterone.

By way of additional examples, some compounds of this invention can bind to the human glucocorticoid receptor. In some instances, a compound disclosed herein binds the glucocorticoid receptor with an affinity of at least 0.1%, 1%, 5%, 10%, 20%, 30%, 40%, 50%, 60%, 70%, 80%, 90%, or 100% of that of cortisone.

In certain embodiments, the nuclear steroid receptor-targeting epitope (e.g., $B^1$) is an agonist at the androgen receptor. In certain embodiments, the nuclear steroid receptor-targeting epitope is an antagonist at the androgen receptor.

In certain embodiments, the nuclear steroid receptor-targeting epitope (e.g., $B^1$) is steroidal (or is derived from a steroidal compound) (e.g., dihydrotestosterone). In certain embodiments, the nuclear steroid receptor-targeting epitope is non-steroidal (or is derived from a non-steroidal compound) (e.g., enzalutamide, apalutamide, AZD9496 and bicalutamide).

The analogs are derived from the known nuclear steroid receptor-targeting epitope described herein (e.g., $B^1$) and are modified to be conjugated to at least one nuclear steroid payload, optionally via a linking moiety. The analogs, even after modification to arrive at the compounds described herein, maintain biological activity, which is comparable to that observed in the original, unmodified nuclear steroid receptor-targeting epitope. In certain embodiments, the compounds exhibit a binding activity or inhibition which is at least about 98%, about 95%, about 90%, about 85%, about 80%, about 75%, about 70%, about 65%, about 60%, about 55%, or about 50%, or about 5-50% of that observed in the original, unmodified nuclear steroid receptor-targeting epitope.

In certain embodiments, the analogs are derived from a known nuclear receptor-targeting epitope (e.g., $B^1$), such as a known nuclear steroid receptor-targeting epitope. In certain embodiments, $B^1$ binds to an estrogen receptor, glucocorticoid receptor, progesterone receptor, or androgen receptor. In certain embodiments, the term "derived from" as used in reference to a nuclear receptor-targeting epitope, means that at most, one non-hydrogen atom of an original, unmodified nuclear receptor-targeting compound (i.e., a known nuclear steroid receptor-targeting compound) is replaced by a covalent bond to the nuclear payload, optionally via a linking moiety. Exemplary non-hydrogen atoms include, but are not limited to, —$CH_3$, —OH, =O, and —$NH_2$. In certain embodiments, the term "derived from" as used in reference to a nuclear receptor-targeting epitope, means that at most, one non-hydrogen atom of an original, unmodified nuclear receptor-targeting compound (i.e., a known nuclear steroid receptor-targeting compound) is replaced by a covalent bond to the nuclear payload, optionally via a linking moiety. In certain embodiments, one hydrogen atom bound to a heteroatom (e.g., N, O, or S) of the original, unmodified nuclear receptor-targeting compound (i.e., a known nuclear steroid receptor-targeting compound) is replaced by a covalent bond to the nuclear payload, optionally via a linking moiety. In certain embodiments, the term "derived from" means that one or more atoms (e.g., hydrogen, methyl, or hydroxy) is replaced by a direct covalent bond to $L^1$.

In certain embodiments, the nuclear steroid receptor-targeting epitope (e.g., $B^1$) is an androgen receptor-targeting epitope. As used herein, the term "androgen receptor-targeting epitope" is intended to refer to the portion of the compound which binds to the androgen receptor and can functionally be an androgen receptor agonist or androgen receptor antagonist (including partial androgen receptor agonists or partial androgen receptor antagonists) and in some embodiments, is capable of binding to the receptor and the ligand receptor complex shuttling from the cytoplasm into the nucleus of a cell. The "androgen receptor" (AR), also known as NR3C4 (nuclear receptor subfamily 3, group C, member 4), is a type of nuclear receptor that, when activated by binding an androgen receptor binder (e.g., an androgenic hormone such as testosterone, or dihydrotestosterone) in the cytoplasm, is capable of translocating the androgenic hormone into the nucleus.

Exemplary androgen receptor-targeting epitopes which can be used in the compounds described herein include (e.g., $B^1$) but are not limited to, an androgen receptor agonist, a selective androgen-receptor modulator (SARM) (e.g., enobosarm), an androgen receptor antagonist (e.g., bicalutamide, flutamide, nilutamide, or enzalutamide), a selective estrogen receptor modulator (SERM) (e.g., tamoxifen, toremifene, or raloxifene), an estrogen receptor antagonist (e.g., fulvestrant), a progestin (e.g., megestrol acetate), an estrogen (e.g., estramustine), ketoconazole, abiraterone, darolutamide, or an analog thereof.

In certain embodiments, the nuclear steroid receptor-targeting epitope (e.g., $B^1$) is a selective androgen receptor modulator (SARM). In certain embodiments, the compound comprises at least one nuclear steroid receptor-targeting epitope independently comprises an epitope derived from testosterone, a testosterone ester (e.g., testosterone enanthate, propionate, cypionate, etc., or an analog thereof), enobosarm, BMS-564929, PS178990, LGD-4033 (ligandrol), LGD-2941, AC-262,356, JNJ-28330835, JNJ-37654032, JNJ-26146900, LGD-2226, LGD-3303, LGD-121071, LG-120907, S-40503, S-23, testolone (RAD-140), acetothiolutamide, andarine (S-4), LG-121071, TFM-4AS-1, YK-11, MK-0773 (PF-05314882), GSK2849466, GSK2881078, GSK8698, GSK4336, ACP-105, TT701, LY2452473 (TT-701), 1-(2-hydroxy-2-methyl-3-phenoxypropanoyl)-indoline-4-carbonitrile-derivatives (J Med Chem. 2014, 57(6), 2462-71), or an analog thereof.

In certain embodiments, a single atom on the nuclear receptor-targeting epitope ($B^1$) as disclosed herein is replaced for attachment to the remainder of the compound (e.g., the moiety -$L^1$-$B^1$). In certain embodiments, a halogen atom on a nuclear receptor-targeting epitope disclosed herein is replaced for attachment to the remainder of the compound. In certain embodiments, a hydrogen atom on a nuclear receptor-targeting epitope disclosed herein is replaced for attachment to the remainder of the compound. In certain embodiments, the hydrogen atom is on a heteroatom. In certain embodiments, the hydrogen atom is on a nitrogen. In certain embodiments, the hydrogen atom is on an oxygen. In certain embodiments, the hydrogen atom is on a carbon.

In certain embodiments, $B^1$ is of Formula IIA:

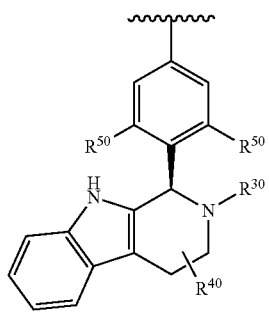

IIA wherein:
the wavy bond refers to the point of connection to $L^1$;
$R^{30}$ is hydrogen, $C_{1-12}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;
$R^{40}$ is hydrogen, $C_{1-12}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;
each $R^{50}$ is independently halo, cyano, nitro, —$OR^{170}$, —$SR^{170}$, —$NR^{170}R^{180}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl or amino as valency permits;
each $R^{100}$ is independently oxo, halo, cyano, nitro, —$OR^{170}$, —$SR^{170}$, —$SF_5$, —$NR^{170}R^{180}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(=O)R^{170}$, —$C(=O)OR^{170}$, —$OC(=O)OR^{170}$, —$OC(=O)R^{170}$, —$C(=O)NR^{170}R^{180}$, —$OC(=O)NR^{170}R^{180}$, —$NR^{170}C(=O)NR^{170}R^{180}$, —$S(=O)_{1-2}R^{170}$, —$S(=O)_{1-2}NR^{170}R^{180}$, —$NR^{170}S(=O)_{1-2}R^{180}$, —$NR^{170}S(=O)_{1-2}NR^{170}R^{180}$, —$NR^{170}C(=O)R^{180}$, —$NR^{170}C(=O)OR^{180}$ or —$C=NOR^{17}$, wherein each $C_{1-12}$ alkyl, $C_{2-12}$ alkenyl, $C_{2-12}$ alkynyl, $C_{3-10}$ cycloalkyl, heterocyclyl, aryl, and heteroaryl of $R^{100}$ are independently optionally substituted with one or more halo or $C_{1-12}$ alkyl optionally substituted by oxo, halo, hydroxyl or amino as valency permits; and
each $R^{170}$ and $R^{180}$ is independently hydrogen or $C_{1-12}$ alkyl optionally substituted with oxo, halo, hydroxyl or amino as valency permits; or $R^{170}$ and $R^{180}$ are taken together with the atoms to which they are attached to form heterocyclyl optionally substituted by halo or $C_{1-12}$ alkyl optionally substituted by oxo, halo, hydroxyl or amino.

In certain embodiments, $B^1$ is of Formula IIB:

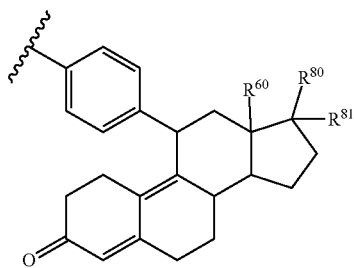

IIB wherein:
the wavy bond refers to the point of connection to $L^1$;
$R^{60}$ is hydrogen, $C_{1-12}$ alkyl, $C_{2-12}$ alkenyl, $C_{2-12}$ alkynyl, or $C_{3-12}$ cycloalkyl, wherein each $C_{1-12}$ alkyl, $C_{2-12}$ alkenyl, $C_{2-12}$ alkynyl, or $C_{3-12}$ cycloalkyl is optionally independently substituted with one to five $R^{100}$ as valency permits;
$R^{80}$ is hydrogen, hydroxy, $C_{1-12}$ alkyl, $C_{2-12}$ alkenyl, $C_{2-12}$ alkynyl, $C_{1-12}$ alkoxy, or $C_{3-12}$ cycloalkyl, wherein each $C_{1-12}$ alkyl, $C_{2-12}$ alkenyl, $C_{2-12}$ alkynyl, or $C_{1-12}$ alkoxy, $C_{3-12}$ cycloalkyl is optionally independently substituted with one to five $R^{100}$ as valency permits;
$R^{81}$ is hydrogen, hydroxy, $C_{1-12}$ alkyl, $C_{2-12}$ alkenyl, $C_{2-12}$ alkynyl, $C_{1-12}$ alkoxy, or $C_{3-12}$ cycloalkyl, wherein each $C_{1-12}$ alkyl, $C_{2-12}$ alkenyl, $C_{2-12}$ alkynyl, $C_{1-12}$ alkoxy, or $C_{3-12}$ cycloalkyl is optionally independently substituted with one to five $R^{100}$ as valency permits;
or $R^{80}$ and $R^{81}$ are taken together with the atom to which they are attached to form heterocyclyl optionally substituted by halo or $C_{1-12}$ alkyl optionally substituted by oxo, halo, hydroxyl or amino;
each $R^{100}$ is independently oxo, halo, cyano, nitro, —$OR^{170}$, —$SR^{170}$, —$SF_5$, —$NR^{170}R^{180}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(=O)R^{170}$, —$C(=O)OR^{170}$, —$OC(=O)OR^{170}$, —$OC(=O)R^{170}$, —$C(=O)NR^{170}R^{180}$, —$OC(=O)NR^{170}R^{180}$, —$NR^{170}C(=O)NR^{170}R^{180}$, —$S(=O)_{1-2}R^{170}$, —$S(=O)_{1-2}NR^{170}R^{180}$, —$NR^{170}S(=O)_{1-2}R^{180}$, —$NR^{170}S(=O)_{1-2}NR^{170}R^{180}$, —$NR^{170}C(=O)R^{180}$, —$NR^{170}C(=O)OR^{180}$ or —$C=NOR^{17}$, wherein each $C_{1-12}$ alkyl, $C_{2-12}$ alkenyl, $C_{2-12}$ alkynyl, $C_{3-10}$ cycloalkyl, heterocyclyl, aryl, and heteroaryl of $R^{100}$ are independently optionally substituted with one or more halo or $C_{1-12}$ alkyl optionally substituted by oxo, halo, hydroxyl or amino as valency permits; and
each $R^{170}$ and $R^{180}$ is independently hydrogen or $C_{1-12}$ alkyl optionally substituted with oxo, halo, hydroxyl or amino as valency permits; or $R^{170}$ and $R^{180}$ are taken together with the atoms to which they are attached to form heterocyclyl optionally substituted by halo or $C_{1-12}$ alkyl optionally substituted by oxo, halo, hydroxyl or amino.

In certain embodiments, $B^1$ is of Formula IIC:

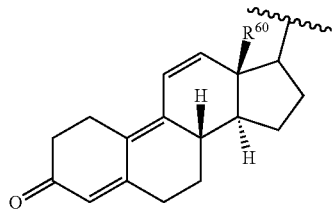

IIC wherein:
the wavy bond refers to the point of connection to $L^1$;
$R^{60}$ is hydrogen, $C_{1-12}$ alkyl, $C_{2-12}$ alkenyl, $C_{2-12}$ alkynyl, or $C_{3-12}$ cycloalkyl, wherein each $C_{1-12}$ alkyl, $C_{2-12}$ alkenyl, $C_{2-12}$ alkynyl, or $C_{3-12}$ cycloalkyl is optionally independently substituted with one to five $R^{100}$ as valency permits;
each $R^{100}$ is independently oxo, halo, cyano, nitro, —$OR^{170}$, —$SR^{170}$, —$SF_5$, —$NR^{170}R^{180}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(=O)R^{170}$, —$C(=O)OR^{170}$, —$OC(=O)OR^{170}$, —$OC(=O)R^{170}$, —$C(=O)NR^{170}R^{180}$, —$OC(=O)NR^{170}R^{180}$, —$NR^{170}C(=O)NR^{170}R^{180}$, —$S(=O)_{1-2}R^{170}$, —$S(=O)_{1-2}NR^{170}R^{180}$, —$NR^{170}S(=O)_{1-2}R^{180}$, —$NR^{170}S$ $(=O)_{1-2}NR^{170}R^{180}$, $-NR^{170}C(=O)R^{180}$, $-NR^{170}C(=O)OR^{180}$ or $-C=NOR^{17}$, wherein each $C_{1-12}$ alkyl, $C_{2-12}$ alkenyl, $C_{2-12}$ alkynyl, $C_{3-10}$ cycloalkyl, heterocyclyl, aryl, and heteroaryl of $R^{100}$ are independently optionally substituted with one or more halo or $C_{1-12}$ alkyl optionally substituted by oxo, halo, hydroxyl or amino as valency permits; and each $R^{170}$ and $R^{180}$ is independently hydrogen or $C_{1-12}$ alkyl optionally substituted with oxo, halo, hydroxyl or amino as valency permits; or $R^{170}$ and $R^{180}$ are taken together with the atoms to which they are attached to form heterocyclyl optionally substituted by halo or $C_{1-12}$ alkyl optionally substituted by oxo, halo, hydroxyl or amino.

In certain embodiments, $B^1$ is of Formula IID:

IID wherein:
the wavy bond refers to the point of connection to $L^1$;
A" and A''' are each independently O or S;
$R^a$ and $R^b$ are each independently $CH_3$ or $CH_2CH_3$; or $R^a$ and $R^b$ together with the atom to which they are attached form a $C_{3-5}$ cycloalkyl, oxirane, oxetane or tetrahydrofuran;
B, $B^{10}$, $B^2$, $B^3$, B', $B^{1'}$, $B^{2'}$ and $B^{3'}$ are each independently $CR^c$ or N;
each $R^c$ is independently hydrogen, fluoro, CN, or methyl;
D is NH, O, S, $CH_2$ or C=O;
X" is CN, halo, or $NO_2$;
Y" is $CH_3$, $CH_2R^d$, $CHF_2$, or $CF_3$;
$R^d$ is halo;
Z''' is H, $C_{1-2}$ alkyl, $C_2$ alkenyl or $NO_2$; or
X" and Y" together form a wherein the broken lines indicate bonds to the ring;
or Y" and Z''' together form a wherein each === is a single or double bond, and wherein the broken lines indicate bonds to the ring; and
Z' is CH or N.

In certain embodiments, $B^1$ is of Formula IIE:

IIE wherein:
the wavy bond refers to the point of connection to L;
Q is wherein bond a is attached to ring a and bond b is attached to ring b;
$R^a$ and $R^b$ are each independently $-CH_3$ or $-CH_2CH_3$; or $R^a$ and $R^b$ together with the atom to which they are attached form a $C_{3-5}$ cycloalkyl, oxiranyl, oxetanyl, or tetrahydrofuranyl;
A and A' are each independently O or S;
E, $E^1$, $E^2$, and $E^3$ are each independently $CR^c$ or N, and each $R^c$ is independently hydrogen, halo, CN, or methyl;
$E^4$ is CF, CH or N;
$Q^1$ is a bond, $CH_2$, C=O, or (C=O)NH;
$Q^2$ is NH, O, S, $CH_2$, NH(C=O), C(=O)NH, or C=O;
$R^{44}$, $R^{45}$ and $R^{46}$ are each independently hydrogen, CN, or $C_{1-2}$ alkyl;
t is 0, 1, 2, 3 or 4;
each $R^e$ is independently halo, cyano, $C_{1-4}$ alkyl, or $C_{1-4}$ haloalkyl;

$R^{41}$ is halo, CN, or $NO_2$;
$R^{42}$ is halo, $CH_3$, $CH_2F$, $CHF_2$, or $CF_3$; or
$R^{41}$ and $R^{42}$ together form a

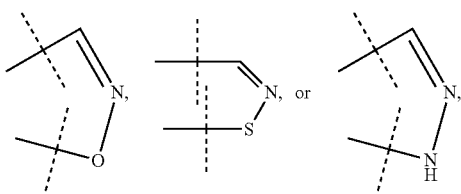

wherein the broken lines indicate bonds to ring a;
$R^{43}$ is hydrogen, halo, $C_{1-2}$ alkyl, $C_2$ alkenyl, $NO_2$, $CF_3$; or
$R^{42}$ and $R^{43}$ together form a

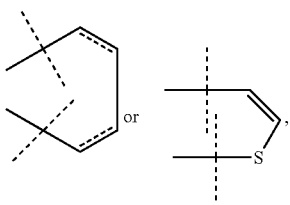

wherein each === is a single or double bond, and where the broken lines indicate bonds to ring a.

In certain embodiments, $B^1$ is:

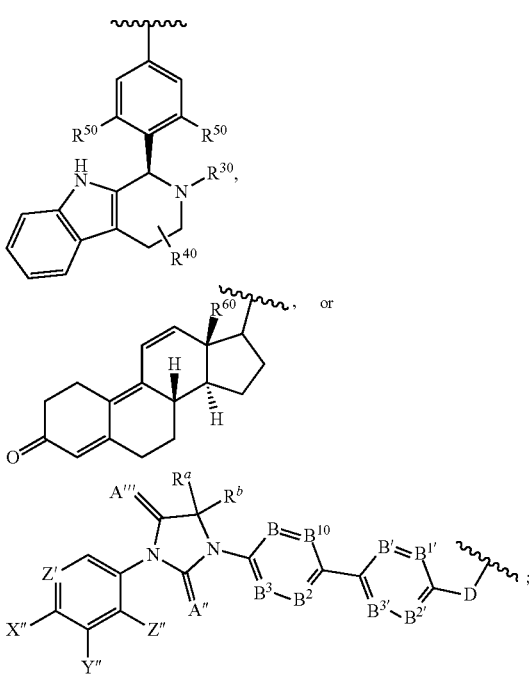

wherein:
$R^{30}$ is hydrogen, $C_{1-12}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;
$R^{40}$ is hydrogen, $C_{1-12}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;
each $R^{50}$ is independently halo, cyano, nitro, $-OR^{170}$, $-SR^{170}$, $-NR^{170}R^{180}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl or amino as valency permits;
$R^{60}$ is hydrogen, $C_{1-12}$ alkyl, $C_{2-12}$ alkenyl, $C_{2-12}$ alkynyl, or $C_{3-12}$ cycloalkyl, wherein each $C_{1-12}$ alkyl, $C_{2-12}$ alkenyl, $C_{2-12}$ alkynyl, or $C_{3-12}$ cycloalkyl is optionally independently substituted with one to five $R^{100}$ as valency permits;
each $R^{100}$ is independently oxo, halo, cyano, nitro, $-OR^{170}$, $-SR^{170}$, $-SF_5$, $-NR^{170}R^{180}$, $C_{1-12}$ alkyl, $C_{2-12}$ alkenyl, $C_{2-12}$ alkynyl, $C_{3-10}$ cycloalkyl, heterocyclyl, aryl, heteroaryl, $-C(=O)R^{170}$, $-C(=O)OR^{170}$, $-OC(=O)OR^{170}$, $-OC(=O)R^{170}$, $-C(=O)NR^{170}R^{180}$, $-OC(=O)NR^{170}R^{180}$, $-NR^{170}C(=O)NR^{170}R^{180}$, $-S(=O)_{1-2}R^{170}$, $-S(=O)_{1-2}NR^{170}R^{180}$, $-NR^{170}S(=O)_{1-2}R^{180}$, $-NR^{170}S(=O)_{1-2}NR^{170}R^{180}$, $-NR^{170}C(=O)R^{180}$, $-NR^{170}C(=O)OR^{180}$ or $-C=NOR^{17}$, wherein each $C_{1-12}$ alkyl, $C_{2-12}$ alkenyl, $C_{2-12}$ alkynyl, $C_{3-10}$ cycloalkyl, heterocyclyl, aryl, and heteroaryl of $R^{100}$ are independently optionally substituted with one or more halo or $C_{1-12}$ alkyl optionally substituted by oxo, halo, hydroxyl or amino as valency permits;
each $R^{170}$ and $R^{18}$ is independently hydrogen or $C_{1-12}$ alkyl optionally substituted with oxo, halo, hydroxyl or amino as valency permits; or $R^{170}$ and $R^{180}$ are taken together with the atoms to which they are attached to form heterocyclyl optionally substituted by halo or $C_{1-12}$ alkyl optionally substituted by oxo, halo, hydroxyl or amino.

A" and A''' are each independently O or S;
$R^a$ and $R^b$ are each independently $CH_3$ or $CH_2CH_3$; or $R^a$ and $R^b$ together with the atom to which they are attached form a $C_{3-5}$ cycloalkyl, oxirane, oxetane or tetrahydrofuran;
B, $B^{10}$, $B^2$, $B^3$, B', B1', $B^{2'}$ and $B^{3'}$ are each independently $CR^c$ or N;
each $R^c$ is independently hydrogen, fluoro, CN, or methyl;
D is NH, O, S, $CH_2$ or C=O;
X" is CN, halo, or $NO_2$;
Y" is $CH_3$, $CH_2R^d$, $CHF_2$, or $CF_3$;
$R^d$ is halo;
Z''' is H, $C_{1-2}$ alkyl, $C_2$ alkenyl or $NO_2$; or
X" and Y" together form a

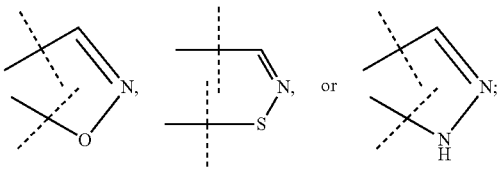

or Y" and Z''' together form a

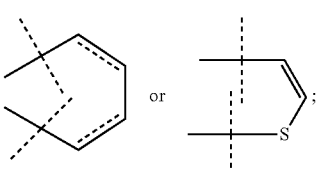

and
Z' is CH or N.

In certain embodiments, B¹ is:

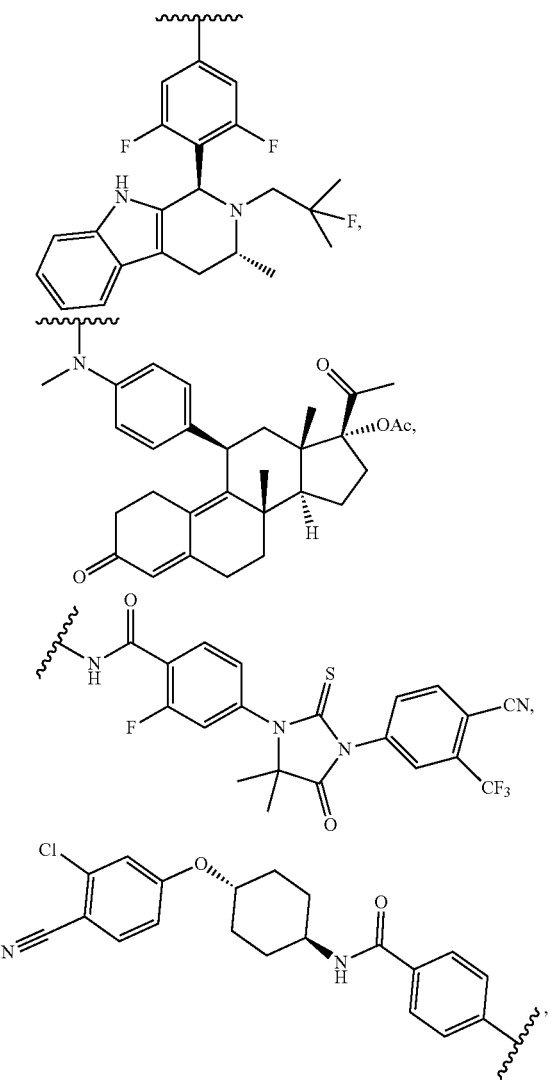

where the wavy bond refers to the point of connection to L¹.

In certain embodiments, B¹ is:

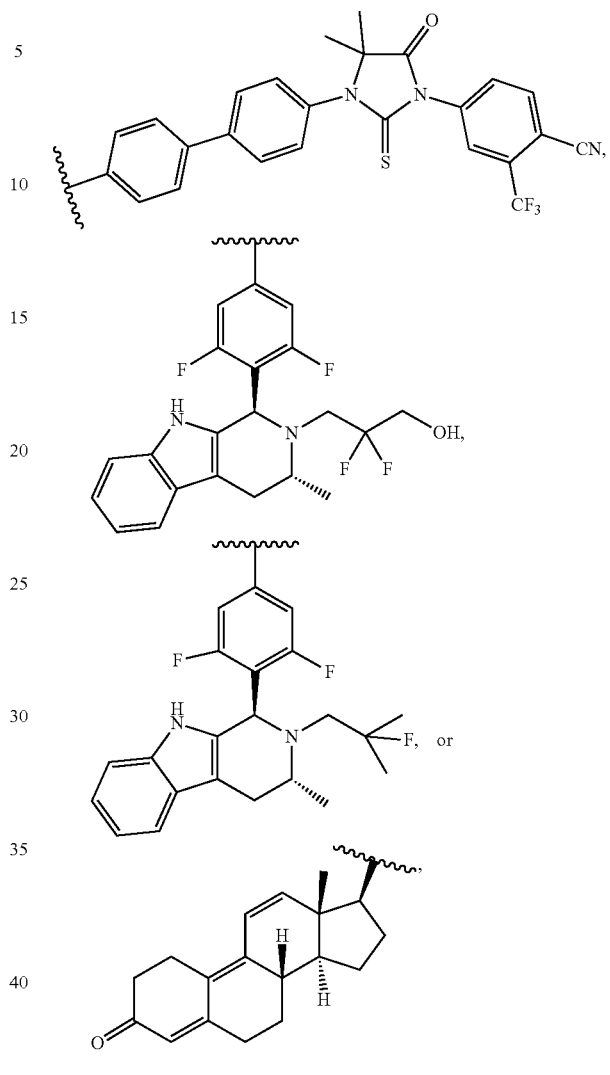

or a stereoisomer or a mixture of stereoisomers thereof or an analog thereof, where the wavy line indicates the point of attachment to the nuclear payload, optionally via a linking moiety.

In certain embodiments, B¹ is derived from, progesterone, enobosarm, bicalutamide, apalutamide, testosterone, dihydrotestosterone, testosterone, 19-nortestosterone, progesterone, andarine, cortisol, prednisone, flutamide, nilutamide, enzalutamide, tamoxifen, toremifene, raloxifene, bazedoxifene, ospemifene, megestrol acetate, estramustine, abiraterone, LGD-2941, BMS-564929, ostarine, ulipristal acetate, asoprisnil (J867), mifepristone, telapristone (CDB-4124, Proellex, Progenta), or an analog thereof.

In certain embodiments, B¹ is derived from, progesterone, enobosarm, bicalutamide, apalutamide, testosterone, dihydrotestosterone, flutamide, nilutamide, enzalutamide, tamoxifen, toremifene, raloxifene, bazedoxifene, ospemifene, megestrol acetate, abiraterone, LGD-2941, BMS-564929, ostarine, or an analog thereof.

In certain embodiments, B¹ comprises a nuclear receptor-targeting epitope derived from:

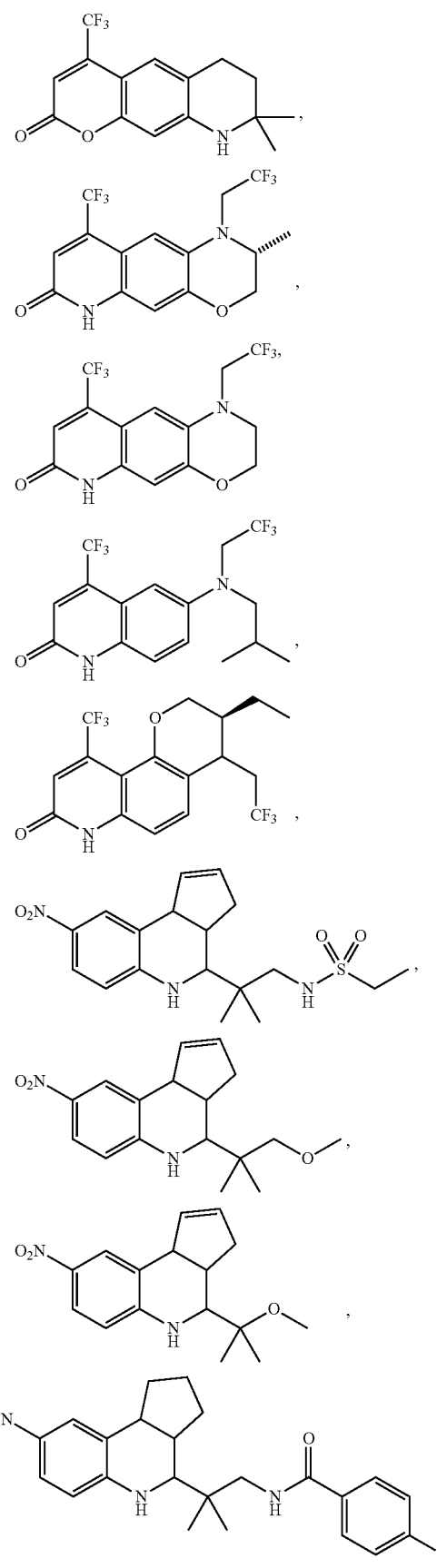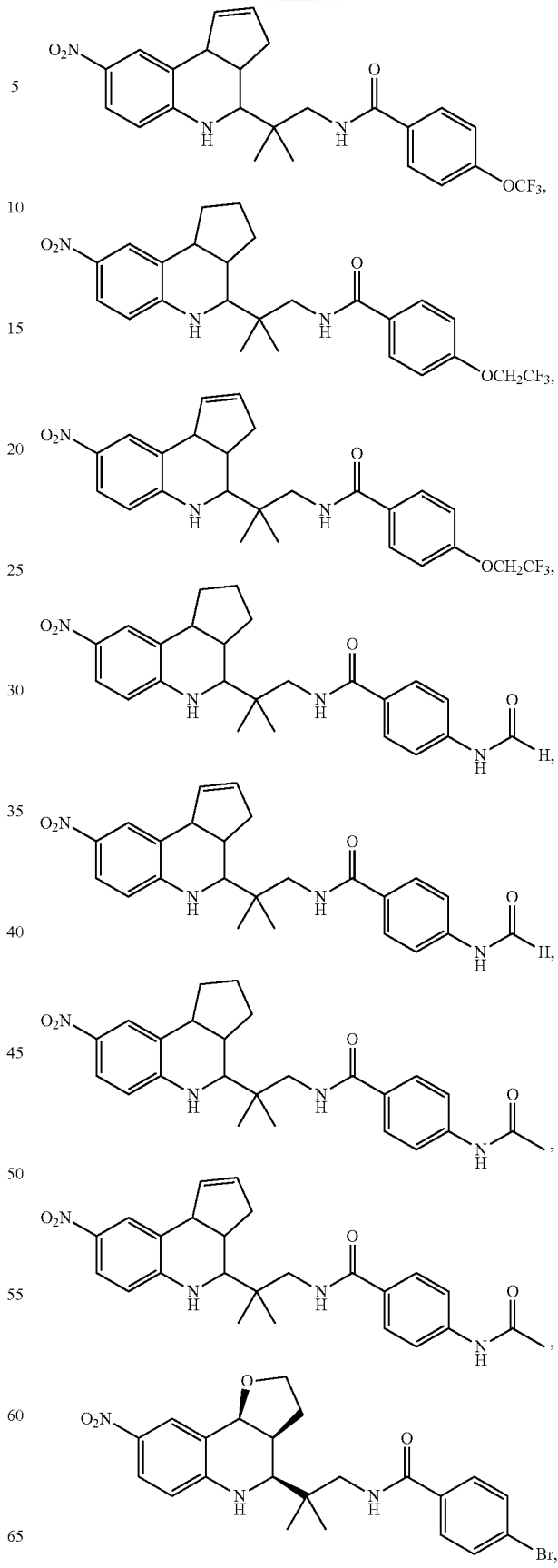

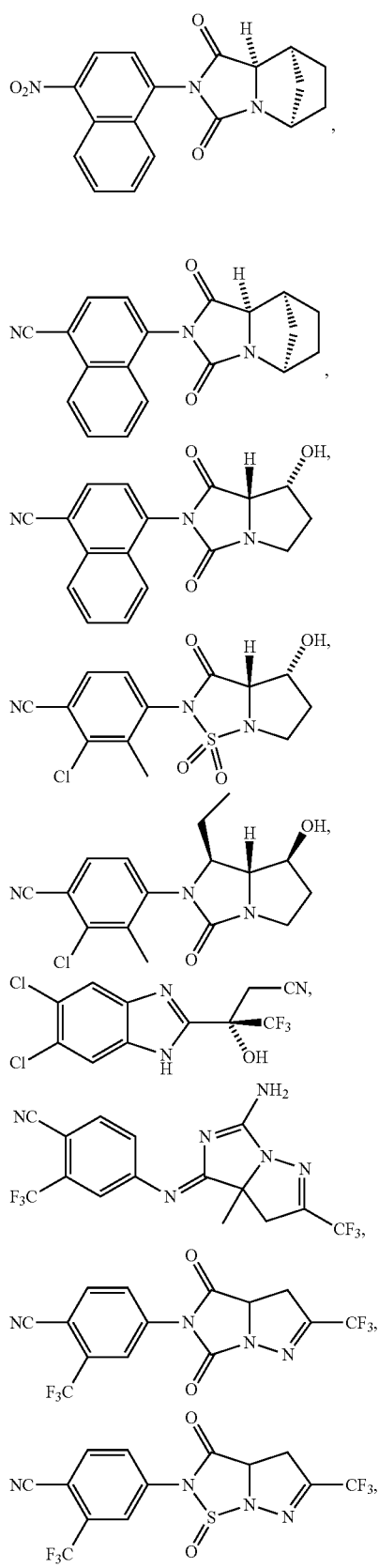
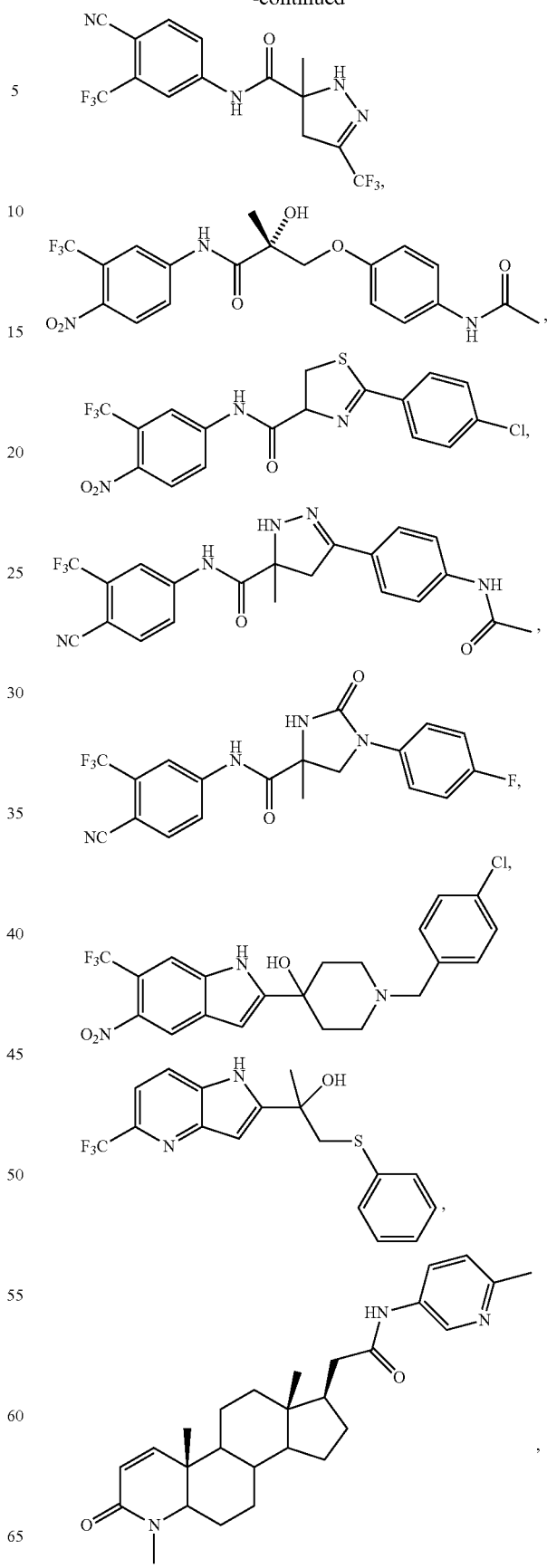

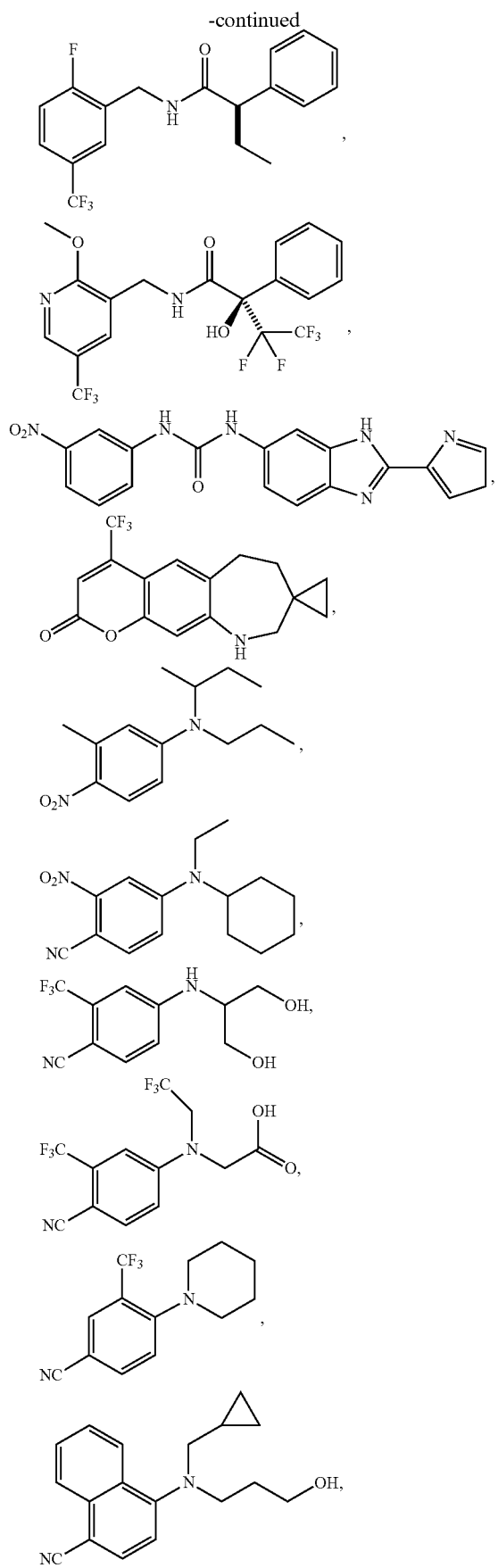
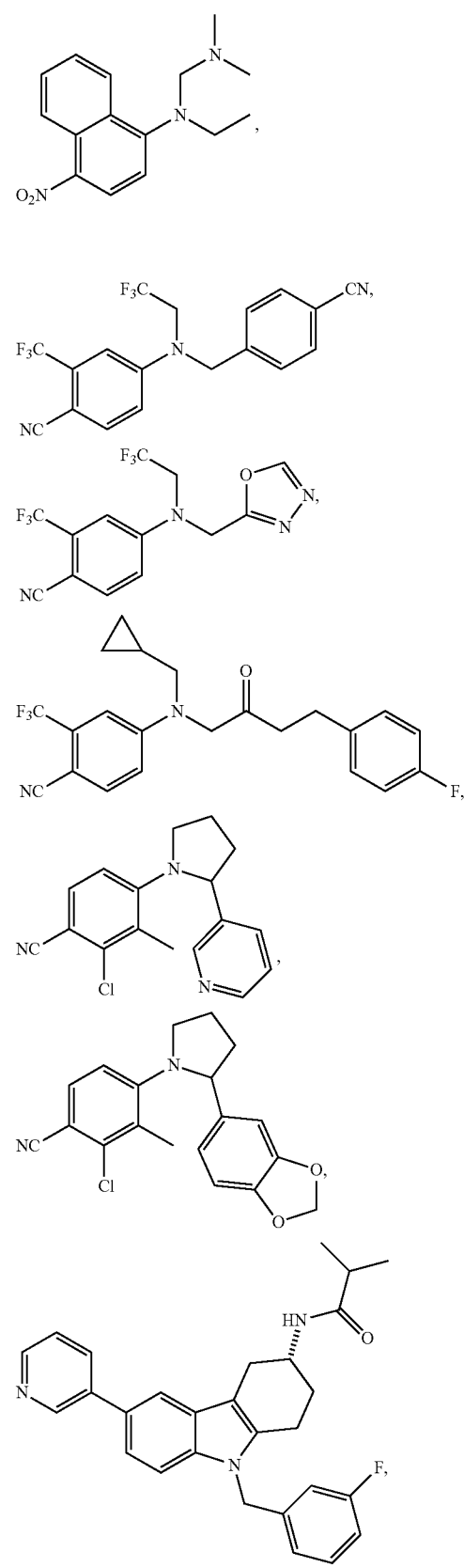

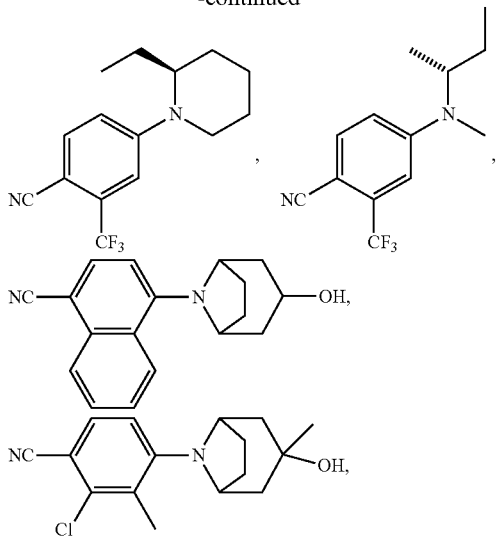

or a stereoisomer or a mixture of stereoisomers thereof or an analog thereof, wherein at least one hydrogen atom is replaced by a direct covalent bond to $A^1$, optionally via a linking moiety.

These and other selective androgen receptor modulator (SARMs) which can be used as a nuclear steroid receptor-targeting epitope in $B^1$ described herein can be found in U.S. Pat. Nos. 6,462,038, 6,777,427, WO2001/027086, WO2004/013104, WO2004/000816, WO2004/0113309, US2006/0211756, US2006/0063819, US2005/245485, US2005/250741, US2005/277681, WO2006/060108, WO2004/041277, WO2003/034987, US2006/0148893, US2006/0142387, WO2005/000795, WO2005/085185, WO2006/133216, WO2006/044707, WO2006/124447, WO2007/002181, WO2005/108351, WO2005/115361, and US2006/0160845.

In certain embodiments, $B^1$ is a selective estrogen receptor modulator (SERM). In certain embodiments, $B^1$ comprises an epitope derived from anordrin, bazedoxifene, broparestrol (Acnestrol), clomifene (Clomid), cyclofenil (Sexovid), lasofoxifene (Fablyn), ormeloxifene (Centron, Novex, Novex-DS, Sevista), ospemifene (Osphena, deaminohydroxytoremifene), raloxifene (Evista), tamoxifen (Nolvadex), toremifene (Fareston; 4-chlorotamoxifen), acolbifene, afimoxifene (4-hydroxytamoxifen; metabolite of tamoxifen), elacestrant, enclomifene ((E)-clomifene), endoxifen (4-hydroxy-N-desmethyltamoxifen; metabolite of tamoxifen), zuclomifene ((Z)-clomifene), bazedoxifene, arzoxifene, brilanestrant, clomifenoxide (clomiphene N-oxide; metabolite of clomifene), droloxifene (3-hydroxytamoxifen), etacstil, fispemifene, GW-7604 (4-hydroxyetacstil), idoxifene (pyrrolidino-4-iodotamoxifen), levormeloxifene ((L)-ormeloxifene), miproxifene, nafoxidine, nitromifene (CI-628), panomifene, pipendoxifene (ERA-923), trioxifene, keoxifene, LY117018, onaprostone, fareston (toremifine citrate) or zindoxifene (D-16726), or an analog thereof.

In certain embodiments, the SERM is classified structurally as a triphenylethylene (tamoxifen, clomifene, toremifene, droloxifene, idoxifene, ospemifene, fispemifene, afimoxifene, etc., or an analog thereof), a benzothiophene (raloxifene, arzoxifene, etc., or an analog thereof), an indole (bazedoxifene, zindoxifene, pipendoxifene, etc., or an analog thereof), a tetrahydronaphthalene (lasofoxifene, nafoxidine, etc., or an analog thereof), or a benzopyran (acolbifene, ormeloxifene, levormeloxifene, etc., or an analog thereof).

In certain embodiments, $B^1$ is a selective estrogen receptor downregulator (SERD). In certain embodiments, the compound comprises at least one nuclear steroid receptor-targeting epitope independently comprises an epitope derived from fulvestrant, brilanestrant (ARN-810), etacstil (GW5638), AZD9496, giredestrant (GDC-9545) or GW7604.

In certain embodiments, $B^1$ is a selective progesterone receptor modulator (SPRM). In certain embodiments, B comprises an epitope derived from ulipristal acetate, asoprisnil (J867), mifepristone, telapristone (CDB-4124, Proellex, Progenta), or an analog thereof.

In certain embodiments, $B^1$ comprises an epitope derived from, estrogen, estetrol, estriol, estrone, progesterone, enobosarm, bicalutamide, apalutamide, testosterone, dihydrotestosterone, estradiol, flutamide, nilutamide, enzalutamide, tamoxifen, toremifene, raloxifene, bazedoxifene, ospemifene, megestrol acetate, estramustine, abiraterone, LGD-2941, BMS-564929, ostarine, or an analog thereof.

In certain embodiments, at least one nuclear steroid receptor-targeting epitope is an androgen receptor-targeting epitope, and comprises:

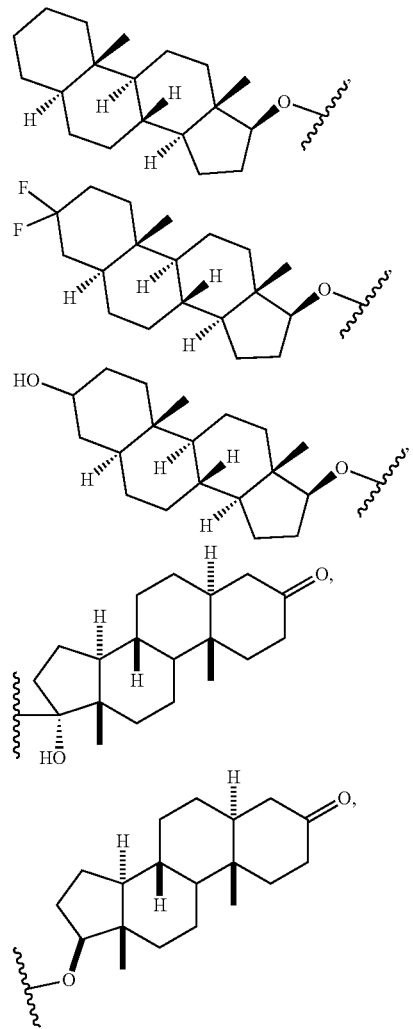

-continued
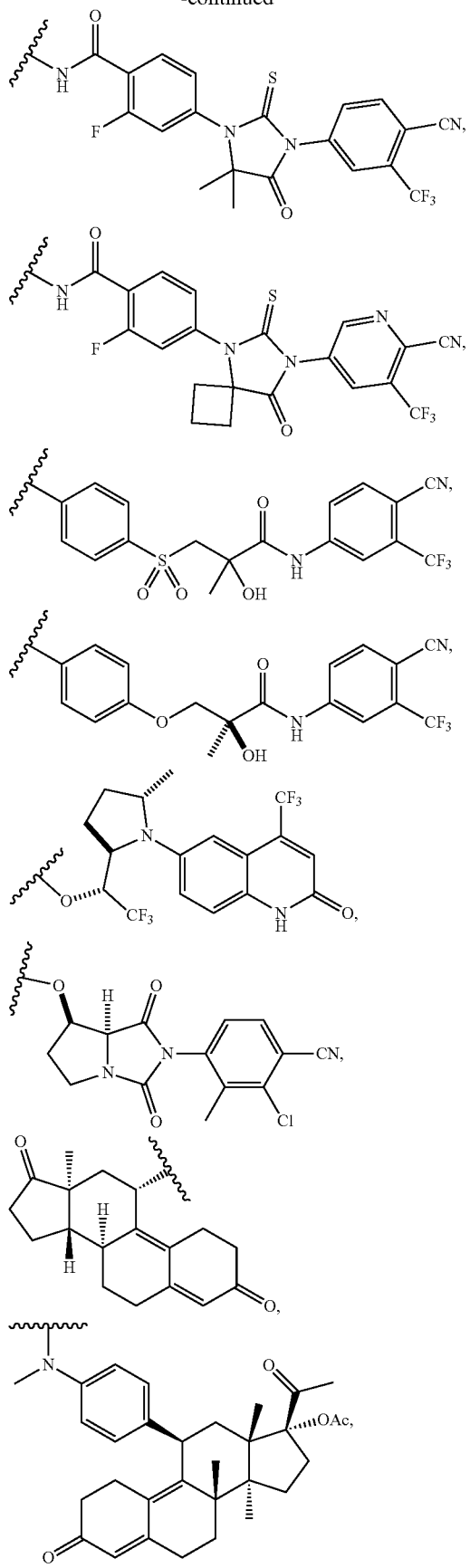
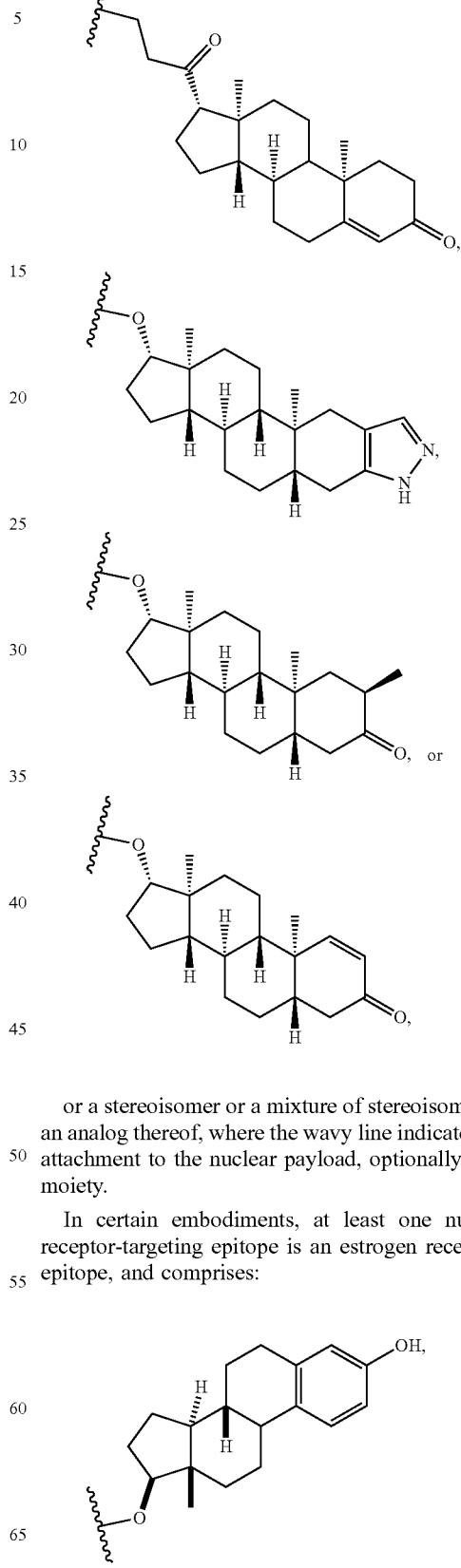
or a stereoisomer or a mixture of stereoisomers thereof or an analog thereof, where the wavy line indicates the point of attachment to the nuclear payload, optionally via a linking moiety.
In certain embodiments, at least one nuclear steroid receptor-targeting epitope is an estrogen receptor-targeting epitope, and comprises:
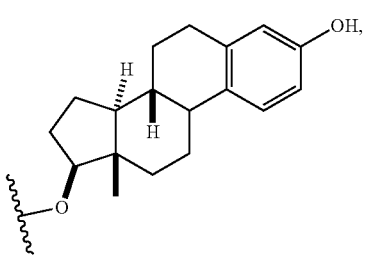

71
-continued
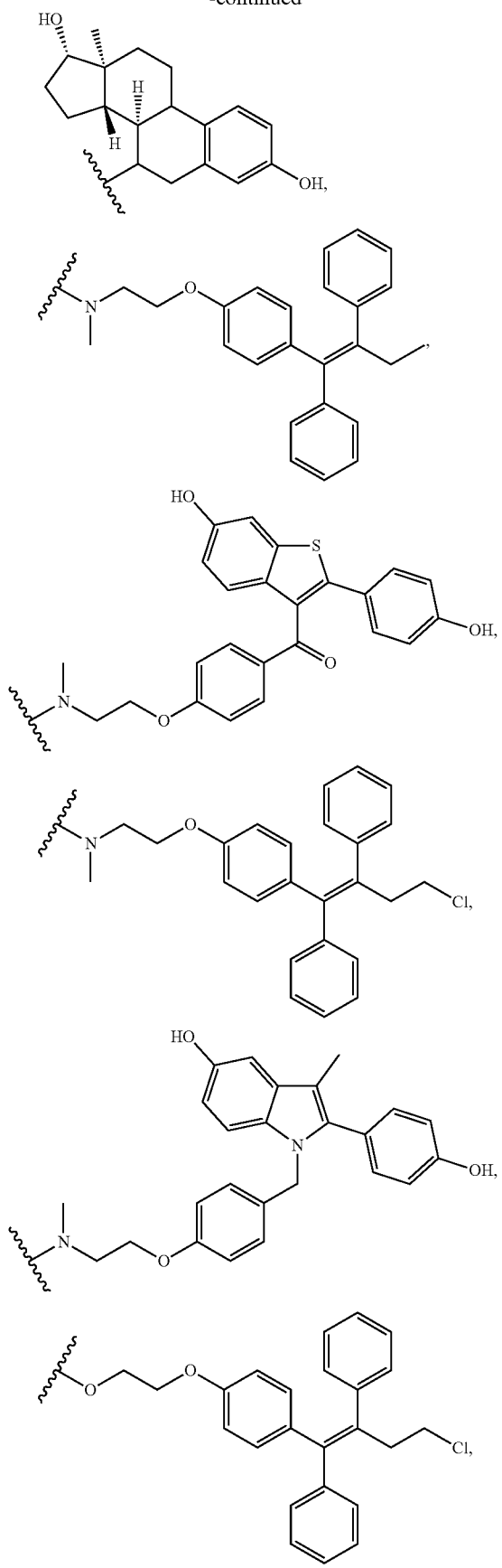
72
-continued
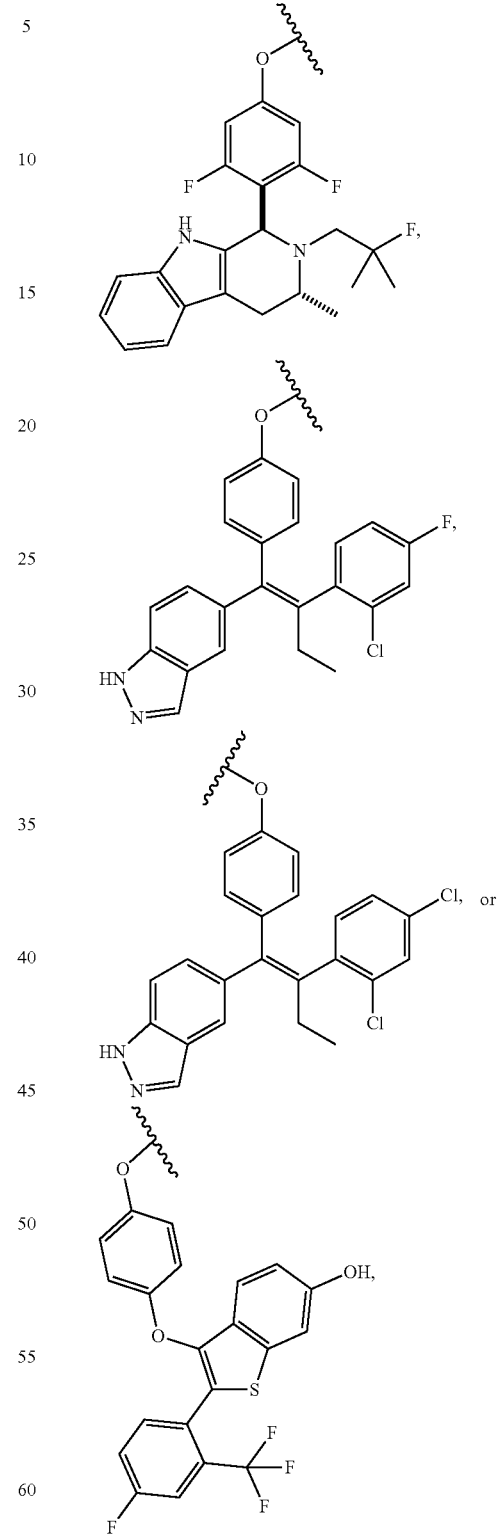
or a stereoisomer or a mixture of stereoisomers thereof or an analog thereof, where the wavy line indicates the point of attachment to the nuclear payload, optionally via a linking moiety.

In certain embodiments, at least one nuclear steroid receptor-targeting epitope is an estrogen receptor-targeting epitope, and comprises:
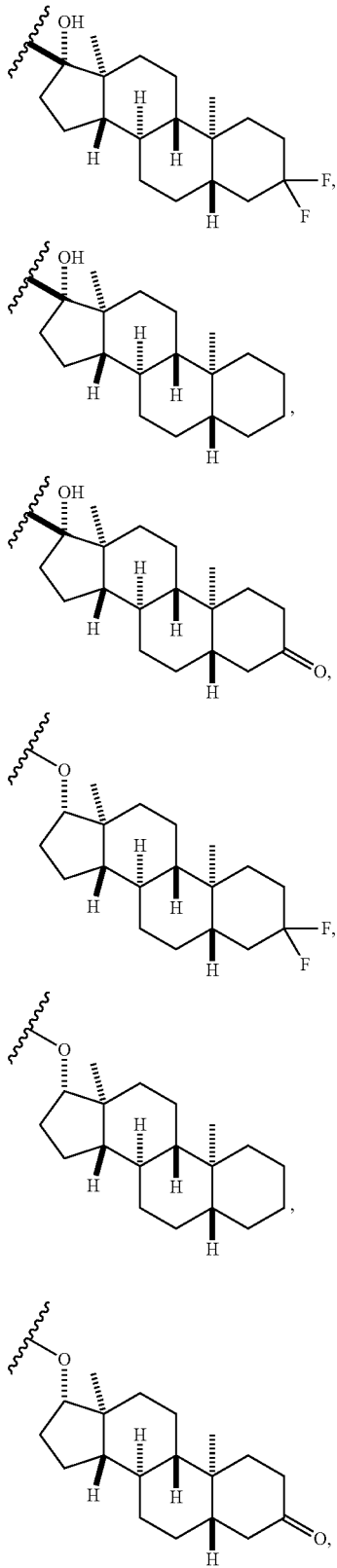
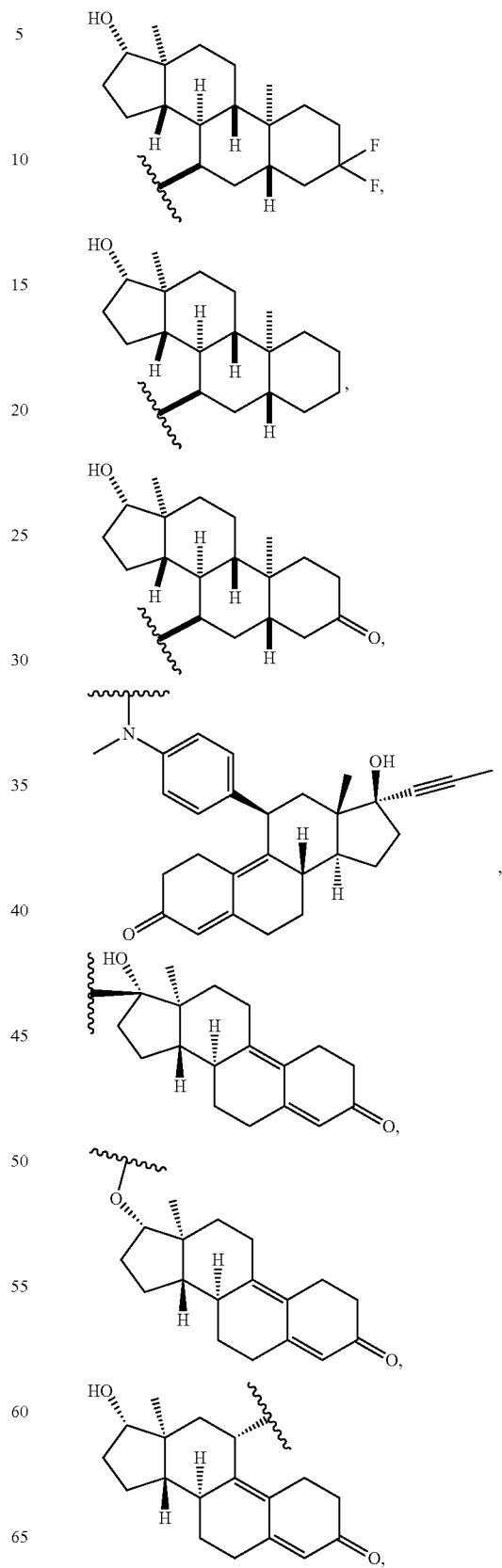
-continued -continued
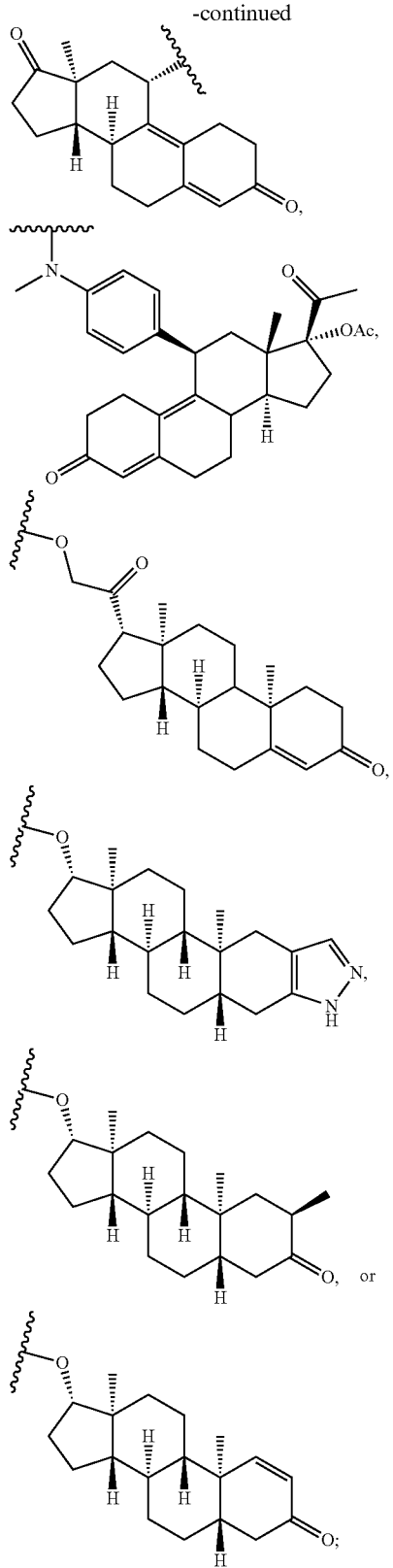
or a stereoisomer or a mixture of stereoisomers thereof or an analog thereof, where the wavy line indicates the point of attachment to the nuclear payload, optionally via a linking moiety.
In certain embodiments, at least one nuclear steroid receptor-targeting epitope comprises:
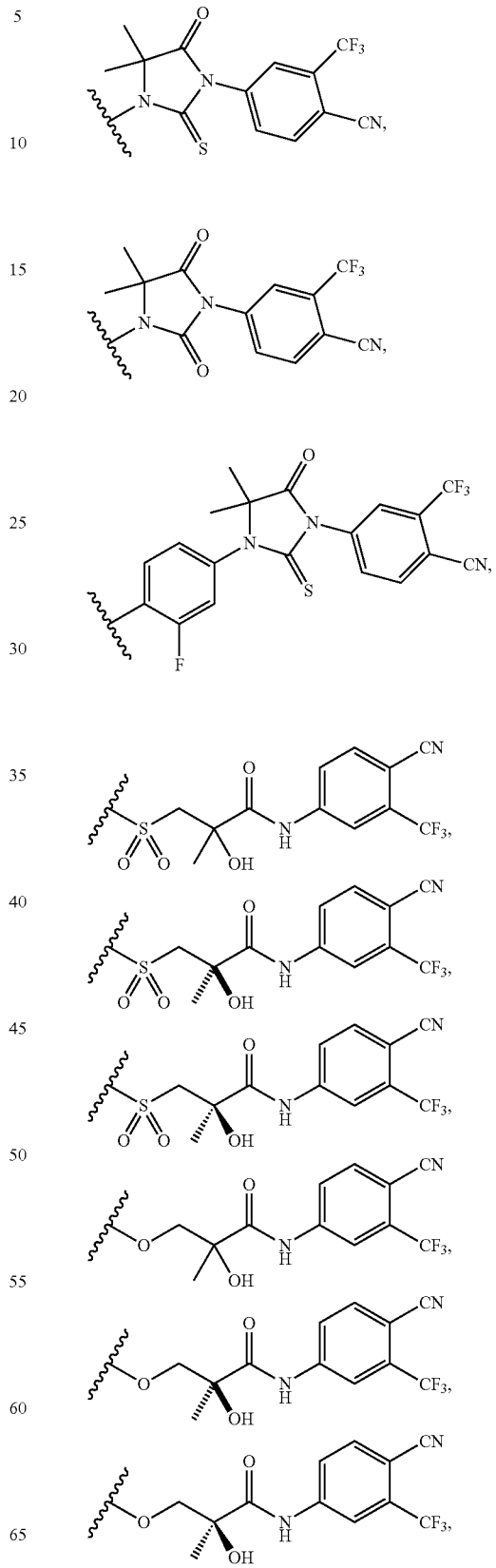

77
-continued
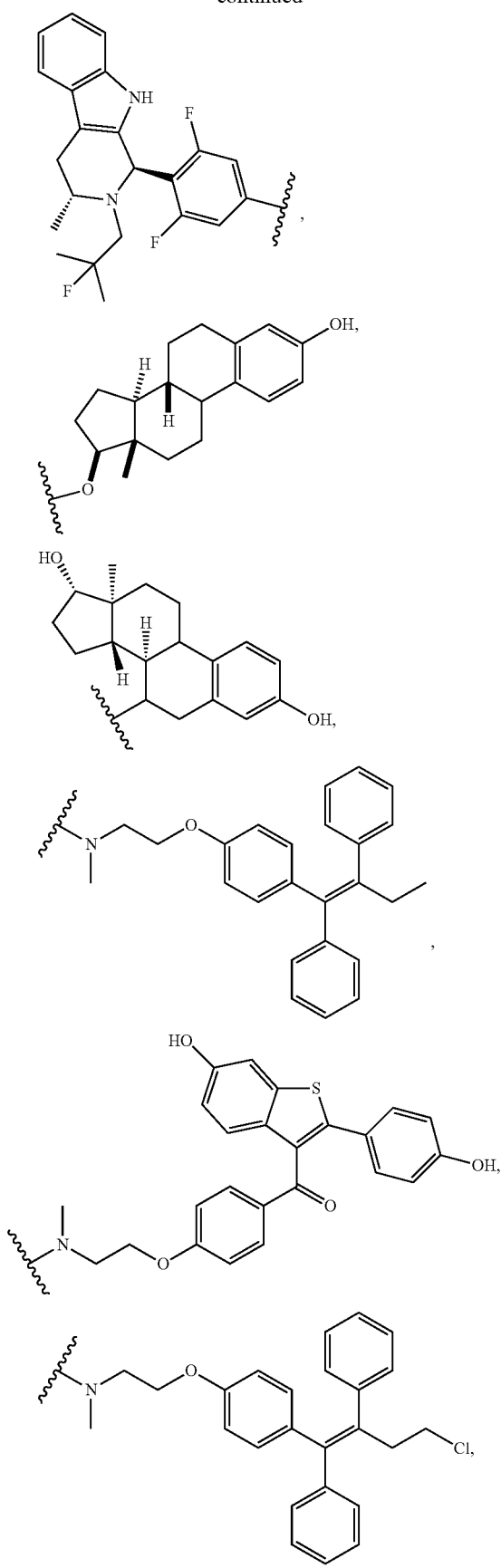
78
-continued
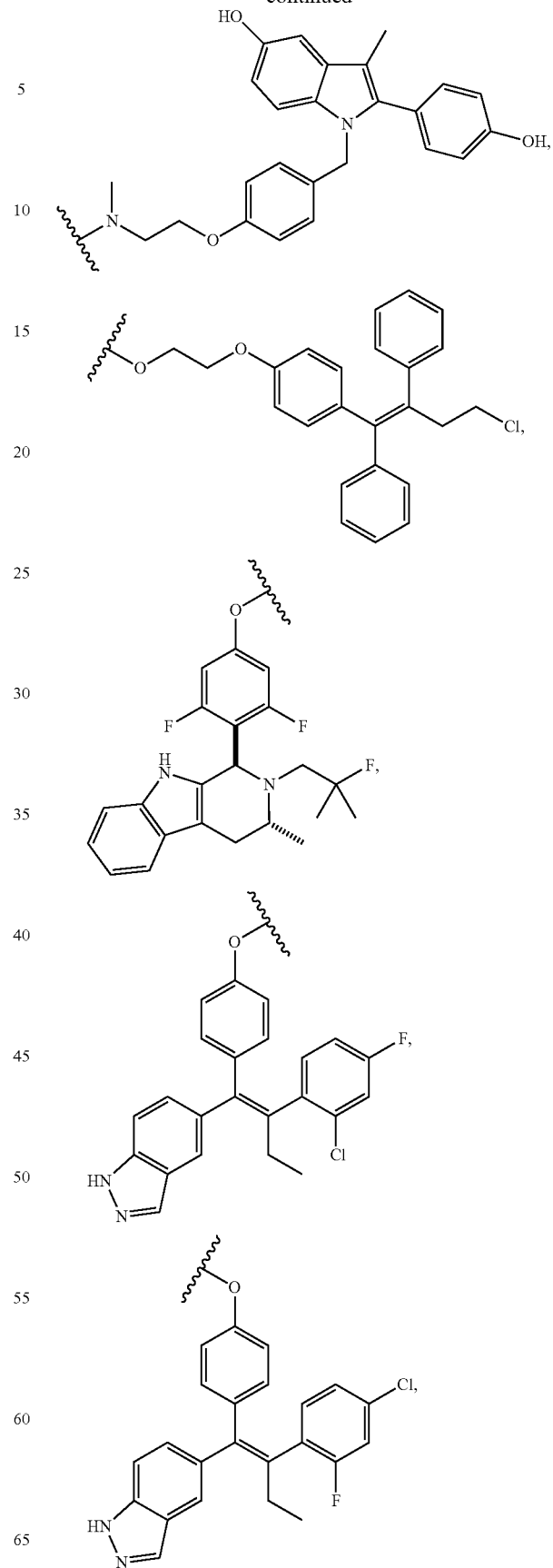

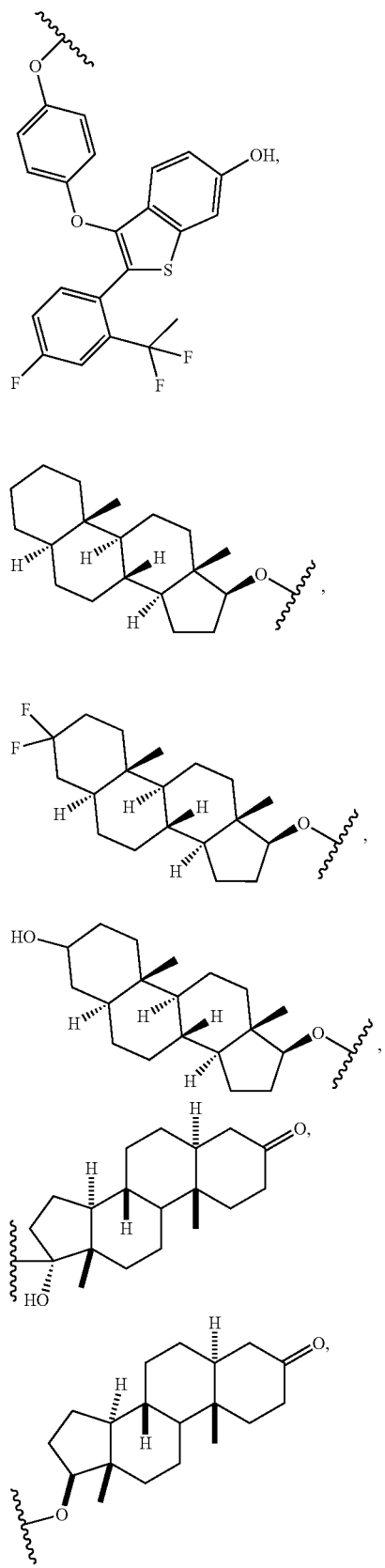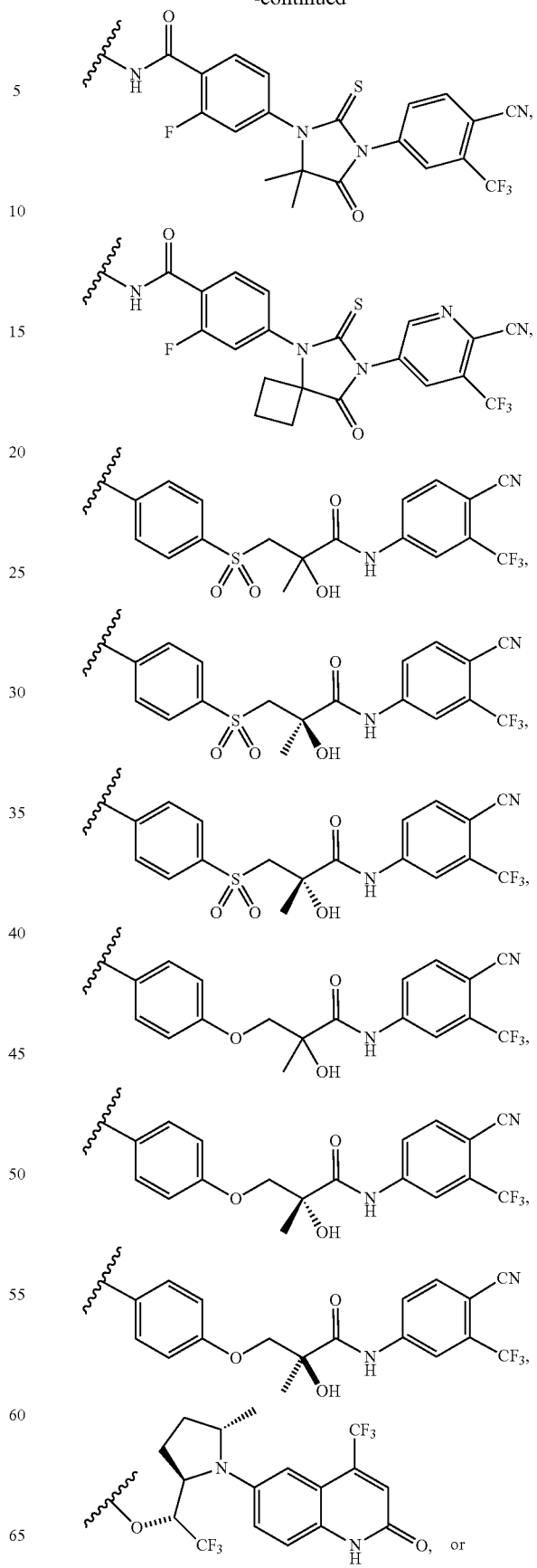

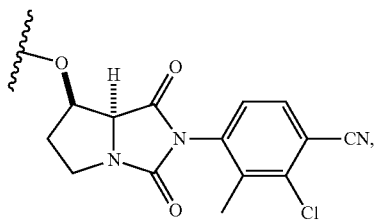
or a stereoisomer or a mixture of stereoisomers thereof or an analog thereof, where the wavy line indicates the point of attachment to the nuclear payload, optionally via a linking moiety.
In certain embodiments, at least one nuclear steroid receptor-targeting epitope comprises:
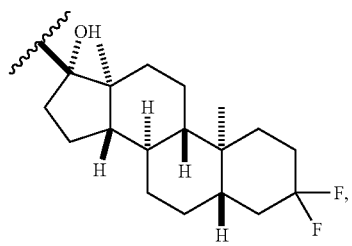
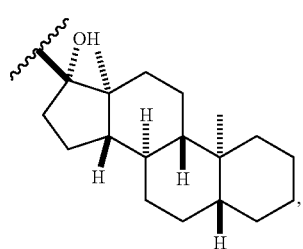
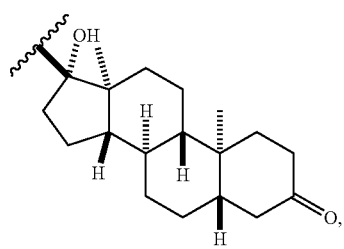
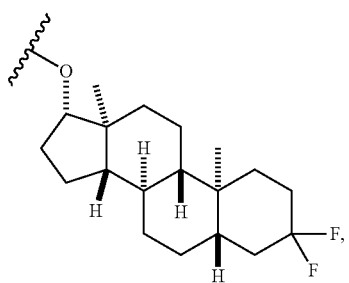
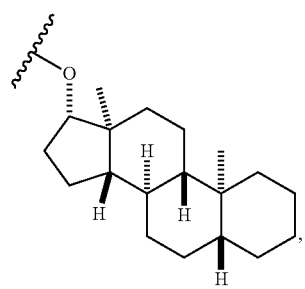
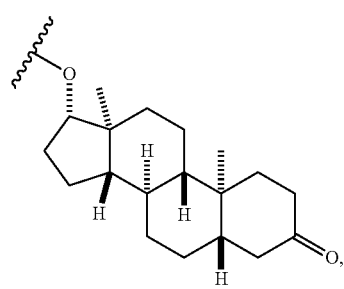
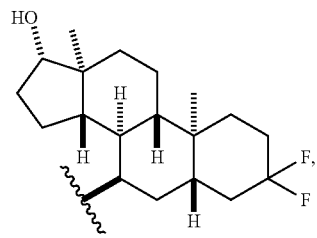
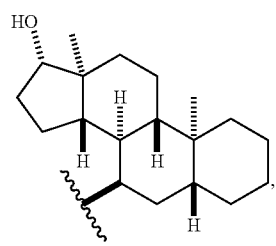
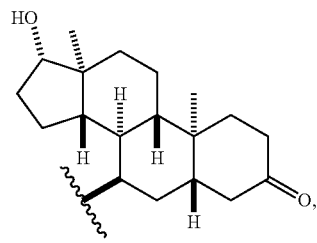
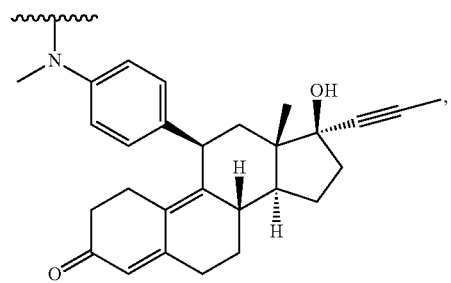

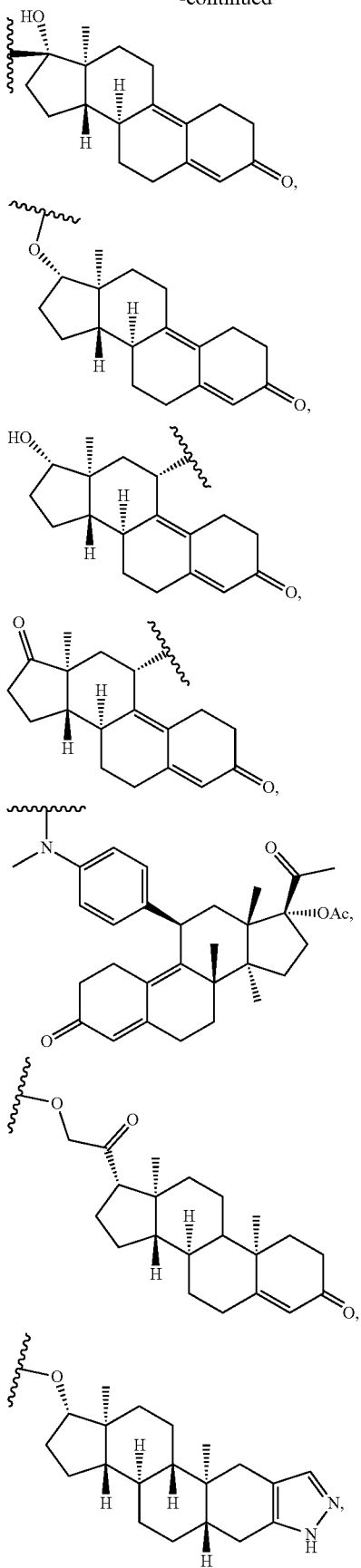

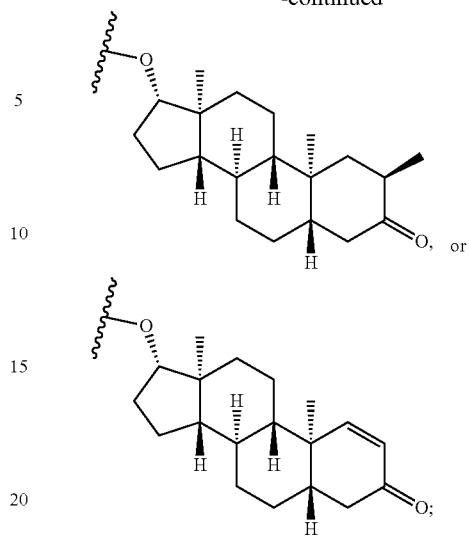

or a stereoisomer or a mixture of stereoisomers thereof or an analog thereof, where the wavy line indicates the point of attachment to the nuclear payload, optionally via a linking moiety.

In certain embodiments, the nuclear steroid receptor-targeting epitope is not, or does not contain, a peptide, protein, nanoparticle or antibody.

Linking Moiety

The "linking moiety" of any compounds described herein can be biocleavable (e.g., acid labile) or non-biocleavable. Linking moieties can be linear, branched, saturated, unsaturated, all-carbon or heteroatomic. Linking moieties can also contain one or more rings that are fused, saturated, unsaturated, as well as be all-carbon or heteroatomic. In certain embodiments, the linking moiety is a non-biocleavable linking moiety. In certain embodiments, the linking moiety is a biocleavable linking moiety. In certain embodiments, a nuclear payload is bonded to one nuclear steroid receptor-targeting epitope via a non-biocleavable linking moiety and one or more nuclear steroid receptor-targeting epitope(s) via a biocleavable linking moiety. In certain embodiments, the biocleavable linking moiety is an acid-labile linking moiety. In some embodiments, the linking moiety comprises a hydrazone linkage.

It is contemplated that any linking moiety can be used in the compounds described herein, provided that it does not significantly interfere with or disrupt the desired binding of the nuclear payload or the nuclear receptor-targeting epitope.

In some embodiments, the linking moiety is alkylene, heteroalkylene, alkenylene, heteroalkenylene, alkynylene, heteroalkynylene, arylene, heteroarylene, cycloalkylene or heterocycloalkylene; wherein each alkylene, heteroalkylene, alkenylene, heteroalkenylene, alkynylene, heteroalkynylene, may optionally comprise an arylene, heteroarylene, cycloalkylene or heterocycloalkylene; and further wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl.

In certain embodiments, the linking moiety $L^1$ is of the formula:

$$-(L^a)_q-,$$

wherein:

each $L^a$ is —$NR^{110}$—, —O—, —$S(O)_{0-2}$—, —$NR^{110}C(O)$—, —$C(O)NR^{110}$—, —$NR^{110}C(O)NR^{110}$—, —$NR^{110}S(O)_2$—, —$S(O)_2NR^{110}$—, —$NR^{110}S(O)_2NR^{110}$—, —$CR^{120}=N—NR^{110}$—, —$NR^{110}—N=CR^{120}$—, —C(O)—, —OC(O)—, —OC(O)O—, —C(O)O—, alkylene, alkenylene, alkynylene, arylene, cycloalkylene, heterocyclylene, or heteroarylene, wherein each alkylene, alkenylene, alkynylene, arylene, cycloalkylene, heterocyclylene, or heteroarylene is independently optionally substituted with one to five substituents independently selected from oxo, halo, $C_{1-4}$ alkyl, $C_{1-4}$ haloalkyl, $C_{1-4}$ alkoxy, $C_{1-4}$ haloalkoxy, aryl, heteroaryl, cycloalkyl, and heterocyclyl;

each $R^{110}$ is independently hydrogen, $C_{1-4}$ alkyl, $C_{1-4}$ haloalkyl, $C_{1-4}$ alkoxy, $C_{1-4}$ haloalkoxy aryl, heteroaryl, cycloalkyl, or heterocyclyl;

each $R^{120}$ is independently hydrogen, $C_{1-4}$ alkyl, $C_{1-4}$ haloalkyl, $C_{1-4}$ alkoxy, $C_{1-4}$ haloalkoxy aryl, heteroaryl, cycloalkyl, or heterocyclyl; and q is an integer from 0 to 20.

In certain embodiments, the linking moiety $L^1$ is of the formula:

$$—Y^{10}—(CHR^{130})_{n'}—Y^{20}—(CHR^{140})_{n''}—Y^{30}—(CHR^{150})_{m''}—Y^{40}—$$

wherein:

each of $Y^{10}$, $Y^{20}$, $Y^{30}$, and $Y^{40}$ are independently a bond, —$NR^{110}$—, —O—, —$S(O)_{0-2}$—, —$NR^{110}C(O)$—, —$C(O)NR^{110}$—, —$NR^{110}C(O)NR^{110}$—, —$NR^{110}S(O)_2$—, —$S(O)_2NR^{110}$—, —$NR^{110}S(O)_2NR^{110}$—, —$CR^{120}=N—NR^{110}$—, —$NR^{110}—N=CR^{120}$—, —C(O)—, —OC(O)—, —OC(O)O—, —$(CH_2CH_2O)_{1-5}$—, —C(O)O—, alkylene, alkenylene, alkynylene, arylene, cycloalkylene, heterocyclylene, and heteroarylene; wherein each alkylene, alkenylene, alkynylene, arylene, cycloalkylene, heterocyclylene, or heteroarylene is independently optionally substituted with one to five substituents independently selected from oxo, halo, $C_{1-4}$ alkyl, $C_{1-4}$ haloalkyl, $C_{1-4}$ alkoxy, or $C_{1-4}$ haloalkoxy;

each $R^{110}$ is independently hydrogen, $C_{1-4}$ alkyl, $C_{1-4}$ haloalkyl, $C_{1-4}$ alkoxy, $C_{1-4}$ haloalkoxy aryl, heteroaryl, cycloalkyl, or heterocyclyl;

each $R^{120}$ is independently hydrogen, $C_{1-4}$ alkyl, $C_{1-4}$ haloalkyl, $C_{1-4}$ alkoxy, $C_{1-4}$ haloalkoxy aryl, heteroaryl, cycloalkyl, or heterocyclyl;

each $R^{130}$ is independently hydrogen, $C_{1-4}$ alkyl, $C_{1-4}$ haloalkyl, $C_{1-4}$ alkoxy, $C_{1-4}$ haloalkoxy aryl, heteroaryl, cycloalkyl, or heterocyclyl;

each $R^{140}$ is independently hydrogen, $C_{1-4}$ alkyl, $C_{1-4}$ haloalkyl, $C_{1-4}$ alkoxy, $C_{1-4}$ haloalkoxy aryl, heteroaryl, cycloalkyl, or heterocyclyl;

each $R^{150}$ is independently hydrogen, $C_{1-4}$ alkyl, $C_{1-4}$ haloalkyl, $C_{1-4}$ alkoxy, $C_{1-4}$ haloalkoxy aryl, heteroaryl, cycloalkyl, or heterocyclyl; and n', n", and m" are each independently 0, 1, 2, 3, 4, 5, 6, 7, or 8.

In certain embodiments, the linking moiety $L^1$ is of the formula:

$$—Y^{10}—(CH_2)_{n'}—Y^{20}—(CH_2)_{p'}—Y^{30}—$$

wherein each of $Y^{10}$, $Y^{20}$, and $Y^{30}$ are independently a bond, optionally substituted alkylene, optionally substituted heteroalkylene, optionally substituted arylene, optionally substituted heteroarylene, optionally substituted cycloalkylene, optionally substituted heterocyclylene, —$CR^{110}R^{120}$—, —$NR^{110}$—, —O—, —$S(O)_{0-2}$—, —$NR^{110}C(O)$—, —$C(O)NR^{110}$—, —$NR^{110}S(O)_2$—, —$S(O)_2NR^{110}$—, —$CR^{120}=N—NR^{110}$—, —$NR^{110}—N=CR^{120}$—, —OC(O)—, or —C(O)—;

each $R^{110}$ is independently hydrogen, $C_{1-4}$ alkyl, $C_{1-4}$ haloalkyl, aryl, heteroaryl, cycloalkyl or heterocyclyl;

each $R^{120}$ is independently hydrogen, $C_{1-4}$ alkyl, $C_{1-4}$ haloalkyl, aryl, heteroaryl, cycloalkyl or heterocyclyl; and n' and p' are each independently 0, 1, 2, 3, 4, 5, 6, 7, or 8.

In certain embodiments, each alkylene, alkenylene, alkynylene, arylene, or heteroarylene of $Y^{10}$, $Y^{20}$, and $Y^{30}$ is independently optionally substituted with one to five substituents independently selected from oxo, halo, $C_{1-4}$ alkyl, $C_{1-4}$ haloalkyl, $C_{1-4}$ alkoxy, or $C_{1-4}$ haloalkoxy.

In certain embodiments, the linking moiety is of the formula:

$$—Y^{10}—(CH_2)_{n'}—Y^{20}—(CH_2)_{m''}—Y^{30}—$$

wherein:

each of $Y^{10}$, $Y^{20}$, and $Y^{30}$ are independently a —$NR^{110}$—, —O—, —$S(O)_{0-2}$—, —$NR^{110}C(O)$—, —$C(O)NR^{110}$—, —$NR^{110}S(O)_2$—, —$S(O)_2NR^{110}$—, —$CR^{120}=N—NR^{110}$—, —$NR^{110}—N=CR^{120}$—, —C(O)—, arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene, or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{110}$ is independently $C_{1-4}$ alkyl, $C_{1-4}$ haloalkyl, aryl, heteroaryl, cycloalkyl or heterocyclyl;

each $R^{120}$ is independently $C_{1-4}$ alkyl, $C_{1-4}$ haloalkyl, aryl, heteroaryl, cycloalkyl or heterocyclyl; and n' and m" are each independently 0, 1, 2, 3, 4, 5, 6, 7, or 8.

In certain embodiments, the linking moiety is not a bond. In certain embodiments, each $R^{110}$ is independently hydrogen, $C_{1-4}$ alkyl, $C_{1-4}$ haloalkyl, aryl, heteroaryl, cycloalkyl or heterocyclyl; and each $R^{120}$ is independently hydrogen, $C_{1-4}$ alkyl, $C_{1-4}$ haloalkyl, aryl, heteroaryl, cycloalkyl or heterocyclyl.

In certain embodiments, the linking moiety is of the formula:

$$—Y^{10}—(CH_2)_{n'}—Y^{20}—(CH_2)_{m''}—Y^{30}—$$

wherein:

each of $Y^{10}$, $Y^{20}$, and $Y^{30}$ are independently a —$NR^{110}$—, —O—, —$S(O)_{0-2}$—, —$NR^{110}C(O)$—, —$C(O)NR^{110}$—, —$NR^{110}S(O)_2$—, —$S(O)_2NR^{110}$—, —$CR^{120}=N—NR^{110}$—, —$NR^{110}—N=CR^{120}$—, —C(O)—, arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene, or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{110}$ is independently hydrogen, $C_{1-4}$ alkyl, $C_{1-4}$ haloalkyl, aryl, heteroaryl, cycloalkyl or heterocyclyl;

each $R^{120}$ is independently hydrogen, $C_{1-4}$ alkyl, $C_{1-4}$ haloalkyl, aryl, heteroaryl, cycloalkyl or heterocyclyl; and n' and m" are each independently 0, 1, 2, 3, 4, 5, 6, 7, or 8.

In certain embodiments, the linking moiety is of the formula:

$$—Y^{10}—(CH_2)_{n'}—Y^{20}—(CH_2)_{p'}—Y^{30}—$$

wherein each of $Y^{10}$, $Y^{20}$, and $Y^{30}$ are independently a bond, optionally substituted alkylene, optionally substituted heteroalkylene, optionally substituted arylene, optionally substituted heteroarylene, optionally substituted cycloalkylene, optionally substituted heterocyclylene, —CR$^{110}$R$^{120}$—, —NR$^{110}$—, —O—, —S(O)$_{0-2}$—, —NR$^{110}$C(O)—, —C(O)NR$^{110}$—, —NR$^{110}$S(O)$_2$—, —S(O)$_2$NR$^{110}$—, —CR$^{120}$=N—NR$^{110}$—, —NR$^{110}$—N=CR$^{120}$—, or —C(O)—;

each R$^{110}$ is independently hydrogen, C$_{1-4}$ alkyl, C$_{1-4}$ haloalkyl, aryl, heteroaryl, cycloalkyl or heterocyclyl;

each R$^{120}$ is independently hydrogen, C$_{1-4}$ alkyl, C$_{1-4}$ haloalkyl, aryl, heteroaryl, cycloalkyl or heterocyclyl; and n' and p' are each independently 0, 1, 2, 3, 4, 5, 6, 7, or 8.

In certain embodiments, L$^1$ comprises a non-biocleavable moiety.

In certain embodiments, L$^1$ comprises an optionally substituted C$_{4-7}$ atom alkylene, optionally substituted C$_{4-7}$ atom heterocyclylene, or optionally substituted C$_{4-7}$ atom heteroalkylene.

In certain embodiments, L$^1$ comprises an optionally substituted heterocyclylene and or optionally substituted heteroalkylene.

In certain embodiments, L$^1$ is optionally substituted C$_{4-10}$ atom heteroalkylene.

In certain embodiments, L$^1$ is a bond.

In certain embodiments, L$^1$ is a 4-12 atom alkylene or heteroalkylene linking moiety containing CH$_2$ and up to 2 heteroatoms each independently selected from NH, O or S, and optionally one C=O. In certain embodiments, L$^1$ is a 4-11 atom alkylene or heteroalkylene linking moiety containing CH$_2$ and up to 2 heteroatoms each independently selected from NH, O or S, and optionally one C=O. In certain embodiments, L$^1$ is a 4-10 atom alkylene or heteroalkylene linking moiety containing CH$_2$ and up to 2 heteroatoms each independently selected from NH, O or S, and optionally one C=O. In certain embodiments, L$^1$ is a 4-9 atom alkylene or heteroalkylene linking moiety containing CH$_2$ and up to 2 heteroatoms each independently selected from NH, O or S, and optionally one C=O. In certain embodiments, L$^1$ is a 4-8 atom alkylene or heteroalkylene linking moiety containing CH$_2$ and up to 2 heteroatoms each independently selected from NH, O or S, and optionally one C=O. In certain embodiments, L$^1$ is a 4-7 atom alkylene or heteroalkylene linking moiety containing CH$_2$ and up to 2 heteroatoms each independently selected from NH, O or S, and optionally one C=O. In certain embodiments, L$^1$ is a 4-6 atom alkylene or heteroalkylene linking moiety containing CH$_2$ and up to 2 heteroatoms each independently selected from NH, O or S, and optionally one C=O.

In certain embodiments, the linking moiety is of the Formula:

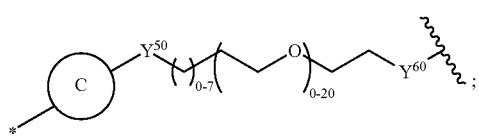

wherein
ring C is a 3-10 membered cycloalkylene or 3-10 membered heterocyclylene; wherein each 3-10 membered cycloalkylene or 3-10 membered heterocyclylene is independently optionally substituted with one to five substituents independently selected from oxo, halo, C$_{1-4}$ alkyl, C$_{1-4}$ haloalkyl, C$_{1-4}$ alkoxy, or C$_{1-4}$ haloalkoxy;

each of Y$^{50}$ and Y$^{60}$ are independently a bond, —NR$^{110}$—, —O—, —S(O)$_{0-2}$—, —NR$^{110}$C(O)—, —C(O)NR$^{110}$—, —NR$^{110}$C(O)NR$^{110}$—, —NR$^{110}$S(O)$_2$—, —S(O)$_2$NR$^{110}$—, —NR$^{110}$S(O)$_2$NR$^{110}$—, —CR$^{120}$=N—NR$^{110}$—, —NR$^{110}$—N=CR$^{120}$—, —C(O)—, —OC(O)—, —OC(O)O—, —(CH$_2$CH$_2$O)$_{1-5}$—, —C(O)O—, alkylene, alkenylene, alkynylene, arylene, cycloalkylene, heterocyclylene, and heteroarylene; wherein each alkylene, alkenylene, alkynylene, arylene, cycloalkylene, heterocyclylene, or heteroarylene is independently optionally substituted with one to five substituents independently selected from oxo, halo, C$_{1-4}$ alkyl, C$_{1-4}$ haloalkyl, C$_{1-4}$ alkoxy, or C$_{1-4}$ haloalkoxy;

each R$^{110}$ is independently hydrogen, C$_{1-4}$ alkyl, C$_{1-4}$ haloalkyl, aryl, heteroaryl, cycloalkyl or heterocyclyl;

each R$^{120}$ is independently hydrogen, C$_{1-4}$ alkyl, C$_{1-4}$ haloalkyl, aryl, heteroaryl, cycloalkyl or heterocyclyl; and wherein the "*" and the wavy line represent a covalent bond.

In certain embodiments, each alkylene, alkenylene, alkynylene, arylene, cycloalkylene, heterocyclylene, or heteroarylene of Y$^{50}$ and Y$^{60}$ is independently optionally substituted with one to five substituents independently selected from halo, C$_{1-4}$ alkyl, C$_{1-4}$ haloalkyl, C$_{1-4}$ alkoxy, or C$_{1-4}$ haloalkoxy.

In certain embodiments, the linking moiety is of the Formula:

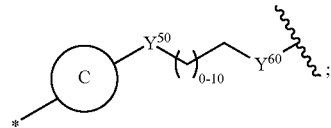

wherein
ring C is a 3-10 membered cycloalkylene or 3-10 membered heterocyclylene; wherein each 3-10 membered cycloalkylene or 3-10 membered heterocyclylene is independently optionally substituted with one to five substituents independently selected from oxo, halo, C$_{1-4}$ alkyl, C$_{1-4}$ haloalkyl, C$_{1-4}$ alkoxy, or C$_{1-4}$ haloalkoxy;

each of Y$^{50}$ and Y$^{60}$ are independently a bond, —NR$^{110}$—, —O—, —S(O)$_{0-2}$—, —NR$^{110}$C(O)—, —C(O)NR$^{110}$—, —NR$^{110}$C(O)NR$^{110}$—, —NR$^{110}$S(O)$_2$—, —S(O)$_2$NR$^{110}$—, —NR$^{110}$S(O)$_2$NR$^{110}$—, —CR$^{120}$=N—NR$^{110}$—, —NR$^{110}$—N=CR$^{120}$—, —C(O)—, —OC(O)—, —OC(O)O—, —(CH$_2$CH$_2$O)$_{1-5}$—, —C(O)O—, alkylene, alkenylene, alkynylene, arylene, cycloalkylene, heterocyclylene, and heteroarylene; wherein each alkylene, alkenylene, alkynylene, arylene, cycloalkylene, heterocyclylene, or heteroarylene is independently optionally substituted with one to five substituents independently selected from oxo, halo, C$_{1-4}$ alkyl, C$_{1-4}$ haloalkyl, C$_{1-4}$ alkoxy, or C$_{1-4}$ haloalkoxy;

each R$^{110}$ is independently hydrogen, C$_{1-4}$ alkyl, C$_{1-4}$ haloalkyl, aryl, heteroaryl, cycloalkyl or heterocyclyl;

each R$^{120}$ is independently hydrogen, C$_{1-4}$ alkyl, C$_{1-4}$ haloalkyl, aryl, heteroaryl, cycloalkyl or heterocyclyl; and wherein the "*" and the wavy line represent a covalent bond.

In certain embodiments, each of Y$^{50}$ and Y$^{60}$ are independently a bond, —NR$^{110}$—, —O—, —S(O)$_{0-2}$—, —NR¹¹⁰C(O)—, —C(O)NR¹¹⁰—, —NR¹¹⁰C(O)NR¹¹⁰—, —NR¹¹⁰S(O)₂—, —S(O)₂NR¹¹⁰—, —NR¹¹⁰S(O)₂NR¹¹⁰—, —CR¹²⁰=N—NR¹¹⁰—, —NR¹¹⁰—N=CR¹²⁰—, —C(O)—, —OC(O)—, —OC(O)O—, —(CH₂CH₂O)₁₋₅—, —C(O)O—.

In certain embodiments, the linking moiety is of the formula:

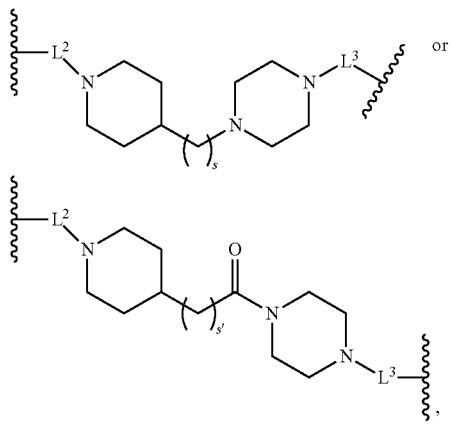

or

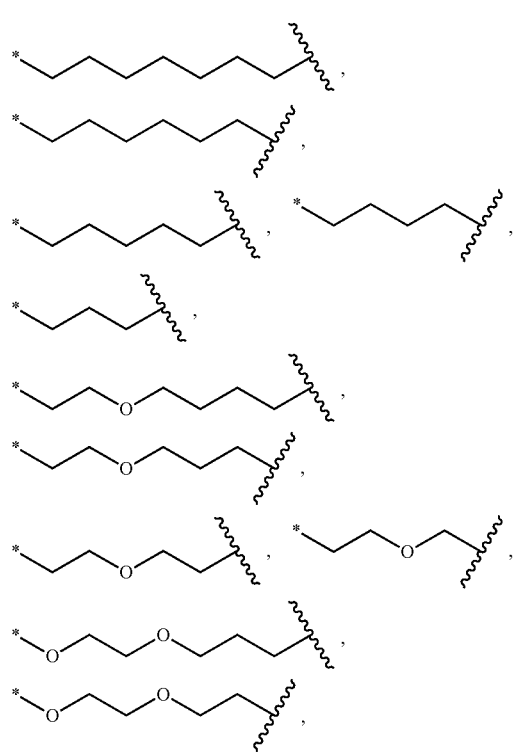

wherein:

L² is attached to ring b and L³ is attached to A;

L² and L³ are each independently selected from a bond, CH₂, CH₂CH₂, or C=O;

s is 1, 2, or 3; and s' is 0 or 1.

In certain embodiments, the linking moiety is of the formula:

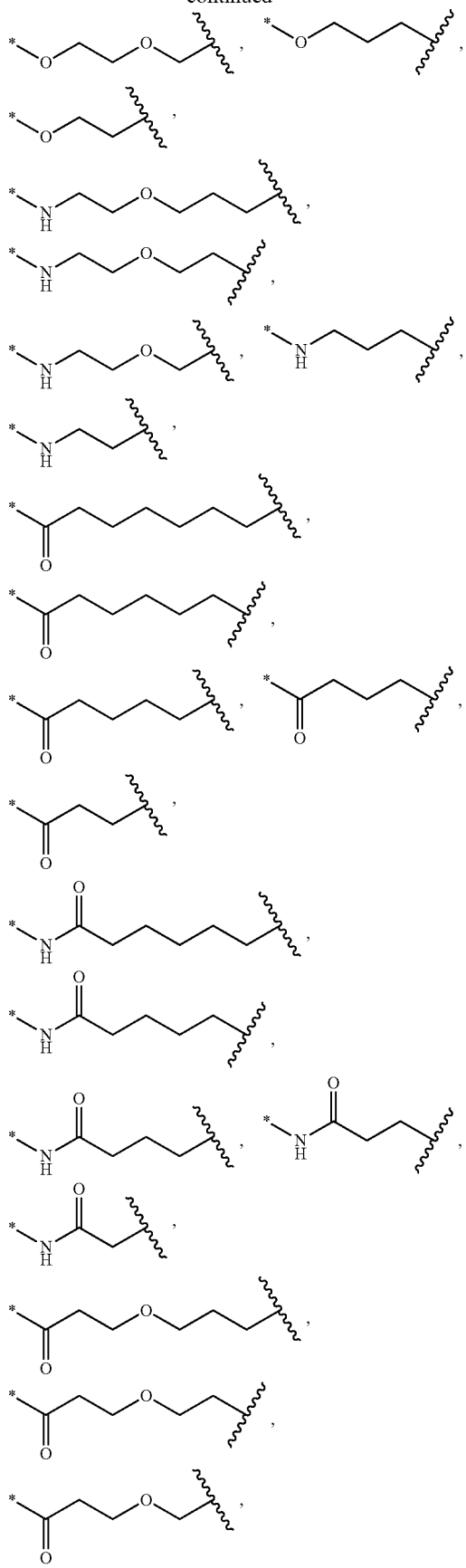

91
-continued
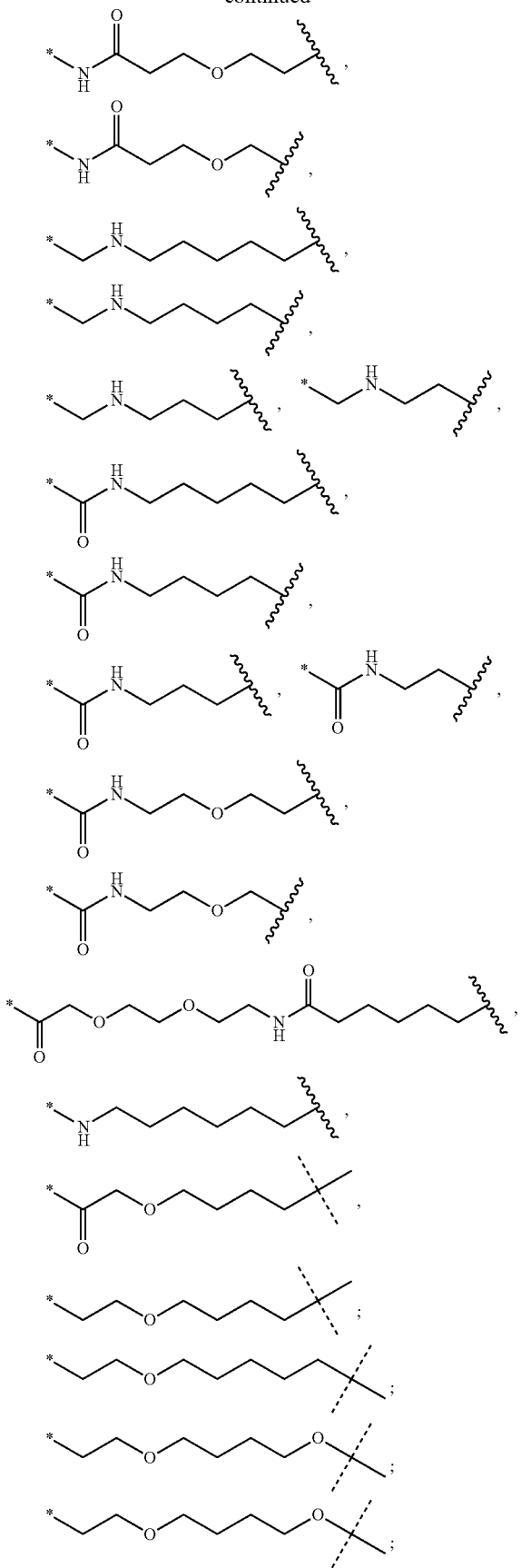
92
-continued
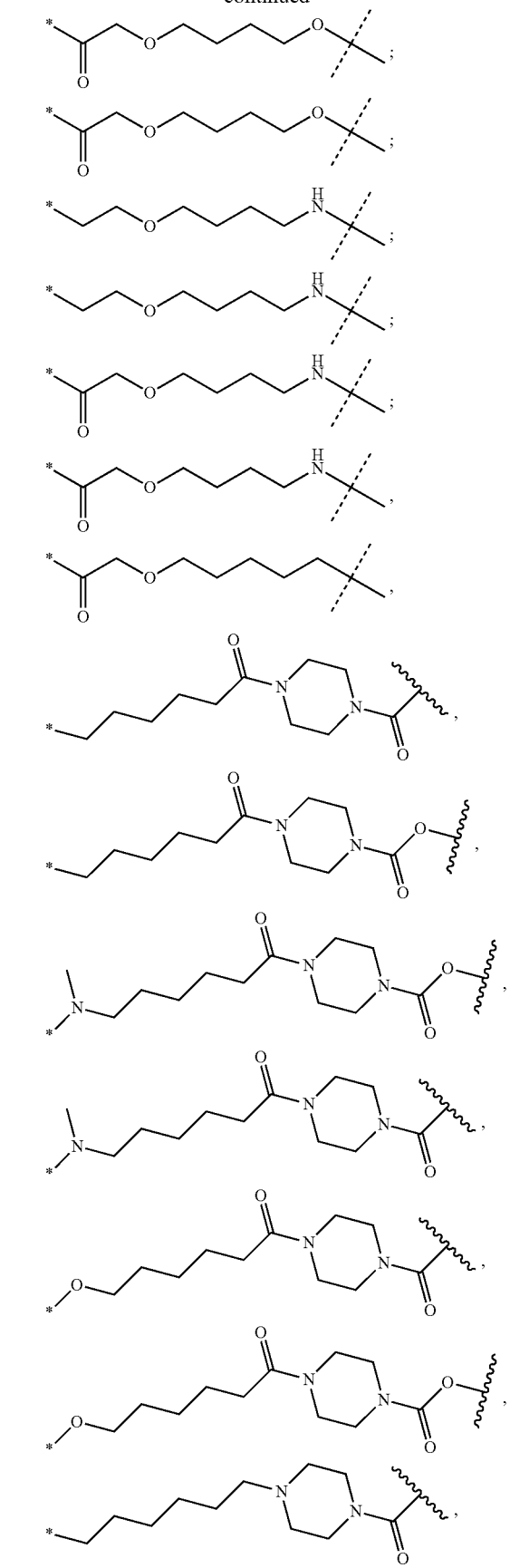

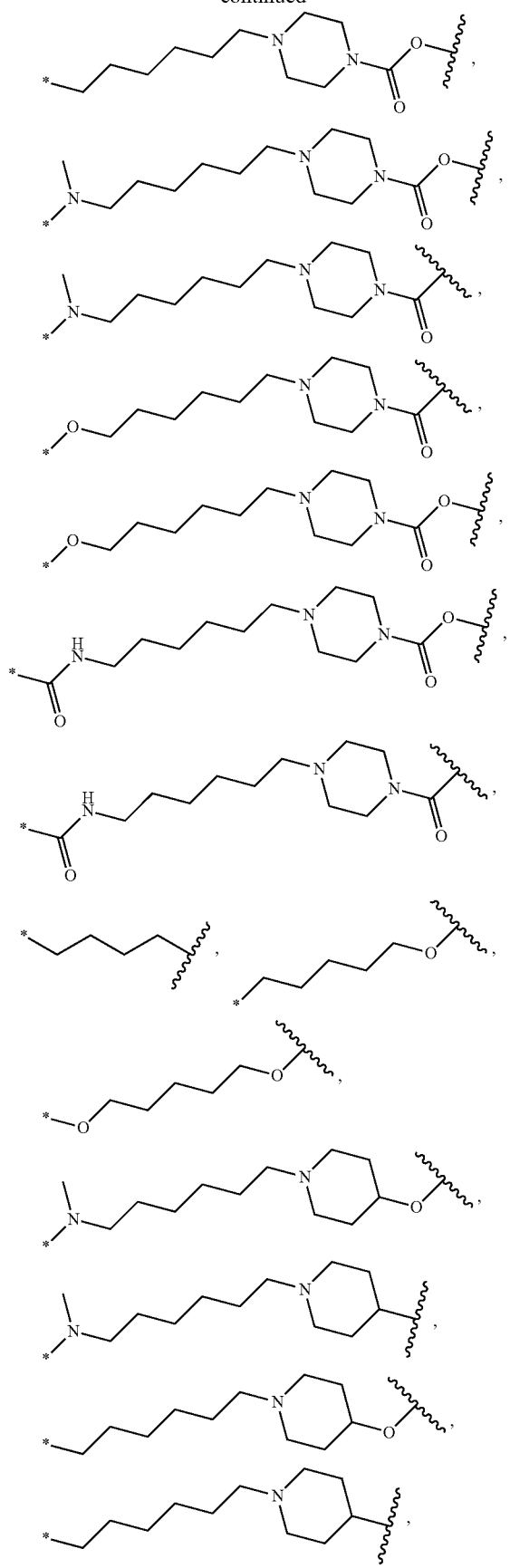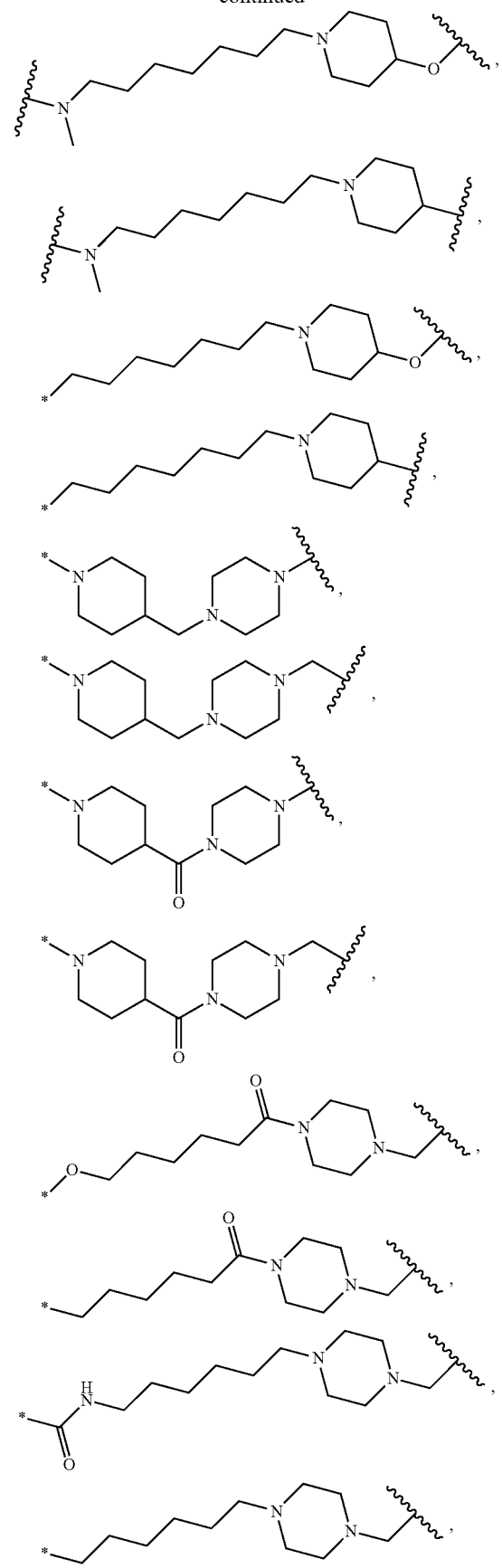

95
-continued
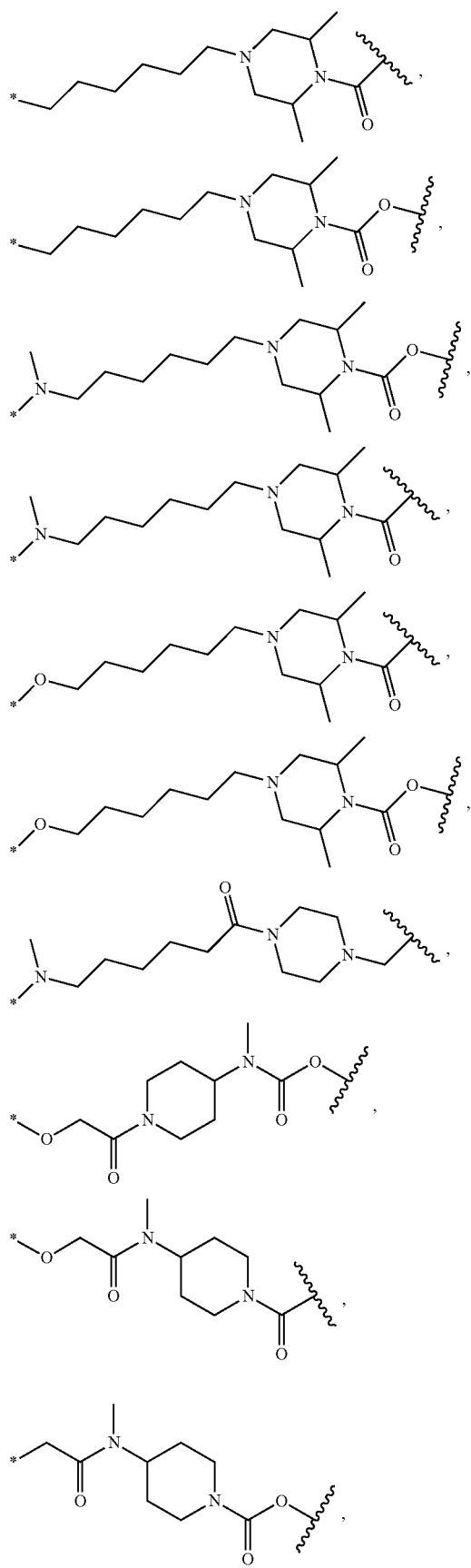
96
-continued
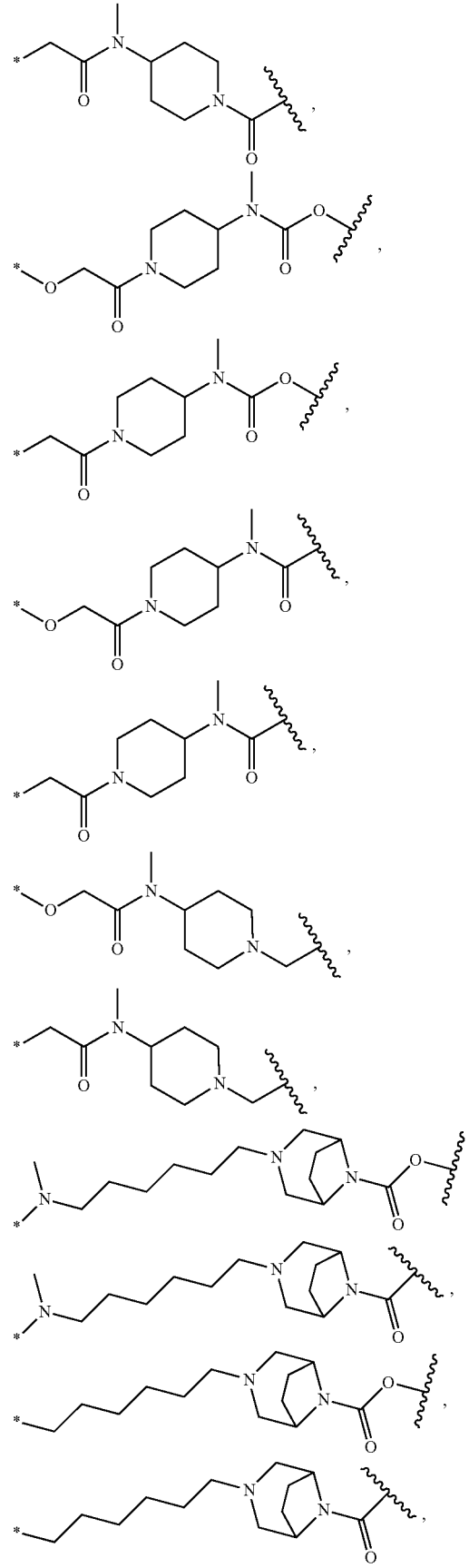

97
-continued
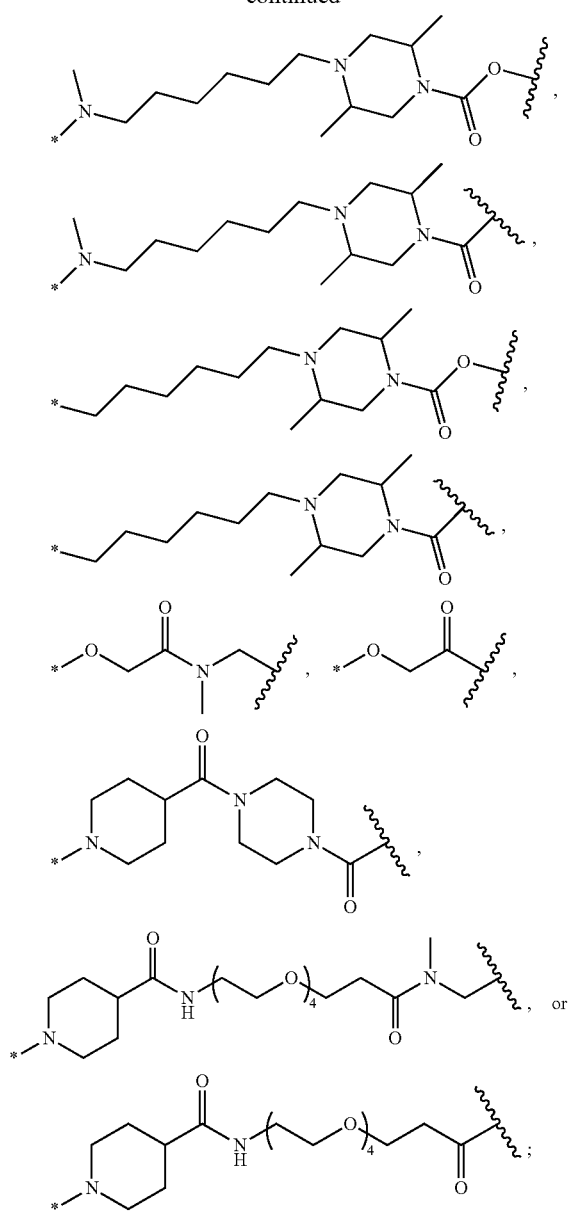
where the "*" and the wavy or dashed line represent a covalent bond.
In certain embodiments, the linking moiety is of the formula:
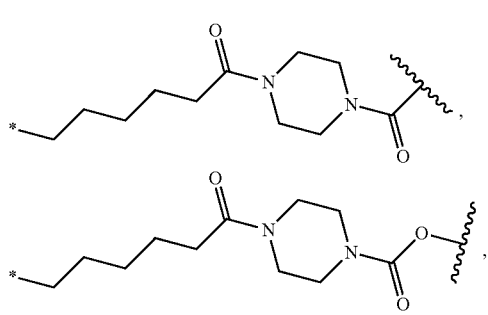
98
-continued
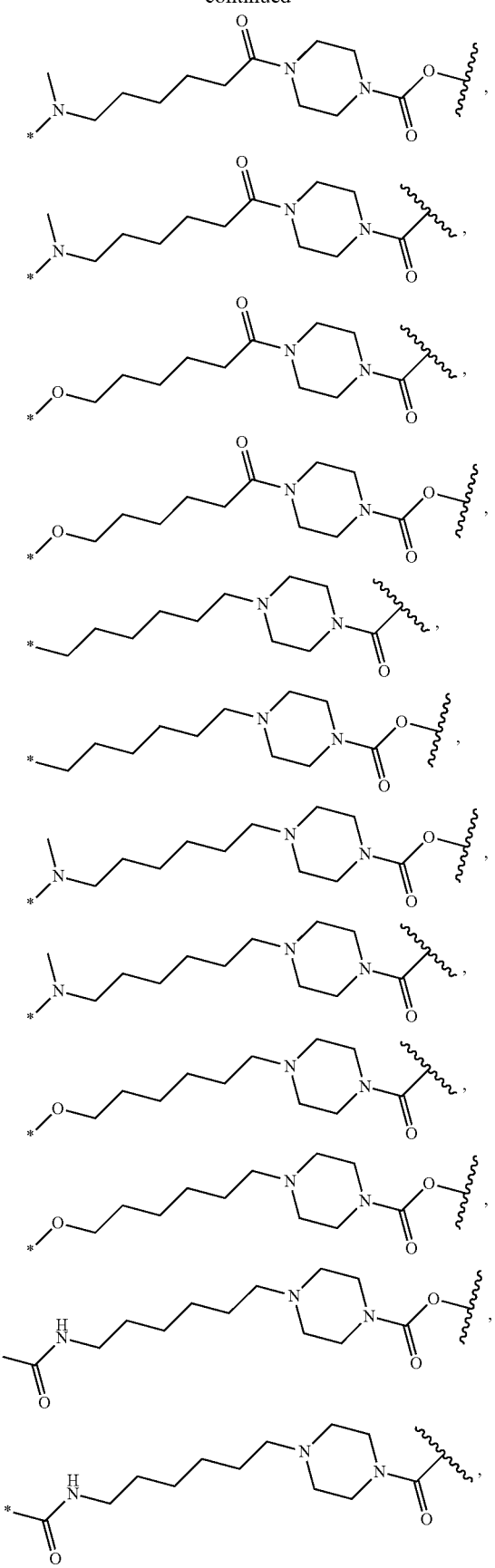

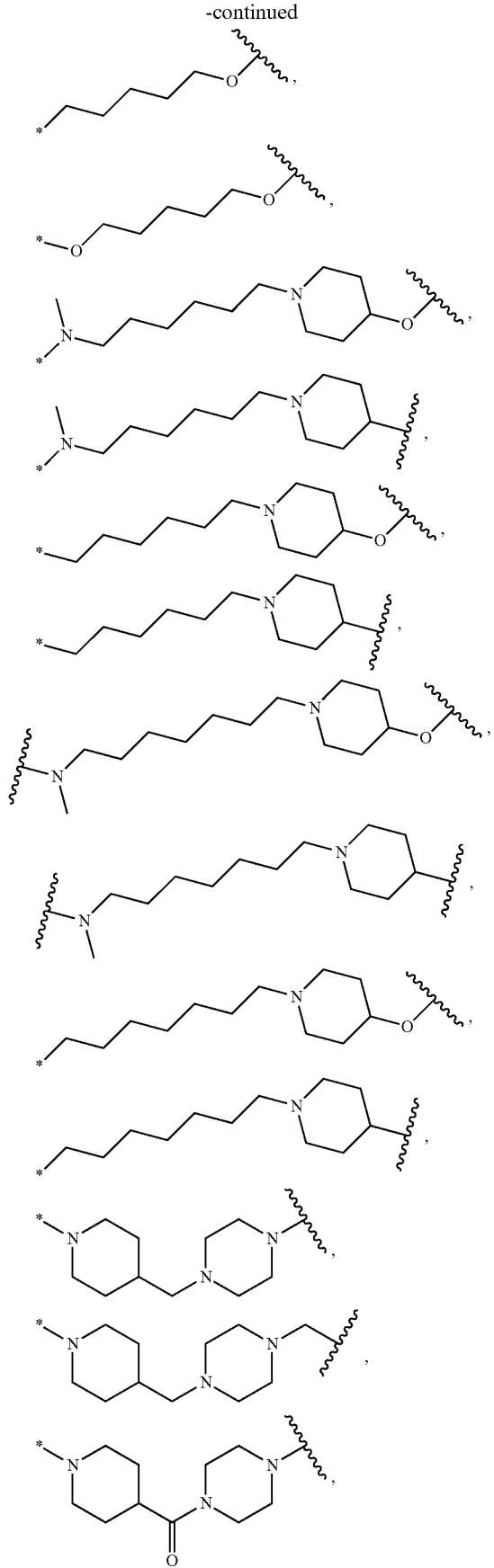
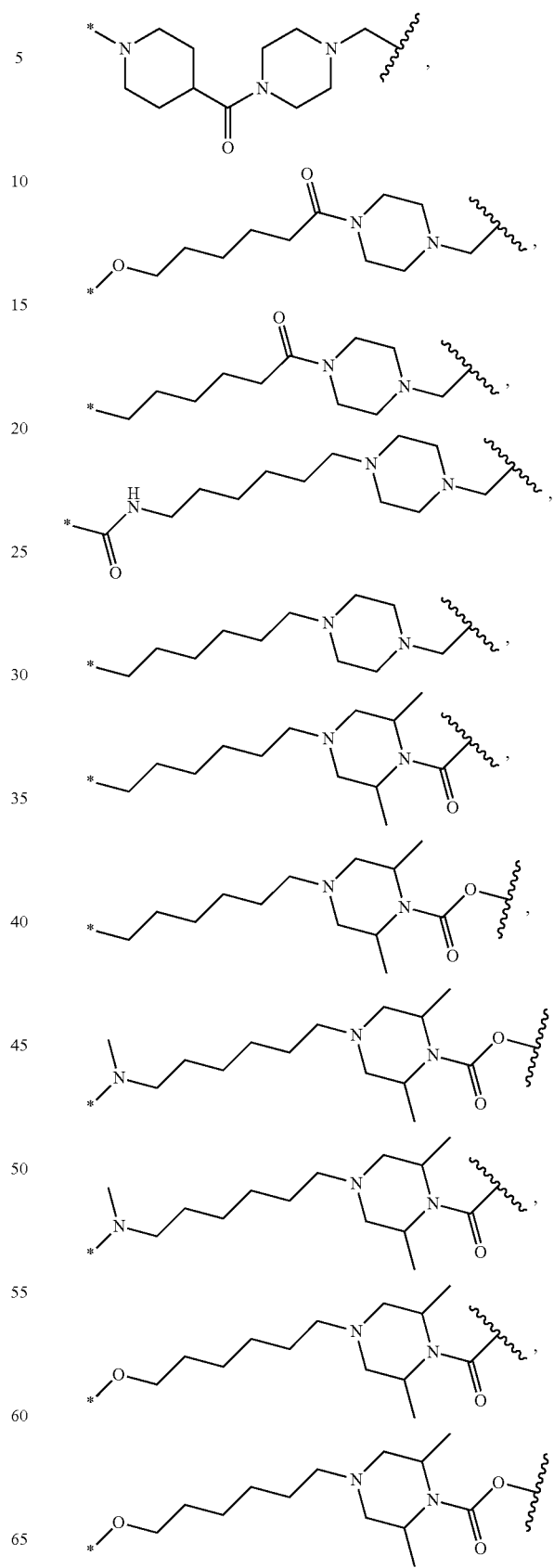

101
-continued
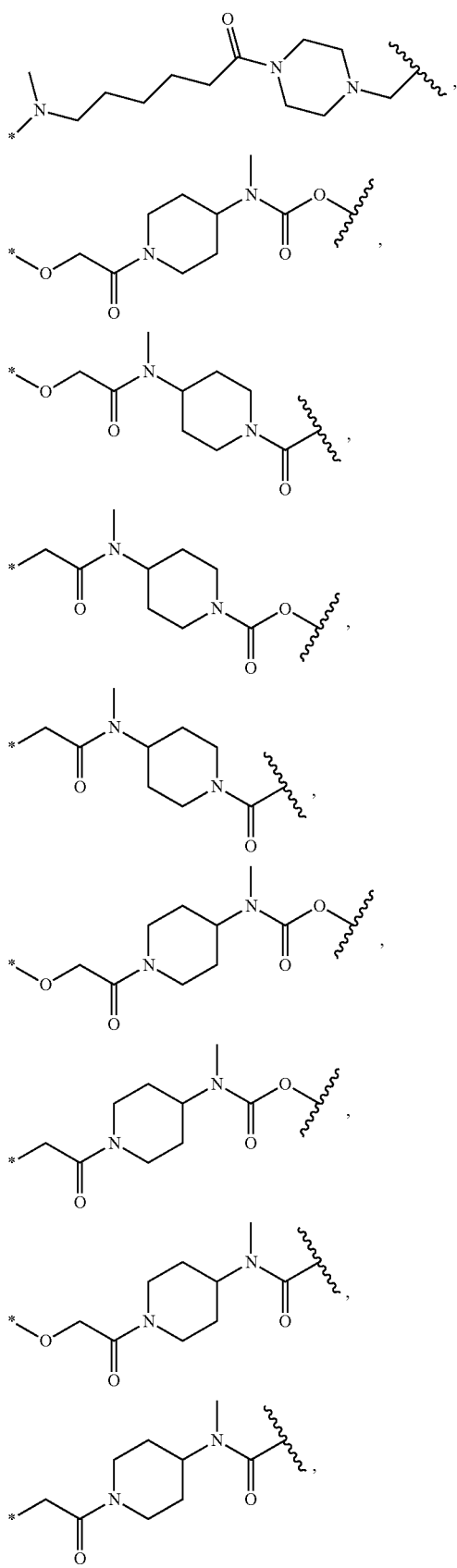
102
-continued
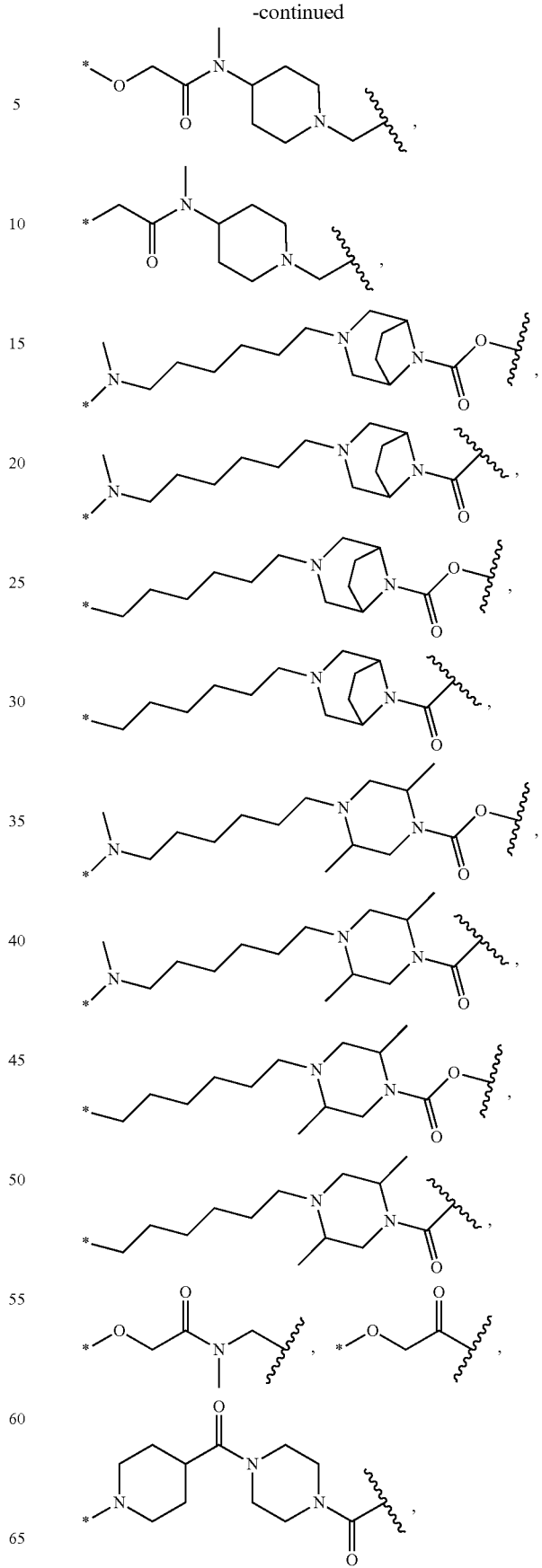

103
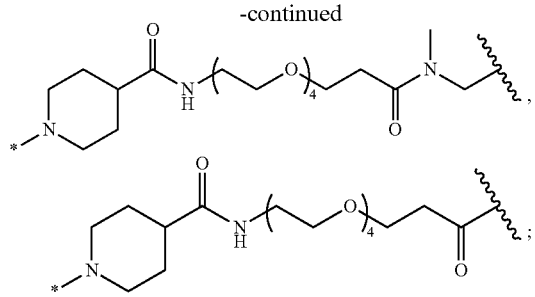
wherein the "*" and the wavy line represent a covalent bond.
In certain embodiments, the linking moiety is of the formula:
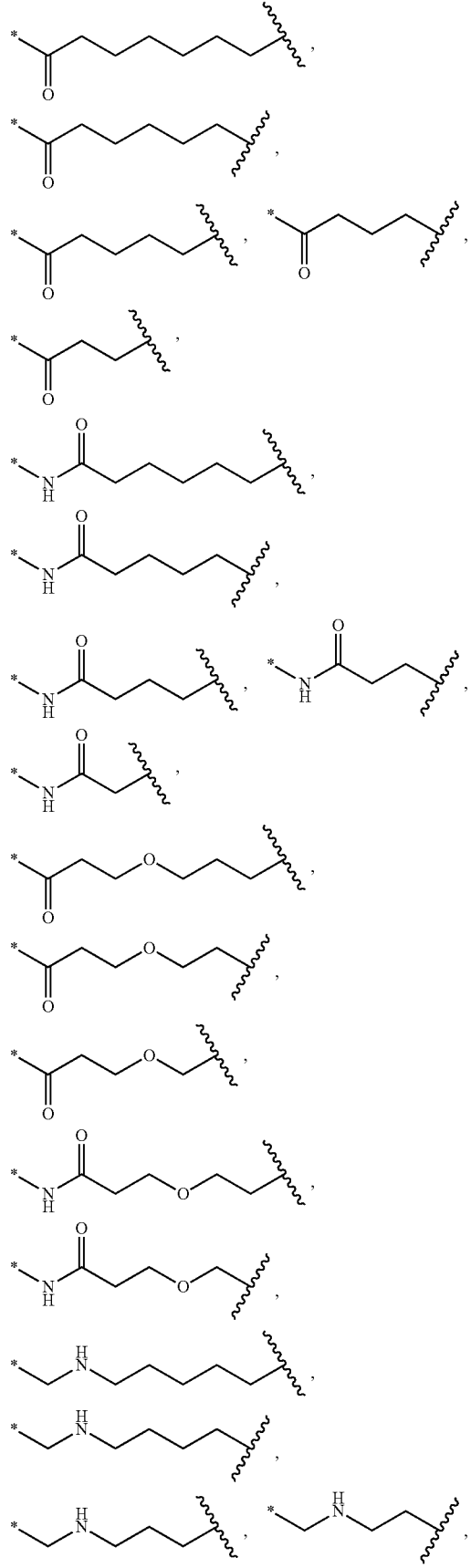

-continued
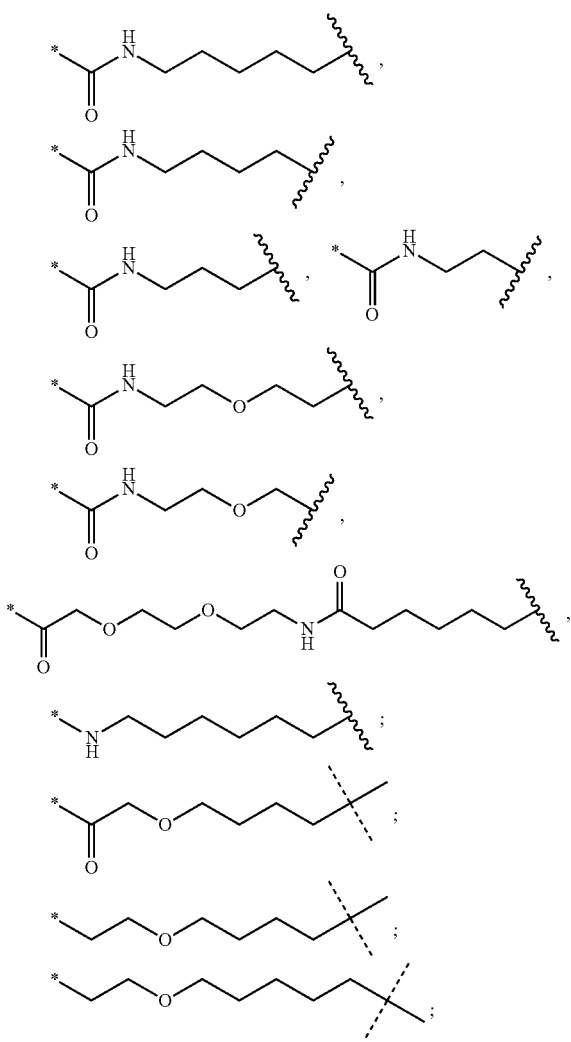
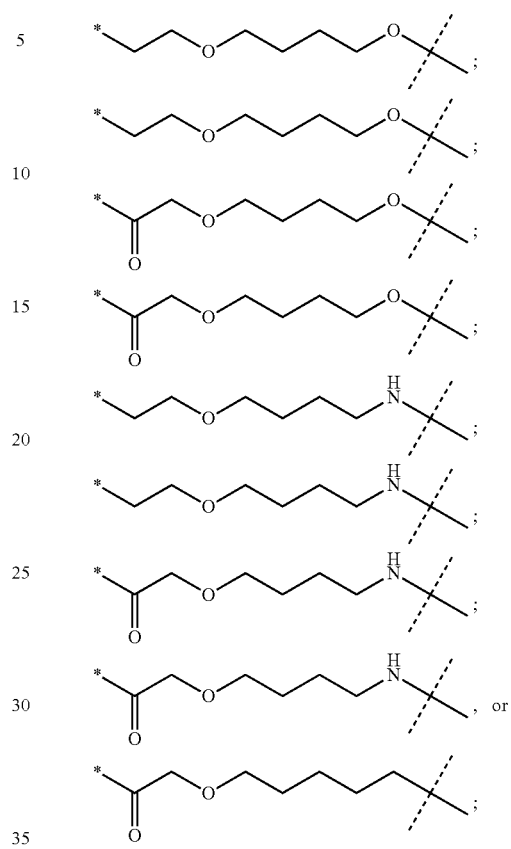
where the "*" and the dashed or wavy line represent a covalent bond.
In certain embodiments, provided is a compound as in Table 1 or a stereoisomer, mixture of stereoisomers, hydrate, solvate, isotopically enriched analog, or pharmaceutically acceptable salt thereof.
TABLE 1
| No. | Structure |
|-----|-----------|
| 1 | 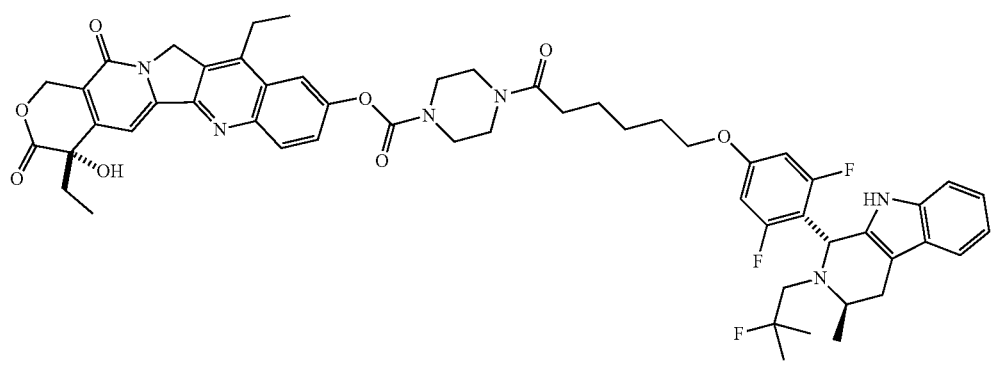 |

TABLE 1-continued

| No. | Structure |
|-----|-----------|
| 2 | 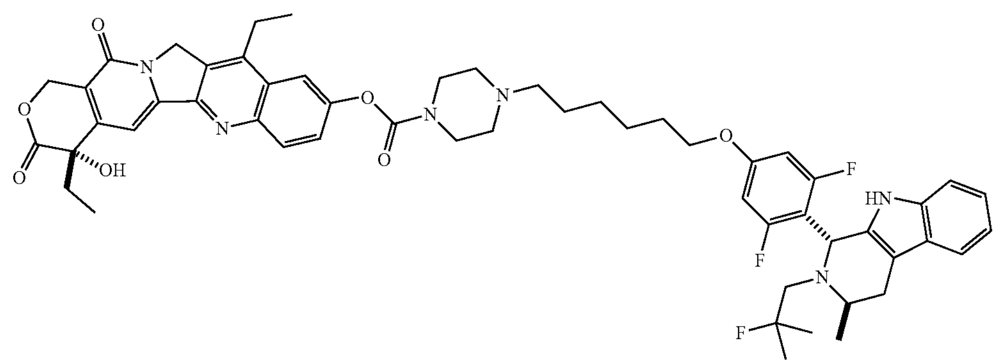 |
| 3 | 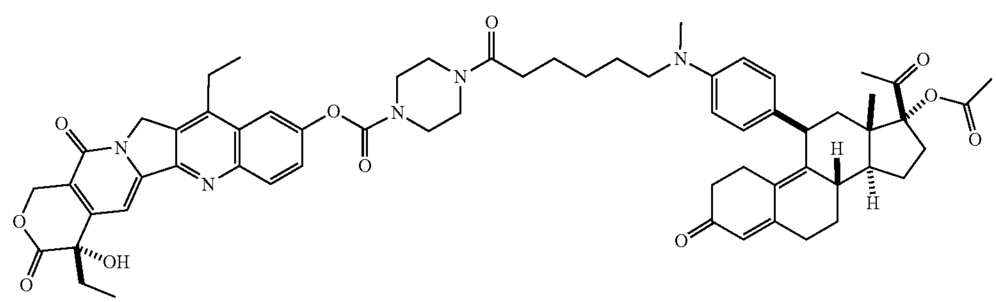 |
| 4a | 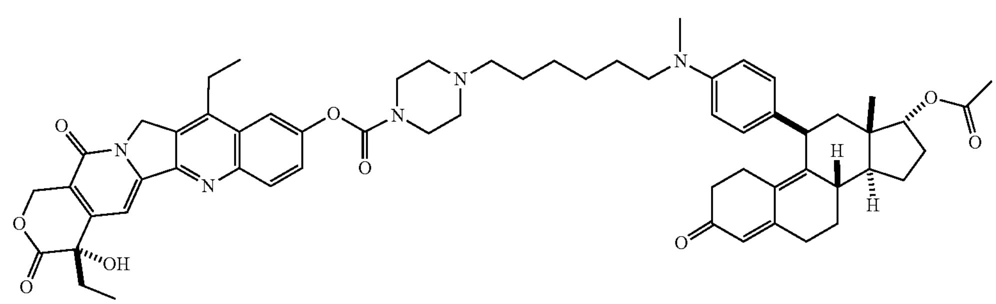 |
| 4 | 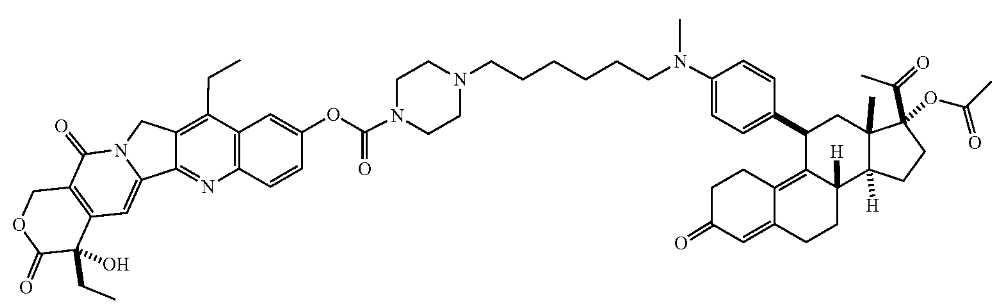 |

TABLE 1-continued
| No. | Structure |
|---|---|
| 5 | 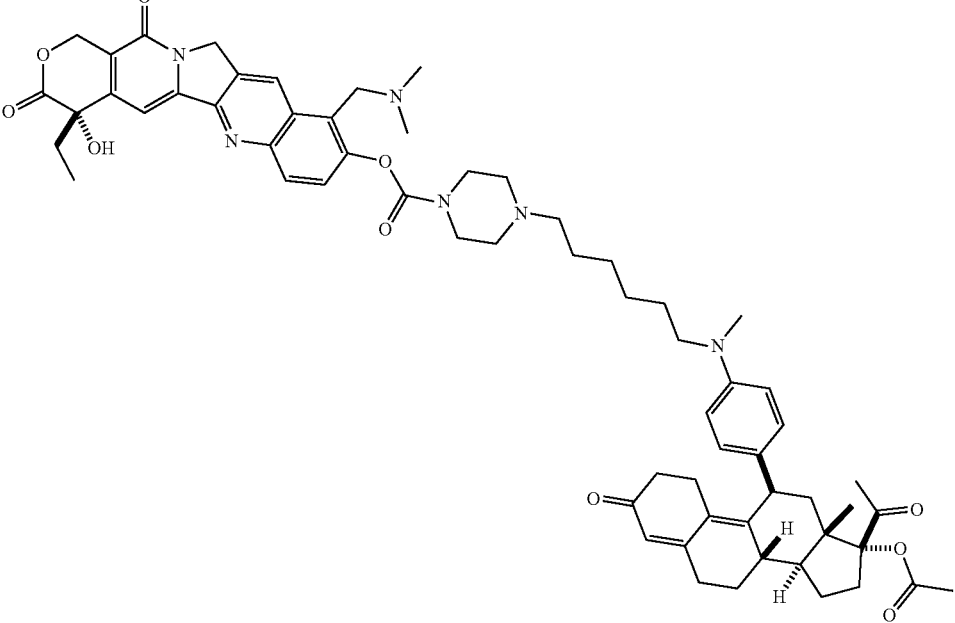 |
| 6 | 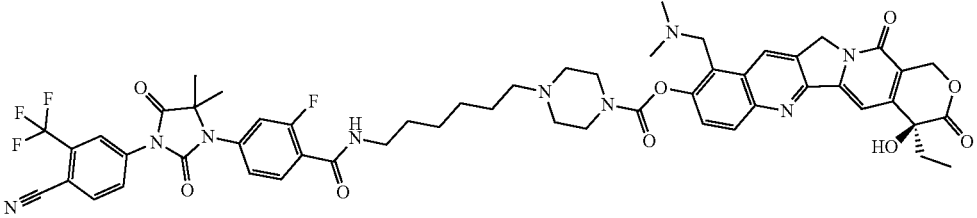 [SMILES: CC[C@@]1(O)C(=O)OCc2c1cc1n(c2=O)Cc2cc3c(CN(C)C)c(OC(=O)N4CCN(CCCCCCNC(=O)c5ccc(N6C(=O)N(c7ccc(C#N)c(C(F)(F)F)c7)C(=O)C6(C)C)cc5F)CC4)ccc3nc2-1] |
| 7 | 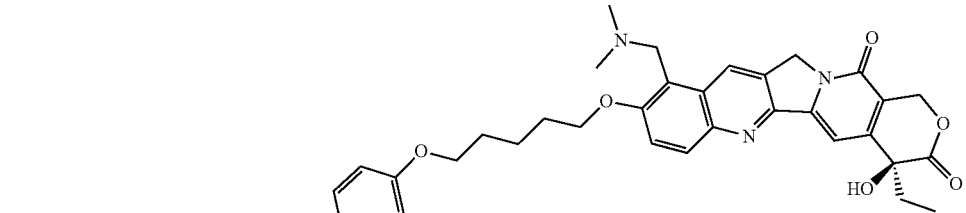 |
| 8 | 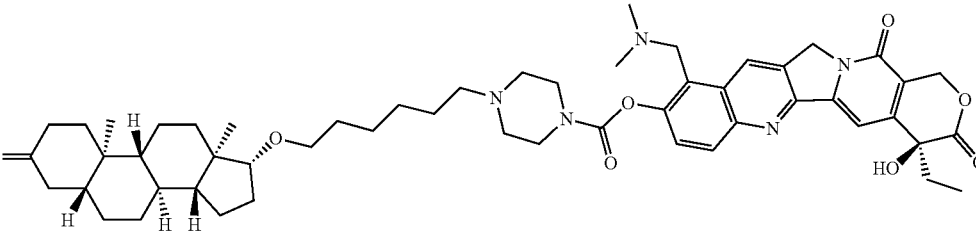 |

TABLE 1-continued

| No. | Structure |
|---|---|
| 9 | 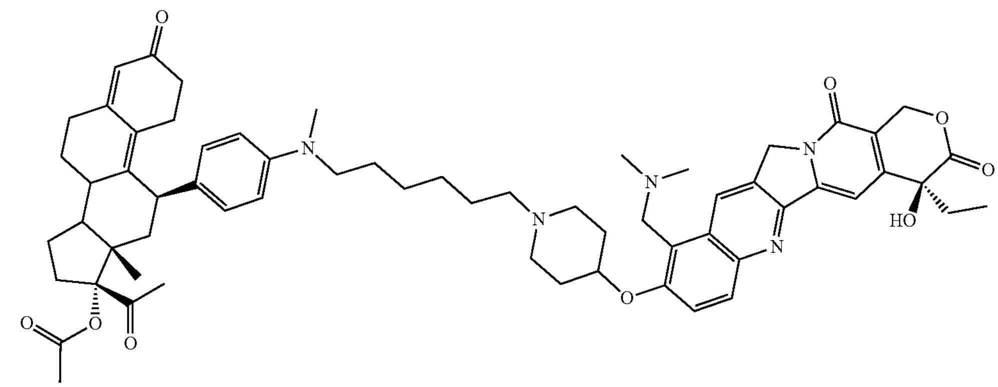 [SMILES: CC[C@@]1(O)C(=O)OCc2c1cc1n(c2=O)Cc2cc3c(CN(C)C)c(OC4CCN(CCCCCCN(C)c5ccc([C@H]6C[C@@]7(C)C(CC[C@]7(OC(C)=O)C(C)=O)C7CCC8=CC(=O)CCC8=C76)cc5)CC4)ccc3nc2-1] |
| 10 | 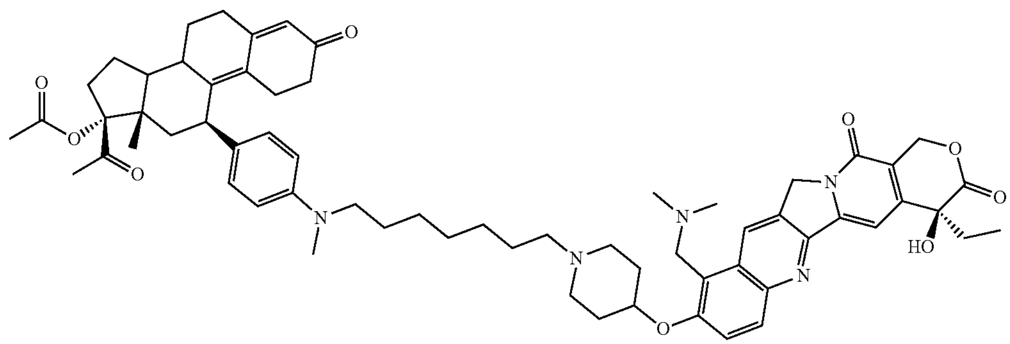 [SMILES: CC[C@@]1(O)C(=O)OCc2c1cc1n(c2=O)Cc2cc3c(CN(C)C)c(OC4CCN(CCCCCCCN(C)c5ccc([C@H]6C[C@@]7(C)C(CC[C@]7(OC(C)=O)C(C)=O)C7CCC8=CC(=O)CCC8=C76)cc5)CC4)ccc3nc2-1] |
| 11 | 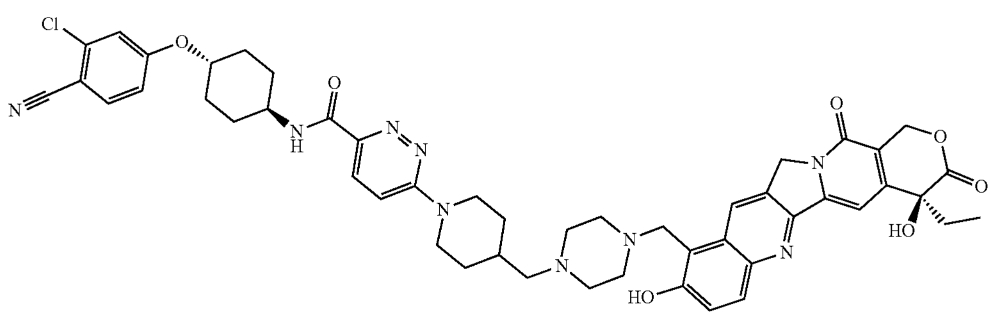 [SMILES: CC[C@@]1(O)C(=O)OCc2c1cc1n(c2=O)Cc2cc3c(CN4CCN(CC5CCN(c6ccc(C(=O)N[C@H]7CC[C@H](Oc8ccc(C#N)c(Cl)c8)CC7)nn6)CC5)CC4)c(O)ccc3nc2-1] |
| 12 | 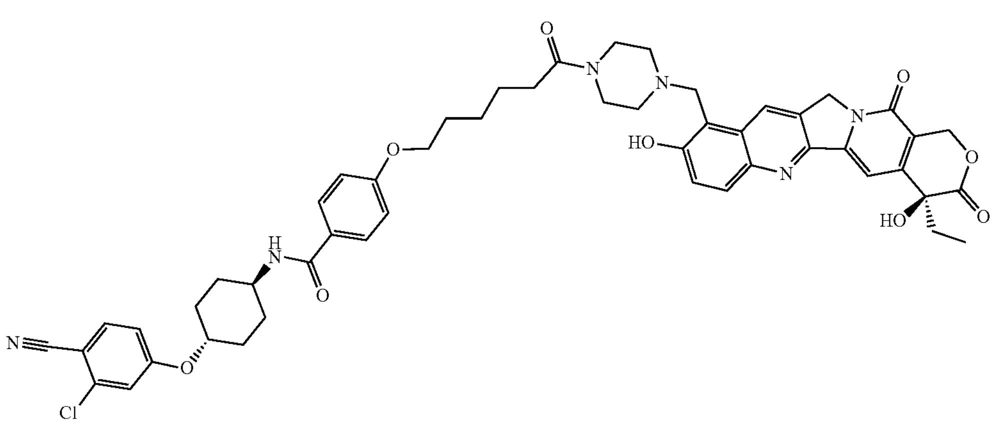 [SMILES: CC[C@@]1(O)C(=O)OCc2c1cc1n(c2=O)Cc2cc3c(CN4CCN(C(=O)CCCCCOc5ccc(C(=O)N[C@H]6CC[C@H](Oc7ccc(C#N)c(Cl)c7)CC6)cc5)CC4)c(O)ccc3nc2-1] |

TABLE 1-continued
| No. | Structure |
|---|---|
| 13 | 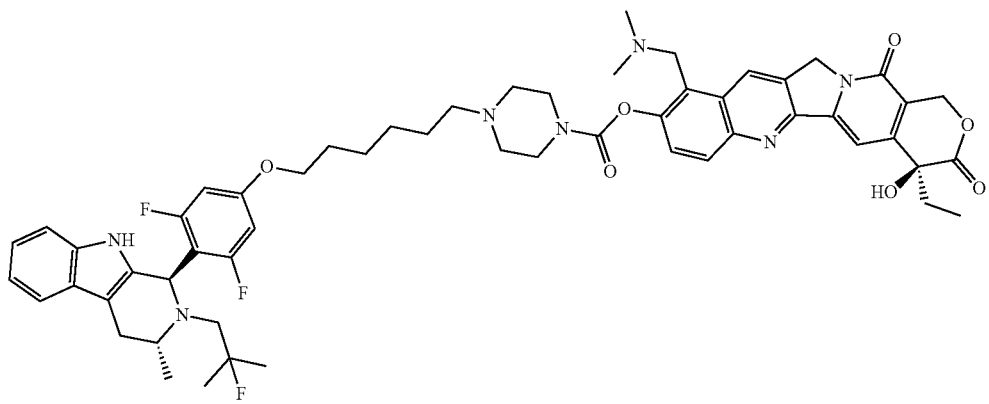 [SMILES: CC[C@@]1(O)C(=O)OCc2c1cc1n(c2=O)Cc2cc3c(CN(C)C)c(OC(=O)N4CCN(CCCCCCOc5cc(F)c([C@@H]6c7[nH]c8ccccc8c7C[C@@H](C)N6CC(C)(C)F)c(F)c5)CC4)ccc3nc2-1] |
| 14 | 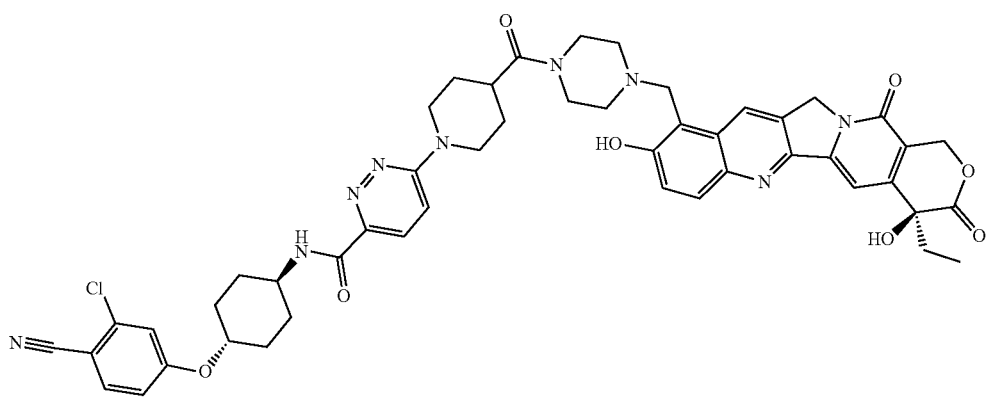 [SMILES: CC[C@@]1(O)C(=O)OCc2c1cc1n(c2=O)Cc2cc3c(CN4CCN(C(=O)C5CCN(c6ccc(C(=O)N[C@H]7CC[C@H](Oc8ccc(C#N)c(Cl)c8)CC7)nn6)CC5)CC4)c(O)ccc3nc2-1] |
| 15 | 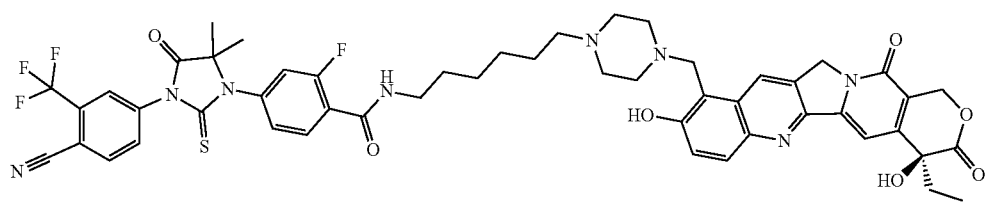 [SMILES: CC[C@@]1(O)C(=O)OCc2c1cc1n(c2=O)Cc2cc3c(CN4CCN(CCCCCCNC(=O)c5ccc(N6C(=S)N(c7ccc(C#N)c(C(F)(F)F)c7)C(=O)C6(C)C)cc5F)CC4)c(O)ccc3nc2-1] |
| 16 | 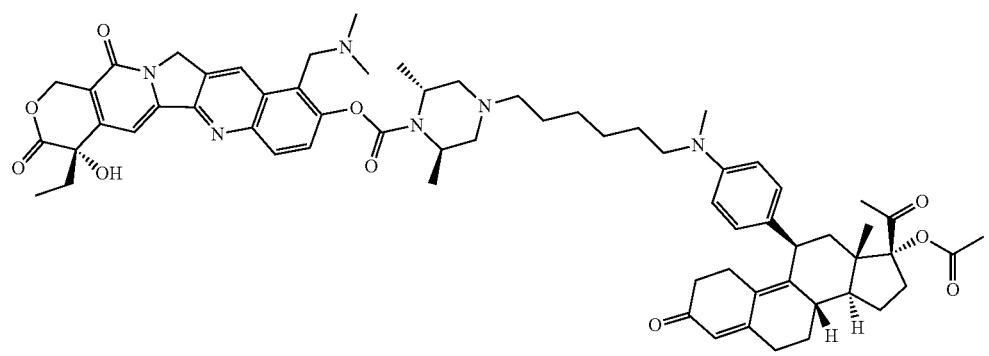 [SMILES: CC[C@@]1(O)C(=O)OCc2c1cc1n(c2=O)Cc2cc3c(CN(C)C)c(OC(=O)N4[C@H](C)CN(CCCCCCN(C)c5ccc([C@H]6C[C@@]7(C)[C@@H](CC[C@]7(OC(C)=O)C(C)=O)[C@@H]7CCC8=CC(=O)CCC8=C76)cc5)C[C@H]4C)ccc3nc2-1] |

| No. | Structure |
|---|---|
| 17 | 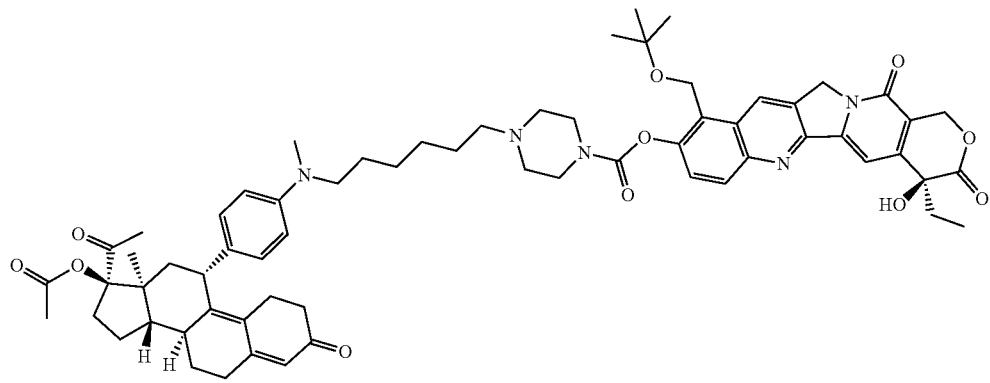 [SMILES: CC[C@@]1(O)C(=O)OCc2c1cc1n(c2=O)Cc2cc3c(COC(C)(C)C)c(OC(=O)N4CCN(CCCCCCN(C)c5ccc([C@H]6C[C@@]7(C)[C@@H](CC[C@]7(OC(C)=O)C(C)=O)[C@@H]7CCC8=CC(=O)CCC8=C76)cc5)CC4)ccc3nc2-1] |
| 18 | 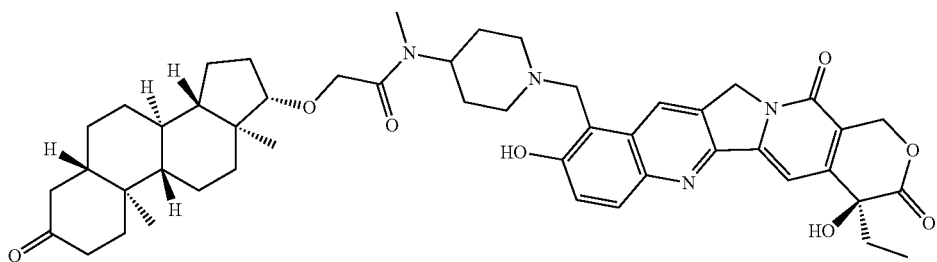 [SMILES: CC[C@@]1(O)C(=O)OCc2c1cc1n(c2=O)Cc2cc3c(CN4CCC(N(C)C(=O)CO[C@H]5CC[C@H]6[C@@H]7CC[C@H]8CC(=O)CC[C@]8(C)[C@H]7CC[C@]56C)CC4)c(O)ccc3nc2-1] |
| 19 | 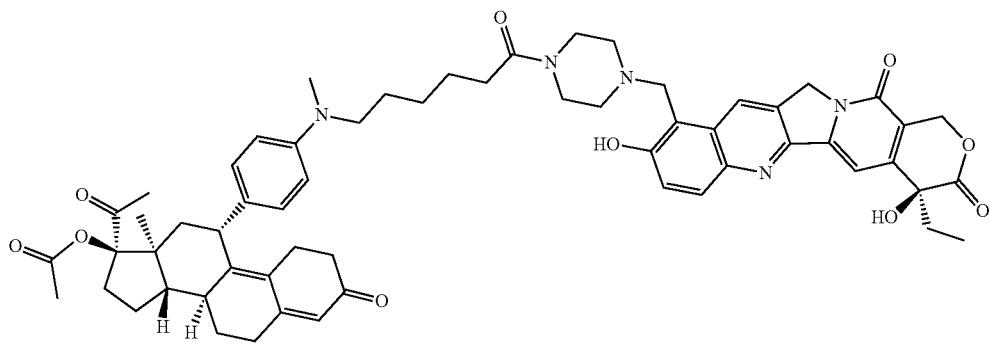 [SMILES: CC[C@@]1(O)C(=O)OCc2c1cc1n(c2=O)Cc2cc3c(CN4CCN(C(=O)CCCCCN(C)c5ccc([C@H]6C[C@@]7(C)[C@@H](CC[C@]7(OC(C)=O)C(C)=O)[C@@H]7CCC8=CC(=O)CCC8=C76)cc5)CC4)c(O)ccc3nc2-1] |
| 20 | 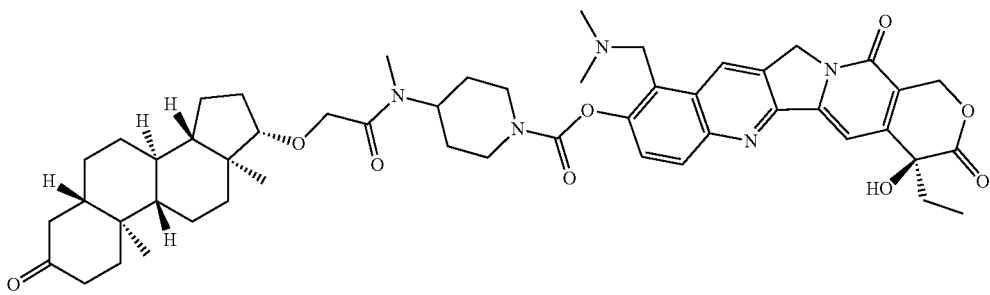 [SMILES: CC[C@@]1(O)C(=O)OCc2c1cc1n(c2=O)Cc2cc3c(CN(C)C)c(OC(=O)N4CCC(N(C)C(=O)CO[C@H]5CC[C@H]6[C@@H]7CC[C@H]8CC(=O)CC[C@]8(C)[C@H]7CC[C@]56C)CC4)ccc3nc2-1] |

TABLE 1-continued

| No. | Structure |
|---|---|
| 21 | 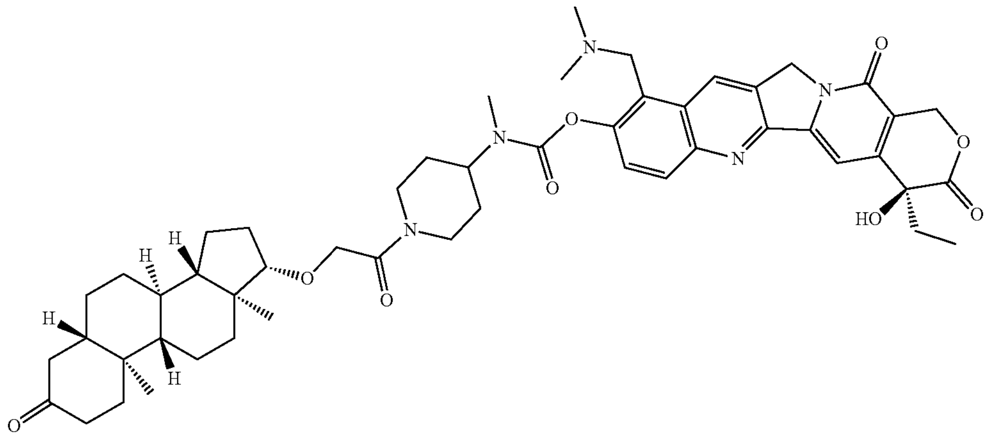 [SMILES: CC[C@@]1(O)C(=O)OCc2c1cc1n(c2=O)Cc2cc3c(CN(C)C)c(OC(=O)N(C)C4CCN(C(=O)CO[C@H]5CC[C@H]6[C@@H]7CC[C@H]8CC(=O)CC[C@]8(C)[C@H]7CC[C@]56C)CC4)ccc3nc2-1] |
| 22 | 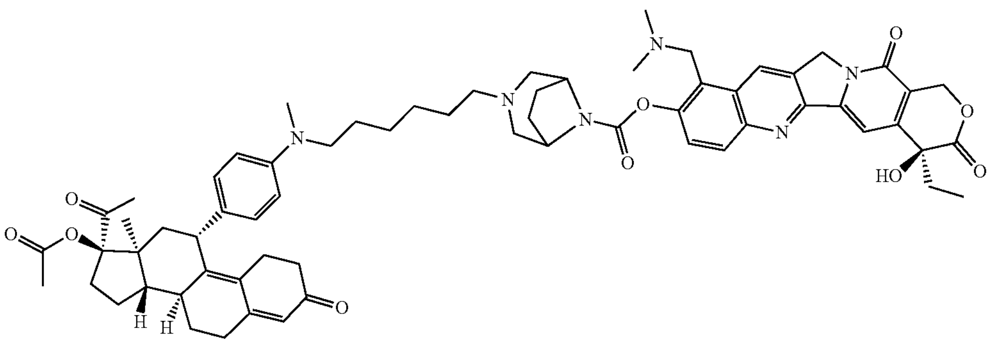 [SMILES: CC[C@@]1(O)C(=O)OCc2c1cc1n(c2=O)Cc2cc3c(CN(C)C)c(OC(=O)N4C5CCC4CN(CCCCCCN(C)c4ccc([C@H]6C[C@@]7(C)[C@@H](CC[C@]7(OC(C)=O)C(C)=O)[C@@H]7CCC8=CC(=O)CCC8=C76)cc4)C5)ccc3nc2-1] |
| 23 | 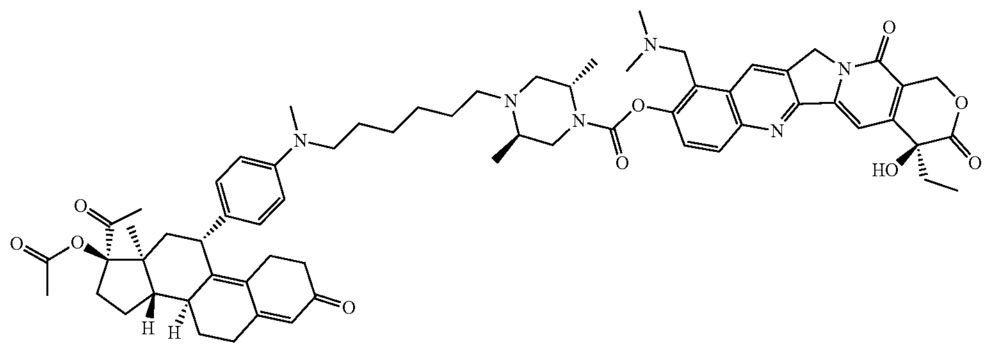 [SMILES: CC[C@@]1(O)C(=O)OCc2c1cc1n(c2=O)Cc2cc3c(CN(C)C)c(OC(=O)N4C[C@@H](C)N(CCCCCCN(C)c5ccc([C@H]6C[C@@]7(C)[C@@H](CC[C@]7(OC(C)=O)C(C)=O)[C@@H]7CCC8=CC(=O)CCC8=C76)cc5)C[C@@H]4C)ccc3nc2-1] |
| 24 | 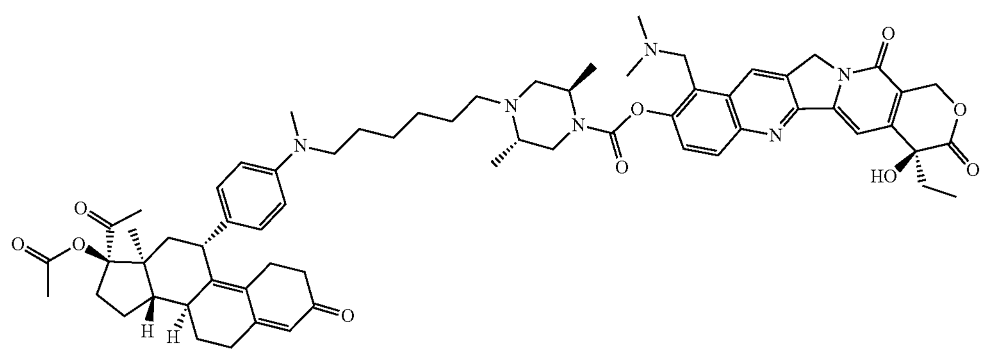 [SMILES: CC[C@@]1(O)C(=O)OCc2c1cc1n(c2=O)Cc2cc3c(CN(C)C)c(OC(=O)N4C[C@H](C)N(CCCCCCN(C)c5ccc([C@H]6C[C@@]7(C)[C@@H](CC[C@]7(OC(C)=O)C(C)=O)[C@@H]7CCC8=CC(=O)CCC8=C76)cc5)C[C@H]4C)ccc3nc2-1] |

TABLE 1-continued

| No. | Structure |
|---|---|
| 25 | 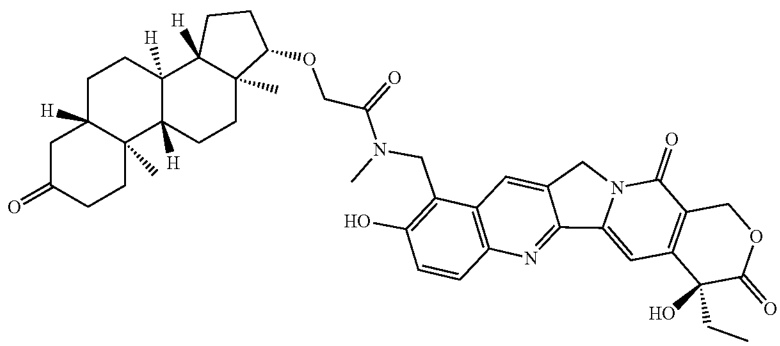 [SMILES: CC[C@@]1(O)C(=O)OCc2c1cc1n(c2=O)Cc2cc3c(CN(C)C(=O)CO[C@H]4CC[C@H]5[C@@H]6CC[C@H]7CC(=O)CC[C@]7(C)[C@H]6CC[C@]45C)c(O)ccc3nc2-1] |
| 26 | 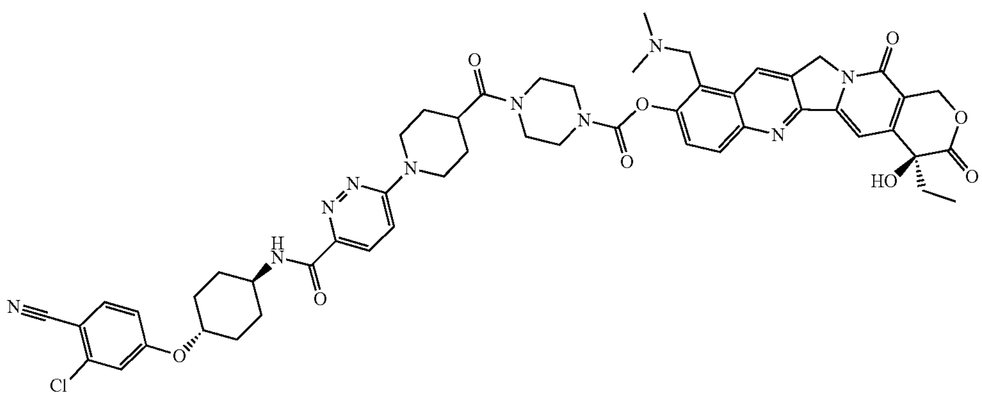 [SMILES: CC[C@@]1(O)C(=O)OCc2c1cc1n(c2=O)Cc2cc3c(CN(C)C)c(OC(=O)N4CCN(C(=O)C5CCN(c6ccc(C(=O)N[C@H]7CC[C@H](Oc8ccc(C#N)c(Cl)c8)CC7)nn6)CC5)CC4)ccc3nc2-1] |
| 27 | 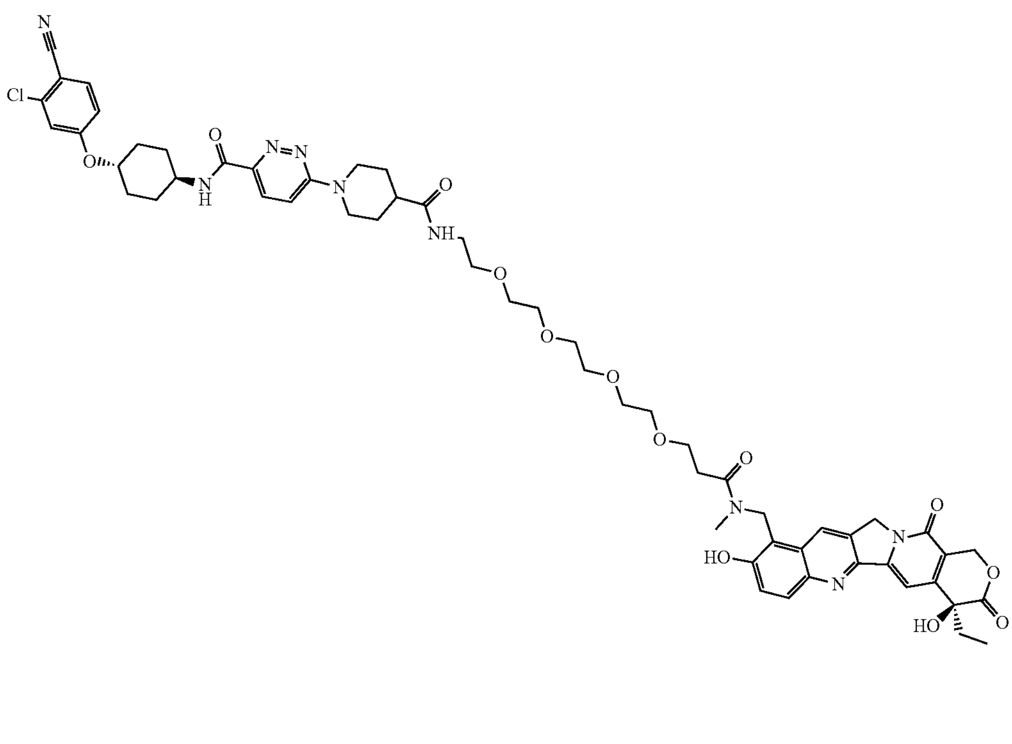 [SMILES: CC[C@@]1(O)C(=O)OCc2c1cc1n(c2=O)Cc2cc3c(CN(C)C(=O)CCOCCOCCOCCOCCNC(=O)C4CCN(c5ccc(C(=O)N[C@H]6CC[C@H](Oc7ccc(C#N)c(Cl)c7)CC6)nn5)CC4)c(O)ccc3nc2-1] |

TABLE 1-continued

| No. | Structure |
|---|---|
| 28 | 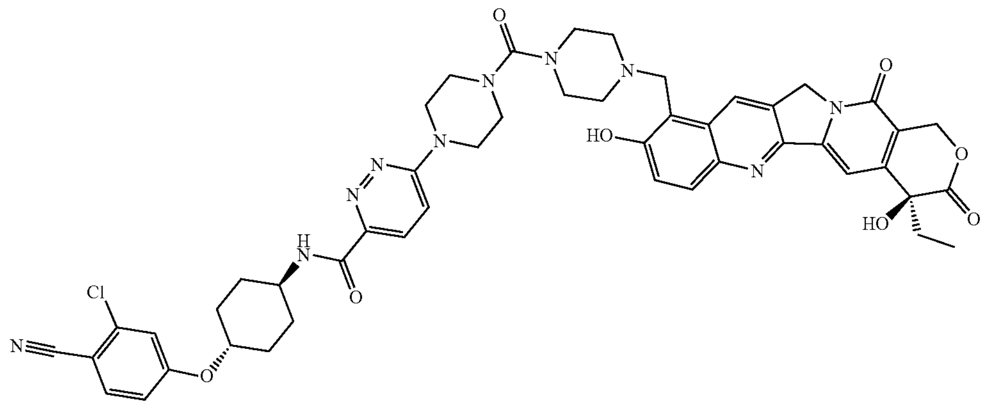 [SMILES: CC[C@@]1(O)C(=O)OCc2c1cc1n(c2=O)Cc2cc3c(CN4CCN(C(=O)N5CCN(c6ccc(C(=O)N[C@H]7CC[C@H](Oc8ccc(C#N)c(Cl)c8)CC7)nn6)CC5)CC4)c(O)ccc3nc2-1] |
| 29 | 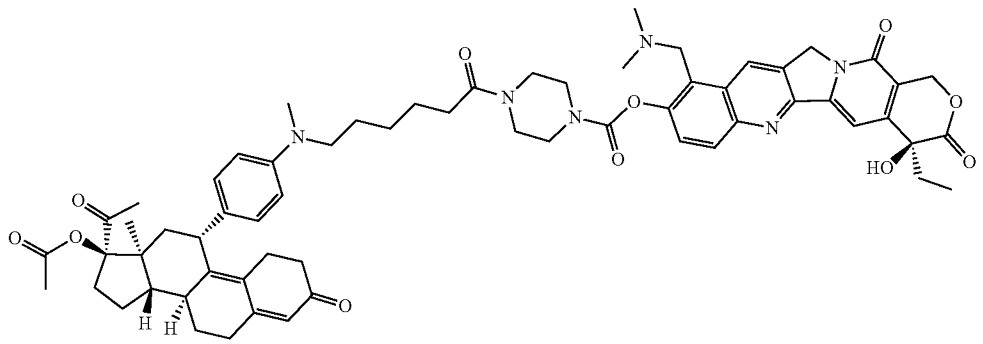 [SMILES: CC[C@@]1(O)C(=O)OCc2c1cc1n(c2=O)Cc2cc3c(CN(C)C)c(OC(=O)N4CCN(C(=O)CCCCCN(C)c5ccc([C@H]6C[C@@]7(C)[C@@H](CC[C@]7(OC(C)=O)C(C)=O)[C@@H]7CCC8=CC(=O)CCC8=C76)cc5)CC4)ccc3nc2-1] |
| 30 | 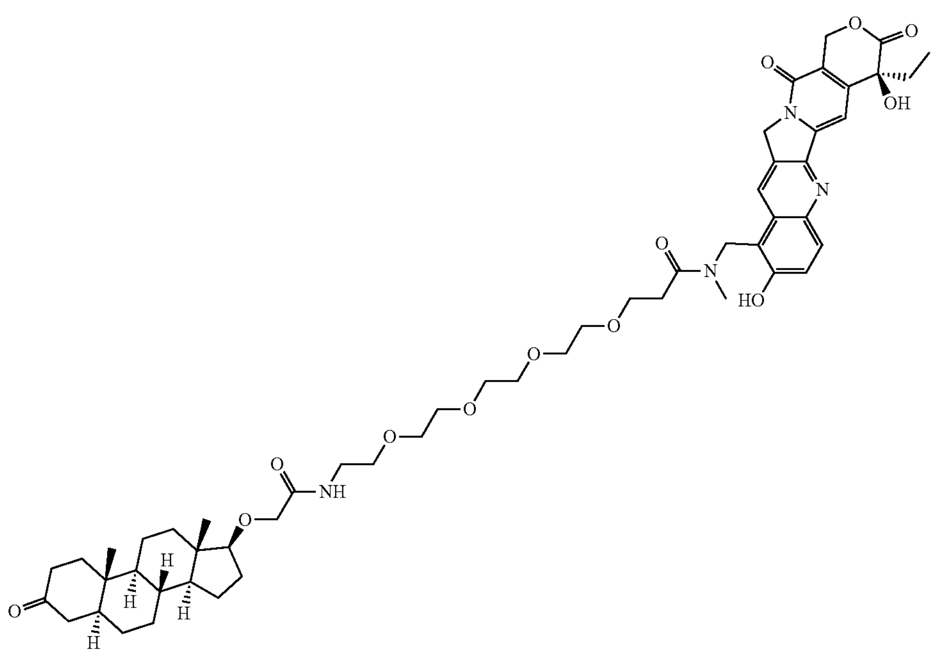 |

Methods of Treatment

Provided herein are compounds which can be used to treat, prevent, and/or delay the onset and/or development of cancer. Accordingly, in certain embodiments, provided is a method for the treatment of cancer, comprising administering to a subject in need of treatment a therapeutically-effective amount of a compound or composition described herein. Certain embodiments provide a method of potentiation of cytotoxic cancer therapy in a subject in recognized need of such treatment comprising administering to the subject a therapeutically acceptable amount of a compound or composition described herein.

It is contemplated that a patient having any cancer may benefit from being treated with the compounds and compositions described herein. Accordingly, in certain embodiments, the cancer is liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, Waldenström macroglobulinemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoides, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, trophoblastic neoplasms, or prostatic carcinoma. In certain embodiments, the cancer is bladder cancer, a blood cancer, such as leukemia (e.g., chronic leukemia, chronic lymphocytic leukemia (CLL, etc.) or lymphoma (e.g., Hodgkin lymphoma, non-Hodgkin lymphoma, low grade lymphoma, high grade lymphoma), lung cancer (e.g., small cell lung cancer), breast cancer, fallopian tube cancer, glioblastoma multiforme, head and neck cancer, esophageal cancer, ovarian cancer, pancreatic cancer, peritoneal cancer, prostate cancer, testicular cancer, skin cancer (e.g., melanoma) or uterine cancer. In certain embodiments, the cancer is bladder cancer, breast cancer, fallopian tube cancer, ovarian cancer, prostate cancer, peritoneal cancer, testicular cancer, endometrial cancer, or uterine cancer.

In certain embodiments, the cancer is chronic lymphocytic leukemia (CLL), Hodgkin lymphoma, non-Hodgkin lymphoma, Waldenström macroglobulinemia, polycythemia vera, trophoblastic neoplasms, and ovarian carcinoma.

In certain embodiments, the compounds and compositions as described herein are tailored to target cancers which overexpress a specific receptor, such as, but not limited to, androgen receptors, estrogen receptors, progesterone receptors, and/or glucocorticoid receptors by including an epitope which targets that specific nuclear receptor. The epitope can be derived from a steroid hormone or any non-steroidal drug which targets that particular receptor.

In certain embodiments, provided is a method of treating or preventing an androgen receptor overexpressing cancer, comprising administering an effective amount of a compound, or a pharmaceutically acceptable salt or solvate thereof, comprising at least one nuclear payload and at least one androgen receptor-targeting epitope to an individual in need thereof. Specific cancers which are contemplated to be treated by such methods include, but are not limited to, prostate, breast, triple negative breast cancer, bladder, or liver cancer. Also provided is a method of treating or preventing metastatic castration-resistant prostate cancer (mCRPC), comprising administering an effective amount of a compound or composition as described herein, or a pharmaceutically acceptable salt or solvate thereof, to an individual in need thereof.

In certain embodiments, provided is a method of treating or preventing an androgen receptor overexpressing cancer, comprising administering an effective amount of a compound, or a pharmaceutically acceptable salt or solvate thereof, comprising at least one nuclear payload and at least one androgen receptor-targeting epitope to an individual in need thereof. In certain embodiments, the cancer is prostate, breast, triple negative breast cancer, bladder, or liver cancer.

In certain embodiments, the androgen receptor-targeting epitope comprises an androgen receptor agonist, a selective androgen-receptor modulator (SARM), an androgen receptor antagonist, a selective estrogen receptor modulator (SERM), an estrogen receptor antagonist, a progestin, or an estrogen. In certain embodiments, the androgen receptor-targeting epitope comprises enobosarm, bicalutamide, flutamide, nilutamide, enzalutamide, tamoxifen, toremifene, raloxifene, fulvestrant, megestrol acetate, estramustine, ketoconazole, abiraterone, darolutamide, or an analog thereof. In certain embodiments, the androgen receptor-targeting epitope comprises enobosarm, bicalutamide, flutamide, nilutamide, enzalutamide, tamoxifen, toremifene, raloxifene, fulvestrant, megestrol acetate, estramustine, ketoconazole, abiraterone, or an analog thereof. In certain embodiments, the nuclear payload comprises a topoisomerase inhibitor.

In certain embodiments, provided is a method of treating or preventing an estrogen and/or progesterone receptor overexpressing cancer, comprising administering an effective amount of a compound, or a pharmaceutically acceptable salt or solvate thereof, comprising at least one nuclear payload and at least one estrogen and/or progesterone receptor-targeting epitope to an individual in need thereof. Specific cancers which are contemplated to be treated by such methods include, but are not limited to, breast, uterine, or ovarian cancer.

In certain embodiments, provided is a method of treating or preventing a glucocorticoid receptor overexpressing cancer, comprising administering an effective amount of a compound, or a pharmaceutically acceptable salt or solvate thereof, comprising at least one nuclear payload and at least one glucocorticoid receptor-targeting epitope to an individual in need thereof. Specific cancers which are contemplated to be treated by such methods include, but are not limited to, breast, uterine, or ovarian cancer. Specific cancers which are contemplated to be treated by such methods include, but are not limited to, prostate, possibly breast, uterine, ovarian.

Breast cancer includes ductal carcinoma in situ (DCIS) and invasive breast cancer. Breast cancers can occur in milk ducts, milk-producing lobules and connective tissues. Breast cancer includes estrogen receptor (ER) negative and hormone receptor (HR) negative, and also can be categorized as Group 3 (HER-2 positive) or Group 4 (basal-like).

Prostate cancer is a cancer which develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease. Rates of detection of prostate cancers vary widely across the world, with South and East Asia detecting less frequently than in Europe, and especially the United States. Prostate cancer develops most frequently in men over the age of fifty and is one of the most prevalent types of cancer in men. However, many men who develop prostate cancer never have symptoms, undergo no therapy, and eventually die of other causes. This is because cancer of the prostate is, in most cases, slow-growing, and because most of those affected are over the age of 60. Hence, they often die of causes unrelated to prostate cancer. Many factors, including genetics and diet, have been implicated in the development of prostate cancer. The presence of prostate cancer may be indicated by symptoms, physical examination, prostate specific antigen (PSA), or biopsy. There is concern about the accuracy of the PSA test and its usefulness in screening. Suspected prostate cancer is typically confirmed by taking a biopsy of the prostate and examining it under a microscope. Further tests, such as CT scans and bone scans, may be performed to determine whether prostate cancer has spread. Combination with primarily surgery and radiation therapy, or other treatments such as hormonal therapy, chemotherapy, proton therapy, cryosurgery, high intensity focused ultrasound (HIFU) are also contemplated.

Certain embodiments provide a method of inhibiting one or more topoisomerases in a subject in recognized need of such treatment comprising administering to the subject a therapeutically acceptable amount of a compound or composition described herein. In one embodiment, provided herein is a method of treating a disease ameliorated by the inhibition of one or more topoisomerases comprising administering to a subject in need of treatment a therapeutically-effective amount of a compound or composition described herein.

Certain embodiments provide a method of treating leukemia, colon cancer, glioblastomas, lymphomas, melanomas, carcinomas of breast, or cervical carcinomas in a subject in recognized need of such treatment comprising administering to the subject a therapeutically acceptable amount of a compound or composition described herein.

In some embodiments, provided herein is a method of treatment of a cancer deficient in Homologous Recombination (HR) dependent DNA double strand break (DSB) repair pathway, which includes administering to a subject in need of treatment a therapeutically-effective amount of a compound or composition described herein. In certain embodiments, the cancer includes one or more cancer cells having a reduced or abrogated ability to repair DNA DSB by HR relative to normal cells. In some embodiments, the cancer cells have a BRCA1 or BRCA2 deficient phenotype. In some embodiments, the cancer cells are deficient in BRCA1 or BRCA2. In some embodiments, the methods provided herein involve treatment of an individual who is heterozygous for a mutation in a gene encoding a component of the HR dependent DNA DSB repair pathway. In certain embodiment, the individual is heterozygous for a mutation in BRCA1 and/or BRCA2. In some embodiments, the method of treatment of a cancer includes treatment of breast, ovary, pancreas and/or prostate cancer. In some embodiments, the method of treatment of a cancer further includes administration of ionizing radiation or a chemotherapeutic agent.

The primary function of the DNA mismatch repair (MMR) system is to eliminate single-base mismatches and insertion-deletion loops that may arise during DNA replication. Insertion-deletion loops result from gains or losses of short repeat units within microsatellite sequences, also known as microsatellite instability (MSI). At least six different MMR proteins are required. For mismatch recognition, the MSH2 protein forms a heterodimer with either MSH6 or MSH3 depending on the type of lesion to be repaired (MSH6 is required for the correction of single-base mispairs, whereas both MSH3 and MSH6 may contribute to the correction of insertion-deletion loops). A heterodimer of MLH1 and PMS2 coordinates the interplay between the mismatch recognition complex and other proteins necessary for MMR. These additional proteins may include at least exonuclease 1 (EXO1), possibly helicase(s), proliferating cell nuclear antigen (PCNA), single-stranded DNA-binding protein (RPA), and DNA polymerases δ and ε. In addition to PMS2, MLH1 may heterodimerize with two additional proteins, MLH3 and PMS1. Recent observations indicate that PMS2 is required for the correction of single-base mismatches, and PMS2 and MLH3 both contribute to the correction of insertion-deletion loops. Additional homologs of the human MMR proteins are known that are required for functions other than MMR. These proteins include MSH4 and MSH5 that are necessary for meiotic (and possibly mitotic) recombination but are not presumed to participate in MMR.

Germline mutations of human MMR genes cause susceptibility to hereditary nonpolyposis colon cancer (HNPCC), one of the most common cancer syndromes in humans. An excess of colon cancer and a defined spectrum of extracolonic cancers, diagnosed at an early age and transmitted as an autosomal dominant trait, constitute the clinical definition of the syndrome. MSI, the hallmark of HNPCC, occurs in approximately 15% to 25% of sporadic tumors of the colorectum and other organs as well. According to international criteria, a high degree of MSI (MSI-H) is defined as instability at two or more of five loci or ≥30% to 40% of all microsatellite loci studied, whereas instability at fewer loci is referred to as MSI-low (MSI-L). MSI occurs in a substantial proportion (2% to 50% of tumors) among non-HNPCC cancers (e.g., cancers of the breast, prostate, and lung). On the basis of the proportion of unstable markers, categories MSS, MSI-L, and MSI-H can be distinguished in these cancers in analogy to HNPCC cancers. In one embodiment is a method for treating a cancer deficient in mismatch DNA repair pathway. In another embodiment is a method for treating a cancer demonstrating microsatellite instability due to reduced or impaired DNA repair pathways. In another embodiment is a method for treating a cancer demonstrating genomic instability due to reduced or impaired DNA repair pathways.

In certain embodiments, a compound or composition described herein, may be used in the preparation of a medicament for the treatment of cancer which is deficient in Homologous Recombination (HR) dependent DNA double strand break (DSB) repair activity, or in the treatment of a patient with a cancer which is deficient in HR dependent DNA DSB repair activity, which includes administering to said patient a therapeutically-effective amount of the compound or composition.

The HR dependent DNA DSB repair pathway repairs double-strand breaks (DSBs) in DNA via homologous mechanisms to reform a continuous DNA helix. The components of the HR dependent DNA DSB repair pathway include, but are not limited to, ATM (NM_000051), RAD51 (NM_002875), RAD51L1 (NM_002877), RAD51C (NM_002876), RAD51L3 (NM_002878), DMC1 (NM_007068), XRCC$_2$ (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS11M_00248_5). Other proteins involved in the HR dependent DNA DSB repair pathway include regulatory factors such as EMSY (Wood, et al., Science, 291, 1284-1289 (2001); Khanna et al., Nat. Genet. 27(3): 247-254 (2001); and Hughes-Davies, et al., Cell, 115, pp 523-535).

In some embodiments, a cancer which is deficient in HR dependent DNA DSB repair includes one or more cancer cells which have a reduced or abrogated ability to repair DNA DSBs through that pathway, relative to normal cells, i.e. the activity of the HR dependent DNA DSB repair pathway are reduced or abolished in the one or more cancer cells.

In certain embodiments, the activity of one or more components of the HR dependent DNA DSB repair pathway is abolished in the one or more cancer cells of an individual having a cancer which is deficient in HR dependent DNA DSB repair. Components of the HR dependent DNA DSB repair pathway include the components listed above.

In some embodiments, the cancer cells have a BRCA1 and/or a BRCA2 deficient phenotype, i.e., BRCA1 and/or BRCA2 activity is reduced or abolished in the cancer cells. In certain embodiments, cancer cells with this phenotype are deficient in BRCA1 and/or BRCA2, i.e., expression and/or activity of BRCA1 and/or BRCA2 is reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor or by an epigenetic mechanism such as gene promoter methylation.

BRCA1 and BRCA2 are tumor suppressors whose wild-type alleles are frequently lost in tumors of heterozygous carriers. BRCA1 and/or BRCA2 mutations are associated with breast cancer. Amplification of the EMSY gene, which encodes a BRCA2 binding factor, is associated with breast and ovarian cancer (Jasin M., *Oncogene,* 21(58), 8981-93 (2002); Tutt, et al, *Trends Mol. Med.,* 8(12), 571-6, (2002); and Radice, P. J., *Exp Clin Cancer Res.,* 21(3 Suppl), 9-12 (2002)).

Carriers of mutations in BRCA1 and/or BRCA2 are also at elevated risk of cancer of the ovary, prostate and pancreas.

In some embodiments, the individual is heterozygous for one or more variations, such as mutations and polymorphisms, in BRCA1 and/or BRCA2 or a regulator thereof. The detection of variation in BRCA1 and BRCA2 is described, for example in EP 699 754, EP 705 903, Neuhausen, S. L. and Ostrander, E. A., Genet. Test, 1, 75-83 (1992); Janatova M., et al, *Neoplasma,* 50(4), 246-50 (2003). Determination of amplification of the BRCA2 binding factor EMSY is described in Hughes-Davies, et al., *Cell,* 115, 523-535.

In certain instances, mutations and polymorphisms associated with cancer are detected at the nucleic acid level by detecting the presence of a variant nucleic acid sequence or at the protein level by detecting the presence of a variant (i.e. a mutant or allelic variant) polypeptide.

In certain embodiments, it is contemplated that the compounds described herein are useful for patients who have relapsed or become refractory. The term "relapsed" refers to disease (or cancer) that reappears or grows again after a period of remission. The term "refractory" is used to describe when the cancer does not respond to treatment or when the response to treatment does not last very long. For example, the compounds herein may be useful for treating cancer in patients who have previously been treated with the cancer therapies described herein, e.g. enzalutamide.

Certain embodiments provide a method of treating a viral infection in a subject in recognized need of such treatment comprising administering to the subject a therapeutically acceptable amount of a compound or composition described herein. In certain embodiments, compounds and compositions described herein can be used to treat RNA virus Enterovirus 71 (a causative agent of hand, foot, and mouth disease), Kaposi's sarcoma associated herpesvirus, HIV infection, Ebola virus, simian virus 40, parvoviruses, adenoviruses, herpesviruses, and other DNA viruses.

In certain embodiments, compounds and compositions described herein can be used to augment the effects of cancer immunotherapy. In certain embodiments, compounds and compositions described herein can be used to stimulate or attenuate immunological responses outside of cancer.

In certain embodiments, compounds and compositions described herein can be used to prevent the expression of pathogen-associated inflammatory genes. In certain embodiments, compounds and compositions described herein can be used to treat a *Staphylococcus aureus* infection in a subject in need of such treatment.

In certain embodiments, compounds and compositions described herein can be used to treat autoimmune disorders, such as lupus in a subject in need of such treatment.

In certain embodiments, compounds and compositions described herein can be used to treat a neurological or developmental disorder, such as Rett Syndrome or Angelman Syndrome, in a subject in need of such treatment.

Compositions

Compositions, including pharmaceutical compositions, of any of the compounds detailed herein are embraced by this disclosure. Thus, provided herein are pharmaceutical compositions comprising a compound of the disclosure, or a pharmaceutically acceptable salt thereof, and a pharmaceutically acceptable carrier or excipient. The pharmaceutical compositions provided herein may take a form suitable for oral, buccal, parenteral (e.g., intravenous, intramuscular, infusion or subcutaneous injection), nasal, topical or rectal administration, or a form suitable for administration by inhalation.

A compound as described herein may, in one aspect, be in a purified form. Compositions comprising a compound as described herein, or a salt thereof, are provided, such as compositions of substantially pure compounds. In some embodiments, a composition comprising a compound as described herein, or a salt thereof, is in substantially pure form. Unless otherwise stated, "substantially pure" refers to a composition which contains no more than 35% impurity, wherein the impurity denotes a compound other than the desired compound, or a salt thereof, which comprises the majority of the composition. In one variation, a composition of substantially pure compound, or a salt thereof, is provided wherein the composition contains no more than 25% impurity. In another variation, a composition of substantially pure compound, or a salt thereof, is provided wherein the composition contains or no more than 20% impurity. In still another variation, a composition of substantially pure compound, or a salt thereof, is provided wherein the composition contains or no more than 10% impurity. In a further variation, a composition of substantially pure compound, or a salt thereof, is provided wherein the composition contains or no more than 5% impurity. In another variation, a composition of substantially pure compound, or a salt thereof, is provided wherein the composition contains or no more than 3% impurity. In still another variation, a composition of substantially pure compound, or a salt thereof, is provided wherein the composition contains or no more than 1% impurity. In a further variation, a composition of substantially pure compound, or a salt thereof, is provided wherein the composition contains or no more than 0.5% impurity.

In certain embodiments, pharmaceutical compositions are formulated in any manner, including using one or more physiologically acceptable carriers comprising excipients and/or auxiliaries which facilitate processing of the active compounds into pharmaceutical compositions. In some embodiments, proper formulation is dependent upon the route of administration chosen. In various embodiments, any techniques, carriers, and excipients are used as suitable.

Provided herein are pharmaceutical compositions that include a compound described herein and a pharmaceutically acceptable diluent(s), excipient(s), and/or carrier(s). In addition, in some embodiments, the compounds described herein are administered as pharmaceutical compositions in which compounds described herein are mixed with other active ingredients, as in combination therapy.

A pharmaceutical composition, as used herein, refers to a mixture of a compound described herein with other chemical components, such as carriers, stabilizers, diluents, dispersing agents, suspending agents, thickening agents, and/or excipients. In certain embodiments, a pharmaceutical composition facilitates administration of the compound to an organism. In some embodiments, practicing the methods of treatment or use provided herein, includes administering or using a pharmaceutical composition comprising a therapeutically effective amount of a compound provided herein. In specific embodiments, the methods of treatment provided for herein include administering such a pharmaceutical composition to a mammal having a disease or condition to be treated. In one embodiment, the mammal is a human. In some embodiments, the therapeutically effective amount varies widely depending on the severity of the disease, the age and relative health of the subject, the potency of the compound used and other factors. In various embodiments, the compounds described herein are used singly or in combination with one or more therapeutic agents as components of mixtures.

In certain embodiments, the pharmaceutical compositions provided herein are formulated for intravenous injections. In certain aspects, the intravenous injection formulations provided herein are formulated as aqueous solutions, and, in some embodiments, in physiologically compatible buffers such as Hank's solution, Ringer's solution, or physiological saline buffer. In certain embodiments, the pharmaceutical compositions provided herein are formulated for transmucosal administration. In some aspects, transmucosal formulations include penetrants appropriate to the barrier to be permeated. In certain embodiments, the pharmaceutical compositions provided herein are formulated for other parenteral injections, appropriate formulations include aqueous or nonaqueous solutions, and in one embodiment, with physiologically compatible buffers or excipients.

In certain embodiments, the pharmaceutical compositions provided herein are formulated for oral administration. In certain aspects, the oral formulations provided herein comprise compounds described herein that are formulated with pharmaceutically acceptable carriers or excipients. Such carriers enable the compounds described herein to be formulated as tablets, powders, pills, dragees, capsules, liquids, gels, syrups, elixirs, slurries, suspensions and the like, for oral ingestion by a patient to be treated.

In some embodiments, pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are optionally added, such as the cross-linked croscarmellose sodium, polyvinylpyrrolidone, agar, or alginic acid or a salt thereof such as sodium alginate.

In certain embodiments, provided herein is a pharmaceutical composition formulated as dragee cores with suitable coatings. In certain embodiments, concentrated sugar solutions are used in forming the suitable coating, and optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs and/or pigments are added to tablets, dragees and/or the coatings thereof for, e.g., identification or to characterize different combinations of active compound doses.

In certain embodiments, pharmaceutical compositions which are used include orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In certain embodiments, in soft capsules, the active compounds are dissolved or suspended in suitable liquids, such as fatty oils, liquid paraffin, or liquid polyethylene glycols. In addition, stabilizers are optionally added. In certain embodiments, the formulations for oral administration are in dosages suitable for such administration.

In certain embodiments, the pharmaceutical compositions provided herein are formulated for buccal or sublingual administration. In certain embodiments, buccal or sublingual compositions take the form of tablets, lozenges, or gels formulated in a conventional manner. In certain embodiments, parenteral injections involve bolus injection or continuous infusion. In some embodiments, formulations for injection are presented in unit dosage form, e.g., in ampoules or in multi-dose containers, with an added preservative. In some embodiments, the pharmaceutical composition described herein is in a form suitable for parenteral injection as a sterile suspensions, solutions or emulsions in oily or aqueous vehicles, and optionally contains formulatory agents such as suspending, stabilizing and/or dispersing agents. Pharmaceutical formulations for parenteral administration include aqueous solutions of the active compounds in water-soluble form. In some embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In certain embodiments, aqueous injection suspensions contain substances which increase the viscosity of the suspension, such as sodium carboxymethyl cellulose, sorbitol, or dextran. Optionally, the suspensions also contain suitable stabilizers or agents which increase the solubility of the compounds to allow for the preparation of highly concentrated solutions. In alternative embodiments, the active ingredient is in powder form for constitution with a suitable vehicle, e.g., sterile pyrogen-free water, before use.

In some embodiments, the compounds described herein are administered topically. In specific embodiments, the compounds described herein are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and/or preservatives.

In certain embodiments, the pharmaceutical compositions provided herein are formulated for transdermal administration of compounds described herein. In some embodiments, administration of such compositions employs transdermal delivery devices and transdermal delivery patches. In certain embodiments, the compositions are lipophilic emulsions or buffered, aqueous solutions, dissolved and/or dispersed in a polymer or an adhesive. Such patches include those constructed for continuous, pulsatile, or on demand delivery of pharmaceutical agents. In some embodiments, transdermal delivery of the compounds described herein is accomplished by use of iontophoretic patches and the like. In certain embodiments, the rate of absorption is slowed by using rate-controlling membranes or by trapping the compound within a polymer matrix or gel. Conversely, absorption enhancers are optionally used to increase absorption. Absorption enhancer and carrier include absorbable pharmaceutically acceptable solvents that assist in passage of the compound through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In certain embodiments, the pharmaceutical compositions provided herein are formulated for administration by inhalation. In certain embodiments, in such pharmaceutical compositions formulated for inhalation, the compounds described herein are in a form as an aerosol, a mist or a powder. In some embodiments, pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In certain aspects of a pressurized aerosol, the dosage unit is determined by providing a valve to deliver a metered amount. In certain embodiments, capsules and cartridges of, such as, by way of example only, gelatin for use in an inhaler or insufflator is formulated containing a powder mix of the compound described herein and a suitable powder base such as lactose or starch.

In some embodiments, the compounds described herein are formulated in rectal compositions such as enemas, rectal gels, rectal foams, rectal aerosols, suppositories, jelly suppositories, or retention enemas. In certain embodiments, rectal compositions optionally contain conventional suppository bases such as cocoa butter or other glycerides, as well as synthetic polymers such as polyvinylpyrrolidone, PEG, and the like. In certain suppository forms of the compositions, a low-melting wax such as, but not limited to, a mixture of fatty acid glycerides, optionally in combination with cocoa butter is first melted.

In various embodiments provided herein, the pharmaceutical compositions are formulated in a conventional manner using one or more physiologically acceptable carriers comprising excipients and auxiliaries which facilitate processing of the active compounds into pharmaceutically acceptable preparations. In certain embodiments, proper formulation is dependent upon the route of administration chosen. In various embodiments, any of the techniques, carriers, and excipients is used as suitable. In some embodiments, pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

In certain embodiments, the pharmaceutical compositions include at least one pharmaceutically acceptable carrier, diluent or excipient and a compound described herein described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds described herein exist as tautomers. All tautomers are included within the scope of the compounds presented herein. Additionally, included herein are the solvated and unsolvated forms of the compounds described herein. Solvated compounds include those that are solvated with pharmaceutically acceptable solvents such as water, ethanol, and the like. The solvated forms of the compounds presented herein are also considered to be disclosed herein. In some embodiments, the pharmaceutical compositions described herein include other medicinal or pharmaceutical agents, carriers, adjuvants, such as preserving, stabilizing, wetting or emulsifying agents, solution promoters, salts for regulating the osmotic pressure, and/or buffers. In additional embodiments, the pharmaceutical compositions described herein also contain other therapeutically valuable substances.

Methods for the preparation of compositions containing the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. In various embodiments, the compositions are in liquid solutions or suspensions, solid forms suitable for solution or suspension in a liquid prior to use, or as emulsions. These compositions optionally contain minor amounts of nontoxic, auxiliary substances, such as wetting or emulsifying agents, pH buffering agents, and so forth.

In some embodiments, a composition comprising a compound described herein takes the form of a liquid where the agents are present in solution, in suspension or both. In some embodiments, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

Useful aqueous suspension optionally contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions optionally comprise an mucoadhesive polymer, selected for example from carboxymethylcellulose, carbomer (acrylic acid polymer), poly (methylmethacrylate), polyacrylamide, polycarbophil, acrylic acid/butyl acrylate copolymer, sodium alginate and dextran.

Useful compositions optionally include solubilizing agents to aid in the solubility of a compound described herein. The term "solubilizing agent" generally includes agents that result in formation of a micellar solution or a true solution of the agent. Solubilizing agents include certain acceptable nonionic surfactants, for example polysorbate 80, and ophthalmically acceptable glycols, polyglycols, e.g., polyethylene glycol 400, and glycol ethers.

Useful compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Certain useful compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Some useful compositions optionally include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Certain useful compositions optionally one or more antioxidants to enhance chemical stability where required. Suitable antioxidants include, by way of example only, ascorbic acid and sodium metabisulfite.

In some embodiments, aqueous suspension compositions are packaged in single-dose non-reclosable containers. In alternative embodiments, multiple-dose reclosable containers are used, in which case it is typical to include a preservative in the composition.

In various embodiments, any delivery system for hydrophobic pharmaceutical compounds is employed. Liposomes and emulsions are examples of delivery vehicles or carriers for hydrophobic drugs. In certain embodiments, certain organic solvents such as N-methylpyrrolidone are employed. In some embodiments, the compounds are delivered using a sustained-release system, such as semipermeable matrices of solid hydrophobic polymers containing the therapeutic agent. Various sustained-release materials are utilized in the embodiments herein. In certain embodiments, sustained-release capsules release the compounds for a few weeks up to over 100 days. In some embodiments, depending on the chemical nature and the biological stability of the therapeutic reagent, additional strategies for protein stabilization are employed.

In certain embodiments, the formulations or compositions described herein benefit from and/or optionally comprise antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Dosing and Treatment Regimens

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. In some embodiments, amounts effective for this use will depend on the severity and course of the disease or condition, previous therapy, the patient's health status, weight, and response to the drugs, and the judgment of the treating physician. In certain instances, it is considered appropriate for the caregiver to determine such therapeutically effective amounts by routine experimentation (including, but not limited to, a dose escalation clinical trial).

In certain prophylactic applications, compositions containing the compounds described herein are administered to a patient susceptible to or otherwise at risk of a particular disease, disorder or condition. In some embodiments, the amount administered is defined to be a "prophylactically effective amount or dose." In certain embodiments of this use, the precise amounts of compound administered depend on the patient's state of health, weight, and the like. In some embodiments, it is considered appropriate for the caregiver to determine such prophylactically effective amounts by routine experimentation (e.g., a dose escalation clinical trial). In certain embodiments, when used in a patient, effective amounts for this use will depend on the severity and course of the disease, disorder or condition, previous therapy, the patient's health status and response to the drugs, and the judgment of the treating physician.

In certain instances, a patient's condition does not improve or does not significantly improve following administration of a compound or composition described herein and, upon the doctor's discretion the administration of the compounds is optionally administered chronically, that is, for an extended period of time, including throughout the duration of the patient's life in order to ameliorate or otherwise control or limit the symptoms of the patient's disease or condition.

In certain cases wherein the patient's status does improve or does not substantially improve, upon the doctor's discretion the administration of the compounds are optionally given continuously; alternatively, the dose of drug being administered is optionally temporarily reduced or temporarily suspended for a certain length of time (i.e., a "drug holiday"). In certain embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes a reduction from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, once improvement of the patient's conditions has occurred, a maintenance dose is administered if necessary. In some embodiments, the dosage, e.g., of the maintenance dose, or the frequency of administration, or both, are reduced, as a function of the symptoms, to a level at which the improved disease, disorder or condition is retained. In certain embodiments, however, patients are optionally given intermittent treatment on a long-term basis upon any recurrence of symptoms.

In certain embodiments, the amount of a given agent that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In certain embodiments, however, doses employed for adult human treatment is in the range of about 0.02 to about 5000 mg per day, in a specific embodiment about 1 to about 1500 mg per day. In various embodiments, the desired dose is conveniently presented in a single dose or as divided doses administered simultaneously (or over a short period of time) or at appropriate intervals, for example as two, three, four or more sub-doses per day.

In some embodiments, the pharmaceutical compositions described herein are in a unit dosage form suitable for single administration of precise dosages. In some instances, in unit dosage form, the formulation is divided into unit doses containing appropriate quantities of one or more compound. In certain embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In alternative embodiments, multiple-dose reclosable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In certain embodiments, the daily dosages appropriate for the compounds described herein described herein are from about 0.01 to about 10 mg/kg per body weight. In some embodiments, an indicated daily dosage in the larger subject, including, but not limited to, humans, is in the range from about 0.5 mg to about 1,000 mg, conveniently administered in divided doses, including, but not limited to, up to four times a day or in extended release form. In certain embodiments, suitable unit dosage forms for oral administration comprise from about 1 to about 50 mg active ingredient. The foregoing ranges are merely suggestive, as the number of variables in regard to an individual treatment regime is large, and considerable excursions from these recommended values are not uncommon. In certain embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

In certain embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. In certain embodiments, compounds exhibiting high therapeutic indices are disclosed. In some embodiments, the data obtained from cell culture assays and animal studies is used in formulating a range of dosage for use in human. In specific embodiments, the dosage of such compounds lies within a range of circulating concentrations that include the $ED_{50}$ with minimal toxicity. In certain embodiments, the dosage varies within this range depending upon the dosage form employed and the route of administration utilized.

In certain embodiments, the disclosed compounds exhibit an increased affinity for a nuclear target, increased potency or increased therapeutic index as compared to an unmodified nuclear payload from which the compound was derived. In certain embodiments, this higher affinity, potency or therapeutic index may provide benefits, such as allowing for the administration of lower doses and thus reduced potential for toxicity, improvement in therapeutic index and decreased overall cost of therapy. In certain embodiments, the daily dosages appropriate for administration of the compounds described herein is less than 100% of the recommended daily dose of the unmodified nuclear payload, or less than about 90%, or less than about 80% or less than about 70%, or less than about 60%, or less than about 50%, or less than about 40%, or from about 20% to about 90%, or from about 30% to about 90%, or from about 40% to about 90%, or from about 50% to about 90%, or from about 60% to about 90%, or from about 70% to about 90%, or from about 20% to about 80%, or from about 30% to about 80%, or from about 40% to about 80%, or from about 50% to about 80%, or from about 60% to about 80%, or from about 70% to about 80%, or from about 20% to about 70%, or from about 30% to about 70%, or from about 40% to about 70%, or from about 50% to about 70%, or from about 60% to about 70%, of the recommended daily dose of the unmodified nuclear payload.

In certain embodiments, the compounds described herein are used in the preparation or manufacture of medicaments for the treatment of diseases or conditions that are mediated by a topoisomerase inhibitor or in which inhibition of one or more topoisomerase ameliorates the disease or condition. In some embodiments, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

Combination Therapy

Compounds described herein can also be used in combination with other active ingredients. Such combinations are selected based on the condition to be treated, cross-reactivities of ingredients and pharmaco-properties of the combination. In one embodiment, the disclosure provides a use of a compound as described herein used in combination with another agent or therapy method, such as another cancer treatment. For example, when treating cancer, the compositions can be combined with other anti-cancer compounds (such as paclitaxel or rapamycin).

It is also possible to combine a compound of the disclosure with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-cancer effect denotes an anti-cancer effect that is greater than the predicted purely additive effects of the individual compounds of the combination.

Administration of the compounds and compositions of the present disclosure to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described active agent(s). These therapies include but are not limited to chemotherapy, radiotherapy, immunotherapy, gene therapy and surgery.

In some embodiments, provided herein is a method for the treatment of cancer, comprising administering to a subject in need of treatment a therapeutically-effective amount of a compound or composition described herein in combination with ionizing radiation or one or more chemotherapeutic agents. In some embodiments, the compound described herein is administered simultaneously with ionizing radiation or one or more chemotherapeutic agents. In other embodiments, the compound described herein is administered sequentially with ionizing radiation or one or more chemotherapeutic agents.

In certain embodiments, provided herein is a method for the treatment of cancer, which includes administering to a subject in need of treatment a therapeutically-effective amount of a compound or composition described herein in combination with ionizing radiation and one or more chemotherapeutic agents. In some embodiments, the compound described herein is administered simultaneously with ionizing radiation and one or more chemotherapeutic agents. In other embodiments, the compound described herein is administered sequentially with ionizing radiation and one or more chemotherapeutic agents.

In certain embodiments, provided herein is a method for the treatment of cancer, which includes administering to a subject in need of treatment a therapeutically-effective amount of a compound or composition described herein in combination with ionizing radiation. In certain embodiments, the radiation is administered at a dose of less than about 2.5 Gy per day, or about 2.0 Gy per day, or about 1.8 Gy per day, or about 1.6 Gy per day, or about 1.4 Gy per day, or about 1.2 Gy per day. In certain embodiments, a dose of less than about 2.5 Gy, or about 2.0 Gy, or about 1.8 Gy, or about 1.6 Gy, or about 1.4 Gy, or about 1.2 Gy is administered about 5 times per week. In certain embodiments, the radiation is administered at a dose of less than about 2.5 Gy per day, or about 2.0 Gy per day, or about 1.8 Gy per day, or about 1.6 Gy per day, or about 1.4 Gy per day, or about 1.2 Gy per day. In certain embodiments, a dose of less than about 2.5 Gy, or about 2.0 Gy, or about 1.8 Gy, or about 1.6 Gy, or about 1.4 Gy, or about 1.2 Gy is administered about 6 times per week. It is contemplated that by administering radiation in combination with a compound or composition described herein, prostate specific chemical prostatectomy can be achieved while avoiding detrimental side effects, such as the impotence and incontinence of surgical prostatectomy due to disruption of vessels and nerves.

Cancer therapies can also include a variety of combination therapies with both chemical and radiation based treatments. Combination chemotherapies include the use of chemotherapeutic agents such as, cisplatin, etoposide, irinotecan, camptostar, topotecan, paclitaxel, docetaxel, epothilones, taxotere, tamoxifen, 5-fluorouracil, methotrexate, temozolomide, cyclophosphamide, SCH 66336, R115777, L778,123, BMS 214662, IRESSA® (gefitinib), TARCEVAR® (erlotinib hydrochloride), antibodies to EGFR, GLEEVEC® (imatinib), intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, Mitomycin-C, L-Asparaginase, teniposide, 17α-Ethinylestradiol, Diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesterone acetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, Avastin, herceptin, Bexxar, Velcade, Zevalin, Trisenox, Xeloda, Vinorelbine, Porfimer, Erbitux® (cetuximab), Liposomal, Thiotepa, Altretamine, Melphalan, Trastuzumab, Lerozole, Fulvestrant, Exemestane, Ifosfomide, Rituximab, $C_{225}$, Campath, carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, paclitaxel, gemcitabine, navelbine, farnesylprotein transferase inhibitors, transplatinum, 5-fluorouracil, vincristine, vinblastine and methotrexate, or any analog or derivative variant of the foregoing.

In certain embodiments, a compound described herein is administered in combination with a CDK inhibitor (e.g., a CDK2, CDK4, CDK6 inhibitor, or a CDK 4/6 inhibitor).

Other factors that cause DNA damage, such as radiotherapy, have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (e.g., 3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

In yet another embodiment, the secondary treatment is a secondary gene therapy in which a therapeutic polynucleotide is administered before, after, or at the same time a first chemotherapeutic agent. Delivery of the chemotherapeutic agent in conjunction with a vector encoding a gene product will have a combined anti-hyperproliferative effect on target tissues.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Administration of the compound or composition as described herein may precede or follow the other anti-cancer agent or treatment by intervals ranging from minutes to weeks. In embodiments where the other anti-cancer agent and expression construct are applied separately, one would generally ensure that a significant period of time did not elapse between the time of each delivery, such that the agent and expression construct would still be able to exert an advantageously combined effect on a cell. For example, in such instances, it is contemplated that one may contact a cell, tissue or organism with two, three, four or more modalities substantially simultaneously (i.e., within less than about a minute) with the active agent(s). In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 6 hours, about 8 hours, about 9 hours, about 12 hours, about 15 hours, about 18 hours, about 21 hours, about 24 hours, about 28 hours, about 31 hours, about 35 hours, about 38 hours, about 42 hours, about 45 hours, to about 48 hours or more prior to and/or after administering the active agent(s). In certain other embodiments, an agent may be administered within from about 1 day, about 2 days, about 3 days, about 4 days, about 5 days, about 6 days, about 8 days, about 9 days, about 12 days, about 15 days, about 16 days, about 18 days, about 20 days, to about 21 days prior to and/or after administering the active agent(s). In some situations, it may be desirable to extend the time period for treatment significantly, however, where several weeks (e.g., about 1, about 2, about 3, about 4, about 6, or about 8 weeks or more) lapse between the respective administrations.

Kits

Kits for use to achieve anti-cancer effects comprising a compound or composition described herein are provided. In certain embodiments, the kit comprises a unit dose of a compound or composition described herein and instructions for administering the same. In certain aspects, the kit further comprises a second drug suitable for anti-cancer therapy, or instructions for co-administering an additional anti-cancer therapy (such as radiation or gene therapy). In another aspect, kits for use to achieve anti-cancer effects comprise a low dose (e.g., less than about 500 mg/day, or less than about 400 mg/day, or less than about 300 mg/day, or less than about 200 mg/day) of a compound or composition described herein and a second drug suitable for anti-cancer therapy. In yet another variation, kits for use to achieve anti-cancer effects comprise a high dose (e.g., greater than about 500 mg/day) of a compound or composition as described herein and a second drug suitable for anti-cancer therapy.

Methods of Manufacturing a Medicament

In a further aspect of the disclosure, use of the compounds and compositions described herein in the manufacture of a medicament is provided. In particular, the manufacture of a medicament for use in the treatment of cancer, or diseases or conditions which can be mediated, at least in part, by blocking DNA repair and/or transcription activation, such as by inhibition of one or more topoisomerase, are provided. Further, pharmaceutical compositions of a compound described herein are also intended for use in the manufacture of a medicament for use in treatment of diseases or conditions which can be mediated, at least in part, by inhibition of one or more topoisomerase.

NUMBERED EMBODIMENTS

Embodiment 1: A compound of Formula I, II, or III, or stereoisomer, mixture of stereoisomers, hydrate, solvate, isotopically enriched analog, or pharmaceutically acceptable salt thereof:

A¹-(L¹-B¹)_{m'}    I

A¹-L¹-(B¹)_{m'}    II

A¹-L¹-B¹    III wherein:
A¹ is a topoisomerase inhibitor or analog thereof;
m' is 1, 2 or 3;
each B¹ is independently a nuclear receptor-targeting epitope; and
L¹ is a linking moiety.

Embodiment 2: The compound of embodiment 1, or stereoisomer, mixture of stereoisomers, hydrate, solvate, isotopically enriched analog, or pharmaceutically acceptable salt thereof, wherein A¹ is selected from:

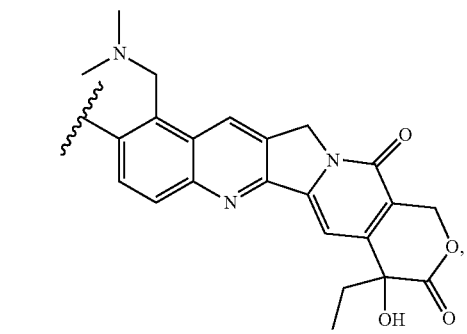

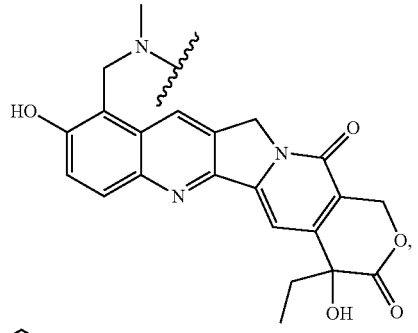

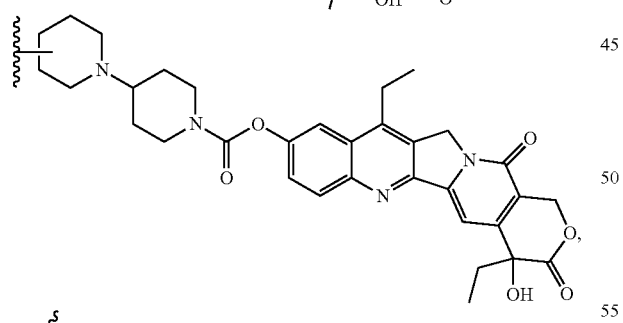

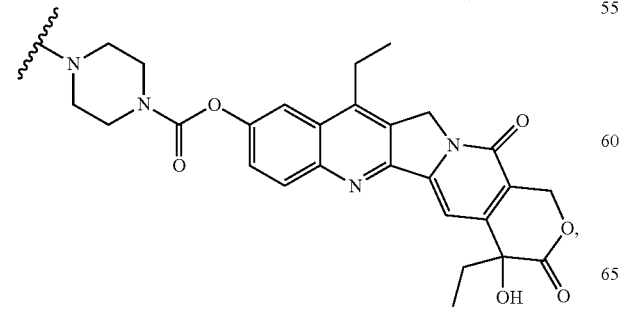

-continued

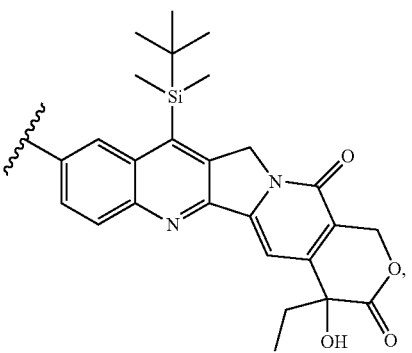

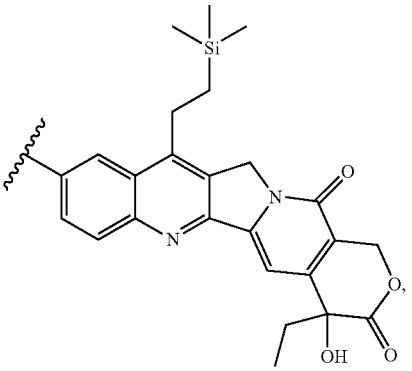

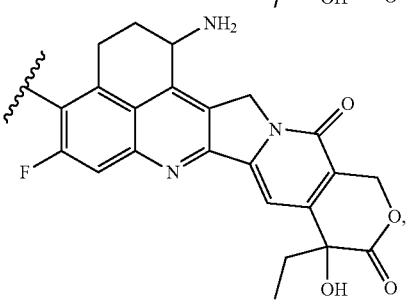

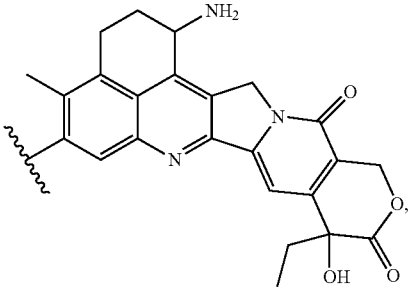

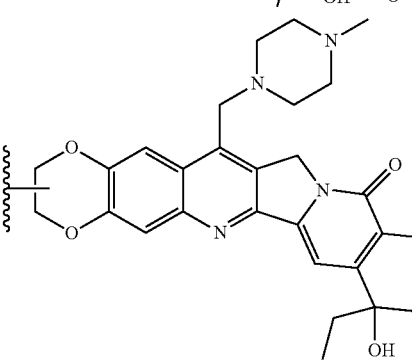

-continued

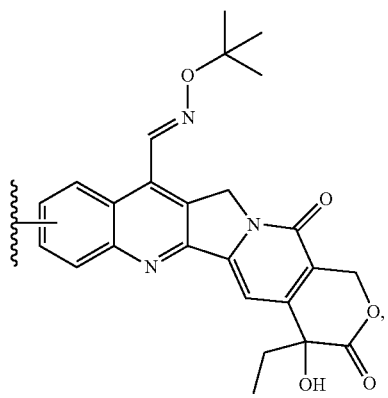

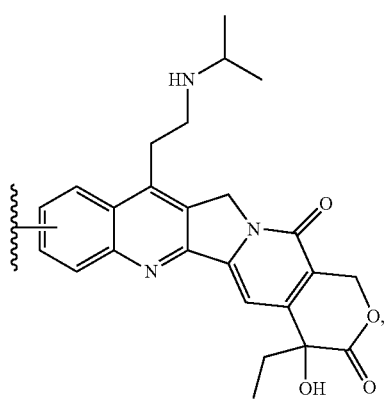

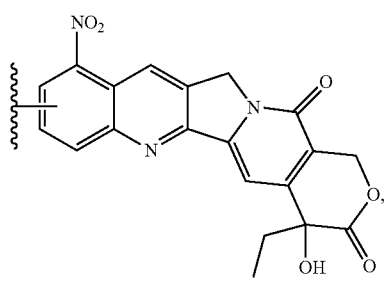

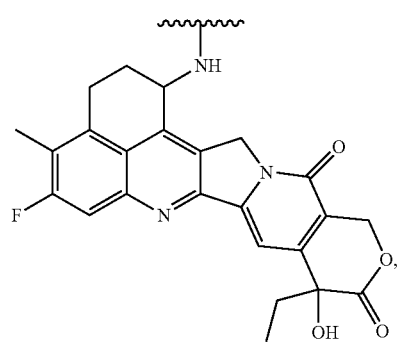

-continued

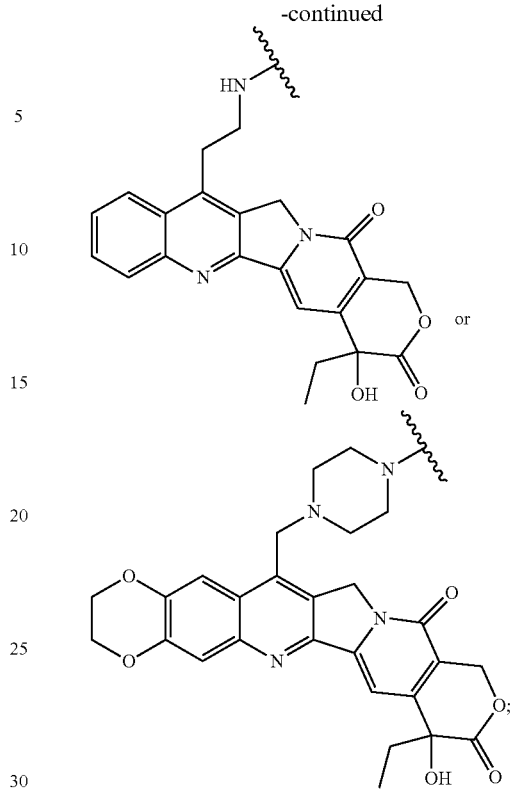

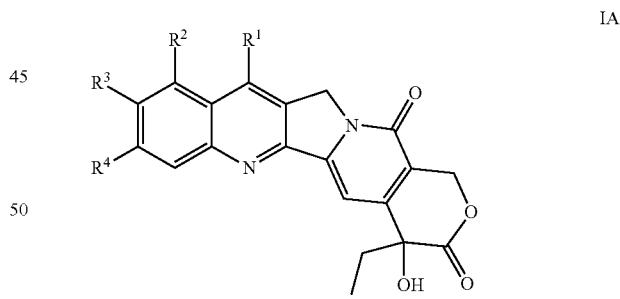

where the wavy line indicates the point of attachment to -L$^1$-B$^1$.

Embodiment 3: The compound of embodiment 1 or 2, wherein m' is 1.

Embodiment 4: A compound of Formula IA, or stereoisomer, mixture of stereoisomers, hydrate, solvate, isotopically enriched analog, or pharmaceutically acceptable salt thereof:

IA wherein:
R$^1$, R$^2$, R$^3$ and R$^4$ are each independently hydrogen, halo, cyano, nitro, —OR$^{15}$, —SR$^{15}$, —NR$^{15}$R$^{16}$, C$_{1-12}$ alkyl, C$_{2-12}$ alkenyl, C$_{2-12}$ alkynyl, C$_{3-10}$ cycloalkyl, heterocyclyl, aryl, heteroaryl, —C(=O)R$^{15}$, —C(=O)OR$^{15}$, —OC(=O)R$^{15}$, —C(=O)NR$^{15}$R$^{16}$, —NR$^{15}$C(=O)R$^{16}$, —NR$^{15}$C(=O)OR$^{16}$, —S(=O)$_{1-2}$R$^{15}$, —S(=O)$_{1-2}$NR$^{15}$R$^{16}$, —NR$^{15}$S(=O)$_{1-2}$R$^{16}$, —Si(R$^{15}$)$_3$, or —C=NOR$^{15}$, wherein each alkyl, alkenyl, alkynyl, cycloalkyl, heterocyclyl, aryl and heteroaryl of R$^1$, R$^2$, R$^3$ and R$^4$ are independently optionally substituted with one or more R$^{10}$ as valency permits;

or $R^1$ and $R^2$ are taken together with the atoms to which they are attached to form a $C_{3-10}$ cycloalkyl, heterocyclyl, aryl, or heteroaryl, optionally substituted with one or more $R^{10}$ as valency permits;

or $R^2$ and $R^3$ are taken together with the atoms to which they are attached to form a $C_{3-10}$ cycloalkyl, heterocyclyl, aryl, or heteroaryl, optionally substituted with one or more $R^{10}$ as valency permits;

or $R^3$ and $R^4$ are taken together with the atoms to which they are attached to form a $C_{3-10}$ cycloalkyl, heterocyclyl, aryl, or heteroaryl, optionally substituted with one or more $R^{10}$ as valency permits;

each $R^{10}$ is independently halo, cyano, nitro, —$OR^{17}$, —$SR^{17}$, —$SF_5$, —$NR^{17}R^{18}$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)$R^{17}$, —C(=O)$OR^{17}$, —OC(=O)$OR^{17}$, —OC(=O)$R^{17}$, —C(=O)$NR^{17}R^{18}$, —OC(=O)$NR^{17}R^{18}$, —$NR^7C$(=O)$NR^{17}R^{18}$, —S(=O)$_{1-2}R^{17}$, —S(=O)$_{1-2}NR^{17}R^{18}$, —$NR^{17}S$(=O)$_{1-2}R^{18}$, —$NR^{17}S$(=O)$_{1-2}NR^{17}R^{18}$, —$NR^{17}C$(=O)$R^{18}$, —$NR^{17}C$(=O)$OR^{18}$, —Si($R^{17}$)$_3$, or —C=$NOR^{17}$, wherein each alkyl, alkenyl, alkynyl, cycloalkyl, heterocyclyl, aryl and heteroaryl of $R^{10}$ are independently optionally substituted with one or more halo or $C_{1-12}$ alkyl optionally substituted by oxo, halo, hydroxyl or amino as valency permits; and each $R^{15}$ and $R^{16}$ is independently hydrogen, $C_{1-12}$ alkyl, $C_{2-12}$ alkenyl, $C_{2-12}$ alkynyl, or $C_{3-12}$ cycloalkyl, wherein each $C_{1-12}$ alkyl, $C_{2-12}$ alkenyl, $C_{2-12}$ alkynyl, or $C_{3-12}$ cycloalkyl is optionally independently substituted with oxo, halo, hydroxyl or amino as valency permits; or $R^{15}$ and $R^{16}$ are taken together with the atoms to which they are attached to form heterocyclyl optionally substituted by halo or $C_{1-12}$ alkyl optionally substituted by oxo, halo, hydroxyl or amino; and each $R^{17}$ and $R^{18}$ is independently hydrogen, $C_{1-12}$ alkyl, $C_{2-12}$ alkenyl, $C_{2-12}$ alkynyl, or $C_{3-12}$ cycloalkyl, wherein each $C_{1-12}$ alkyl, $C_{2-12}$ alkenyl, $C_{2-12}$ alkynyl, or $C_{3-12}$ cycloalkyl is optionally substituted with oxo, halo, hydroxyl or amino as valency permits; or $R^{17}$ and $R^{18}$ are taken together with the atoms to which they are attached to form heterocyclyl optionally substituted by halo or $C_{1-12}$ alkyl optionally substituted by oxo, halo, hydroxyl or amino;

where one or more atoms (e.g., hydrogen, methyl, hydroxy, etc.) is replaced by a direct covalent bond to at least one nuclear receptor-targeting epitope(s), optionally via a linking moiety (e.g., -$L^1$-$B^1$) as defined herein.

Embodiment 5: A compound of Formula IB, or stereoisomer, mixture of stereoisomers, hydrate, solvate, isotopically enriched analog, or pharmaceutically acceptable salt thereof:

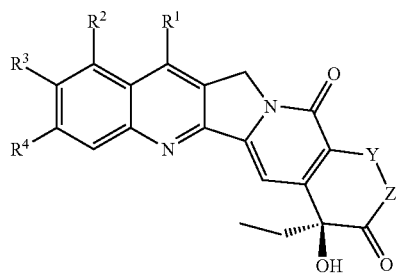

IB wherein:
$R^1$ is hydrogen or -$L^1$-$B^1$;
$R^2$ is hydrogen, $NH_2$, $NO_2$, or -$L^1$-$B^1$;
$R^3$ is hydrogen, halo, methyl, methoxy, or -$L^1$-$B^1$;
$R^4$ is hydrogen, halo, methyl, or methoxy; or
$R^3$ and $R^4$ together form a —O—$CH_2$—O— or —O—$CH_2CH_2$—O—;
Y is a bond, —$CH_2$—, or —$CH_2$—$CH_2$—; and
Z is a bond or O.

Embodiment 6: The compound of embodiment 5, wherein only one of $R^1$, $R^2$ or $R^3$ is -$L^1$-$B^1$.

Embodiment 7: The compound of embodiment 5, wherein $R^2$ is -$L^1$-$B^1$.

Embodiment 8: The compound of embodiment 5, wherein $R^3$ is -$L^1$-$B^1$.

Embodiment 9: The compound of any preceding embodiment, wherein $L^1$ is of the formula:

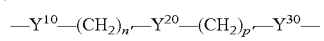

wherein each of $Y^{10}$, $Y^{20}$, and $Y^{30}$ are independently a bond, optionally substituted alkylene, optionally substituted heteroalkylene, optionally substituted arylene, optionally substituted heteroarylene, optionally substituted cycloalkylene, optionally substituted heterocyclylene, —$CR^{110}R^{120}$—, —$NR^{110}$—, —O—, —S(O)$_{0-2}$—, —$NR^{110}C(O)$—, —C(O)$NR^{110}$—, —$NR^{110}S(O)_2$—, —S(O)$_2NR^{110}$—, —$CR^{120}$=N—$NR^{110}$—, —$NR^{110}$—N=$CR^{120}$—, or —C(O)—;

each $R^{110}$ is independently hydrogen, $C_{1-4}$ alkyl, $C_{1-4}$ haloalkyl, aryl, heteroaryl, cycloalkyl or heterocyclyl;

each $R^{120}$ is independently hydrogen, $C_{1-4}$ alkyl, $C_{1-4}$ haloalkyl, aryl, heteroaryl, cycloalkyl or heterocyclyl; and n' and p' are each independently 0, 1, 2, 3, 4, 5, 6, 7, or 8.

Embodiment 10: The compound of any preceding embodiment, wherein $L^1$ comprises a non-biocleavable moiety.

Embodiment 11: The compound of any preceding embodiment, wherein $L^1$ is an optionally substituted alkylene or optionally substituted heteroalkylene.

Embodiment 12: The compound of any preceding embodiment, wherein $L^1$ comprises an optionally substituted $C_{4-7}$ atom alkylene, optionally substituted $C_{4-7}$ atom heterocyclylene, or optionally substituted $C_{4-7}$ atom heteroalkylene.

Embodiment 13: The compound of any preceding embodiment, wherein $L^1$ is optionally substituted $C_{4-10}$ atom heteroalkylene.

Embodiment 14: The compound of any preceding embodiment, wherein $L^1$ is a 4-7 atom alkylene or heteroalkylene linking moiety containing $CH_2$ and up to 2 heteroatoms each independently selected from NH, O or S, and optionally one C=O.

Embodiment 15: The compound of any preceding embodiment, wherein the linking moiety is of the formula:

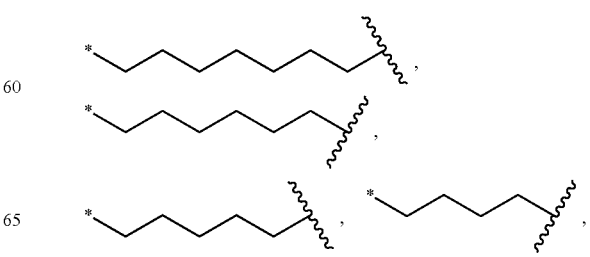

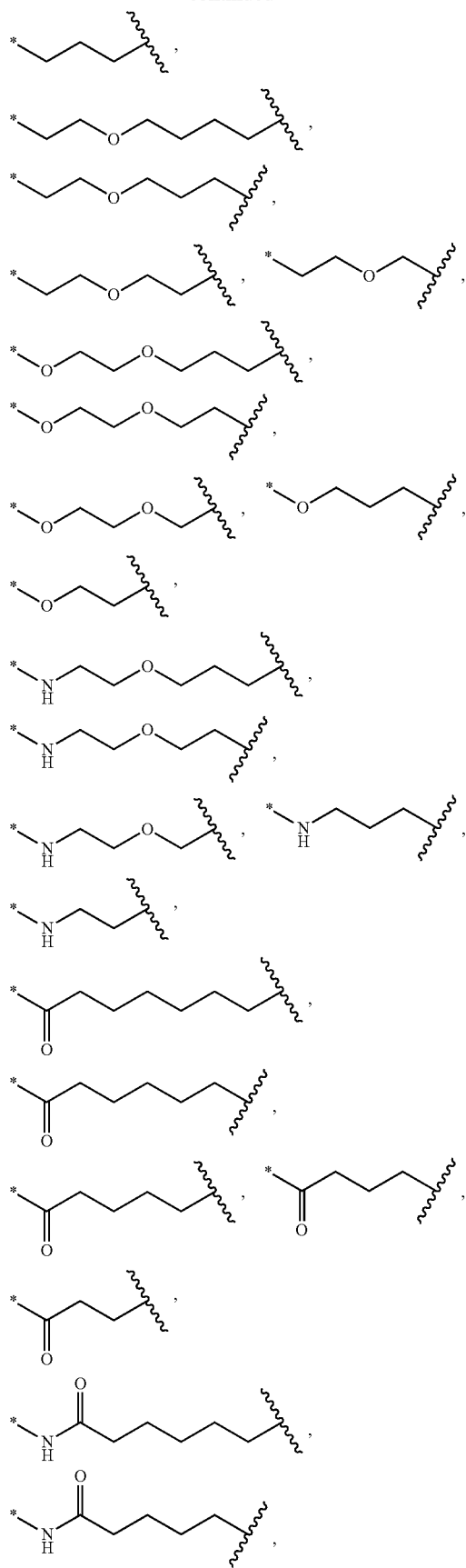
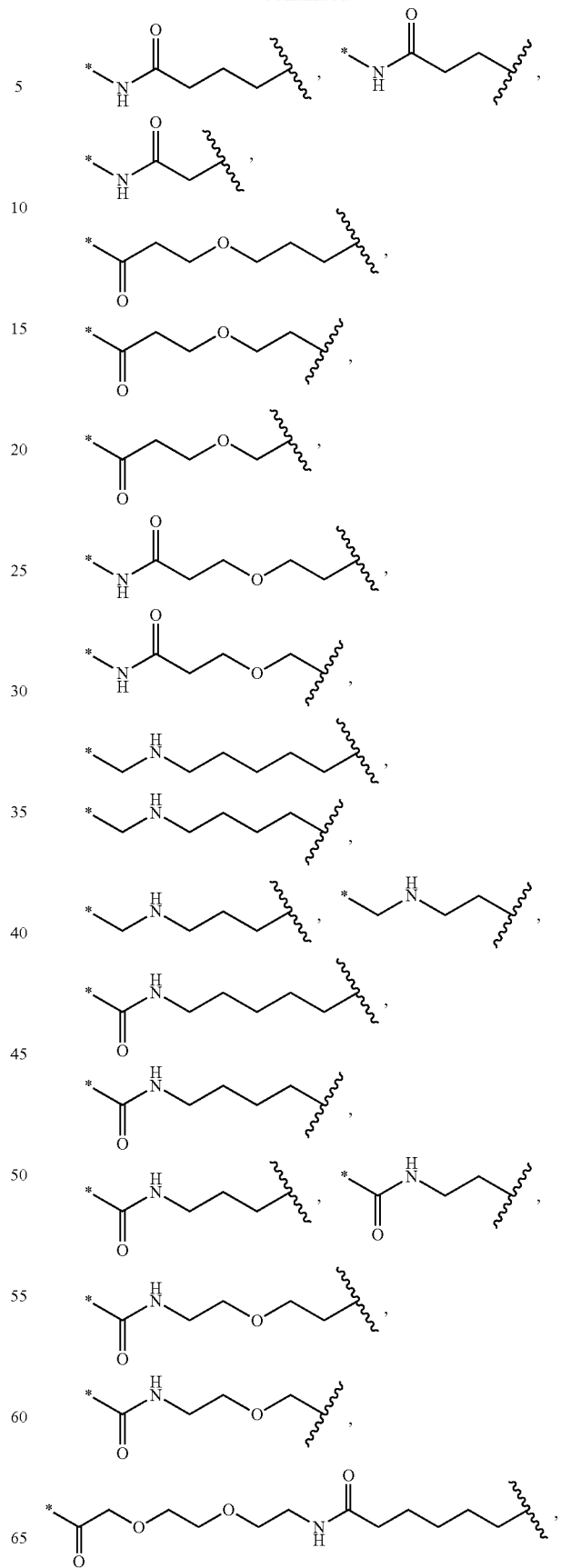

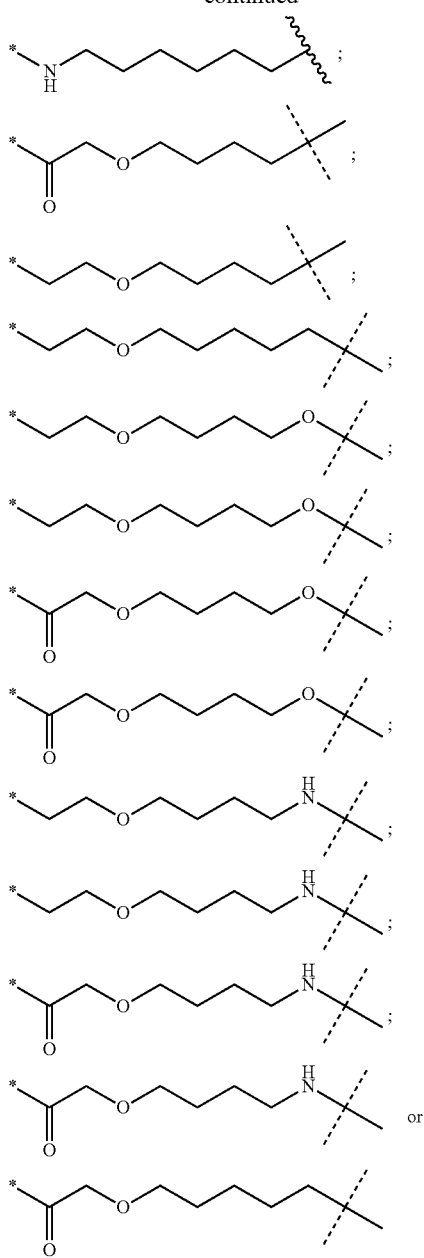

where the "*" and the wavy line represent a covalent bond.

Embodiment 16: The compound of any preceding embodiment, wherein the compound maintains a biological activity which is comparable to that observed in the original, unmodified topoisomerase inhibitor.

Embodiment 17: The compound of any preceding embodiment, wherein the compound inhibits a topoisomerase with an $IC_{50}$ of less than about 5,000 nM.

Embodiment 18: The compound of any preceding embodiment, wherein the compound binds to topoisomerase I.

Embodiment 19: The compound of any preceding embodiment, wherein the compound comprises a nuclear receptor-targeting epitope derived from:

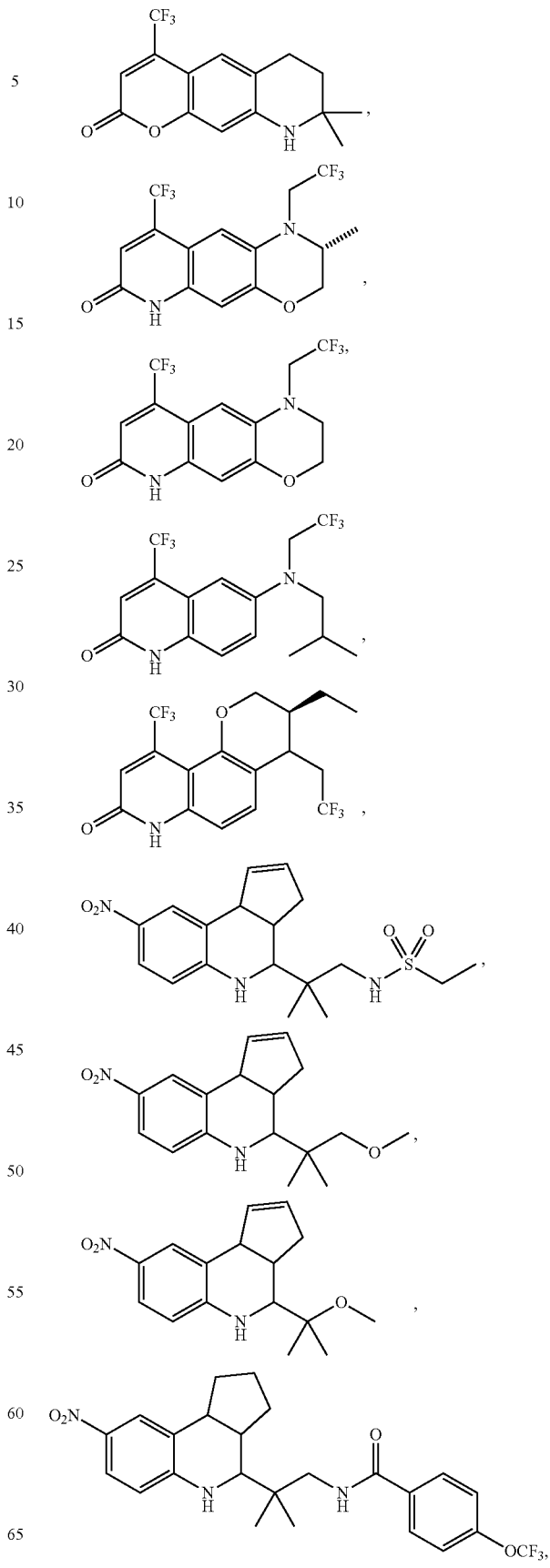

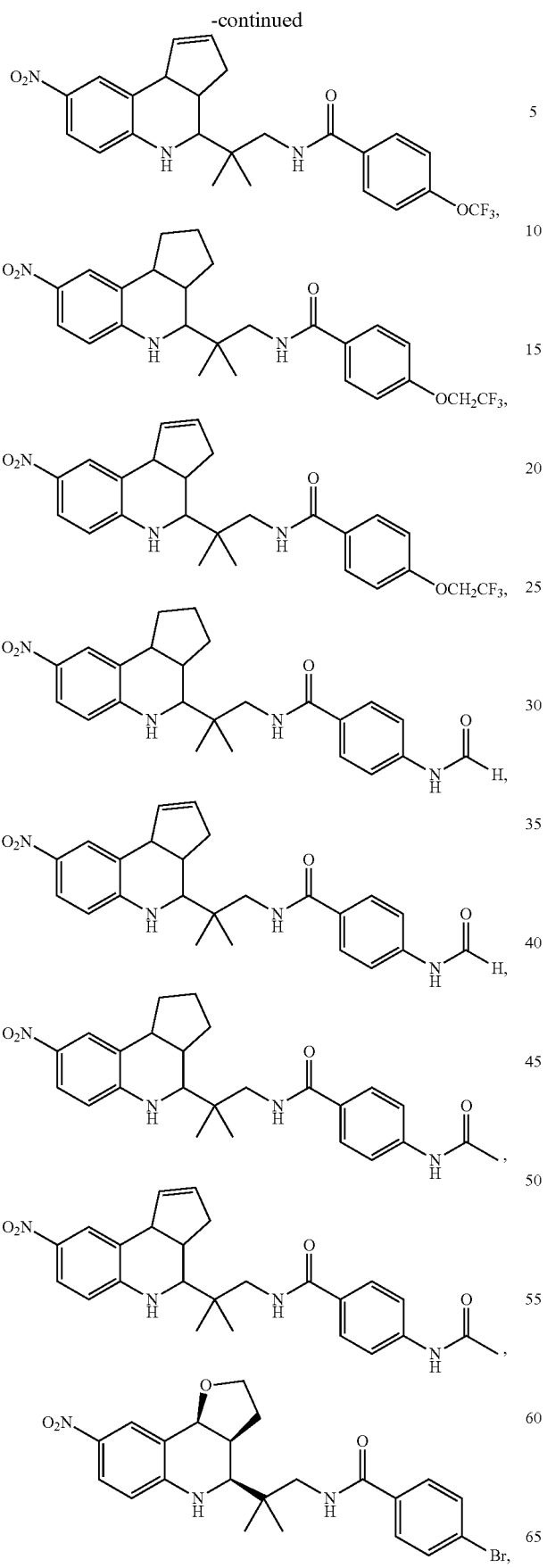
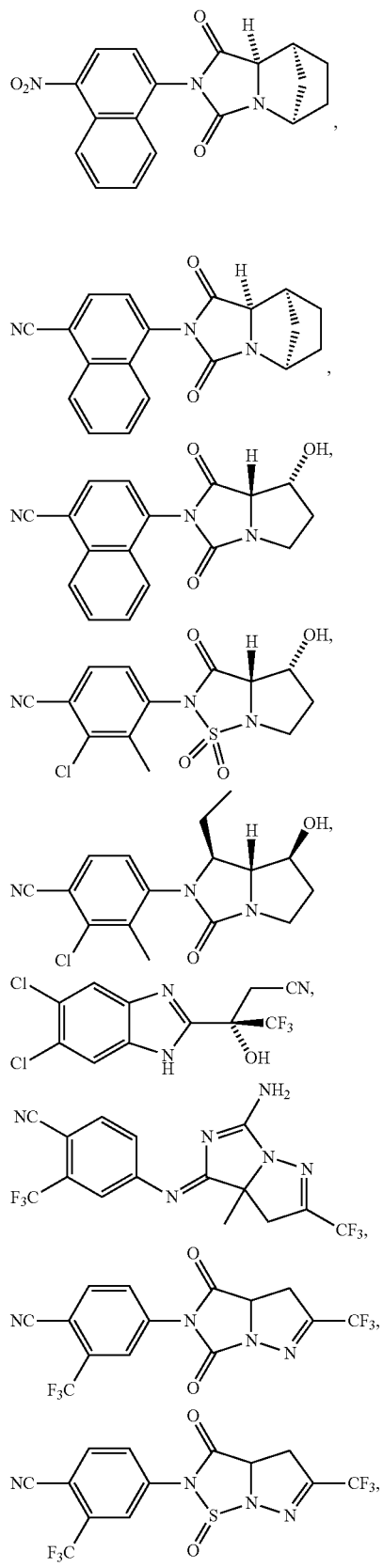

153
-continued
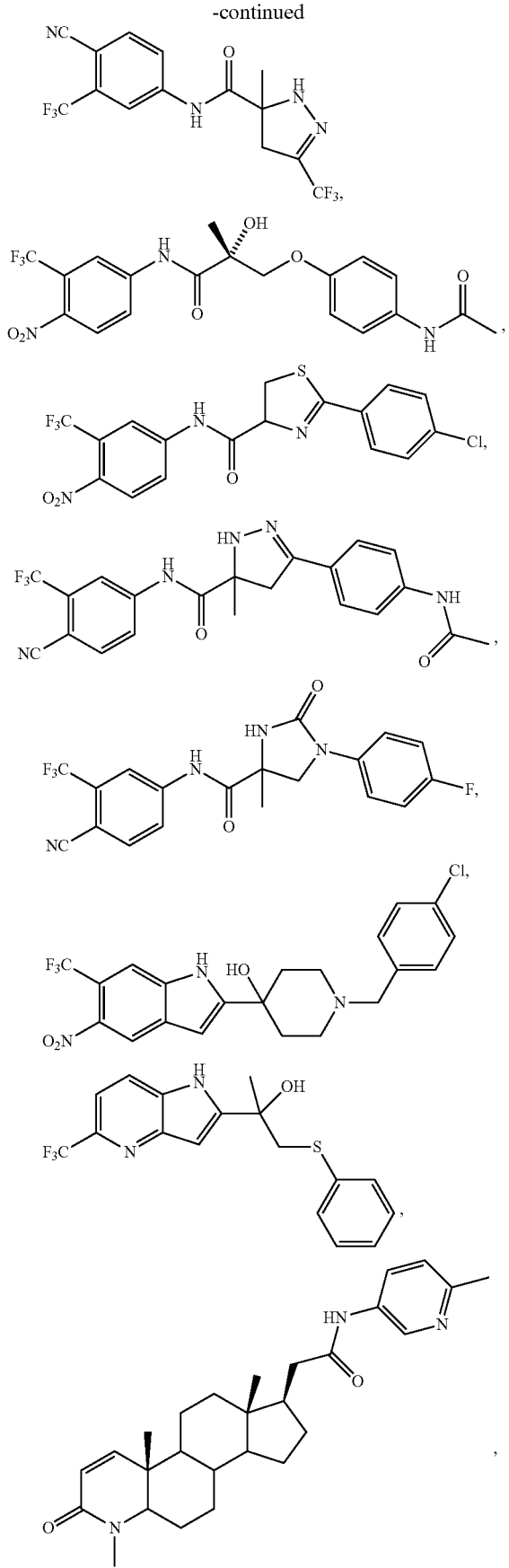
154
-continued
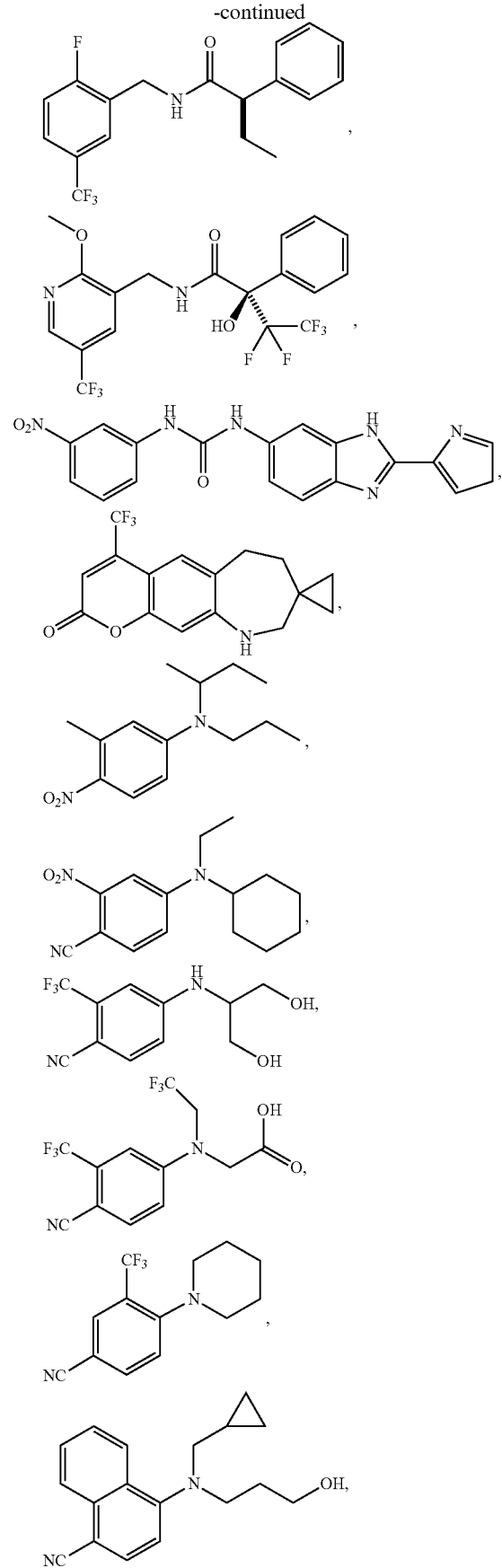

-continued

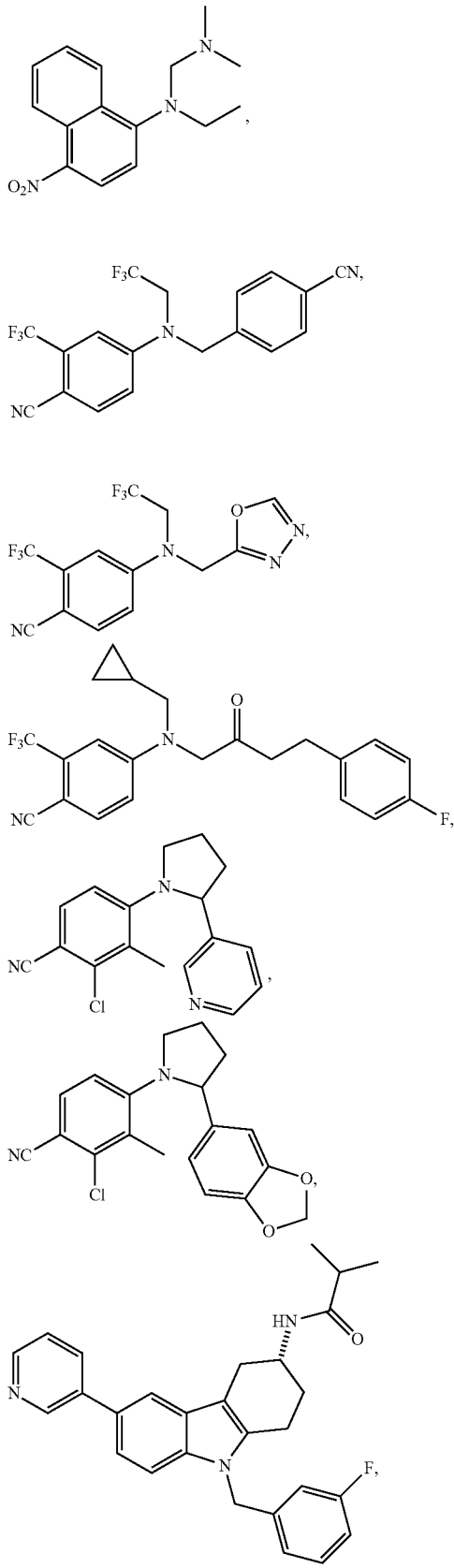

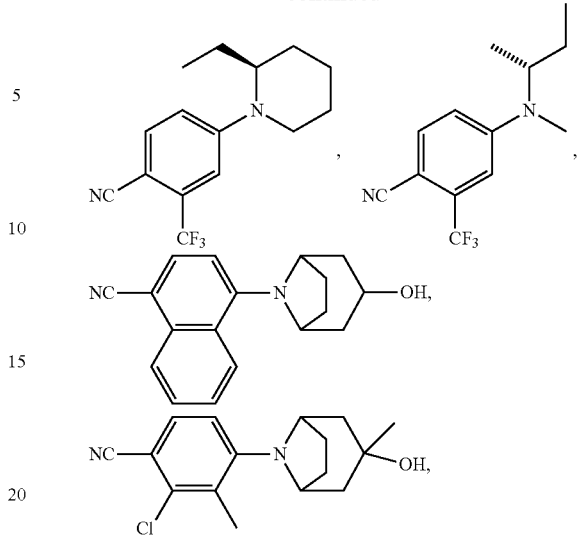

or a stereoisomer or a mixture of stereoisomers thereof or an analog thereof, wherein at least one hydrogen atom is replaced by a direct covalent bond to $A^1$, optionally via a linking moiety.

Embodiment 20: Compound 1, 2, 3, 4, or 5, as provided in Table 1 or a stereoisomer, mixture of stereoisomers, hydrate, solvate, isotopically enriched analog, or pharmaceutically acceptable salt thereof.

Embodiment 21: A pharmaceutical composition comprising a compound as in any preceding embodiment, or a stereoisomer, mixture of stereoisomers, hydrate, solvate, isotopically enriched analog, or pharmaceutically acceptable salt thereof, and a pharmaceutically acceptable excipient.

Embodiment 22: A method of treating or preventing cancer, comprising administering an effective amount of the pharmaceutical composition embodiment 21 to an individual in need thereof.

Embodiment 23: The method of embodiment 21, wherein the administering comprises oral administration.

Embodiment 24: The method of embodiment 21, further comprising administering an additional chemotherapeutic agent.

Embodiment 25: The method of embodiment 24, wherein the additional chemotherapeutic agent is cisplatin or etoposide, irinotecan, camptostar, topotecan, paclitaxel, docetaxel, epothilones, taxotere, tamoxifen, 5-fluorouracil, methotrexate, temozolomide, cyclophosphamide, SCH 66336, R115777, L778123, BMS 214662, gefitinib, erlotinib hydrochloride, antibodies to EGFR, matinib, intron, cytarabine, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, drostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesterone acetate, leuprolide, flutamide, toremifene, goserelin, carboplatin, hydroxyurea, amsacrine, procarbazine, mitotane, mitoxantrone, levamisole, navelbene, anastrazole, capecitabine, droloxifenehexamethylmelamine, avastin, herceptin, bexxar, velcade, zevalin, trisenox, xeloda, vinorelbine, porfimer, cetuximab, liposomal, Thiotepa, Altretamine, Trastuzumab, lertozole, fulvestrant, exemestane, rituximab, C225, Campath, carboplatin, procarbazine, mechlorethamine, cyclophosphamide, camptothecin, melphalan, busulfan, nitrosurea, dactinomycin, daunorubicin, doxorubicin, bleomycin, plicomycin, mitomycin, etoposide (VP 16), raloxifene, estrogen receptor binding agents, paclitaxel, gemcitabine, navelbine, farnesyl-protein transferase inhibitors, transplatinum, and methotrexate, or an analog or derivative thereof.

Embodiment 26: The method of any one of embodiments 22-25, further comprising administering radiotherapy to the patient.

Embodiment 27: The method of any one of embodiments 22-26, wherein the cancer is a BRCA positive cancer.

Embodiment 28: The method of any one of embodiments 22-27, wherein the cancer is a solid tumor.

Embodiment 29: The method of any one of embodiments 22-28, wherein the cancer is a cancer affecting B cells.

Embodiment 30: The method of any one of embodiments 22-29, wherein the cancer is liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, Waldenström macroglobulinemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, trophoblastic neoplasms, or prostatic carcinoma.

Embodiment 31: The method of embodiment 22, wherein the cancer is a neuroblastoma, brainstem glioma, Ewing's, non-small cell lung cancer, colorectal cancer, breast cancer, non-Hodgkin lymphoma, endometrial cancer, or oligodendroglioma.

Embodiment 32: A method of treating or preventing a neuro-genetic disease or disorder, comprising administering an effective amount of the pharmaceutical composition embodiment 21 to an individual in need thereof.

Embodiment 33: The method of embodiment 32, wherein the neuro-genetic disease or disorder is Angelman's syndrome.

EXAMPLES

The disclosure is further illustrated by the following examples. The examples below are non-limiting are merely representative of various aspects of the disclosure. Solid and dotted wedges within the structures herein disclosed illustrate relative stereochemistry, with absolute stereochemistry depicted only when specifically stated or delineated.

Compounds having the structure of any compound, Formula, or any sub-formula described herein can be synthesized using standard synthetic techniques known to those of skill in the art. Compounds of the present disclosure can be synthesized using the general synthetic procedures set forth in the General Methods or the Synthetic Examples.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Synthetic Procedures

Example 1

Synthesis of (S)-4,11-diethyl-4-hydroxy-3,14-dioxo-3,4,12,14-tetrahydro-1H-pyrano[3',4':6,7]indolizino[1,2-b]quinolin-9-yl 4-(6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanoyl)piperazine-1-carboxylate (Compound 1)

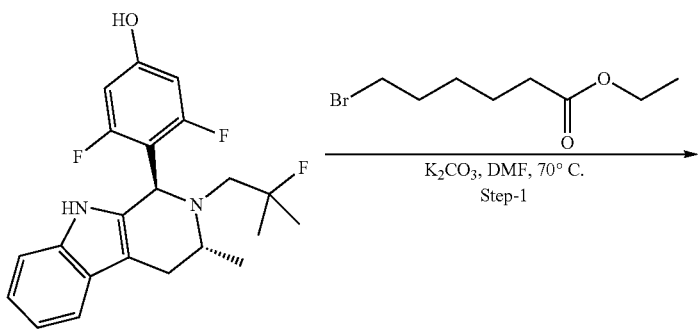

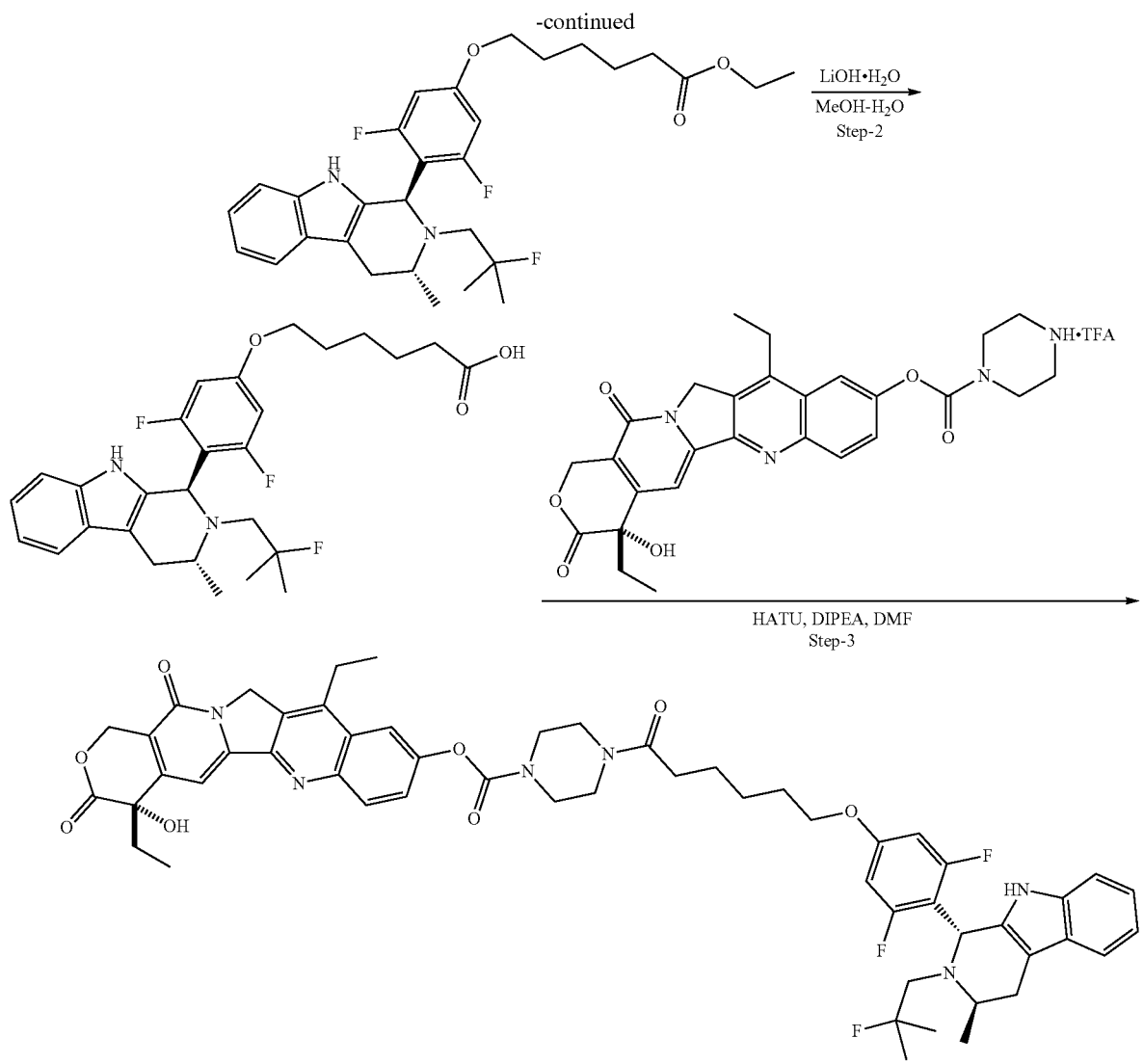

Step-1: Preparation of ethyl 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanoate: To a mixture of 3,5-difluoro-4-((1R,3R)-2-(2-fluoro-2-methylpropyl)-3-methyl-2,3,4,9-tetrahydro-1H-pyrido[3,4-b]indol-1-yl)phenol (776 mg, 2.0 mmol, 1.0 eq) and ethyl 6-bromohexanoate (600 mg, 2.2 mmol, 1.1 eq) in DMF (200 mL) was added K$_2$CO$_3$ (550 mg, 4.0 mmol, 2.0 eq) and stirred at RT for 16 h. The progress of the reaction was monitored by TLC analysis. Upon completion, the mixture was diluted with ice-cold water (30 mL) and extracted with EtOAc (50 mL×2). The combined organic layers were washed with brine (20 mL×4), dried over anhydrous sodium sulphate and concentrated under reduced pressure to obtain crude product which was purified by silica gel column chromatography to afford the title compound (900 mg, 85%).

Step-2: Preparation of 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanoic acid: To a solution of ethyl 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanoate (265 mg, 0.5 mmol, 1.0 eq) in MeOH (10 mL) was added LiOH·H$_2$O (95 mg, 2.5 mmol, 5.0 eq) and water (2 mL). The progress of the reaction was monitored by TLC analysis. Upon completion, the mixture was concentrated and acidified with aqueous citric acid (20 mL) to pH ~3 and extracted with DCM (50 mL×2). The combined organic layers were washed with brine (20 mL×4), dried over anhydrous sodium sulphate and concentrated under reduced pressure to afford the title compound (150 mg, 60%) which was used without further purification.

Step-3: Preparation of (S)-4,11-diethyl-4-hydroxy-3,14-dioxo-3,4,12,14-tetrahydro-1H-pyrano[3',4':6,7]indolizino[1,2-b]quinolin-9-yl 4-(6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanoyl)piperazine-1-carboxylate (1): To a stirred solution of 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanoic acid (125 mg, 0.25 mmol, 1.0 eq) in DMF (5 mL) was added HATU (141 mg, 0.37 mmol, 1.5 eq) and stirred at RT for 15 min. To this solution were added DIPEA (0.18 mL, 1.0 mmol, 2.0 eq) and (S)-4,11-diethyl-4-hydroxy-3,14-dioxo-3,4,12,14-tetrahydro-1H-pyrano[3',4':6,7]indolizino[1,2-b]quinolin-9-yl 4-(2,2,2-trifluoroacetyl)-4l4-piperazine-1-carboxylate (150 mg, 0.25 mmol, 1.0 eq) and stirred at RT for 2 h. Upon completion, the mixture was diluted with ice-cold water (30 mL) and extracted with DCM (50 mL×2). The combined organic layers were washed with brine (20 mL×4), dried over anhydrous sodium sulphate and concentrated under reduced pressure to obtain crude product which was purified by silica gel column chromatography to obtain the desired product which was again triturated with acetone/n-pentane (1:5) and dried to afford the title compound (22 mg, 6%). LCMS: 989.5 [M+H]$^+$; $^1$H NMR (400 MHz, DMSO-d$_6$): δ10.52 (s, 1H), 8.19 (d, J=9.6 Hz, 1H), 8.01 (d, J=2.6 Hz, 1H), 7.69 (dd, J=9.2, 2.2 Hz, H), 7.38 (d, J=7.0 Hz, 1H) 7.32 (s, 1H), 7.17 (d, J=7.9 Hz, 1H), 7.04-6.88 (m, 2H), 6.64 (s, 1H), 6.67 (s, 1H), 6.53 (s, 1H), 5.44 (s, 2H), 5.34 (s, 2H), 5.12 (m, 1H), 4.04-3.90 (m, 2H), 3.69-3.45 (m, 10H), 3.26-2.56 (m., 6H), 2.21-2.45 (m, 3H), 1.98-1.43 (m, 8H), 1.29 (t, J=7.7 Hz, 4H), 1.22-1.03 (m, 6H), 0.88 (t, J=7.2 Hz, 3H).

Example 2

Synthesis of (S)-4,11-diethyl-4-hydroxy-3,14-dioxo-3,4,12,14-tetrahydro-1H-pyrano[3',4':6,7]indolizino[1,2-b]quinolin-9-yl 4-(6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)piperazine-1-carboxylate (Compound 2)

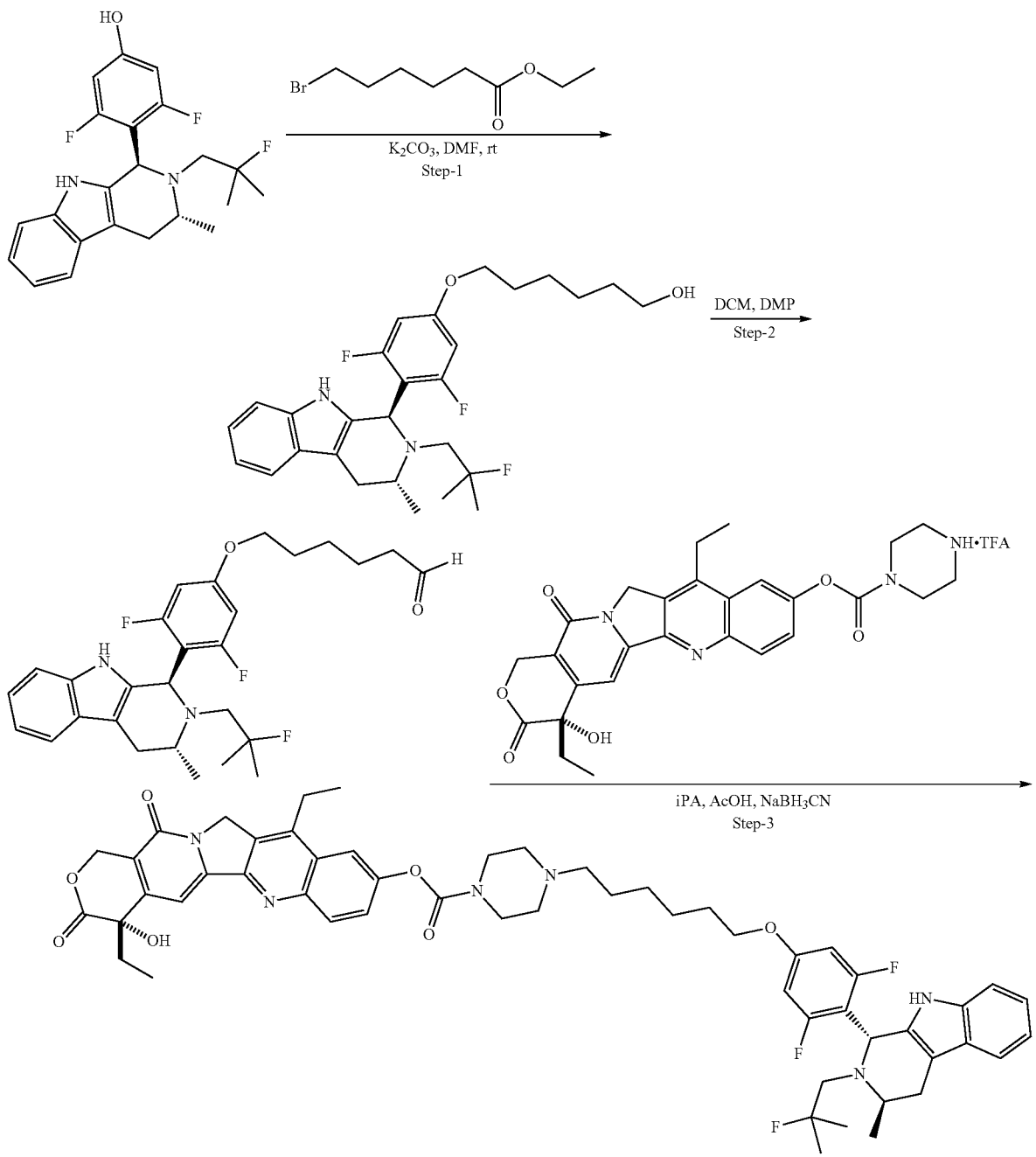

Step-1: Preparation of 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexan-1-ol: To a mixture of 3,5-difluoro-4-((1R,3R)-2-(2-fluoro-2-methylpropyl)-3-methyl-2,3,4,9-tetrahydro-1H-pyrido[3,4-b]indol-1-yl)phenol (776 mg, 2.0 mmol, 1.0 eq) and 6-bromohexan-1-ol (396 mg, 2.2 mmol, 1.1 eq) in DMF (10 mL) was added $K_2CO_3$ (552 mg, 4.0 mmol, 2.0 eq) and stirred at RT overnight. Progress of the reaction was monitored by TLC analysis. Upon completion, the reaction mixture was diluted with ice-cold water (30 mL) and extracted with EtOAc (50 mL×2). The combined organic layers were washed with brine (20 mL×4), dried over anhydrous sodium sulfate and concentrated under reduced pressure to obtain crude product which was purified by silica gel column chromatography to afford the title compound (800 mg, 82%).

Step-2: Preparation of 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanal: To a solution of 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexan-1-ol (489 mg, 1.0 mmol, 1.0 eq) in DCM (50 mL) was added DMP (510 mg, 1.2 mmol, 1.2 eq) and stirred at RT for 2 h. The reaction mixture was then diluted with DCM (50 mL), washed with sodium thiosulfate solution (20 mL×2), dried over anhydrous sodium sulphate and concentrated under reduced pressure to obtain the crude product was used in next step without further purification.

Step-3: Preparation of (S)-4,11-diethyl-4-hydroxy-3,14-dioxo-3,4,12,14-tetrahydro-1H-pyrano[3',4':6,7]indolizino[1,2-b]quinolin-9-yl 4-(6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)piperazine-1-carboxylate (2): To a stirred solution of (S)-4,11-diethyl-4-hydroxy-3,14-dioxo-3,4,12,14-tetrahydro-1H-pyrano[3',4':6,7]indolizino[1,2-b]quinolin-9-yl 4-(2,2,2-trifluoroacetyl)-4l4-piperazine-1-carboxylate (240 mg, 0.4 mmol, 1.0 eq) and 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanal (389 mg, 0.8 mmol, 2.0 eq) in IPA (20 mL) was added acetic acid (0.1 mL) and stirred at RT for 15 min. To this solution was added sodium cyanoborohydride (49 mg, 0.8 mmol, 2.0 eq) and the mixture was stirred at RT overnight. Progress of the reaction was monitored by TLC and LC-MS analysis. Upon completion, the reaction mixture was diluted with saturated aq $NaHCO_3$ (30 mL) and extracted with DCM (50 mL×2). The combined organic layers were washed with brine (20 mL×4), dried over anhydrous sodium sulphate and concentrated under reduced pressure to obtain crude product which was purified by reverse phase chromatography to afford the title compound (72 mg, 18%). LCMS: 975.4 $[M+H]^+$; $^1$H NMR (400 MHz, DMSO-$d_6$): δ 10.53 (s, 1H), 8.18 (d, J=9.2 Hz, 1H), 8.00 (d, J=2.6 Hz, 1H), 7.66 (d, J=9.2 Hz, 1H), 7.39 (d, J=7.8 Hz, 1H), 7.32 (s, 1H), 7.18 (d, J=7.8 Hz, 1H), 6.86-7.05 (m, 2H), 6.66 (d, J=11.4 Hz, 1H), 6.54 (s, 1H), 5.44 (s, 2H), 5.34 (s, 2H), 5.12 (m, 1H), 3.96 (m, 2H), 3.67-3.48 (m, 6H), 3.19 (d, J=6.6 Hz, 3H), 2.86-2.20 (m, 8H), 1.79-1.20 (m, 16H), 1.16 (m, 2H), 1.11 (s, 2H), 1.04 (d, J=6.1 Hz, 3H), 0.88 (t, J=7.2 Hz, 3H).

Example 3

Synthesis of (S)-4,11-diethyl-4-hydroxy-3,14-dioxo-3,4,12,14-tetrahydro-1H-pyrano[3',4':6,7]indolizino[1,2-b]quinolin-9-yl 4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexanoyl)piperazine-1-carboxylate (Compound 3)

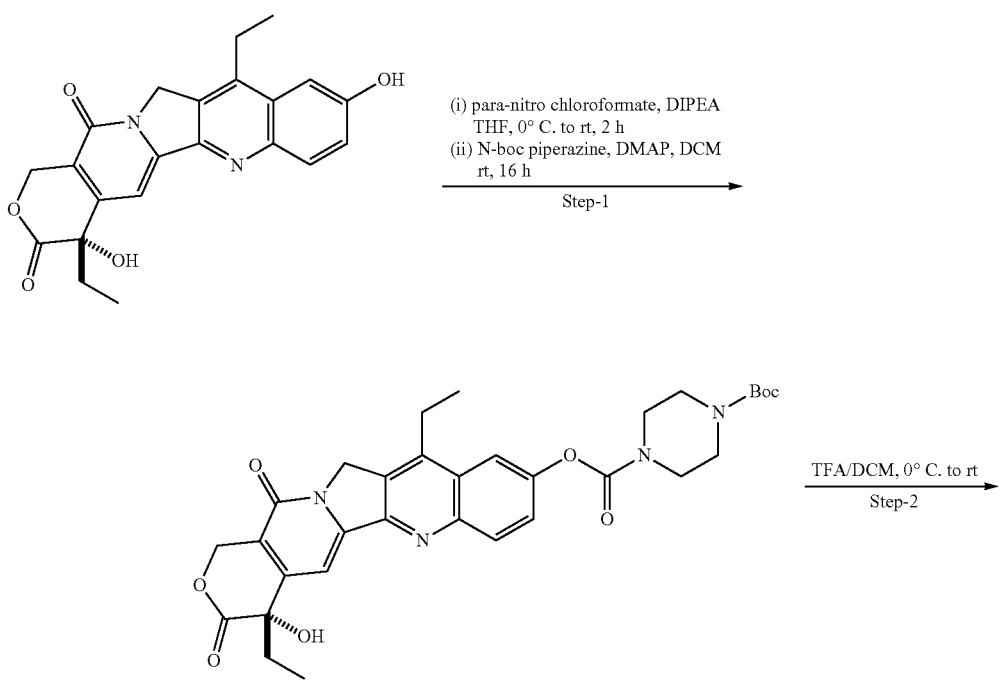

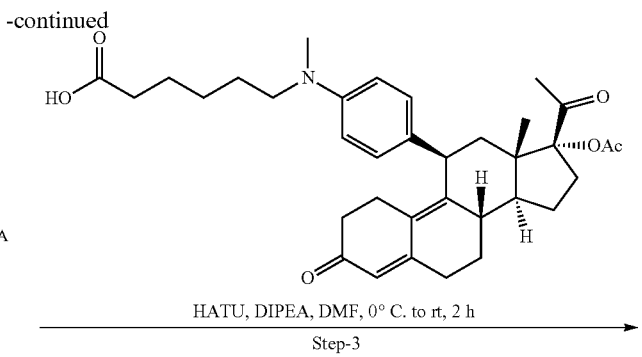

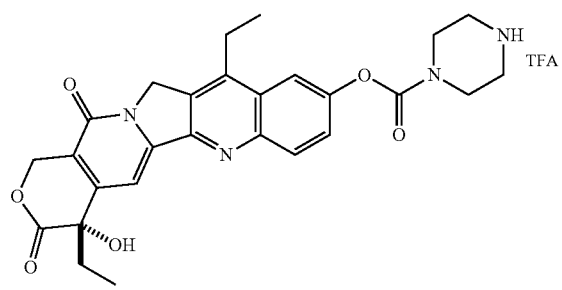

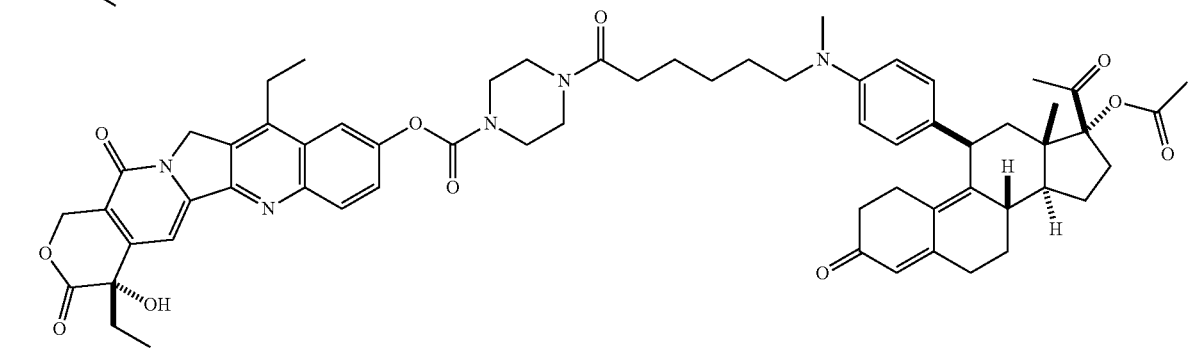

Step-1: Preparation of (S)-1-(tert-butyl) 4-(4,11-diethyl-4-hydroxy-3,14-dioxo-3,4,12,14-tetrahydro-1H-pyrano[3',4':6,7]indolizino[1,2-b]quinolin-9-yl) piperazine-1,4-dicarboxylate: To a stirred solution of 7-ethyl-10-hydroxycamptothecin (0.50 g, 1.27 mmol, 1.0 eq) in THF (10 mL) was added DIPEA (0.34 mL, 1.91 mmol, 1.5 eq) followed by the addition of p-nitro chloroformate (0.30 g, 1.53 mmol, 1.2 eq). The reaction was then allowed to stir at RT for 2 h. Upon completion, the mixture was evaporated under reduced pressure to get the crude which was then treated with diethyl ether to afford a crude residue (700 mg) which was dissolved in DCM (15 mL) followed by the addition of DMAP (153 mg, 1.25 mmol, 1.0 eq) and N-Boc piperazine (467 mg, 2.5 mmol, 2.0 eq). The reaction was then allowed to stir at RT for 16 h. Upon completion, the mixture was diluted with DCM (50 mL) followed by washing with brine (2×50 mL). The organic layer was then dried over anhydrous sodium sulfate, filtered and evaporated under reduced pressure to afford a crude residue which was purified by CombiFlash chromatography to afford the title compound (300 mg, 39%).

Step-3: Preparation of (S)-4,11-diethyl-4-hydroxy-3,14-dioxo-3,4,12,14-tetrahydro-1H-pyrano[3',4':6,7]indolizino[1,2-b]quinolin-9-yl piperazine-1-carboxylate triflate: To a stirred solution of (S)-1-(tert-butyl) 4-(4,11-diethyl-4-hydroxy-3,14-dioxo-3,4,12,14-tetrahydro-1H-pyrano[3',4':6,7]indolizino[1,2-b]quinolin-9-yl) piperazine-1,4-dicarboxylate (0.30 g, 0.50 mmol, 1.0 eq) in DCM (5 ML) was added TFA (0.5 mL) at 0° C. dropwise. The resulting mixture was then stirred at RT for 30 min. Upon completion, the reaction mass was then evaporated under reduced pressure to get the crude product which was purified by trituration with diethyl ether (2×25 mL) to afford the title compound (220 mg, 90%).

Step-4: Preparation of (S)-4,11-diethyl-4-hydroxy-3,14-dioxo-3,4,12,14-tetrahydro-1H-pyrano[3',4':6,7]indolizino[1,2-b]quinolin-9-yl 4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexanoyl)piperazine-1-carboxylate (3): To a stirred solution of 6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexanoic acid (0.26 g, 0.46 mmol, 1.0 eq) in DMF (5 mL) was added HATU (0.22 g, 5.8 mmol, 1.5 eq). The reaction was then allowed to stir at 0° C. for 10 min. (S)-4,11-Diethyl-4-hydroxy-3,14-dioxo-3,4,12,14-tetrahydro-1H-pyrano[3',4':6,7]indolizino[1,2-b]quinolin-9-yl piperazine-1-carboxylate triflate (0.2 g, 3.9 mmol, 1.0 eq) dissolved in DMF (5 mL) and DIPEA (0.2 mL, 11.7 mmol, 3.0 eq) were added drop wise to the reaction mass at 0° C. The reaction was then allowed to stir at RT for 2 h. Upon completion, the reaction was diluted with DCM (50 mL) followed by washing with ice cold water (2×50 mL). The organic layer was dried over anhydrous sodium sulfate, filtered and evaporated under reduced pressure to afford crude residue which was purified by Reversed Phase HPLC to afford the title compound (76 mg, 18%). LCMS: 1062 [M+H]$^+$; $^1$H NMR (400 MHz, DMSO-d$_6$): δ 8.19 (d, J=9.2 Hz, 1H), 8.02 (s, 1H), 7.70 (d, J=9.2 Hz, 1H), 7.33 (s, 1H), 6.99 (d, J=8.3 Hz, 2H), 6.48-6.67 (m, 3H), 5.67 (s, 1H), 5.44 (s, 2H), 5.35 (s, 2H), 4.40 (m, 1H) 3.58 (m, 8H), 3.21 (dd, J=16.0, 7.24 Hz, 5H), 2.83 (s, 6H), 2.60-2.71 (m, 3H), 2.34 (d, J=9.6 Hz, 4H), 2.06-2.15 (m, 3H), 2.00 (s, 3H), 1.83-1.93 (m, 4H), 1.75 (s, 3H), 1.70 (m, 3H), 1.54 (m, 4H), 1.29 (t, J=7.7 Hz, 7H), 0.88 (t, J=7.4 Hz, 3H).

Example 4

Synthesis of (S)-4,11-diethyl-4-hydroxy-3,14-dioxo-3,4,12,14-tetrahydro-1H-pyrano[3',4':6,7]indolizino[1,2-b]quinolin-9-yl 4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)piperazine-1-carboxylate (Compound 4)

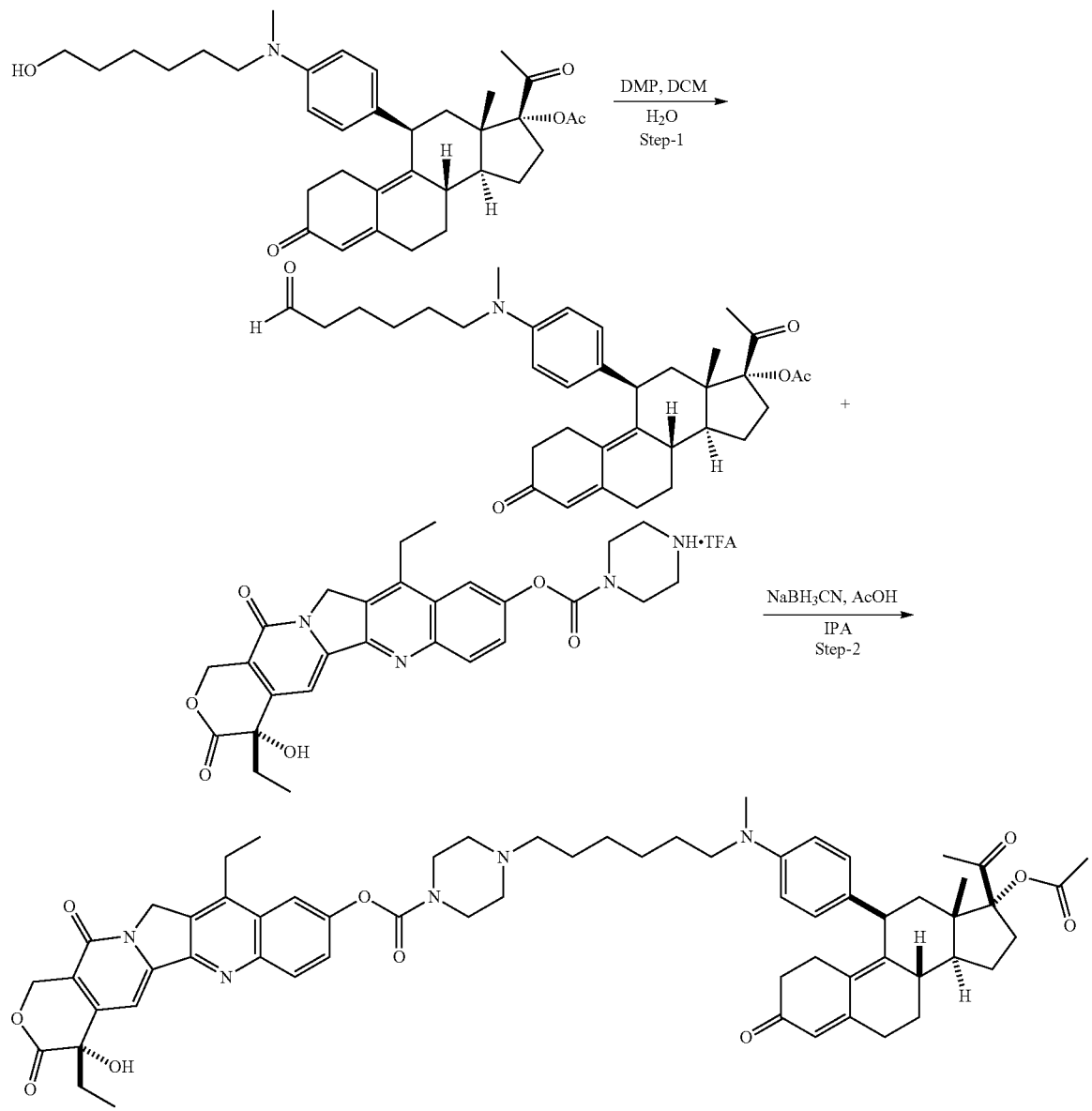

Step-1: Preparation of (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate: To a solution of (8S,11R,13S,14S,17R)-17-acetyl-11-(4-(((6-hydroxyhexyl)(methyl)amino)phenyl)-13-methyl-3-oxo-2,3,6,7,8,11,12,13,14,15,16,17-dodecahydro-1H-cyclopenta[a]phenanthren-17-yl acetate (281 mg, 0.5 mmol, 1.0 eq) in DCM (20 mL) was added DMP (424 mg, 1.0 mmol, 2.0 eq) followed by water (18 mg, 1.0 mmol, 2.0 eq) and stirred at RT for 2 h. The reaction mixture was then diluted with DCM (50 mL) and washed with sodium thiosulfate solution (20 mL×2), dried over anhydrous sodium sulfate and concentrated under reduced pressure to obtain the crude product which was used in next step without further purification.

Step-2: Preparation of (S)-4,11-diethyl-4-hydroxy-3,14-dioxo-3,4,12,14-tetrahydro-1H-pyrano[3',4':6,7]indolizino[1,2-b]quinolin-9-yl 4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)piperazine-1-carboxylate (4): To a stirred solution of (S)-4,11-diethyl-4-hydroxy-3,14-dioxo-3,4,12,14-tetrahydro-1H-pyrano[3',4':6,7]indolizino[1,2-b]quinolin-9-yl 4-(2,2,2-trifluoroacetyl)-4l4-piperazine-1-carboxylate triflate (120 mg, 0.2 mmol, 1.0 eq) and (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate (224 mg, 0.4 mmol, 2.0 eq) in IPA (5 mL) was added acetic acid (0.05 mL) and stirred at RT for 15 min. To this solution was added sodium cyanoborohydride (25 mg, 0.4 mmol, 2.0 eq) and stirred at RT overnight. Progress of the reaction was monitored by TLC and LC-MS analysis. Upon completion, the reaction mixture was diluted with saturated aq NaHCO$_3$ (30 mL) and extracted with DCM (50 mL×2). The combined organic layers were washed with brine (20 mL×4), dried over anhydrous sodium sulphate and concentrated under reduced pressure to obtain crude product which was purified by reverse phase chromatography to afford the title compound (12 mg, 6%). LCMS: 1049.0 [M+H]$^+$; $^1$H NMR (400 MHz, DMSO-d$_6$): δ 8.18 (d, J=8.8 Hz, 1H), 8.00 (d, J=2.2 Hz, 1H), 7.67 (d, J=10.5 Hz, 1H), 7.32 (s, 1H), 6.98 (d, J=8.2 Hz, 2H), 6.46-6.70 (m, 3H), 5.67 (s, 1H), 5.44 (s, 2H), 5.34 (s, 2H), 4.39 (m, 1H), 3.65 (m, 2H), 3.46 (m, 2H), 3.04-3.27 (m, 6H), 2.8-2.62 (m, 8H), 2.27-1.23 (m, 36H), 0.88 (t, J=7.2 Hz, 3H).

Example 5

Synthesis of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)piperazine-1-carboxylate (Compound 5)

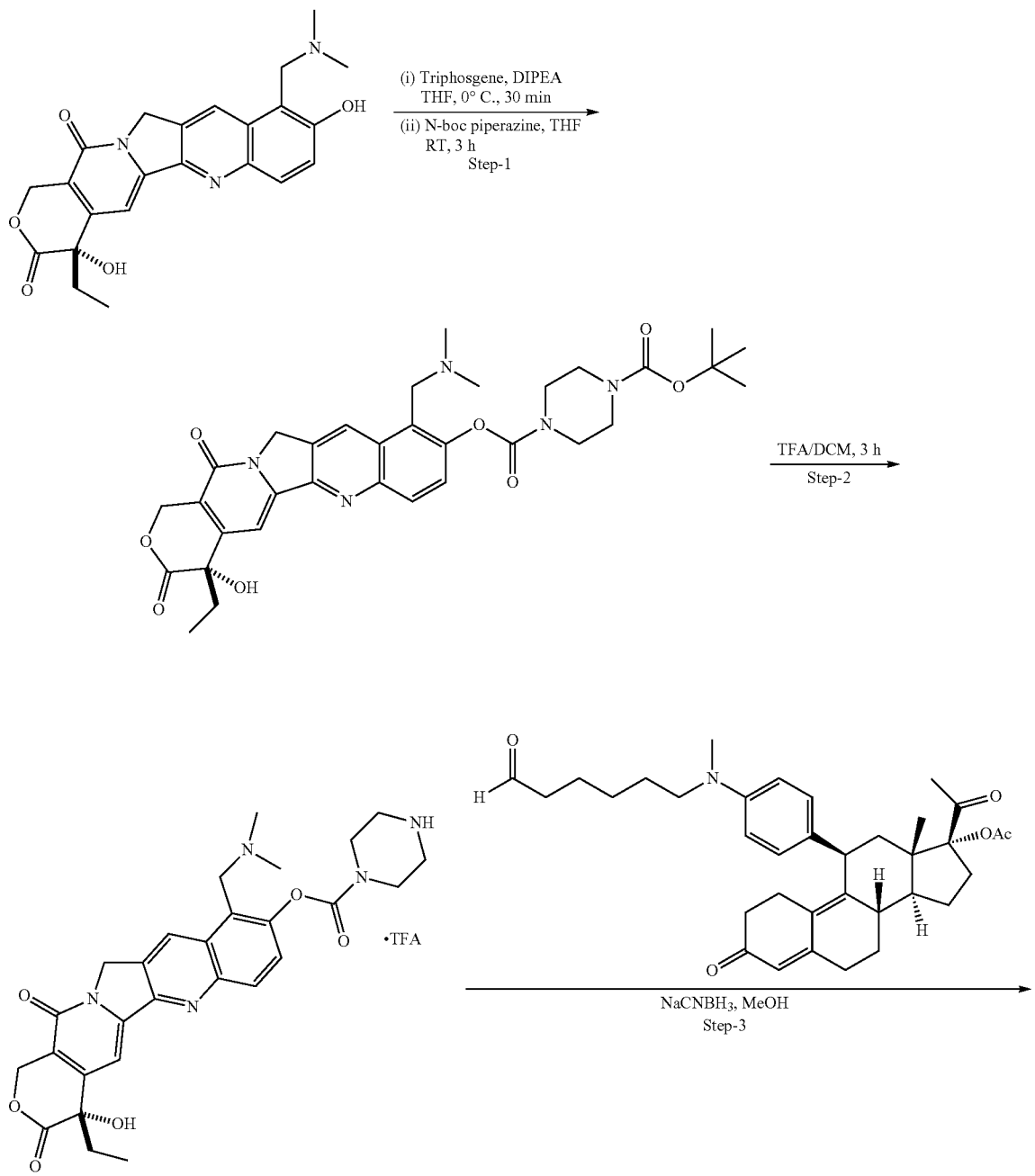

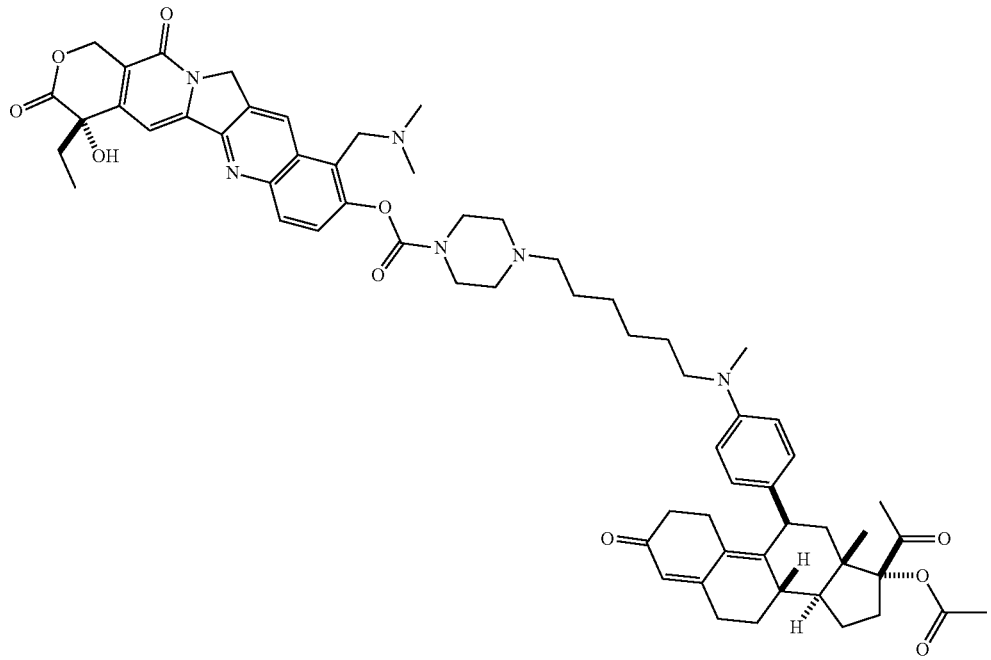

Step-1: Preparation of (S)-1-(tert-butyl) 4-(10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl) piperazine-1,4-dicarboxylate: To a stirred solution of topotecan hydrochloride (2 g, 4.75 mmol, 1.0 eq) in anhydrous THF (100 mL):DCM (100 mL) was added DIPEA (3.3 mL, 19 mmol, 4.0 eq) and triphosgene (2.8 g, 9.5 mmol, 2.0 eq) dissolved in DCM (15 ml) at 0° C. dropwise. The mixture was stirred at 0° C. for 30 min followed by the addition of N-Boc piperazine (1.32 g, 7.12 mmol, 1.5 eq) dissolved in DCM (15 mL). The resultant mixture was stirred at RT for 3 h. The progress of the reaction was monitored by TLC and LC-MS. Upon completion, the mixture was diluted with water (50 mL) and extracted with DCM (50 mL×5). The combined organic layers were washed with saturated NaHCO$_3$ (50 mL), water (50 mL), brine (50 mL), dried over anhydrous sodium sulfate and concentrated under reduced pressure. The residue was purified by CombiFlash chromatography to afford the desired compound (0.35 g, 12%).

Step-2: Preparation of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl piperazine-1-carboxylate triflate: To a stirred solution of (S)-1-(tert-butyl) 4-(10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl) piperazine-1,4-dicarboxylate (0.35 g, 0.55 mmol) in DCM (5 mL) was added trifluoroacetic acid (1 mL) at 0° C. dropwise and the resulting solution was stirred RT for 3 h. The reaction was monitored by LC-MS. Upon completion, the mixture was concentrated under reduced pressure to afford the crude product which was triturated with diethyl ether to afford the title compound (0.28 g, 95%).

Step-3: Preparation of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino) hexyl)piperazine-1-carboxylate (5): To a stirred solution of (S)-10-((dimethylamino)methyl)-4-ethyl-4-hydroxy-3,14-dioxo-3,4,12,14-tetrahydro-1H-pyrano[3',4':6,7]indolizino [1,2-b]quinolin-9-yl piperazine-1-carboxylate triflate (0.25 g, 0.46 mmol, 1.0 eq) and (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate (0.28 g, 0.50 mmol, 1.1 eq) in MeOH (12 mL) was added acetic acid (0.2 ml) and the mixture was stirred at RT for 15 min. Sodium cyanoborohydride (0.058 g, 0.92 mmol, 2.0 eq) was then added to the mixture and the resultant mixture was stirred at RT for 3 h. The progress of the reaction was monitored by TLC and LCMS analysis. Upon completion, the mixture was diluted with water (30 mL) and extracted with DCM (30 mL×3). The combined organic layers were washed with saturated NaHCO$_3$ (20 mL), water (20 mL), brine (20 mL), dried over anhydrous sodium sulfate and concentrated under reduced pressure to obtain a crude which was purified by Reversed Phase HPLC to afford the title compound (0.01 g, 2%). LCMS: 1078 [M+H]$^+$; $^1$H NMR (500 MHz, DMSO-d$_6$): δ8.94 (s, 1H), 8.11 (d, J=9.2 Hz, 1H), 7.63 (d, J=9.2 Hz, 1H), 7.34 (s, 1H), 6.99 (d, J=8.2 Hz, 2H), 6.59 (d, J=8.2 Hz, 2H), 6.55 (s, 1H), 5.68 (s, 2H), 5.43 (s, 4H), 5.32 (s, 4H), 4.40 (d, J=7.0 Hz, 2H), 3.75 (s, 4H), 3.70 (s, 4H), 3.46 (s, 4H), 3.25 (s, 2H), 2.82 (s, 6H), 2.43-0.81 (m, 32H), 0.24 (s, 3H).

Example 6

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(6-(4-(3-(4-cyano-3-(trifluoromethyl)phenyl)-5,5-dimethyl-4-oxo-2-thioxoimidazolidin-1-yl)-2-fluorobenzamido)hexyl)piperazine-1-carboxylate (Compound 6)

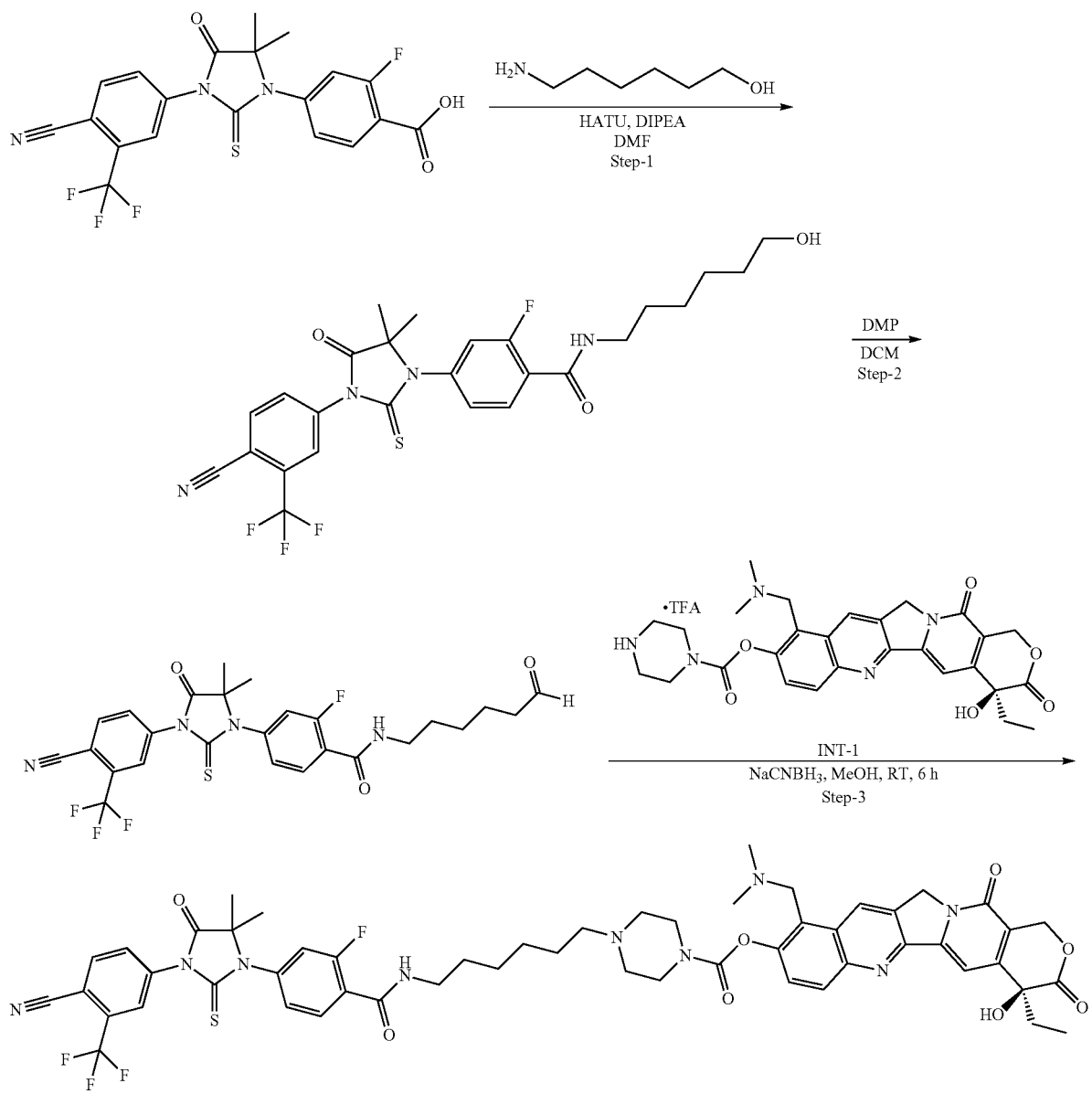

Step-1: Preparation of 4-(3-(4-Cyano-3-(trifluoromethyl)phenyl)-5,5-dimethyl-4-oxo-2-thioxoimidazolidin-1-yl)-2-fluoro-N-(6-hydroxyhexyl)benzamide To a stirred solution of 4-(3-(4-cyano-3-(trifluoromethyl)phenyl)-5,5-dimethyl-4-oxo-2-thioxoimidazolidin-1-yl)-2-fluorobenzoic acid (0.9 g, mmol, 2.0 mmol, 1.0 eq.) in DMF (5 mL) was added HATU (1.14 g, 3.0 mmol, 1.5 eq.) and stirred at RT for 15 minutes. To this solution were added DIPEA (1.67 mL, 10.0 mmol, 5.0 eq.) and 6-aminohexan-1-ol (284 mg, 2.4 mmol, 1.2 eq.) and stirred at RT for 1 h. After completion of reaction, reaction mixture was diluted with ice-cold water (30 mL) and extracted with DCM (50 mL×2). The combined organic layers were washed with brine solution (20 mL×4), dried over anhydrous sodium sulfate and concentrated under reduced pressure to obtain crude product which was purified by silica gel column chromatography to give the desired product (700 mg, 63.5%). LCMS: 551.3 [M+H]$^+$.

Step-2: Preparation of 4-(3-(4-Cyano-3-(trifluoromethyl)phenyl)-5,5-dimethyl-4-oxo-2-thioxoimidazolidin-1-yl)-2-fluoro-N-(6-oxohexyl)benzamide To a solution of 4-(3-(4-cyano-3-(trifluoromethyl)phenyl)-5,5-dimethyl-4-oxo-2-thioxoimidazolidin-1-yl)-2- fluoro-N-(6-hydroxyhexyl)benzamide (275 mg, 0.5 mmol, 1.0 eq.) in DCM (20 mL) was added DMP (255 mg, 0.6 mmol, 1.2 eq.) and stirred at RT for 2 h. Reaction mixture was then diluted with DCM (50 mL) and washed with sodium thiosulfate solution (20 mL×2), dried over anhydrous sodium sulfate and concentrated under reduced pressure to obtain the crude product which was used in next step as such. LCMS: 549.4 [M+H]$^+$.

Step-3: Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(6-(4-(3-(4-cyano-3-(trifluoromethyl)phenyl)-5,5-dimethyl-4-oxo-2-thioxoimidazolidin-1-yl)-2-fluorobenzamido)hexyl)piperazine-1-carboxylate (Compound 6)

To a stirred solution of compound 4-(3-(4-cyano-3-(trifluoromethyl)phenyl)-5,5-dimethyl-4-oxo-2-thioxoimidazolidin-1-yl)-2-fluoro-N-(6-oxohexyl)benzamide (225 mg, 0.5 mmol, 1.0 eq.) and INT-1 (315 mg, 0.5 mmol, 1.0 eq.) in methanol (10 mL) was added acetic acid (0.2 mL) and stirred at RT for 15 minutes. To this solution was added sodium cyanoborohydride (126 mg, 2.0 mmol, 4.0 eq.) and stirred at RT for overnight. Progress of the reaction was monitored by TLC and LCMS analysis. After completion of reaction, reaction mixture was diluted with saturated aqueous NaHCO$_3$ (30 mL) and extracted with DCM (50 mL×2). Combined organic layer was washed with brine solution (20 mL×4), dried over anhydrous sodium sulfate and concentrated under reduced pressure to obtain crude product which was purified by reverse phase chromatography to give the desired product (18 mg, 3.4%) (formate salt).

$^1$H NMR (400 MHz, DMSO-d$_6$): δ 8.94 (s, 1H), 8.48 (br s, 2H), 8.40 (d, J=7.89 Hz, 1H), 8.29 (s, 1H), 8.11 (d, J=9.65 Hz, 2H), 7.76 (s, 1H), 7.63 (d, J=9.21 Hz, 1H), 7.43 (d, J=10.96 Hz, 1H), 7.34 (s, 2H), 6.54 (br s, 1H), 5.43 (s, 2H), 5.31 (s, 2H), 3.75 (br s, 4H), 3.48 (br s, 3H), 2.34 (d, J=13.59 Hz, 6H), 2.20 (s, 6H), 1.85 (d, J=14.03 Hz, 2H), 1.54 (s, 8H), 1.36 (br s, 4H), 1.23 (br s, 2H), 0.89 (t, J=7.24 Hz, 3H). LCMS: 1067 [M+H]$^+$.

Example 7

Preparation of N-((1r,4r)-4-(3-Chloro-4-cyanophenoxy)cyclohexyl)-4-((5-(((S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy)pentyl)oxy)benzamide (Compound 7)

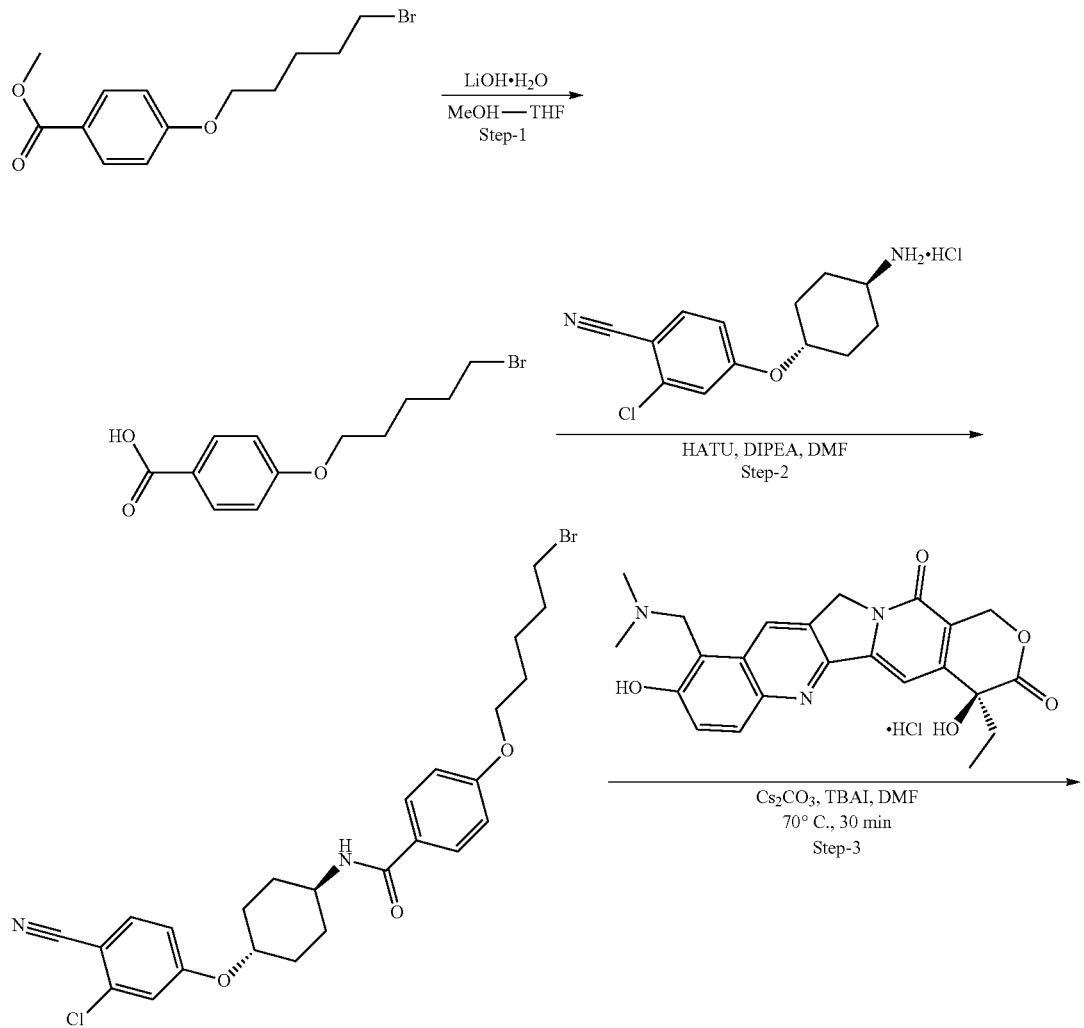

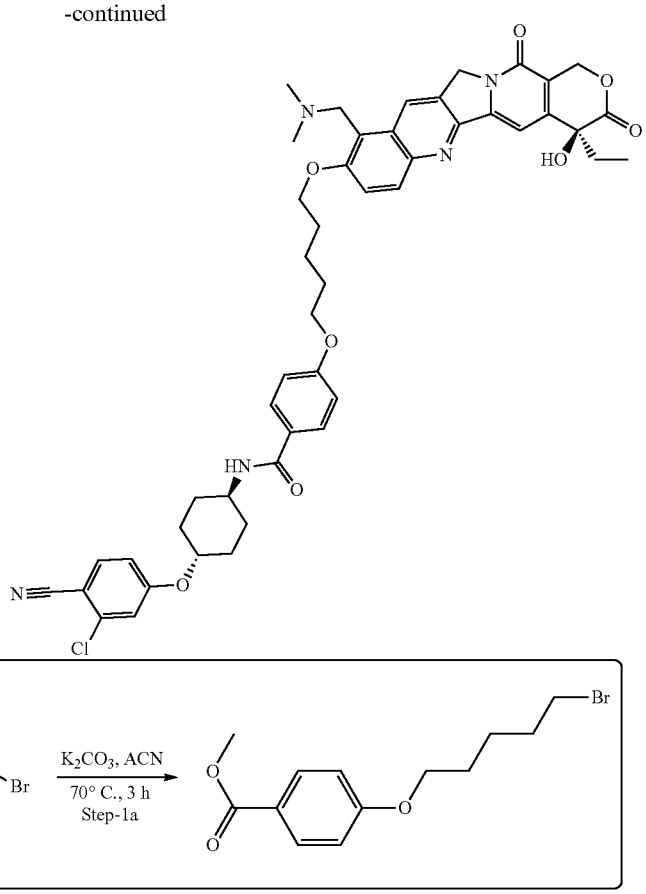

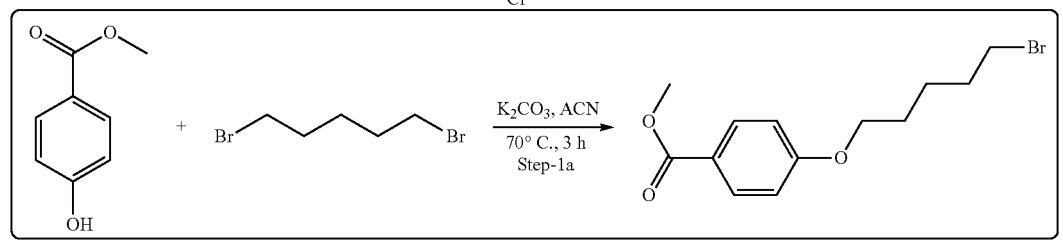

Step-1a: Preparation of Methyl 4-(5-Bromopentyloxy)benzoate

To a stirred solution of methyl 4-hydroxybenzoate (8 g, 52.63 mmol, 1.0 eq.) in acetonitrile (80 mL) was added K₂CO₃ (21.7 g, 157.8 mmol, 3 eq.) at RT and the mixture was stirred at same temperature for 30 minutes. 1,5-dibromopentane (24.0 g, 105.2 mmol, 2.0 eq.) was then added and the resulting reaction mixture was heated at 90° C. for 1 h. The progress of the reaction was monitored by TLC and LC-MS. After completion, the mixture was diluted with H₂O (150 mL) and extracted with EtOAc (200 mL×2). The combined organic layers were washed with water (100 mL×3), brine (100 mL), dried over anhydrous sodium sulfate, filtered and concentrated under reduced pressure to afford crude which was purified by CombiFlash Chromatography to afford title compound (11.5 g, 73%). LCMS: 301 [M+H]⁺.

Step-1: Preparation of 4-(5-Bromopentyloxy)benzoic acid

To a solution of methyl 4-(5-bromopentyloxy)benzoate (6.6 g, 22.0 mmol, 1.0 eq.) in THF:MeOH (30 mL:15 mL) was added LiOH·H₂O (9.0 g, 220.0 mmol, 10 eq.) dissolved in H₂O (5 mL) and the mixture was stirred at RT for 2 h. Progress of the reaction was monitored by TLC. After completion, the mixture was concentrated under reduced pressure and the residue obtained was acidified using 2N—HCl acid (pH ~3) at ice-cold condition to form a precipitate which was then filtered over Buchner funnel to afford the title compound (5 g, 79%). LCMS: 287.0 [M+H]⁺.

Step-2: Preparation of 4-(5-Bromopentyloxy)-N-((1r,4r)-4-(3-chloro-4-cyanophenoxy)cyclohexyl)benzamide To a stirred solution of 4-(5-bromopentyloxy)benzoic acid (1.5 g, 5.24 mmol, 1.0 eq.) in DMF (15 mL) was added HATU (2.3 g, 6.29 mmol, 1.2 eq.) and the mixture was stirred at RT for 15 minutes. DIPEA (4.8 mL, 26.22 mmol, 5.0 eq.) and 4-((1r,4r)-4-aminocyclohexyloxy)-2-chlorobenzonitrile hydrochloride (1.4 g, 5.24 mmol, 1.0 eq.) were then successively added and the resulting reaction mixture was stirred at RT for 2 h. Progress of the reaction was monitored by TLC and LC-MS. After completion, the mixture was diluted with ice-cold water (30 mL) and the precipitate obtained was filtered over Buchner funnel, washed with water (100 mL), n-pentane (100 mL) to afford the title product (2 g, 74%). LCMS: 519 [M+H]⁺.

Step-3: Preparation of N-((1r,4r)-4-(3-Chloro-4-cyanophenoxy)cyclohexyl)-4-((5-(((S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy)pentyl)oxy)benzamide (Compound 7)

To a stirred solution of Topotecan hydrochloride (0.45 g, 0.98 mmol, 1.0 eq.) in DMF (8 mL) was added Cs₂CO₃ (0.640 g, 1.96 mmol, 2.0 eq.) and the mixture was stirred at RT for 20 minutes. TBAI (0.072 g, 0.19 mmol, 0.2 eq.) and 4-(5-bromopentyloxy)-N-((1r,4r)-4-(3-chloro-4-cyanophenoxy) cyclohexyl)benzamide (2.04 g, 3.93 mmol, 4.0 eq.) were then added to the mixture and the resultant mixture was heated at 70° C. for 30 minutes. The progress of the reaction was monitored by TLC and LC-MS. After completion, the mixture was diluted with ice-cold water (30 mL) and the precipitate obtained was filtered over Buchner funnel to obtain a crude residue which was purified by reverse phase chromatography to afford the title compound (0.065 g, 7%). $^1$H NMR (400 MHz, DMSO-d$_6$): δ 8.80-8.78 (m, 1H), 8.12-8.09 (m, 2H), 7.90-7.60 (m, 3H), 7.41-7.38 (m., 1H), 7.29 (s, 1H), 7.14 (d, J=8.77 Hz, 1H), 6.97 (d, J=8.33 Hz, 2H), 6.49 (s, 1H), 5.51-5.43 (m, 2H), 5.29-5.27 (m, 2H), 4.55-5.52 (m., 2H), 4.24-4.22 (m, 2H), 4.09-4.06 (m, 2H), 3.85-3.82 (m., 3H), 2.34-2.32 (m, 2H), 2.2-2.18 (m, 4H), 2.13-2.11 (m, 1H), 2.07-1.87 (m, 6H), 1.77-1.75 (m, 2H), 1.69-1.67 (m, 2H), 1.51 (d, J=7.89 Hz, 3H), 1.24 (m, 2H), 0.88 (t, J=7.45 Hz, 3H). LCMS: 860 [M+H]$^+$.

Example 8

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(6-((((5R,8S,9R,10R,13R,14R,17R)-10,13-dimethyl-3-oxohexadecahydro-1H-cyclopenta[a]phenanthren-17-yl)oxy)hexyl)piperazine-1-carboxylate (Compound 8)

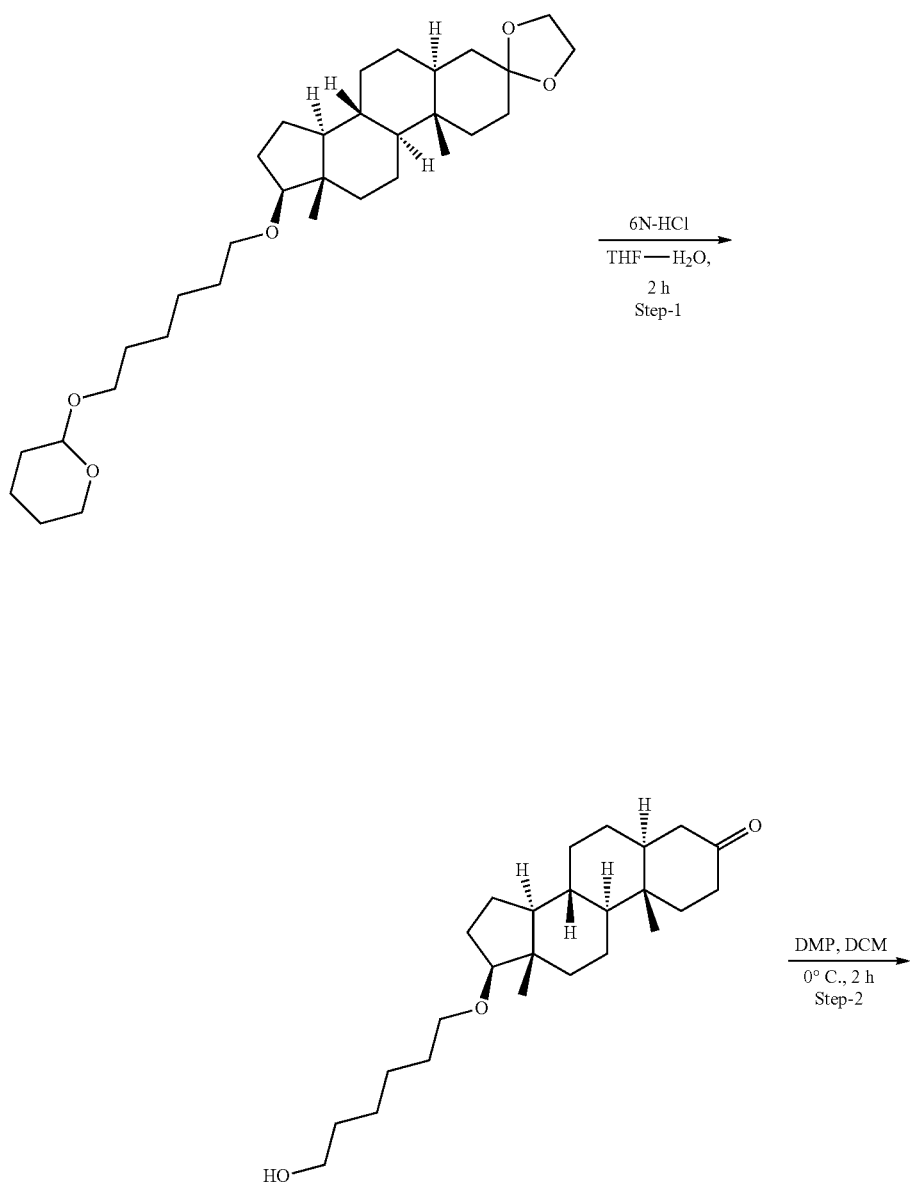

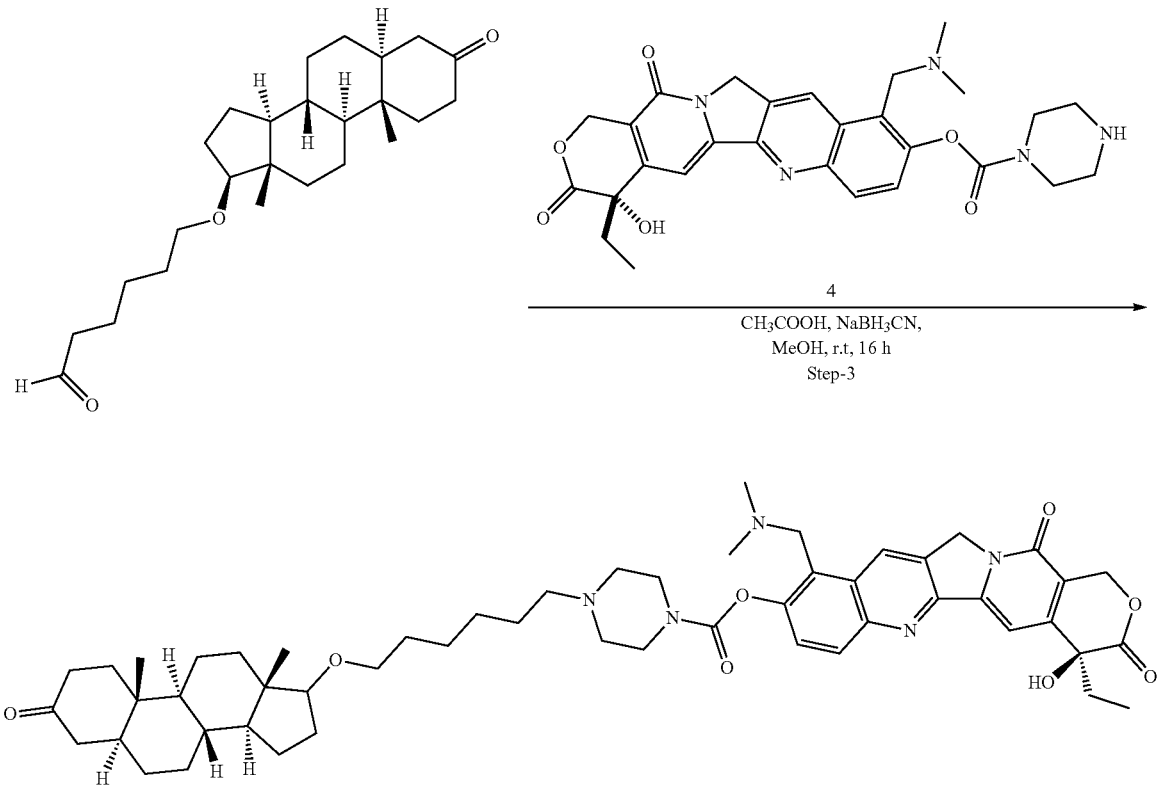

Step-1: Preparation of (5S,8R,9S,10S,13S,14S,17S)-17-(6-Hydroxyhexyloxy)-10,13-dimethyltetradecahydro-1H-cyclopenta[a]phenanthren-3(2H)-one To a stirred solution of (5S,8R,9S,10S,13S,14S,17S)-10,13-dimethylhexadecahydrospiro[cyclopenta[a]phenanthrene-3,2'-[1,3]dioxolan]-17-ol (0.86 g, 1.66 mmol, 1.0 eq.) in THF (21 mL), water (4.0 mL) was added 6 N—HCl (13 mL) at RT and the resultant mixture was stirred at 0° C. for 2 h. After completion of the reaction (monitored by TLC), the reaction mixture was diluted with saturated NaHCO$_3$ (50 mL) (pH ~8). The aqueous layer was extracted with EtOAc (50 mL). The organic layer was washed with NaHCO$_3$ (50 mL), dried over anhydrous sodium sulfate, filtered and evaporated under reduced pressure to get the desired product (0.7 g, 42%). LCMS: 391.5 [M+H]$^+$.

Step-2: Preparation of 6-((5S,8R,9S,10S,13S,14S,17S)-10,13-Dimethyl-3-oxohexadecahydro-1H-cyclopenta[a]phenanthren-17-yloxy)hexanal To a stirred solution of (5S,8R,9S,10S,13S,14S,17S)-10,13-dimethylhexadecahydrospiro[cyclopenta[a]phenanthrene-3,2'-[1,3]dioxolan]-17-ol (0.70 g, 1.61 mmol, 1.0 eq.) in DCM (10 ml) was added DMP (1.39 mL, 2.41 mmol). The reaction mixture was allowed to stir at 0° C. for 1 h. After completion of the reaction (monitored by TLC), the reaction mixture was diluted with water (50 mL) and extracted with EtOAc (100 mL). The organic layer was dried over anhydrous sodium sulfate, filtered and evaporated under reduced pressure to get the desired product (0.60 g, 99.99%). LCMS: 389.30 [M+H]$^+$.

Step-3: Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(6-(((5R,8S,9R,10R,13R,14R,17R)-10,13-dimethyl-3-oxohexadecahydro-1H-cyclopenta[a]phenanthren-17-yl)oxy)hexyl)piperazine-1-carboxylate (Compound 8)

To a stirred solution of 6-((5S,8R,9S,10S,13S,14S,17S)-10,13-dimethyl-3-oxohexadecahydro-1H-cyclopenta[a]phenanthren-17-yloxy)hexanal (0.70 g, 1.80 mmol, 1.0 eq.) in Methanol (10 mL), was added Topotecan (0.60 g, 1.80 mmol, 1.0 eq.) and acetic acid (0.2 mL) at 0° C. for 1 h, followed by addition of NaBH$_3$CN (0.18 g, 3.60 mmol, 2.0 eq.). The resultant mixture was stirred at RT for 16 h. After completion of the reaction (monitored by TLC), the reaction mixture was basified with NaHCO$_3$ solution (100 mL) and extracted with DCM (200 mL). The organic layer was washed with water (200 mL), dried over anhydrous sodium sulfate, filtered and evaporated under reduced pressure to get the crude. Crude was then purified by CombiFlash [silica gel 100-200 mesh, Elution—0-6% MeOH in DCM] to get the desired product (0.20 g, 13%). $^1$H NMR (400 MHz, DMSO-d$_6$): δ 8.95 (s, 1H), 8.29 (s, 1H), 8.11 (d, J=8.77 Hz, 1H), 7.63 (d, J=8.77 Hz, 1H), 7.34 (s, 1H), 6.52 (s, 1H), 5.43 (s, 2H), 5.32 (br s, 2H), 3.76 (br s, 2H), 3.70 (br s, 2H), 3.47 (br s, 2H), 3.38 (br s, 1H), 2.26 (br s, 1H), 2.20-1.16 (d, 37H), 0.97 (s, 3H), 0.89 (t, J=7.24 Hz, 4H), 0.79-0.56 (m, 4H). LCMS: 907.19 [M+H]$^+$.

Example 9
Preparation of (11R,13S,17R)-17-Acetyl-11-(4-((6-(4-(((S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy)piperidin-1-yl)hexyl)(methyl)amino)phenyl)-13-methyl-3-oxo-2,3,6,7,8,11,12,13,14,15,16,17-dodecahydro-1H-cyclopenta[a]phenanthren-17-yl acetate (Compound 9)
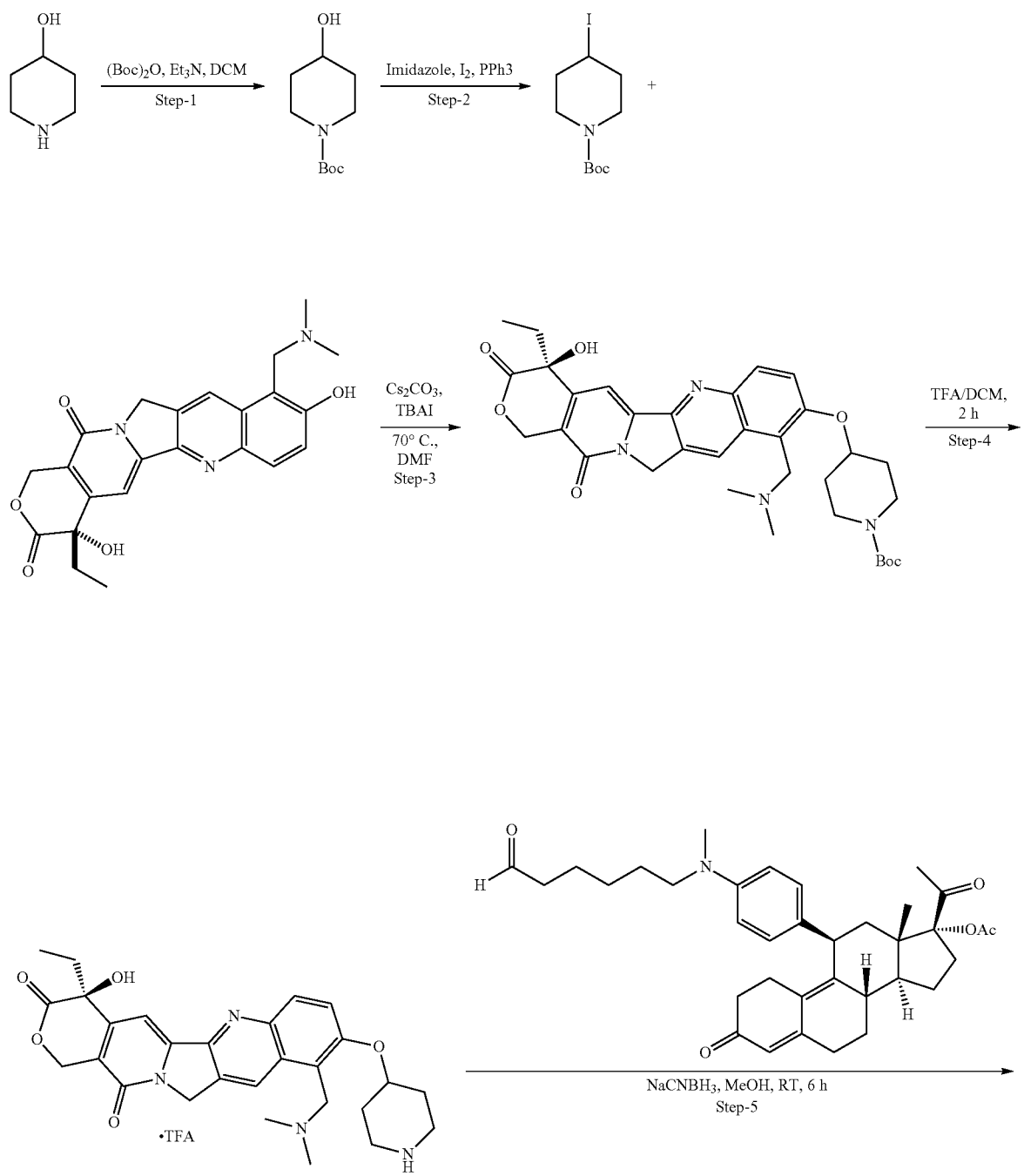

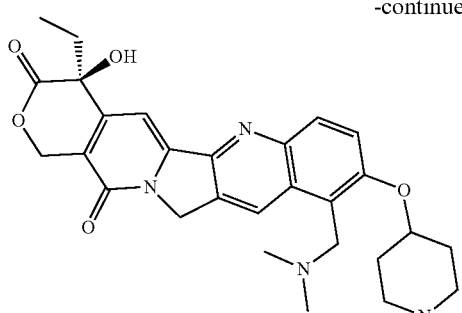

-continued

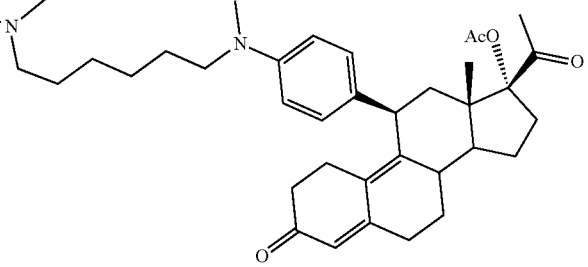

Step-1: Preparation of tert-Butyl 4-Hydroxypiperidine-1-carboxylate

To a stirred solution of 4-hydroxypiperidine (10 g, 99.01 mmol, 1.0 eq.) in DCM (200 mL) were successively added Boc-anhydride (25.5 g, 118.8 mmol, 1.2 eq.) and TEA (16.52 mL, 118.8 mmol, 1.2 eq.) and the mixture was stirred at RT for 18 h. The reaction was monitored by TLC and LC-MS. After completion, the mixture was diluted with $H_2O$ (100 mL) and extracted with DCM (30 mL×3). The combined organic layers were washed with water (100 mL), brine (50 mL), dried over anhydrous sodium sulfate and concentrated under reduced pressure to afford the title compound (19 g, 95% yield). $^1$H NMR (400 MHz, $CDCl_3$): δ 3.91-3.79 (m, 3H), 3.08-3.00 (m, 2H), 1.90-1.81 (m, 2H), 1.51-1.41 (m, 11H).

Step-2: Preparation of tert-Butyl 4-Iodopiperidine-1-carboxylate

To a stirred solution of N-Boc-4-hydroxypiperidine (19 g, 94.52 mmol, 1.0 eq.) in DCM (200 mL) were added triphenylphosphine (32.2 g, 122.8 mmol, 1.3 eq.) and imidazole (10.2 g, 151.2 mmol, 1.6 eq.) followed by addition of iodine (23.81 g, 94.5 mmol, 1.0 eq.) at 0° C. portion-wise. The resultant mixture was then stirred at ambient temperature for 4 h and monitored by TLC. After completion, the mixture was diluted with water (100 mL) and extracted with diethyl ether (150 mL). The organic layer was washed with water (300 mL), and brine (100 mL), dried over anhydrous sodium sulfate and concentrated under reduced pressure to afford a crude residue which was purified by CombiFlash chromatography to afford the title compound (13.9 g, 47% yield). $^1$H NMR (400 MHz, $CDCl_3$): δ 4.43 (m, 1H), 3.57 (dt, J=3.6, 13.6 Hz, 2H), 3.26 (dt, J=6.0, 3.6 Hz, 2H), 2.01 (m, 4H), 1.44 (s, 9H).

Step-3: Preparation of (S)-tert-Butyl 4-((10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy)piperidine-1-carboxylate To a stirred solution of (S)-10-((dimethylamino)methyl)-4-ethyl-4,9-dihydroxy-1H-pyrano[3',4':6,7]indolizino[1,2-b]quinoline-3,14(4H,12H)-dione (3 g, 6.55 mmol, 1.0 eq.) in DMF (25 mL) was added $Cs_2CO_3$ (4.26 g, 13.11 mmol, 2.0 eq.) the mixture was stirred at RT for 15 minutes. TBAI (0.484 g, 1.31 mmol, 0.2 eq.) and tert-butyl 4-iodopiperidine-1-carboxylate (8.2 g, 26.22 mmol, 4.0 eq.) were then successively added to the mixture and the mixture was heated at 70° C. for 30 minutes. The progress of the reaction was monitored by TLC and LC-MS. After completion, the mixture was quenched with ice-cold water and the precipitate obtained was filtered over Büchner funnel, washed with $H_2O$ (100 mL) and dried under vacuum to afford a crude residue which was purified by CombiFlash chromatography to afford the title compound (0.65 g, 15%). LCMS: 605 [M+H]$^+$.

Step-4: Preparation of (S)-10-((Dimethylamino)methyl)-4-ethyl-4-hydroxy-9-(piperidin-4-yloxy)-1H-pyrano[3',4':6,7]indolizino[1,2-b]quinoline-3,14(4H,12H)-dione To a stirred solution of (S)-tert-butyl 4-((10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy)piperidine-1-carboxylate (0.65 g, 1 mmol) in DCM (8 mL) was added trifluoroacetic acid (2 mL) at 0° C. slowly and the resultant mixture was stirred RT for 2 h. The reaction was monitored by TLC and LC-MS. After completion, the mixture was concentrated under reduced pressure to obtain a crude residue which was triturated with diethyl ether (10 mL×2) to afford the title compound (0.35 g, 64%). LCMS: 505 [M+H]$^+$.

Step-5: Preparation of ((11R,13S,17R)-17-Acetyl-11-(4-((6-(4-(((S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy)piperidin-1-yl)hexyl)(methyl)amino)phenyl)-13-methyl-3-oxo-2,3,6,7,8,11,12,13,14,15,16,17-dodecahydro-1H-cyclopenta[a]phenanthren-17-yl acetate (Compound 9)

To a stirred solution of (S)-10-((dimethylamino)methyl)-4-ethyl-4-hydroxy-9-(piperidin-4-yloxy)-1H-pyrano[3',4':6, 7]indolizino[1,2-b]quinoline-3,14(4H,12H)-dione (0.30 g, 0.48 mmol, 1.0 eq.) and (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate (0.804 g, 1.44 mmol, 3.0 eq.) in anhydrous methanol (12 mL) was added acetic acid (0.2 ml) at RT and the mixture was stirred at same temperature for 30 minutes. Sodium cyanoborohydride (0.06 g, 0.96 mmol) was then slowly added and the resulting reaction mixture was stirred at RT for 6 h. The reaction was monitored by TLC & LC-MS. After completion, the mixture was diluted with H$_2$O (30 mL) and extracted with DCM (30 mL×3). The combined organic layers were washed with saturated NaHCO$_3$ (20 mL), water (20 mL), brine (20 mL), dried over anhydrous sodium sulfate and concentrated under reduced pressure on obtain a crude residue which was purified by Reversed Phase chromatography to afford the title compound (25 mg, 4%). $^1$H NMR (400 MHz, DMSO-d$_6$): δ 8.80 (s, 1H), 8.18-8.01 (m, 1H), 7.93-7.69 (m, 1H), 7.29 (s, 1H), 6.97 (d, J=8.55 Hz, 2H), 6.58 (d, J=8.55 Hz, 2H), 6.50 (s, 2H), 5.66 (s, 1H), 5.42 (s, 2H), 5.28 (s, 2H), 4.39 (d, J=6.80 Hz, 2H), 4.28 (m, 2H), 3.86 (s, 3H), 3.27-3.16 (m, 3H), 2.82 (s, 7H), 2.74-2.64 (m, 9H), 2.38-2.25 (m, 8H), 2.25-2.12 (m, 13H), 2.05-1.93 (m, 6H), 1.93-1.76 (m, 3H), 1.76-1.55 (m, 2H), 1.41 (m, 1H), 0.88 (t, J=7.21 Hz, 3H). LCMS: 1048 [M+H]$^+$.

Example 10

Preparation of (11R,13S,17R)-17-Acetyl-11-(4-((7-(4-(((S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy)piperidin-1-yl)heptyl)(methyl)amino)phenyl)-13-methyl-3-oxo-2,3,6,7,8,11,12,13,14,15,16,17-dodecahydro-1H-cyclopenta[a]phenanthren-17-yl-acetate (Compound 10)

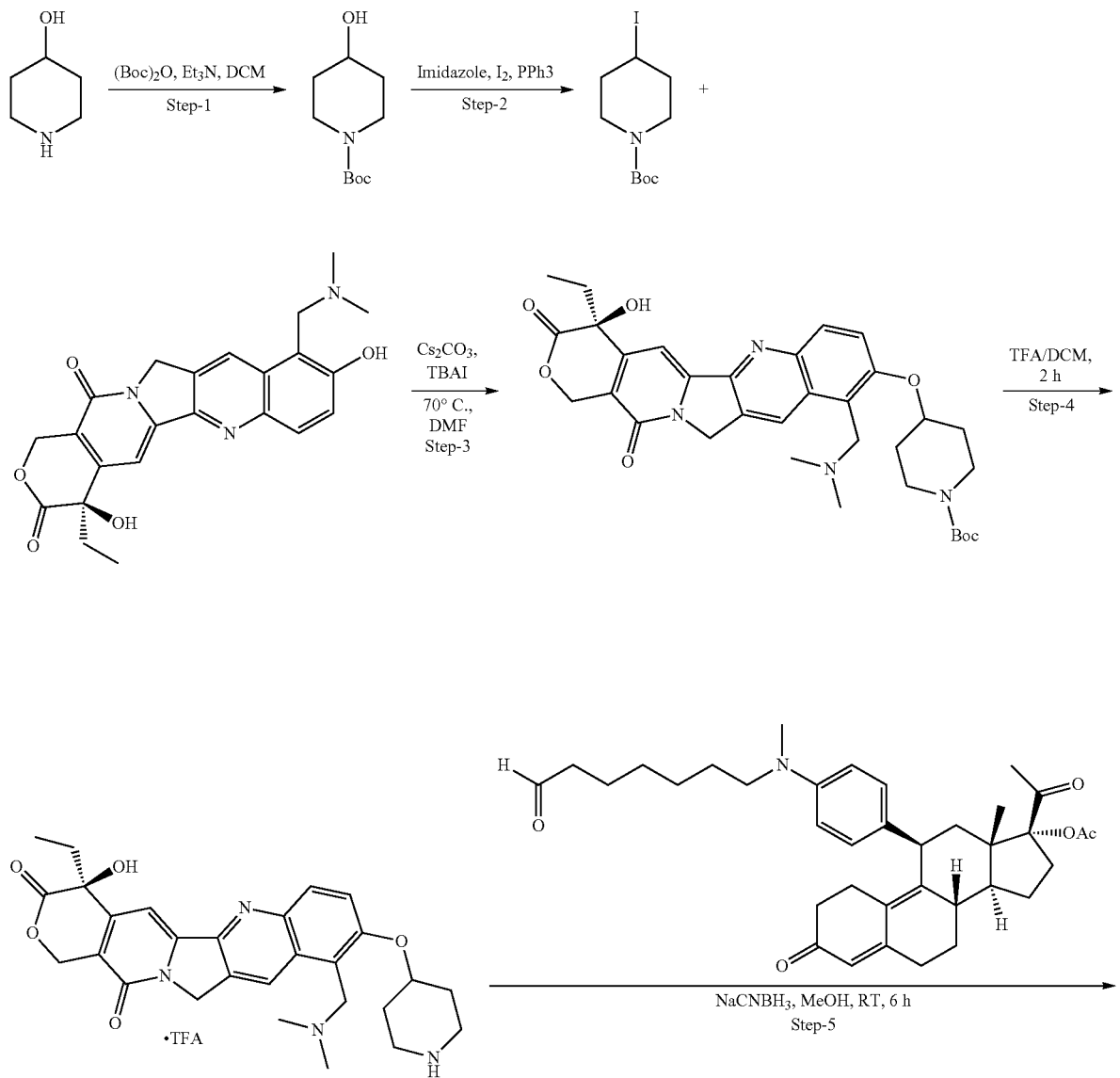

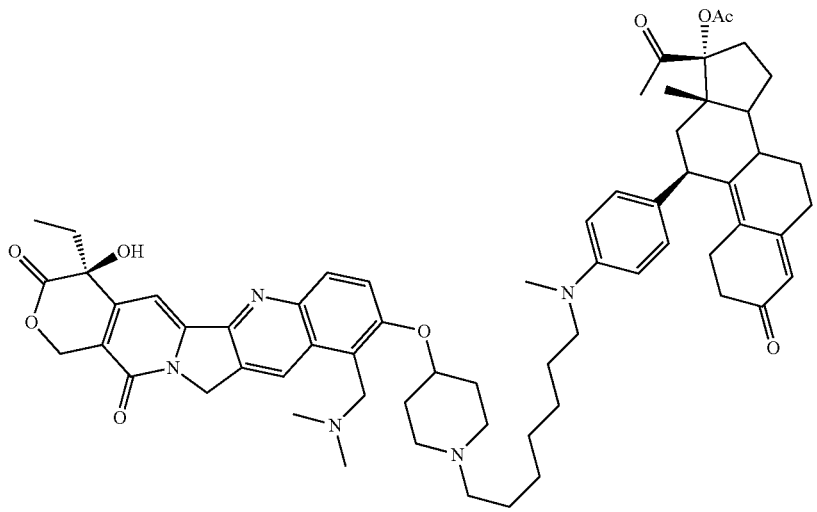
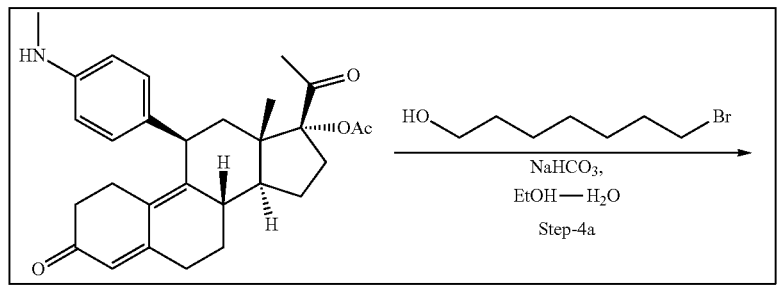
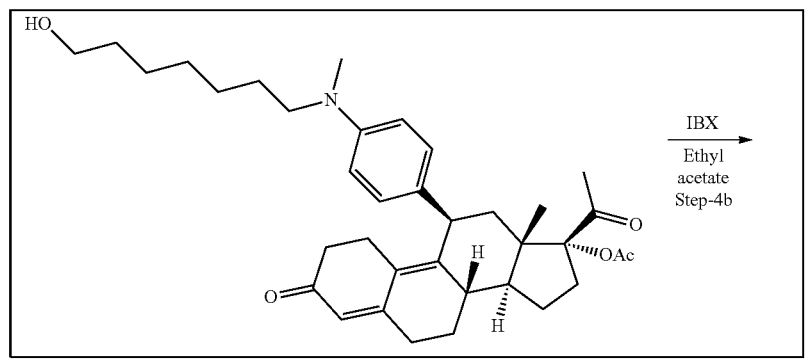
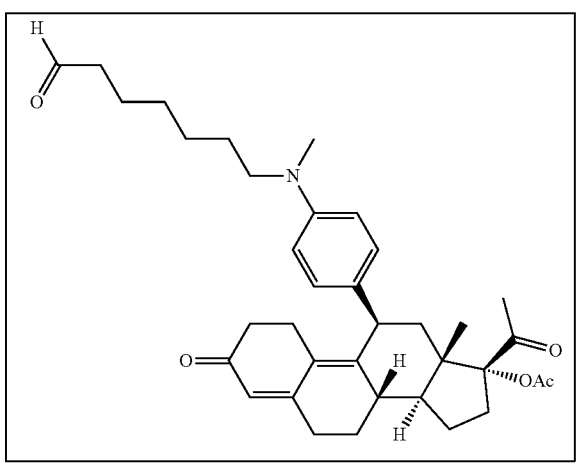

Step-1: Preparation of tert-Butyl 4-Hydroxypiperidine-1-carboxylate

To a stirred solution of 4-hydroxypiperidine (10 g, 99.01 mmol, 1.0 eq.) in DCM (200 mL) were successively added Boc-anhydride (25.5 g, 118.8 mmol, 1.2 eq.) and TEA (16.5 mL, 118.8 mmol, 1.2 eq.) and the mixture was stirred at RT for 18 h. The reaction was monitored by TLC & LC-MS. After completion, the mixture was diluted with H$_2$O (100 mL) and extracted with DCM (30 mL×3). The combined organic layers were washed with water (100 mL), brine (50 mL), dried over anhydrous sodium sulfate and concentrated under reduced pressure to afford the title compound (19 g, 95% yield). $^1$H NMR (400 MHz, CDCl$_3$): δ 3.91-3.79 (m, 3H), 3.08-3.00 (m, 2H), 1.90-1.81 (m, 2H), 1.51-1.41 (m, 11H).

Step-2: Preparation of tert-Butyl 4-Iodopiperidine-1-carboxylate

To a stirred solution of N-Boc-4-hydroxypiperidine (19 g, 94.52 mmol, 1.0 eq.) in DCM (200 mL) were added triphenylphosphine (32.2 g, 122.8 mmol, 1.3 eq.) and imidazole (10.2 g, 151.2 mmol, 1.6 eq.) followed by addition of iodine (23.81 g, 94.5 mmol, 1.0 eq.) at 0° C. portion-wise. The resultant mixture was then stirred at ambient temperature for 4 h and monitored by TLC. After completion, the mixture was diluted with water (100 mL) and extracted with diethyl ether (150 mL). The organic layer was washed with water (300 mL), and brine (100 mL), dried over anhydrous sodium sulfate and concentrated under reduced pressure to afford a crude residue which was purified by CombiFlash chromatography to afford the title compound (13.9 g, 47% yield). $^1$H NMR (400 MHz, CDCl$_3$): δ 4.43 (m, 1H), 3.57 (dt, J=3.6, 13.6 Hz, 2H), 3.26 (dt, J=6.0, 3.6 Hz, 2H), 2.01 (m, 4H), 1.44 (s, 9H).

Step-3: Preparation of (S)-tert-Butyl 4-((10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy)piperidine-1-carboxylate To a stirred solution of (S)-10-((dimethylamino)methyl)-4-ethyl-4,9-dihydroxy-1H-pyrano[3',4':6,7]indolizino[1,2-b]quinoline-3,14(4H,12H)-dione (3 g, 6.55 mmol, 1.0 eq.) in DMF (25 mL) was added Cs$_2$CO$_3$ (4.26 g, 13.11 mmol, 2.0 eq.) the mixture was stirred at RT for 15 minutes. TBAI (0.48 g, 1.31 mmol, 0.2 eq.) and tert-butyl 4-iodopiperidine-1-carboxylate (8.2 g, 26.22 mmol, 4.0 eq.) were then successively added to the mixture and the mixture was heated at 70° C. for 30 minutes. The progress of the reaction was monitored by TLC and LC-MS. After completion, the mixture was quenched with ice-cold water and the precipitate obtained was filtered over Büchner funnel, washed with H$_2$O (100 mL) and dried under vacuum to afford a crude residue which was purified by CombiFlash chromatography to afford the title compound (0.65 g, 15%). LCMS: 605 [M+H]$^+$.

Step-4: Preparation of (S)-10-((Dimethylamino)methyl)-4-ethyl-4-hydroxy-9-(piperidin-4-yloxy)-1H-pyrano[3',4':6,7]indolizino[1,2-b]quinoline-3,14(4H,12H)-dione To a stirred solution of (S)-tert-butyl 4-((10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy)piperidine-1-carboxylate (0.65 g, 1 mmol, 1.0 eq.) in DCM (8 mL) was added trifluoroacetic acid (2 mL) at 0° C. slowly and the resultant mixture was stirred RT for 2 h. The reaction was monitored by TLC and LC-MS. After completion, the mixture was concentrated under reduced pressure to obtain a crude residue which was triturated with diethyl ether (10 mL×2) to afford the title compound (0.35 g, 64%). LCMS: 505 [M+H]$^+$.

Step-4a: Preparation of (8S,11R,13S,14S,17R)-17-Acetyl-11-(4-((7-hydroxyheptyl)(methyl)amino) phenyl)-13-methyl-3-oxo-2,3,6,7,8,11,12,13,14,15, 16,17-dodecahydro-1H-cyclopenta[a]phenanthren-17-yl Acetate To a stirred suspension of 7-bromo heptanol (3.17 g, 16.2 mmol, 3.0 eq.) in EtOH:H$_2$O (25 mL:5 mL) was added NaHCO$_3$ (pH ~8-9) followed by addition of (8S,11R,13S, 14S,17R)-17-acetyl-13-methyl-11-(4-(methylamino)phenyl)-3-oxo-2,3,6,7,8,11,12,13,14,15,16,17-dodecahydro-1H-cyclopenta[a]phenanthren-17-yl acetate (2.5 g, 5.42 mmol, 1.0 eq.) dissolved in EtOH (20 mL) and the resultant mixture was heated at 80° C. for 16 h. After completion, the mixture was diluted with water (100 mL) and extracted with DCM (200 mL×3). The combined organic layers were dried over anhydrous sodium sulfate, concentrated under reduced pressure to obtain a crude residue which was purified by CombiFlash Chromatography to afford the title compound (1.1 g, 35%). LCMS: 576 [M+H]$^+$.

Step-4b: Synthesis of (8S,11R,13S,14S,17R)-17-acetyl-13-methyl-11-(4-(methyl(7-oxoheptyl)amino) phenyl)-3-oxo-2,3,6,7,8,11,12,13,14,15,16,17-dodecahydro-1H-cyclopenta[a]phenanthren-17-yl Acetate To a stirred solution of (8S,11R,13S,14S,17R)-17-acetyl-11-(4-((7-hydroxyheptyl) (methyl)amino)phenyl)-13-methyl-3-oxo-2,3,6,7,8,11,12,13,14,15,16,17-dodecahydro-1H-cyclopenta[a]phenanthren-17-yl acetate (1 g, 1.73 mmol, 1.0 eq.) in EtOAc (100 mL) was added 2-iodoxybenzoic acid (1.2 g, 4.34 mmol, 2.5 eq.) portion-wise at 0° C. and the mixture was allowed to stir at 80° C. for 2 h. After completion, the mixture was diluted with DCM (300 mL). The organic layer was washed with saturated solution of Na$_2$S$_2$O$_3$ (100 mL×2), NaHCO$_3$ solution (100 mL×2), then with water (100 mL) and dried over anhydrous sodium sulfate, concentrated to afford the title compound (0.9 g, 90%) which was taken to next step without further purification. LCMS: 574 [M+H]$^+$.

Step-5: Preparation of (11R,13S,17R)-17-Acetyl-11-(4-((7-(4-(((S)-10((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy) piperidin-1-yl)heptyl)(methyl)amino)phenyl)-13-methyl-3-oxo-2,3,6,7,8,11,12,13,14,15,16,17-dodecahydro-1H-cyclopenta[a]phenanthren-17-yl Acetate (Compound 10)

To a stirred solution of (S)-10-((dimethylamino)methyl)-4-ethyl-4-hydroxy-9-(piperidin-4-yloxy)-1H-pyrano[3',4':6, 7]indolizino[1,2-b]quinoline-3,14(4H,12H)-dione (0.3 g, 0.48 mmol, 1.0 eq.) and (8S,11R,13S,14S,17R)-17-acetyl-13-methyl-11-(4-(methyl(7-oxoheptyl)amino) phenyl)-3-oxo-2,3,6,7,8,11,12,13,14,15,16,17-dodecahydro-1H-cyclopenta[a]phenanthren-17-yl acetate (0.80 g, 1.44 mmol, 3.0 eq.) in anhydrous methanol (12 mL) was added acetic acid (0.2 ml) at RT and the mixture was stirred at same temperature for 30 minutes. Sodium cyanoborohydride (0.06 g, 0.96 mmol) was then slowly added to the mixture and the resultant mixture was stirred at RT for 6 h. The reaction was monitored by TLC & LC-MS. After completion, the mixture was diluted with H$_2$O (30 mL) and extracted with DCM (30 mL×3). The combined organic layers were washed with saturated NaHCO$_3$ (20 mL), water (20 mL), brine (20 mL), dried over anhydrous sodium sulfate and concentrated under reduced pressure on obtain a crude residue which was purified by reverse phase chromatography to afford the title compound (20 mg, 2%). $^1$H NMR (400 MHz, DMSO-d$_6$): δ 8.78 (s, 1H), 8.07 (d, J=9.2 Hz, 1H), 7.76 (d, J=9.2 Hz, 1H), 7.27 (s, 1H), 7.03-6.88 (m, 2H), 6.56 (d, J=8.8 Hz, 2H), 6.48 (s, 1H), 5.65 (s, 1H), 5.40 (s, 2H), 5.26 (s, 2H), 4.66 (br s, 1H), 4.37 (d, J=7.9 Hz, 2H), 3.85 (s, 3H), 3.22 (d, J=7.0 Hz, 2H), 2.80 (s, 6H), 2.72 (s, 2H), 2.20 (s, 3H), 2.13 (d, J=14.0 Hz, 3H), 2.08 (s, 3H), 1.97 (s, 3H), 1.93-1.78 (m, 7H), 1.73 (s, 3H), 1.71-1.52 (m, 8H), 1.42 (s, 8H), 1.26 (s, 8H), 0.86 (t, J=7.5 Hz, 3H). LCMS: 1062 [M+H]$^+$.

Example 11

Preparation of N-((1r,4r)-4-(3-Chloro-4-cyanophenoxy)cyclohexyl)-6-(4-((4-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperazin-1-yl)methyl)piperidin-1-yl)pyridazine-3-carboxamide (Compound 11)

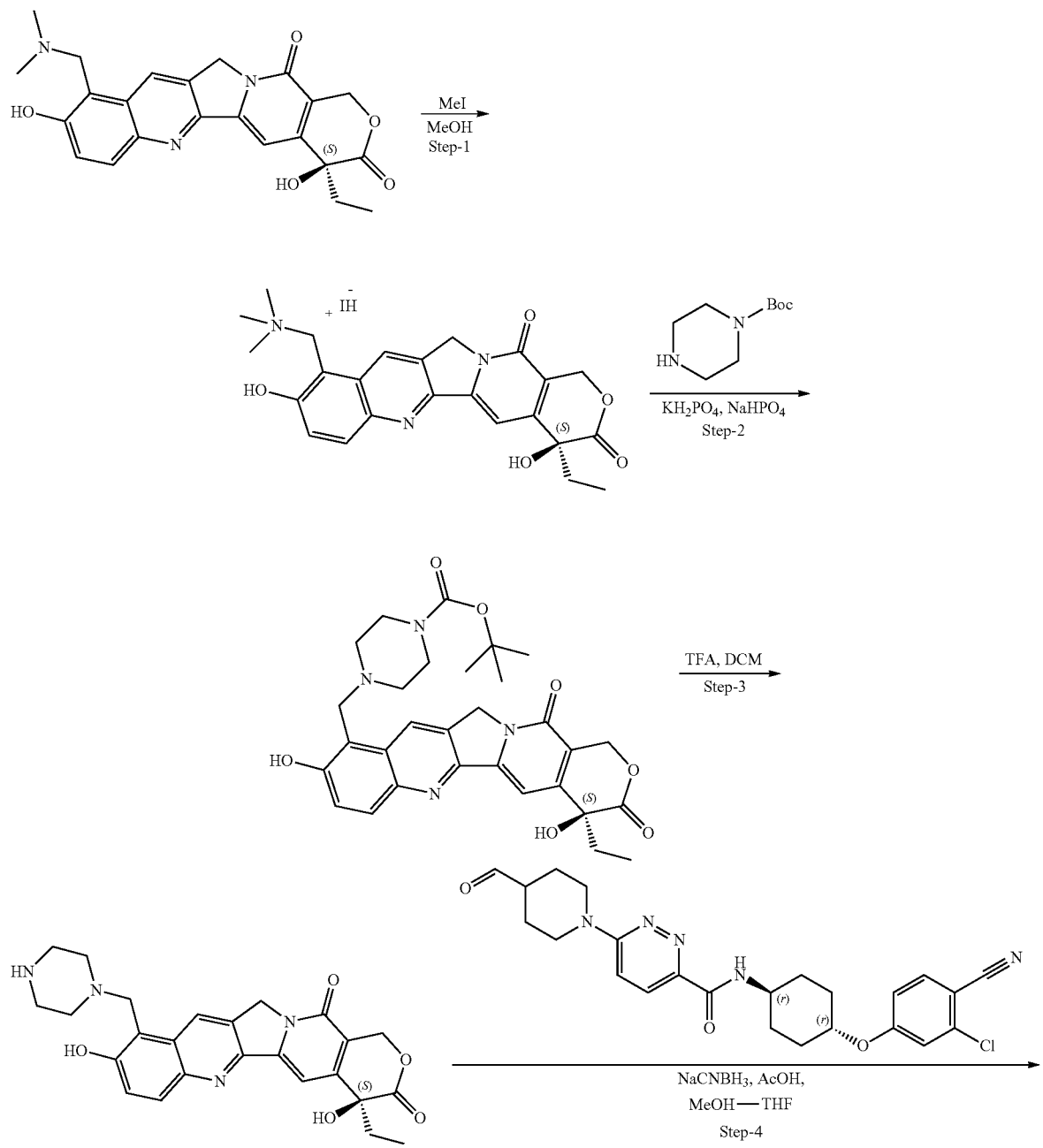

-continued

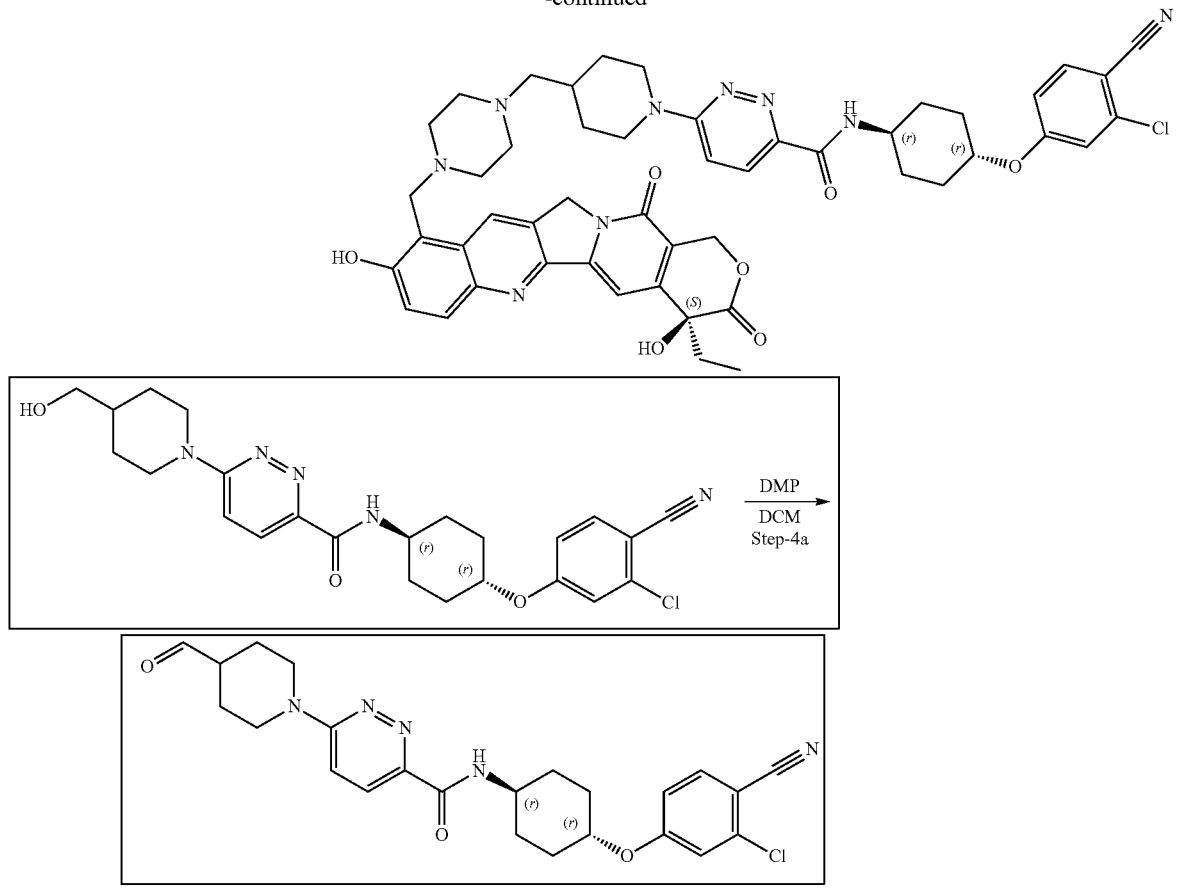

Step-1: Preparation of (S)-1-(4-Ethyl-4,9-dihydroxy-3,14-dioxo-3,4,12,14-tetrahydro-1H-pyrano[3',4':6,7]indolizino[1,2-b]quinolin-10-yl)-N,N,N-trimethylmethanaminium Iodide To a solution of (S)-10-((dimethylamino)methyl)-4-ethyl-4,9-dihydroxy-1H-pyrano[3',4':6,7]indolizino[1,2-b]quinoline-3,14(4H,12H)-dione (2.0 g, 4.75 mmol, 1.0 eq.) in MeOH (50 mL), was added methyl iodide (2.60 g, 19.0 mmol, 4 eq.) at RT and the mixture was stirred at same temperature for 3 h. After 3 h, the mixture was concentrated under reduced pressure to afford the quaternary salt which was washed with diethyl ether and dried under reduced pressure to afford title compound (2.0 g, 76%).

Step-2: Preparation of (S)-tert-Butyl 4-((4-Ethyl-4,9-dihydroxy-3,14-dioxo-3,4,12,14-tetrahydro-1H-pyrano[3',4':6,7]indolizino[1,2-b]quinolin-10-yl)methyl)piperazine-1-carboxylate To a solution of (S)-1-(4-ethyl-4,9-dihydroxy-3,14-dioxo-3,4,12,14-tetrahydro-1H-pyrano[3',4':6,7]indolizino[1,2-b]quinolin-10-yl)-N,N,N-trimethylmethanaminium iodide (2.0 g, 3.55 mmol, 1.0 eq.) and N-Boc-piperazine (1.18 g, 5.32 mmol, 1.5 eq.) in Na$_2$HPO$_4$:KH$_2$PO$_4$ (pH ~7) (20 mL) was stirred at 100° C. for 3 h. The reaction was monitored by TLC. After completion, the mixture was diluted with NaHCO$_3$ (50 mL) and extracted with 10% MeOH in EtOAc (200 mL×3). The combined organic layers were dried over anhydrous sodium sulfate, filtered and concentrated under reduced pressure to afford crude residue which was purified by CombiFlash chromatography to afford title compound (0.25 g, 12%). LCMS: 563 [M+H]$^+$.

Step-3: Preparation of (S)-4-Ethyl-4,9-dihydroxy-10-(piperazin-1-ylmethyl)-1H-pyrano[3',4':6,7]indolizino[1,2-b]quinoline-3,14(4H,12H)-dione To a stirred solution of (S)-tert-butyl 4-((4-ethyl-4,9-dihydroxy-3,14-dioxo-3,4,12,14-tetrahydro-1H-pyrano[3',4':6,7]indolizino[1,2-b]quinolin-10-yl)methyl)piperazine-1-carboxylate (0.25 g, 0.44 mmol, 1.0 eq.) in DCM (5 mL) was added TFA (0.5 mL) at 0° C. dropwise and the mixture was stirred at RT for 2 h. The reaction was monitored by TLC. After completion, the mixture was quenched with saturated NaHCO$_3$ solution (100 mL) and extracted with 10% MeOH in EtOAc (100 mL×3). The combined organic layers were washed with water (50 mL), brine (50 mL), dried over anhydrous sodium sulfate, filtered and concentrated under reduced pressure to afford title compound (0.200 g, 97%). LCMS: 463 [M+H]$^+$.

Step-4a: Preparation of N-((1r,4r)-4-(3-Chloro-4-cyanophenoxy)cyclohexyl)-6-(4-formylpiperidin-1-yl)pyridazine-3-carboxamide To a solution of N-((1r,4r)-4-(3-chloro-4-cyanophenoxy)cyclohexyl)-6-(4-(hydroxymethyl)piperidin-1-yl)pyridazine-3-carboxamide (0.8 g, 1.7 mmol, 1.0 eq.) in DCM (20 mL) was added DMP (1.44 g, 3.41 mmol, 2.0 eq.)

at 0° C. and the reaction mixture was stirred at room temperature for 2 h. The reaction was monitored by TLC. After completion, the mixture was diluted with DCM (100 mL) and washed with sat NaHCO$_3$ (100 mL×2), dried over anhydrous sodium sulfate, filtered and concentrated under reduced pressure to afford crude which was purified by CombiFlash chromatography to afford title compound (0.5 g, 62%). LCMS: 468 [M+H]$^+$.

Step-4: Preparation of N-((1r,4r)-4-(3-Chloro-4-cyanophenoxy)cyclohexyl)-6-(4-((4-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperazin-1-yl)methyl)piperidin-1-yl)pyridazine-3-carboxamide (Compound 11)

To a solution of N-((1r,4r)-4-(3-chloro-4-cyanophenoxy)cyclohexyl)-6-(4-formylpiperidin-1-yl)pyridazine-3-carboxamide (200 mg, 0.432 mmol, 1.0 eq.) and (S)-4-ethyl-4,9-dihydroxy-10-(piperazin-1-ylmethyl)-1H-pyrano[3',4':6,7]indolizino[1,2-b]quinoline-3,14(4H,12H)-dione (0.3 g, 0.65 mmol, 1.0 eq.) in methanol:THF (5:2) (14 mL) was added catalytic amount acetic acid (0.1 mL) and the reaction mixture was stirred at RT for 2 h. Sodium cyanoborohydride (0.07 g, 1.08 mmol, 2.5 eq.) was then added to the mixture and continue to stirred for 1 h. The reaction was monitored by TLC. After completion, the mixture was concentrated under reduced pressure then diluted with H$_2$O (50 mL) and extracted with EtOAc (200 mL×2). The combined organic layers were washed with water (100 mL×2), brine (100 mL), dried over anhydrous sodium sulfate, filtered and concentrated under reduced pressure to afford crude residue which washed with methanol to afford title compound (0.06 g, 15%). $^1$H NMR (400 MHz, DMSO-d$_6$): δ 8.73 (s, 1H), 8.58 (d, J=8.33 Hz, 1H), 7.98 (d, J=9.21 Hz, 1H), 7.85 (d, J=8.77 Hz, 1H), 7.79 (d, J=9.21 Hz, 1H), 7.47-7.36 (m, 2H), 7.32 (d, J=9.65 Hz, 1H), 7.26 (s, 1H), 7.13 (dd, J=8.77, 2.19 Hz, 1H), 6.48-6.38 (br s, 1H), 5.41 (s, 2H), 5.25 (s, 2H) 4.61-4.40 (m, 3H), 4.10 (s, 3H), 2.99 (t, J=12.06 Hz, 3H), 2.67 (m, 3H), 2.61 (m, 3H), 2.03-2.21 (m, 4H), 1.95-1.72 (m, 7H), 1.71-1.57 (m, 4H), 1.57-1.43 (m, 2H), 1.10 (d, J=11.84 Hz, 2H), 0.88 (t, J=7.45 Hz, 3H). LCMS: 914 [M+H]$^+$.

Example 12

Preparation of N-((1r,4r)-4-(3-Chloro-4-cyanophenoxy)cyclohexyl)-4-((6-(4-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperazin-1-yl)-6-oxohexyl)oxy)benzamide (Compound 12)

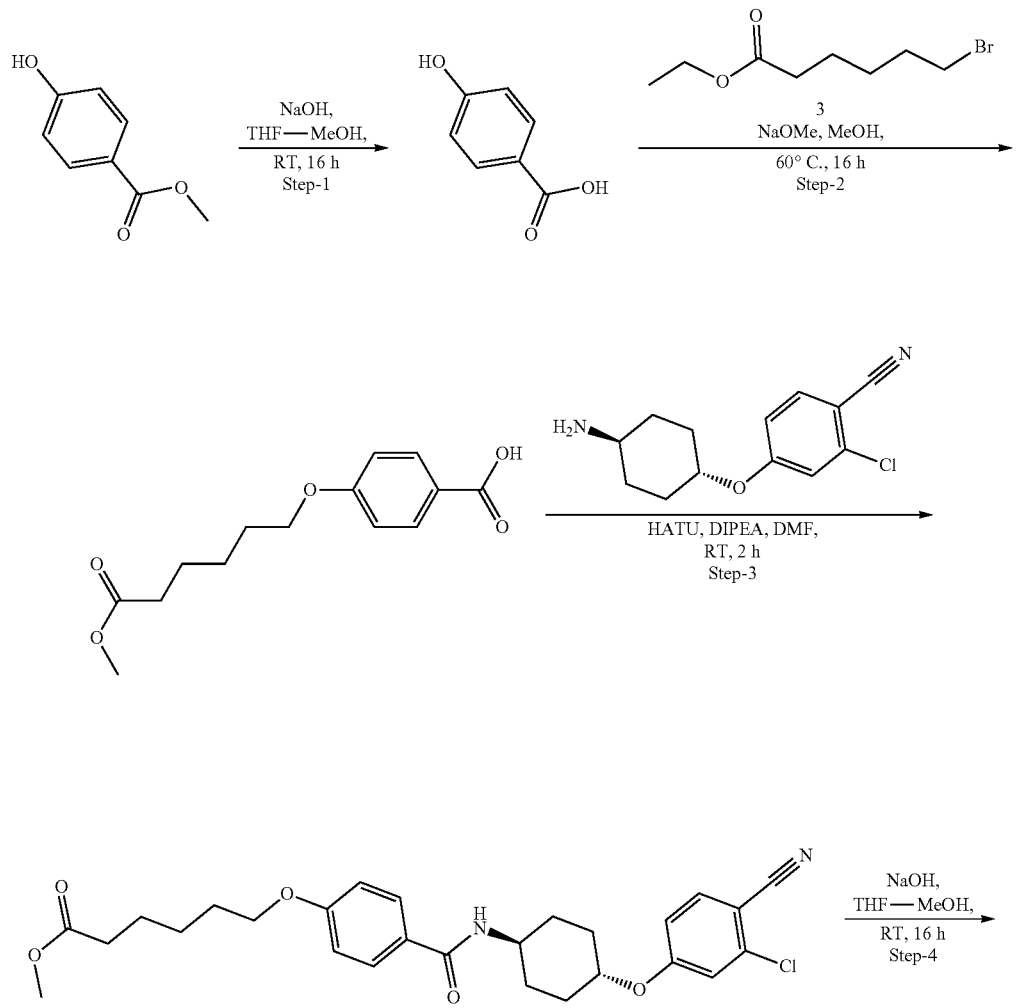

-continued
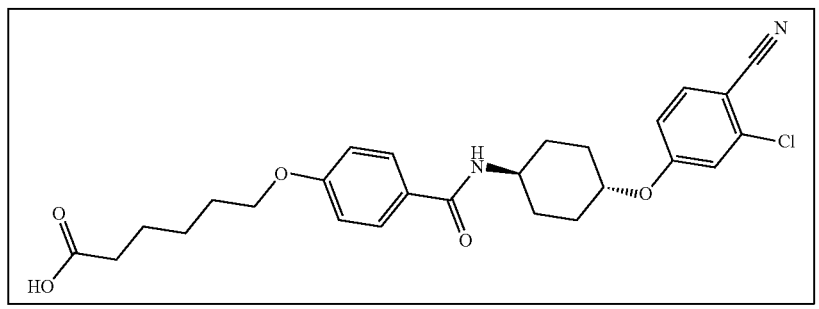
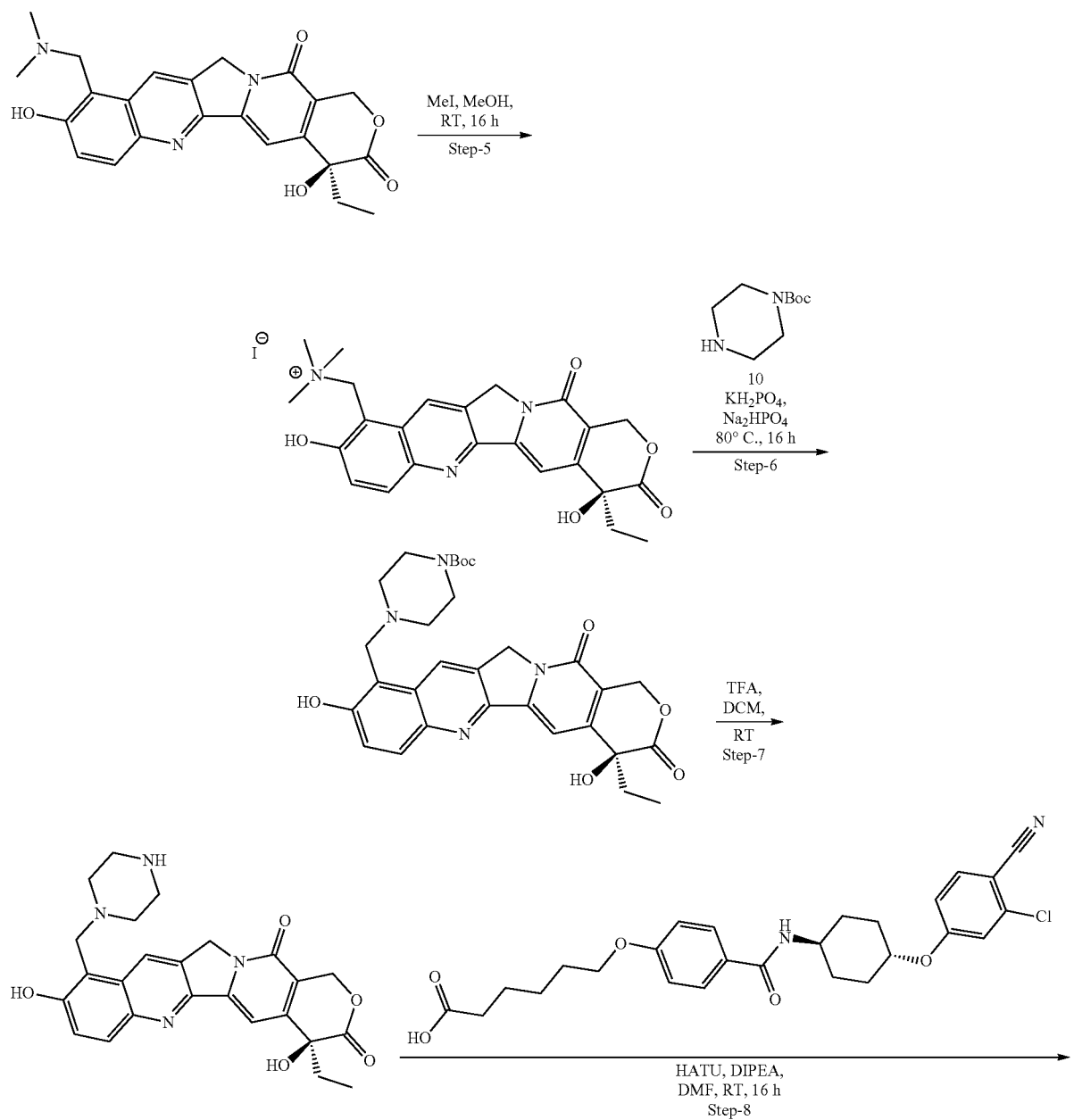

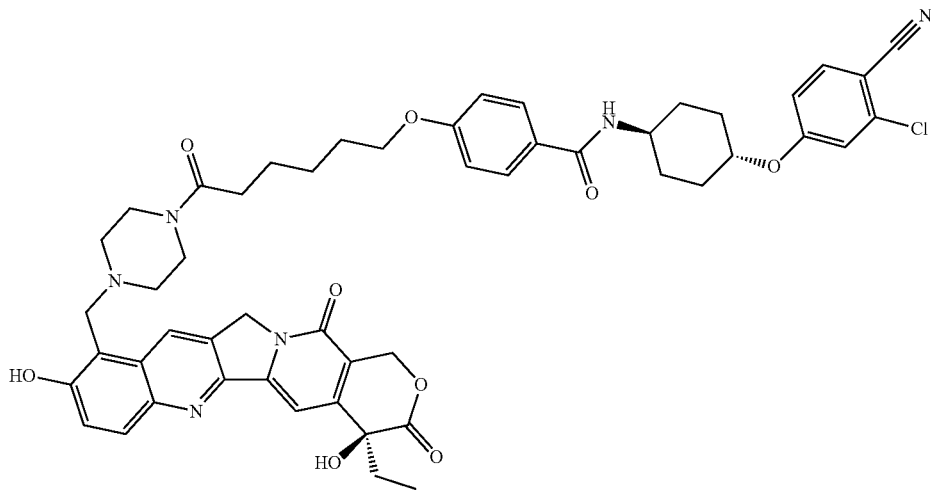

Step-1: Preparation of 4-Hydroxybenzoic acid

To a solution of methyl paraben (5 g, 32.89 mmol, 1.0 eq.) in THF:MeOH (1:1, 100 mL) was added solution of 4N NaOH (13.1 g, 328 mmol, 10.0 eq.) in water (80 mL) and the mixture was stirred at RT for 16 h. The reaction was monitored using TLC. After completion, the mixture was concentrated under reduced pressure and the residue obtained was acidified with conc. HCl to pH 3-2. The precipitated solid was filtered over Büchner funnel, washed with cold water and dried to afford the title compound (2.5 g, 55%). LCMS: 139 [M+H]$^+$.

Step-2: Preparation of 4-(6-Methoxy-6-oxohexyloxy)benzoic acid

4-Hydroxybenzoic acid (500 mg, 3.62 mmol, 1.0 eq.) was added to a solution of sodium methoxide (410 mg, 7.60 mmol, 2.1 eq.) in methanol (30 mL) and the mixture was stirred at RT for 5 min, followed by the addition of ethyl 5-bromohexanoate (1.13 g, 5.43 mmol, 1.5 eq.). The resultant mixture was stirred at 50° C. for 16 h. The reaction was monitored using TLC. After completion, the volatiles were removed under reduced pressure and the residue was dissolved in water. The aqueous layer was washed with ether (50 mL) and then acidified to pH 3-4 using dilute hydrochloric acid. The precipitated solid was collected by filtration, washed with water and dried to afford the title compound (463 mg, 48%). LCMS: 267 [M+H]$^+$.

Step-3: Preparation of Methyl 6-(4-((1r,4r)-4-(3-Chloro-4-cyanophenoxy)cyclohexylcarbamoyl)phenoxy)hexanoate To a solution of 4-(6-methoxy-6-oxohexyloxy)benzoic acid (350 mg, 1.31 mmol, 1.0 eq.) in a dry DMF (5 mL) was added HATU (750 mg, 1.97 mmol, 1.5 eq.) at 0° C. and stirred for 30 min. To this mixture was added 4-(((1r,4r)-4-aminocyclohexyloxy)-2-chlorobenzonitrile (327 mg, 1.31 mmol, 1.0 eq.) followed by addition of DIPEA (247 mg, 1.97 mmol, 1.5 eq.). The resultant mixture was stirred at room temperature for 2 h. After completion, the mixture was diluted with water (30 mL) and extracted with EtOAc (30 mL×3). The combined organic layers were washed with water (30 mL×2), brine (30 mL), dried over anhydrous sodium sulfate, filtered and evaporated to afford the title compound which was used as such for next step without purification (600 mg). LCMS: 499 [M+H]$^+$.

Step-4: Preparation of 6-(4-((1r,4r)-4-(3-Chloro-4-cyanophenoxy)cyclohexylcarbamoyl)phenoxy) hexanoic Acid To a solution of methyl 6-(4-((1r,4r)-4-(3-chloro-4-cyanophenoxy)cyclohexylcarbamoyl) phenoxy)hexanoate (600 mg, 1.20 mmol, 1.0 eq.) in THF:MeOH (1:1, 10 mL) was added 4M NaOH (144 mg, 3.60 mmol, 3.0 eq.) and stirred at RT for 1 h. The progress of the reaction was monitored using TLC. After completion, the mixture was concentrated under reduced pressure and acidified with conc. HCl to pH 3-4. The solid obtained was then filtered on Büchner funnel and washed with water, diethyl ether, pentane and dried under vacuum to afford the title compound (500 mg, 86%) which was used directly for next step without purification. LCMS: 485 [M+H]$^+$.

Step-5: Preparation of (S)-1-(4-Ethyl-4,9-dihydroxy-3,14-dioxo-3,4,12,14-tetrahydro-1H-pyrano[3',4':6,7]indolizino[1,2-b]quinolin-10-yl)-N,N,N-trimethylmethanaminium Iodide To a suspension of (S)-10-((dimethylamino)methyl)-4-ethyl-4,9-dihydroxy-1H-pyrano[3',4':6,7]indolizino[1,2-b]quinoline-3,14(4H,12H)-dione (190 mg, 0.451 mmol, 1.0 eq.) in MeOH (5 mL) was added MeI (0.9 mL) and the mixture was stirred at RT for 16 h. After completion, the volatiles were removed under reduced pressure to afford the title compound (240 mg, 96%).

Step-6: Preparation of (S)-tert-Butyl 4-((4-ethyl-4,9-dihydroxy-3,14-dioxo-3,4,12,14-tetrahydro-1H-pyrano[3',4':6,7]indolizino[1,2-b]quinolin-10-yl)methyl)piperazine-1-carboxylate To a suspension of (S)-1-(4-ethyl-4,9-dihydroxy-3,14-dioxo-3,4,12,14-tetrahydro-1H-pyrano[3',4':6,7]indolizino

[1,2-b]quinolin-10-yl)-N,N,N-trimethylmethanaminium iodide (1.2 g, 2.13 mmol, 1.0 eq.) in 0.1 M KH$_2$PO$_4$ (22 mL) and 0.1 M Na$_2$HPO$_4$ (34 mL) was added tert-butyl piperazine-1-carboxylate (670 mg, 3.60 mmol, 1.7 eq.) and the resultant mixture was heated at 80° C. for 16 h and monitored using LCMS. After completion, the mixture was acidified with dil. HCl to pH 6-6.5 and extracted with DCM (30 mL×3). The combined organic layers were washed with brine, dried over sodium sulfate and evaporated to afford the title compound which was used directly for next step without purification (1.2 g, 99%). LCMS: 563 [M+H]$^+$.

Step-7: Preparation of (S)-4-Ethyl-4,9-dihydroxy-10-(piperazin-1-ylmethyl)-1H-pyrano[3',4':6,7]indolizino[1,2-b]quinoline-3,14(4H,12H)-dione To a solution of (S)-tert-butyl 4-((4-ethyl-4,9-dihydroxy-3,14-dioxo-3,4,12,14-tetrahydro-1H-pyrano[3',4':6,7]indolizino[1,2-b]quinolin-10-yl)methyl)piperazine-1-carboxylate (1.2 g, 2.13 mmol, 1.0 eq.) in DCM (20 mL) was added TFA (2 mL) and the mixture was stirred at RT for 16 h. After completion, the volatiles were removed under reduced pressure to afford the title compound (700 mg, 71%). LCMS: 463 [M+H]$^+$.

Step-8: Preparation of N-((1r,4r)-4-(3-Chloro-4-cyanophenoxy)cyclohexyl)-4-((6-(4-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperazin-1-yl)-6-oxohexyl)oxy)benzamide (Compound 12)

To a solution of 6-(4-((1r,4r)-4-(3-chloro-4-cyanophenoxy)cyclohexylcarbamoyl)phenoxy)hexanoic acid (100 mg, 0.206 mmol, 1.0 eq.) in a dry DMF (5 mL) was added HATU (117 mg, 0.309 mmol, 1.5 eq.) at 0° C. and stirred for 30 min. To this reaction mixture was added (S)-4-ethyl-4,9-dihydroxy-10-(piperazin-1-ylmethyl)-1H-pyrano[3',4':6,7]indolizino[1,2-b]quinoline-3,14(4H,12H)-dione (95 mg, 0.206 mmol, 1.0 eq.) followed by addition of DIPEA (78 mg, 0.618 mmol, 3.0 eq.). The resultant mixture was stirred at room temperature for 2 h. After completion, the mixture was diluted with water (30 mL) and extracted with EtOAc (30 mL×3). The combined organic layers were washed with water (30 mL×2), brine (30 mL), dried over anhydrous sodium sulfate, filtered and evaporated to give crude product which was purified by preparative to afford the title compound (20 mg, 5%). $^1$H NMR (400 MHz, DMSO-d$_6$): δ 8.77 (s, 1H), 8.12 (t, J=8 Hz, 1H), 7.99 (d, J=8 Hz, 1H), 7.85 (d, J=8 Hz, 1H), 7.81 (d, J=8 Hz, 2H), 7.47 (d, J=12 Hz, 1H), 7.38 (s, 1H), 7.26 (s, 1H), 7.13 (d, J=12 Hz, 1H), 6.96 (d, J=8 Hz, 2H), 6.49 (br s, 1H), 5.41 (s, H), 5.25 (s, 2H), 4.53 (m, 1H), 4.02 (m, 4H), 3.80 (m, 2H), 2.33 (t, J=6 Hz, 2H), 2.08 (m, 3H), 1.88 (m, 4H), 1.73 (t, J=8 Hz, 2H), 1.46 (m, 8H), 0.88 (t, J=8 Hz, 3H). LCMS: 929 [M+H]$^+$.

Example 13

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(6-(3,5-difluoro-4-((1S,3S)-2-(2-fluoro-2-methylpropyl)-3-methyl-2,3,4,9-tetrahydro-1H-pyrido[3,4-b]indol-1-yl)phenoxy)hexyl)piperazine-1-carboxylate (Compound 13)

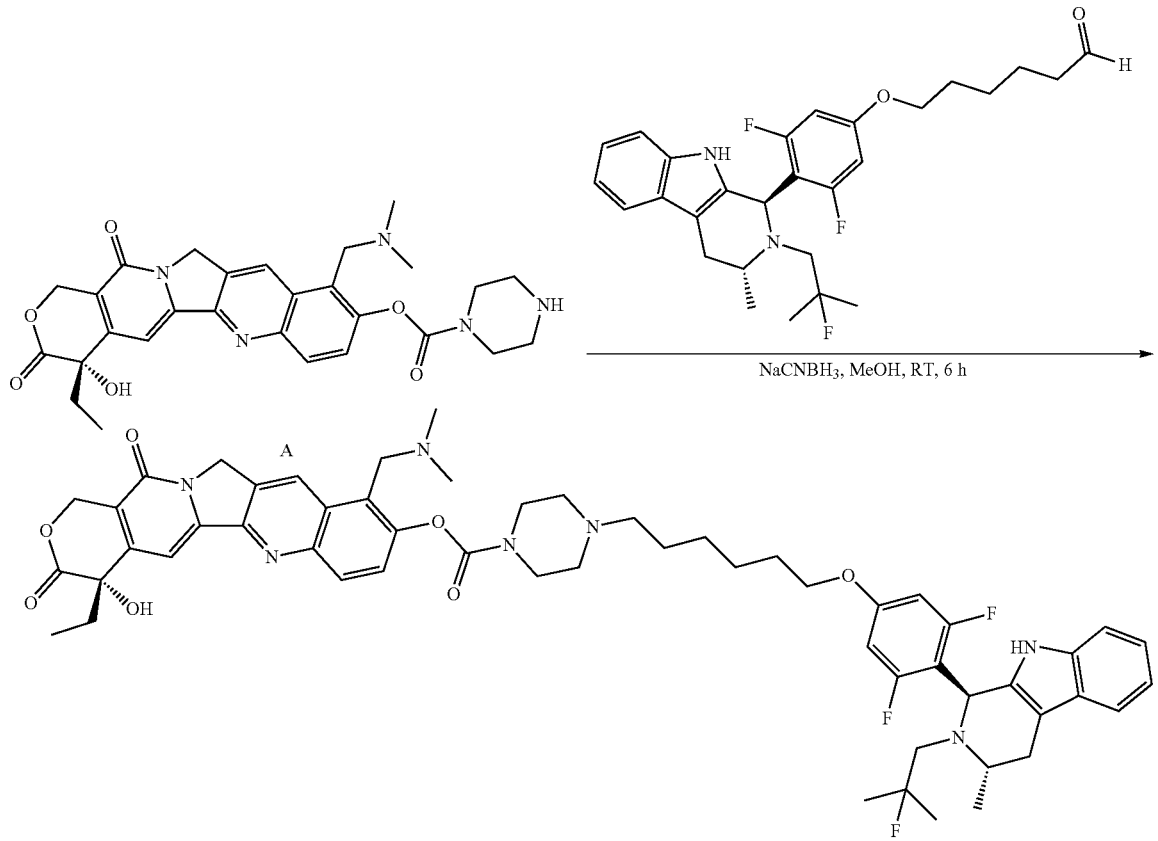

To a stirred solution of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl piperazine-1-carboxylate (266 mg, 0.5 mmol, 1.0 eq.) and 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanal (243 mg, 0.5 mmol, 1.0 eq.) in MeOH (5 mL) was added acetic acid (0.5 mL) and stirred at RT for 15 min. To this solution was added NaBH$_3$CN (64 mg, 1.0 mmol, 2.0 eq.) and stirred at RT overnight. Progress of the reaction was monitored by TLC and LC-MS analysis. After completion of reaction, reaction mixture was diluted with saturated aq. NaHCO$_3$ (30 mL) and extracted with DCM (50 mL×2). Combined organic layers were washed with brine solution (20 mL×4), dried over anhydrous sodium sulfate and concentrated under reduced pressure to obtain crude product which was purified by reverse phase chromatography to obtain the desired product (24 mg, 5%). $^1$H NMR (400 MHz, DMSO-d$_6$): δ 10.51 (s, 1H), 8.94 (s, 1H), 8.18-8.07 (m, 2H), 7.62 (d, J=9.2 Hz, 1H), 7.44-7.32 (m, 2H), 7.18 (d, J=7.9 Hz, 1H), 7.05-6.91 (m, 2H), 6.64 (d, J=11.0 Hz, 1H), 6.54 (br s, 1H), 5.43 (s, 2H), 5.31 (s, 2H), 5.12 (br s, 1H), 3.98 (t, J=6.4 Hz, 2H), 3.83-3.62 (m, 5H), 2.93-2.76 (m, 2H), 2.45-2.25 (m, 10H), 2.20 (s, 6H), 1.87 (dt, J=14.0, 7.0 Hz, 2H), 1.76-1.62 (m, 3H), 1.54-1.44 (m, 8H), 1.44-1.29 (m, 2H), 1.22-1.04 (m, 6H), 0.88 (t, J=7.2 Hz, 3H). LCMS: 1004 [M+H]$^+$.

Example 14

Preparation of N-((1r,4r)-4-(3-Chloro-4-cyanophenoxy)cyclohexyl)-6-(4-(4-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperazine-1-carbonyl)piperidin-1-yl)pyridazine-3-carboxamide (Compound 14)

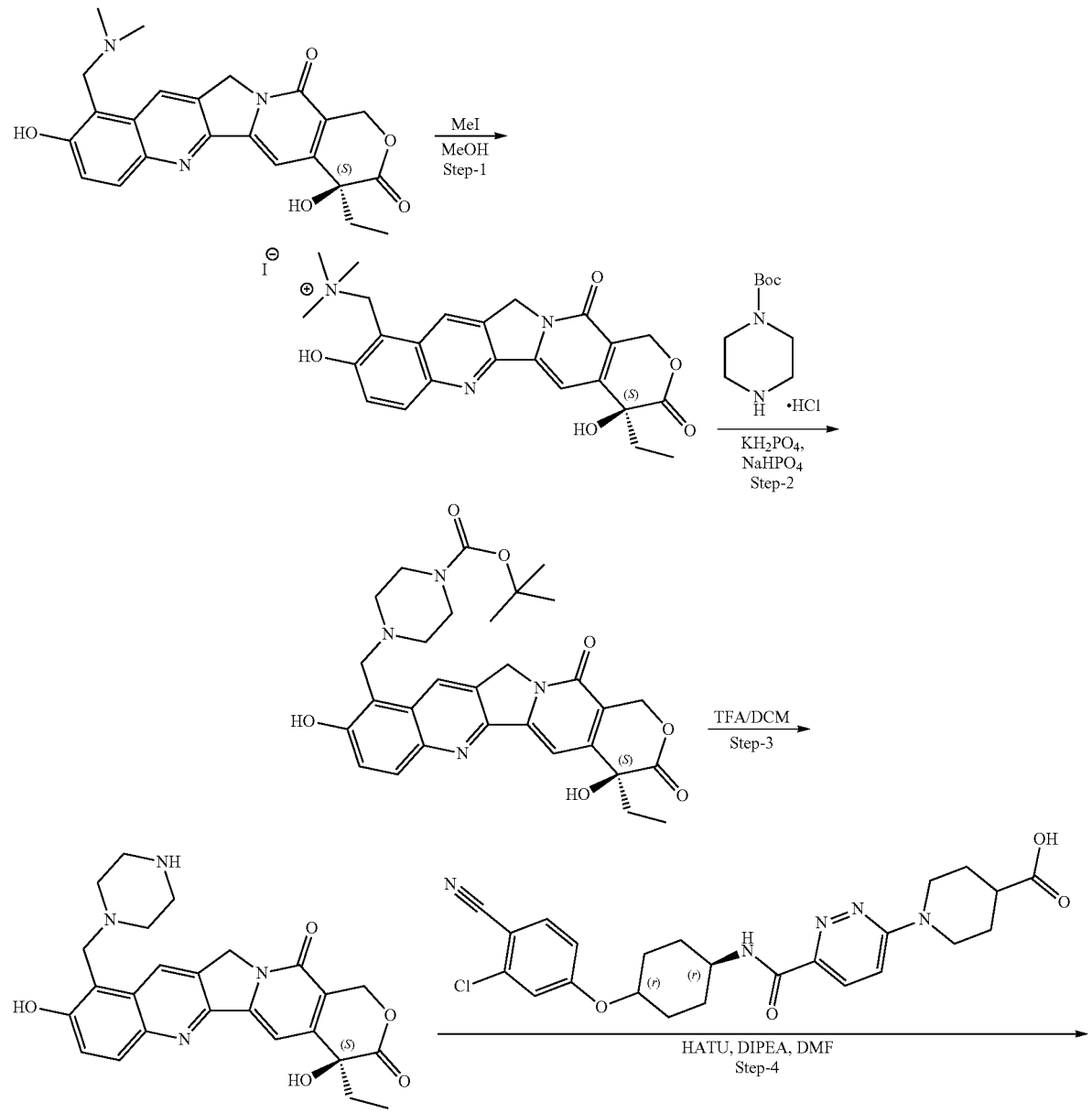

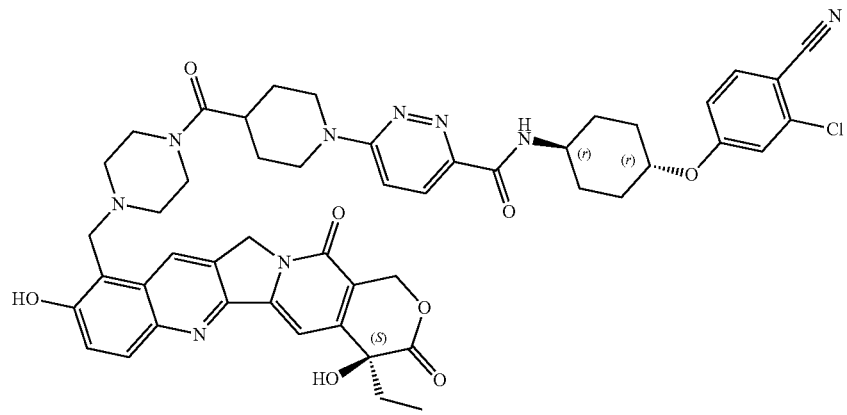

Step-1: Preparation of (S)-1-(4-Ethyl-4,9-dihydroxy-3,14-dioxo-3,4,12,14-tetrahydro-1H-pyrano[3',4':6,7]indolizino[1,2-b]quinolin-10-yl)-N,N,N-trimethylmethanaminium Iodide To a solution of (S)-10-((dimethylamino)methyl)-4-ethyl-4,9-dihydroxy-1H-pyrano[3',4':6,7]indolizino[1,2-b]quinoline-3,14(4H,12H)-dione (2.0 g, 4.75 mmol, 1.0 eq.) in MeOH (50 mL), was added methyl iodide (2.60 g, 19.0 mmol, 4 eq.) at RT and the mixture was stirred at same temperature for 3 h. After 3 h, the mixture was concentrated under reduced pressure to afford quaternary salt of compound which washed with diethyl ether and dried under reduced pressure to afford title compound (2.0 g, 76%).

Step-2: Preparation of (S)-tert-Butyl 4-((4-ethyl-4,9-dihydroxy-3,14-dioxo-3,4,12,14-tetrahydro-1H-pyrano[3',4':6,7]indolizino[1,2-b]quinolin-10-yl)methyl)piperazine-1-carboxylate To a solution of (S)-1-(4-ethyl-4,9-dihydroxy-3,14-dioxo-3,4,12,14-tetrahydro-1H-pyrano[3',4':6,7]indolizino[1,2-b]quinolin-10-yl)-N,N,N-trimethylmethanaminium iodide (2.0 g, 3.55 mmol, 1.0 eq.) and Boc-piperazine hydrochloride (1.18 g, 5.32 mmol, 1.5 eq.) in $Na_2HPO_4$:$KH_2PO_4$ (pH ~7) (20 mL) was heated at 100° C. for 3 h. The reaction was monitored by TLC. After completion, the mixture was diluted with $NaHCO_3$ (50 mL) and extracted with 10% MeOH in EtOAc (200 mL×3). The combined organic layers were dried over anhydrous sodium sulfate, filtered and concentrated under reduced pressure to afford crude residue which was purified by CombiFlash chromatography to afford the title compound (0.25 g, 12%). LCMS: 563 [M+H]$^+$.

Step-3: Preparation of (S)-4-Ethyl-4,9-dihydroxy-10-(piperazin-1-ylmethyl)-1H-pyrano[3',4':6,7]indolizino[1,2-b]quinoline-3,14(4H,12H)-dione To a stirred solution of (S)-tert-butyl 4-((4-ethyl-4,9-dihydroxy-3,14-dioxo-3,4,12,14-tetrahydro-1H-pyrano[3',4':6,7]indolizino[1,2-b]quinolin-10-yl)methyl)piperazine-1-carboxylate (0.25 g, 0.44 mmol, 1.0 eq.) in DCM (5 mL) was added TFA (0.5 mL) at 0° C. dropwise and the mixture was stirred at RT for 2 h. The reaction was monitored by TLC. After completion, the mixture was quenched with saturated $NaHCO_3$ solution (100 mL) and extracted with 10% MeOH in EtOAc (100 mL×3). The combined organic layer was washed with water (50 mL), brine (50 mL), dried over anhydrous sodium sulfate, filtered and concentrated under reduced pressure to afford the title compound (0.200 g, 97%). LCMS: 463 [M+H]$^+$.

Step-4: Preparation of N-((1r,4r)-4-(3-Chloro-4-cyanophenoxy)cyclohexyl)-6-(4-(4-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperazine-1-carbonyl)piperidin-1-yl)pyridazine-3-carboxamide (Compound 14)

To a stirred solution of 1-(6-(((1r,4r)-4-(3-chloro-4-cyanophenoxy)cyclohexyl)carbamoyl)pyridazin-3-yl)piperidine-4-carboxylic acid (0.170 g, 0.35 mmol, 1.0 eq.) in DMF (8 mL) was added HATU (0.401 g, 1.05 mmol, 3.0 eq.) at 0° C. and the resulting mixture was stirred at same temperature for 10 min. DIPEA (0.3 mL, 1.75 mmol, 5.0 eq.) and (S)-4-ethyl-4,9-dihydroxy-10-(piperazin-1-ylmethyl)-1H-pyrano[3',4':6,7]indolizino[1,2-b]quinoline-3,14(4H,12H)-dione (0.325 g, 0.70 mmol, 1.2 eq.) were then successively added to the mixture and the mixture was stirred at RT for 1 h. The reaction was monitored by TLC & LCMS. After completion, water (10 mL) was added and the resulting precipitate was filtered over Büchner funnel. The solid obtained was washed with water (5 mL×2) and n-pentane (5 mL×2), dried under vacuum to obtain a crude product which was purified by Combiflash chromatography to afford the title compound (0.055 g, 16%). $^1$H NMR (400 MHz, DMSO-$d_6$): δ 8.79 (s, 1H), 8.59 (d, J=8.33 Hz, 1H), 8.00 (d, J=9.21 Hz, 1H), 7.86 (s, 1H), 7.81 (d, J=9.65 Hz, 1H), 7.48 (d, J=9.21 Hz, 1H), 7.42-7.29 (m, 2H), 7.26 (s, 1H), 7.13 (dd, J=8.77, 2.19 Hz, 1H), 6.49 (m, 1H), 5.42 (s, 2H), 5.26 (s, 2H), 4.58-4.41 (m, 3H), 4.03 (m, 2H), 3.87 (m, 1H), 3.57 (m, 2H), 3.46 (m, 3H), 3.16-3.08 (m, 2H), 3.02 (m, 1H), 2.67 (m, 1H), 2.58 (m, 2H), 2.35-2.27 (m, 1H), 2.10 (d, J=10.09 Hz, 2H), 1.94-1.78 (m, 4H), 1.73 (d, J=12.28 Hz, 2H), 1.67-1.45 (m, 4H), 1.23 (s, 2H), 0.95-0.78 (m, 3H). LCMS: 928 [M+H]$^+$.

Example 15
Preparation of (S)-4-(3-(4-Cyano-3-(trifluoromethyl)phenyl)-5,5-dimethyl-4-oxo-2-thioxoimidazolidin-1-yl)-N-(6-(4-((4-ethyl-4,9-dihydroxy-3,14-dioxo-3,4,12,14-tetrahydro-1H-pyrano[3',4':6,7]indolizino[1,2-b]quinolin-10-yl)methyl)piperazin-1-yl)hexyl)-2-fluorobenzamide (Compound 15)
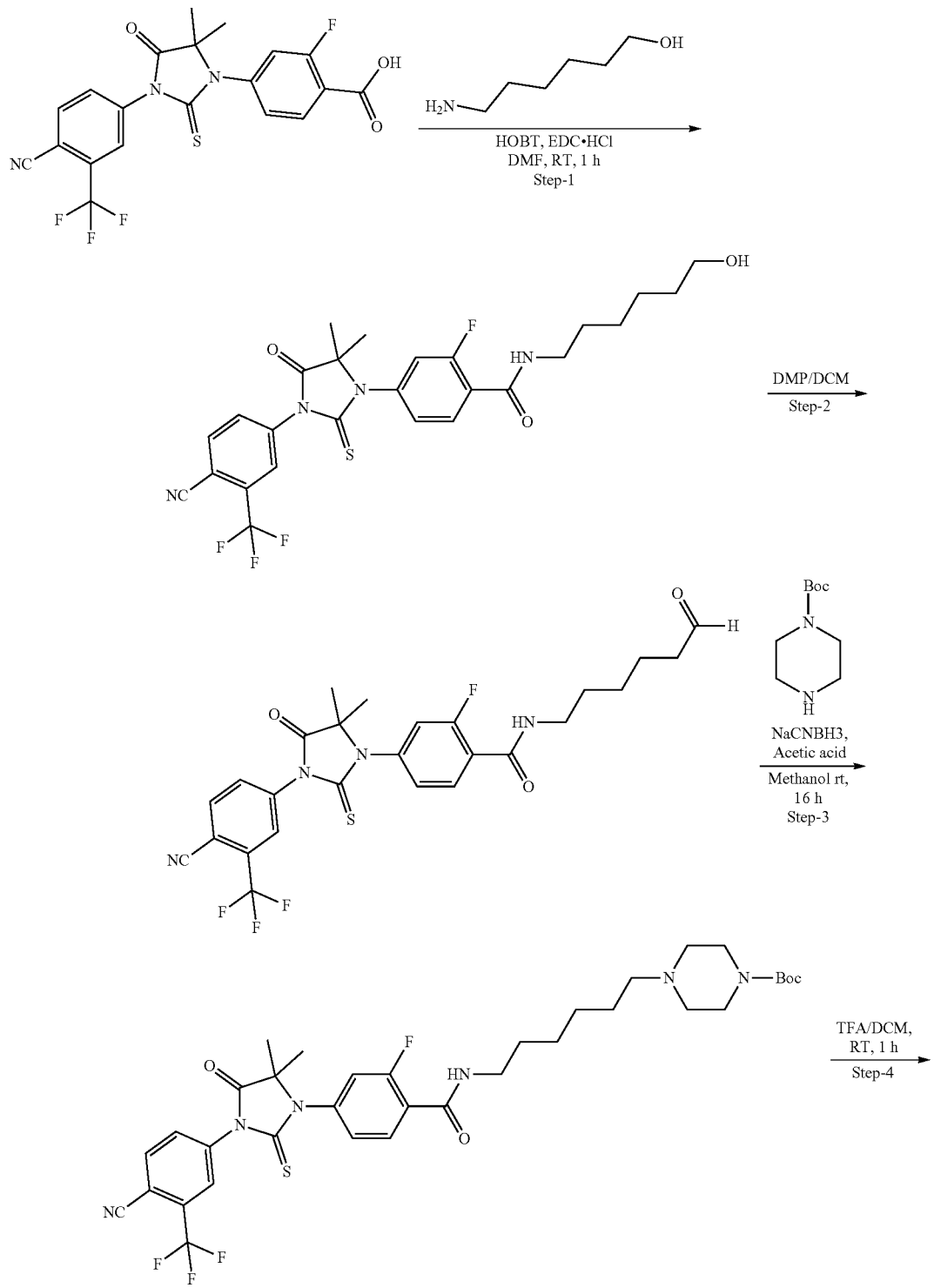

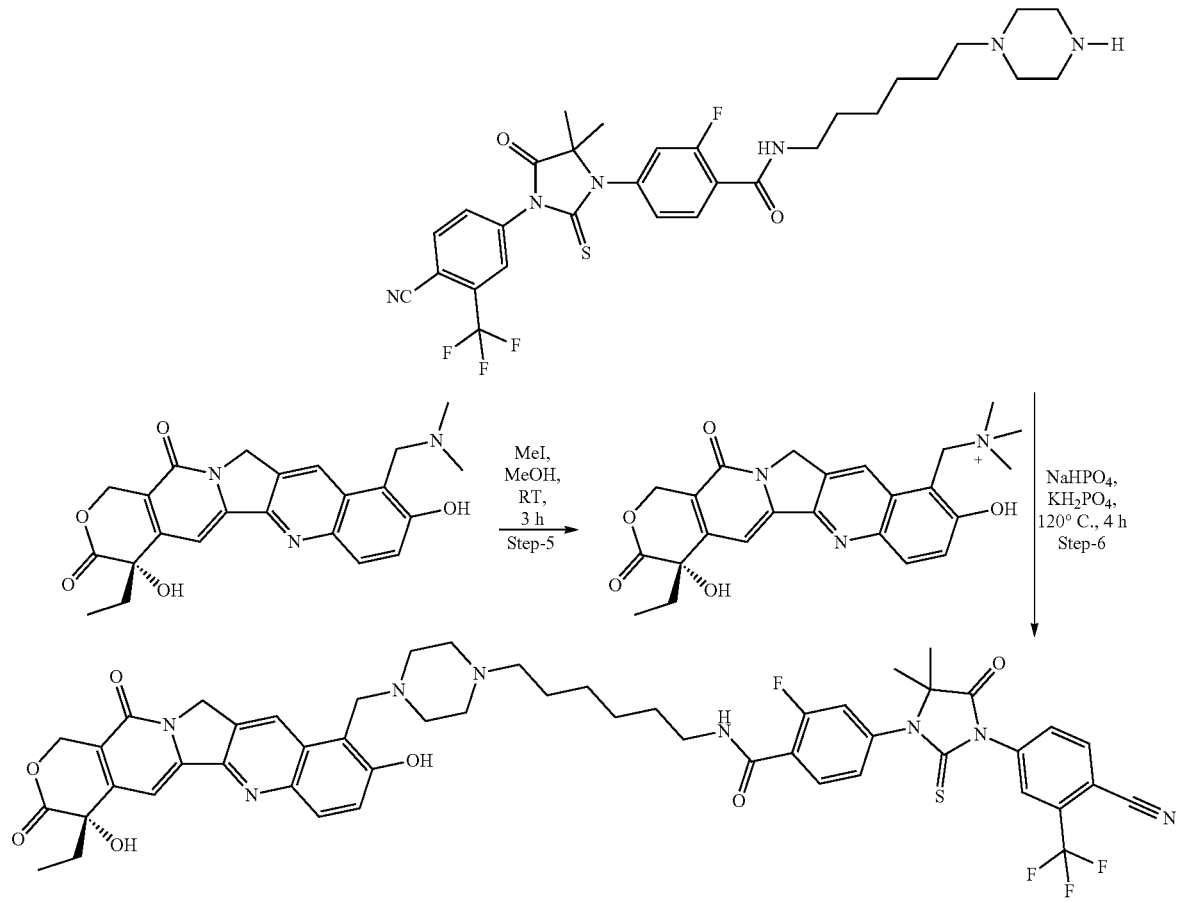

Step-1: Preparation of 4-(3-(4-Cyano-3-(trifluoromethyl)phenyl)-5,5-dimethyl-4-oxo-2-thioxoimidazolidin-1-yl)-2-fluoro-N-(6-hydroxyhexyl)benzamide To a stirred solution of 4-(3-(4-cyano-3-(trifluoromethyl)phenyl)-5,5-dimethyl-4-oxo-2-thioxoimidazolidin-1-yl)-2-fluorobenzoic acid (2.0 g, 4.43 mmol, 1.0 eq.) in DMF (10 mL), EDC.HCl (1.27 g 6.64 mmol, 1.5 eq.), HOBT (1.01 g 6.64 mmol, 1.5 eq.) and 6-aminohexan-1-ol (0.56 g 4.87 mmol, 1.1 eq.) were added and the reaction mixture was allowed to stir at RT for 1 h. After completion of reaction, the reaction mixture (reaction was monitored by TLC analysis) was quenched with ice-cold water (400 mL×2) and extracted with EtOAc (200 mL×2). The combined organic layer was dried with $Na_2SO_4$, concentrated under reduced pressure to obtain a crude residue which was purified by CombiFlash Chromatography to afford the title compound (1.80 g, 75%). LCMS: 551.2 [M+H]$^+$.

Step-2: Preparation of 4-(3-(4-Cyano-3-(trifluoromethyl)phenyl)-5,5-dimethyl-4-oxo-2-thioxoimidazolidin-1-yl)-2-fluoro-N-(6-oxohexyl)benzamide To a stirred solution of 4-(3-(4-cyano-3-(trifluoromethyl)phenyl)-5,5-dimethyl-4-oxo-2-thioxoimidazolidin-1-yl)-2-fluoro-N-(6-hydroxyhexyl)benzamide (0.60 g, 1.09 mmol, 1.0 eq.) in DCM (10 mL). DMP (0.77 g, 1.82 mmol, 1.67 eq.) was added and the reaction mixture was allowed to stir at RT for 1 h. (The reaction was monitored by TLC). After completion, the mixture was diluted with $H_2O$ (200 mL×2) and extracted with DCM (50 mL×2). The combined organic layer was dried with $Na_2SO_4$ and concentrated under reduced pressure to obtain the desired product (400 mg, 67%). LCMS: 549.2 [M+H]$^+$.

Step-3: Preparation of tert-Butyl 4-(6-(4-(3-(4-cyano-3-(trifluoromethyl)phenyl)-5,5-dimethyl-4-oxo-2-thioxoimidazolidin-1-yl)-2-fluorobenzamido)hexyl)piperazine-1-carboxylate To a stirred solution of 4-(3-(4-cyano-3-(trifluoromethyl)phenyl)-5,5-dimethyl-4-oxo-2-thioxoimidazolidin-1-yl)-2-fluoro-N-(6-oxohexyl)benzamide (0.40 g, 0.72 mmol, 1.0 eq.) and tert-butyl piperazine-1-carboxylate (0.24 g, 1.08 mmol, 1.5 eq.) in methanol (5 mL), acetic acid (0.02 mL) and $NaCNBH_3$ (0.03 g, 0.54 mmol, 1.0 eq.) was added the reaction mixture was allowed to stir at RT for 16 h. After completion of reaction, the reaction mixture (reaction was monitored by TLC analysis) was quenched with $Na_2HCO_3$ (200 mL×2) and extracted with DCM (50 mL×2). The combined organic layer was washed with $H_2O$ (50 mL×2) and dried with $Na_2SO_4$ and concentrated under reduced pressure to obtain a crude residue which was purified by CombiFlash Chromatography to obtain a desired product (0.30 g, 76%). LCMS: 719.8 [M+H]$^+$.

Step-4: Preparation of 4-(3-(4-Cyano-3-(trifluoromethyl)phenyl)-5,5-dimethyl-4-oxo-2-thioxoimidazolidin-1-yl)-2-fluoro-N-(6-(piperazin-1-yl)hexyl)benzamide To a stirred solution of tert-butyl 4-(6-(4-(3-(4-cyano-3-(trifluoromethyl)phenyl)-5,5-dimethyl-4-oxo-2-thioxoimidazolidin-1-yl)-2-fluorobenzamido)hexyl)piperazine-1-carboxylate (0.30 g, 0.39 mmol, 1.0 eq.) in DCM (10 mL), TFA (1.5 mL) was added and the reaction mixture was allowed to stir at RT for 1 h. After completion of the reaction, the reaction mixture (reaction was monitored by TLC analysis) was quenched with water (100 mL×2) and extracted with DCM (50 mL×2). The combined organic layer was dried over $Na_2SO_4$ and concentrated under reduced pressure to obtain a desired product (0.25 g, 96%). LCMS: 620.2 $[M+H]^+$.

Step-5: Preparation of (S)-1-(4-ethyl-4,9-dihydroxy-3,14-dioxo-3,4,12,14-tetrahydro-1H-pyrano[3',4':6,7]indolizino[1,2-b]quinolin-10-yl)-N,N,N-trimethylmethanaminium To a stirred solution of (S)-10-((dimethylamino)methyl)-4-ethyl-4,9-dihydroxy-1,12-dihydro-14H-pyrano[3',4':6,7]indolizino[1,2-b]quinoline-3,14(4H)-dione (2.5 g, 5.93 mmol, 1.0 eq.) in methanol (50 mL). Methyl iodide (5 mL) was added and the reaction mixture was allowed to stir at RT for 1 h. After completion of the reaction, the reaction mixture (reaction was monitored by TLC analysis) was concentrated under reduced pressure and triturated with diethyl ether (50 mL) to obtain a desired product (2.3 g, 92%). LCMS: 436.4 $[M+H]^+$.

Step-6: Preparation of (S)-4-(3-(4-Cyano-3-(trifluoromethyl)phenyl)-5,5-dimethyl-4-oxo-2-thioxoimidazolidin-1-yl)-N-(6-(4-((4-ethyl-4,9-dihydroxy-3,14-dioxo-3,4,12,14-tetrahydro-1H-pyrano[3',4':6,7]indolizino[1,2-b]quinolin-10-yl)methyl)piperazin-1-yl)hexyl)-2-fluorobenzamide (Compound 15)

To a stirred solution of 4-(3-(4-cyano-3-(trifluoromethyl)phenyl)-5,5-dimethyl-4-oxo-2-thioxoimidazolidin-1-yl)-2-fluoro-N-(6-(piperazin-1-yl)hexyl)benzamide (0.30 g, 0.68 mmol, 1.0 eq.) and (S)-10-((dimethylamino)methyl)-4-ethyl-4,9-dihydroxy-1,12-dihydro-14H-pyrano[3',4':6,7]indolizino[1,2-b]quinoline-3,14(4H)-dione (0.42 g, 0.68 mmol, 1.0 eq.) in $KHPO_4$ and $NaHPO_4$ (20 mL). The reaction mixture was allowed to stir at 120° for 16 h. After completion of reaction, the reaction mixture (reaction was monitored by TLC analysis) was quenched with $Na_2HCO_3$ (50 mL×2) and extracted with 10%, MeOH in DCM (20 mL×2). The combined organic layer was washed with $H_2O$ (50 mL×2) and dried over $Na_2SO_4$ and concentrated under reduced pressure to obtain a crude residue which was purified by reverse phase chromatography to obtain a desired product (0.03 g, 6%). LCMS: 996.1 $[M+H]^+$.

Example 16

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl (2R,6R)-4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)-2,6-dimethylpiperazine-1-carboxylate (Compound 16)

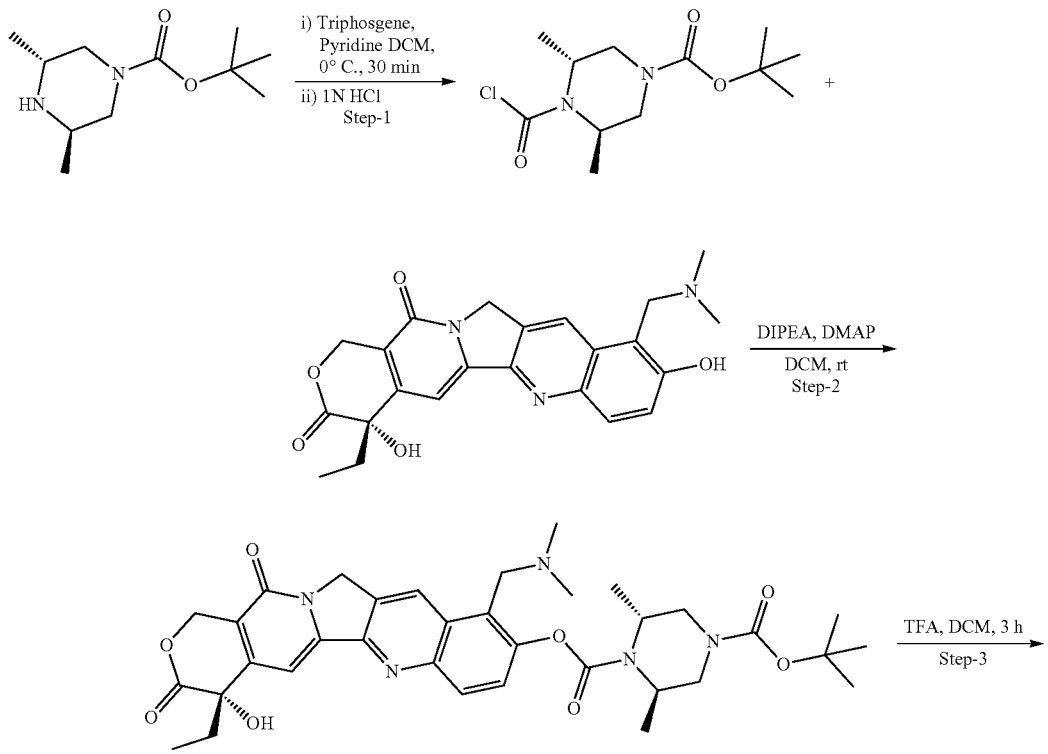

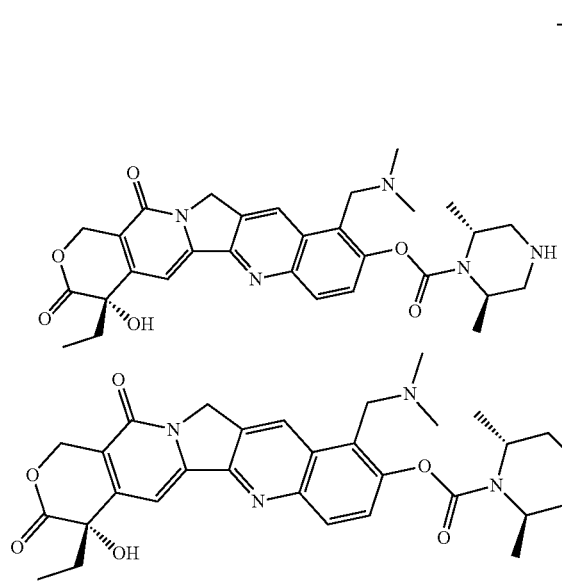
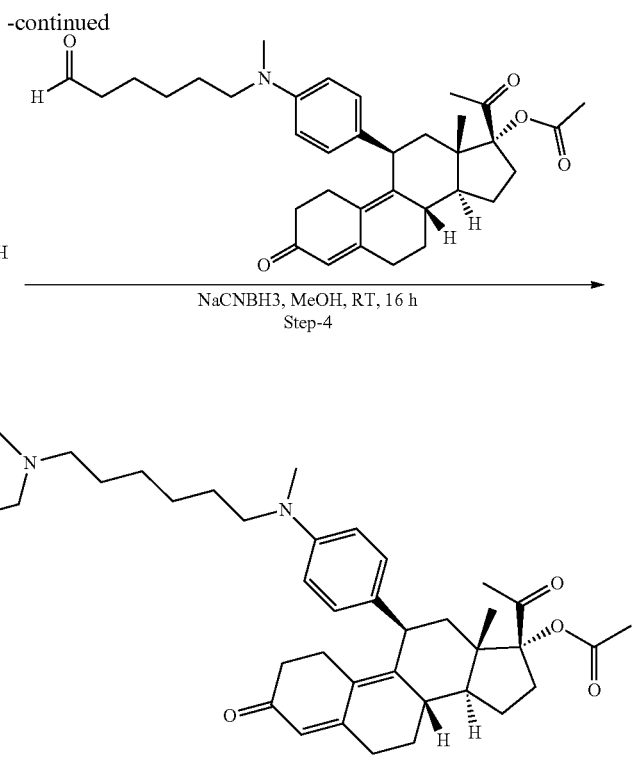

Step-1: Preparation of tert-butyl (3R,5R)-4-(chlorocarbonyl)-3,5-dimethylpiperazine-1-carboxylate To a stirred solution of tert-butyl (3R,5R)-3,5-dimethylpiperazine-1-carboxylate (1.5 g, 7.0 mmol, 1.0 eq.) in DCM (30 mL) and pyridine (1.4 mL, 17.4 mmol, 2.5 eq.), triphosgene (already dissolved in DCM, 15 mL) (1.03 g, 3.49 mmol, 0.5 eq.) was added dropwise at 0° C. The resultant mixture was stirred at RT for 1 h. The progress of the reaction was monitored by TLC and LC-MS. Upon completion, the reaction mixture was acidified with 1N HCl (40 mL) and extracted with DCM (30 mL×5). The combined organic layer was washed with $H_2O$ (200 mL), dried over anhydrous sodium sulfate and concentrated under reduced pressure to afford the desired compound (1.28 g, 67.3%). $^1$H NMR (400 MHz, $CDCl_3$): δ 3.69-3.61 (m, 4H) 3.48 (m, 2H) 1.46 (s, 9H), 1.4 (m, 6H).

Step-2: Preparation of 4-(tert-Butyl) 1-((S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl) (2R,6R)-2,6-dimethylpiperazine-1,4-dicarboxylate To a stirred solution of (S)-10-((dimethylamino)methyl)-4-ethyl-4,9-dihydroxy-1,12-dihydro-14H-pyrano[3',4':6,7]indolizino[1,2-b]quinoline-3,14(4H)-dione (1.30 g, 3.08 mmol, 1.0 eq.) in DCM (50 mL) were added DIPEA (2.7 mL, 15.4 mmol, 5.0 eq.) and DMAP (0.094 g, 0.77 mmol, 0.25 eq.). The mixture was stirred at RT for 5 min, followed by the addition of tert-butyl (3R,5R)-4-(chlorocarbonyl)-3,5-dimethylpiperazine-1-carboxylate (1.28 g, 4.63 mmol, 1.5 eq.) dissolved in DCM (20 mL) slowly. The resultant mixture was stirred at RT for 16 h. The progress of the reaction was monitored by TLC and LCMS. Upon completion, the reaction mixture was concentrated on rotary-evaporator and water was added to provide the desired product. The resulting solid was filtered, washed with pentane and dried over vacuum (1.2 g, 59%). LCMS: 661.1 [M+H]$^+$.

Step-3: Preparation of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl (2R,6R)-2,6-dimethylpiperazine-1-carboxylate To a stirred solution of 4-(tert-butyl) 1-((S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl) (2R,6R)-2,6-dimethylpiperazine-1,4-dicarboxylate (1.2 g, 1.8 mmol) in DCM (20 mL) was added trifluoroacetic acid (2 mL) at 0° C. dropwise and the resulting solution was stirred RT for 3 h. The reaction was monitored by LCMS. Upon completion, the mixture was concentrated under reduced pressure to afford the crude product which was triturated with diethyl ether (200 mL) to afford the desired compound (0.95 g, 94%). LCMS: 561.2 [M+H]$^+$.

Step-4: Preparation of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl (2R,6R)-4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)-2,6-dimethylpiperazine-1-carboxylate (Compound 16)

To a stirred solution of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl (2R,6R)-2,6-dimethylpiperazine-1-carboxylate (0.95 g, 1.4 mmol, 1.0 eq.) and (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate (2.3 g, 4.2 mmol, 3.0 eq.) in methanol (10 mL) was added acetic acid (0.5 mL) and stirred at RT for 16 h. The reaction mixture was cooled to 0° C. and sodium cyanoborohydride (0.176 g, 2.8 mmol, 2.0 eq.) was added and stirred for 30 min. Reaction mixture was then warmed to RT and stirred again for 2 h. Progress of the reaction was monitored by TCL analysis. Added water to reaction mass which was filtered and dried to give the desired compound (0.013 g, 1%). $^1$H NMR (500 MHz, DMSO-$d_6$): δ 8.95 (s, 1H), 8.24 (s, 1H), 8.10 (d, J=9.06 Hz, 1H), 7.58 (d, J=9.06 Hz, 1H), 7.34 (s, 1H), 7.08-6.85 (m, J=8.58 Hz, 2H), 6.67-6.55 (m, J=8.58 Hz, 3H), 5.67 (s, 1H), 5.43 (s, 2H), 5.31 (s, 2H), 4.39 (m, 1H), 4.10 (m, 2H), 3.77 (m, 2H), 3.20 (m, 3H), 2.90-2.77 (m, 5H), 2.76-2.66 (m, 6H), 2.48-2.23 (m, 19H), 2.20 (s, 6H), 2.17-2.02 (m, 5H), 2.00 (s, 5H), 1.95-1.77 (m, 5H), 1.77-1.62 (m, 3H), 1.41 (d, J=6.20 Hz, 3H). LCMS: 1106.3 [M+H]$^+$.

Example 17

Preparation of (S)-10-(tert-Butoxymethyl)-4-ethyl-4-hydroxy-3,14-dioxo-3,4,12,14-tetrahydro-1H-pyrano[3',4':6,7]indolizino[1,2-b]quinolin-9-yl 4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)piperazine-1-carboxylate (Compound 17)

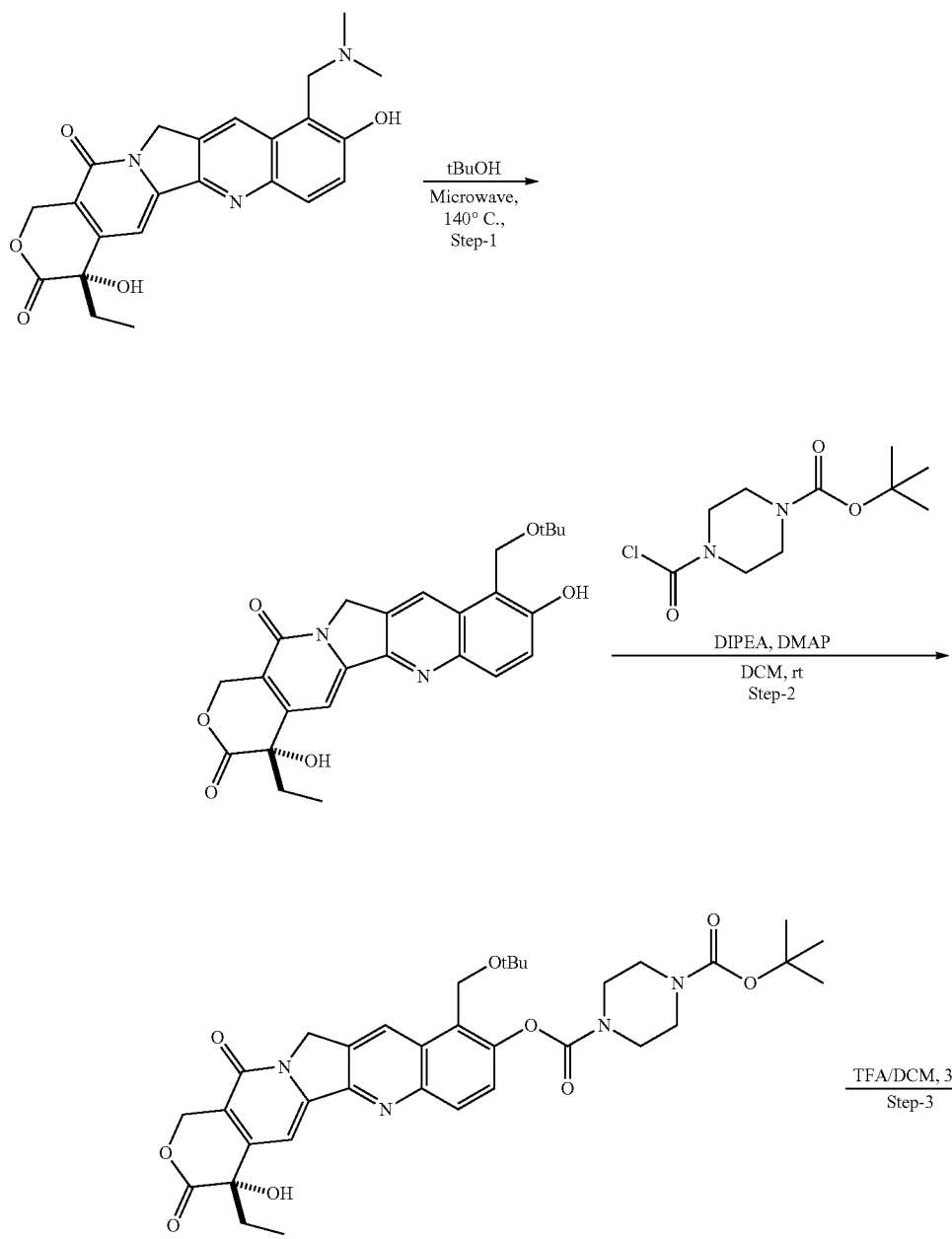

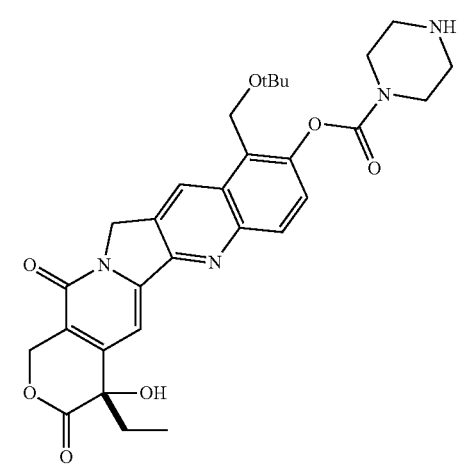
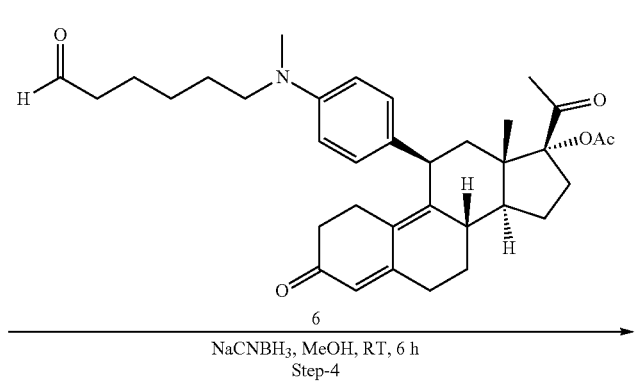

-continued

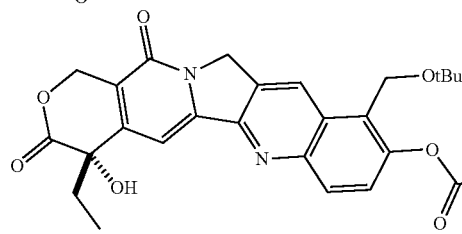

$\xrightarrow{\text{6}}$
NaCNBH₃, MeOH, RT, 6 h
Step-4

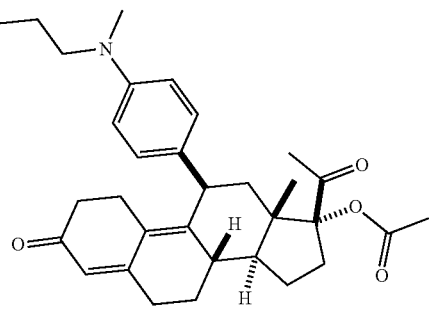

Step-1: Preparation of (S)-10-(tert-Butoxymethyl)-4-ethyl-4,9-dihydroxy-1,12-dihydro-14H-pyrano[3',4':6,7]indolizino[1,2-b]quinoline-3,14(4H)-dione A stirred solution of (S)-10-((dimethylamino)methyl)-4-ethyl-4,9-dihydroxy-1,12-dihydro-14H-pyrano[3',4':6,7]indolizino[1,2-b]quinoline-3,14(4H)-dione (1.0 g, 2.19 mmol, 1.0 eq.) in t-BuOH (10 mL) was allowed to stir at 140° for 5 Min under MW irradiation. After completion, the mixture was diluted with H₂O (50 mL×2) and extracted with DCM (50 mL×2). The combined organic layer was washed with H₂O (50 mL×2) and dried with Na₂SO₄ and concentrated under reduced pressure to obtain a crude residue which was purified by silica gel column chromatography (Combiflash, Elution: 0-3% MeOH in DCM) to obtain the desired product (0.110 g, 11%). LCMS: 451.3 [M+H]⁺.

Step-2: Preparation of (S)-1-(10-(tert-Butoxymethyl)-4-ethyl-4-hydroxy-3,14-dioxo-3,4,12,14-tetrahydro-1H-pyrano[3',4':6,7]indolizino[1,2-b]quinolin-9-yl) 4-(tert-butyl)piperazine-1,4-dicarboxylate To a stirred solution of (S)-10-(tert-butoxymethyl)-4-ethyl-4,9-dihydroxy-1,12-dihydro-14H-pyrano[3',4':6,7]indolizino[1,2-b]quinoline-3,14(4H)-dione (0.110 g, 0.24 mmol, 1.0 eq.) in DCM (10 mL), DIPEA (0.6 mL, 1.21 mmol, 5.0 eq.) and DMAP (0.0084 g, 0.06 mmol, 0.25 eq.) were added. The reaction mixture was then allowed to stir at RT for 5 min. and tert-butyl 4-(chlorocarbonyl)piperazine-1-carboxylate (0.026 g, 0.026 mmol, 1.2 eq.) was added. The reaction mixture was allowed to stir at RT for 16 h. After completion of reaction, the reaction mixture (reaction was monitored by TLC analysis) was diluted with H₂O (50 mL×2) and extracted with DCM (50 mL×2). The combined organic layer was dried over Na₂SO₄ and concentrated under reduced pressure to obtain a crude residue which was purified by silica gel column chromatography (Combiflash, Elution: 0-3% MeOH in DCM) to obtain the desired product (0.140 g, 87%). LCMS: 663.1 [M+H]⁺.

Step-3: Preparation of (S)-10-(tert-Butoxymethyl)-4-ethyl-4-hydroxy-3,14-dioxo-3,4,12,14-tetrahydro-1H-pyrano[3',4':6,7]indolizino[1,2-b]quinolin-9-yl piperazine-1-carboxylate To a stirred solution of (S)-1-(10-(tert-butoxymethyl)-4-ethyl-4-hydroxy-3,14-dioxo-3,4,12,14-tetrahydro-1H-pyrano[3',4':6,7]indolizino[1,2-b]quinolin-9-yl)-4-(tert-butyl)piperazine-1,4-dicarboxylate (0.140 g, 0.211 mmol, 1.0 eq.) in DCM (10 mL), TFA (0.5 mL) was added and the reaction mixture was allowed to stir at RT for 1 h. After completion of the reaction, the reaction mixture (reaction was monitored by TLC analysis) was quenched with Na₂HCO₃ (50 mL×2) and extracted with DCM (50 mL×2).

The combined organic layer was dried with Na₂SO₄ and concentrated under reduced pressure to obtain the desired product (0.090 g, 76%). LCMS: 563.2 [M+H]⁺.

Step-4: Preparation of (S)-10-(tert-Butoxymethyl)-4-ethyl-4-hydroxy-3,14-dioxo-3,4,12,14-tetrahydro-1H-pyrano[3',4':6,7]indolizino[1,2-b]quinolin-9-yl 4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)piperazine-1-carboxylate (Compound 17)

To a stirred solution of (S)-10-(tert-butoxymethyl)-4-ethyl-4-hydroxy-3,14-dioxo-3,4,12,14-tetrahydro-1H-pyrano[3',4':6,7]indolizino[1,2-b]quinolin-9-yl piperazine-1-carboxylate (0.090 g, 0.160 mmol, 1.0 eq.) and (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate (0.107 g, 0.192 mmol, 1.2 eq.) in methanol (10 mL), acetic acid (0.2 mL) and NaCNBH₃ (0.014 g, 0.32 mmol, 2.0 eq.) were added. The reaction mixture was allowed to stir at RT for 2 h. After completion of reaction, the reaction mixture (reaction was monitored by TLC analysis) was quenched with Na₂HCO₃ (50 mL×2) and extracted with DCM (50 mL×2). The combined organic layer was washed with H₂O (50 mL×2) and dried with Na₂SO₄ and concentrated under reduced pressure to obtain a crude residue which was purified by silica gel column chromatography (Combiflash, Elution: 0-3% MeOH in DCM) to obtain the desired product (0.016 g, 9%). ¹H NMR (400 MHz, DMSO-d₆): δ 8.83 (s, 1H), 8.14 (d, J=9.1 Hz, 1H), 7.65 (d, J=9.1 Hz, 1H), 7.34 (s, 1H), 6.98 (d, J=8.6 Hz, 2H), 6.64-6.49 (m, 3H), 5.67 (s, 1H), 5.43 (s, 2H), 5.34 (s, 2H), 4.77 (s, 2H), 4.40 (d, J=6.2 Hz, 1H), 3.68 (br s, 2H), 3.46 (br s, 3H), 3.25 (d, J=6.7 Hz, 3H), 2.82 (s, 3H), 2.33 (br s, 3H), 2.22 (br s, 1H), 2.19-2.00 (m, 10H), 1.88 (d, J=7.6 Hz, 4H), 1.73 (d, J=19.6 Hz, 2H), 1.45 (br s, 4H), 1.39-1.26 (m, 18H), 1.22 (s, 3H), 0.89 (t, J=7.2 Hz, 3H), 0.24 (s, 3H). LCMS: 1107.2 [M+H]⁺.

Example 18

Preparation of 2-(((5S,8R,9S,10S,13S,14S,17S)-10,13-Dimethyl-3-oxohexadecahydro-1H-cyclopenta[a]phenanthren-17-yl)oxy)-N-(1-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperidin-4-yl)-N-methylacetamide (Compound 18)

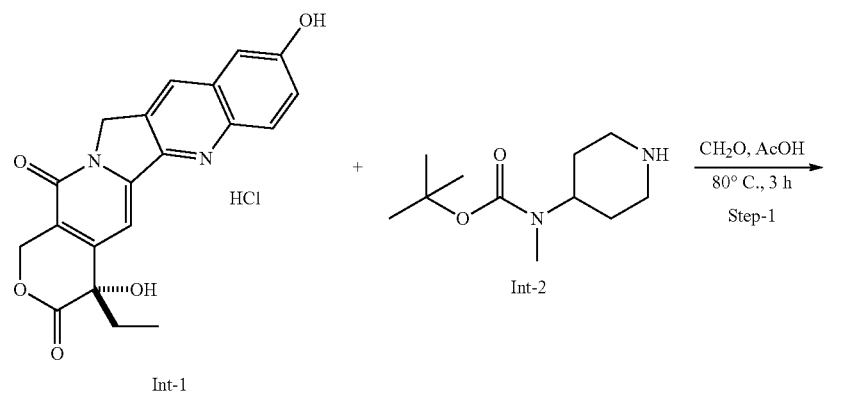

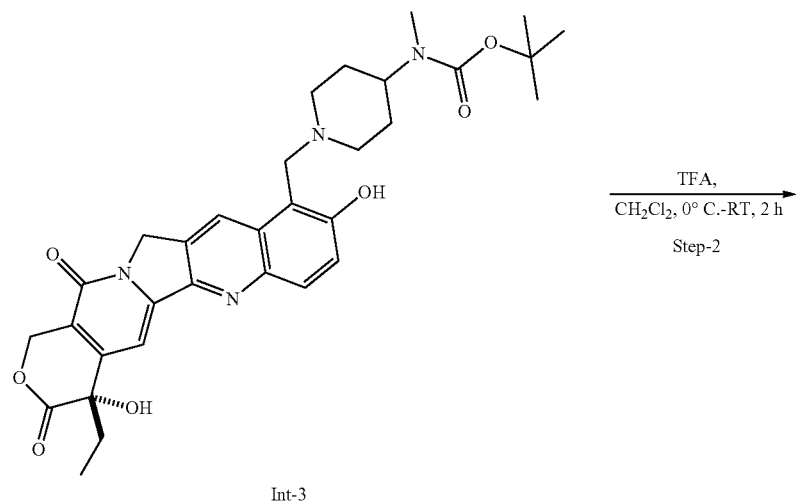

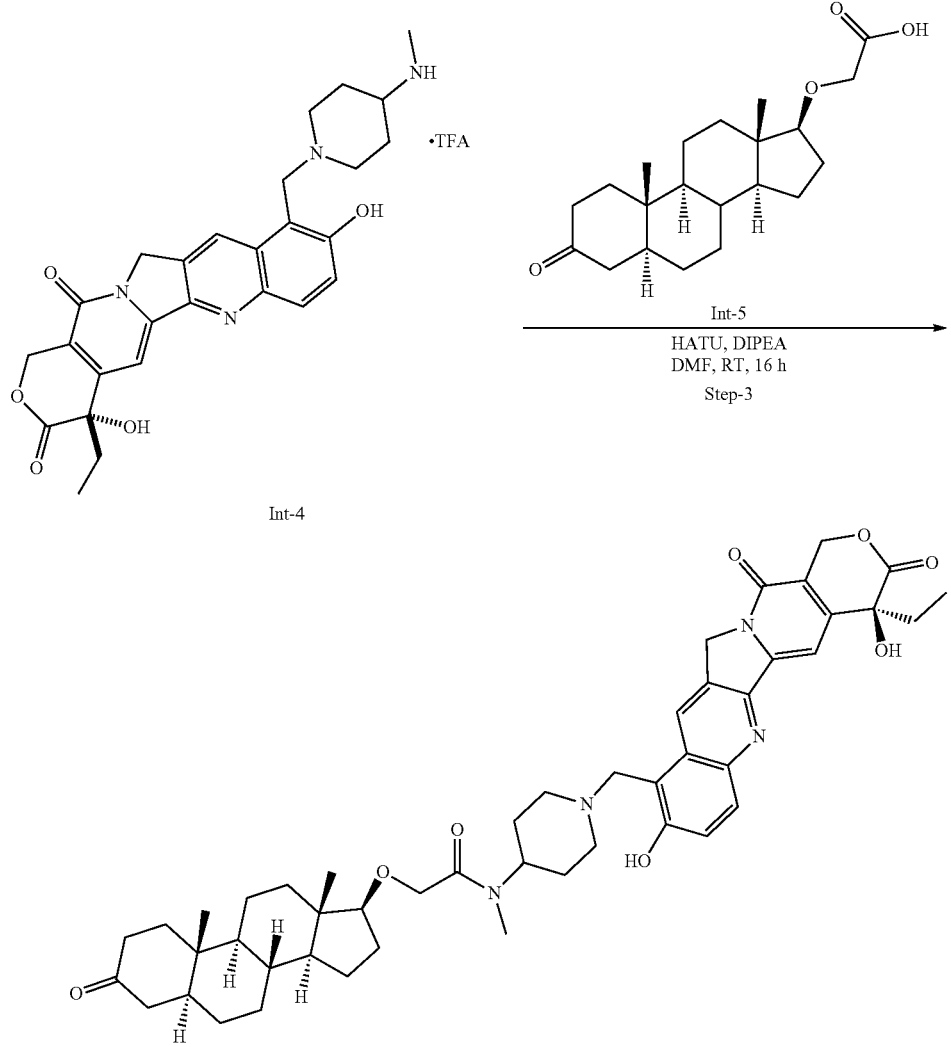

Step-1: Synthesis of tert-Butyl (S)-(1-((4-Ethyl-4,9-dihydroxy-3,14-dioxo-3,4,12,14-tetrahydro-1H-pyrano[3',4':6,7]indolizino[1,2-b]quinolin-10-yl)methyl)piperidin-4-yl)(methyl)carbamate (Int-3)

To a stirred solution of (S)-4-ethyl-4,9-dihydroxy-1,12-dihydro-14H-pyrano[3',4':6,7]indolizino[1,2-b]quinoline-3,14(4H)-dione (Int-1, 1.0 g, 2.74 mmol, 1.0 eq.) and tert-butyl methyl(piperidin-4-yl)carbamate (Int-2, 881 mg, 4.12 mmol, 1.5 eq.) in acetic acid (10 mL) was added 37% solution of formaldehyde (0.3 mL, 3.29 mmol, 1.5 eq.) at room temperature. The reaction mixture was heated to 80° C. and stirred for 3 h in a sealed tube. Progress of the reaction was monitored by TLC. After completion of the reaction, solvents were evaporated under reduced pressure to get the crude product. The crude product was basified with aq. ammonia until the pH reached 9, filtered the solid and washed with water, dried under vacuum to afford Int-3 (1.1 g, 68%). $^1$H NMR (400 MHz, DMSO-$d_6$) δ 8.72 (s, 1H) 7.97 (d, J=9.39 Hz, 1H) 7.41 (d, J=9.00 Hz, 1H) 7.25 (s, 1H) 6.37 (br s, 1H) 5.41 (s, 2H) 5.19-5.29 (m, 2H) 4.08 (s, 2H) 3.03 (br d, J=10.96 Hz, 2H) 2.66 (s, 3H) 2.24 (br t, J=11.15 Hz, 2H) 1.77-1.95 (m, 3H) 1.68 (br d, J=11.35 Hz, 2H) 1.55 (br s, 2H) 1.39 (s, 9H) 0.87 (t, J=7.24 Hz, 3H) (1H exchangeable hydrogen was not seen in spectra). LCMS: 591.2 [M+H]$^+$.

Step-2: Synthesis of (S)-4-Ethyl-4,9-dihydroxy-10-((4-(methylamino)piperidin-1-yl)methyl)-1,12-dihydro-14H-pyrano[3',4':6,7]indolizino[1,2-b]quinoline-3,14(4H)-dione.TFA salt (Int-4)

To a stirred solution of tert-butyl (S)-(1-((4-ethyl-4,9-dihydroxy-3,14-dioxo-3,4,12,14-tetrahydro-1H-pyrano[3',4':6,7]indolizino[1,2-b]quinolin-10-yl)methyl)piperidin-4-yl) (methyl)carbamate (Int-3, 1.1 g, 1.86 mmol, 1.0 eq.) in DCM (20 mL) under nitrogen atmosphere was added TFA (1.8 mL, 18.6 mmol, 10 eq.) at 0° C. The reaction mixture was allowed to warm up to room temperature and stirred for 2 h. Progress of the reaction was monitored by TLC. After completion of the reaction, solvents were evaporated under reduced pressure, washed with diethyl ether (10 mL) and dried under vacuum to afford Int-4 (900 mg, 98%) as a TFA salt. $^1$H NMR (400 MHz, DMSO-$d_6$) δ 11.36 (br s, 1H) 9.70 (br s, 1H) 8.85-8.90 (m, 2H) 8.19 (d, J=9.13 Hz, 1H) 7.65 (d, J=9.38 Hz, 1H) 7.23-7.34 (m, 1H) 6.50 (br s, 1H) 5.43 (s, 2H) 5.28 (s, 2H) 4.71 (br s, 2H) 3.65 (br d, J=1.63 Hz, 2H) 3.38 (q, J=7.00 Hz, 1H) 3.25 (br s, 2H) 2.58 (s, 3H) 2.19

(br d, J=10.26 Hz, 2H) 1.77-1.94 (m, 4H) 0.89 (t, J=7.32 Hz, 3H). LCMS: 491.45 [M+H]⁺.

Step-3: Synthesis of 2-(((5S,8R,9S,10S,13S,14S, 17S)-10,13-dimethyl-3-oxohexadecahydro-1H-cyclopenta[a]phenanthren-17-yl)oxy)-N-(1-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperidin-4-yl)-N-methylacetamide (18)

To a stirred solution of (S)-4-ethyl-4,9-dihydroxy-10-((4-(methylamino)piperidin-1-yl)methyl)-1,12-dihydro-14H-pyrano[3',4':6,7]indolizino[1,2-b]quinoline-3,14(4H)-dione.TFA salt Int-4 (250 mg, 0.51 mmol, 1.0 eq.) and 2-(((5S, 9S,10S,13S,14S,17S)-10,13-dimethyl-3-oxohexadecahydro-1H-cyclopenta[a]phenanthren-17-yl) oxy)acetic acid Int-5 (195 mg, 0.56 mmol, 1.1 eq.) in DMF (5 mL) were added HATU (273 mg, 0.76 mmol, 1.5 eq.) and DIPEA (0.3 mL, 1.53 mmol, 3 eq.) at room temperature and stirred for 16 h. Progress of the reaction was monitored by TLC. After completion of the reaction, water (20 mL) was added to the reaction mixture, filtered the solid and again washed with water (50 mL), and dried under vacuum to afford the desired product (80 mg, 20%). ¹H NMR (400 MHz, DMSO-d₆) δ 8.74 (br s, 1H) 7.98 (d, J=9.13 Hz, 1H) 7.43 (dd, J=9.13, 5.00 Hz, 1H) 7.26 (s, 1H) 6.47 (br d, J=2.00 Hz, 1H) 5.41 (s, 2H) 5.26 (s, 2H) 4.18-4.33 (m, 1H) 4.09 (br s, 4H) 3.70-3.83 (m, 1H) 3.30-3.40 (m, 3H) 3.05 (br d, J=10.88 Hz, 2H) 2.81 (s, 2H) 2.55 (s, 3H) 2.23-2.34 (m, 3H) 2.08 (br d, J=14.01 Hz, 1H) 1.92-1.85 (m, 6H) 1.67-1.73 (m, 1H) 1.58-1.66 (m, 2H) 1.35-1.56 (m, 6H) 1.16-1.33 (m, 6H) 0.97 (s, 3H) 0.88 (br t, J=7.32 Hz, 3H) 0.72 (s, 3H) (1H exchangeable hydrogen was not seen in spectra). LCMS: 821.7 [M+H]⁺. HPLC purity 97.9%.

Example 19

Preparation of (8S,11R,13S,14S,17R)-17-Acetyl-11-(4-((6-(4-(((S)-4-ethyl-4,9-dihydroxy-3,14-dioxo-3, 4,12,14-tetrahydro-1H-pyrano[3',4':6,7]indolizino[1, 2-b]quinolin-10-yl)methyl)piperazin-1-yl)-6-oxohexyl)(methyl)amino)phenyl)-13-methyl-3-oxo-2,3,6,7,8,11,12,13,14,15,16,17-dodecahydro-1H-cyclopenta[a]phenanthren-17-yl Acetate (Compound 19)

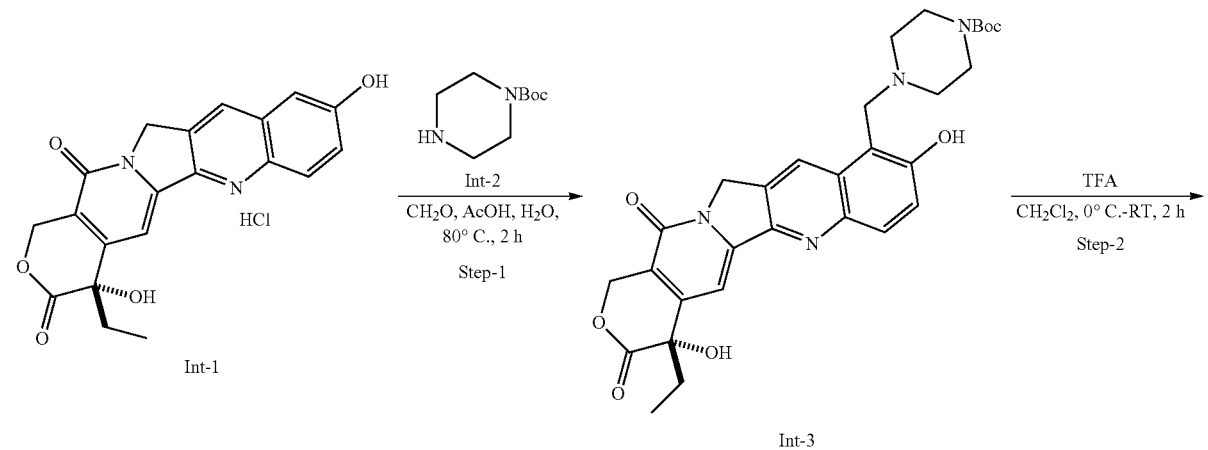

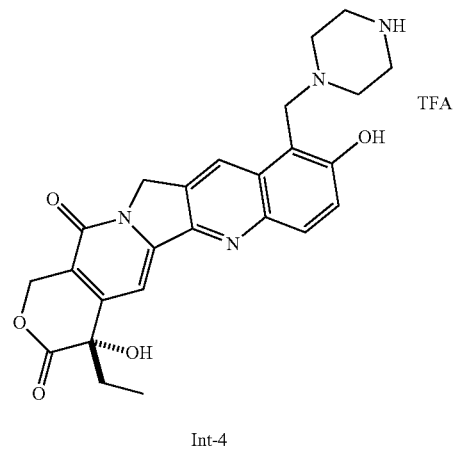

-continued
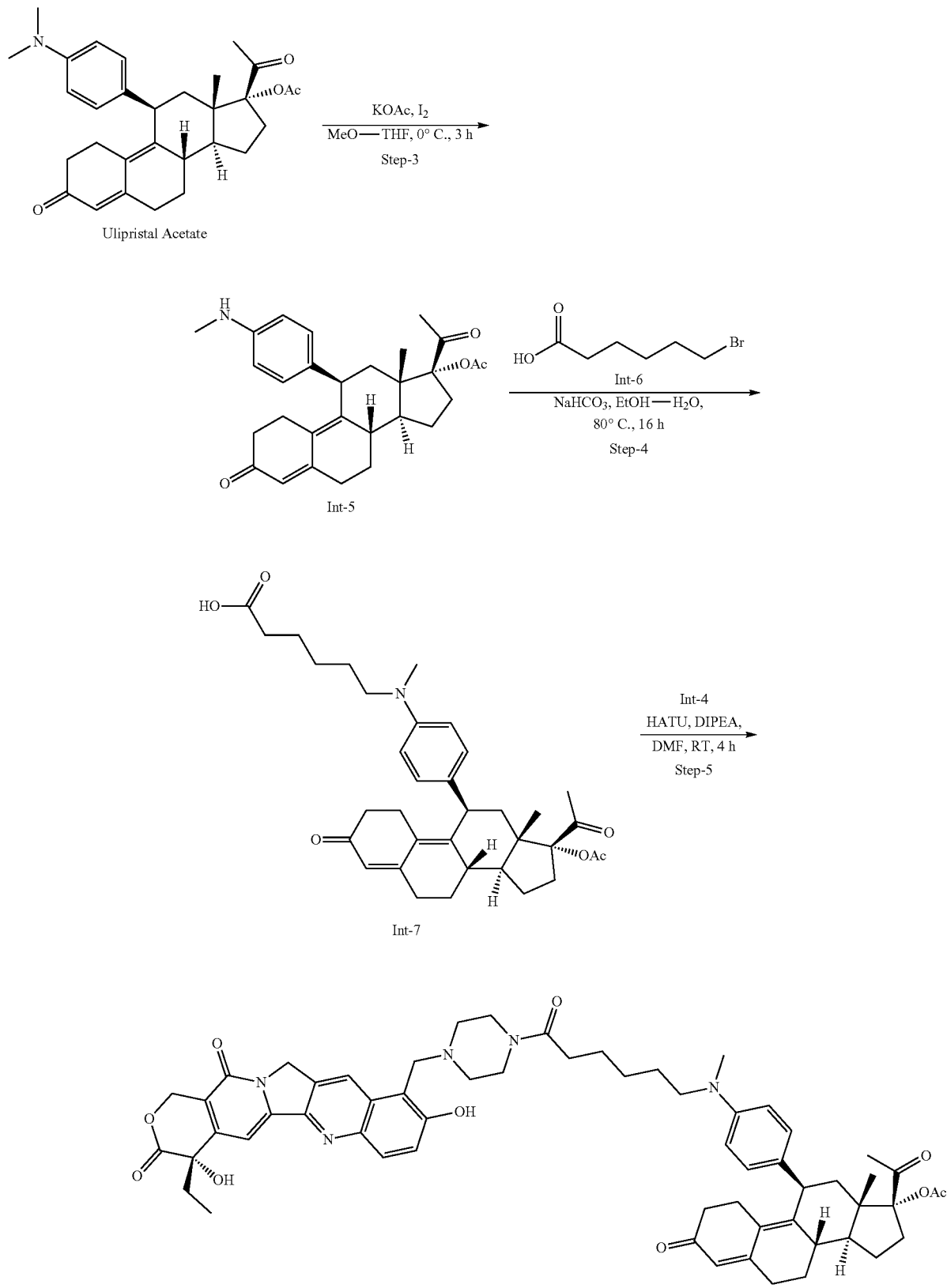

Step-1: Synthesis of tert-Butyl (S)-4-((4-Ethyl-4,9-dihydroxy-3,14-dioxo-3,4,12,14-tetrahydro-1H-pyrano[3',4':6,7]indolizino[1,2-b]quinolin-10-yl)methyl)piperazine-1-carboxylate (Int-3)

To a stirred solution of (S)-4-ethyl-4,9-dihydroxy-1,12-dihydro-14H-pyrano[3',4':6,7]indolizino[1,2-b]quinoline-3,14(4H)-dione.HCl salt Int-1 (2.5 g, 6.86 mmol, 1.0 eq.) and tert-butyl piperazine-1-carboxylate Int-2 (1.85 g, 10.3 mmol, 1.5 eq.) in acetic acid (10 mL) under inert atmosphere was added 37% solution of formaldehyde (0.29 mL, 8.24 mmol, 1.2 eq.) at room temperature. The reaction mixture was heated to 80° C. and stirred for 2 h in a sealed tube. Progress of the reaction was monitored by TLC. After completion of the reaction, solvents were evaporated under reduced pressure to get crude compound, the crude compound was basified with aq ammonia until the pH reached to 9, filtered the solid and washed with water (10 mL) and dried under vacuum to afford Int-3 (1.9 g, 50%). LCMS: 463.46 (M-100, Boc group cleavage was observed in LCMS) [M-Boc+H]$^+$.

Step-2: Synthesis of (S)-4-ethyl-4,9-dihydroxy-10-(piperazin-1-ylmethyl)-1,12-dihydro-14H-pyrano[3',4':6,7]indolizino[1,2-b]quinoline-3,14(4H)-dione.TFA salt (Int-4)

To a stirred solution of tert-butyl (S)-4-((4-ethyl-4,9-dihydroxy-3,14-dioxo-3,4,12,14-tetrahydro-1H-pyrano[3',4':6,7]indolizino[1,2-b]quinolin-10-yl)methyl)piperazine-1-carboxylate (Int-3, 2 g, 3.5 mmol, 1.0 eq.) in DCM (20 mL) under nitrogen atmosphere was added TFA (2.7 mL, 35 mmol, 10 eq.) at 0° C. Warmed to room temperature and stirred for 2 h. Progress of the reaction was monitored by TLC. After completion of the reaction, solvents were evaporated under reduced pressure, washed with diethyl ether (10 mL) and dried under vacuum to afford Int-4 (1.4 g, 83%). $^1$H NMR (400 MHz, DMSO-d$_6$) δ 8.86 (br s, 2H) 8.10 (d, J=9.25 Hz, 1H) 7.58 (d, J=9.25 Hz, 1H) 7.21-7.32 (m, 2H) 6.97-7.15 (m, 1H) 6.34-6.64 (m, 1H) 5.42 (s, 2H) 5.26 (s, 2H) 4.40 (s, 2H) 3.10-3.30 (m, 8H) 1.85-1.89 (m, 2H) 0.88 (t, J=7.17 Hz, 3H).

Step-3: Synthesis of (8S,11R,13S,14S,17R)-17-Acetyl-13-methyl-11-(4-(methylamino)phenyl)-3-oxo-2,3,6,7,8,11,12,13,14,15,16,17-dodecahydro-1H-cyclopenta[a]phenanthren-17-yl Acetate (Int-5)

To a stirred solution of Ulipristal acetate (2.0 g, 4.2 mmol, 1.0 eq.) in methanol (30 mL) and THF (30 mL) were added potassium acetate (4.12 g, 4.2 mmol, 10 eq.) and Iodine (2.65 g, 21 mmol, 5 eq.) at 0° C. and stirred for 3 h. Progress of the reaction was monitored by TLC. After completion of the reaction, solvent were evaporated under reduced pressure, to this reaction mixture was added saturated solution of sodium thiosulphate (100 mL), filtered the solid and washed with diethyl ether (30 mL), and dried under vacuum to afford Int-5 (1.7 g, 87%). $^1$H NMR (400 MHz, DMSO-d$_6$) δ 7.00 (br d, J=8.31 Hz, 1H) 6.91 (br d, J=8.31 Hz, 1H) 6.74 (br d, J=8.80 Hz, 1H) 6.44 (br d, J=8.80 Hz, 1H) 5.67 (s, 1H) 4.66-4.75 (m, 1H) 4.39 (br dd, J=19.32, 6.60 Hz, 1H) 2.75 (s, 3H) 2.61 (br d, J=4.40 Hz, 2H) 2.34 (br dd, J=11.74, 3.42 Hz, 2H) 2.13-2.24 (m, 3H) 2.10 (s, 3H) 1.99-2.05 (m, 3H) 1.91 (s, 3H) 1.61-1.78 (m, 3H) 1.24-1.47 (m, 3H) 0.23 (s, 3H). LCMS: 462.15 [M+H]$^+$.

Step-4: Synthesis of 6-((4-((8S,11R,13S,14S,17R)-17-Acetoxy-17-acetyl-13-methyl-3-oxo-2,3,6,7,8,11,12,13,14,15,16,17-dodecahydro-1H-cyclopenta[a]phenanthren-11yl)phenyl)(methyl)amino)hexanoic Acid (Int-7)

To a stirred solution of Int-5 (1 g, 2.1 mmol, 1.0 eq.) in ethanol (15 mL) and water (15 mL) were added Int-6 (2.1 g, 10.8 mmol, 5 eq.) and NaHCO$_3$ (1.84 g, 21.6 mmol, 10 eq.) at 0° C. The reaction mixture was heated at 80° C. for 16 h. Progress of the reaction was monitored by TLC. After completion of the reaction, 2M HCl in ethanol (10 mL) was added to this reaction mixture until the pH reached to 6. And extracted with ethyl acetate (2×100 mL). The combined organic extracts were washed with water (50 mL), brine (50 mL) and dried over anhydrous sodium sulphate, filtered and concentrated under vacuum to obtained crude compound. The crude compound obtained was purified by Combiflash column by using 5% methanol in dichloromethane to afford Int-7 (250 mg, 20%). $^1$H NMR (400 MHz, DMSO-d$_6$) δ 6.97 (br d, J=8.22 Hz, 2H) 6.57 (br d, J=8.22 Hz, 2H) 5.57-5.79 (m, 1H) 3.90-4.18 (m, 4H) 3.48-3.50 (m, 1H) 2.67-2.90 (m, 3H) 2.75 (s, 3H) 2.45-2.59 (m, 5H) 2.20 (s, 3H) 1.94-2.18 (m, 6H) 1.95 (s, 3H) 1.62-1.80 (m, 2H) 1.34-1.60 (m, 2H) 1.18-1.31 (m, 2H) 1.15-1.20 (m, 1H) 0.30 (s, 3H) (1H exchangeable hydrogen was not seen in spectra).

Step-5: Synthesis of (8S,11R,13S,14S,17R)-17-Acetyl-11-(4-((6-(4-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperazin-1-yl)-6-oxohexyl)(methyl)amino)phenyl)-13-methyl-3-oxo-2,3,6,7,8,11,12,13,14,15,16,17-dodecahydro-1H-cyclopenta[a]phenanthren-17-yl Acetate (19)

To a stirred solution of 6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11yl)phenyl)(methyl)amino)hexanoic acid Int-7 (200 mg, 0.34 mmol, 1.0 eq.) and (S)-4-ethyl-4,9-dihydroxy-10-(piperazin-1-ylmethyl)-1,12-dihydro-14H-pyrano[3',4':6,7]indolizino[1,2-b]quinoline-3,14(4H)dione.TFA salt (Int-4, 192 mg, 0.41 mmol, 1.2 eq.) in DMF (2 mL) were added HATU (186 mg, 0.52 mmol, 1.5 eq.) and DIPEA (0.090 mL, 0.52 mmol, 1.5 eq.) at room temperature and stirred for 4 h. Progress of the reaction was monitored by TLC. After completion of the reaction, water (20 mL) was added to this reaction mixture, filtered the solid and washed with water (10 mL) and dried under vacuum to obtain crude compound. The crude compound obtained was purified by Combiflash column by using 7% methanol in dichloromethane to afford the desired product (60 mg, 16%). $^1$H NMR (400 MHz, DMSO-d$_6$) δ 11.35 (br s, 1H) 9.65 (br s, 1H) 8.94 (s, 1H) 8.21 (d, J=9.25 Hz, 1H) 7.64 (d, J=9.25 Hz, 1H) 7.30 (s, 1H) 7.02 (br s, 2H) 6.67 (br s, 2H) 5.67 (s, 1H) 5.43 (s, 2H) 5.30 (s, 2H) 4.76 (br s, 2H) 4.41 (br d, J=6.94 Hz, 3H) 3.98-4.08 (m, 10H) 3.49-3.45 (br s, 4H) 3.25 (br s, 2H) 2.85 (s, 3H) 2.56 (br s, 2H) 2.28-2.42 (m, 3H) 2.13 (s, 3H) 2.00 (s, 3H) 1.82-1.94 (m, 2H) 1.63-1.80 (m, 4H) 1.20-1.56 (m, 7H) 0.88 (t, J=7.17 Hz, 3H) 0.22 (s, 3H). LCMS: 511.4 [M/2+H]$^+$, 1018.6 [M−H]$^-$. HPLC purity 95.1%.

Example 20
Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl (1-(2-(((5S,8R,9S,10S,13S,14S,17S)-10,13-dimethyl-3-oxohexadecahydro-1H-cyclopenta[a]phenanthren-17-yl)oxy)acetyl)piperidin-4-yl)(methyl)carbamate (Compound 21)
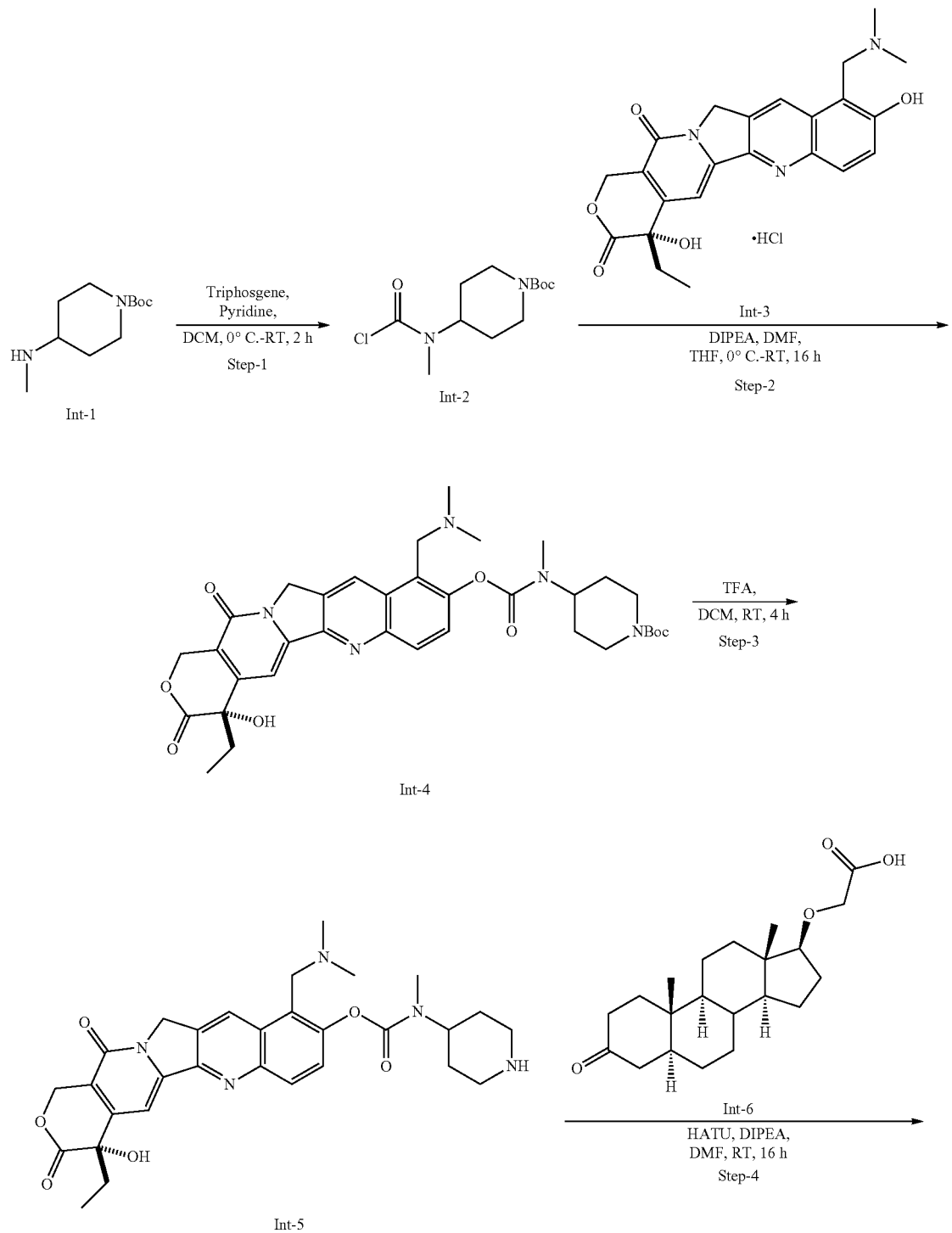

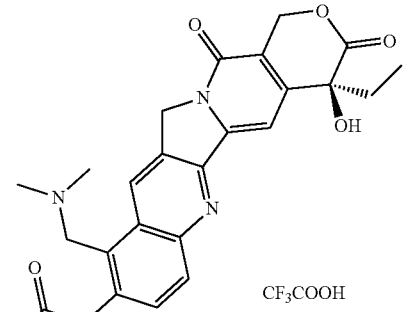
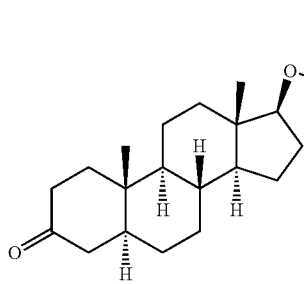

Step-1: Synthesis of tert-Butyl 4-((chlorocarbonyl)(methyl)amino)piperidine-1-carboxylate (Int-2)

To a stirred solution of tert-butyl 4-(methylamino)piperidine-1-carboxylate (Int-1, 2.0 g, 9.3 mmol, 1.0 eq.) in DCM (30 mL) were added pyridine (1.10 mL, 13 mmol, 1.5 eq.) at 0° C. followed by triphosgene (830 mg, 2.7 mmol, 0.3 eq.). Warmed to room temperature and stirred for 2 h. Progress of the reaction was monitored by TLC. After completion of the reaction, the reaction mixture was washed with water (60 mL) and extracted with DCM (2×60 mL). The combined organic extracts were washed with water (100 mL), brine (100 mL) and dried over anhydrous sodium sulphate, filtered, and concentrated under vacuum to afford Int-2 (2.0 g, crude) which was used in next step without further purification.

Step-2: Synthesis of tert-Butyl (S)-4-((((10-((dimethylamino)methyl)-4-ethyl-4-hydroxy-3,14-dioxo-3,4,12,14-tetrahydro-1H-pyrano[3',4':6,7]indolizino[1,2-b]quinolin-9yl)oxy)carbonyl)(methyl)amino)piperidine-1-carboxylate (Int-4)

To a stirred solution of tert-butyl 4-((chlorocarbonyl)(methyl)amino)piperidine-1-carboxylate (Int-2, 2 g, 7.2 mmol, 1.0 eq.) in DMF (15 mL) and THF (15 mL) were added (S)-10-((dimethylamino)methyl)-4-ethyl-4,9-dihydroxy-1,12-dihydro-14H-pyrano[3',4':6,7]indolizino[1,2-b]quinoline-3,14(4H)-dione.HCl salt (Int-3, 1.71 g, 3.6 mmol, 0.5 eq.) and DIPEA (8 mL, 38 mmol, 5 eq.) at 0° C. Warmed to room temperature and stirred for 16 h. Progress of the reaction was monitored by TLC. After completion of the reaction, the reaction mixture was washed with water (100 mL) and extracted with ethyl acetate (2×100 mL). The combined organic extracts were washed with water (100 mL), brine (100 mL) and dried over anhydrous sodium sulphate, filtered and concentrated under vacuum to obtain crude compound. The crude compound obtained was purified by Combiflash column by using 5% methanol in dichloromethane to afford Int-4 (690 mg, 24%). $^1$H NMR (400 MHz, DMSO-$d_6$) δ 8.94 (s, 1H) 8.10 (br d, J=9.29 Hz, 1H) 7.62 (br d, J=9.29 Hz, 1H) 7.30-7.33 (m, 1H) 6.52 (br s, 1H) 5.42 (s, 2H) 5.30 (s, 2H) 3.87-4.19 (m, 4H) 3.75 (br s, 2H) 3.01-3.05 (m, 4H) 2.66-2.94 (m, 3H) 2.25 (s, 3H) 1.66 (s, 6H) 1.41 (s, 9H) 0.88 (br t, J=7.34 Hz, 3H). LCMS: 661.4 [M+H]$^+$.

Step-3: Synthesis of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl methyl(piperidin-4-yl)carbamate (Int-5)

To a stirred solution of tert-butyl (S)-4-((((10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)oxy) carbonyl)(methyl)amino)piperidine-1-carboxylate (Int-4, 700 mg, 1 mmol, 1.0 eq.) in DCM (15 mL) under nitrogen atmosphere was added TFA (1.2 mL, 20 mmol, 20 eq.) at 0° C. Warmed to room temperature and stirred for 4 h. Progress of the reaction was monitored by TLC. After completion of the reaction, solvents were evaporated under reduced pressure, washed with diethyl ether (10 mL) and dried under vacuum to afford Int-5 (570 mg, 98%) as TFA salt. $^1$H NMR (400 MHz, DMSO-$d_6$) δ 10.15 (br s, 1H) 9.11 (s, 1H) 8.41-9.01 (m, 1H) 8.32 (d, J=8.80 Hz, 1H) 7.81 (d, J=8.80 Hz, 1H) 7.37 (s, 1H) 6.56 (br s, 1H) 5.40 (s, 2H) 5.32 (br s, 2H) 4.80-482 (m, 1H) 4.22-428 (s, 2H) 3.50-3.58 (m, 4H) 3.13 (s, 3H) 2.81 (s, 6H) 2.03 (br d, J=13.21 Hz, 2H) 1.79-1.95 (m, 4H) 0.89 (br t, J=7.09 Hz, 3H). LCMS: 560.2 [M+H]$^+$.

Step-4: Synthesis of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl (1-(2-(((5S,8R,9S,10S,13S,14S,17S)-10,13-dimethyl-3-oxohexadecahydro-1H-cyclopenta[a]phenanthren-17-yl)oxy)acetyl)piperidin-4-yl)(methyl)carbamate (21)

To a stirred solution of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl methyl(piperidin-4-yl)carbamate TFA salt (Int-5, 300 mg, 5.3 mmol, 1.0 eq.) and 2-(((5S,9S,10S,13S,14S,17S)-10,13-dimethyl-3-oxohexadecahydro-1H-cyclopenta[a]phenanthren-17-yl) oxy)acetic acid (Int-6, 183 mg, 5.3 mmol, 1.0 eq.) in DMF (15 mL) were added HATU (406 mg, 10.6 mmol, 2.0 eq.) and NaHCO$_3$ (225 mg, 26.5 mmol, 3.0 eq.) at room temperature and stirred for 16 h. Progress of the reaction was monitored by TLC. After completion of the reaction, water (20 mL) was added to this reaction mixture, filtered the solid and washed with water (50 mL) and dried under vacuum to obtain crude compound. The crude compound was purified by prep. HPLC method to afford the desired product (142 mg, 29%). $^1$H NMR (400 MHz, DMSO-d$_6$) δ 9.83 (br s, 1H) 9.15 (s, 1H) 8.39 (d, J=9.26 Hz, 1H) 7.89 (d, J=9.26 Hz, 1H) 7.44 (s, 1H) 6.61 (br s, 1H) 5.51 (s, 2H) 5.40 (s, 2H) 4.89 (br s, 2H) 4.54 (br dd, J=9.69, 1.56 Hz, 1H) 4.35-4.50 (m, 1H) 4.17 (d, J=5.38 Hz, 2H) 4.02-4.11 (m, 1H) 3.44 (br d, J=8.13 Hz, 1H) 3.11 (s, 3H) 2.80-2.90 (m, 2H) 2.92 (s, 6H) 2.64-2.77 (m, 1H) 2.42-2.52 (m, 1H) 2.31-2.41 (m, 1H) 2.09-2.19 (m, 1H) 1.78-2.05 (m, 10H) 1.64-1.73 (m, 2H) 1.55-1.63 (m, 2H) 1.41-1.54 (m, 4H) 1.23-1.39 (m, 6H) 1.05 (s, 3H) 0.96 (br t, J=7.32 Hz, 3H) 0.80 (s, 3H). LCMS: 893.0 [M+H]$^+$. HPLC purity 97.90%.

Example 21

Preparation of 2-(((5S,8R,9S,10S,13S,14S,17S)-10,13-Dimethyl-3-oxohexadecahydro-1H-cyclopenta[a]phenanthren-17-yl)oxy)-N—(((S)-4-ethyl-4,9-dihydroxy-3,14-dioxo-3,4,12,14-tetrahydro-1H-pyrano[3',4':6,7]indolizino[1,2-b]quinolin-10-yl)methyl)-N-methylacetamide (Compound 25)

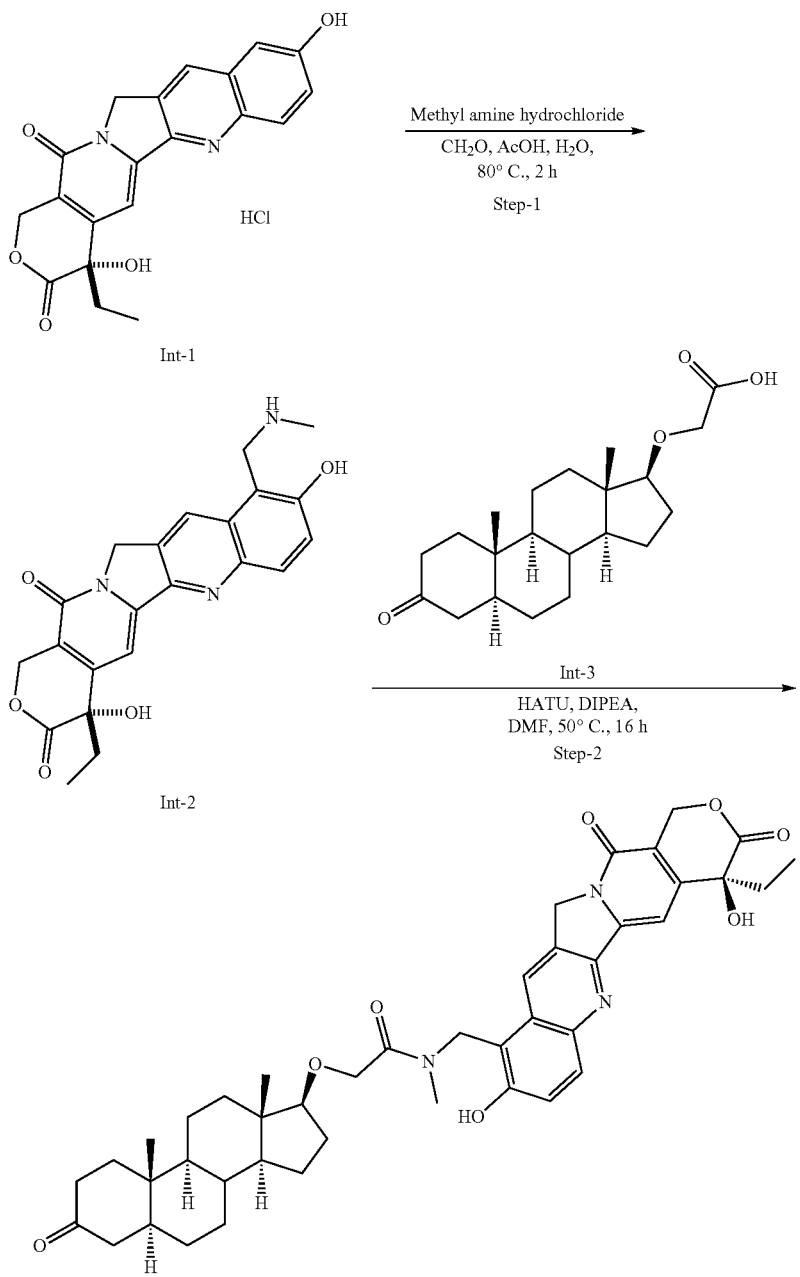

Step-1: Synthesis of (S)-4-Ethyl-4,9-dihydroxy-10-((methylamino)methyl)-1,12-dihydro-14H-pyrano[3',4':6,7]indolizino[1,2-b]quinoline-3,14(4H)-dione (Int-2)

To a stirred solution of (S)-4-ethyl-4,9-dihydroxy-1,12-dihydro-14H-pyrano[3',4':6,7]indolizino[1,2-b]quinoline-3,14(4H)-dione (Int-1, 2.0 g, 5.4 mmol, 1.0 eq.) and methyl amine hydrochloride (255 mg, 8.2 mmol, 1.5 eq.) in acetic acid (20 mL) was added 37% solution of formaldehyde (197 mg, 6.59 mmol, 1.2 eq.) at room temperature. The reaction mixture was heated to 80° C. and stirred for 2 h in a sealed tube. Progress of the reaction was monitored by TLC. After completion of the reaction, solvents were evaporated under reduced pressure to get crude compound. The crude compound was basified with aq ammonia until the pH reached to 9, filtered the solid and washed with water, dried under vacuum to afford Int-2 (1.7 g, 50%). $^1$H NMR (400 MHz, DMSO-$d_6$) δ 8.70 (s, 1H) 7.97 (d, J=9.29 Hz, 1H) 7.40 (d, J=9.29 Hz, 1H) 7.24 (s, 1H) 5.41 (s, 2H) 5.22 (s, 2H) 5.20 (br s, 1H) 4.37 (s, 2H) 2.46 (s, 3H) 1.82-1.93 (m, 3H) 0.88 (br t, J=6.85 Hz, 3H). LCMS: 408.4 [M+H]$^+$.

Step-2: Synthesis of 2-(((5S,8R,9S,10S,13S,14S,17S)-10,13-Dimethyl-3-oxohexadecahydro-1H-cyclopenta[a]phenanthren-17-yl)oxy)-N—(((S)-4-ethyl-4,9-dihydroxy-3,14-dioxo-3,4,12,14-tetrahydro-1H-pyrano[3',4':6,7]indolizino[1,2-b]quinolin-10-yl)methyl)-N-methylacetamide (25)

To a stirred solution of (S)-4-ethyl-4,9-dihydroxy-10-((methylamino)methyl)-1,12-dihydro-14H-pyrano[3',4':6,7]indolizino[1,2-b]quinoline-3,14(4H)-dione (Int-2, 500 mg, 1.22 mmol, 1.0 eq.) and 2-(((5S,9S,10S,13S,14S,17S)-10,13-dimethyl-3-oxohexadecahydro-1H-cyclopenta[a]phenanthren-17-yl)oxy)acetic acid (Int-3, 427 mg, 1.22 mmol, 1.0 eq.) in DMF (5 mL) were added HATU (879 mg, 2.45 mmol, 2.0 eq.) and DIPEA (0.64 mL, 3.68 mmol, 3.0 eq.) at room temperature. The reaction mixture was heated to 50° C. and stirred for 16 h. Progress of the reaction was monitored by TLC. After completion of the reaction, the reaction mixture was washed with water (100 mL) and extracted with 10% methanol in DCM (2×100 mL). The combined organic extracts were concentrate under reduced pressure to obtain crude compound. The crude compound obtained was purified by Combiflash column by using 10% methanol in DCM to afford the desired product (160 mg, 16%). $^1$H NMR (400 MHz, DMSO-$d_6$) δ 10.67 (s, 1H) 8.76 (s, 1H) 8.04 (d, J=9.26 Hz, 1H) 7.58 (d, J=9.26 Hz, 1H) 7.28 (s, 1H) 6.30 (s, 1H) 5.37 (d, J=5.50 Hz, 2H) 5.20-5.34 (m, 2H) 5.07 (d, J=19.26 Hz, 1H) 4.81 (d, J=14.01 Hz, 1H) 4.29 (d, J=13.76 Hz, 1H) 4.00 (d, J=13.63 Hz, 1H) 2.80 (m, 3H) 2.23-2.39 (m, 2H) 2.02-2.18 (m, 2H) 1.80-1.98 (m, 3H) 1.68-1.78 (m, 1H) 1.54-1.67 (m, 1H) 0.91-1.33 (m, 13H) 0.87 (t, J=7.25 Hz, 3H) 0.77 (s, 3H) 0.46 (s, 3H) 0.05-0.13 (m, 3H). LCMS: 738.35 [M+H]$^+$. HPLC purity 97.5%.

Example 22

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(1-(6-(((1r,4r)-4-(3-chloro-4-cyanophenoxy)cyclohexyl)carbamoyl)pyridazin-3-yl)piperidine-4-carbonyl)piperazine-1-carboxylate (Compound 26)

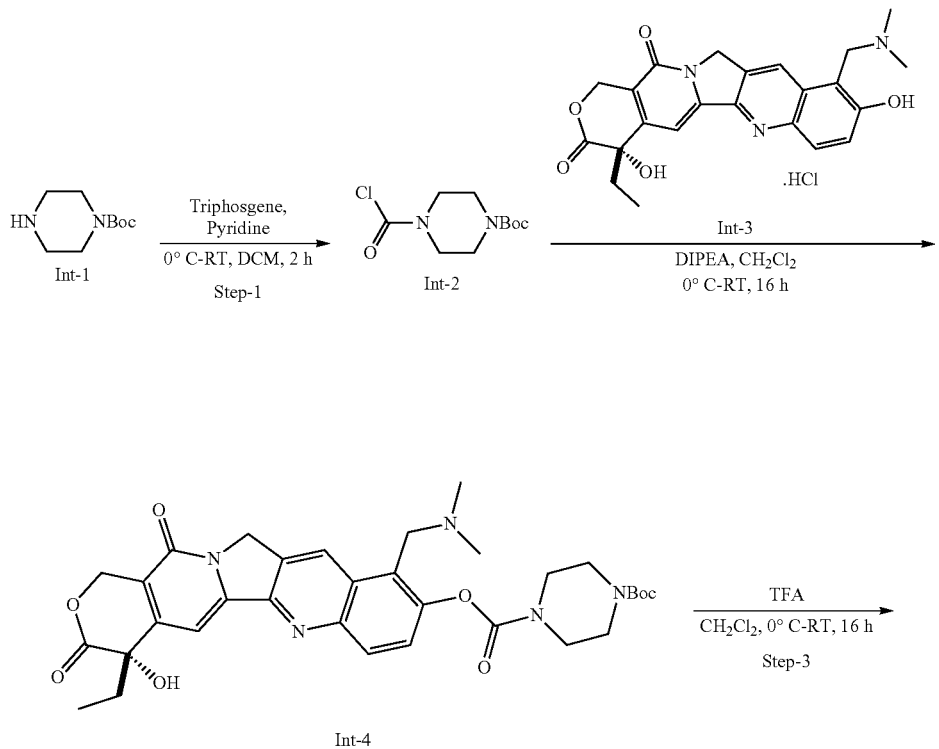

-continued
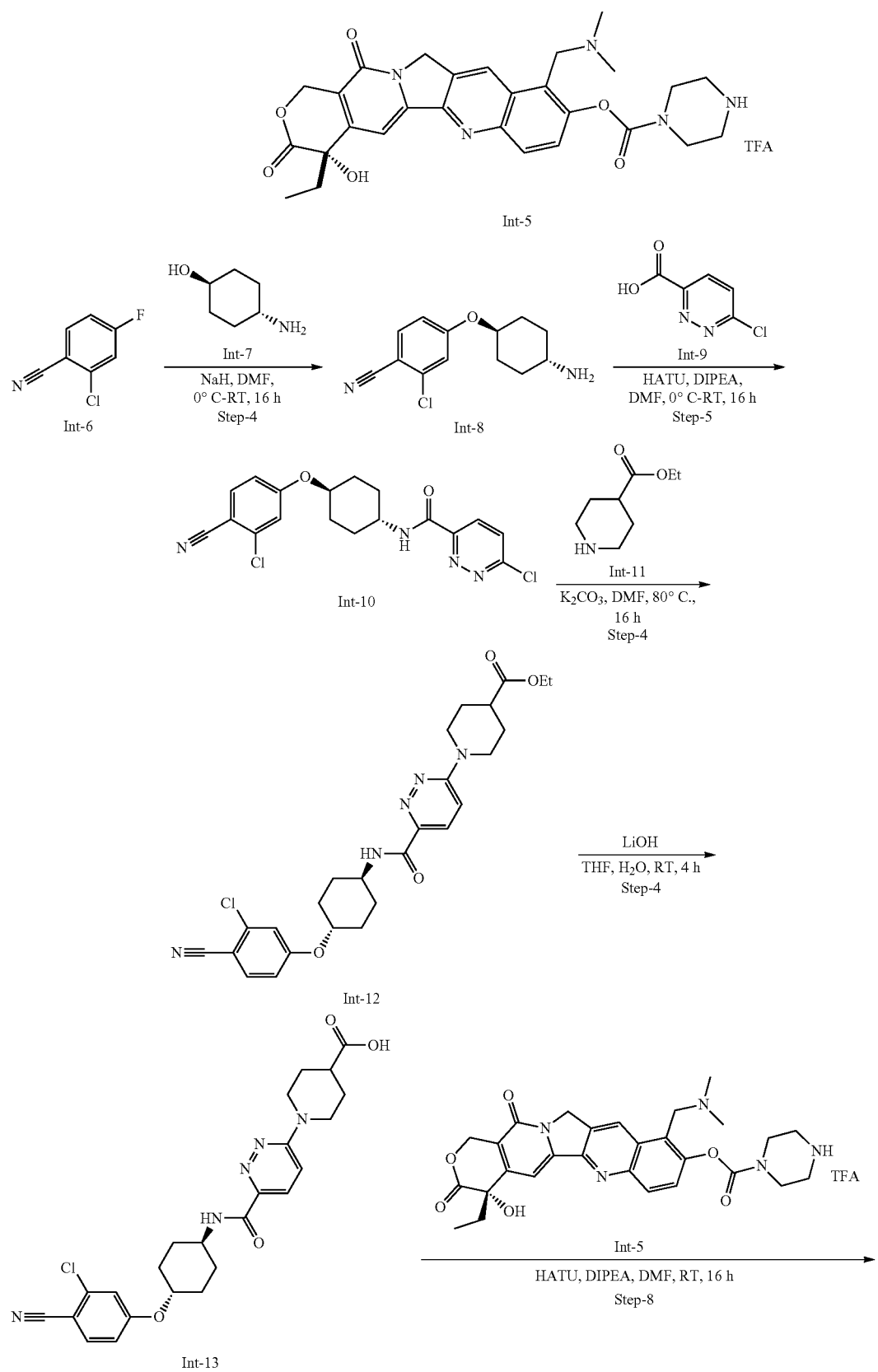

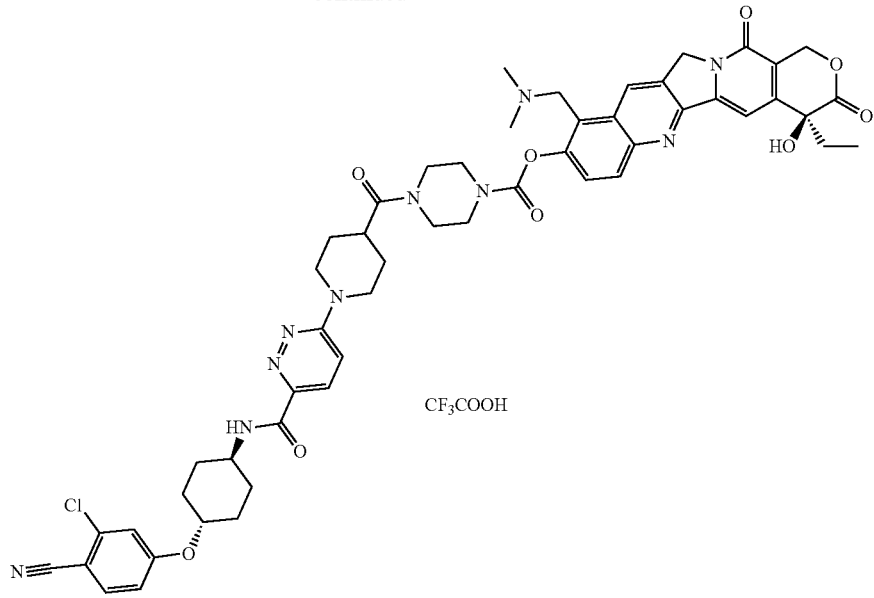 [SMILES: CC[C@@]1(O)C(=O)OCc2c1cc1n(c2=O)Cc2cc3c(CN(C)C)c(OC(=O)N4CCN(C(=O)C5CCN(c6ccc(C(=O)N[C@H]7CC[C@H](Oc8ccc(C#N)c(Cl)c8)CC7)nn6)CC5)CC4)ccc3nc2-1 ; "CF3COOH"]

Step-1: Synthesis of tert-Butyl 4-(Chlorocarbonyl)piperazine-1-carboxylate (Int-2)

To a stirred solution of tert-butyl piperazine-1-carboxylate (Int-1, 5 g, 26.8 mmol, 1.0 eq.) in DCM (100 mL) were added pyridine (2.97 g, 37.6 mmol, 1.4 eq.) and triphosgene (3.19 g, 10.7 mmol, 0.4 eq.) at 0° C. Warmed to room temperature and stirred for 2 h. Progress of the reaction was monitored by TLC. After completion of the reaction, the reaction mixture was washed with water (100 mL) and extracted with DCM (2×100 mL). The combined organic extracts were again washed with water (200 mL), brine (200 mL) and dried over anhydrous sodium sulphate, filtered and concentrated under vacuum to afford Int-2 (6.0 g, 90%). $^1$H NMR (400 MHz, DMSO-$d_6$) δ 3.64 (br d, J=4.40 Hz, 2H) 3.52 (br s, 2H) 3.27-3.47 (m, 3H) 2.93-3.21 (m, 1H) 1.41 (s, 9H).

Step-2: Synthesis of (S)-1-(tert-Butyl) 4-(10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl)piperazine-1,4-dicarboxylate (Int-4)

To a stirred solution of (S)-10-((dimethylamino)methyl)-4-ethyl-4,9-dihydroxy-1,12-dihydro-14H-pyrano[3',4':6,7]indolizino[1,2-b]quinoline-3,14(4H)-dione HCl salt (Int-3, 10 g, 23.7 mmol, 1.0 eq.) in DCM (250 mL) were added DIPEA (15.3 g, 118 mmol, 5 eq.) and DMAP (724 mg, 5.9 mmol, 0.25 eq.) followed by addition of tert-butyl 4-(chlorocarbonyl)piperazine-1-carboxylate (Int-2, 5.89 g, 23.7 mmol, 1 eq.) in DCM (mL) drop wise over a period of 10 min at 0° C. and stirred for 16 h. Progress of the reaction was monitored by TLC. After completion of the reaction, the reaction mixture was washed with water (100 mL) and extracted with DCM (3×100 mL). The combined organic extracts were again washed with water (200 mL), brine (200 mL) and dried over anhydrous sodium sulphate, filtered and concentrated under vacuum to get crude compound. The crude compound obtained was purified by Combiflash column by using 7% methanol in DCM to afford Int-4 (10 g, 66%). $^1$H NMR (400 MHz, DMSO-$d_6$) δ 8.95 (s, 1H) 8.11 (d, J=9.29 Hz, 1H) 7.65 (d, J=9.29 Hz, 1H) 7.34 (s, 1H) 6.53 (s, 1H) 5.43 (s, 2H) 5.31 (s, 2H) 3.67-3.79 (m, 4H) 3.41-3.55 (m, 6H) 2.20 (s, 6H) 1.80-1.93 (m, 2H) 1.44 (s, 9H) 0.89 (br t, J=7.34 Hz, 3H). LCMS: 634.2 [M+H]$^+$.

Step-3: Synthesis of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl piperazine-1-carboxylate TFA salt (Int-5)

To a stirred solution of (S)-1-(tert-butyl) 4-(10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl) piperazine-1,4-dicarboxylate (Int-4, 1 g, 15 mmol, 1.0 eq.) in DCM (20 mL) under nitrogen atmosphere was added TFA (3 mL) at 0° C. Warmed to room temperature and stirred for 16 h. Progress of the reaction was monitored by TLC. After completion of the reaction, solvents were evaporated under reduced pressure, washed with diethyl ether (20 mL) and dried under vacuum to afford Int-5 (1.02 g, crude) as a TFA salt which was used in next step without further purification. $^1$H NMR (400 MHz, DMSO-$d_6$) δ 10.12 (br s, 1H) 9.03-9.27 (m, 2H) 8.35 (br d, J=9.29 Hz, 1H) 7.86 (br d, J=9.29 Hz, 1H) 7.37 (s, 1H) 6.57 (br s, 1H) 5.45 (br s, 2H) 5.33 (br s, 2H) 4.86 (br s, 2H) 3.90-3.95 (m, 2H) 3.68-3.71 (m, 2H) 3.30 (br d, J=12.23 Hz, 2H) 2.89 (s, 6H) 1.80-1.95 (m, 3H) 1.08 (br t, J=7.09 Hz, 1H) 0.89 (br t, J=6.85 Hz, 3H). LCMS: 534.2 [M+H]$^+$.

Step-4: Synthesis of 4-(((1r,4r)-4-Aminocyclohexyl)oxy)-2-chlorobenzonitrile (Int-8)

To a stirred solution of (1r,4r)-4-aminocyclohexan-1-ol (Int-7, 11.1 g, 96 mmol, 1.0 eq.) in DMF (120 mL) under nitrogen atmosphere was added NaH (4.62 g, 192 mmol, 2 eq.) at 0° C. Warmed to room temperature and stirred for 45 min. To this reaction mixture was added 2-chloro-4-fluorobenzonitrile (Int-6, 15 g, 96 mmol, 1.0 eq.) in DMF (30 mL) drop wise over a period of 10 min at room temperature and stirred for 16 h. Progress of the reaction was monitored by TLC. After completion of the reaction, water (100 mL) was added to this reaction mixture, solvents were evaporated under reduced pressure and washed with water (200 mL) and extracted with ethyl acetate (3×500 mL). The combined organic extracts were washed with water (500 mL) and brine (500 mL), dried over anhydrous sodium sulfate, filtered and concentrated under vacuum to afford Int-8 (20 g, crude) which was used in next step without further purification. LCMS: 251.2 [M+H]$^+$.

Step-5: Synthesis of 6-Chloro-N-((1r,4r)-4-(3-chloro-4-cyanophenoxy)cyclohexyl)pyridazine-3-carboxamide (Int-10)

A mixture of 4-(((1r,4r)-4-aminocyclohexyl)oxy)-2-chlorobenzonitrile 6-chloropyridazine-3-carboxylic acid (Int-8, 20 g, 80 mmol, 1.0 eq.) and 6-chloropyridazine-3-carboxylic acid (Int-9, 12.6 g, 80 mmol, 1.0 eq.) in DMF (200 mL) were added HATU (36.4 g, 96 mmol, 1.2 eq.) and DIPEA (28 mL, 217 mmol, 2.0 eq.) at 0° C. Reaction mixture was stirred at RT for 16 h. Progress of the reaction was monitored by TLC. After completion of the reaction, solvents were evaporated under reduced pressure and washed with water (500 mL) and extracted with ethyl acetate (3×800 mL). The combined organic extracts were washed with water (500 mL) and brine (500 mL), dried over anhydrous sodium sulfate, filtered and concentrated under vacuum to get crude compound. The crude compound was purified by silica gel column chromatography by eluting with 80% ethyl acetate in hexane to afford Int-10 (10.7 g, 31%). $^1$H NMR (400 MHz, DMSO-d$_6$) δ 9.15 (d, J=7.83 Hz, 1H) 8.22 (d, J=8.80 Hz, 1H) 8.10 (d, J=8.80 Hz, 1H) 7.86 (d, J=8.80 Hz, 1H) 7.40 (d, J=1.96 Hz, 1H) 7.14 (dd, J=8.80, 2.45 Hz, 1H) 4.47-4.59 (m, 1H) 3.84-3.99 (m, 1H) 2.12 (br d, J=11.25 Hz, 2H) 1.90 (br d, J=10.76 Hz, 2H) 1.62-1.78 (m, 2H) 1.45-1.59 (m, 2H).

Step-6: Synthesis of Ethyl 1-(6-(((1r,4r)-4-(3-Chloro-4-cyanophenoxy)cyclohexyl)carbamoyl)pyridazin-3-yl)piperidine-4-carboxylate (Int-12)

To a stirred solution of 6-chloro-N-((1r,4r)-4-(3-chloro-4-cyanophenoxy)cyclohexyl) pyridazine-3-carboxamide (Int-10, 3 g, 7.6 mmol, 1.0 eq.) and ethyl piperidine-4-carboxylate (Int-11, 1.2 mL, 7.6 mmol, 1.0 eq.) in DMF (30 mL) was added potassium carbonate (1.6 g, 11.6 mmol, 1.5 eq.) at room temperature 0° C. The reaction mixture was heated to 80° C. and stirred for 16 h. Progress of the reaction was monitored by TLC. After completion of the reaction, solvents were evaporated under reduced pressure and washed with water (100 mL) and extracted with ethyl acetate (3×100 mL). The combined organic extracts were washed with water (500 mL) and brine (500 mL), dried over anhydrous sodium sulfate, filtered and concentrated under vacuum to get crude compound. The crude compound was purified by silica gel column chromatography by eluting with 60% ethyl acetate in heptane to afford Int-12 (3.2 g, 44%). $^1$H NMR (400 MHz, DMSO-d$_6$) δ 8.59 (br d, J=8.31 Hz, 1H) 7.82 (dd, J=15.16, 9.29 Hz, 2H) 7.30-7.41 (m, 2H) 7.12 (dd, J=8.80, 2.45 Hz, 1H) 4.47-4.57 (m, 1H) 4.36 (br d, J=13.20 Hz, 2H) 4.06 (q, J=6.85 Hz, 2H) 3.77-3.92 (m, 1H) 3.09-3.22 (m, 2H) 2.63-2.74 (m, 1H) 2.09 (br d, J=9.29 Hz, 2H) 1.89 (br t, J=10.27 Hz, 4H) 1.42-1.70 (m, 6H) 1.17 (t, J=7.09 Hz, 3H). LCMS: 512.45 [M+H]$^+$.

Step-7: Synthesis of 1-(6-(((1r,4r)-4-(3-Chloro-4-cyanophenoxy)cyclohexyl)carbamoyl)pyridazin-3-yl)piperidine-4-carboxylic Acid (Int-13)

To a stirred solution of ethyl 1-(6-(((1r,4r)-4-(3-chloro-4-cyanophenoxy)cyclohexyl)carbamoyl)pyridazin-3-yl)piperidine-4-carboxylate (Int-12, 3.5 g, 6.8 mmol, 1.0 eq.) in THF (30 mL) and water (17 mL) was added LiOH (500 mg, 20.8 mmol, 3.0 eq.) at room temperature and for 4 h. Progress of the reaction was monitored by TLC. After completion of the reaction, solvents were evaporated under reduced pressure, to this mixture was added water (30 mL) and acidified with conc. HCl until the pH reached to 6 and extracted with ethyl acetate (3×100 mL). The combined organic extracts were washed with water (500 mL) and brine (500 mL), dried over anhydrous sodium sulfate, filtered and concentrated under vacuum to afford Int-13 (2.8 g, 80%). $^1$H NMR (400 MHz, DMSO-d$_6$) δ 8.60 (d, J=8.31 Hz, 1H) 7.83 (dd, J=19.56, 9.29 Hz, 2H) 7.30-7.44 (m, 2H) 7.07-7.20 (m, 1H) 4.46-4.62 (m, 1H) 4.34 (br d, J=13.69 Hz, 2H) 3.78-3.95 (m, 2H) 3.10-3.22 (m, 2H) 2.10 (br d, J=12.23 Hz, 2H) 1.89 (br d, J=11.25 Hz, 4H) 1.46-1.70 (m, 6H) (1H exchangeable hydrogen was not seen in spectra). LCMS: 482.2 [M+H]$^+$.

Step-8: Synthesis of (S)-10-((Dimethylamino) methyl)-4-ethyl-4-hydroxy-3,14-dioxo-3,4,12,14-tetrahydro-1H-pyrano[3',4':6,7]indolizino[1,2-b]quinolin-9-yl 4-(1-(6-(((1r,4r)-4-(3-chloro-4-cyanophenoxy)cyclohexyl)carbamoyl)pyridazin-3-yl)piperidine-4-carbonyl)piperazine-1-carboxylate TFA salt (26)

To a stirred solution of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl piperazine-1-carboxylate TFA salt (Int-5, 295 mg, 5.53 mmol, 1.0 eq.) and 1-(6-(((1r,4r)-4-(3-chloro-4-cyanophenoxy)cyclohexyl) carbamoyl)pyridazin-3-yl)piperidine-4-carboxylic acid (Int-13, 259 mg, 5.53 mmol, 1.0 eq.) in DMF (8 mL) were added HATU (306 mg, 8.05 mmol, 1.5 eq.) and DIPEA (0.2 mL, 16.5 mmol, 3.0 eq.) at 0° C. Reaction mixture was stirred at RT for 16 h. Progress of the reaction was monitored by TLC. After completion of the reaction, the reaction mixture was washed with water (60 mL) and extracted with 10% methanol in DCM (2×60 mL). The combined organic extracts were washed with water (500 mL) and brine (500 mL), dried over anhydrous sodium sulfate, filtered and concentrated under vacuum to get crude compound. The crude compound was purified by prep. HPLC method (0.5% TFA in ACN) in TFA method to afford the desired TFA salt (166 mg, 30%). $^1$H NMR (400 MHz, DMSO-d$_6$) δ 9.65-9.83 (m, 1H) 9.11 (s, 1H) 8.58 (d, J=8.00 Hz, 1H) 8.35 (d, J=9.26 Hz, 1H) 7.79-7.92 (m, 3H) 7.34-7.43 (m, 3H) 7.14 (dd, J=8.76, 2.38 Hz, 1H) 6.43-6.67 (m, 1H) 5.45 (s, 2H) 5.35 (s, 2H) 4.84 (br d, J=0.88 Hz, 2H) 4.54 (br s, 2H) 3.60-3.92 (m, 10H) 3.06-3.22 (m, 3H) 2.91 (s, 6H) 2.06-2.16 (m, 2H) 1.85-1.95 (m, 4H) 1.75-1.84 (m, 2H) 1.47-1.70 (m, 6H) 0.90 (t, J=7.32 Hz, 3H). LCMS: 999.65 [M+H]$^+$. HPLC purity 98.9%.

Example 23
Preparation of N-((1r,4r)-4-(3-Chloro-4-cyanophenoxy)cyclohexyl)-6-(4-((1-((S)-4-ethyl-4,9-dihydroxy-3,14-dioxo-3,4,12,14-tetrahydro-1H-pyrano[3',4':6,7]indolizino[1,2-b]quinolin-10-yl)-2-methyl-3-oxo-6,9,12,15-tetraoxa-2-azaheptadecan-17-yl)carbamoyl)piperidin-1-yl)pyridazine-3-carboxamide (Compound 27)
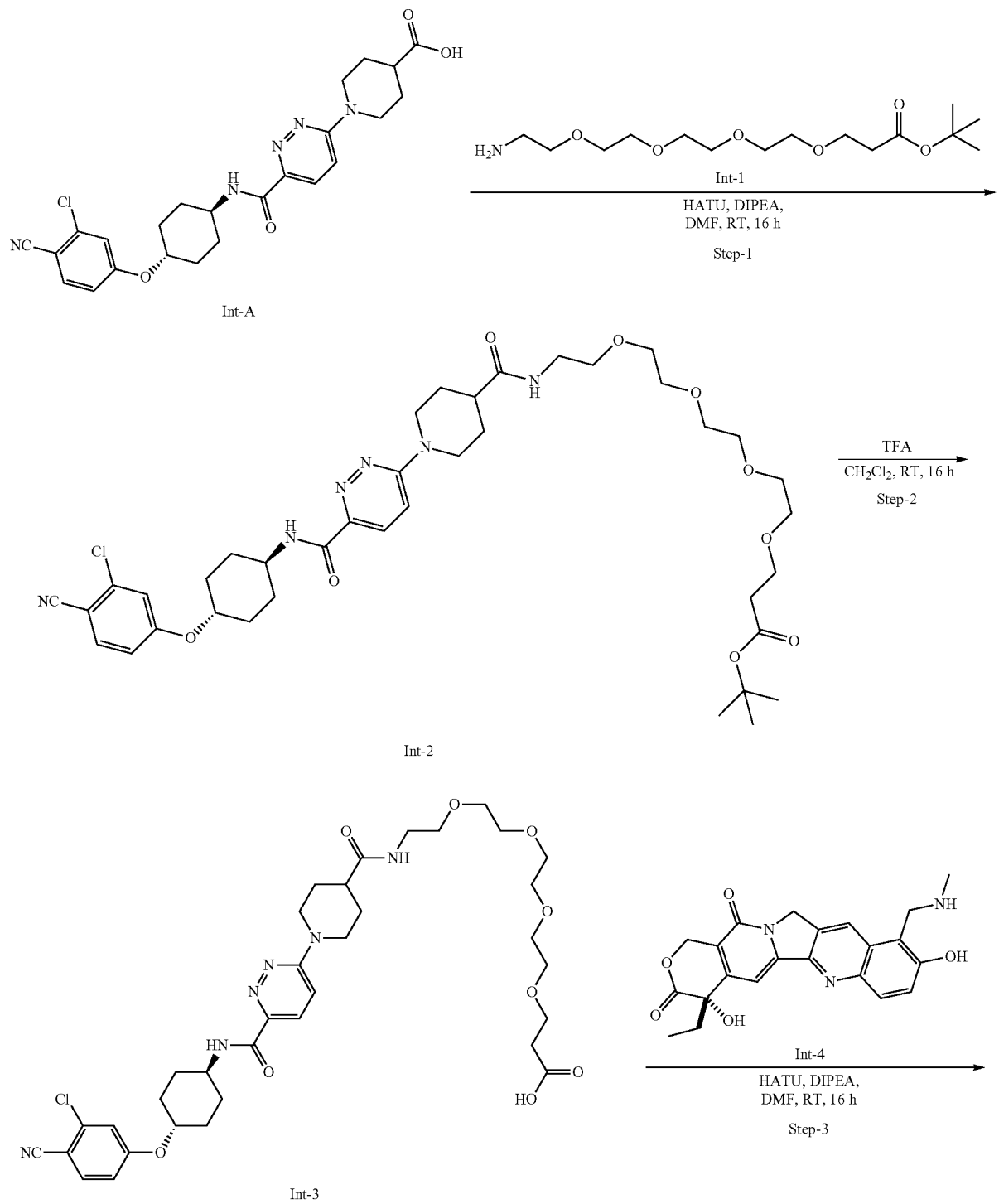

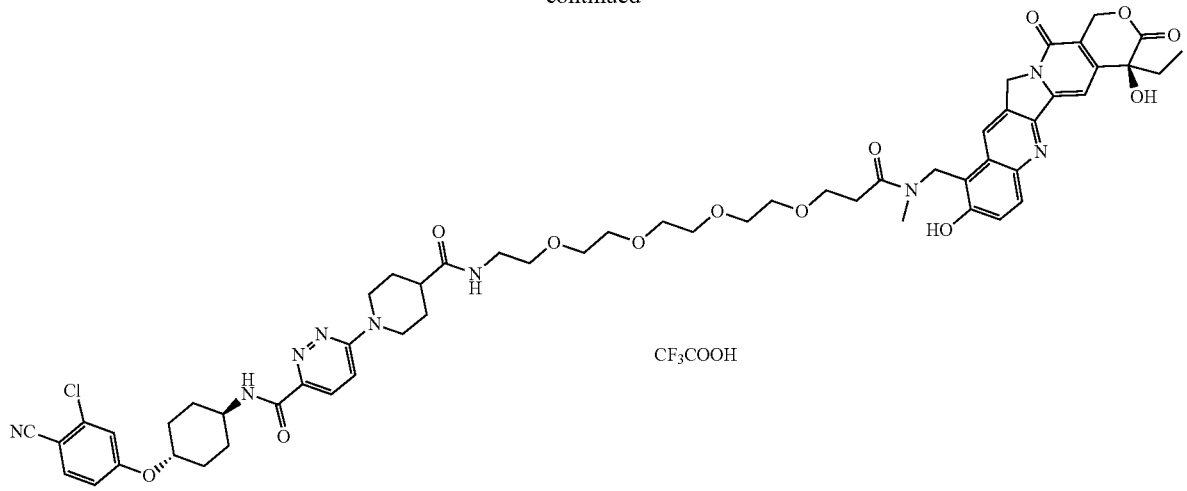

Step-1: Synthesis of tert-butyl 1-(1-(6-(((1r,4r)-4-(3-Chloro-4-cyanophenoxy)cyclohexyl)carbamoyl) pyridazin-3-yl)piperidin-4-yl)-1-oxo-5,8,11,14-tetraoxa-2-azaheptadecan-17-oate (Int-2)

To a stirred solution of 1-(6-(((1r,4r)-4-(3-chloro-4-cyanophenoxy)cyclohexyl) carbamoyl)pyridazin-3-yl)piperidine-4-carboxylic acid (Int-A, 600 mg, 1.2 mmol, 1.0 eq.) and tert-butyl 1-amino-3,6,9,12-tetraoxapentadecan-15-oate (Int-1, 400 mg, 1.2 mmol, 1.1 eq.) in DMF (4 mL) were added HATU (800 mg, 1.8 mmol, 1.5 eq.) and DIPEA (0.64 mL, 3.6 mmol, 3 eq.) at 0° C. Reaction mixture was stirred at RT for 16 h. Progress of the reaction was monitored by TLC. After completion of the reaction, the reaction mixture was washed with water (100 mL) and extracted with 10% methanol in DCM (2×100 mL). The combined organic extracts were washed with brine (500 mL), dried over anhydrous sodium sulfate, filtered and concentrated under vacuum to get crude compound. The crude compound was purified by Combiflash column by eluting with 10% methanol in DCM to afford Int-2 (860 mg, 88%). $^1$H NMR (400 MHz, DMSO-$d_6$) δ 8.60 (br d, J=7.82 Hz, 1H) 7.72-7.98 (m, 3H) 7.28-7.45 (m, 2H) 7.06-7.21 (m, 1H) 4.38-4.61 (m, 3H) 3.86 (br d, J=7.21 Hz, 1H) 3.58 (br t, J=5.50 Hz, 2H) 3.50 (br s, 12H) 3.40 (br d, J=4.65 Hz, 2H) 3.19 (br d, J=5.14 Hz, 2H) 3.04 (br t, J=11.98 Hz, 2H) 2.38-2.45 (m, 3H) 2.10 (br d, J=8.44 Hz, 2H) 1.90 (br d, J=9.17 Hz, 2H) 1.76 (br d, J=11.25 Hz, 2H) 1.46-1.69 (m, 6H) 1.38 (s, 9H). LCMS: 787.70; [M+H]$^+$.

Step-2: Synthesis of 1-(1-(6-(((1r,4r)-4-(3-Chloro-4-cyanophenoxy)cyclohexyl)carbamoyl)pyridazin-3-yl)piperidin-4-yl)-1-oxo-5,8,11,14-tetraoxa-2-azaheptadecan-17-oic Acid (Int-3)

To a stirred solution of tert-butyl 1-(1-(6-(((1r,4r)-4-(3-chloro-4-cyanophenoxy)cyclohexyl) carbamoyl) pyridazin-3-yl)piperidin-4-yl)-1-oxo-5,8,11,14-tetraoxa-2-azaheptadecan-17-oate (Int-2, 850 mg, 1.23 mmol, 1.0 eq.) in DCM (10 mL) under nitrogen atmosphere was added TFA (1.5 mL, 10 eq.) at 0° C. Warmed to room temperature and stirred for 16 h. Progress of the reaction was monitored by TLC. After completion of the reaction, solvents were evaporated under reduced pressure, washed with diethyl ether (20 mL) and dried under vacuum to afford Int-3 (600 mg, 76%). $^1$H NMR (400 MHz, DMSO-$d_6$) δ 8.59 (d, J=8.19 Hz, 1H) 7.76-7.96 (m, 3H) 7.30-7.45 (m, 2H) 7.13 (dd, J=8.80, 2.45 Hz, 1H) 4.36-4.61 (m, 4H) 3.77-3.93 (m, 1H) 3.60 (t, J=6.36 Hz, 2H) 3.45-3.53 (m, 11H) 3.40 (t, J=5.87 Hz, 2H) 3.19 (q, J=5.79 Hz, 2H) 3.05 t, J=11.68 Hz, 2H) 2.44-250 (m, 3H) 2.10 (br d, J=9.90 Hz, 2H) 1.90 (br d, J=10.51 Hz, 2H) 1.76 (br d, J=10.64 Hz, 2H) 1.45-1.69 (m, 6H) (1H exchangeable hydrogen was not seen in spectra). LCMS: 731.45 [M+H]$^+$.

Step-3: Synthesis of N-((1r,4r)-4-(3-Chloro-4-cyanophenoxy)cyclohexyl)-6-(4-((1-((S)-4-ethyl-4,9-dihydroxy-3,14-dioxo-3,4,12,14-tetrahydro-1H-pyrano[3',4':6,7]indolizino[1,2-b]quinolin-10-yl)-2-methyl-3-oxo-6,9,12,15-tetraoxa-2-azaheptadecan-17-yl)carbamoyl)piperidin-1-yl)pyridazine-3-carboxamide (27)

To a stirred solution of 1-(1-(6-(((1r,4r)-4-(3-chloro-4-cyanophenoxy)cyclohexyl) carbamoyl)pyridazin-3-yl)piperidin-4-yl)-1-oxo-5,8,11,14-tetraoxa-2-azaheptadecan-17-oic acid (Int-3, 300 mg, 0.41 mmol, 1.0 eq.) and (S)-4-ethyl-4,9-dihydroxy-10-((methylamino)methyl)-1,12-dihydro-14H-pyrano[3',4':6,7]indolizino[1,2-b]quinoline-3,14(4H)-dione (Int-4, 160 mg, 0.41 mmol, 1 eq.) in DMF (8 mL) were added HATU (230 mg, 0.61 mmol, 1.5 eq.) and DIPEA (0.2 mL, 1.23 mmol, 3 eq.) at 0° C. Reaction mixture was stirred at RT for 16 h. Progress of the reaction was monitored by TLC. After completion of the reaction, the reaction mixture was washed with water (100 mL) and extracted with ethyl acetate (2×100 mL). The combined organic extracts were washed with brine (500 mL), dried over anhydrous sodium sulfate, filtered and concentrated under vacuum to get crude compound. The crude compound was purified by prep. HPLC to afford the desired product (52 mg, 11%). $^1$H NMR (400 MHz, DMSO-$d_6$) δ 10.66 (s, 1H) 8.69 (s, 1H) 8.56 (d, J=8.13 Hz, 1H) 8.03 (d, J=9.26 Hz, 1H) 7.76-7.90 (m, 3H) 7.55 (d, J=9.26 Hz, 1H) 7.30-7.42 (m, 2H) 7.26 (s, 1H) 7.13 (dd, J=8.88, 2.38 Hz, 1H) 6.30-6.61 (m, 1H) 5.41 (s, 2H) 5.23 (s, 2H) 4.93-5.06 (m, 2H) 4.49-4.57 (m, 1H) 4.45 (br d, J=13.01 Hz, 2H) 3.85 (br d, J=8.00 Hz, 1H) 3.70 (t, J=6.57 Hz, 3H) 3.34-3.53 (m, 11H) 3.50 (s, 3H) 3.13-3.21 (m, 2H) 2.95-3.10 (m, 3H) 2.83 (s, 2H) 2.59 (t, J=6.57 Hz, 2H) 2.05-2.14 (m, 2H) 1.85-1.90 (m, 4H) 1.75 (br d, J=10.51 Hz, 2H) 1.47-1.66 (m, 6H) 0.87 (t, J=7.32 Hz, 3H). LCMS: 1120.80 [M+H]$^+$. HPLC purity 99.7%.

Example 24

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(2-(((5S,8R,9S,10S,13S,14S,17S)-10,13-dimethyl-3-oxohexadecahydro-1H-cyclopenta[a]phenanthren-17-yl)oxy)-N-methylacetamido)piperidine-1-carboxylate (Compound 20)

Preparation of 2-(((5S,8R,9S,10S,13S,14S,17S)-10,13-Dimethyl-3-oxohexadecahydro-1H-cyclopenta[a]phenanthren-17-yl)oxy)acetic acid (Int-A)

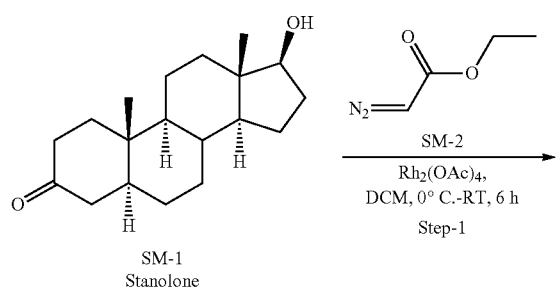

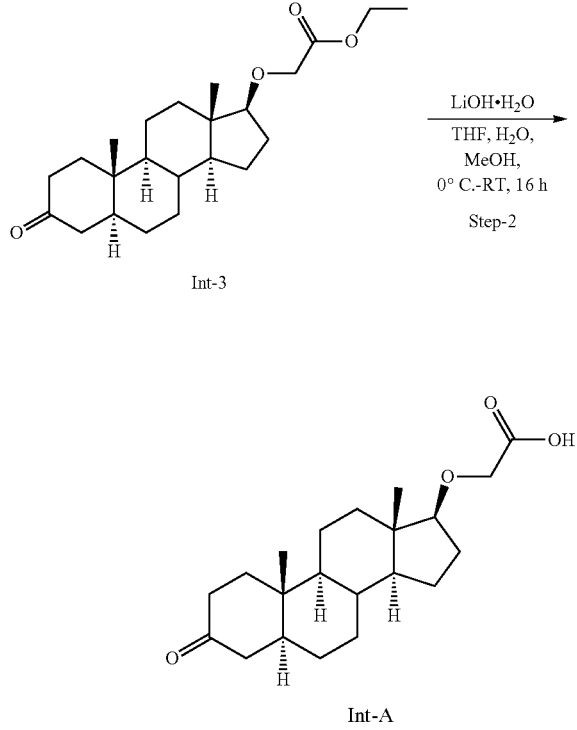

Step-1: Preparation of ethyl 2-(((5S,8R,9S,10S,13S,14S,17S)-10,13-Dimethyl-3-oxohexadecahydro-1H-cyclopenta[a]phenanthren-17-yl)oxy)acetate (Int-3)

A stirred solution of stanolone (SM-1, 2.0 g, 6.88 mmol, 1.0 eq.) in DCM (20 mL) were added Rhodium(II)acetate dimer (213 mg, 0.48 mmol, 0.07 eq.) followed by ethyl 2-diazoacetate (SM-2, 785 mg, 6.88 mmol, 1.0 eq.) dropwise at 0° C. Warmed to room temperature and stirred for 3 h. Progress of the reaction was monitored by TLC. After completion of the reaction, the reaction mixture was quenched with water (25 mL) and extracted with DCM (2×30 mL). The combined organic extracts were washed with brine (50 mL) and dried over anhydrous sodium sulphate, filtered and concentrated under vacuum to obtain crude compound. The crude compound obtained was purified by combiflash column chromatography by eluting with 18% ethyl acetate in n-heptane to afford Int-3 (1.25 g, 48%). $^1$H NMR (400 MHz, DMSO-$d_6$) δ 4.06-4.16 (m, 3H) 4.05 (s, 2H) 3.37 (t, J=8.31 Hz, 1H) 2.35-2.46 (m, 1H) 2.30 (t, J=14.43 Hz, 1H) 2.08 (dd, J=13.21, 1.96 Hz, 1H) 1.76-2.00 (m, 3H) 1.31-1.66 (m, 6H) 1.14-1.30 (m, 10H) 0.97 (s, 3H) 0.76-0.96 (m, 1H) 0.72 (s, 3H) 0.64-0.71 (m, 1H). LCMS: 377.41 [M+H]$^+$.

Step-2: Preparation of 2-(((5S,9S,10S,13S,14S,17S)-10,13-dimethyl-3-oxohexadecahydro-1H-cyclopenta[a]phenanthren-17-yl)oxy)acetic acid (Int-A)

A stirred solution of ethyl 2-(((5S,9S,10S,13S,14S,17S)-10,13-dimethyl-3-oxohexadecahydro-1H-cyclopenta[a]phenanthren-17-yl)oxy)acetate (Int-3, 1.2 g, 3.18 mmol, 1.0 eq.) in THF (10 mL), methanol (3 mL), and water (3 mL) was added lithium hydroxide monohydrate (1.07 g, 25.4 mmol, 8.0 eq.) at 0° C. The reaction mixture was allowed to warm up to room temperature and stirred for 16 h. Progress of the reaction was monitored by TLC. After completion of the reaction, the reaction mixture was diluted with water (25 mL) and extracted with ethyl acetate (2×20 mL). Aqueous layer was neutralized with aq. citric acid solution and extracted with 10% methanol in DCM (2×20 mL). The combined organic extract was washed with brine (50 mL) and dried over anhydrous sodium sulphate, filtered and concentrated under vacuum to afford Int-A (1.0 g, 90%). $^1$H NMR (400 MHz, DMSO-$d_6$) δ 12.46 (br s, 1H) 3.97 (s, 2H) 3.37 (t, J=8.31 Hz, 1H) 2.41 (td, J=14.67, 6.36 Hz, 1H) 2.30 (t, J=14.43 Hz, 1H) 2.08 (dd, J=13.21, 1.96 Hz, 1H) 1.77-1.99 (m, 4H) 1.61 (dd, J=12.96, 3.18 Hz, 1H) 1.31-1.56 (m, 6H) 1.11-1.32 (m, 6H) 0.78-0.97 (m, 5H) 0.72 (s, 3H). LCMS: 347.44 [M−H]$^-$.

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(2-(((5S,8R,9S,10S,13S,14S,17S)-10,13-dimethyl-3-oxohexadecahydro-1H-cyclopenta[a]phenanthren-17-yl)oxy)-N-methylacetamido)piperidine-1-carboxylate
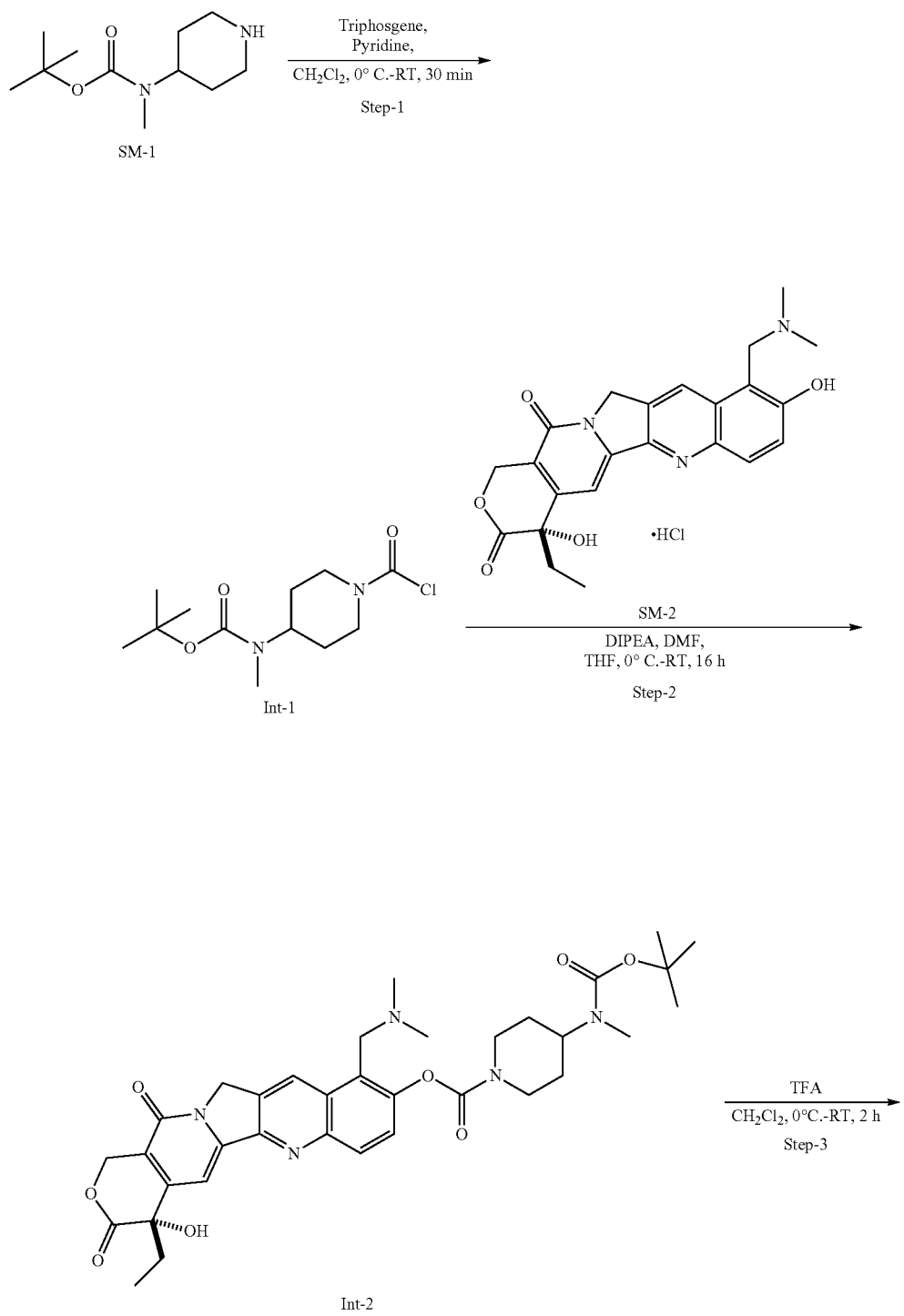

-continued

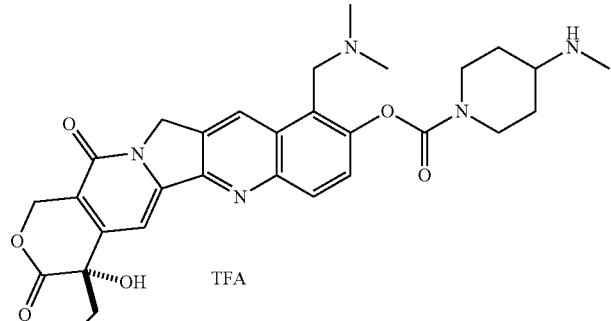

TFA

Int-3

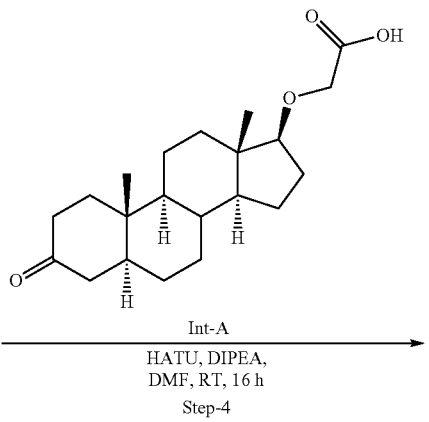

Int-A
→
HATU, DIPEA,
DMF, RT, 16 h
Step-4

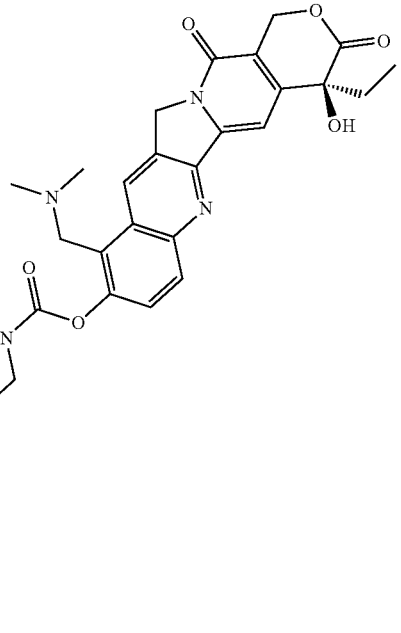

Step-1: Preparation of tert-Butyl (1-(chlorocarbonyl)piperidin-4-yl)(methyl)carbamate (Int-1)

To a stirred solution of tert-butyl methyl(piperidin-4-yl)carbamate (SM-1, 1.6 g, 7.47 mmol, 1.0 eq.) in DCM (15 mL) were added pyridine (1 mL, 11.2 mmol, 1.5 eq.) and triphosgene solution (3 mL in DCM) dropwise at 0° C. The reaction mixture was allowed to warm up to room temperature and stirred for 30 min. Progress of the reaction was monitored by TLC (non-polar spot was observed). After completion of the reaction, the reaction mixture was poured into ice cold water (40 mL) and extracted with DCM (2×25 mL). The combined organic extract was washed with brine (50 mL) and dried over anhydrous sodium sulphate, filtered and concentrated under vacuum to afford Int-1 (2.05 g, crude) which was used in next step without further purification. $^1$H NMR (400 MHz, CDCl$_3$) δ 4.30-4.52 (m, 2H) 4.11-4.30 (m, 1H) 3.11 (t, J=12.76 Hz, 1H) 2.90 (t, J=12.26 Hz, 1H) 2.73 (s, 3H) 1.56-1.86 (m, 4H) 1.47 (s, 9H).

Step-2: Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-((tert-butoxycarbonyl)(methyl)amino)piperidine-1-carboxylate (Int-2)

To a stirred solution of tert-butyl (1-(chlorocarbonyl)piperidin-4-yl)(methyl)carbamate (Int-1, 2.05 g, 7.42 mmol, 1.0 eq.) and (S)-10-((dimethylamino)methyl)-4-ethyl-4,9-dihydroxy-1,12-dihydro-14H-pyrano[3',4':6,7]indolizino[1,2-b]quinoline-3,14(4H)-dione (SM-2, 1.72 g, 3.62 mmol, 0.5 eq.), in DMF (15 mL) and THF (15 mL) was added DIPEA (6 mL, 36.2 mmol, 5 eq.) at 0° C. The reaction mixture allowed to warm up to room temperature and stirred for 16 h. Progress of the reaction was monitored by TLC. After completion of the reaction, the reaction mixture was quenched with ice cold water (30 mL) and extracted with ethyl acetate (2×30 mL). The combined organic extracts were washed with brine (50 mL) and dried over anhydrous sodium sulphate, filtered and concentrated under vacuum to obtained crude compound. The crude compound obtained was purified by combiflash column chromatography by eluting with 7% methanol in dichloromethane to afford Int-2 (1.6 g, 69%). $^1$H NMR (400 MHz, DMSO-$d_6$) δ 8.94 (s, 1H) 8.11 (d, J=9.17 Hz, 1H) 7.64 (d, J=9.17 Hz, 1H) 7.33 (s, 1H) 6.53 (br s, 1H) 5.75 (s, 2H) 5.43 (s, 2H) 5.31 (s, 2H) 4.04-4.41 (m, 2H) 2.91-3.43 (m, 2H) 2.74 (s, 3H) 2.69-2.72 (m, 1H) 2.49 (s, 3H) 2.21 (s, 3H) 1.81-1.97 (m, 2H) 1.58-1.78 (m, 2H) 1.42 (s, 9H) 1.25-1.39 (m, 2H) 0.81-0.95 (m, 3H). LCMS: 662.5 [M+H]$^+$.

Step-3: Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(methylamino)piperidine-1-carboxylate TFA salt (Int-3)

To a stirred solution of (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-((tert-butoxycarbonyl)(methyl) amino)piperidine-1-carboxylate (Int-2, 1.6 g, 2.4 mmol, 1.0 eq.) in DCM (18 mL) was added TFA (2 mL) at 0° C. The reaction mixture was allowed to stir at room temperature for 2 h. Progress of the reaction was monitored by TLC. After completion of the reaction, solvents were evaporated under reduced pressure to get the crude compound which was triturated with ethyl acetate (30 mL), filtered the solid and dried under vacuum to afford of Int-3 (900 mg, 69%). $^1$H NMR (400 MHz, DMSO-$d_6$) δ 9.98 (br s, 1H) 9.12 (s, 1H) 8.76 (br s 2H) 8.34 (d, J=9.29 Hz, 1H) 7.81 (d, J=9.29 Hz, 1H) 7.37 (s, 1H) 6.54 (br s, 1H) 5.40 (s, 2H) 5.34 (s, 2H) 4.79 (s, 2H) 4.15-4.21 (m, 2H) 2.90-3.21 (m, 2H) 2.89 (br s, 6H) 2.64 (t, J=5.14 Hz, 4H) 2.12 (d, J=10.76 Hz, 2H) 1.82-1.94 (m, 4H) 0.89 (t, J=7.09 Hz, 3H). LCMS: 562.2 [M+H]$^+$.

Step-4: Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(2-(((5S,8R,9S,10S,13S,14S,17S)-10,13-dimethyl-3-oxohexadecahydro-1H-cyclopenta[a]phenanthren-17-yl)oxy)-N-methylacetamido)piperidine-1-carboxylate To a stirred solution of 2-(((5S,9S,10S,13S,14S,17S)-10,13-dimethyl-3-oxohexadecahydro-1H-cyclopenta[a]phenanthren-17-yl)oxy)acetic acid (Int-A, 300 mg, 0.862 mmol, 1.0 eq.) and (S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(methylamino)piperidine-1-carboxylate TFA salt (Int-3, 725 mg, 1.29 mmol, 1.5 eq.) in DMF (20 mL) were added NaHCO$_3$ (362 mg, 4.31 mmol, 5.0 eq.) and HATU (655 mg, 1.72 mmol, 2 eq.) at room temperature and stirred for 16 h. Progress of the reaction was monitored by TLC. After completion of the reaction, the reaction mixture was quenched with ice cold water (20 mL), filtered the solid and washed with excess water (50 mL) and dried under vacuum to obtain crude compound. The crude compound was purified by combiflash column chromatography to afford the desired product (155.2 mg, 20%). $^1$H NMR (400 MHz, DMSO-$d_6$) δ 9.58-9.81 (m, 1H) 9.10 (s, 1H) 8.34 (d, J=9.38 Hz, 1H) 7.86 (d, J=9.13 Hz, 1H) 7.38 (s, 1H) 6.55 (br s, 1H) 5.45 (s, 2H) 5.35 (s, 2H) 4.84 (br s, 2H) 4.32-4.56 (m, 2H) 4.08-4.22 (m, 3H) 3.89-4.06 (m, 1H) 3.36 (t, J=8.63 Hz, 2H) 3.13-3.28 (m, 1H) 2.97-3.11 (m, 1H) 2.89 (br s, 8H) 2.76 (s, 1H) 2.42 (td, J=14.66, 6.57 Hz, 1H) 2.25-2.35 (m, 1H) 2.03-2.16 (m, 1H) 1.79-1.99 (m, 8H) 1.71-1.79 (m, 1H) 1.50-1.67 (m, 4H) 1.33-1.49 (m, 3H) 1.14-1.33 (m, 6H) 0.98 (s, 3H) 0.89 (t, J=7.32 Hz, 4H) 0.75 (br d, J=5.88 Hz, 3H). LCMS: 892.8 [M+H]$^+$. HPLC Purity: 99.7%.

Example 25

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 3-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)-3,8-diazabicyclo[3.2.1]octane-8-carboxylate (Compound 22)

Preparation (8S,11R,13S,14S,17R)-17-Acetyl-13-methyl-11-(4-(methyl(7-oxoheptyl)amino)phenyl)-3-oxo-2,3,6,7,8,11,12,13,14,15,16,17-dodecahydro-1H-cyclopenta[a]phenanthren-17-yl Acetate (Int-C)

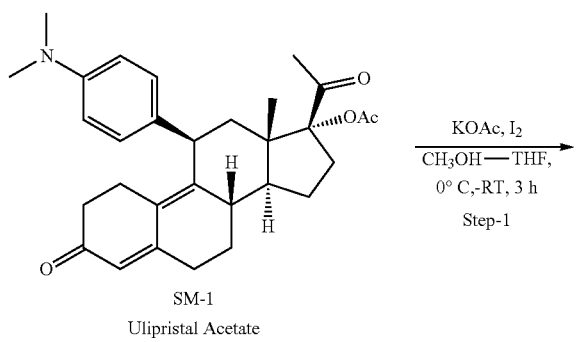

SM-1
Ulipristal Acetate

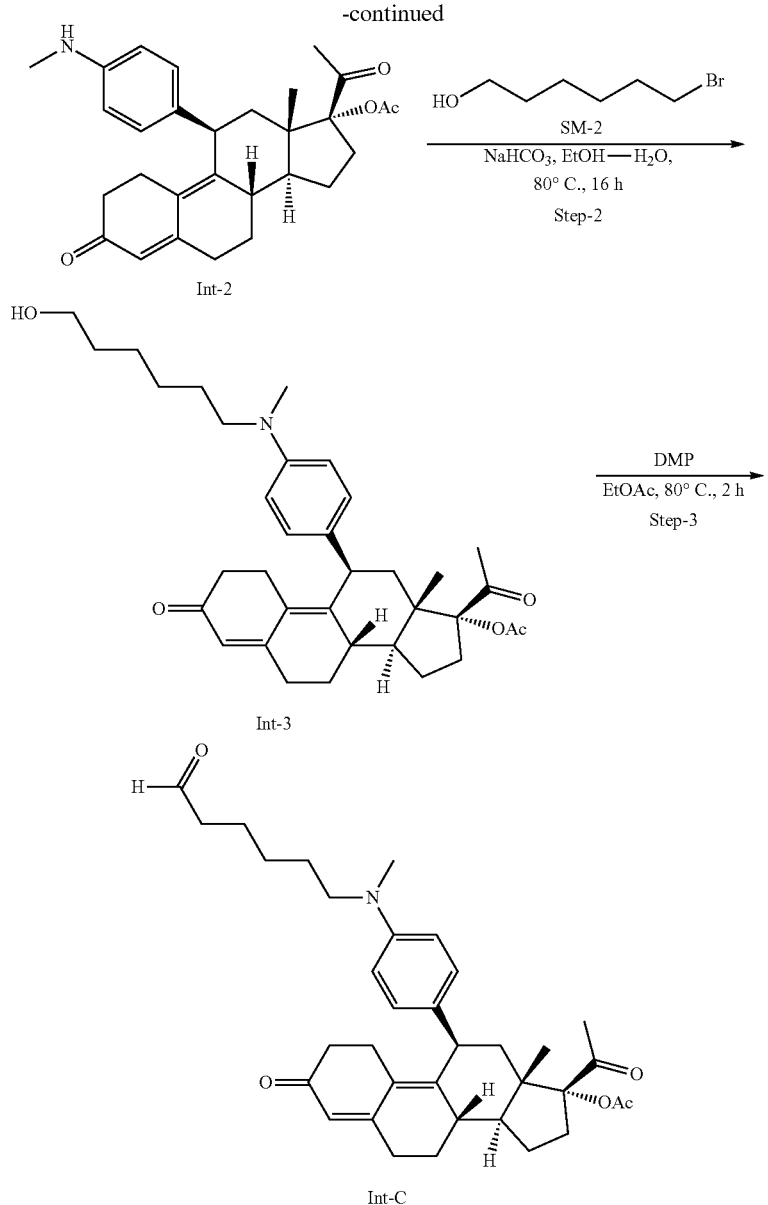

Step-1: Preparation of (8S,11R,13S,14S,17R)-17-Acetyl-13-methyl-11-(4-(methylamino)phenyl)-3-oxo-2,3,6,7,8,11,12,13,14,15,16,17-dodecahydro-1H-cyclopenta[a]phenanthren-17-yl Acetate (Int-2)

To a stirred solution of SM-1 (10 g, 21 mmol, 1.0 eq.) in methanol (150 mL) and THF (150 mL) were added KOAc (20.6 g, 210 mmol, 10 eq.) and iodine (13.1 g, 105 mmol, 5 eq.) at 0° C. The reaction mixture was allowed to warm up to room temperature and stirred for 3 h. Progress of the reaction was monitored by TLC. After completion of the reaction, the reaction mixture was quenched with sodium thiosulfate ($Na_2S_2O_3$) solution (50 g in 30 mL water) and extracted with ethyl acetate (2×200 mL). The combined organic extracts were washed with brine (100 mL) and dried over anhydrous sodium sulphate, filtered and concentrated under vacuum to afford Int-2 (8.0 g, 82%) which was used in next step without further purification. $^1$H NMR (400 MHz, DMSO-$d_6$) δ 11.91 (br s, 1H) 6.91 (d, J=8.31 Hz, 2H) 6.44 (d, J=8.31 Hz, 2H) 5.67 (s, 1H) 4.37 (m, 1H) 2.75 (s, 2H) 2.61 (d, J=4.40 Hz, 3H) 2.30-2.40 (m, 1H) 2.07-2.16 (s, 5H) 1.99 (s, 6H) 1.63-1.77 (m, 2H) 1.21-1.45 (m, 5H) 0.86 (t, J=6.60 Hz, 1H) 0.16-0.28 (m, 3H). LCMS: 462.28 [M+H]$^+$.

Step-2: Preparation of (8S,11R,13S,14S,17R)-17-Acetyl-11-(4-(((6-hydroxyhexyl)(methyl)amino)phenyl)-13-methyl-3-oxo-2,3,6,7,8,11,12,13,14,15,16,17-dodecahydro-1H-cyclopenta[a]phenanthren-17-yl Acetate (Int-3)

To a solution of (8S,11R,13S,14S,17R)-17-acetyl-13-methyl-11-(4-(methylamino)phenyl)-3-oxo-2,3,6,7,8,11,12,13,14,15,16,17-dodecahydro-1H-cyclopenta[a]phenanthren-17-yl acetate (Int-2, 4 g, 8.67 mmol, 1.0 eq.) and 6-bromohexan-1-ol (SM-2, 7.81 g, 43.38 mmol, 5 eq.) in ethanol (40 mL) and water (40 mL) was added NaHCO$_3$ (7.37 g, 86.76 mmol, 10 eq.) at room temperature. The reaction mixture was heated to 80° C. and stirred for 16 h. Progress of the reaction was monitored by TLC. After completion of the reaction, the reaction mixture was filtered through a pad of celite bed and washed with ethyl acetate (40 mL). Filtrate was concentrated under reduced pressure, diluted with water (120 mL) and extracted with ethyl acetate (2×200 mL). The combined organic extracts were washed with brine (100 mL) and dried over anhydrous sodium sulphate, filtered and concentrated under vacuum to obtained crude compound. The crude compound obtained was purified by combiflash chromatography by eluting with 70% ethyl acetate in heptane to afford Int-3 (2.6 g, 53%). $^1$H NMR (400 MHz, DMSO-d$_6$) δ 6.98 (d, J=7.89 Hz, 2H) 6.58 (d, J=7.89 Hz, 2H) 5.67 (br s, 1H) 4.24-4.51 (m, 2H) 3.36 (d, J=5.70 Hz, 2H) 3.23 (d, J=6.58 Hz, 2H) 2.69-2.86 (m, 4H) 2.55 (s, 3H) 2.29-2.44 (m, 1H) 2.05-2.26 (m, 5H) 1.87-2.04 (m, 6H) 1.63-1.77 (m, 2H) 1.34-1.49 (m, 6H) 1.27 (br s, 6H) 0.23 (br s, 3H). LCMS: 562.40 [M+H]$^+$.

Step-3: Preparation of (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate (Int-C)

To a stirred solution of Int-3 (500 mg, 0.891 mmol, 1 eq.) in ethyl acetate (40 mL), was added Dess-Martin periodinane (DMP) (1.1 g, 2.67 mmol, 3 eq.) portionwise at 0° C. The reaction mixture was heated to 80° C. and stirred for 2 h. Progress of the reaction was monitored by TLC. After completion of the reaction, the reaction mixture was quenched with 50% aqueous Na$_2$S$_2$O$_3$ solution (10 mL), sat. NaHCO$_3$ solution (15 mL) and extracted with ethyl acetate (2×25 mL). The combined organic extracts were washed with brine (100 mL) and dried over anhydrous sodium sulphate, filtered and concentrated under vacuum to afford Int-C (450 mg, 92%). $^1$H NMR (400 MHz, DMSO-d$_6$) δ 9.64 (s, 1H) 6.98 (d, J=8.31 Hz, 2H) 6.58 (d, J=8.80 Hz, 2H), 5.67 (s, 1H) 4.39 (d, J=5.87 Hz, 1H) 3.22 (t, J=6.60 Hz, 2H) 2.55-2.80 (m, 5H) 2.51-2.54 (m, 2H) 2.40 (t, J=7.09 Hz, 2H) 1.96-2.15 (m, 12H) 1.56-1.69 (m, 2H) 1.11-1.59 (m, 10H) 0.23 (s, 3H). LCMS: 560.4 [M+H]$^+$.

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 3-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)-3,8-diazabicyclo[3.2.1]octane-8-carboxylate

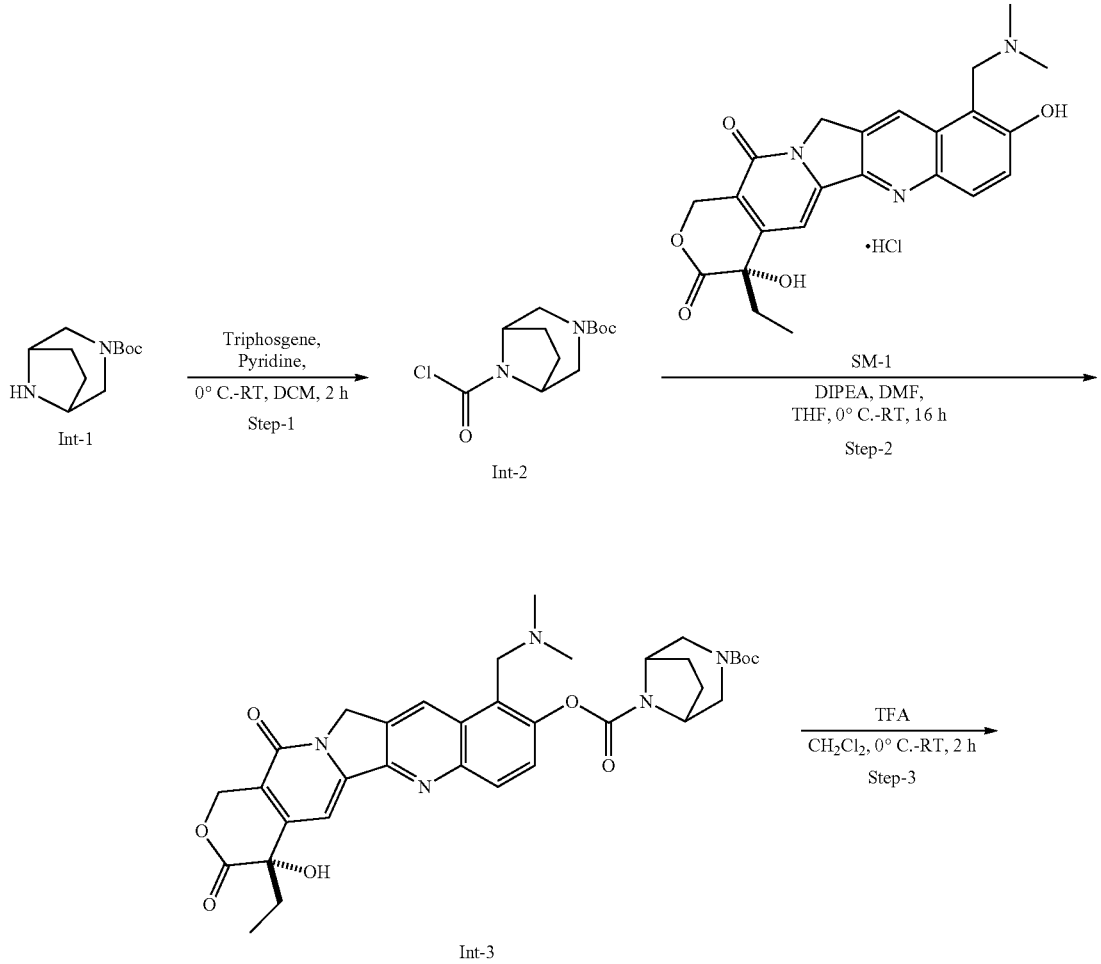

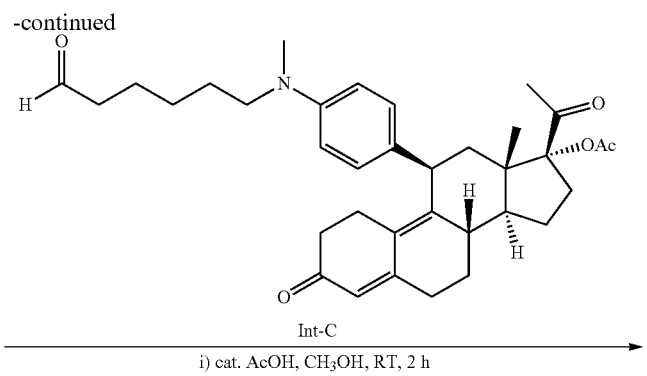

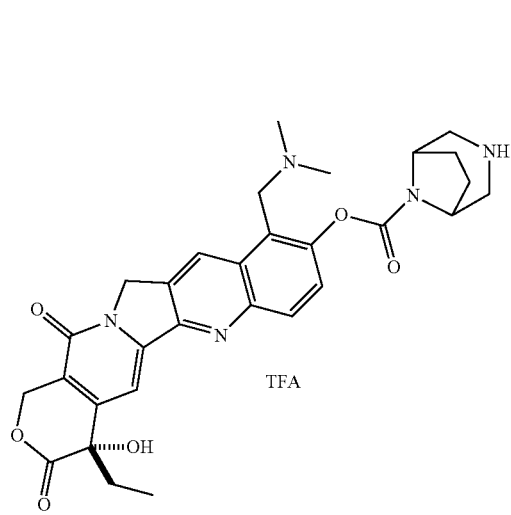

Int-4

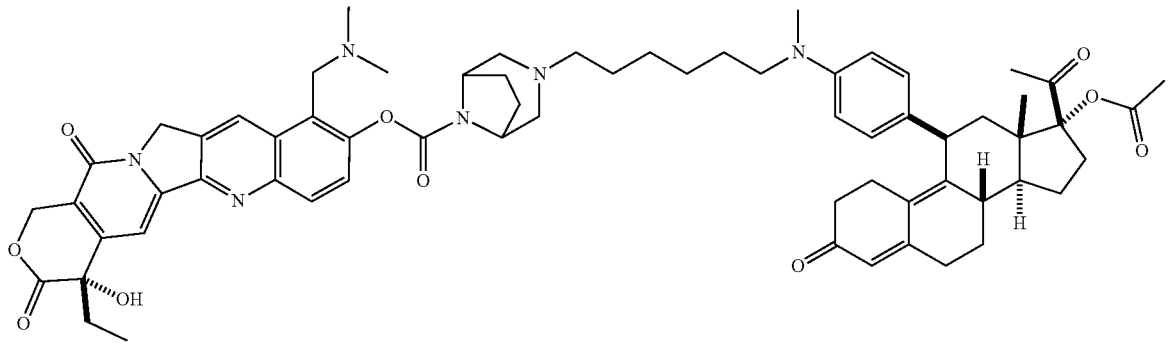

Step-1: Preparation of tert-Butyl 8-(Chlorocarbonyl)-3,8-diazabicyclo[3.2.1]octane-3-carboxylate (Int-2)

To a stirred solution of tert-butyl 3,8-diazabicyclo[3.2.1]octane-3-carboxylate (Int-1, 2.0 g, 9.34 mmol, 1.0 eq.) in DCM (25 mL) were added pyridine (1.1 mL, 14.01 mmol, 1.5 eq.) and triphosgene (0.83 g, 2.8 mmol, 0.3 eq.) solution in DCM (5 mL) drop wise over a period of 10 min at 0° C. The reaction mixture was allowed to warm up to room temperature and stirred for 2 h. Progress of the reaction was monitored by TLC (non-polar spot was observed). After completion of the reaction, the reaction mixture was poured into ice cold water (40 mL) and extracted with DCM (2×25 mL). The combined organic extracts were washed with brine (100 mL) and dried over anhydrous sodium sulphate, filtered and concentrated under vacuum to afford Int-2 (2.0 g, crude) which was used in next step without further purification. $^1$H NMR (400 MHz, DMSO-$d_6$) δ 4.29-4.48 (m, 2H) 3.67-3.95 (m, 2H) 2.86-3.22 (m, 2H) 1.89-2.06 (m, 2H) 1.56-1.65 (m, 2H) 1.31-1.51 (m, 9H).

Step-2: Preparation of 3-(tert-Butyl) 8-((S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl) 3,8-diazabicyclo[3.2.1]octane-3,8-dicarboxylate (Int-3)

To a stirred solution of tert-butyl 8-(chlorocarbonyl)-3,8-diazabicyclo[3.2.1]octane-3-carboxylate (Int-2, 2.0 g, 7.24 mmol, 1 eq.) and (S)-10-((dimethylamino) methyl)-4-ethyl-4,9-dihydroxy-1,12-dihydro-14H-pyrano[3',4':6,7]indolizino[1,2-b]quinoline-3,14(4H)-dione HCl salt (SM-1, 1.71 g, 3.6 mmol, 0.5 eq.) in THF (15 mL) and DMF (15 mL) was added DIPEA (6.3 mL, 36.23 mmol, 5 eq.) at 0° C. The reaction mixture was allowed to warm up to room temperature and stirred for 16 h. Progress of the reaction was monitored by TLC. After completion of the reaction, the reaction mixture was quenched with water (50 mL), filtered the solid and dried under reduced pressure to get crude compound. The crude compound was purified by combiflash column chromatography by eluting with 8% methanol in DCM to afford Int-3 (550 mg, 23%). $^1$H NMR (400 MHz, DMSO-$d_6$) δ 8.96 (s, 1H) 8.12 (d, J=9.29 Hz, 1H) 7.70 (d, J=8.80 Hz, 1H) 7.34 (s, 1H) 6.53 (s, 1H) 5.43 (s, 2H) 5.32 (s, 2H) 4.55 (br s, 1H) 4.29 (br s, 1H) 3.72-3.78 (m, 3H) 2.20 (s, 5H) 1.93-2.11 (m, 2H) 1.80-1.95 (m, 2H) 1.71 (d, J=7.34 Hz, 2H) 1.44 (s, 9H) 1.27-1.37 (m, 2H) 1.23 (s, 2H) 0.89 (t, J=7.09 Hz, 3H). LCMS: 660.25 [M+H]$^+$.

Step-3: Preparation of (S)-10-((dimethylamino) methyl)-4-ethyl-4-hydroxy-3,14-dioxo-3,4,12,14-tetrahydro-1H-pyrano[3',4':6,7]indolizino[1,2-b]quinolin-9-yl3,8-diazabicyclo[3.2.1]octane-8-carboxylate TFA salt (Int-4)

To a stirred solution of 3-(tert-butyl) 8-((S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl)3,8-diazabicyclo[3.2.1]octane-3,8-dicarboxylate (Int-3, 550 mg, 0.834 mmol, 1.0 eq.) in DCM (20 mL) was added TFA (1 mL, 8.34 mmol, 10 eq.) at 0° C. The reaction mixture was allowed to warm up to room temperature and stirred for 2 h. Progress of the reaction was monitored by TLC. After completion of the reaction, solvents were evaporated under reduced pressure to get crude compound, the crude compound was triturated with ethyl acetate (25 mL), filtered the solid and dried under vacuum to afford Int-4 (530 mg, 94%). $^1$H NMR (400 MHz, DMSO-$d_6$) δ 10.03 (br s, 1H) 9.56 (br s, 1H) 9.13 (s, 1H) 9.01 (br s, 1H) 8.36 (d, J=9.29 Hz, 1H) 7.97 (d, J=9.29 Hz, 1H) 7.38 (s, 1H) 6.57 (br s, 1H) 5.45 (s, 2H) 5.34 (s, 2H) 4.70-4.96 (m, 2H) 4.45 (br s, 1H) 3.30 (br s, 6H) 2.88 (br s, 5H) 2.05-2.18 (m, 3H) 1.89-1.92 (m 3H) 0.89 (t, J=7.34 Hz, 3H). LCMS: 560.45 [M+H]$^+$.

Step-4: Preparation of (S)-10-((Dimethylamino) methyl)-4-ethyl-4-hydroxy-3,14-dioxo-3,4,12,14-tetrahydro-1H-pyrano[3',4':6,7]indolizino[1,2-b] quinolin-9-yl 3-(6-((4-((8S,11R,13S,14S,17R)-17-acetoxy-17-acetyl-13-methyl-3-oxo-2,3,6,7,8,11,12, 13,14,15,16,17-dodecahydro-1H-cyclopenta[a] phenanthren-11-yl)phenyl)(methyl)amino)hexyl)-3, 8-diazabicyclo[3.2.1]octane-8-carboxylate A stirred solution of common (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate (Int-C, 398 mg, 0.713 mmol, 1 eq.) and (S)-10-((dimethylamino)methyl)-4-ethyl-4-hydroxy-3,14-dioxo-3,4,12,14-tetrahydro-1H-pyrano[3',4':6,7] indolizino[1,2-b]quinolin-9-yl 3,8-diazabicyclo[3.2.1]octane-8-carboxylate (Int-4, 400 mg, 0.713 mmol, 1 eq.) in methanol (30 mL) and 1,2-dichloroethane (8 mL) was added catalytic amount of glacial acetic acid (0.1 mL) at room temperature and stirred for 2 h. To this reaction mixture was added NaCNBH$_3$ (89 mg, 1.42 mmol, 2 eq.) at 0° C. The reaction mixture was allowed to warm up to room temperature and stirred for 16 h. Progress of the reaction was monitored by TLC. After completion of the reaction, solvents were evaporated under reduced pressure, quenched with ice cold water (20 mL) and extracted with 10% methanol in DCM (2×25 mL). The combined organic extracts were washed with brine (100 mL) and dried over anhydrous sodium sulphate, filtered and concentrated under vacuum to obtained crude compound. The crude compound obtained was purified by combiflash column chromatography by eluting with 8-10% methanol in DCM to afford the desired product (41.8 mg, 5%). $^1$H NMR (400 MHz, DMSO-$d_6$) δ 8.95 (s, 1H) 8.11 (d, J=9.26 Hz, 1H) 7.63 (d, J=9.26 Hz, 1H) 7.34 (s, 1H) 6.98 (d, J=8.63 Hz, 2H) 6.59 (d, J=8.75 Hz, 2H) 6.51 (s, 1H) 5.67 (s, 1H) 5.43 (s, 2H) 5.32 (s, 2H) 4.46 (br s, 1H) 4.39 (d, J=6.13 Hz, 1H) 4.21 (d, J=1.50 Hz, 1H) 3.79 (s, 2H) 3.18-3.31 (m, 2H) 2.79-2.85 (m, 3H) 2.73 (d, J=11.51 Hz, 2H) 2.65-2.71 (m, 3H) 2.52-2.57 (m, 3H) 2.42 (d, J=10.88 Hz, 1H) 2.28-2.39 (m, 4H) 2.20 (s, 6H) 2.15 (d, J=14.01 Hz, 3H) 2.06-2.11 (m, 4H) 2.00 (s, 4H) 1.83-1.93 (m, 6H) 1.62-1.77 (m, 3H) 1.37-1.53 (m, 6H) 1.20-1.36 (m, 6H) 0.81-0.94 (m, 3H). LCMS: 1103.04 [M+H]$^+$. HPLC Purity: 51.2%.

Example 26

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl (2S,5R)-4-(6-((4-((8S,11R,13S,14S,17R)-17-acetoxy-17-acetyl-13-methyl-3-oxo-2,3,6,7,8,11,12,13, 14,15,16,17-dodecahydro-1H-cyclopenta[a] phenanthren-11-yl)phenyl)(methyl)amino)hexyl)-2, 5-dimethylpiperazine-1-carboxylate (Compound 23)

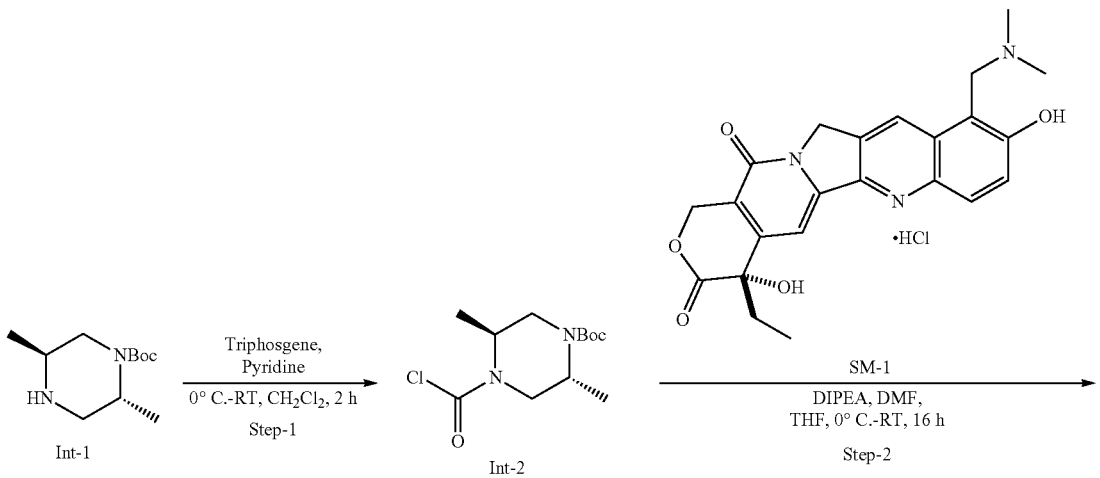

265

266

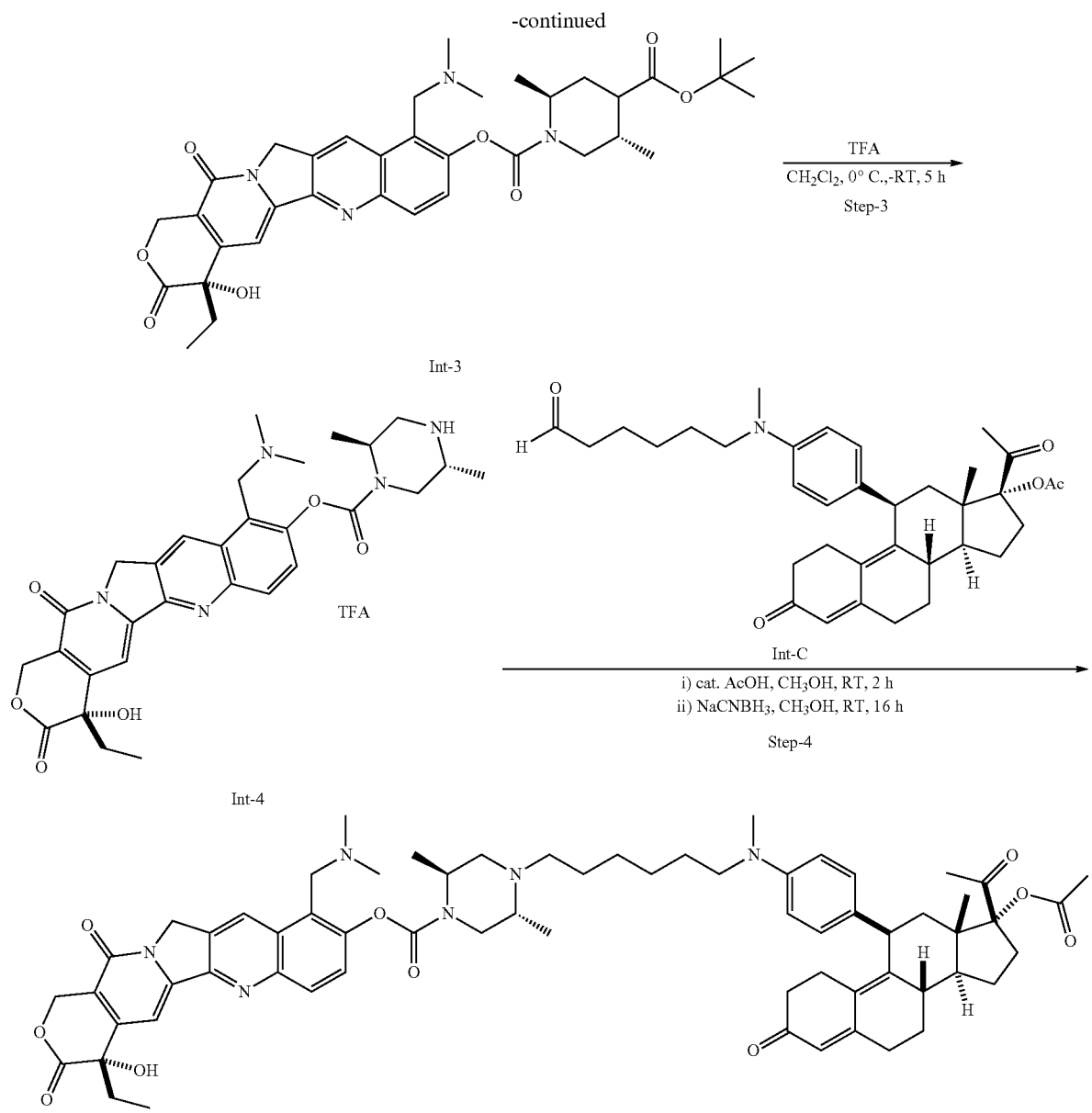

Step-1: Preparation of tert-Butyl (2R,5S)-4-(Chlorocarbonyl)-2,5-dimethylpiperazine-1-carboxylate (Int-2)

To a stirred solution of tert-butyl (2R,5S)-2,5-dimethylpiperazine-1-carboxylate (Int-1, 2.0 g, 9.34 mmol, 1.0 eq.) in DCM (25 mL) were added pyridine (1.1 mL, 13.99 mmol, 1.5 eq.) triphosgene (0.83 g, 2.79 mmol, 0.3 eq.) solution in DCM (5 mL) drop wise over a period of 10 min at 0° C. The reaction mixture was allowed to warm up to room temperature and stirred for 2 h. Progress of the reaction was monitored by TLC (non-polar spot was observed). After completion of the reaction, the reaction mixture was poured into ice cold water (40 mL) and extracted with DCM (2×25 mL). The combined organic extracts were washed with brine (100 mL) and dried over anhydrous sodium sulphate, filtered and concentrated under vacuum to afford Int-2 (2.57 g, crude) which was used in next step without further purification. $^1$H NMR (400 MHz, DMSO-$d_6$) δ 4.09-4.53 (m, 2H) 3.45-3.69 (m, 2H) 3.07-3.42 (m, 2H) 1.41 (s, 9H) 0.99-1.24 (m, 6H).

Step-2: Preparation of 1-(tert-Butyl) 4-((S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl) (2R,5S)-2,5-dimethylpiperazine-1,4-dicarboxylate (Int-3)

To a solution of tert-butyl (2R,5S)-4-(chlorocarbonyl)-2,5-dimethylpiperazine-1-carboxylate (Int-2, 2.57 g, 9.31 mmol, 1 eq.) and (S)-10-((dimethylamino)methyl)-4-ethyl-4,9-dihydroxy-1,12-dihydro-14H-pyrano[3',4':6,7]indolizino[1,2-b]quinoline-3,14(4H)-dione HCl salt (SM-1, 2.21 g, 4.65 mmol, 0.5 eq.) in THF (20 mL) and DMF (20 mL) was added DIPEA (8.1 mL, 46.5 mmol, 5 eq.) at 0° C. The reaction mixture was allowed to warm up to room temperature and stirred for 16 h. Progress of the reaction was monitored by TLC. After completion of the reaction, the reaction mixture was quenched with water (40 mL) and extracted with ethyl acetate (2×25 mL). The combined organic extracts were washed with brine (100 mL) and dried over anhydrous sodium sulphate, filtered and concentrated under vacuum to obtained crude compound. The crude compound obtained was purified by combiflash column chromatography by eluting with 5% methanol in DCM to afford Int-3 (1.4 g, 22%). $^1$H NMR (400 MHz, DMSO-$d_6$) δ 8.95 (br s, 1H) 8.12 (d, J=9.29 Hz, 1H) 7.70 (d, J=8.80 Hz, 1H) 7.33 (s, 1H) 6.53 (s, 1H) 5.43 (s, 2H) 5.31 (s, 2H) 4.12-4.61 (m, 3H) 3.60-4.09 (m, 5H) 2.20 (d, J=6.36 Hz, 6H) 1.80-1.96 (m, 2H) 1.44 (s, 9H) 1.25-1.44 (m, 3H) 1.18 (d, J=6.85 Hz, 3H) 0.78-0.91 (m, 3H). LCMS: 662.2 [M+H]$^+$.

Step-3: Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl (2S,5R)-2,5-dimethylpiperazine-1-carboxylate TFA salt (Int-4)

To a stirred solution of 1-(tert-butyl) 4-((S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl) (2R,5S)-2,5-dimethylpiperazine-1,4-dicarboxylate (Int-3, 1.4 g, 2.11 mmol, 1.0 eq.) in DCM (15 mL) was added TFA (1.2 mL, 21.18 mmol, 10 eq.) at 0° C. The reaction mixture was allowed to warm up to room temperature and stirred for 5 h. Progress of the reaction was monitored by TLC. After completion of the reaction, solvents were evaporated under reduced pressure to get crude compound, the crude compound was triturated with ethyl acetate (25 mL), filtered the solid and dried under vacuum to afford Int-4 (1.01 g, 71%). $^1$H NMR (400 MHz, DMSO-$d_6$) δ 10.00 (br s, 1H) 9.11 (br s, 3H) 8.41 (d, J=9.29 Hz, 1H) 7.84 (d, J=8.80 Hz, 1H) 7.37 (s, 1H) 6.57 (br s, 1H) 5.45 (s, 2H) 5.34 (s, 2H) 4.83 (br s, 1H) 4.40-4.65 (m, 1H) 3.65-4.09 (m, 4H) 3.14 (br d, J=12.72 Hz, 2H) 2.87 (br s, 6H) 1.79-1.98 (m, 2H) 1.41 (br s, 6H) 0.89 (t, J=6.85 Hz, 3H); LCMS: 562.40 [M+H]$^+$.

Step-4: Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl (2S,5R)-4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)-2,5-dimethylpiperazine-1-carboxylate A stirred solution of common (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate (Int-C, 249 mg, 0.445 mmol, 1 eq.) and (S)-10-((dimethylamino)methyl)-4-ethyl-4-hydroxy-3,14-dioxo-3,4,12,14-tetrahydro-1H-pyrano[3',4':6,7] indolizino[1,2-b]quinolin-9-yl (2S,5R)-2,5-dimethylpiperazine-1-carboxylate TFA salt (Int-4, 250 mg, 0.445 mmol, 1 eq.) in methanol (20 mL) and 1,2-dichloroethane (5 mL) was added catalytic amount of glacial acetic acid (0.1 mL) at room temperature and stirred for 2 h. To this reaction mixture was added NaCNBH3 (56 mg, 0.891 mmol, 2 eq.) at 0° C. The reaction mixture was allowed to warm up to room temperature and stirred for 16 h. Progress of the reaction was monitored by TLC. After completion of the reaction, solvents were evaporated under reduced pressure, quenched with ice cold water (20 mL) and extracted with 10% methanol in DCM (2×25 mL). The combined organic extracts were washed with brine (100 mL) and dried over anhydrous sodium sulphate, filtered and concentrated under vacuum to obtained crude compound. The crude compound obtained was purified by combiflash column chromatography by eluting with 8-10% methanol in DCM to afford the desired product (40 mg, 8%). $^1$H NMR (400 MHz, DMSO-$d_6$) δ 8.71 (s, 1H) 7.87 (d, J=9.26 Hz, 1H) 7.37 (d, J=9.13 Hz, 1H) 7.10 (s, 1H) 6.75 (d, J=8.63 Hz, 2H) 6.36 (d, J=8.76 Hz, 2H) 6.27 (s, 1H) 5.43 (s, 1H) 5.19 (s, 2H) 5.08 (s, 2H) 4.16 (d, J=7.25 Hz, 1H) 3.43-3.60 (m, 2H) 3.01-3.09 (m, 3H) 2.74-2.81 (m, 1H) 2.59 (s, 3H) 2.41-2.55 (m, 3H) 2.32 (br s, 1H) 2.04-2.19 (m, 5H) 1.96 (s, 6H) 1.86 (s, 5H) 1.76 (s, 6H) 1.58-1.69 (m, 4H) 1.38-1.52 (m, 3H) 1.24 (d, J=6.38 Hz, 3H) 0.94-1.20 (m, 13H) 0.71-0.82 (m, 4H) 0.65 (t, J=7.32 Hz, 3H). LCMS: 1104.98 [M+H]$^+$. HPLC Purity: 69.7%.

Example 27

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl (2R,5S)-4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexyl)-2,5-dimethylpiperazine-1-carboxylate (Compound 24)

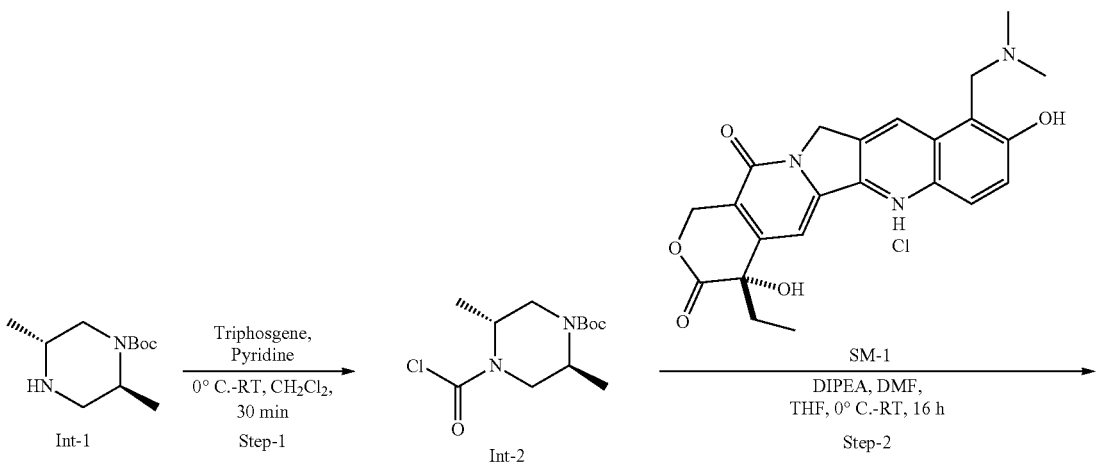

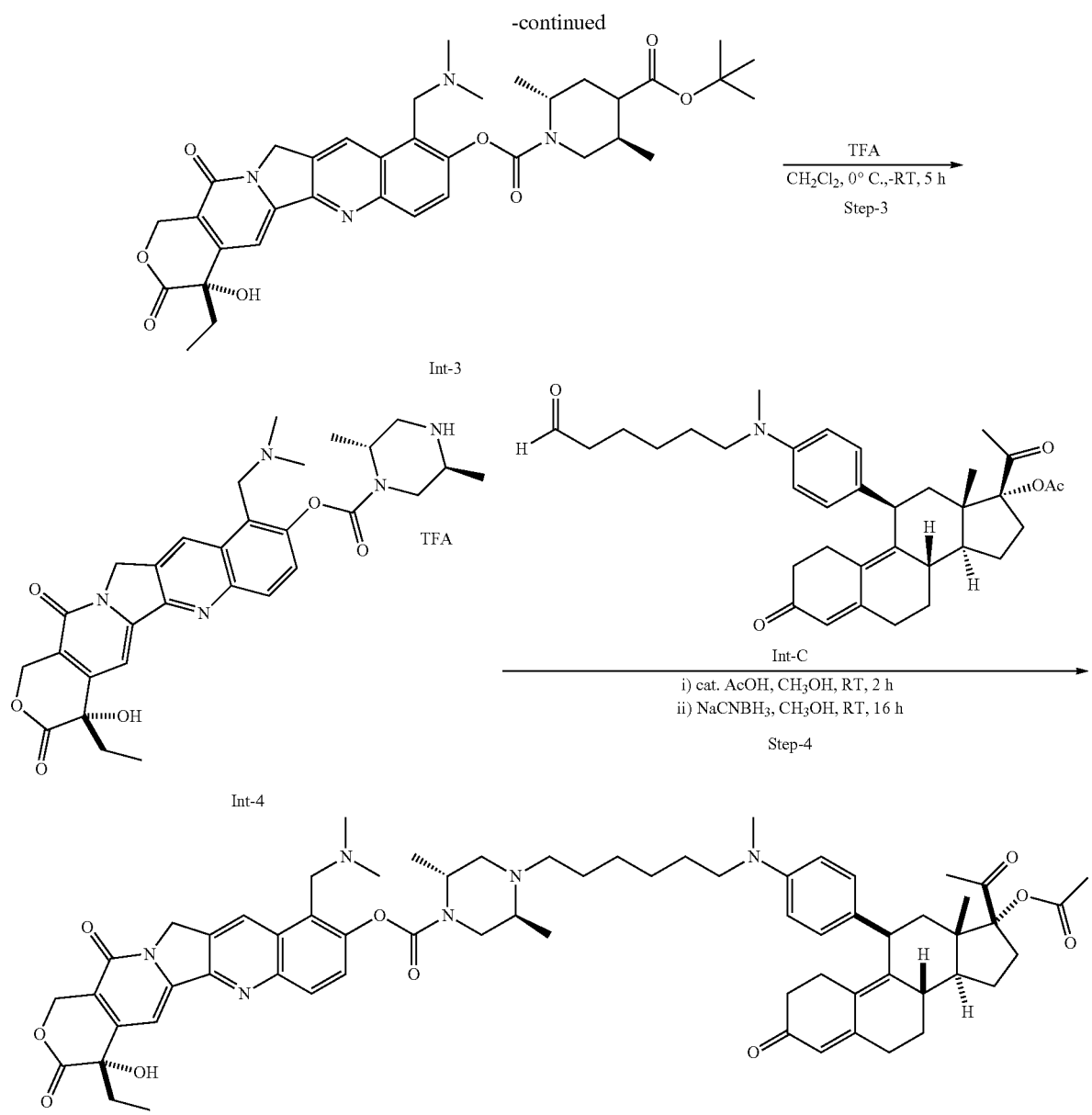

Step-1: Preparation of tert-Butyl (2S,5R)-4-(Chlorocarbonyl)-2,5-dimethylpiperazine-1-carboxylate (Int-2)

To a stirred solution of tert-butyl (2S,5R)-2,5-dimethylpiperazine-1-carboxylate (Int-1, 3.0 g, 13.99 mmol, 1.0 eq.) in DCM (25 mL) were added pyridine (1.7 mL, 20.99 mmol, 1.5 eq.) and triphosgene (1.24 g, 41.99 mmol, 0.3 eq.) solution in DCM (5 mL) drop wise over a period of 10 min at 0° C. The reaction mixture was allowed to warm up to room temperature and stirred for 30 min. Progress of the reaction was monitored by TLC (non-polar spot was observed). After completion of the reaction, the reaction mixture was poured into ice cold water (50 mL) and extracted with DCM (2×30 mL). The combined organic extracts were washed with brine (100 mL) and dried over anhydrous sodium sulphate, filtered and concentrated under vacuum to afford Int-2 (3.7 g, crude) which was used in next step without further purification. $^1$H NMR (400 MHz, DMSO-d$_6$) δ 4.09-4.55 (m, 2H) 3.46-3.69 (m, 2H) 3.13-3.41 (m, 2H) 1.40 (s, 9H) 0.98-1.28 (m, 6H).

Step-2: Preparation of 1-(tert-Butyl) 4-((S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl) (2S,5R)-2,5-dimethyl piperazine-1,4-dicarboxylate (Int-3)

To a solution of tert-butyl (2S,5R)-4-(chlorocarbonyl)-2,5-dimethylpiperazine-1-carboxylate (Int-2, 3.6 g, 13.05 mmol, 2 eq.) and (S)-10-((dimethylamino)methyl)-4-ethyl-4,9-dihydroxy-1,12-dihydro-14H-pyrano[3',4':6,7]indolizino[1,2-b]quinoline-3,14(4H)-dione hydrochloride (SM-1, 3.1 g, 6.52 mmol, 1 eq.) in THF (30 mL) and DMF (30 mL) was added DIPEA (5.67 mL, 32.6 mmol, 5 eq.) at 0° C. The reaction mixture was allowed to warm up to room temperature and stirred for 16 h. Progress of the reaction was monitored by TLC. After completion of the reaction, the reaction mixture was quenched with water (30 mL) and extracted with ethyl acetate (2×25 mL). The combined organic extract was washed with brine (100 mL) and dried over anhydrous sodium sulfate, filtered and concentrated under vacuum to obtained crude compound. The crude compound obtained was purified by combiflash column chromatography by eluting with 10% methanol in DCM to afford Int-3 (2.5 g, 58%). $^1$H NMR (400 MHz, DMSO-d$_6$) δ 8.95 (br s, 1H) 8.11 (d, J=9.29 Hz, 1H) 7.54-7.76 (m, 1H) 7.34 (s, 1H) 6.53 (s, 1H) 5.43 (s, 2H) 5.31 (s, 2H) 4.19-4.41 (m, 2H) 3.61-3.81 (m, 2H) 3.17 (d, J=12.91 Hz, 1H) 2.20 (d, J=6.36 Hz, 6H) 1.80-1.95 (m, 3H) 1.26-1.41 (m, 14H) 1.18 (d, J=6.36 Hz, 3H) 0.89 (t, J=6.36 Hz, 3H). LCMS: 662.4 [M+H]$^+$.

Step-3: Preparation of (S)-10-((Dimethylamino) methyl)-4-ethyl-4-hydroxy-3,14-dioxo-3,4,12,14-tetrahydro-1H-pyrano[3',4':6,7]indolizino[1,2-b] quinolin-9-yl (2R,5S)-2,5-dimethylpiperazine-1-carboxylate TFA salt (Int-4)

To a stirred solution of 1-(tert-butyl) 4-((S)-10-((dimethylamino)methyl)-4-ethyl-4-hydroxy-3,14-dioxo-3,4,12,14-tetrahydro-1H-pyrano[3',4':6,7]indolizino[1,2-b]quinolin-9-yl) (2S,5R)-2,5-dimethylpiperazine-1,4-dicarboxylate (Int-3, 1.5 g, 2.26 mmol, 1.0 eq.) in DCM (20 mL) was added TFA (3 mL)) at 0° C. The reaction mixture was allowed to warm up to room temperature and stirred for 5 h/16 h. Progress of the reaction was monitored by TLC. After completion of the reaction, solvents were evaporated under reduced pressure to get crude compound, the crude compound was triturated with ethyl acetate (30 mL), filtered the solid and dried under vacuum to afford Int-4 (1.20 g, 78%). $^1$H NMR (400 MHz, DMSO-d$_6$) δ 10.01 (br s, 1H) 9.08 (br s, 3H) 8.32 (d, J=9.00 Hz, 1H) 7.80 (d, J=9.39 Hz, 1H) 7.34 (s, 1H) 6.53 (br s, 1H) 5.41 (s, 2H) 5.30 (s, 2H) 4.79 (br s, 2H) 3.91 (br s, 2H) 3.69 (br s, 2H) 3.11 (d, J=12.91 Hz, 1H) 2.84 (br s, 6H) 1.86-1.92 (m, 2H) 1.38 (br s, 6H) 1.21 (d, J=6.65 Hz, 1H) 0.85 (t, J=7.24 Hz, 3H). LCMS: 562.5 [M+H]$^+$.

Step-4: Preparation of (S)-10-((Dimethylamino) methyl)-4-ethyl-4-hydroxy-3,14-dioxo-3,4,12,14-tetrahydro-1H-pyrano[3',4':6,7]indolizino[1,2-b] quinolin-9-yl(2R,5S)-4-(6-((4-((8S,11R,13S,14S, 17R)-17-acetoxy-17-acetyl-13-methyl-3-oxo-2,3,6,7, 8,11,12,13,14,15,16,17-dodecahydro-1H-cyclopenta [a]phenanthren-11-yl)phenyl)(methyl)amino)hexyl)-2,5-dimethylpiperazine-1-carboxylate A stirred solution of common (8S,11R,13S,14S,17R)-17-acetyl-13-methyl-11-(4-(methyl(6-oxohexyl)amino)phenyl)-3-oxo-2,3,6,7,8,11,12,13,14,15,16,17-dodecahydro-1H-cyclopenta[a]phenanthren-17-yl acetate (Int-C, 466 mg, 0.834 mmol, 1 eq.) and (S)-10-((dimethylamino)methyl)-4-ethyl-4-hydroxy-3,14-dioxo-3,4,12,14-tetrahydro-1H-pyrano[3',4':6,7] indolizino[1,2-b]quinolin-9-yl (2R,5S)-2, 5-dimethylpiperazine-1-carboxylate TFA salt (Int-4, 550 mg, 0.834 mmol, 1 eq.) in methanol (25 mL) was added catalytic amount of glacial acetic acid (0.1 mL) at room temperature and stirred for 2 h. To this reaction mixture was added NaCNBH$_3$ (105 mg, 1.67 mmol, 2 eq.) at 0° C. The reaction mixture was allowed to warm up to room temperature and stirred for 16 h. Progress of the reaction was monitored by TLC. After completion of the reaction, the reaction mixture was quenched with ice cold water (25 mL) and extracted with 10% methanol in DCM (2×25 mL). The combined organic extracts were washed with 10% sat. NaHCO$_3$ solution (15 mL), dried over Na$_2$SO$_4$, concentrated under reduced pressure to obtain crude compound. The crude compound was purified by combiflash column chromatography by eluting with 8-10% methanol in DCM to afford the desired product (70 mg, 7%). $^1$H NMR (400 MHz, DMSO-d$_6$) δ 8.95 (s, 1H) 8.11 (d, J=9.25 Hz, 1H) 7.61 (d, J=9.25 Hz, 1H) 7.34 (s, 1H) 6.98 (d, J=8.32 Hz, 2H) 6.59 (d, J=8.32 Hz, 2H) 6.53 (s, 1H) 5.67 (s, 1H) 5.43 (s, 2H) 5.32 (s, 2H) 4.40 (d, J=6.47 Hz, 1H) 3.76 (s, 3H) 3.02 (br s, 1H) 2.63-2.91 (m, 8H) 2.28-2.44 (m, 6H) 2.19 (s, 11H) 2.10 (s, 8H) 2.00 (s, 5H) 1.82-1.93 (m, 5H) 1.19-1.54 (m, 12H) 1.00 (br s, 3H) 0.89 (t, J=7.17 Hz, 3H). LCMS: 1104.98 [M+H]$^+$. HPLC Purity: 56.4%.

Example 28

Preparation of N-((1r,4r)-4-(3-Chloro-4-cyanophenoxy)cyclohexyl)-6-(4-(4-(((S)-4-ethyl-4,9-dihydroxy-3,14-dioxo-3,4,12,14-tetrahydro-1H-pyrano [3',4':6,7]indolizino[1,2-b]quinolin-10-yl)methyl) piperazine-1-carbonyl)piperazin-1-yl)pyridazine-3-carboxamide (Compound 28)

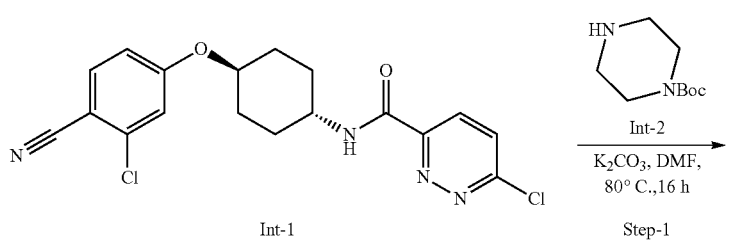

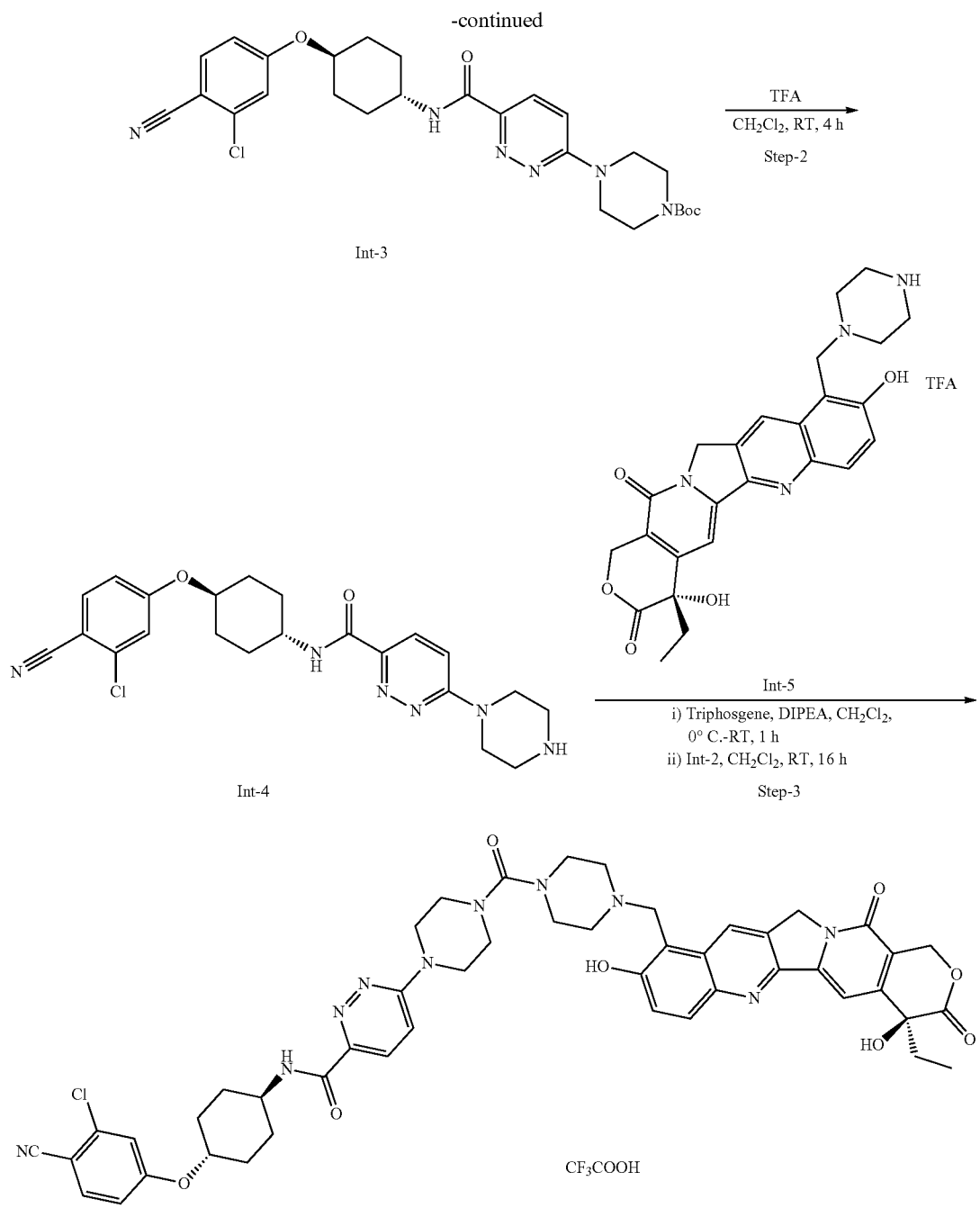

Step-1: Preparation of tert-Butyl 4-(6-(((1r,4r)-4-(3-Chloro-4-cyanophenoxy)cyclohexyl)carbamoyl) pyridazin-3-yl)piperazine-1-carboxylate (Int-3)

To a stirred solution of 6-chloro-N-((1r,4r)-4-(3-chloro-4-cyanophenoxy)cyclohexyl) pyridazine-3-carboxamide (Int-1, 1 g, 2.55 mmol, 1.0 eq.) and tert-butyl piperazine-1-carboxylate (Int-2, 477 mg, 2.55 mmol, 1.0 eq.) in DMF (8 mL) was added potassium carbonate (527 mg, 3.82 mmol, 1.5 eq.) at room temperature. The reaction mixture was heated at 80° C. and stirred for 16 h. Progress of the reaction was monitored by TLC. After completion of the reaction, solvents were evaporated under reduced pressure, washed with water (100 mL) and extracted with ethyl acetate (3×250 mL). The combined organic extracts were washed with brine (80 mL) and dried over anhydrous sodium sulphate, filtered and concentrated under vacuum to obtain crude compound. The crude product was purified by column chromatography by eluting with 5% methanol in DCM to afford Int-3 (370 mg, 26%). $^{1}$H NMR (400 MHz, DMSO-d$_{6}$) δ 8.63 (d, J=8.25 Hz, 1H) 7.86 (dd, J=9.19, 3.06 Hz, 2H) 7.31-7.45 (m, 2H) 7.14 (dd, J=8.76, 2.38 Hz, 1H) 4.47-4.62 (m, 1H) 3.80-3.95 (m, 1H) 3.66-3.79 (m, 4H) 3.43-3.54 (m, 4H) 2.11 (br d, J=10.26 Hz, 2H) 1.91 (br d, J=10.76 Hz, 2H) 1.58-1.72 (m, 2H) 1.48-1.57 (m, 2H) 1.44 (s, 9H). LCMS: 541.2 [M+H]$^{+}$.

Step-2: Preparation of N-((1r,4r)-4-(3-Chloro-4-cyanophenoxy)cyclohexyl)-6-(piperazin-1-yl)pyridazine-3-carboxamide (Int-4)

To a stirred solution of tert-butyl 4-(6-(((1r,4r)-4-(3-chloro-4-cyanophenoxy)cyclohexyl) carbamoyl) pyridazin-3-yl)piperazine-1-carboxylate (Int-3, 350 mg, 0.64 mmol, 1.0 eq.) in DCM (5 mL) under nitrogen atmosphere was added TFA (0.8 mL) at 0° C. Warmed to room temperature and stirred for 16 h. Progress of the reaction was monitored by TLC. After completion of the reaction, solvent was evaporated under reduced pressure, added saturated NaHCO$_3$ solution (25 mL) and extracted with ethyl acetate (2×100 mL). Solvent was evaporated under reduced pressure to afforded Int-4 (255 mg, 89%). $^1$H NMR (400 MHz, DMSO-d$_6$) δ 8.61 (d, J=8.31 Hz, 1H) 7.84 (dd, J=14.67, 9.29 Hz, 2H) 7.39 (s, 1H) 7.32 (br d, J=9.78 Hz, 1H) 7.13 (br d, J=8.80 Hz, 1H) 4.47-4.61 (m, 1H) 3.79-3.91 (m, 1H) 3.64 (br s, 4H) 2.83 (br s, 4H) 2.10 (br d, J=10.76 Hz, 2H) 1.89 (br d, J=11.25 Hz, 2H) 1.43-1.74 (m, 5H). LCMS: 441.2 [M+H]$^+$.

Step-3: Preparation of N-((1r,4r)-4-(3-chloro-4-cyanophenoxy)cyclohexyl)-6-(4-(4-(((S)-4-ethyl-4,9-dihydroxy-3,14-dioxo-3,4,12,14-tetrahydro-1H-pyrano[3',4':6,7]indolizino[1,2-b]quinolin-10-yl)methyl)piperazine-1-carbonyl)piperazin-1-yl)pyridazine-3-carboxamide TFA salt To a stirred solution of N-((1r,4r)-4-(3-chloro-4-cyanophenoxy)cyclohexyl)-6-(piperazin-1-yl)pyridazine-3-carboxamide (Int-1, 220 mg, 0.51 mmol, 1.0 eq.) in DCM (5 mL) were added DIPEA (0.4 mL, 3.1 mmol, 4 eq.) and triphosgene (220 mg, 0.74 mmol, 1.5 eq.) at 0° C. The reaction mixture was allowed to warm up to room temperature and stir for 1 h. Progress of the reaction was monitored by TLC. After completion of the reaction, (S)-4-ethyl-4,9-dihydroxy-10-(piperazin-1-ylmethyl)-1,12-dihydro-14H-pyrano[3',4':6,7]indolizino[1,2-b]quinoline-3,14(4H)-dione TFA salt (Int-2, 231 mg, 0.51 mmol, 1.0 eq.) was added to this reaction mixture and stirred for 16h at room temperature. Progress of the reaction was monitored by TLC. After completion of the reaction, water (80 mL) was added and extracted with DCM (2×60 mL). The combined organic extracts were washed with water (80 mL), brine (80 mL) and dried over anhydrous sodium sulfate, filtered and concentrated under vacuum to obtained crude compound. The crude compound obtained was purified by prep. HPLC using 0.1% TFA in ACN to afford the desired product (68 mg, 13%). $^1$H NMR (400 MHz, DMSO-d$_6$) δ 11.34 (br s, 1H) 9.45-9.66 (m, 1H) 8.97 (br s, 1H) 8.61 (d, J=8.25 Hz, 1H) 8.21 (d, J=8.63 Hz, 1H) 7.80-7.94 (m, 2H) 7.64 (d, J=8.88 Hz, 1H) 7.34-7.41 (m, 2H) 7.30 (s, 1H) 7.13 (dd, J=8.76, 2.25 Hz, 1H) 6.51 (br s, 1H) 5.43 (s, 2H) 5.32 (s, 2H) 4.72-4.85 (m, 2H) 4.53 (br t, J=9.82 Hz, 1H) 3.81-3.92 (m, 1H) 3.70-3.74 (m, 5H) 3.30-3.38 (m, 8H) 3.14-3.24 (m, 1H) 2.06-2.13 (m, 2H) 1.83-1.94 (m, 4H) 1.64 (q, J=11.97 Hz, 2H) 1.30-1.58 (m, 4H) 0.89 (t, J=7.25 Hz, 3H). LCMS: 929.4 [M+H]$^+$. HPLC purity 97.0%.

Example 29

Preparation of (S)-10-((Dimethylamino)methyl)-4-ethyl-4-hydroxy-3,14-dioxo-3,4,12,14-tetrahydro-1H-pyrano[3',4':6,7]indolizino[1,2-b]quinolin-9-yl 4-(6-((4-((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexanoyl)piperazine-1-carboxylate (Compound 29)

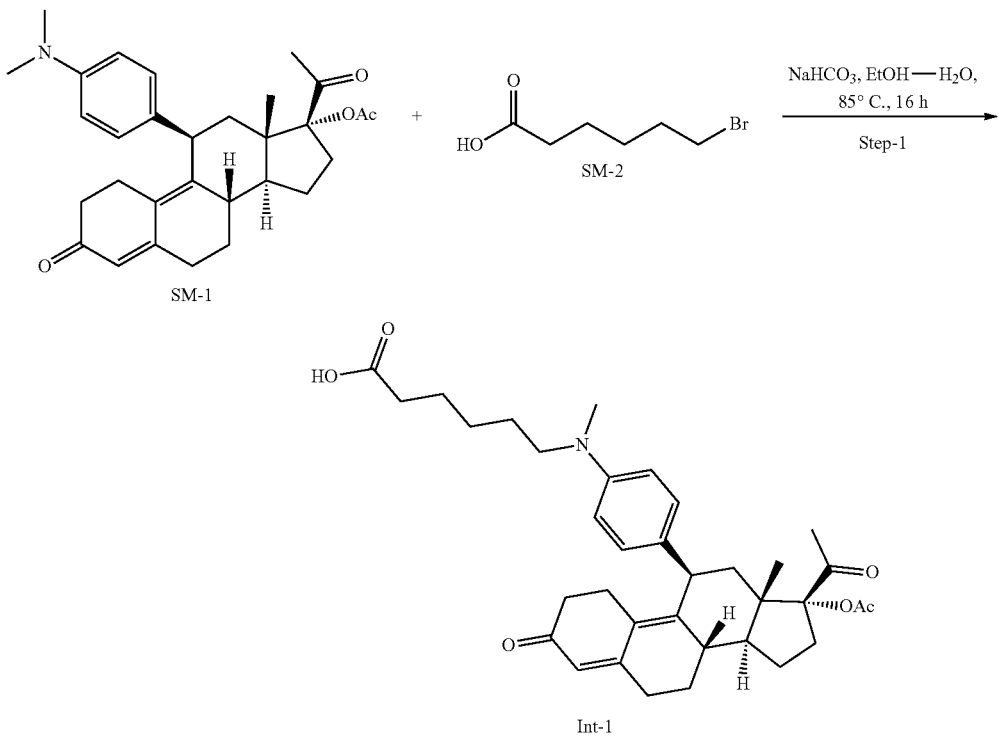

-continued

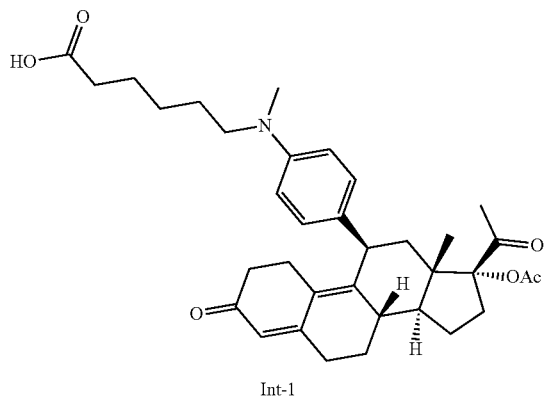

Int-1

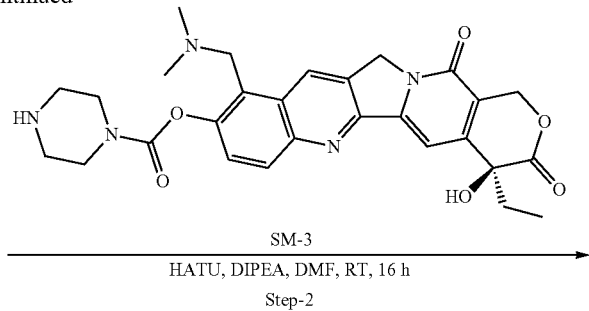

SM-3
→
HATU, DIPEA, DMF, RT, 16 h
Step-2

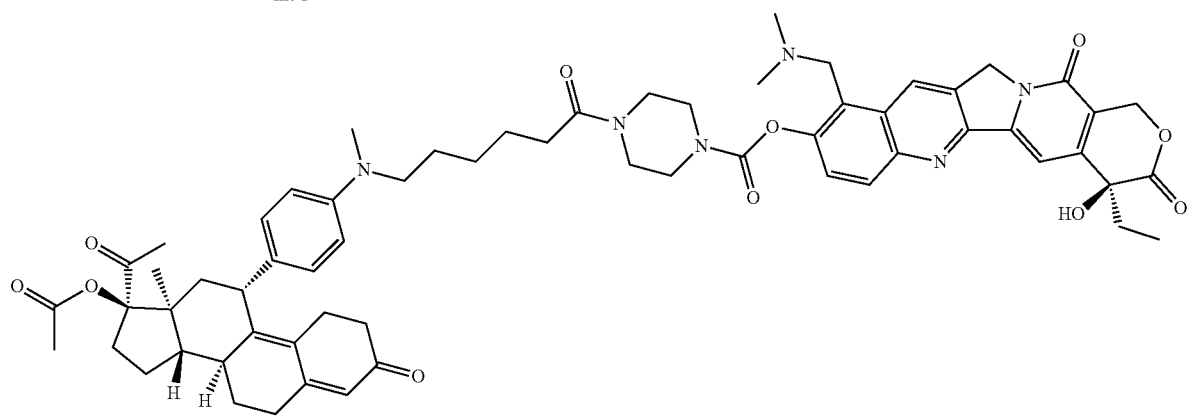

Step-1: Preparation of 6-((4-((8S,11R,13S,14S, 17R)-17-Acetoxy-17-acetyl-13-methyl-3-oxo-2,3,6, 7,8,11,12,13,14,15,16,17-dodecahydro-1H-cyclopenta[a]phenanthren-11-yl)phenyl)(methyl)amino) hexanoic Acid (Int-1)

A flask was charged with (8S,11R,13S,14S,17R)-17-acetyl-13-methyl-11-(4-(methylamino)phenyl)-3-oxo-2,3,6, 7,8,11,12,13,14,15,16,17-dodecahydro-1H-cyclopenta[a] phenanthren-17-yl acetate (SM-1, 700 g, 1.51 mol, 1.0 eq.), 6-bromohexanoic acid (SM-2, 1.48 g, 7.55 mol, 5.0 eq.), $NaHCO_3$ (382 mg, 4.53 mol, 3.0 eq.), EtOH (7 mL, 10 vol.) and $H_2O$ (7 mL, 10 vol.). Reaction mixture was stirred under a nitrogen atmosphere at 85° C. until TLC indicated complete consumption of starting material. The reaction mixture was then cooled to room temperature. Reaction mixture was diluted with water (50 mL) and acidified with citric acid (pH up to ~7), compound was extracted with ethyl acetate (2×100 mL) and combined organic layer was washed with brine solution (100 mL) and dried over sodium sulfate. Filtered organic solvent and concentrated under reduced pressure, Purification by column chromatography ($SiO_2$, EtOAc gradient) to obtain 6-((4-((8S,11R,13S,14S,17R)-17-acetoxy-17-acetyl-13-methyl-3-oxo-2,3,6,7,8,11,12, 13,14, 15,16,17-dodecahydro-1H-cyclopenta[a]phenanthren-11-yl)phenyl)(methyl)amino)hexanoic acid (Int-1, 300 mg, 34% yield). $^1$H NMR (400 MHz, DMSO-$d_6$) δ ppm 11.96 (br s, 1H) 6.98 (d, J=8.31 Hz, 2H) 6.58 (d, J=8.80 Hz, 2H), 5.67 (s, 1H), 4.34 (t, J=4.89 Hz, 2H), 3.95-4.08 (m, 2H), 3.33-3.40 (m, 2H), 3.17-3.26 (m, 1H), 2.81 (s, 3H), 2.58-2.76 (m, 2H), 2.24-2.38 (m, 2H), 2.14-2.22 (m, 2H), 2.10 (s, 3H), 1.99 (d, J=4.40 Hz, 3H), 1.93 (dd, J=13.45, 6.11 Hz, 2H), 1.62-1.77 (m, 2H), 1.45-1.55 (m, 2H), 1.40 (dt, J=14.31, 6.79 Hz, 3H), 1.21-1.33 (m, 4H), 1.17 (t, J=7.09 Hz, 3H). LCMS: 576.4 [M+H]$^+$.

Step-2: Preparation of (S)-10-((Dimethylamino) methyl)-4-ethyl-4-hydroxy-3,14-dioxo-3,4,12,14-tetrahydro-1H-pyrano[3',4':6,7]indolizino[1,2-b] quinolin-9-yl 4-(6-((4-((8S,11R,13S,14S,17R)-17-acetoxy-17-acetyl-13-methyl-3-oxo-2,3,6,7,8,11,12, 13,14,15,16,17-dodecahydro-1H-cyclopenta[a] phenanthren-11-yl)phenyl)(methyl)amino)hexanoyl) piperazine-1-carboxylate A RB flask was charged with 6-((4-((8S,11R,13S,14S, 17R)-17-acetoxy-17-acetyl-13-methyl-3-oxo-2,3,6,7,8,11, 12,13,14,15,16,17-dodecahydro-1H-cyclopenta[a] phenanthren-11-yl)phenyl)(methyl)amino)hexanoic acid (Int-1, 300 g, 0.52 mol, 1.0 eq.) in DMF (3 mL, 10 vol.), (S)-10-((dimethylamino)methyl)-4-ethyl-4-hydroxy-3,14-dioxo-3,4,12,14-tetrahydro-1H-pyrano[3',4':6,7]indolizino [1,2-b]quinolin-9-yl piperazine-1-carboxylate (SM-3, 277 mg, 0.52 mol, 1.0 eq.), HATU (296 mg, 0.78 mol, 1.5 eq.), DIPEA (0.47 mL, 2.6 mol, 5.0 eq.) was added under nitrogen atmosphere at RT. Reaction mixture was stirred at ambient temperature until TLC indicated complete consumption of starting material. The reaction mixture was diluted with $H_2O$ (20 mL) and compound was extracted with ethyl acetate (2×50 mL), combined organic layer was washed with brine solution (50 mL) and dried over sodium sulfate. Filtered organic solvent, concentrated under reduced pressure and purified by preparative HPLC. (Column: X Select CSH C 18 250×30 5μ; Mobilephase 5 mm Ammonium bicarbonate in water; Mobilephase B: 100% Acetonitrile; Gradient: Linear; Flow rate: 30 ml/min), to obtain (S)-10-((dimethylamino)

methyl)-4-ethyl-4-hydroxy-3,14-dioxo-3,4,12,14-tetrahydro-1H-pyrano[3',4':6,7] indolizino[1,2-b]quinolin-9-yl 4-(6-(((8S,11R,13S,14S,17R)-17-acetoxy-17-acetyl-13-methyl-3-oxo-2,3,6,7,8,11,12,13,14,15,16,17-dodecahydro-1H-cyclopenta[a]phenanthren-11-yl)phenyl)(methyl)amino)hexanoyl)piperazine-1-carboxylate (20 mg, 4% yield). $^1$H NMR (400 MHz, DMSO-$d_6$) δ ppm 8.95 (s, 1H), 8.12 (d, J=9.38 Hz, 1H), 7.66 (d, J=9.13 Hz, 1H), 7.34 (s, 1H), 6.99 (d, J=8.63 Hz, 2H), 6.60 (d, J=8.50 Hz, 2H), 6.51 (s, 1H), 5.67 (s, 1H), 5.43 (s, 2H), 5.32 (s, 2H), 4.40 (d, J=7.25 Hz, 1H), 3.77 (m, 2H), 3.71-3.49 (m, 8H), 3.28-3.18 (m, 4H), 2.83 (s, 3H), 2.67 (d, J=1.63 Hz, 4H), 2.38 (d, J=17.64 Hz, 6H), 2.34-2.30 (m, 4H), 2.20 (s, 6H), 2.10 (s, 3H), 2.00 (s, 3H), 1.94-1.82 (m, 2H), 1.75-1.63 (m, 2H), 1.61-1.45 (m, 4H), 1.39-1.21 (m, 4H), 0.89 (t, J=7.32 Hz, 3H), 0.24 (s, 3H). LCMS: 1091.5 [M+H]$^+$.

Example 30

Preparation of 1-(2-(((5S,8R,9S,10S,13S,14S,17S)-10,13-Dimethyl-3-oxohexadecahydro-1H-cyclopenta[a]phenanthren-17-yl)oxy)acetamido)-N—(((S)-4-ethyl-4,9-dihydroxy-3,14-dioxo-3,4,12,14-tetrahydro-1H-pyrano[3',4':6,7]indolizino[1,2-b]quinolin-10-yl)methyl)-N-methyl-3,6,9,12-tetraoxapentadecan-15-amide (Compound 30)

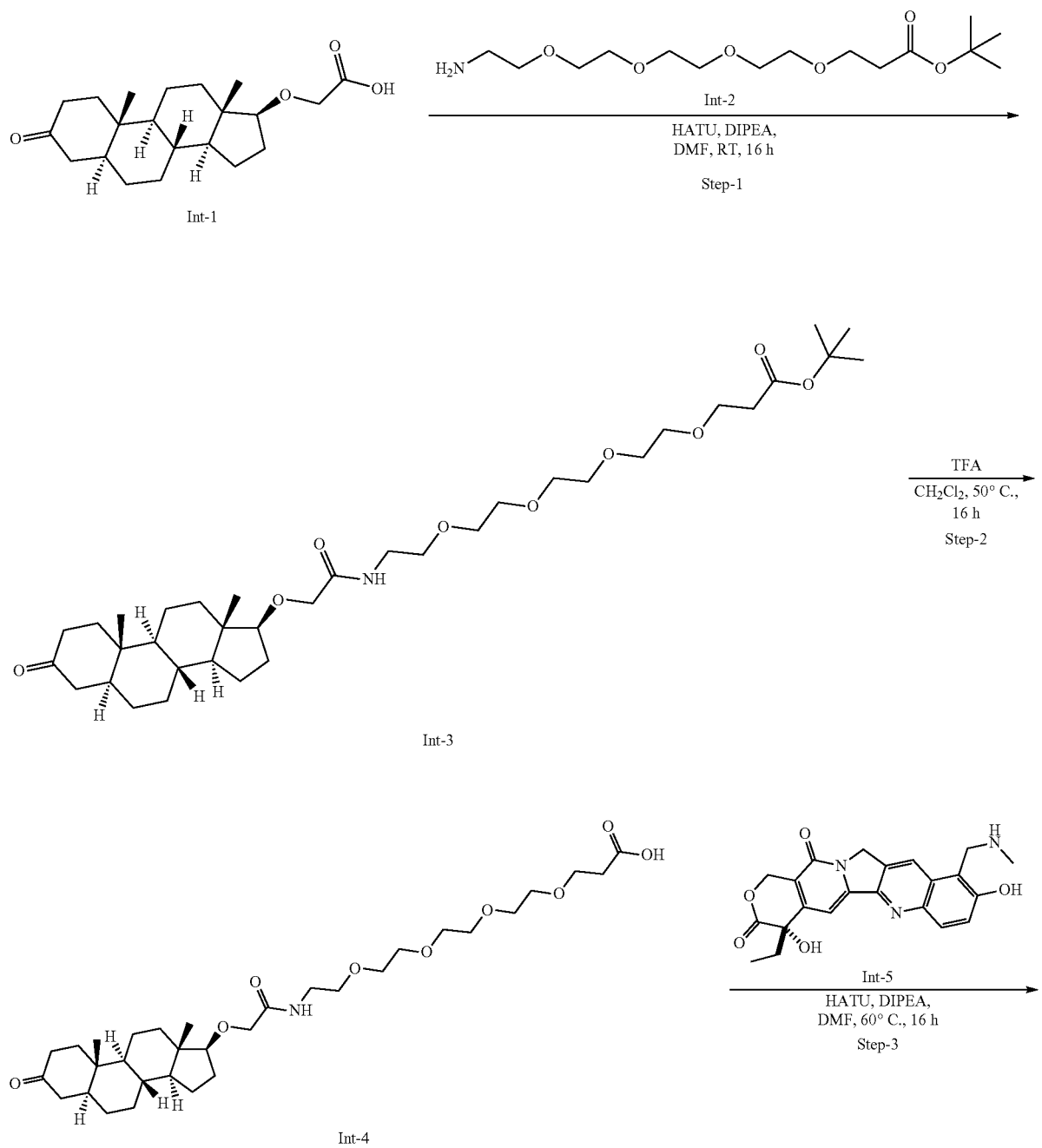

-continued

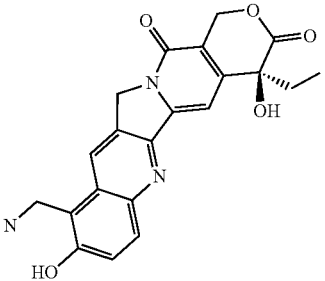
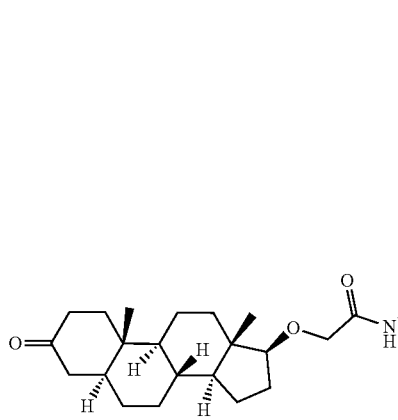

Step-1: Preparation of tert-Butyl 1-(((5S,8R,9S,10S, 13S,14S,17S)-10,13-dimethyl-3-oxohexadecahydro-1H-cyclopenta[a]phenanthren-17-yl)oxy)-2-oxo-6,9, 12,15-tetraoxa-3-aza octadecan-18-oate (Int-3)

To a stirred solution of 2-(((5S,8R,9S,10S,13S,14S,17S)-10,13-dimethyl-3-oxohexadecahydro-1H-cyclopenta[a]phenanthren-17-yl)oxy)acetic acid (Int-1, 500 mg, 1.43 mmol, 1.0 eq.) and tert-butyl 1-amino-3,6,9,12-tetraoxapentadecan-15-oate (Int-2, 459 mg, 1.43 mmol, 1 eq.) in DMF (10 mL) were added HATU (815 mg, 2.14 mmol, 1.5 eq.) and DIPEA (0.74 mL, 4.29 mmol, 3 eq.) at 0° C. and stirred for 16 h. Progress of the reaction was monitored by TLC. After completion of the reaction, the reaction mixture was washed with water (100 mL) and extracted with ethyl acetate (2×100 mL). The combined organic extracts were washed with water (80 mL), brine (80 mL) and dried over anhydrous sodium sulphate, filtered and concentrated under vacuum to obtained crude compound. The crude compound obtained was purified by combiflash column by eluting with 5% methanol in DCM to afford Int-3 (800 mg, 85%). LCMS: 929.4 [M+H]$^+$.

Step-2: Preparation of 1-(((5S,8R,9S,10S,13S,14S, 17S)-10,13-Dimethyl-3-oxohexadecahydro-1H-cyclopenta[a]phenanthren-17-yl)oxy)-2-oxo-6,9,12,15-tetraoxa-3-azaoctadecan-18-oic Acid (Int-4)

To a stirred solution of tert-butyl 1-(((5S,8R,9S,10S,13S,14S,17S)-10,13-dimethyl-3-oxohexadecahydro-1H-cyclopenta[a]phenanthren-17-yl)oxy)-2-oxo-6,9,12,15-tetraoxa-3-azaoctadecan-18-oate (Int-3, 400 mg, 0.61 mmol, 1.0 eq.) in DCM (10 mL) under nitrogen atmosphere was added TFA (0.94 mL, 20 eq.) at 0° C. The reaction mixture was heated to 50° C. and stirred for 16 h. Progress of the reaction was monitored by TLC. After completion of the reaction, solvents were evaporated under reduced pressure, sat. NaHCO$_3$ solution (20 mL) was added, extracted with ethyl acetate (2×100 mL). Solvent was evaporated under reduced pressure to afford Int-4 (320 mg, crude) as an off-white solid which was used in next step without further purification. $^1$H NMR (400 MHz, DMSO-d$_6$) δ 11.91-12.37 (m, 1H) 7.36 (t, J=5.63 Hz, 1H) 3.84 (s, 2H) 3.60 (t, J=6.38 Hz, 2H) 3.48-3.54 (m, 11H) 3.41-3.47 (m, 2H) 3.35 (t, J=8.25 Hz, 1H) 3.28 (q, J=5.84 Hz, 2H) 2.36-2.44 (m, 4H) 2.30 (t, J=14.38 Hz, 1H) 1.82-2.02 (m, 4H) 1.59-1.67 (m, 1H) 1.52 (br d, J=4.13 Hz, 2H) 1.34-1.51 (m, 4H) 1.21-1.32 (m, 6H) 1.09-1.22 (m, 2H) 0.98 (s, 3H) 0.80-0.92 (m, 1H) 0.76 (s, 3H). LCMS: 596.54 [M+H]$^+$.

Step-3: Preparation of 1-(2-(((5S,8R,9S,10S,13S, 14S,17S)-10,13-Dimethyl-3-oxohexadecahydro-1H-cyclopenta[a]phenanthren-17-yl)oxy)acetamido)-N—(((S)-4-ethyl-4,9-dihydroxy-3,14-dioxo-3,4,12, 14-tetrahydro-1H-pyrano[3',4':6,7]indolizino[1,2-b]quinolin-10-yl)methyl)-N-methyl-3,6,9,12-tetraoxapentadecan-15-amide To a stirred solution of 1-(((5S,8R,9S,10S,13S,14S,17S)-10,13-dimethyl-3-oxohexadecahydro-1H-cyclopenta[a]phenanthren-17-yl)oxy)-2-oxo-6,9,12,15-tetraoxa-3-aza octadecan-18-oic acid (Int-4, 250 mg, 0.42 mmol, 1.0 eq.) and (S)-4-ethyl-4,9-dihydroxy-10-((methylamino)methyl)-1,12-dihydro-14H-pyrano[3',4':6,7]indolizino[1,2-b]quinoline-3,14(4H)-dione (Int-5, 170 mg, 0.42 mmol, 1 eq.) in DMF (1 mL) was added HATU (320 mg, 0.84 mmol, 2.0 eq.) and DIPEA (162 mg, 1.26 mmol, 3 eq.) at room temperature. The reaction mixture was heated to 60° C. and stirred for 16 h. Progress of the reaction was monitored by TLC. After completion of the reaction, the reaction mixture was washed with water (100 mL) and extracted with ethyl acetate (2×100 mL). The combined organic extracts were washed with water (100 mL), brine (100 mL) and dried over anhydrous sodium sulphate, filtered and concentrated under vacuum to obtain crude compound. The crude product was purified by prep. HPLC to afford the desired product (23 mg, 6%). $^1$H NMR (400 MHz, DMSO-d$_6$) δ 10.68 (br s, 1H) 8.69 (s, 1H) 8.03 (br d, J=9.13 Hz, 1H) 7.55 (br d, J=9.26 Hz, 1H) 7.32 (br d, J=5.13 Hz, 1H) 7.26 (s, 1H) 6.92-7.23 (m, 1H) 5.40 (s, 2H) 5.22 (s, 2H) 4.99 (br d, J=5.88 Hz, 2H) 3.79 (br s, 2H) 3.70 (t, J=6.50 Hz, 2H) 3.21-3.30 (m, 10H) 2.83 (s, 3H) 2.59 (t, J=6.44 Hz, 2H) 2.33-2.40 (m, 2H) 2.25 (t, J=14.26 Hz, 1H) 2.05 (d, J=13.63 Hz, 1H) 1.74-1.97 (m, 7H) 1.55 (br dd, J=12.57, 2.94 Hz, 1H) 1.31-1.50 (m, 8H) 1.11-1.30 (m, 7H) 1.00-1.10 (m, 1H) 0.92 (s, 3H) 0.87 (t, J=7.25 Hz, 5H) 0.69 (s, 3H) 0.56-0.66 (m, 1H). LCMS: 985.4 [M+H]$^+$. HPLC purity—95.7%.

BIOLOGICAL ASSAYS

The following methods are for evaluating the in vitro biology properties of the test articles.

Biological Example 1 a. AR binding assay: AR in LNCaP cytosol is used for determining the binding affinity of test articles and the reference compound, progesterone (Sigma, Cat: E2785, St. Louis, MO). $IC_{50}$s are determined using 8 concentrations/compound. Cytosol is plated at 200 μg/well (100 μL) into a 96-well conical polypropylene plate (Agilent, Cat: 5042-1385, Santa Clara, CA) and mixed with 3 μL of test compound. After adding 100 μL of $^3$H-methyltrienolone (PerkinElmer, Cat: NET590250UC, San Jose, CA), the plate is sealed and shaken at 300 rpm at 4° C. for 24 hours. Post incubation, 100 μL of radioligand adsorption buffer containing 10 mM Tris-HCl, pH 7.4; 1.5 mM EDTA; 1 mM DTT; 0.25% charcoal; 0.0025% dextran is added to individual wells. Plate is shaken for 15 min at 4° C. followed by centrifugation at 3000 rpm for 30 min at 4° C. 150 μL of supernatant is transferred into scint-tube (PerkinElmer, Cat: 6000192) and mixed with 2 mL of Ultima Gold Cocktail (PerkinElmer, Cat: 6013329). Radioactivity is counted using a TriCarb 2910 TR scintillation counter (PerkinElmer). Inhibition of the radioactivity by test articles is calculated using the equation below:

% Inhibition=(1−(Assay well−Average_LC)/(Average_HC−Average_LC))×100%.

$IC_{50}$ values are calculated and graphed using the model "log(inhibitor) vs. response—Variable slope" included in GraphPad Prism 5 (San Diego, CA). The Ki values are further calculated using the equation below where [L] is the radioligand concentration (1 nM) used in this study. Kd value is 0.332 nM.

$Ki=IC_{50}/(1+[L]/Kd)$ b. AR transactivation: Human AR cloned into a CMV vector backbone is used for the transactivation study. HEK-293 cells are plated at 80,000 cells per well of a 24 well plate in DME+5% csFBS. Twenty four hours later, the cells are transfected using Lipofectamine (Invitrogen, Carlsbad, CA) with 0.25 μg GRE-LUC, 0.01 μg CMV-LUC (renilla luciferase) and 25 ng of the AR in OPTIMEM medium. The cells are treated 24 hrs after transfection with various ligands ($10^{-12}$ to $10^{-5}$ M final concentrations) and luciferase assay performed 48 hours after transfection. Firefly values are normalized to renilla luciferase values and the values represented as relative light units (RLU). Agonist and antagonist assays for the test article are performed in the absence and in the combination with 0.1 nM R1881, respectively. Data are represented as $EC_{50}$ (for agonists) and $IC_{50}$ (for antagonists) values obtained from four parameter logistics curve.

c. Cell culture and proliferation assays: 22RV1 and HT-29 cells are procured from American Type Culture Collection (ATCC). Cells are cultured in medium recommended by the ATCC. Cell culture medium is obtained from Fisher scientific (Waltham, MA) and serum is obtained from Hyclone (San Angelo, TX).

Cells are plated at varying density in the respective growth medium in 96 well plates. 24 hr later, cells are treated, in triplicate or quadruplicate, with test articles prepared in a range of concentrations by series dilution of DMSO stock solutions in growth medium and incubated for three to seven days. The number of viable 22RV1 and HT-29 cells is measured using CellTiter Glo assay (CTG, Promega, Madison, WI) after three days of treatment. Cell viability data are plotted using GraphPad Prism (GraphPad Software, Inc., San Diego, CA). In addition, a nonlinear regression model with a sigmoidal dose response and variable slope within GraphPad Prism is used to calculate the $IC_{50}$ value of individual test articles.

d. Additional cell proliferation assays: Other cancer cell lines are tested in a cell proliferation assays, such as LnCaP, PC-3, MCF-7, HCC1428, BT474, HCT-116, SK-OV-3 or OVCAR3 cancer cells, by the following method. Cells are cultured in medium recommended by the supplier (e.g., ATCC or JCRB Cell Bank), at 37° C. in a 5% $CO_2$ environment. For the proliferation assay, cells are plated in the growth medium in 96 well plates. Seeding density is adjusted according to the cell type. 24 hr later, cells are treated, in triplicate or quadruplicate, with test articles prepared in a range of concentrations by series dilution of DMSO stock solutions in growth medium, and typically incubated for three to seven days, with test article-containing medium replaced after three or four days. The number of viable cells is measured using CellTiter Glo assay (CTG, Promega, Madison, WI) or similar. Cell viability data are plotted using GraphPad Prism (GraphPad Software, Inc., San Diego, CA). In addition, a nonlinear regression model with a sigmoidal dose response and variable slope within GraphPad Prism is used to calculate the $IC_{50}$ value of individual test articles. Similarly, HEK-293 and HeLa calls can also be tested by methods known in the art.

e. Nuclear translocation: LNCaP cells are plated on coverslips in 24 well plates in growth medium. Twenty-four hours after plating, medium is changed to RPMI+1% csFBS and the cells are maintained in this medium for two days. Medium is replaced again and the cells are treated. Cells are fixed 4 hours after treatment and the AR immunostained using AR N20 antibody (Santa Cruz Biotechnology, Santa Cruz, CA). Nucleus is stained with DAPI. Cells are imaged with a confocal microscope.

f. ER binding assay: ERα binding is assessed by the LanthaScreen® TR-FRET ER Alpha Competitive Binding Assay at Thermo Fisher. In this assay, a terbium-labeled anti-GST antibody is used to indirectly label GST-tagged ER Alpha-ligand binding domain (LBD) by binding to its GST tag. Competitive binding to the ER Alpha-LBD (GST) is detected by a test compound's ability to displace a fluorescent ligand (Fluormone™ ES2 Green tracer) from the ER Alpha-LBD (GST), which results in a loss of FRET signal between the Tb-anti-GST antibody and the tracer. When running the assay, Fluormone™ ES2 Green tracer is added to ligand test compounds or solvent controls followed by addition of a mixture of the ER Alpha-LBD (GST) and terbium anti-GST antibody. After an incubation period at room temperature, the TR-FRET ratio of 520:495 emissions are calculated and used to determine the $IC_{50}$ from a dose response curve of the compound.

g. ER and PR functional assays: COS cells are transfected with 25 ng rat progesterone receptor (PR) and 250 ng GRE-LUC or 50 ng human estrogen receptor a (ER) and 250 ng ERE-LUC. Cells are also transfected with 10 ng CMV-renilla LUC in OptiMEM medium using lipofectamine transfection reagent. Twenty-four hours after transfection medium is changed to DME+5% csFBS w/o and treated with compounds in the presence of 0.1 nM progesterone for PR and estradiol for ER. Twenty four hours after treatment, cells are harvested and luciferase assay is performed using dual luciferase assay kit. The firefly values are normalized to renilla luciferase values and represented as a ratio.

h. Evaluation of test compound in mouse xenograft model: To examine the in vivo antitumor activity of test compound, tumor growth experiments are performed in a cell line xenograft model. Male NOD SCID Gamma (NSG) mice are housed as five animals per cage and are allowed free access to water and commercial rodent chow. 22RV1 cells (grown in RPMI+10% FBS) mixed with 50% matrigel basement membrane are implanted subcutaneously in castrated mice. Alternatively, an antiandrogen resistant cell line other than 22RV1, such as MR49F or VCaP, is used. Once the tumors reach 200-500 mm$^3$, the animals are randomized and treated intraperitoneally with vehicle (DMSO:PEG-300:corn oil 10:30:60 ratio) or test compound. Tumors are measured thrice weekly and the volume is calculated using the formula length*width*width*0.5. Animals are sacrificed at the end of 28 days of treatment and the tumors are weighed and stored for further processing. The tumor growth inhibition (TGI) is calculated by comparing the control group's tumor measurements with the other study groups. TGI is calculated for each group using the formula listed below:

$$TGI(\%) = [1 - (TV_{Treatment\_DayN} - TV_{Treatment\_Day0}) / (TV_{Vehicle\_DayN} - TV_{Vehicle\_Day0})] \times 100\%$$

$TV_{Treatment\_DayN}$ is the average tumor volume of a treatment group on a given day, $TV_{Treatment\_Day0}$ is the average tumor volume of the treatment group on the first day of treatment, $TV_{Vehicle\_DayN}$ is the average tumor volume of the vehicle control group on a given day, and $TV_{Vehicle\_Day0}$ is the average tumor volume of the vehicle group on the first day of treatment.

Biological Example 2

AR binding assay: To assess AR binding, test compound (top dose 10 µM, 4 fold serial dilution, 8 point dose response) and control (progesterone) were transferred to the assay plate. Cytosol from LnCaP cells was added to the plate, followed by addition of radiolabeled $^3$H-R1881 at a final concentration of 1 nM. The plate was sealed, and the reaction was incubated at 300 rpm at 4° C. for 24 hrs. Radioligand absorption buffer (10 mM Tris-HCl, pH 7.4; 1.5 mM EDTA; 1 mM DTT; 0.25% charcoal; 0.0025% dextran) was then added to the plate, mixed, and incubated at 4° C. for 15 minutes. The plate was then centrifuged at 3000 rpm for 30 minutes at 4° C. The supernatant was transferred to the scint-tube and Tri-carb was used for scintillation counting. The data was analyzed using GraphPadPrism v5.0 and binding $IC_{50}$ was determined as the concentration where 50% inhibition of radioligand binding was observed.

GR binding assay: To assess GR binding, test compound (top dose 1 µM, 4 fold serial dilution, 8 point dose response) and control (dexamethasone) were transferred to the assay plate. Cytosol from IM-9 cells was added to the plate, followed by addition of radiolabeled $^3$H-Dexamethasone at a final concentration of 1.5 nM. The plate was sealed, and the reaction was incubated at 300 rpm at 4° C. for 24 hrs. Radioligand absorption buffer (10 mM Tris-HCl, pH 7.4; 1.5 mM EDTA; 1 mM DTT; 0.25% charcoal; 0.0025% dextran) was then added to the plate, mixed, and incubated at 4° C. for 15 minutes. The plate was then centrifuged at 3000 pm for 30 minutes at 4° C. The supernatant was transferred to the scint-tube and Tri-carb was used for scintillation counting. The data was analyzed using GraphPadPrism v5.0 and binding $IC_{50}$ was determined as the concentration where 50% inhibition of radioligand binding was observed.

PR binding assay: Progesterone PR-B receptors from human breast carcinoma T47D cells were used in modified $Na_2HPO_4/NaH_2PO_4$ buffer pH 7.4. Compounds were screened at a range of doses (Top dose 40 nM, 4 fold serial dilution, 8 point dose response) and dispensed into the assay plate. Supernatant of $1.2 \times 10^5$ cells aliquot were added to the assay plate and incubated with 0.5 nM [$^3$H]Progesterone for 20 hours at 4° C. Membranes were filtered and washed, the filters were then counted to determine [$^3$H]Progesterone specifically bound. Binding $IC_{50}$ was determined as the concentration where 50% inhibition of radioligand binding was observed.

ER binding assay: ERα binding was assessed using the LanthaScreen® TR-FRET ER Alpha Competitive Binding kit from ThermoFisherScientific. In this assay, a terbium-labeled anti-GST antibody was used to indirectly label GST-tagged ER Alpha-ligand binding domain (LBD) by binding to its GST tag. Competitive binding to the ER Alpha-LBD (GST) was detected by a test compound's ability to displace a fluorescent ligand (Fluormone™ ES2 Green tracer) from the ER Alpha-LBD (GST), which results in a loss of FRET signal between the Tb-anti-GST antibody and the tracer. Briefly, to assess ER binding of the DDC compounds, the test compounds (top dose 10 µM, 4 fold serial dilution, 8 point dose response) and controls were transferred to the assay plate. The Fluormone™ ES2 Green tracer (3 nM final concentration with assay buffer) was added to the assay plate. This was followed by addition of a mixture of the ER Alpha-LBD (GST) and terbium anti-GST antibody. After a 2 h incubation period at room temperature, the plate was read on the Envision plate reader and the TR-FRET ratio of 520:495 emissions were calculated and used to determine the $IC_{50}$ from a dose response curve of the compound.

AR antagonism assay: To evaluate AR antagonist activity, test compound was added to the assay plate (top dose 10 µM, 3 fold serial dilution, 10 point dose response). HEK293 cells stably expressing the full-length androgen receptor were seeded at a density of 20,000 cells/well in the assay plate. The assay plate was then incubated at room temperature for 10 minutes and at 37° C., 5% $CO_2$ for 20 minutes. Testosterone was added to the assay plate at 1 nM final concentration and the assay plate incubated at 37° C., 5% $CO_2$ for 20 h. After the incubation period, Steady-glo was added to the assay plate and mixed at room temperature for 20 minutes on an orbital shaker, before reading out on the EnVision plate reader.

GR antagonism assay: To evaluate GR antagonist activity, test compound was added to the assay plate (top dose 5 µM, 4 fold serial dilution, 8 point dose response). HEK293 cells stably expressing the ligand binding domain of the glucocorticoid receptor were seeded at a density of 40,000 cells/well in the assay plate. The assay plate was then incubated at 37° C., 5% $CO_2$ for 30 minutes. Dexamethasone was added to the assay plate at 1.5 nM final concentration and the assay plate was incubated at 37° C., 5% $CO_2$ for 20 h. After the incubation period, Dual-glo luciferase reagent was added to the assay plate and mixed at room temperature for 20 minutes on an orbital shaker, before reading out on the EnVision plate reader.

PR coactivator antagonist assay: Test compound (Top dose 10 µM, 4 fold serial dilution, 8 point dose response) and/or vehicle was incubated with the 2.5 nM Progesterone Receptor (PR)-LBD and coactivator peptide for 30 minutes at RT. Determination of the amount of complex formed was read spectrofluorimetrically (excitation: 337 nm, emission: 520/490 nm). Test compound-induced inhibition of 10 nM progesterone-induced fluorescence response by 50 percent or more (≥50%) indicates receptor antagonist activity.

ER antagonism assay: To evaluate ER antagonist activity, SK-BR-3 cells were seeded at a density of 30000 cells/well in the assay plate. The assay plate was then incubated at 37° C., 5% CO2 for 24 h. A mixture of ERE plasmid and ER in opti-MEM media was incubated with lipofectamine 3000 in Opti-MEM media and incubated at room temperature for 15 mins. 10 µl of this transfection mix was added to each well of the assay plate and the assay plate was incubated at 37° C., 5% $CO_2$ for 24 h. 100 nM β-Estradiol in 10 µL medium or 10 µL medium (control wells) was added to corresponding wells of assay plate and incubated at 37° C. 5% $CO_2$ for 24 h. After the incubation period, 50 µl of Dual-glo luciferase reagent was added to the assay plate and mixed at room temperature for 20 mins on an orbital shaker, before reading out on the EnVision plate reader. 50 µL of Stop & Glo reagent was added to assay plate, mixed at room temperature for 20 minutes, and read on the Envision plate reader.

Data for certain compounds as tested in the above assays is shown below in Table 2.

TABLE 2

| No. | AR binding | AR antagonism | GR binding | GR antagonism | PR binding | PR antagonism | ER binding | ER antagonism |
|---|---|---|---|---|---|---|---|---|
| 1 | | | | | | | a | b |
| 2 | | | | | | | a | b |
| 3 | a | b | a | b | a | a | | |
| 5 | b | d | a | b | a | a | | |
| 6 | b | b | | | | | | |
| 7 | d | b | | | | | | |
| 8 | b | d | | | | | | |
| 9 | b | d | | | | | | |
| 10 | b | d | | | | | | |
| 11 | b | b | | | | | | |
| 12 | d | b | | | | | | |
| 13 | | | | | | | b | b |
| 14 | b | b | | | | | | |
| 18 | b | d | | | | | | |
| 20 | b | d | | | | | | |
| 21 | b | d | | | | | | | a: $IC_{50}$ = <10 nM;
b: $IC_{50}$ = 10-500 nM;
c: $IC_{50}$ = 501-1,000 nM;
d: $IC_{50}$ = >1,000 nm

Cell viability assay: LNCap, 22Rv1, MCF7, MDAMB361, T47D, and IEC6 cells are seeded at a density of 500-2000 cells/well in 96 well plates, and a 'T0' (timepoint 0) was included along with the assay plate. The plates are then incubated at 37° C., 5% $CO_2$ in a cell culture incubator overnight. On the next day, the 'T0' plate was assayed using CellTiterGlo (Promega, Inc) according to the manufacturer's instructions. The appropriate compounds are diluted in DMSO and added to the assay plate (final DMSO concentration of 0.1-0.2%) on the next day. The assay plates are incubated for 6 days at 37° C., 5% $CO_2$. After the incubation period, the plates are assayed using CellTiterGlo (Promega, Inc) according to the manufacturer's instructions and luminescence was read on the EnVision plate reader. Inhibition of the tested compounds was determined by the following formula: Inhibition rate (%)=(1−(RLU compound−RLU day0)/(RLU control−RLU day0))*100%. GraphPadPrism was used to analyze the data and determine $GI_{50}/IC_{50}$ values.

Data for certain compounds as tested in the above assay is shown below in Table 3.

TABLE 3

| No. | LNCap ($GI_{50}$, nM) | 22RV1 ($GI_{50}$, nM) | T47D ($GI_{50}$, nM) | MCF7 ($GI_{50}$, nM) | MDA-MB-361 ($GI_{50}$, nM) | IEC-6 ($IC_{50}$, nM) |
|---|---|---|---|---|---|---|
| 1 | | | | b | b | |
| 2 | | | | b | b | |
| 3 | b | | b | | | c |
| 4 | b | | b | | | |
| 5 | b | | b | | | c |
| 6 | b | b | | | | b |
| 7 | b | b | | | | c |
| 8 | b | b | | | | d |
| 9 | c | | b | | | d |
| 10 | b | | b | | | |
| 11 | b | b | | | | c |
| 12 | b | c | | | | d |
| 13 | | | | b | b | c |
| 14 | b | b | | | | d |
| 16 | c | | b | b | d | d |
| 17 | d | | d | d | d | d |
| 18 | b | b | | | | d |
| 19 | b | | b | b | b | d |
| 20 | b | b | | | | d |
| 21 | b | b | | | | d |
| 22 | b | | b | | | b |
| 23 | c | | b | | | b |
| 24 | b | | b | | | c |
| 25 | b | b | | | | d |
| 26 | b | b | | | | | a: = <10 nM;
b: = 10-500 nM;
c: = 501-1,000 nM;
d: = >1,000 nm

Biological Example 3

In vitro assay: Compounds as described herein can be tested in an in vitro assay for topoisomerase I activity as described in Nitiss J L, Soans E, Rogojina A, Seth A, Mishina M. Topoisomerase assays. Curr Protoc Pharmacol. 2012; Chapter 3: Unit 3.3-3.3. doi:10.1002/0471141755.ph0303s57.

In vivo xenograft model: The LNCaP-FGC tumor cells are maintained in vitro in RPMI1640 medium supplemented with 10% heat inactivated fetal bovine serum at 37° C. in an atmosphere of 5% $CO_2$ in air. The tumor cells are routinely subcultured twice weekly. The cells growing in an exponential growth phase are harvested and counted for tumor inoculation. Each mouse is inoculated subcutaneously at the right flank with LNCaP-FGC tumor cells (10×10$^6$) in 0.2 mL of PBS mixed with Matrigel (50:50) for tumor development. The treatments are started on day 20 after tumor inoculation when the average tumor volume reached 122 mm$^3$. The test articles or vehicle control are administered to the mice according to the group assignment. Animal body weights are also measured twice weekly. Tumor size is measured twice weekly in two dimensions using a caliper, and the volume expressed in mm$^3$ using the formula: V=0.5 a×b$^2$ where a and b are the long and short diameters of the tumor, respectively. The tumor sizes are then used for the calculation of T/C (tumor/control) and TGI (tumor growth inhibition) values. The T/C value (in percent) is calculated where T and C are the mean volume of the treated and control groups, respectively, on a given day. TGI is calculated for each group using the formula: TGI (%)=[1−(Ti−T0)/(Vi−V0)]×100; Ti is the average tumor volume of a treatment group on PG-D29, T0 is the average tumor volume of the treatment group on the day of treatment start, Vi is the average tumor volume of the vehicle control group on the same day with Ti, and V0 is the average tumor volume of the vehicle group on the day of treatment start. All the mice are taken down on day 30 when the tumor volume of the vehicle treated group reached ~1500-2000 mm³.

What is claimed is:

1. A compound of Formula III, or a stereoisomer, mixture of stereoisomers, or pharmaceutically acceptable salt thereof:

$$A^1\text{-}L^1\text{-}B^1 \qquad \text{III}$$

wherein:
$L^1$ is a covalent bond or a linking moiety;
$B^1$ is a nuclear receptor-targeting epitope selected from the group consisting of;

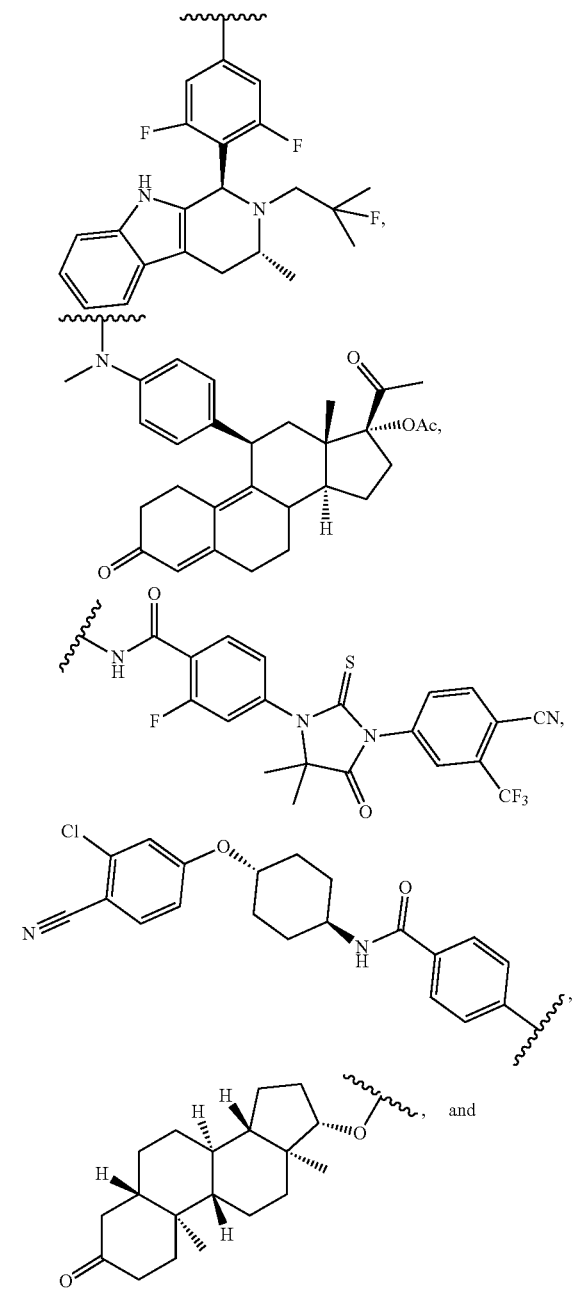

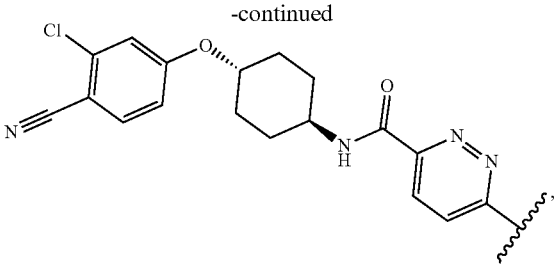

wherein the wavy bond refers to the point of connection to $L^1$; and
$A^1$ is of Formula IA:

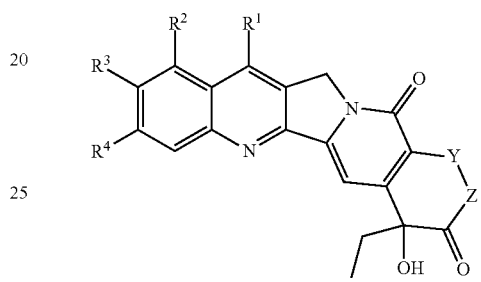

IA wherein:
Y is a bond, —CH₂—, or —CH₂—CH₂—;
Z is a bond or O;
$R^1$, $R^2$, $R^3$, and $R^4$, are each independently hydrogen, halo, cyano, nitro, —OR¹⁵, —SR¹⁵, —NR¹⁵R¹⁶, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R¹⁵, —C(=O)OR¹⁵, —OC(=O)R¹⁵, —C(=O)NR¹⁵R¹⁶, —NR¹⁵C(=O)R¹⁶, —NR¹⁵C(=O)OR¹⁶, —S(=O)₁₋₂R¹⁵, —S(=O)₁₋₂NR¹⁵R¹⁶, —NR¹⁵S(=O)₁₋₂R¹⁶, —Si(R¹⁵)₃, or —C=NOR¹⁵, wherein each alkyl, alkenyl, alkynyl, cycloalkyl, heterocyclyl, aryl and heteroaryl of $R^1$, $R^2$, $R^3$, and $R^4$, are independently optionally substituted with one or more R¹⁰ as valency permits;
or $R^1$ and $R^2$ are taken together with the atoms to which they are attached to form a $C_{3-10}$ cycloalkyl, heterocyclyl, aryl, or heteroaryl, optionally substituted with one or more R¹⁰ as valency permits;
or $R^2$ and $R^3$ are taken together with the atoms to which they are attached to form a $C_{3-10}$ cycloalkyl, heterocyclyl, aryl, or heteroaryl, optionally substituted with one or more R¹⁰ as valency permits;
or $R^3$ and $R^4$ are taken together with the atoms to which they are attached to form a $C_{3-10}$ cycloalkyl, heterocyclyl, aryl, or heteroaryl, optionally substituted with one or more R¹⁰ as valency permits;
each R¹⁰ is independently halo, cyano, nitro, —OR¹⁷, —SR¹⁷, —SF₅, —NR¹⁷R¹⁸, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R¹⁷, —C(=O)OR¹⁷, —OC(=O)OR¹⁷, —OC(=O)R¹⁷, —C(=O)NR¹⁷R¹⁸, —OC(=O)NR¹⁷R¹⁸, —NR¹⁷C(=O)NR¹⁷R¹⁸, —S(=O)₁₋₂R¹⁷, —S(=O)₁₋₂NR¹⁷R¹⁸, —NR¹⁷S(=O)₁₋₂R¹⁸, —NR¹⁷S(=O)₁₋₂NR¹⁷R¹⁸, —NR¹⁷C(=O)R¹⁸, —NR¹⁷C(=O)OR¹⁸, —Si(R¹⁷)₃, or —C=NOR¹⁷, wherein each alkyl, alkenyl, alkynyl, cycloalkyl, heterocyclyl, aryl and heteroaryl of R¹⁰ are independently optionally substituted with one or more halo or C$_{1-12}$ alkyl optionally substituted by oxo, halo, hydroxyl, or amino as valency permits; and each R$^{15}$ and R$^{16}$ is independently hydrogen, C$_{1-12}$ alkyl, C$_{2-12}$ alkenyl, C$_{2-12}$ alkynyl, or C$_{3-12}$ cycloalkyl, wherein each alkyl, alkenyl, alkynyl, or cycloalkyl is optionally independently substituted with oxo, halo, hydroxyl, or amino as valency permits; or R$^{15}$ and R$^{16}$ are taken together with the atoms to which they are attached to form heterocyclyl optionally substituted by halo or C$_{1-12}$ alkyl optionally substituted by oxo, halo, hydroxyl, or amino; and each R$^{17}$ and R$^{18}$ is independently hydrogen, C$_{1-12}$ alkyl, C$_{2-12}$ alkenyl, C$_{2-12}$ alkynyl, or C$_{3-12}$ cycloalkyl, wherein each C$_{1-12}$ alkyl, C$_{2-12}$ alkenyl, C$_{2-12}$ alkynyl, or C$_{3-12}$ cycloalkyl is optionally substituted with oxo, halo, hydroxyl, or amino as valency permits; or R$^{17}$ and R$^{18}$ are taken together with the atoms to which they are attached to form heterocyclyl optionally substituted by halo or C$_{1-12}$ alkyl optionally substituted by oxo, halo, hydroxyl, or amino;

wherein one or more atoms in one of R$^1$, R$^2$, and R$^3$ of Formula IA is replaced by a direct covalent bond to L$^1$.

2. The compound of claim 1, or a stereoisomer, mixture of stereoisomers, or pharmaceutically acceptable salt thereof wherein A$^1$ is of Formula IB:

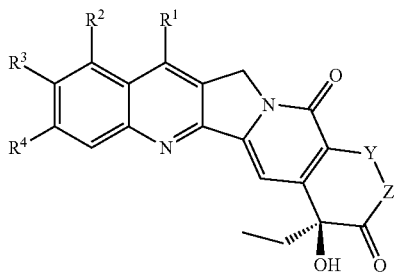

IB wherein:
R$^1$ is hydrogen, —C=NOR$^{15}$, or C$_{1-6}$ alkyl optionally substituted with one or more R$^{10}$;
R$^2$ is hydrogen, C$_{1-6}$ alkyl, —NR$^{17}$R$^{18}$, —NO$_2$, —C$_{1-6}$ alkylene-O—C$_{1-6}$ alkyl, or —C$_{1-6}$ alkylene-NR$^{17}$R$^{18}$; or
R$^1$ and R$^2$ are taken together with the atoms to which they are attached to form a C$_{3-10}$ cycloalkyl optionally substituted with one or more R$^{10}$;
R$^3$ is hydrogen, hydroxy, halo, C$_{1-6}$ alkyl, or —O—C$_{1-6}$ alkyl;
R$^4$ is hydrogen, halo, C$_{1-6}$ alkyl, or —O—C$_{1-6}$ alkyl; or
R$^3$ and R$^4$ together form a —O—CH$_2$—O— or —O—CH$_2$CH$_2$—O—;
Y is a bond, —CH$_2$—, or —CH$_2$—CH$_2$—; and
Z is a bond or O;
wherein one or more atoms in one of R$^1$, R$^2$, and R$^3$ is replaced by a direct covalent bond to L$^1$.

3. The compound of claim 1, or a stereoisomer, mixture of stereoisomers, or pharmaceutically acceptable salt thereof, wherein Y is —CH$_2$— and Z is O.

4. The compound of claim 1, or a stereoisomer, mixture of stereoisomers, or pharmaceutically acceptable salt thereof, wherein Formula IA is:

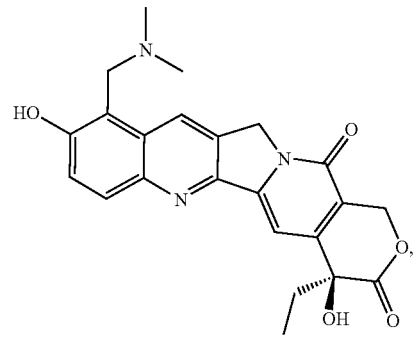

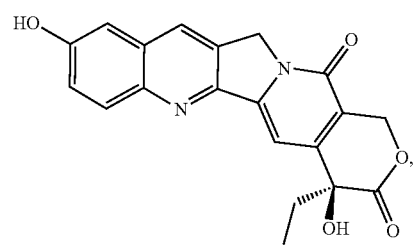

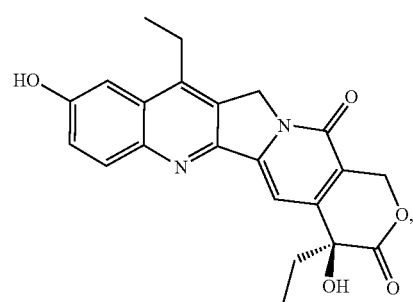

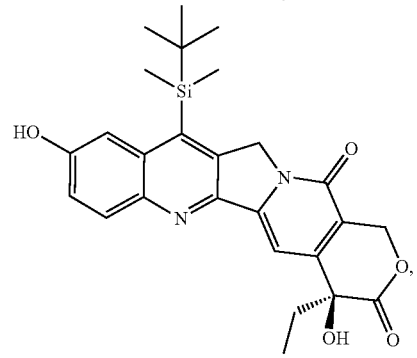

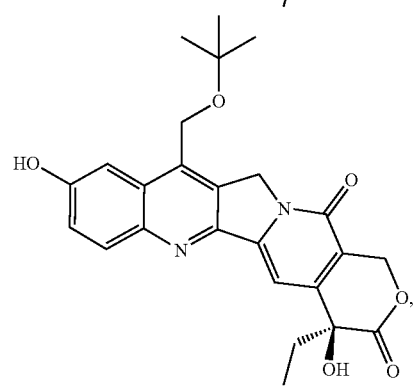

-continued

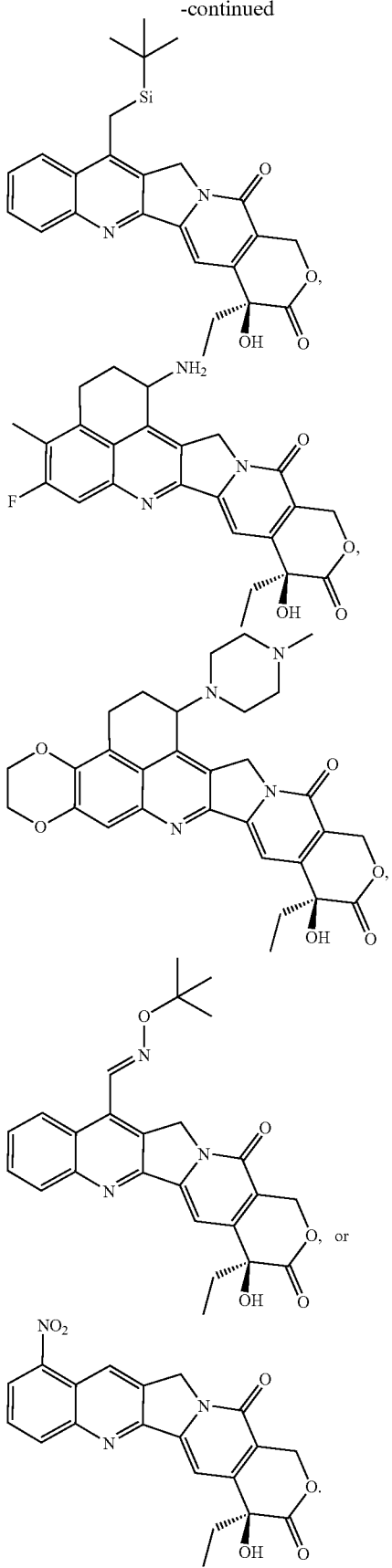

5. The compound of claim 1, or a stereoisomer, mixture of stereoisomers, or pharmaceutically acceptable salt thereof, wherein $A^1$ is:

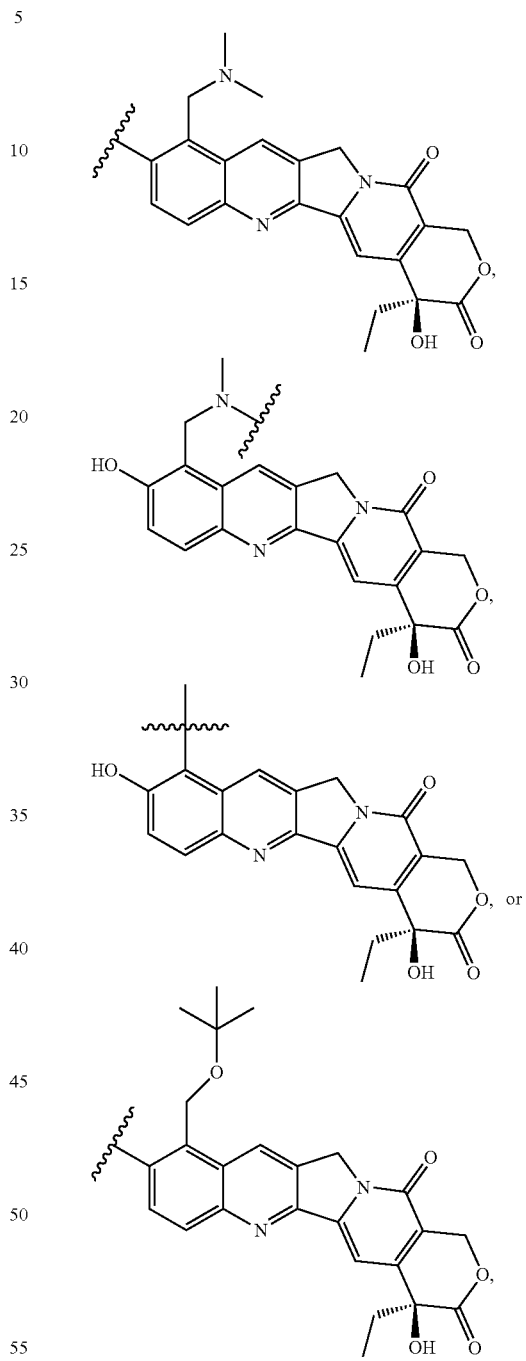

wherein the wavy bond refers to the point of connection to $L^1$.

6. The compound of claim 1, or a stereoisomer, mixture of stereoisomers, or pharmaceutically acceptable salt thereof, wherein $L^1$ is of formula:

$-(L^a)_q-$, wherein:
each $L^a$ is $-NR^{110}-$, $-O-$, $-S(O)_{0-2}-$, $-NR^{110}C(O)-$, $-C(O)NR^{110}-$, $-NR^{110}C(O)NR^{110}-$, —NR$^{110}$S(O)$_2$—, —S(O)$_2$NR$^{110}$—, —NR$^{110}$S(O)$_2$NR$^{110}$—, —CR$^{120}$=N—NR$^{110}$—, —NR$^{110}$—N=CR$^{120}$—, —C(O)—, —OC(O)—, —OC(O)O—, —C(O)O—, alkylene, alkenylene, alkynylene, arylene, cycloalkylene, heterocyclylene, or heteroarylene, wherein each alkylene, alkenylene, alkynylene, arylene, cycloalkylene, heterocyclylene, or heteroarylene is independently optionally substituted with one to five substituents independently selected from oxo, halo, C$_{1-4}$ alkyl, C$_{1-4}$ haloalkyl, C$_{1-4}$ alkoxy, C$_{1-4}$ haloalkoxy, aryl, heteroaryl, cycloalkyl, and heterocyclyl;

each R$^{110}$ is independently hydrogen, C$_{1-4}$ alkyl, C$_{1-4}$ haloalkyl, C$_{1-4}$ alkoxy, C$_{1-4}$ haloalkoxy aryl, heteroaryl, cycloalkyl, or heterocyclyl;

each R$^{120}$ is independently hydrogen, C$_{1-4}$ alkyl, C$_{1-4}$ haloalkyl, C$_{1-4}$ alkoxy, C$_{1-4}$ haloalkoxy aryl, heteroaryl, cycloalkyl, or heterocyclyl; and q is an integer from 0 to 20.

7. The compound of claim 1, or a stereoisomer, mixture of stereoisomers, or pharmaceutically acceptable salt thereof, wherein L$^1$ is of the formula:

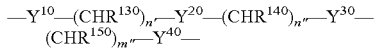

wherein:

each of Y$^{10}$, Y$^{20}$, Y$^{30}$, and Y$^{40}$ are independently a bond, —NR$^{110}$—, —O—, —S(O)$_{0-2}$—, —NR$^{110}$C(O)—, —C(O)NR$^{110}$—, —NR$^{110}$C(O)NR$^{110}$—, —NR$^{110}$S(O)$_2$—, —S(O)$_2$NR$^{110}$—, —NR$^{110}$S(O)$_2$NR$^{110}$—, —CR$^{120}$=N—NR$^{110}$—, —NR$^{110}$—N=CR$^{120}$—, —C(O)—, —OC(O)—, —OC(O)O—, —(CH$_2$CH$_2$O)$_{1-5}$—, —C(O)O—, alkylene, alkenylene, alkynylene, arylene, cycloalkylene, heterocyclylene, and heteroarylene;

wherein each alkylene, alkenylene, alkynylene, arylene, cycloalkylene, heterocyclylene, or heteroarylene is independently optionally substituted with one to five substituents independently selected from oxo, halo, C$_{1-4}$ alkyl, C$_{1-4}$ haloalkyl, C$_{1-4}$ alkoxy, or C$_{1-4}$ haloalkoxy;

each R$^{110}$ is independently hydrogen, C$_{1-4}$ alkyl, C$_{1-4}$ haloalkyl, C$_{1-4}$ alkoxy, C$_{1-4}$ haloalkoxy aryl, heteroaryl, cycloalkyl, or heterocyclyl;

each R$^{120}$ is independently hydrogen, C$_{1-4}$ alkyl, C$_{1-4}$ haloalkyl, C$_{1-4}$ alkoxy, C$_{1-4}$ haloalkoxy aryl, heteroaryl, cycloalkyl, or heterocyclyl;

each R$^{130}$ is independently hydrogen, C$_{1-4}$ alkyl, C$_{1-4}$ haloalkyl, C$_{1-4}$ alkoxy, C$_{1-4}$ haloalkoxy aryl, heteroaryl, cycloalkyl, or heterocyclyl;

each R$^{140}$ is independently hydrogen, C$_{1-4}$ alkyl, C$_{1-4}$ haloalkyl, C$_{1-4}$ alkoxy, C$_{1-4}$ haloalkoxy aryl, heteroaryl, cycloalkyl, or heterocyclyl;

each R$^{150}$ is independently hydrogen, C$_{1-4}$ alkyl, C$_{1-4}$ haloalkyl, C$_{1-4}$ alkoxy, C$_{1-4}$ haloalkoxy aryl, heteroaryl, cycloalkyl, or heterocyclyl; and n', n", and m" are each independently 0, 1, 2, 3, 4, 5, 6, 7, or 8.

8. The compound of claim 1, or a stereoisomer, mixture of stereoisomers, or pharmaceutically acceptable salt thereof, wherein L$^1$ is of the formula:

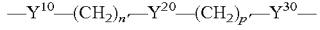

wherein each of Y$^{10}$, Y$^{20}$, and Y$^{30}$ are independently a bond, optionally substituted alkylene, optionally substituted heteroalkylene, optionally substituted arylene, optionally substituted heteroarylene, optionally substituted cycloalkylene, optionally substituted heterocyclylene, —CR$^{110}$R$^{120}$—, —NR$^{110}$—, —O—, —S(O)$_{0-2}$—, —NR$^{110}$C(O)—, —C(O)NR$^{110}$—, —NR$^{110}$S(O)$_2$—, —S(O)$_2$NR$^{110}$—, —CR$^{120}$=N—NR$^{110}$—, —NR$^{110}$—N=CR$^{120}$—, —OC(O)—, or —C(O)—;

each R$^{110}$ is independently hydrogen, C$_{1-4}$ alkyl, C$_{1-4}$ haloalkyl, aryl, heteroaryl, cycloalkyl, or heterocyclyl;

each R$^{120}$ is independently hydrogen, C$_{1-4}$ alkyl, C$_{1-4}$ haloalkyl, aryl, heteroaryl, cycloalkyl, or heterocyclyl; and n' and p' are each independently 0, 1, 2, 3, 4, 5, 6, 7, or 8.

9. The compound of claim 1, or a stereoisomer, mixture of stereoisomers, or pharmaceutically acceptable salt thereof, wherein the linking moiety is of the formula:

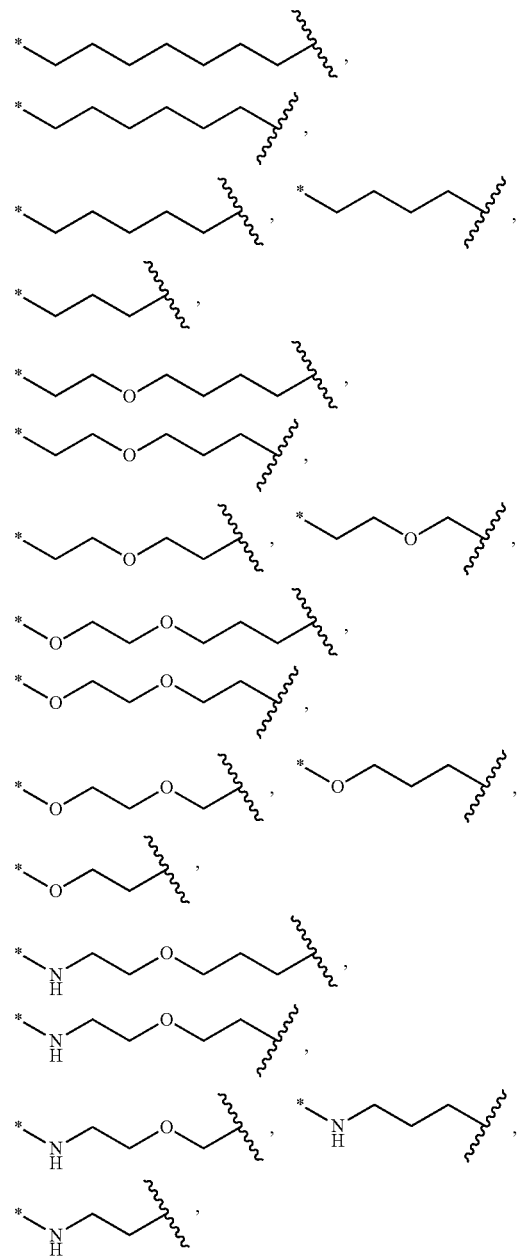

297
-continued
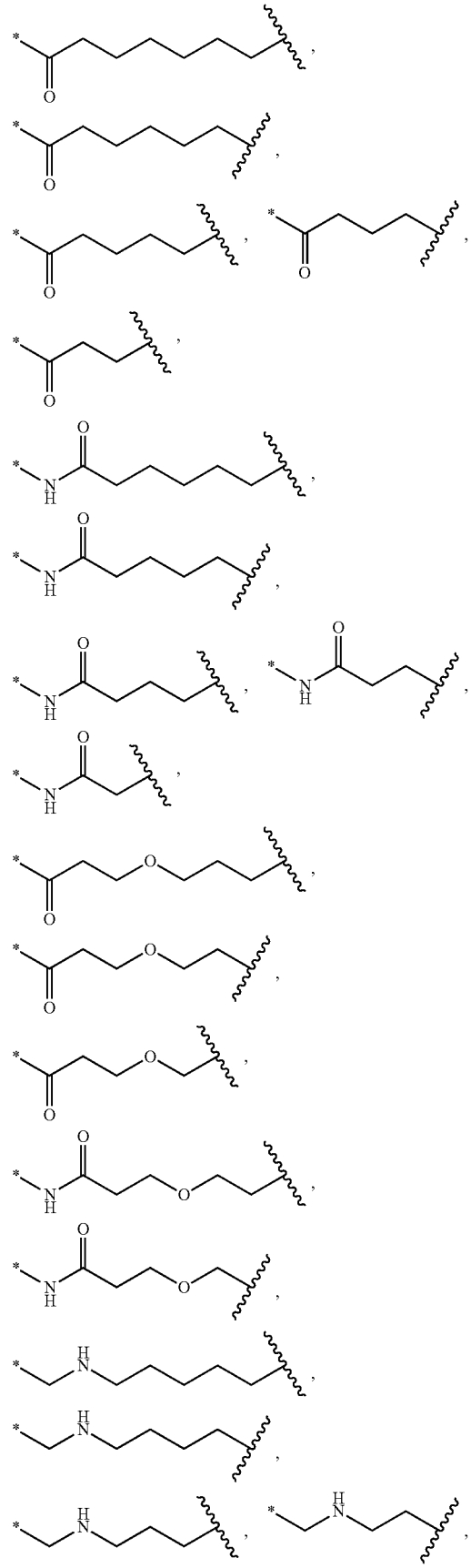
298
-continued
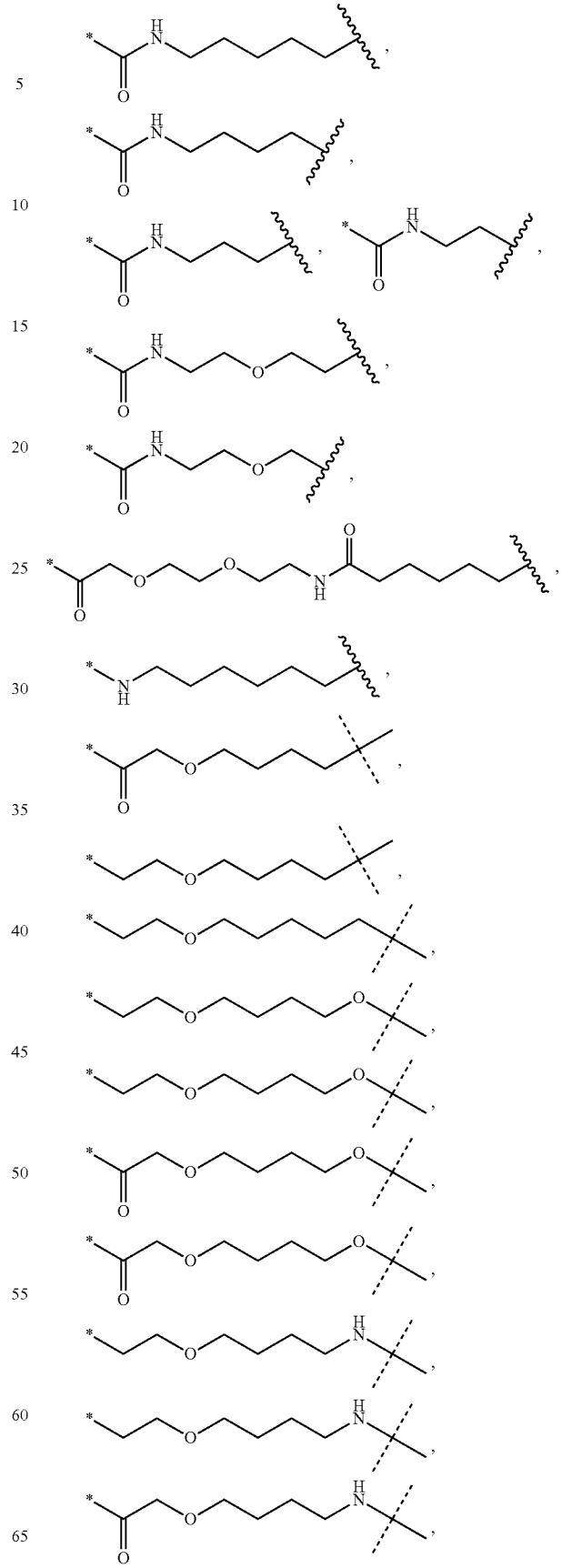

299
-continued
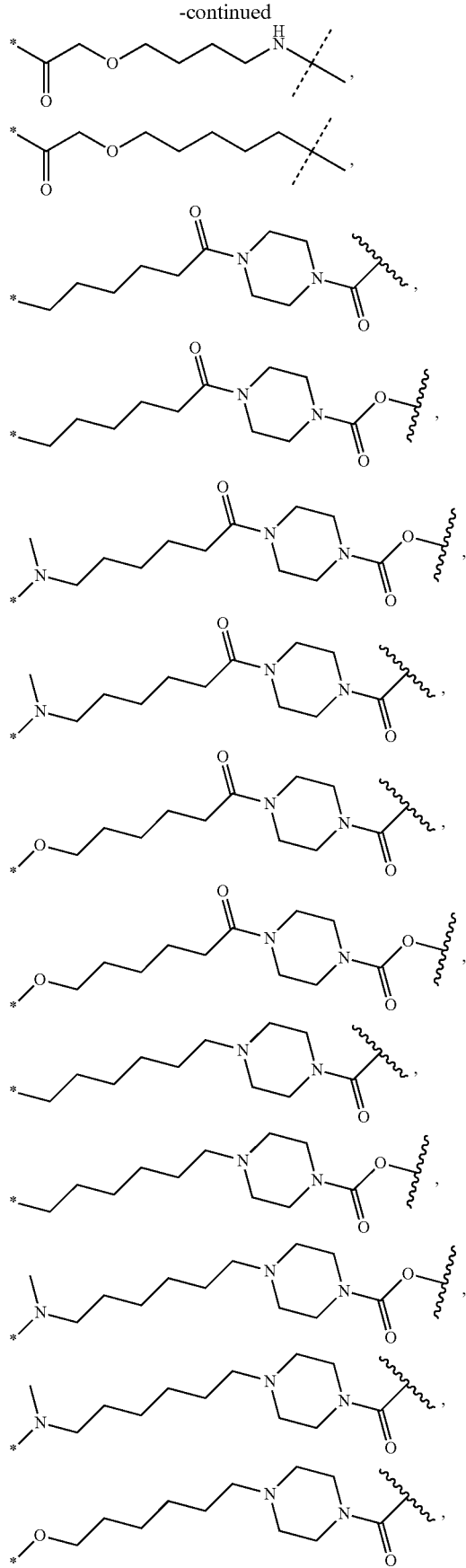
300
-continued
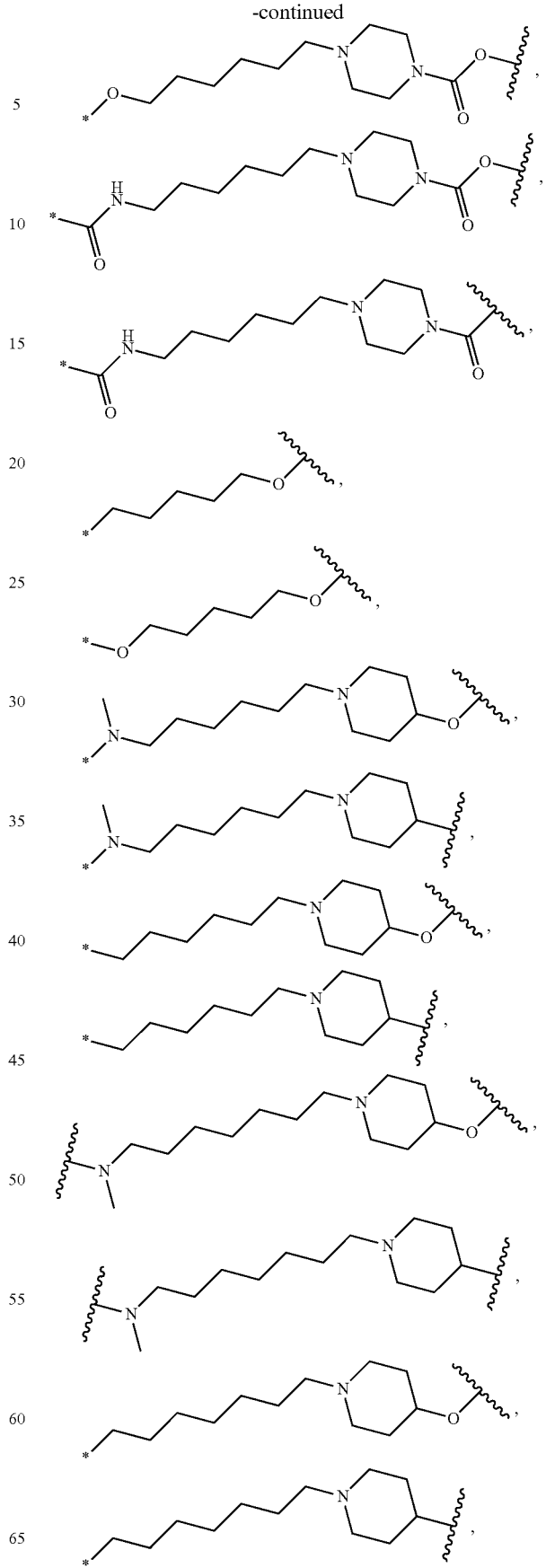

301
-continued
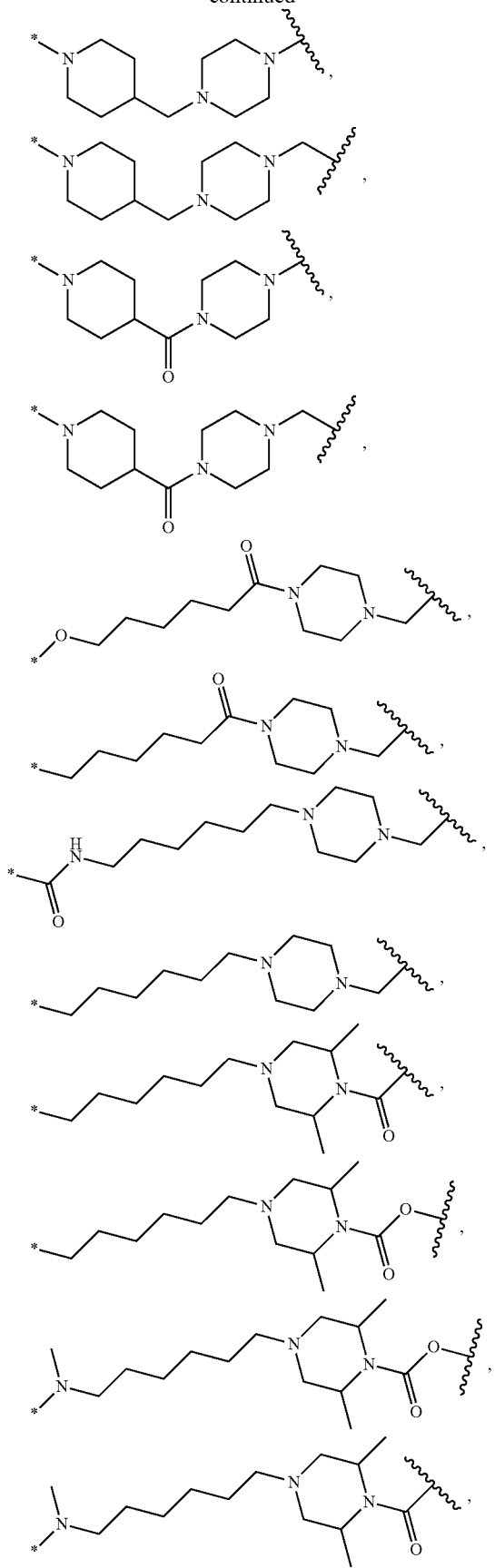
302
-continued
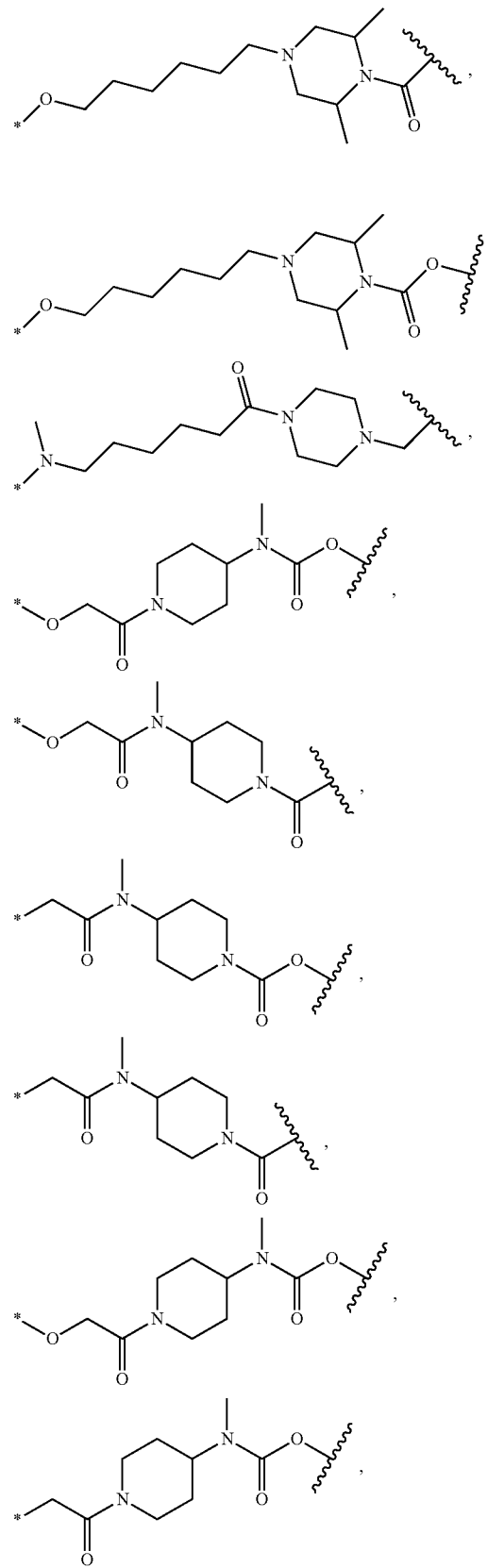

303
-continued
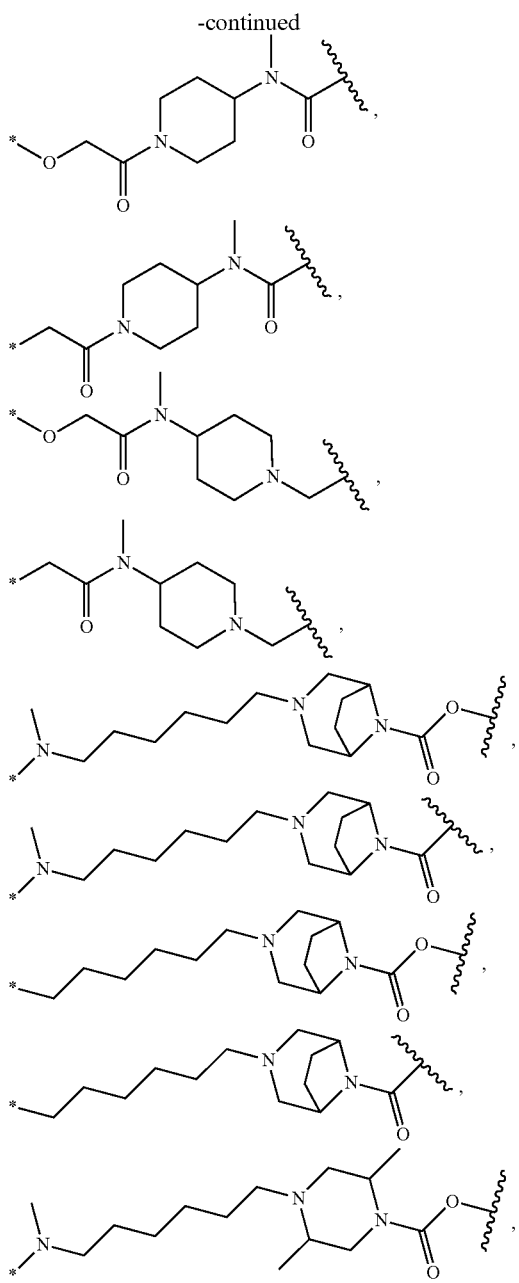
304
-continued
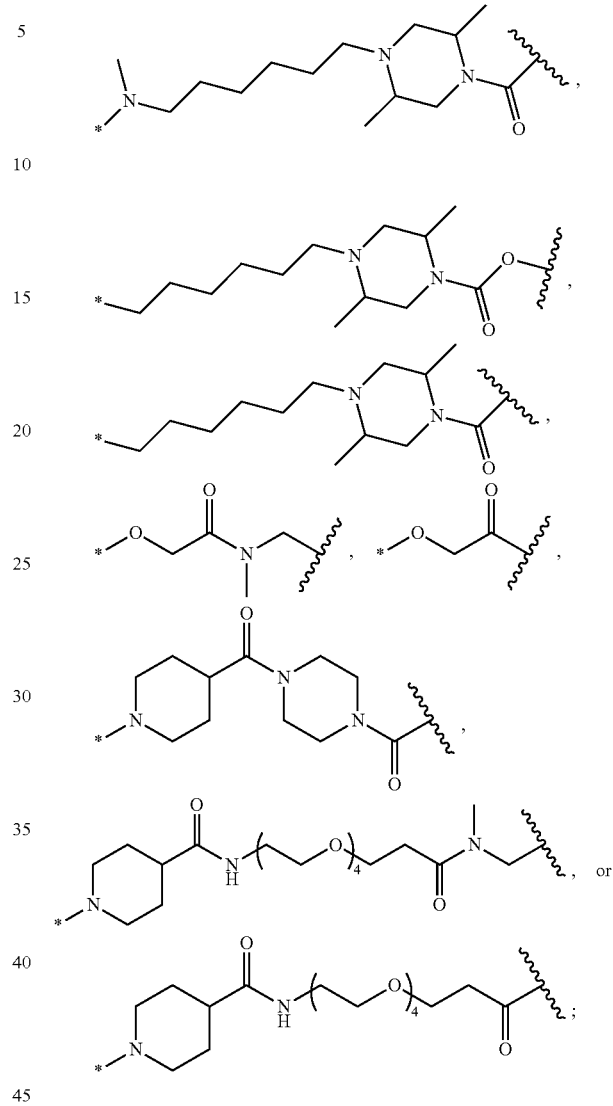
wherein the "*" and the wavy or dashed line each represent a covalent bond.
10. A compound selected from the group consisting of:
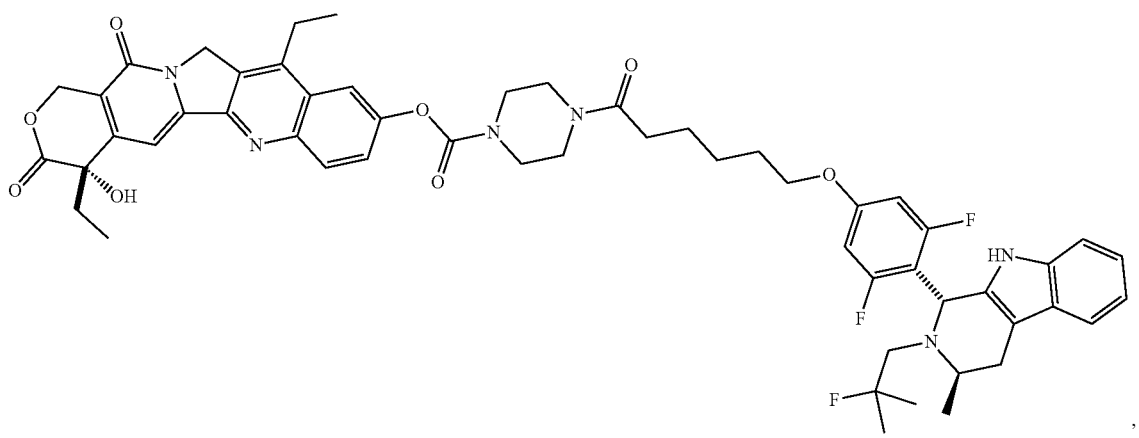

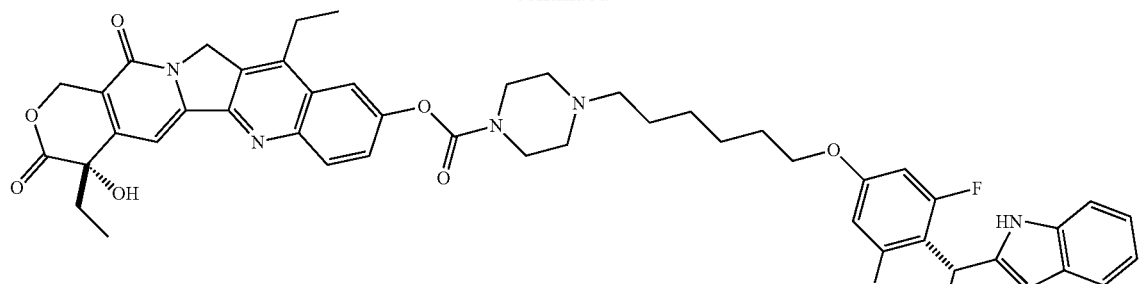
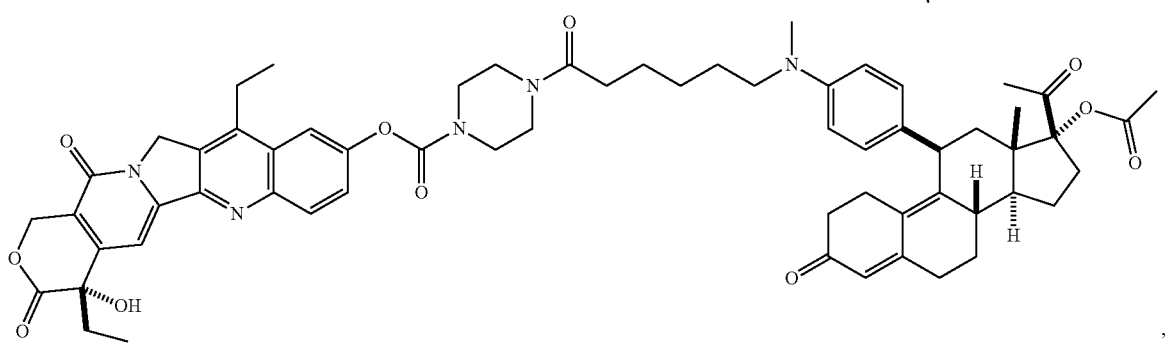
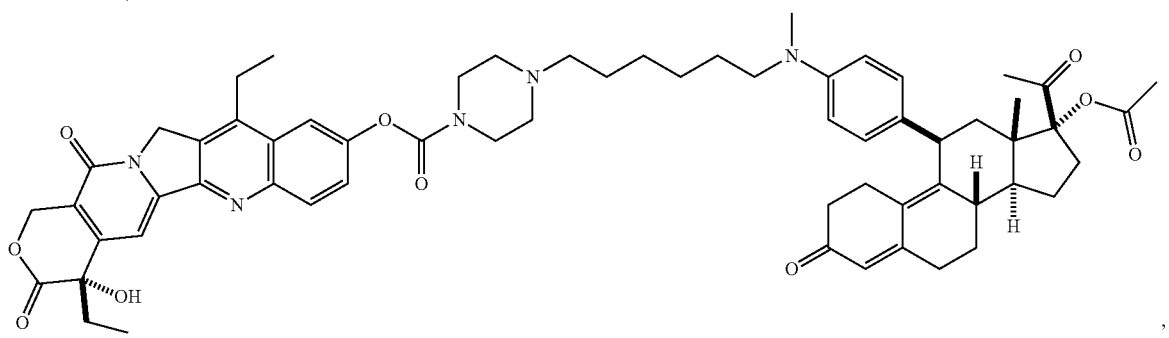
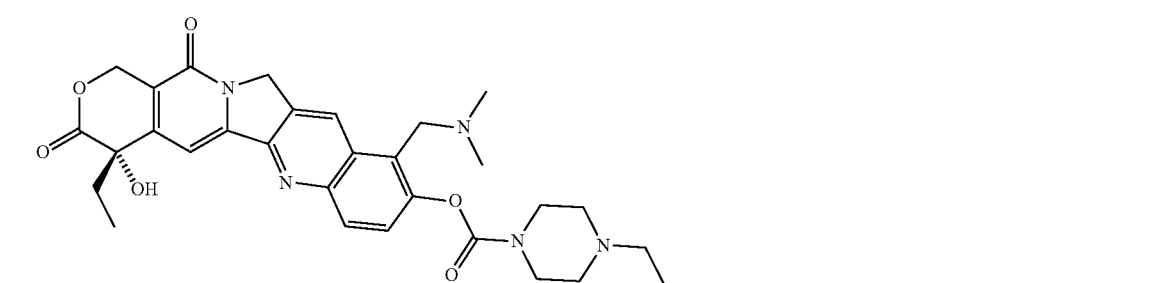
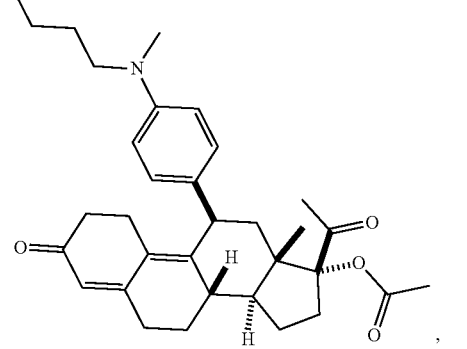

-continued
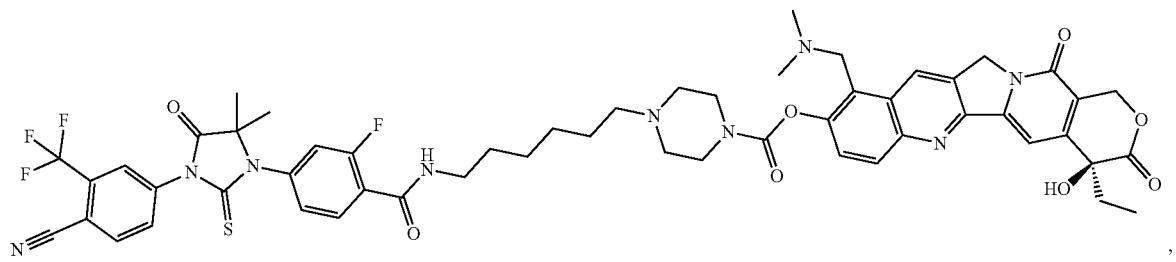
,
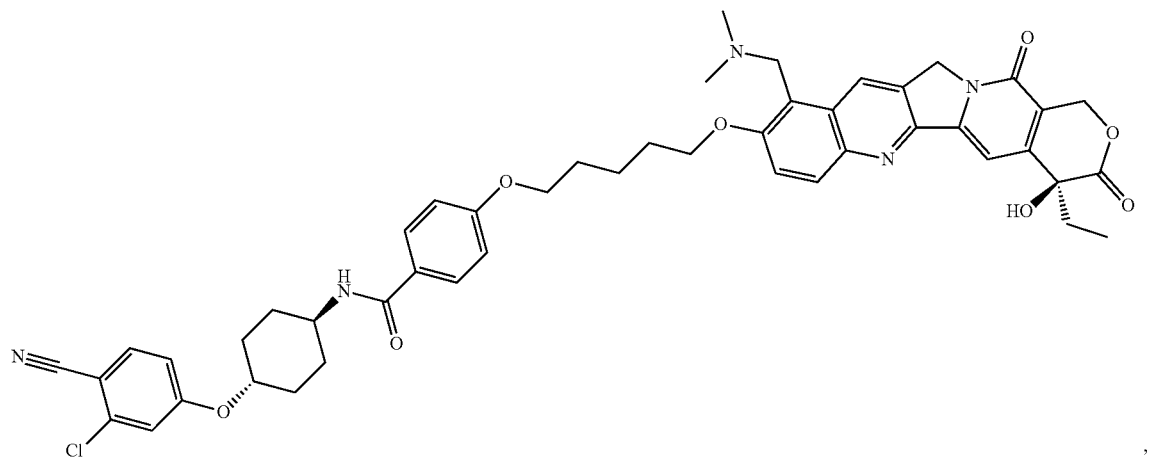
,
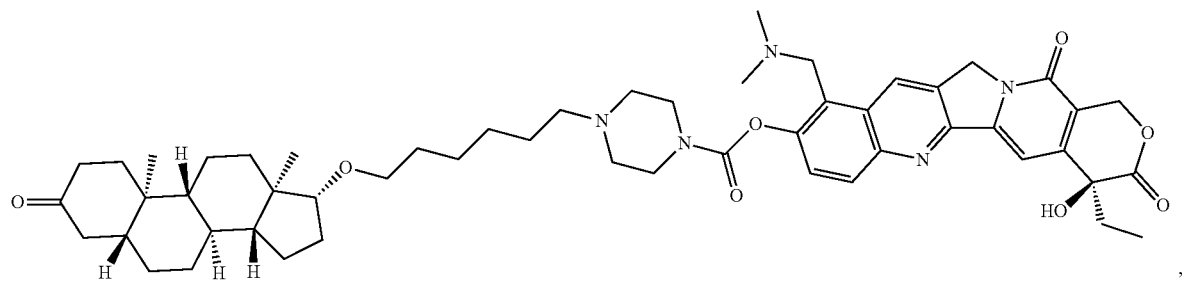
,
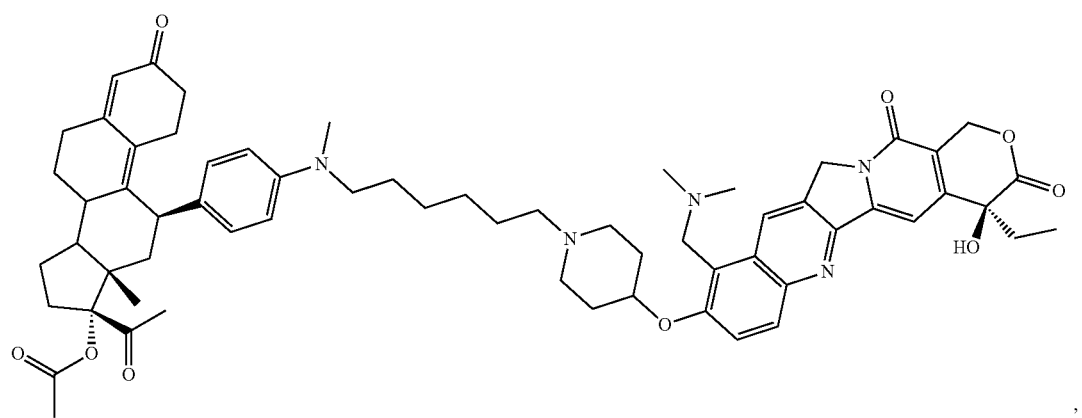
,

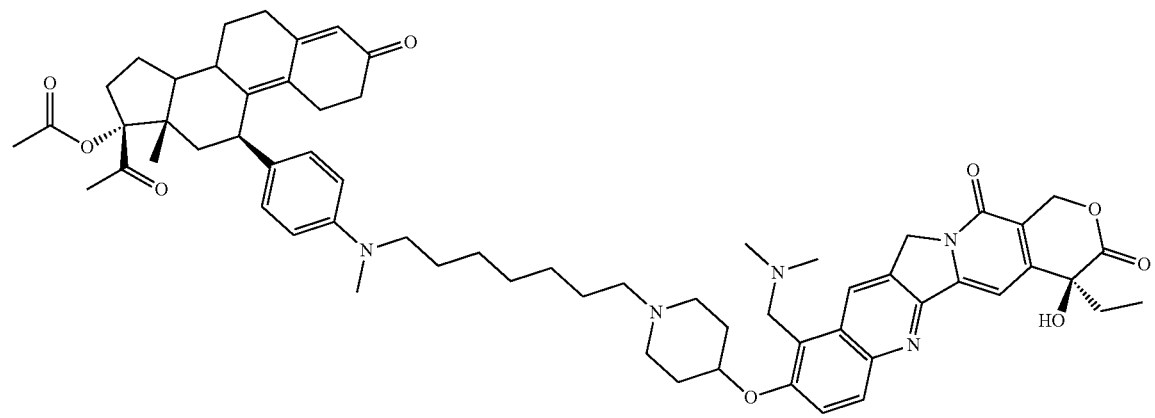
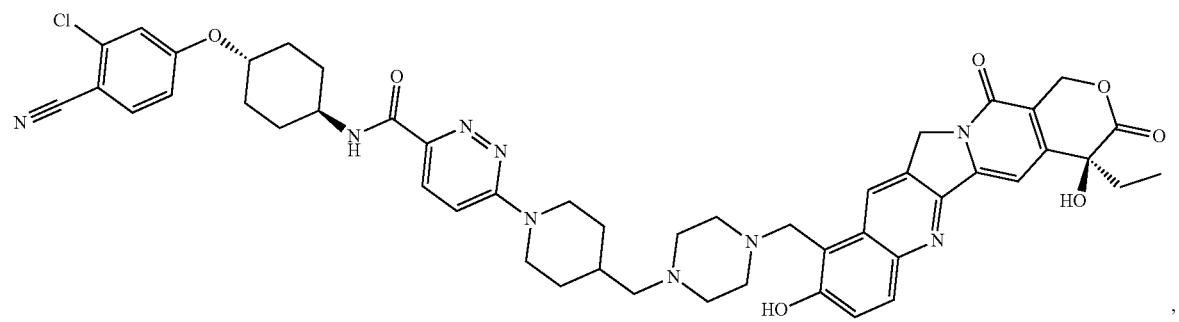
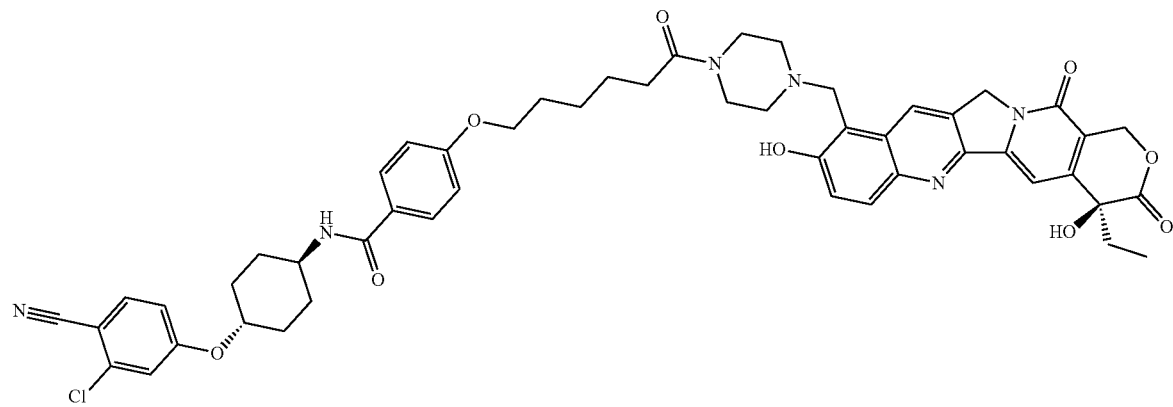
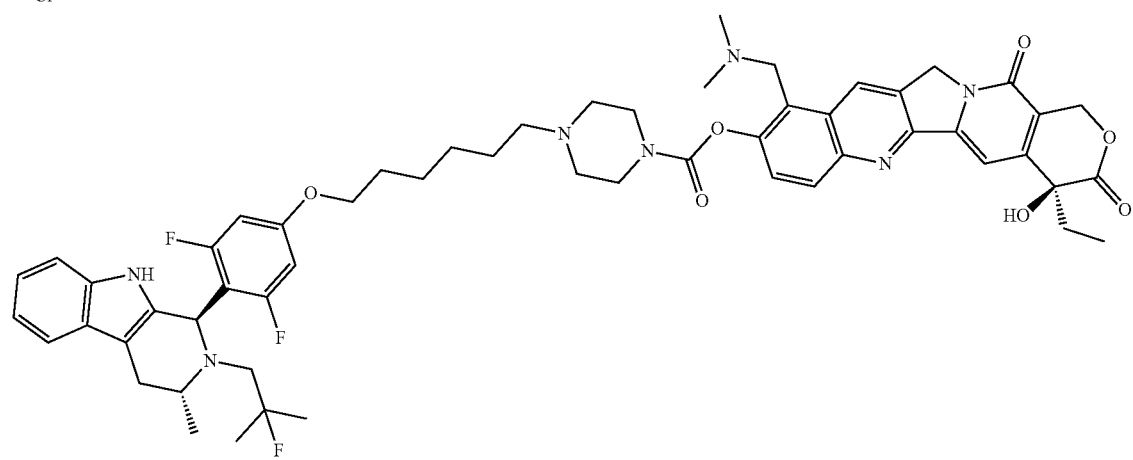

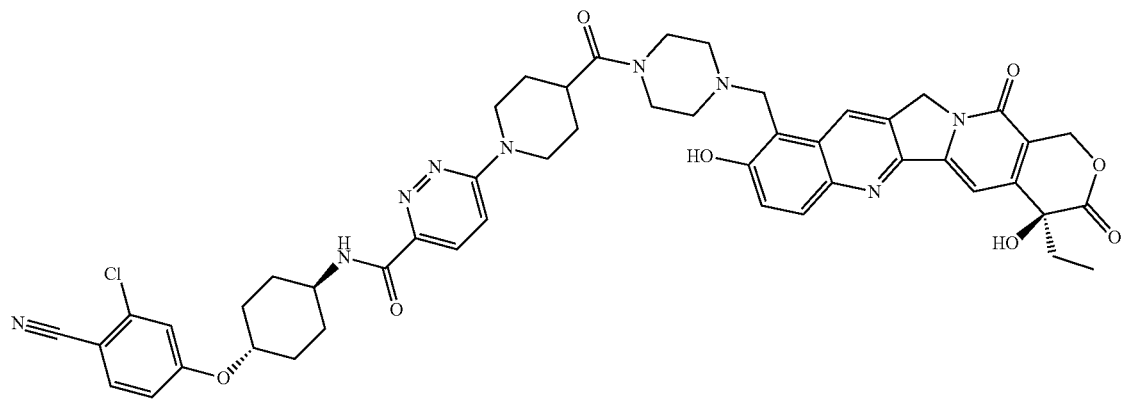
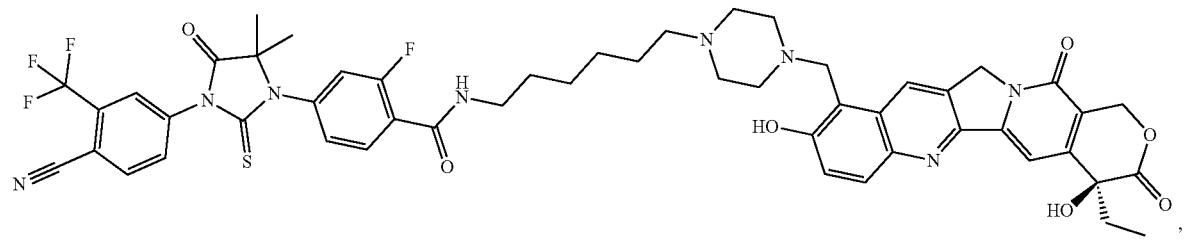
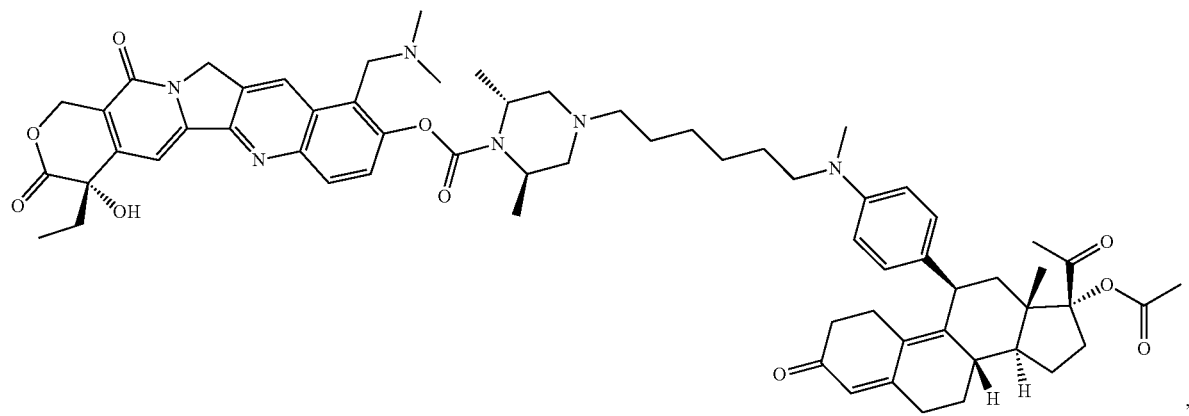
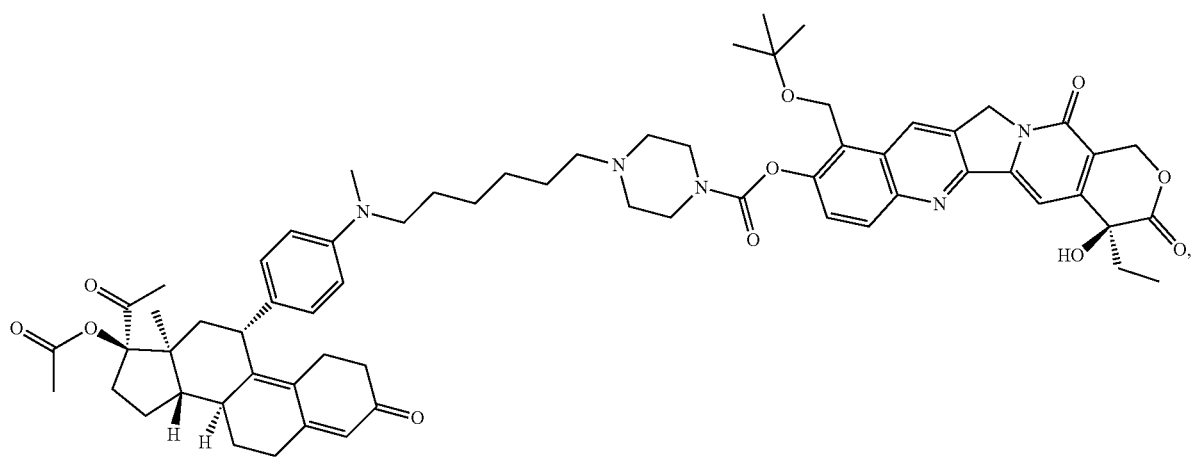

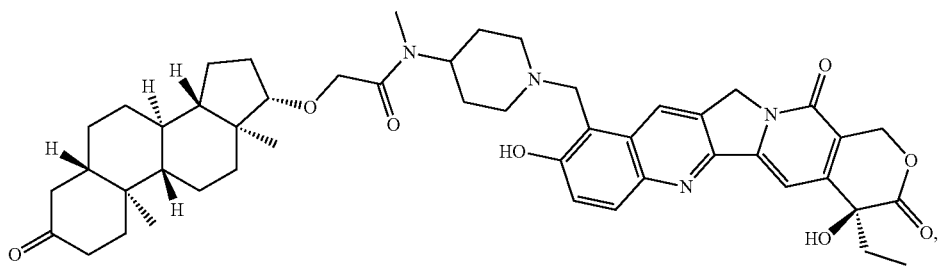
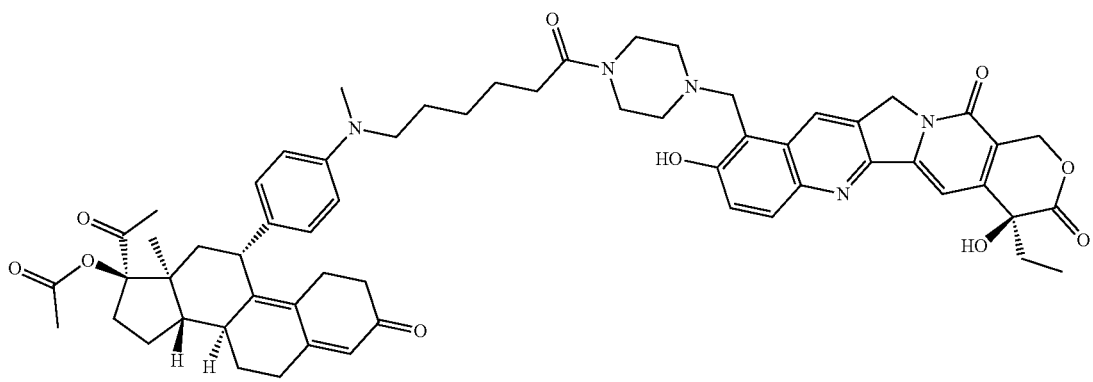
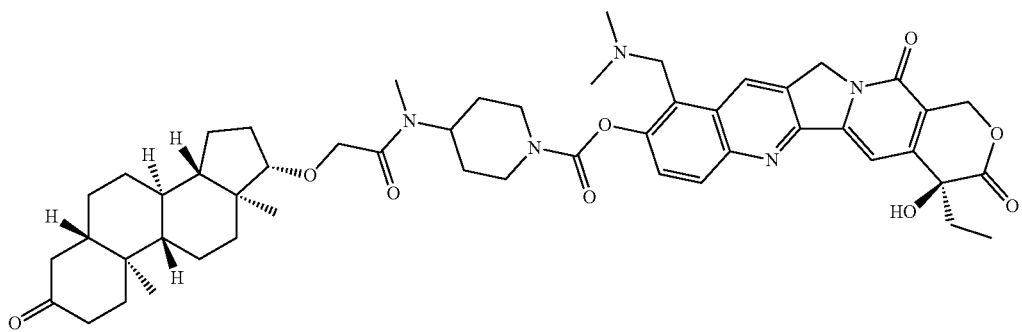
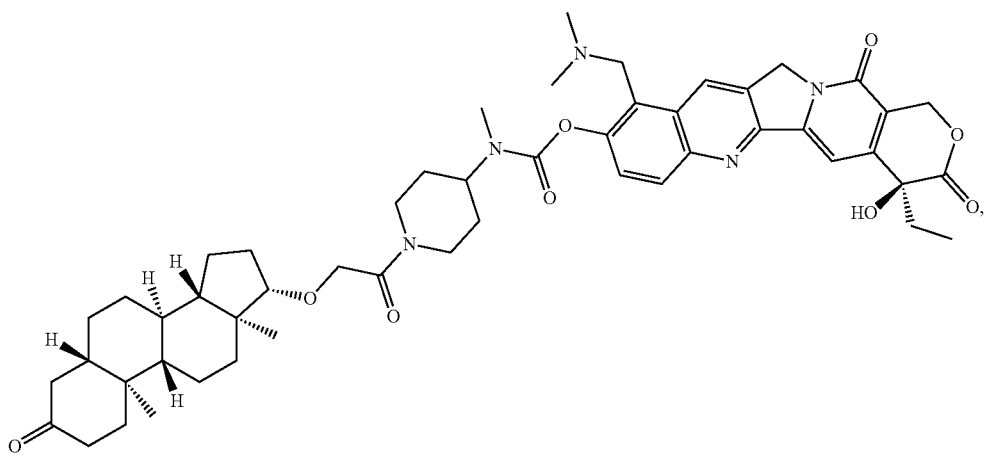

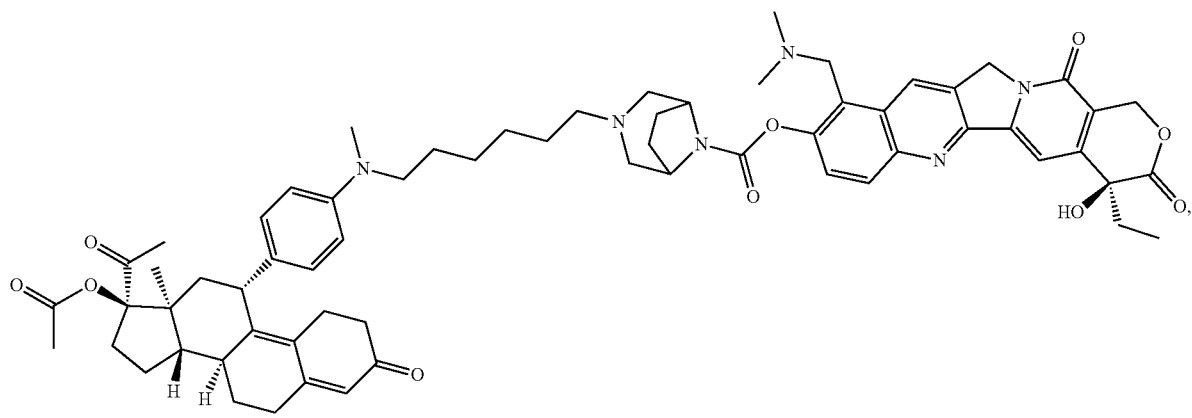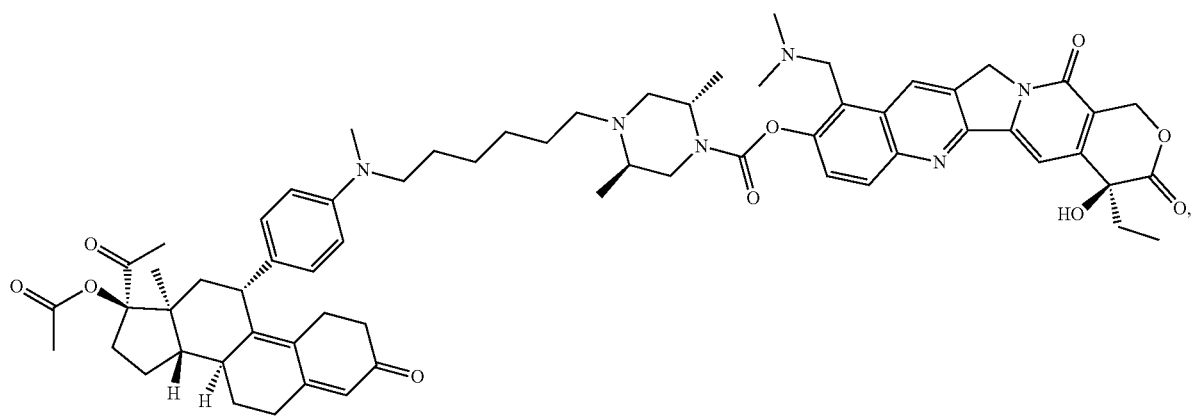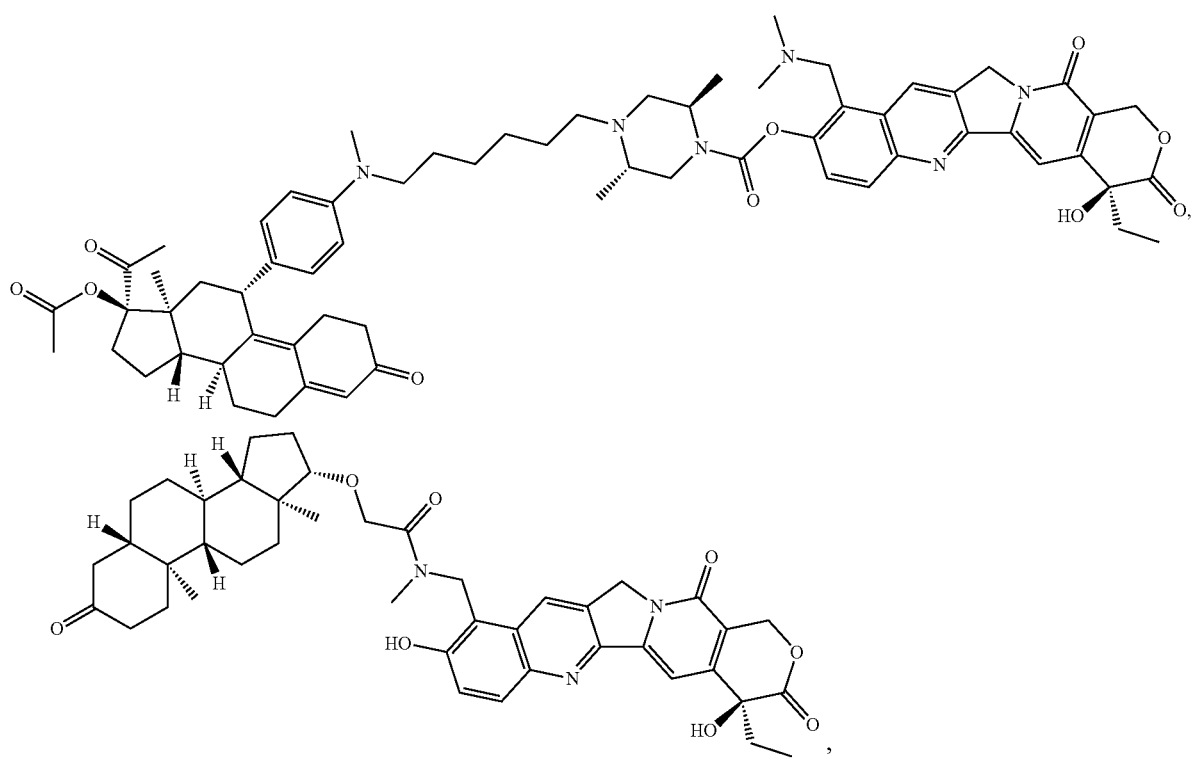

317
318
-continued
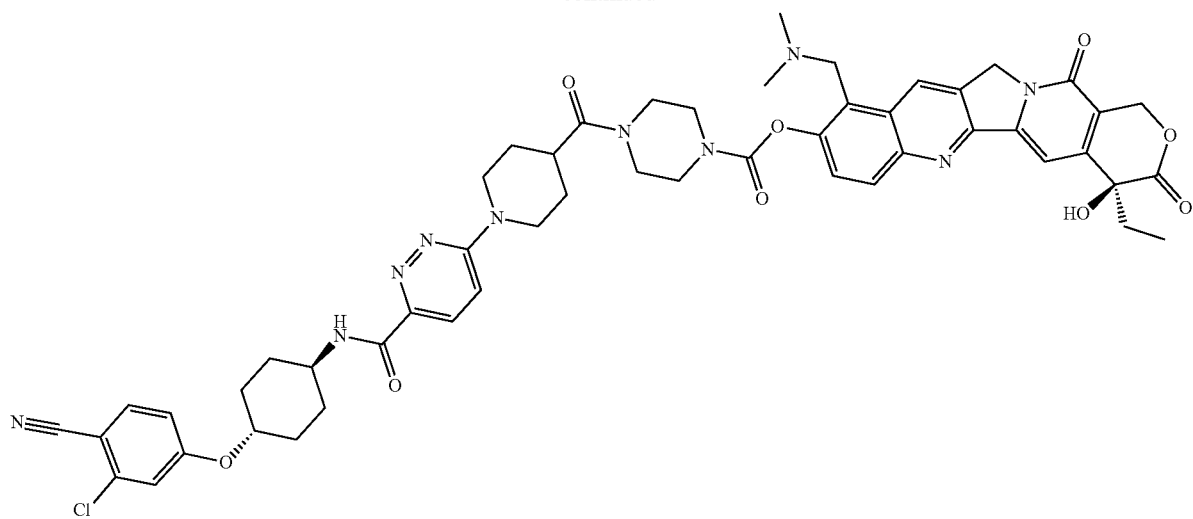
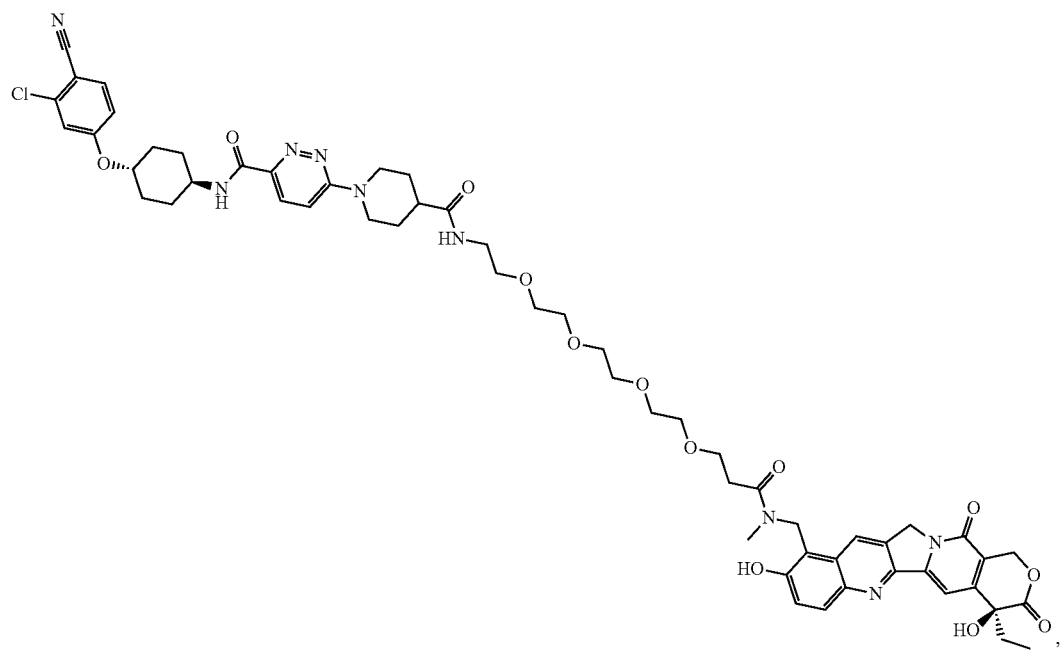
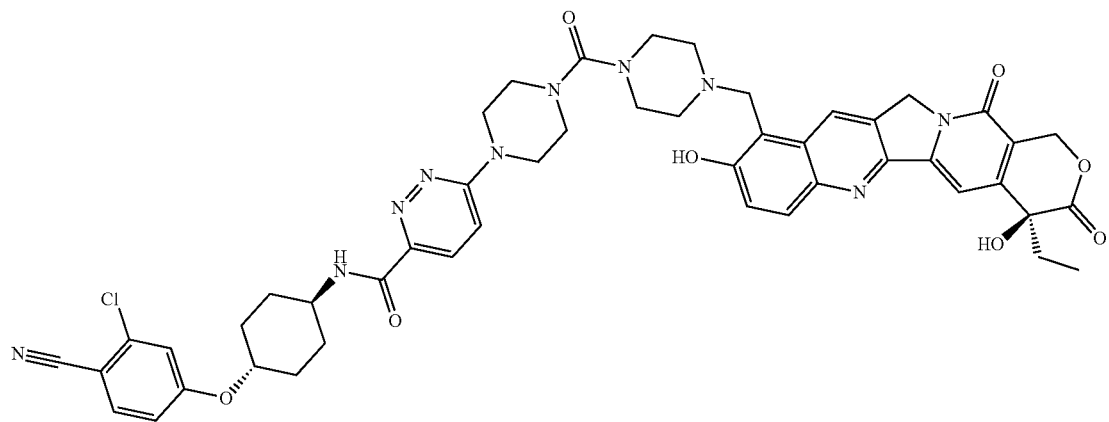

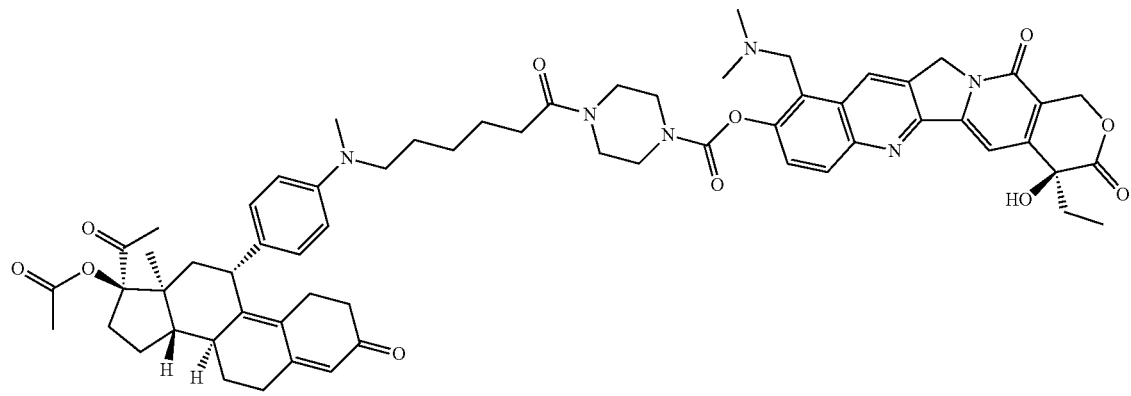

, and

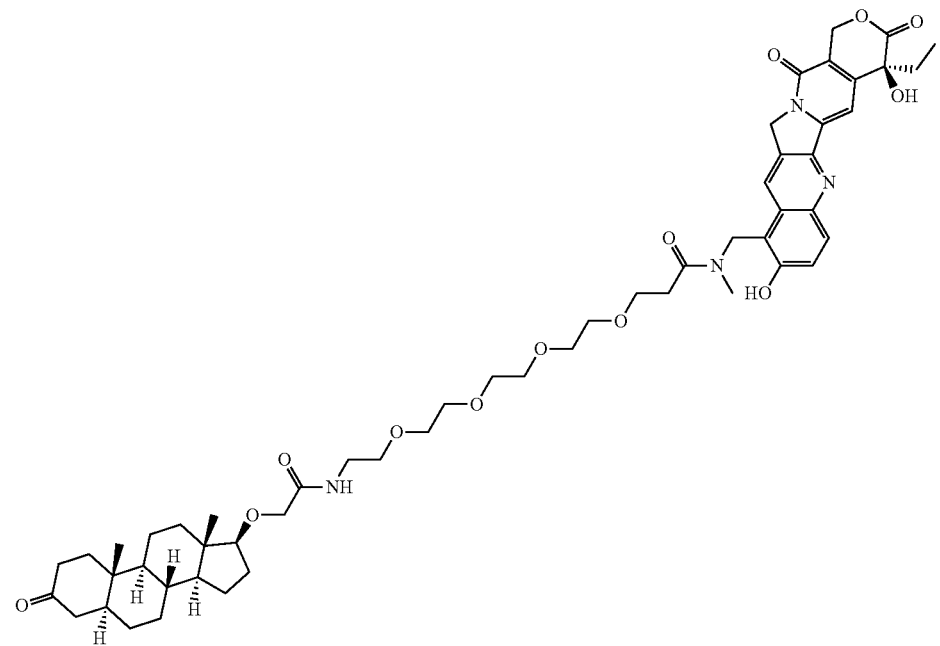

, or a pharmaceutically acceptable salt thereof.

11. A pharmaceutical composition comprising a compound of claim 1, or a stereoisomer, mixture of stereoisomers, or pharmaceutically acceptable salt thereof, and a pharmaceutically acceptable excipient.

12. A method of treating cancer, comprising administering an effective amount of the pharmaceutical composition of claim 11 to an individual in need thereof.

13. The method of claim 12, wherein the cancer is liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, Waldenström macroglobulinemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoides, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, trophoblastic neoplasms, or prostatic carcinoma.

14. The method of claim 12, wherein the cancer is a breast, prostate, or ovarian cancer.

15. The compound of claim 1, or a stereoisomer, mixture of stereoisomers, or pharmaceutically acceptable salt thereof, wherein the compound is a compound of Formula (ID):

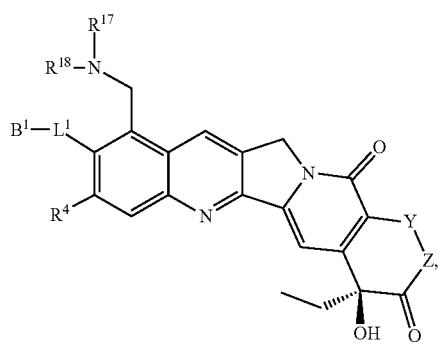

(ID)

wherein:
$R^4$, is hydrogen, halo, methyl, or methoxy; and
each of $R^{17}$ and $R^{18}$ is independently hydrogen, $C_{1-12}$ alkyl, $C_{2-12}$ alkenyl, or $C_{2-12}$ alkynyl, wherein each $C_{1-12}$ alkyl, $C_{2-12}$ alkenyl, or $C_{2-12}$ alkynyl is optionally substituted with oxo, halo, hydroxyl, or amino as valency permits; or $R^{17}$ and $R^{18}$ are taken together with the atoms to which they are attached to form heterocyclyl optionally substituted by halo or $C_{1-12}$ alkyl optionally substituted by oxo, halo, hydroxyl, or amino.

16. The compound of claim 1, or a stereoisomer, mixture of stereoisomers, or pharmaceutically acceptable salt thereof, wherein the compound is a compound of Formula (IF):

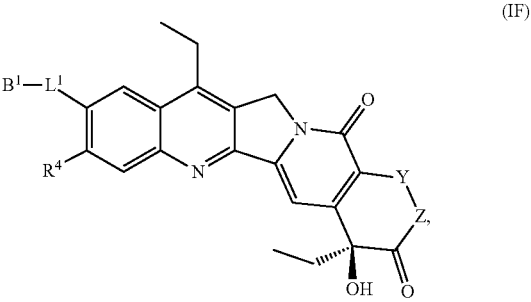

(IF)

wherein $R^4$, is hydrogen, halo, methyl, or methoxy.

17. The compound of claim 1, or a stereoisomer, mixture of stereoisomers, or pharmaceutically acceptable salt thereof, wherein the compound is a compound of Formula (IK):

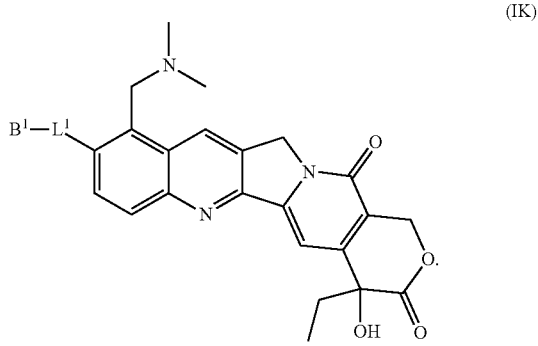

(IK)

18. The compound of claim 10, wherein the compound is:

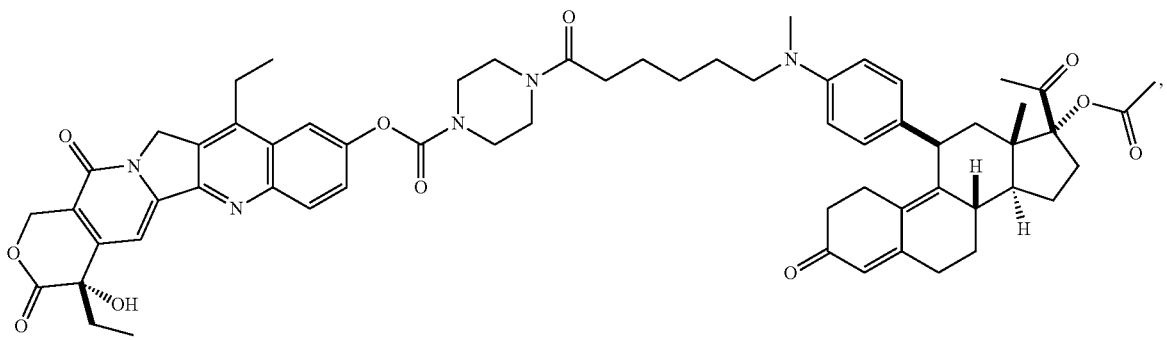

or a pharmaceutically acceptable salt thereof.

19. The compound of claim 10, wherein the compound is
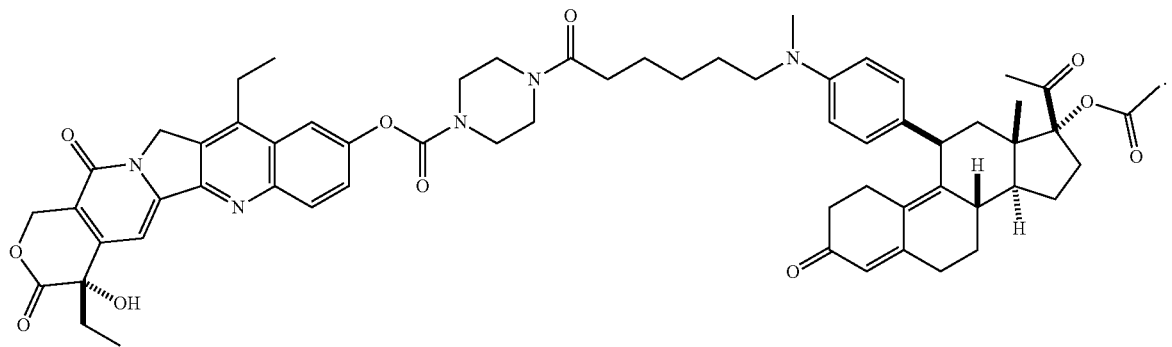
20. The compound of claim 10, wherein the compound is:
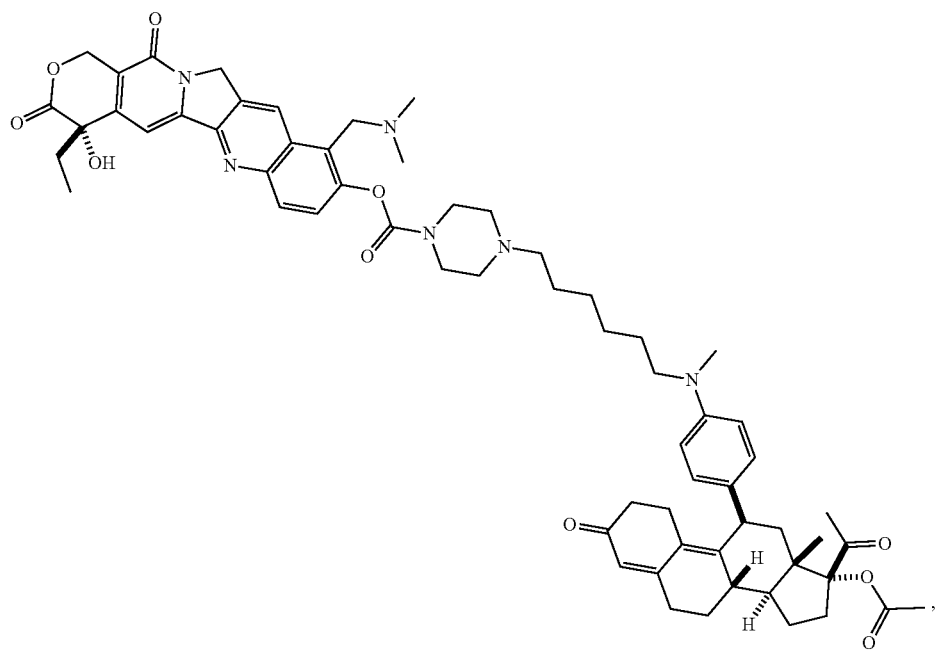
or a pharmaceutically acceptable salt thereof.

21. The compound of claim 10, wherein the compound is:
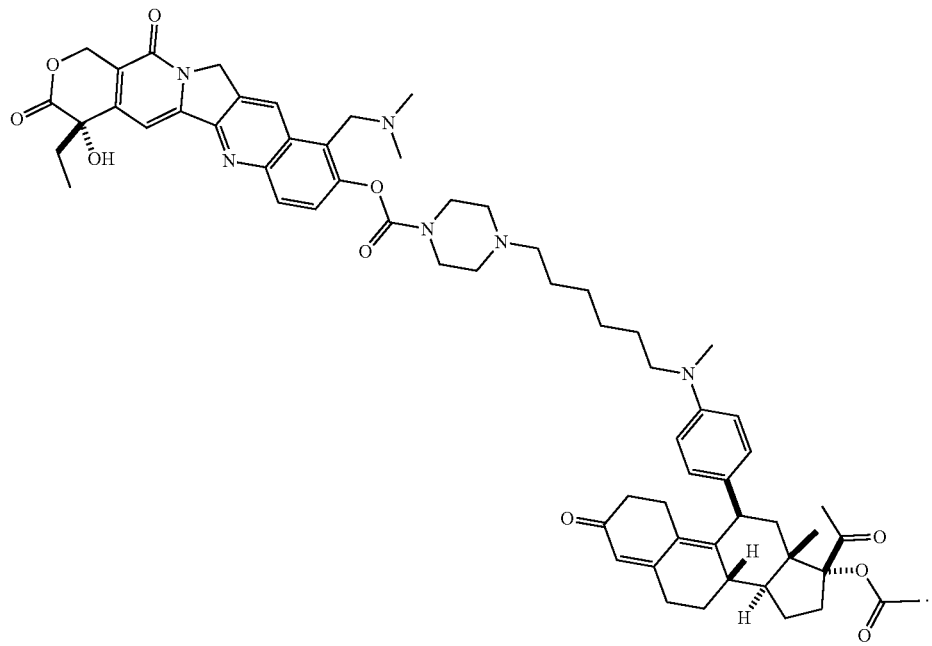
22. The compound of claim 10, wherein the compound is:
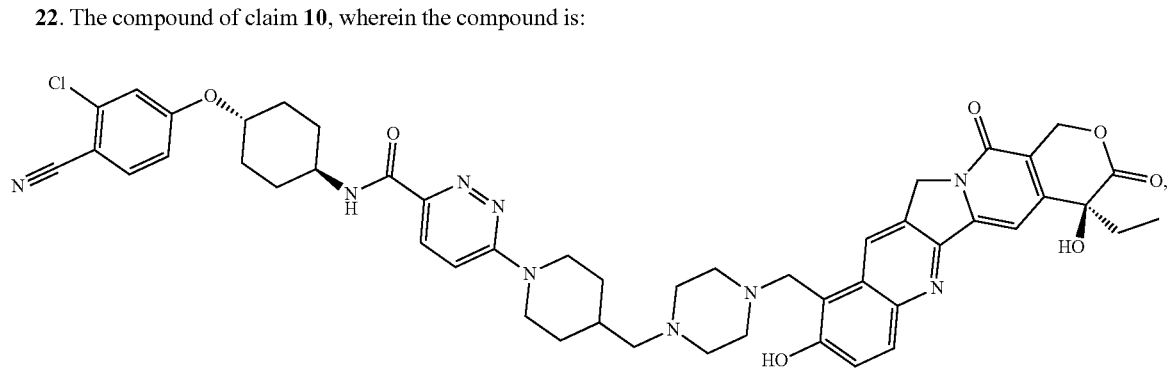
or a pharmaceutically acceptable salt thereof.
23. The compound of claim 10, wherein the compound is:
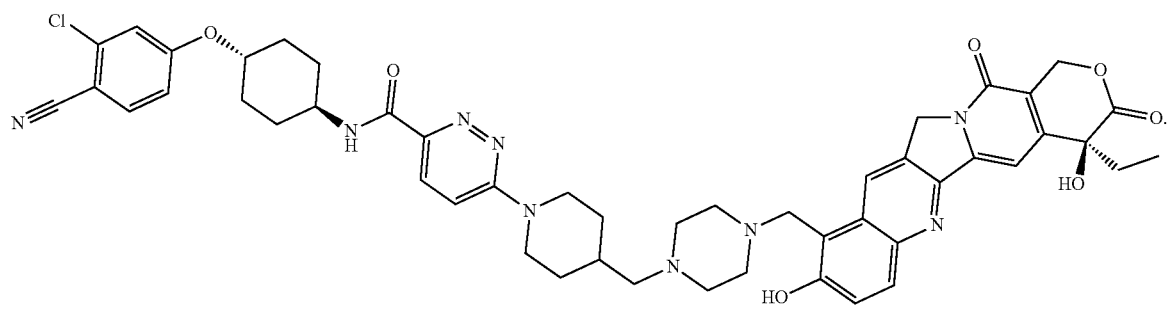 [SMILES: CC[C@@]1(O)C(=O)OCc2c1cc1n(c2=O)Cc2cc3c(CN4CCN(CC5CCN(c6ccc(C(=O)N[C@H]7CC[C@H](Oc8ccc(C#N)c(Cl)c8)CC7)nn6)CC5)CC4)c(O)ccc3nc2-1]

24. The compound of claim 10, wherein the compound is:
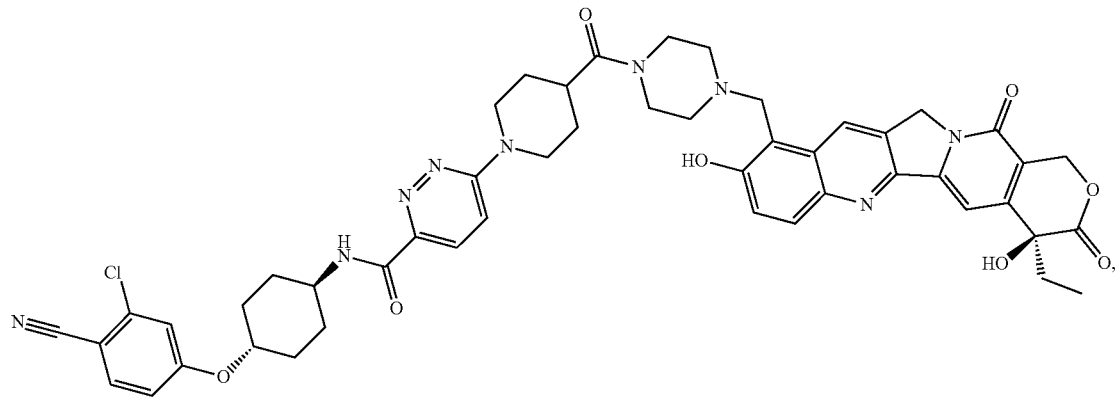 [SMILES: CC[C@@]1(O)C(=O)OCc2c1cc1n(c2=O)Cc2cc3c(CN4CCN(C(=O)C5CCN(c6ccc(C(=O)N[C@H]7CC[C@H](Oc8ccc(C#N)c(Cl)c8)CC7)nn6)CC5)CC4)c(O)ccc3nc2-1]
or a pharmaceutically acceptable salt thereof.
25. The compound of claim 10, wherein the compound is:
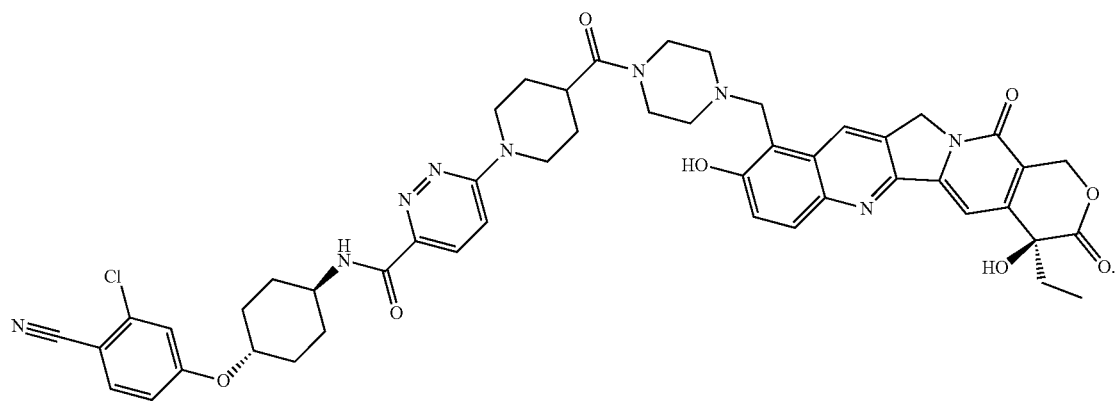 [SMILES: CC[C@@]1(O)C(=O)OCc2c1cc1n(c2=O)Cc2cc3c(CN4CCN(C(=O)C5CCN(c6ccc(C(=O)N[C@H]7CC[C@H](Oc8ccc(C#N)c(Cl)c8)CC7)nn6)CC5)CC4)c(O)ccc3nc2-1]
26. The compound of claim 10, wherein the compound is:
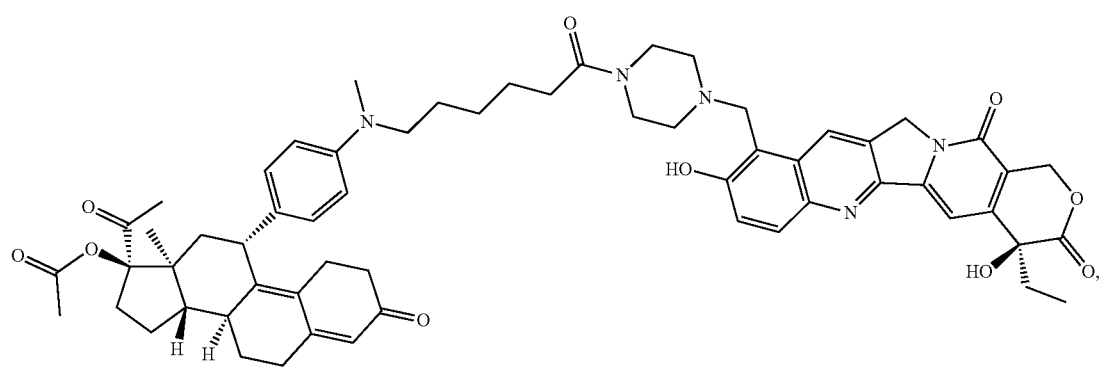 [SMILES: CC[C@@]1(O)C(=O)OCc2c1cc1n(c2=O)Cc2cc3c(CN4CCN(C(=O)CCCCCN(C)c5ccc([C@H]6C[C@@]7(C)[C@@H](CC[C@]7(OC(C)=O)C(C)=O)[C@@H]7CCC8=CC(=O)CCC8=C76)cc5)CC4)c(O)ccc3nc2-1]
or a pharmaceutically acceptable salt thereof.

27. The compound of claim 10, wherein the compound is:
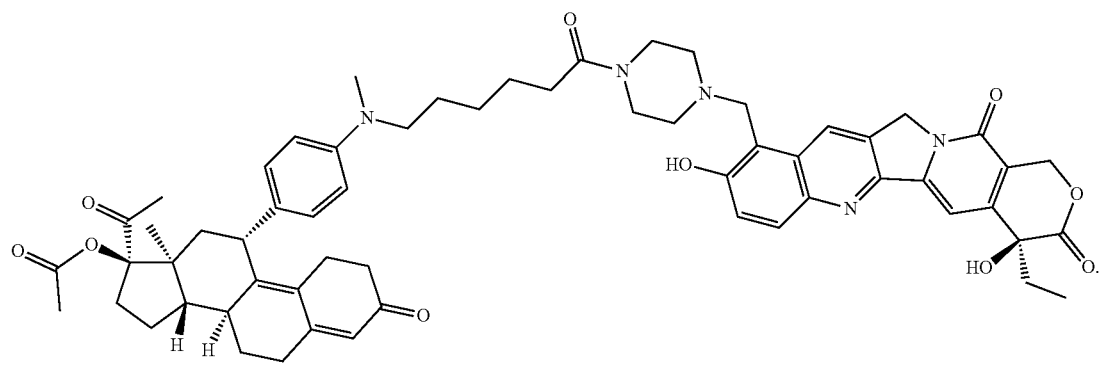 [SMILES: CC[C@@]1(O)C(=O)OCc2c1cc1n(c2=O)Cc2cc3c(CN4CCN(C(=O)CCCCCN(C)c5ccc([C@H]6C[C@@]7(C)[C@@H](CC[C@]7(OC(C)=O)C(C)=O)[C@@H]7CCC8=CC(=O)CCC8=C76)cc5)CC4)c(O)ccc3nc2-1]
28. The compound of claim 10, wherein the compound is:
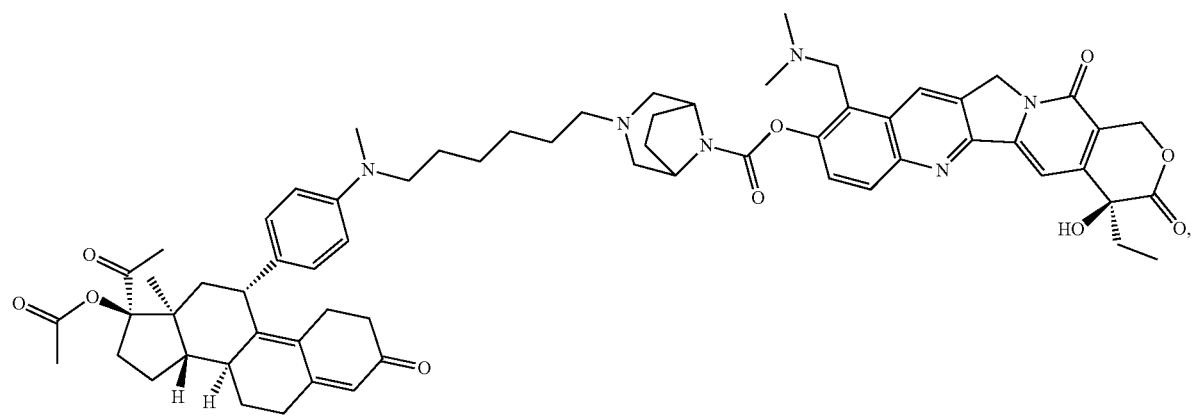 [SMILES: CC[C@@]1(O)C(=O)OCc2c1cc1n(c2=O)Cc2cc3c(CN(C)C)c(OC(=O)N4C5CCC4CN(CCCCCCN(C)c4ccc([C@H]6C[C@@]7(C)[C@@H](CC[C@]7(OC(C)=O)C(C)=O)[C@@H]7CCC8=CC(=O)CCC8=C76)cc4)C5)ccc3nc2-1]
or a pharmaceutically acceptable salt thereof.
29. The compound of claim 10, wherein the compound is:
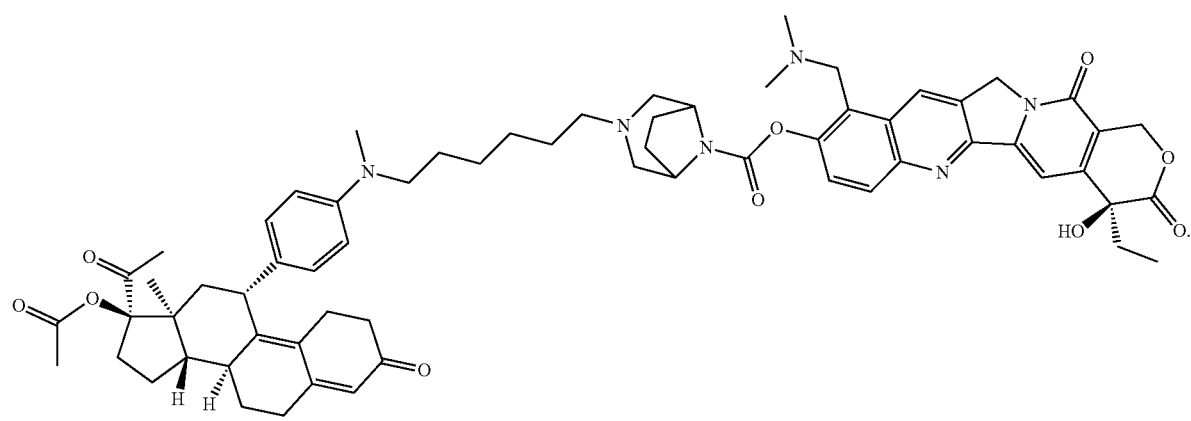 [SMILES: CC[C@@]1(O)C(=O)OCc2c1cc1n(c2=O)Cc2cc3c(CN(C)C)c(OC(=O)N4C5CCC4CN(CCCCCCN(C)c4ccc([C@H]6C[C@@]7(C)[C@@H](CC[C@]7(OC(C)=O)C(C)=O)[C@@H]7CCC8=CC(=O)CCC8=C76)cc4)C5)ccc3nc2-1]

30. The compound of claim 10, wherein the compound is:
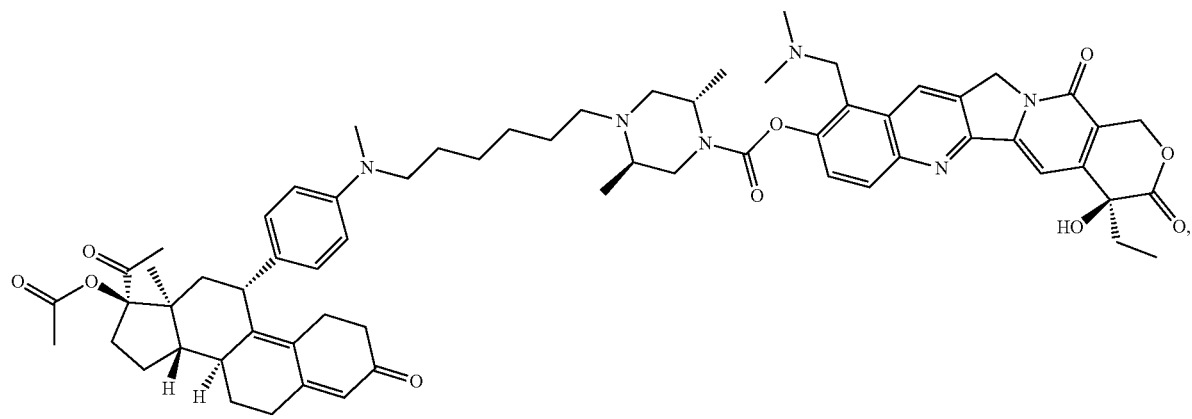 [SMILES: CC[C@@]1(O)C(=O)OCc2c1cc1n(c2=O)Cc2cc3c(CN(C)C)c(OC(=O)N4C[C@@H](C)N(CCCCCCN(C)c5ccc([C@H]6C[C@@]7(C)[C@@H](CC[C@]7(OC(C)=O)C(C)=O)[C@@H]7CCC8=CC(=O)CCC8=C76)cc5)C[C@@H]4C)ccc3nc2-1]
or a pharmaceutically acceptable salt thereof.
31. The compound of claim 10, wherein the compound is:
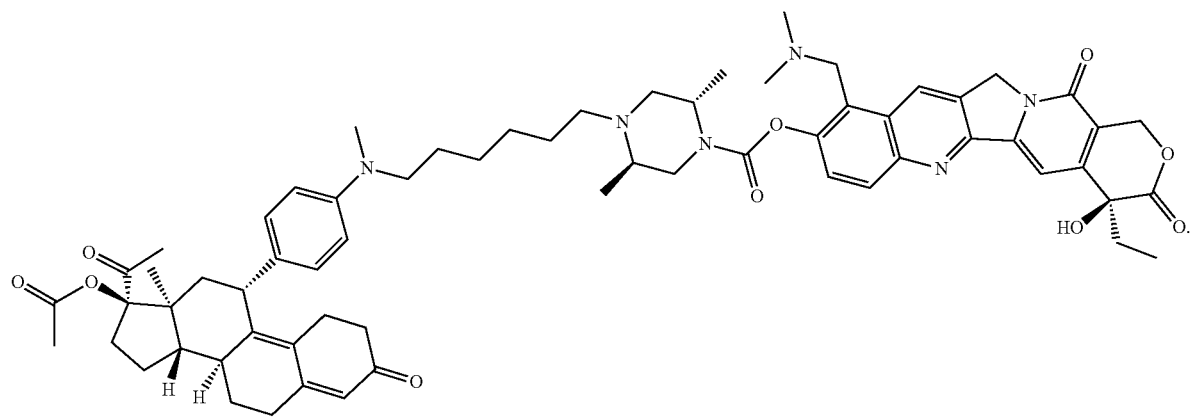 [SMILES: CC[C@@]1(O)C(=O)OCc2c1cc1n(c2=O)Cc2cc3c(CN(C)C)c(OC(=O)N4C[C@@H](C)N(CCCCCCN(C)c5ccc([C@H]6C[C@@]7(C)[C@@H](CC[C@]7(OC(C)=O)C(C)=O)[C@@H]7CCC8=CC(=O)CCC8=C76)cc5)C[C@@H]4C)ccc3nc2-1]
32. The compound of claim 10, wherein the compound is:
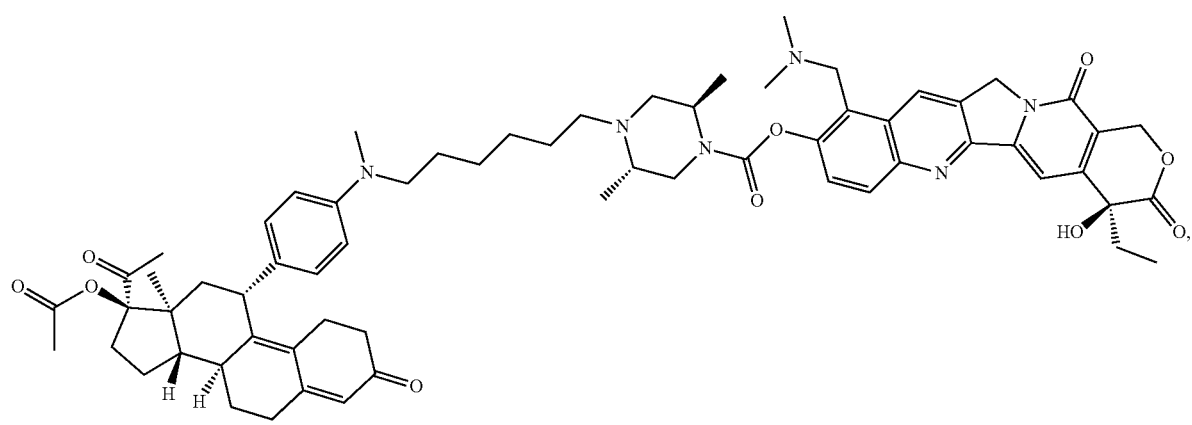 [SMILES: CC[C@@]1(O)C(=O)OCc2c1cc1n(c2=O)Cc2cc3c(CN(C)C)c(OC(=O)N4C[C@H](C)N(CCCCCCN(C)c5ccc([C@H]6C[C@@]7(C)[C@@H](CC[C@]7(OC(C)=O)C(C)=O)[C@@H]7CCC8=CC(=O)CCC8=C76)cc5)C[C@H]4C)ccc3nc2-1]
or a pharmaceutically acceptable salt thereof.

33. The compound of claim 10, wherein the compound is:
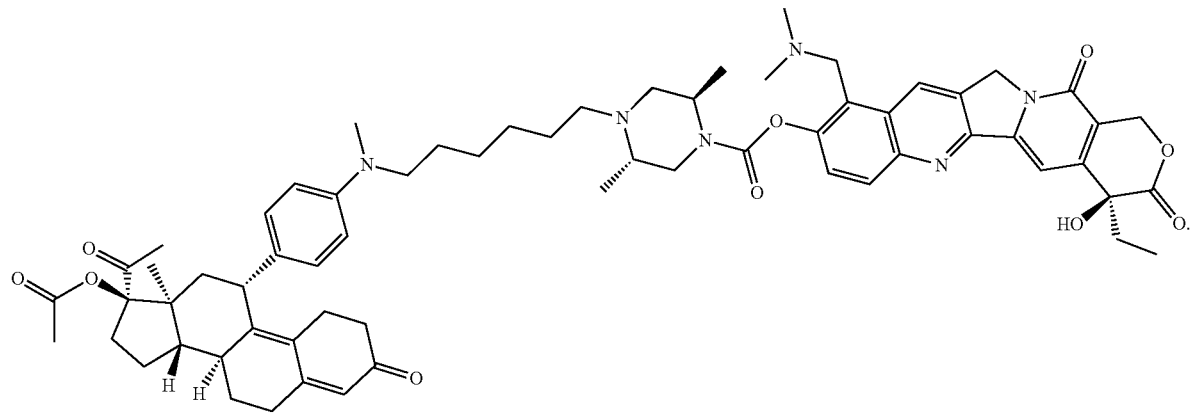 [SMILES: CC[C@@]1(O)C(=O)OCc2c1cc1n(c2=O)Cc2cc3c(CN(C)C)c(OC(=O)N4C[C@H](C)N(CCCCCCN(C)c5ccc([C@H]6C[C@@]7(C)[C@@H](CC[C@]7(OC(C)=O)C(C)=O)[C@@H]7CCC8=CC(=O)CCC8=C76)cc5)C[C@H]4C)ccc3nc2-1]
34. A pharmaceutical composition comprising a compound of claim 10, or a pharmaceutically acceptable salt thereof, and a pharmaceutically acceptable excipient.
* * * * *